(12) United States Patent
Abal Posada et al.

(10) Patent No.: US 9,046,522 B2
(45) Date of Patent: Jun. 2, 2015

(54) MARKERS FOR ENDOMETRIAL CANCER

(75) Inventors: Miguel Abal Posada, Barcelona (ES); Andreas Doll, Barcelona (ES); Antonio Gil Moreno, Barcelona (ES); Tamara Maes, Barcelona (ES); Cristina Perez, Barcelona (ES); Jaume Reventós Puigjaner, Bacelona (ES); Elisabet Rossell, Barcelona (ES)

(73) Assignee: Geadic Biotec, AIE, Barcelona (ES)

( * ) Notice: Subject to any disclaimer, the term of this patent is extended or adjusted under 35 U.S.C. 154(b) by 0 days.

(21) Appl. No.: 13/386,536

(22) PCT Filed: Jul. 23, 2010

(86) PCT No.: PCT/EP2010/004550
§ 371 (c)(1),
(2), (4) Date: Jan. 23, 2012

(87) PCT Pub. No.: WO2011/009637
PCT Pub. Date: Jan. 27, 2011

(65) Prior Publication Data
US 2012/0122726 A1     May 17, 2012

(30) Foreign Application Priority Data
Jul. 24, 2009    (EP) .................................... 09166398

(51) Int. Cl.
*C12Q 1/68* (2006.01)
*G01N 33/574* (2006.01)
*C07K 16/30* (2006.01)

(52) U.S. Cl.
CPC ...... *G01N 33/57442* (2013.01); *C07K 16/3069* (2013.01); *C12Q 1/6886* (2013.01); *C12Q 2600/112* (2013.01); *C12Q 2600/156* (2013.01); *C12Q 2600/16* (2013.01); *G01N 2800/60* (2013.01)

(58) Field of Classification Search
None
See application file for complete search history.

(56) References Cited

U.S. PATENT DOCUMENTS

| 7,014,996 | B1 * | 3/2006 | Macina ........................ 435/6.14 |
| 2005/0164272 | A1 | 7/2005 | Warrington et al. |
| 2007/0287158 | A1 * | 12/2007 | Gorodeski et al. ................ 435/6 |
| 2008/0274470 | A1 | 11/2008 | Le et al. |
| 2009/0075299 | A1 | 3/2009 | Mathew et al. |
| 2009/0175844 | A1 | 7/2009 | Nakamura et al. |

FOREIGN PATENT DOCUMENTS

| JP | 2002-501613 A | 1/2002 |
| JP | 2006-162446 A | 6/2006 |
| JP | 2009-034071 A | 2/2009 |
| WO | WO 98/42865 | 10/1998 |
| WO | WO 2005/034978 A2 | 4/2005 |
| WO | WO 2007/030362 A1 | 3/2007 |
| WO | WO 2007/072220 A2 | 6/2007 |
| WO | WO 2008/122629 A1 | 10/2008 |
| WO | WO 2009/021338 A1 | 2/2009 |
| WO | WO 2009/126969 A2 | 10/2009 |

OTHER PUBLICATIONS

Carta et al. Analysis of candidate genes through a proteomics-based approach in primary cell lines from malignant melanomas and their metastases. Melanoma Research, vol. 15, pp. 235-244, 2005.*
Grimmer et al. Regulation of type II collagen synthesis during osteoarthritis by prolyl-4-hydroxylases. The American Journal of Pathology, vol. 169, No. 2, pp. 491-502, 2006.*
RNAlater® Handbook, Jul. 2006, printed as pp. 1/20-20-20.*
Pollack et al. Microarray analysis reveals a major direct role of DNA copy number alteration in the transcriptional program of human breast tumors. Proceedings of the National Academy of Sciences, USA, vol. 99, No. 20, pp. 12963-12968, Oct. 2002.*
Takacs et al. Echogenic endomeuid collection in postmenoausal women is a significant risk factor for disease. Journal of Ultrasound in Medicine, vol. 24, pp. 1477-1481, 2005.*
The International Search Report received in the corresponding PCT Application No. PCT/EP2010/004550, dated Feb. 21, 2011.
Database GeneBank [Online] NCBI; "P4HB mRNA", Dec. 3, 2006, retrieved from http://www.ncbi.nlm.nih.gov/nuccore/20070124. (XP002603134), NM_000918, GI: 20070124.
"[HG-U133A] Affymetrix Human Genome U133A Array", GEO, Mar. 2002. (XP002527544).
Aresta, et al., "A novel Rho GTPase-activation-protein interacts with Gem, a member of the Ras superfamily of GTPases", *Biochem. J.*, vol. 367, 2002, pp. 57-65.
Clement, et al., "The IKK-related kinases: from innate immunity to oncogenesis", *Cell Research*, vol. 18, 2008, pp. 889-899.
Fiegl, H., et al., "Methylated DNA Collected by Tampons—A New Tool to Detect Endometrial Cancer", *Cancer Epidemiology, Biomarkers & Prevention*, vol. 13, No. 5, 2004, pp. 882-888.
Guo, et al., "Deregulation of IKBKE is associated with Tumor Progression, Poor Prognosis and Cisplatin Resistance in Ovarian Cancer", *The American Journal of Pathology*, vol. 175, No. 1, 2009, pp. 327-333.
Meng, et al., "Increased expression of collagen prolyl 4-hydroxylases in Chinese patients with hereditary gingival fibromatosis", *Archives of Oral Biology*, vol. 52, No. 12, 2007, pp. 1209-1214.

(Continued)

Primary Examiner — Jennifer Dunston
(74) Attorney, Agent, or Firm — Foley & Lardner LLP

(57) ABSTRACT

The invention relates to the surprising finding that biomarkers corresponding to ACAA1, AP1M2, CGN, DDR1, EPS8L2, FASTKD1, GMIP, IKBKE, P2RX4, P4HB, PHKG2, PPFIBP2, PPP1 R16A, RASSF7, RNF183, SIRT6, TJP3, EFEMP2, S0CS2, and DCN are differentially expressed in control samples as compared to samples from patients having endometrial cancer and are therefore useful for detecting endometrial cancer. In particular these biomarkers having excellent sensitivity, specificity, and/or the ability to separate affected from non affected individuals. Furthermore, the inventors found that the differential expression of these biomarkers in primary endometrial cancer tumor tissue is correlated to their expression level in uterine fluid samples as compared to control values. Thus these biomarkers are robust in that they are found to be differentially expressed in several different types of samples from affected individuals.

12 Claims, 14 Drawing Sheets

(56) References Cited

OTHER PUBLICATIONS

Pallet, et al., "Response of human renal tubular cells to cyclosporine and sirolimus: A toxicogenomic study", *Toxicology and Applied Pharmacology*, vol. 229, 2008, pp. 184-196.

Anonymous, "I4907 Sigma Anti-IKK/IKK-i, C-Terminal antibody produced in rabbit", *Sigma Aldrich Labware Cagalog*, Sigma-Aldrich, [Online], Jul. 26, 2007, pp. 1-4. (XP002510910).

Zhu, et al., "Proteomic identification of differential-expressed proteins in squamous cervical cancer", Gynecologic Oncology, vol. 112, 2009, pp. 248-256.

The International Preliminary Report on Patentability received in the corresponding International Patent Application No. PCT/EP2010/004550, dated Jan. 24, 2012.

The Office Communication received in the related European Patent Application No. 10736990.2, dated Nov. 2, 2012.

Chen, et al., "Discordant Protein and mRNA Expression in Lung Adenocarcinomas", Molecular & Cellular Proteomics, 1.4, 2002, pp. 304-313.

Domenyuk V.P. et al., "Identification of new DNA markers of endometrial cancer in patients from the Ukrainian population", Exp Oncol. Jun. 2007;29(2):152-5 (Abstract).

Office Action mailed Jul. 28, 2014 in Russia Application No. 2012106432, with translation.

Office Action Summary issued in corresponding Japanese Application No. 2012-520964 dated Nov. 18, 2014.

Strausberg et al., "*Homo sapiens* prolyl 4-hydroxylase, beta polypeptide, mRNA (dDNA clone Image:3607959)," Database GenBank, Mar. 18, 2009, (URL: http://www.ncbi.nlm.nih.gov/nuccore/17402948)., GenBank Accession No. BC018801.1.

\* cited by examiner

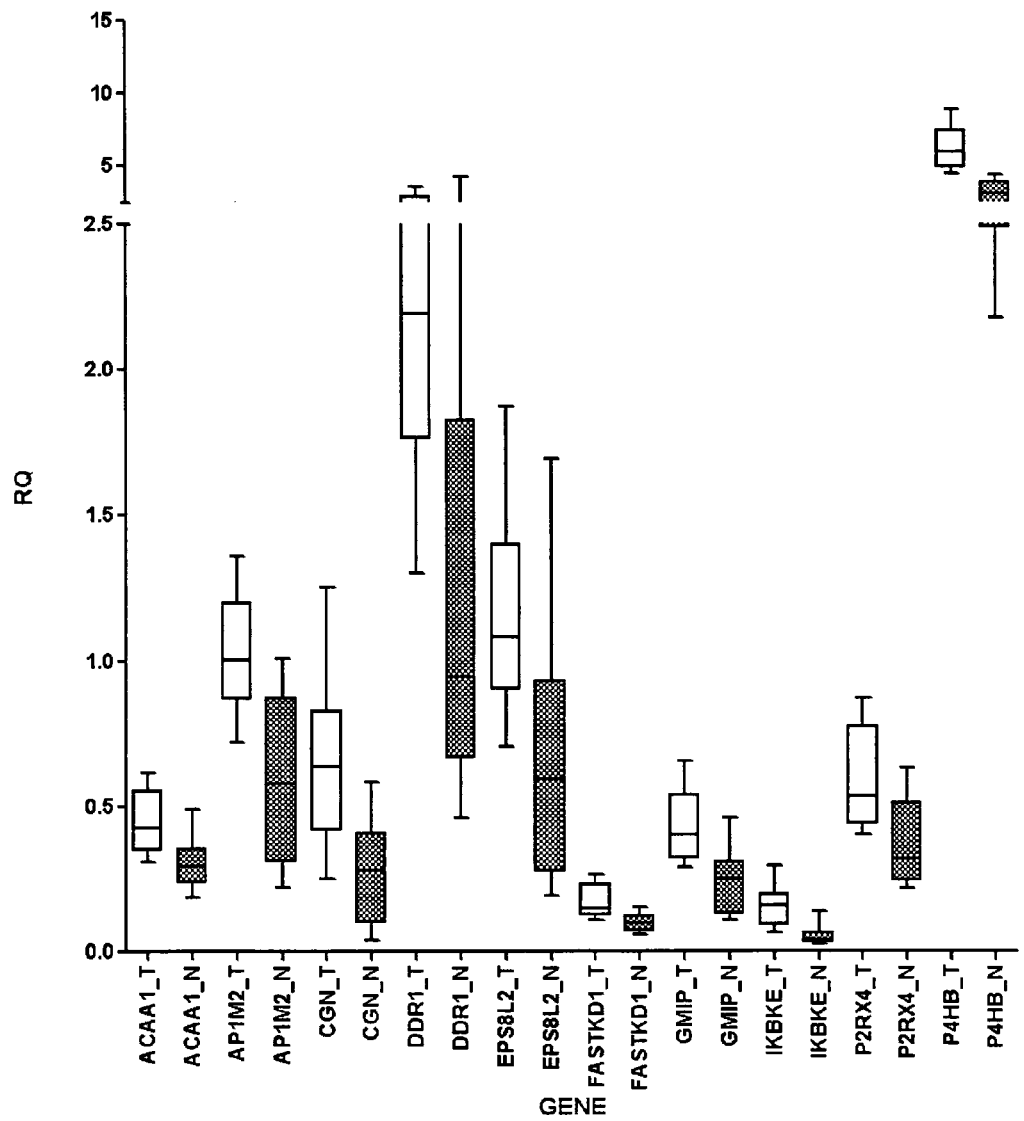

FIG. 3 RNF183 data:
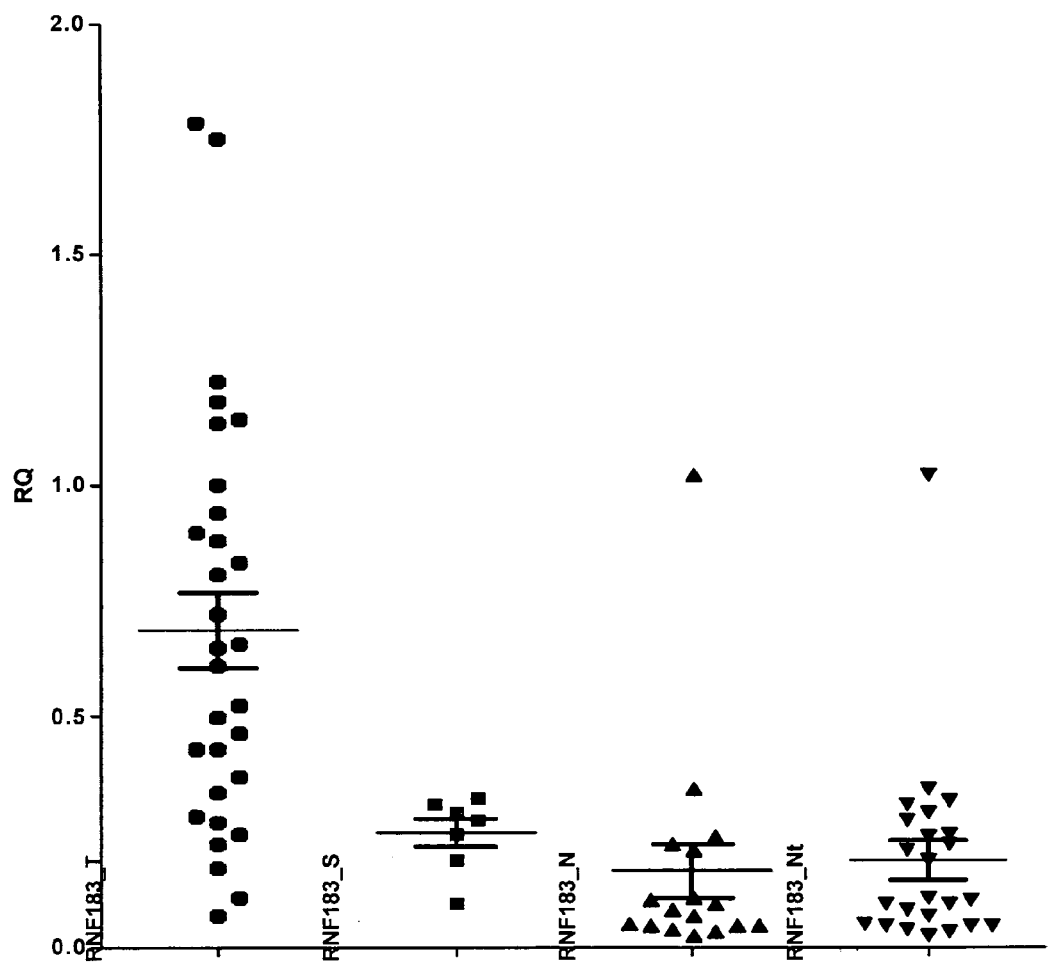

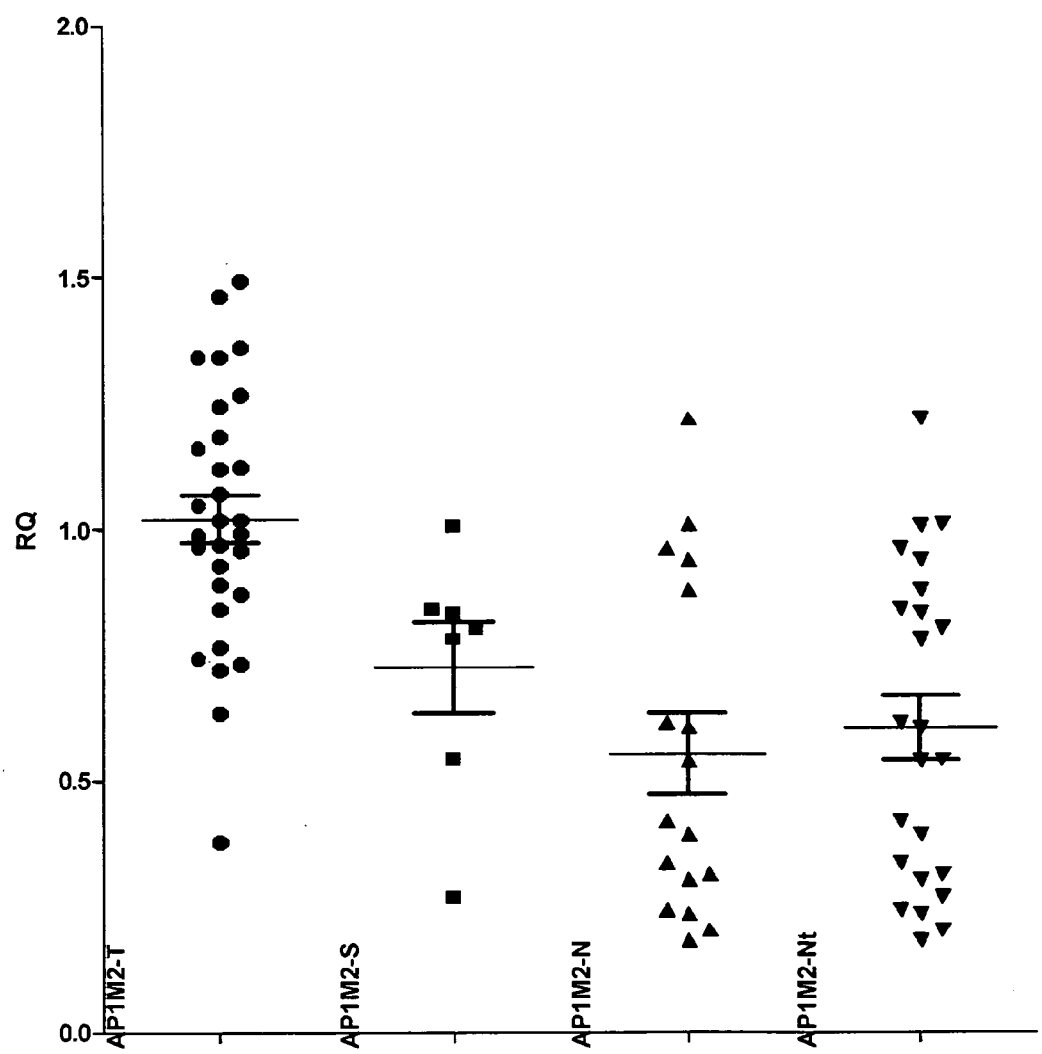
FIG. 4 AP1M2

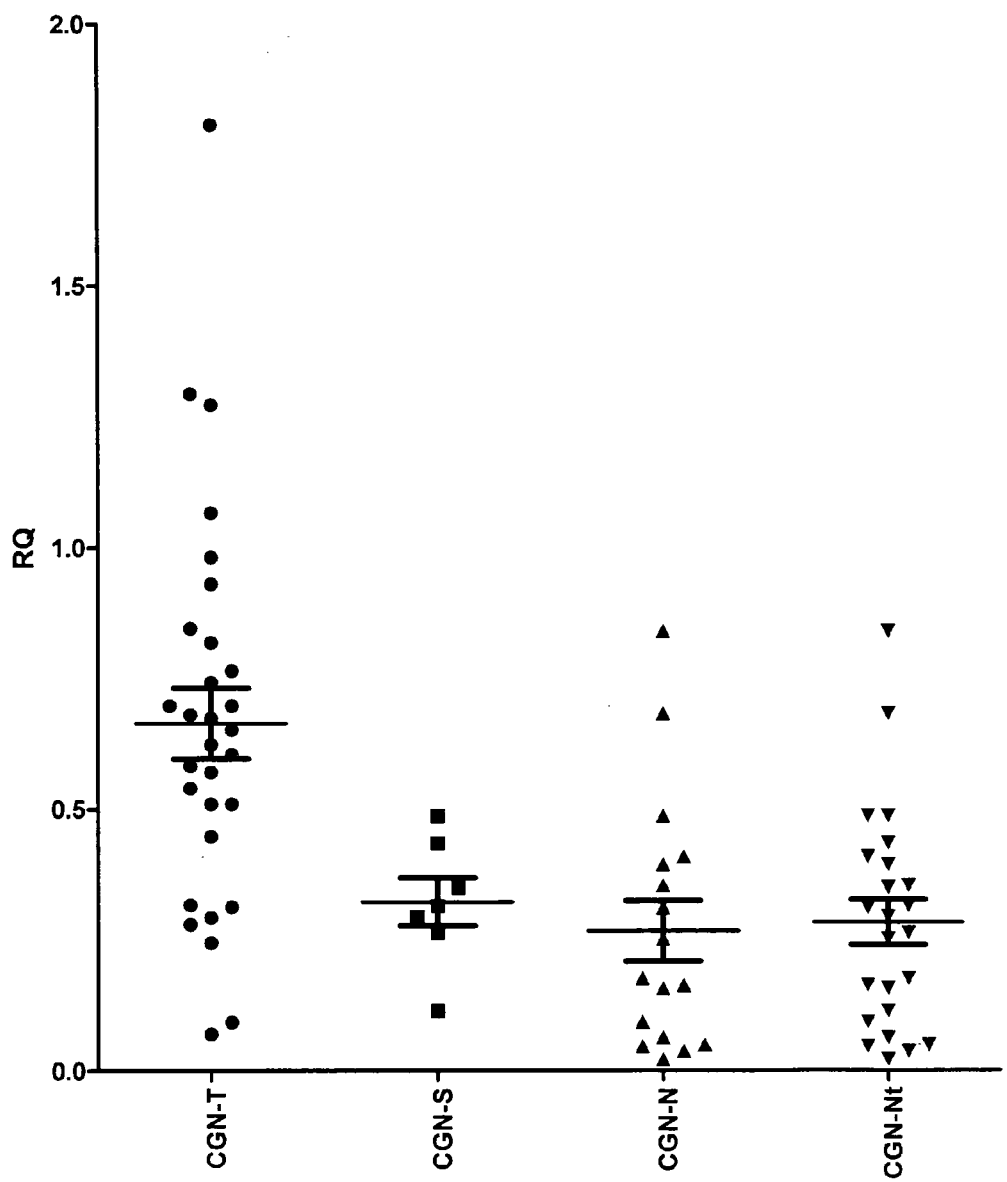
FIG. 5 CGN

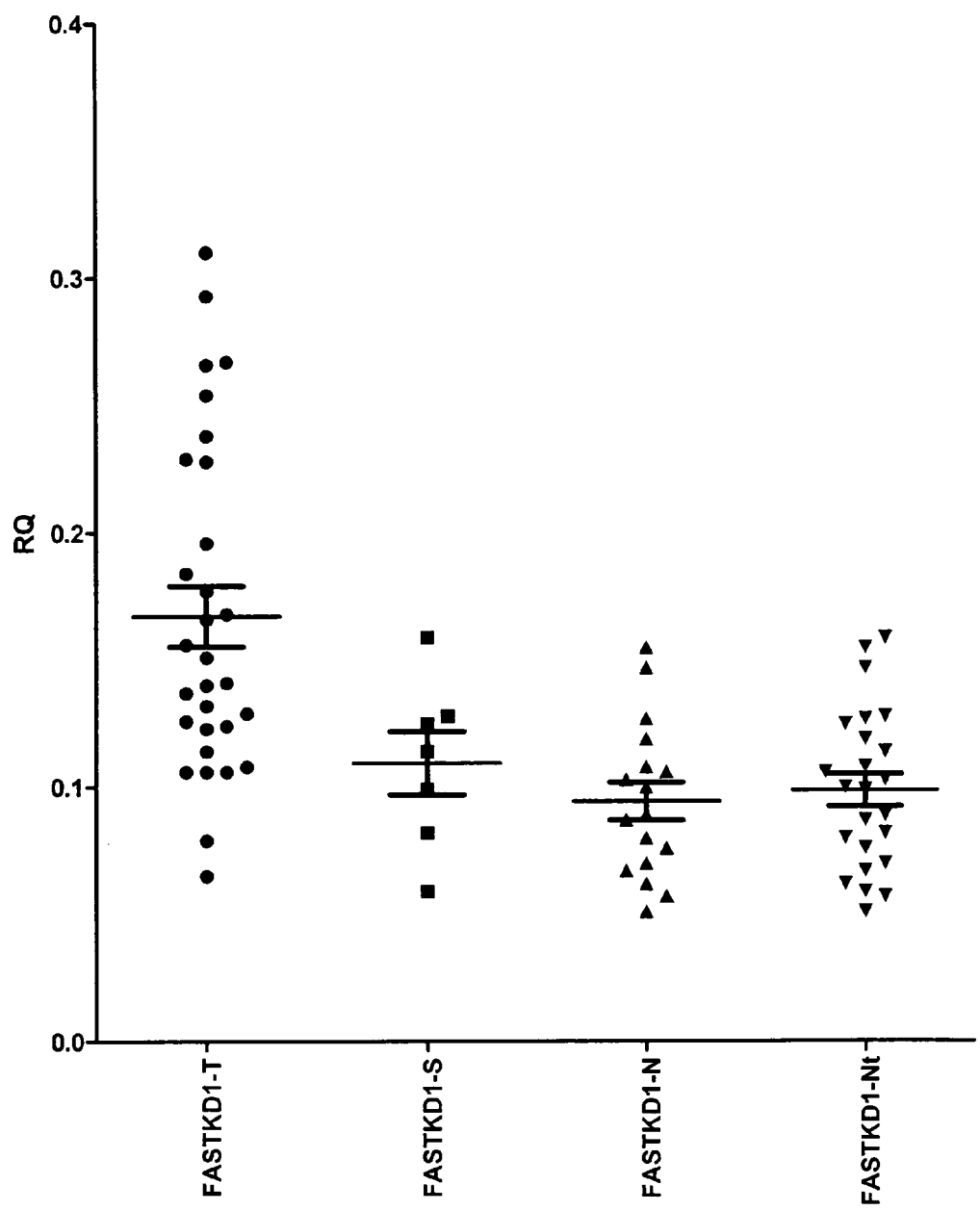
FIG 6. FASTKD1

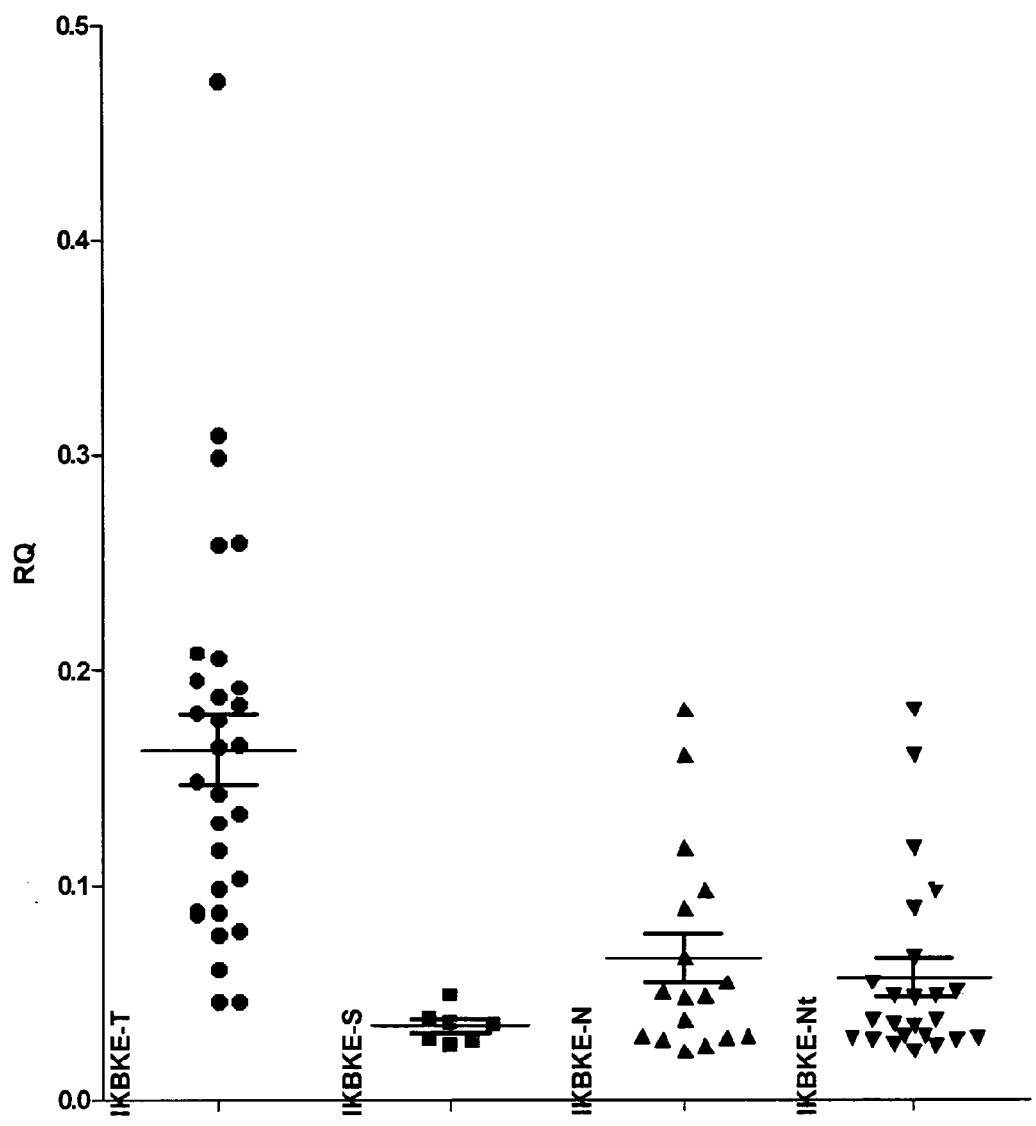
FIG. 7 IKBKE

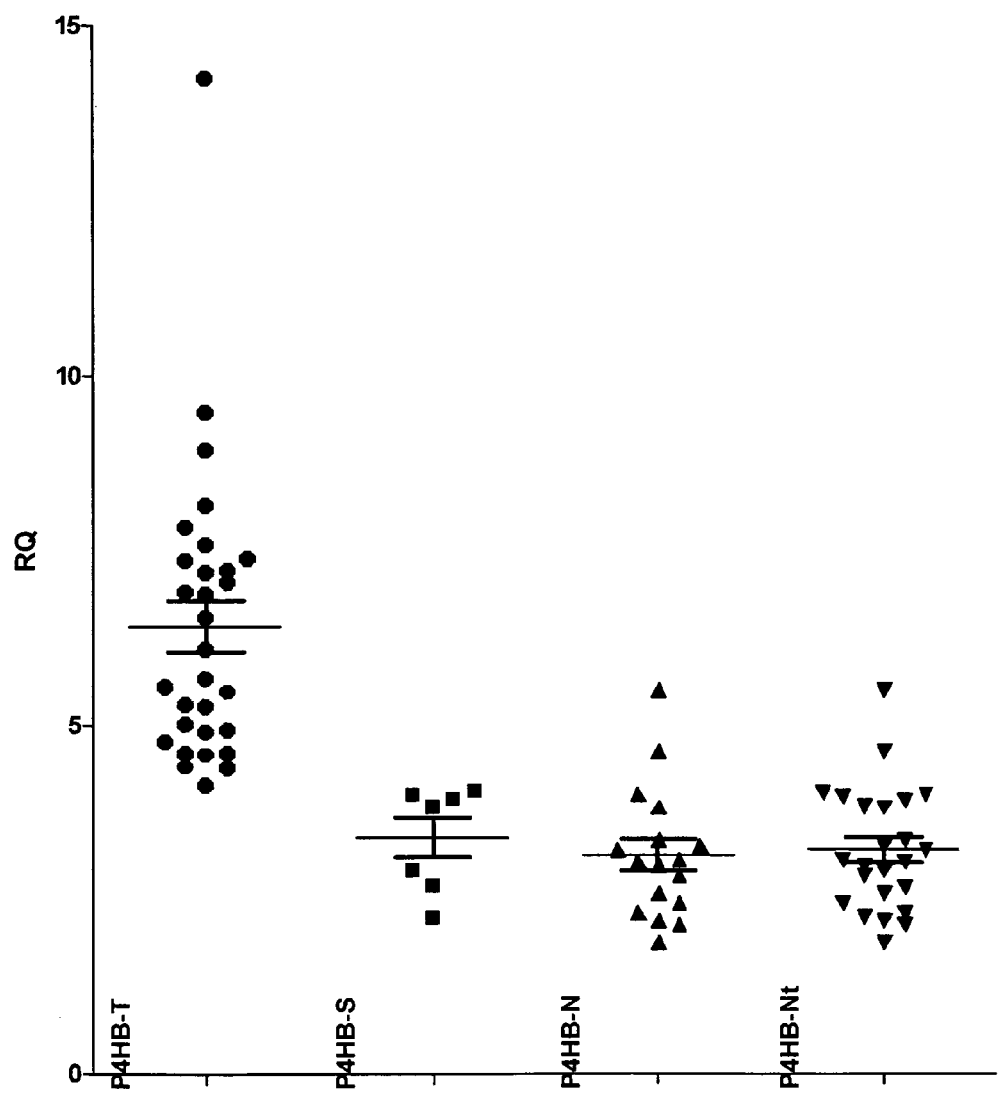
FIG 8. P4HB

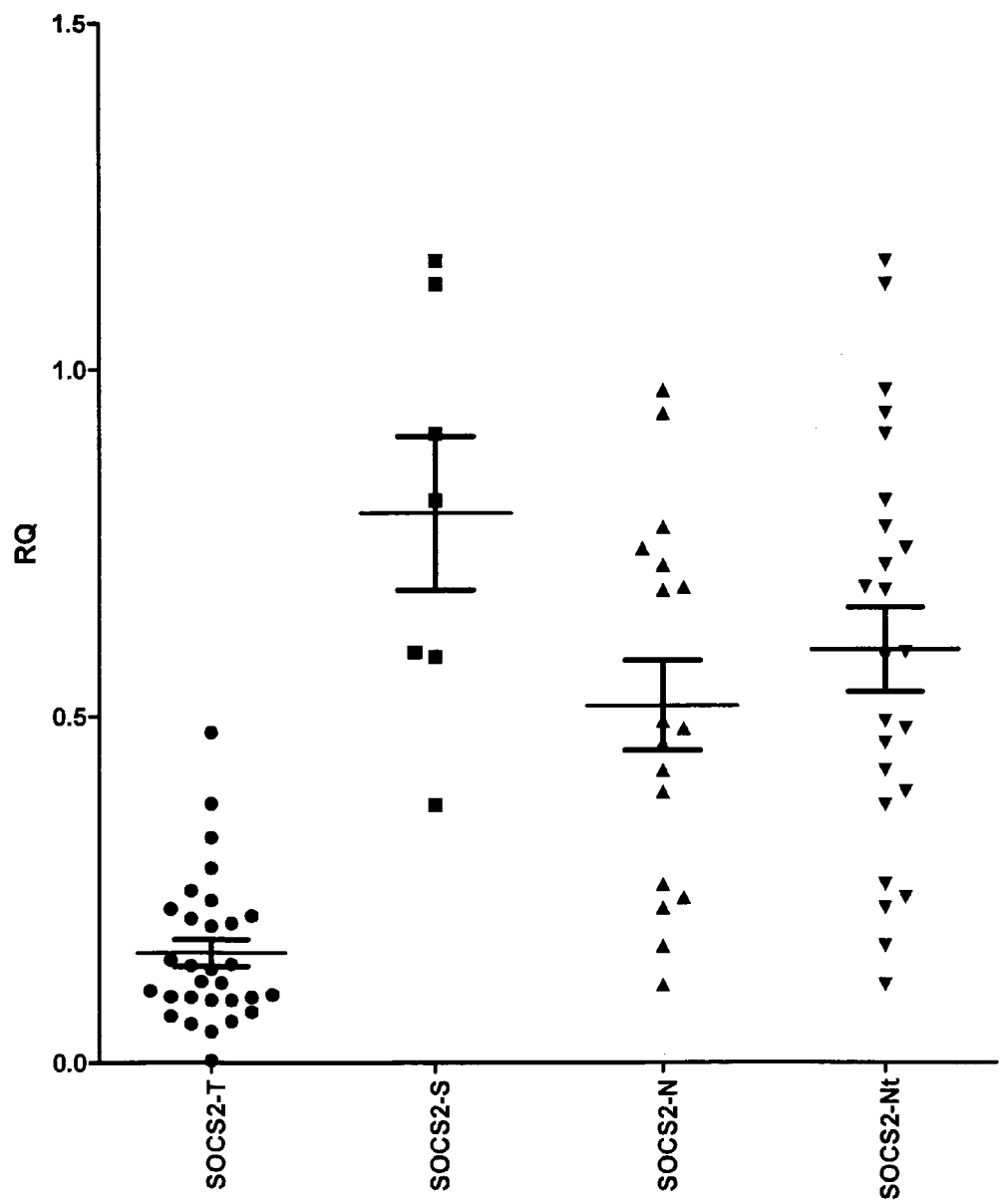
FIG. 9 SOCS2

SEQUENCE LISTING

```
<160> NUMBER OF SEQ ID NOS: 640

<210> SEQ ID NO 1
<211> LENGTH: 1695
<212> TYPE: DNA
<213> ORGANISM: Homo Sapiens

<400> SEQUENCE: 1
atgtggttct gcgcgtgtgc ggacggctgt ctgttaactc cgcggtcagt tcccggactg      60
gtggctggtc tgcagggttg acctgcgcaa tgcagaggct gcaggtagtg ctgggccacc     120 tgagggtcc ggccgattcc ggctggatgc cgcaggccgc gccttgcctg agcggtgccc     180
cgcaggcctc ggccgcggac gtggtggtgg tgcacgggcg gcgcacggcc atctgccggg     240
cgggccgcgg cggcttcaag gacaccaccc ccgacgagct tctctcggca gtcatgaccg     300
cggttctcaa ggacgtgaat ctgaggccgg aacagctggg ggacatctgt gtcggaaatg     360
tgctgcagcc tggggccggg gcaatcatgg cccgaatcgc ccagtttctg agtgacatcc     420
cggagactgt gcctttgtcc actgtcaata gacagtgttc gtcggggcta caggcagtgg     480
ccagcatagc aggtggcatc agaaatgggt cttatgacat tggcatggcc tgtgggggtgg     540 agtccatgtc cctggctgac agagggaacc ctggaaatat tacttcgcgc ttgatggaga     600
aggagaaggc cagagattgc ctgattccta tgggataac ctctgagaat gtggctgagc     660 ggttttggcat ttcacgggag aagcaggata cctttgccct ggcttccag cagaaggcag     720 caagagccca gagcaagggc tgtttccaag ctgagattgt gcctgtgacc accacggtcc     780
atgatgacaa gggcaccaag aggagcatca ctgtgaccca ggatgagggt atccgcccca     840
gcaccaccat ggagggcctg gccaaactga agcctgcctt caagaaagat ggttctacca     900
cagctggaaa ctctagccag gtgagtgatg gggcagctgc catcctgctg gcccggaggt     960
ccaaggcaga agagttgggc cttcccatcc ttgggtcct gaggtcttat gcagtggttg    1020
gggtcccacc tgacatcatg ggcattggac ctgcctatgc catcccagta gctttgcaaa    1080 agcagggct gacagtgagt gacgtggaca tcttcgagat caatgaggcc tttgcaagcc    1140
aggctgccta ctgtgtggag aagctacgac tcccccctga aaggtgaac cccctggggg    1200 gtgcagtggc cttagggcac ccactgggct gcactgggc acgacaggtc atcacgctgc    1260
tcaatgagct gaagcgccgt gggaagaggg catacggagt ggtgtccatg tgcatcggga    1320
```

```
ctggaatggg agccgctgcc gtctttgaat accctgggaa ctgagtgagg tcccaggctg      1380
gaggcgctac gcagacagtc ctgctgctct agcagcaagg cagtaacacc acaaaagcaa      1440
aaccacatgg gaaaactcag cactggtggt ggtggcagtg gacagatcaa ggcacttcaa      1500
ctcatttgga aaatgtgaac actgatgaca tggtatagga gtgggtgggg tgttgagcca      1560
cccatcagac cctctttagc tgtgcaagat aaaagcagcc tgggtcaccc aggccacaag      1620
gccatggtta attcttaagg caaggcaaat ccatggatga aagtgcaat gggcatagta       1680 aaagtgcatg aattt                                                       1695
```

<210> SEQ ID NO 2
<211> LENGTH: 424
<212> TYPE: PRT
<213> ORGANISM: Homo Sapiens

<400> SEQUENCE: 2

```
Met Gln Arg Leu Gln Val Val Leu Gly His Leu Arg Gly Pro Ala Asp
1               5                   10                  15

Ser Gly Trp Met Pro Gln Ala Ala Pro Cys Leu Ser Gly Ala Pro Gln
            20                  25                  30

Ala Ser Ala Ala Asp Val Val Val His Gly Arg Thr Ala Ile
        35                  40                  45

Cys Arg Ala Gly Arg Gly Gly Phe Lys Asp Thr Thr Pro Asp Glu Leu
    50                  55                  60

Leu Ser Ala Val Met Thr Ala Val Leu Lys Asp Val Asn Leu Arg Pro
65                  70                  75                  80

Glu Gln Leu Gly Asp Ile Cys Val Gly Asn Val Leu Gln Pro Gly Ala
                85                  90                  95

Gly Ala Ile Met Ala Arg Ile Ala Gln Phe Leu Ser Asp Ile Pro Glu
            100                 105                 110

Thr Val Pro Leu Ser Thr Val Asn Arg Gln Cys Ser Ser Gly Leu Gln
        115                 120                 125

Ala Val Ala Ser Ile Ala Gly Gly Ile Arg Asn Gly Ser Tyr Asp Ile
    130                 135                 140

Gly Met Ala Cys Gly Val Glu Ser Met Ser Leu Ala Asp Arg Gly Asn
145                 150                 155                 160

Pro Gly Asn Ile Thr Ser Arg Leu Met Glu Lys Glu Lys Ala Arg Asp
                165                 170                 175

Cys Leu Ile Pro Met Gly Ile Thr Ser Glu Asn Val Ala Glu Arg Phe
            180                 185                 190

Gly Ile Ser Arg Glu Lys Gln Asp Thr Phe Ala Leu Ala Ser Gln Gln
        195                 200                 205

Lys Ala Ala Arg Ala Gln Ser Lys Gly Cys Phe Gln Ala Glu Ile Val
    210                 215                 220

Pro Val Thr Thr Thr Val His Asp Asp Lys Gly Thr Lys Arg Ser Ile
225                 230                 235                 240

Thr Val Thr Gln Asp Glu Gly Ile Arg Pro Ser Thr Thr Met Glu Gly
                245                 250                 255

Leu Ala Lys Leu Lys Pro Ala Phe Lys Lys Asp Gly Ser Thr Thr Ala
            260                 265                 270

Gly Asn Ser Ser Gln Val Ser Asp Gly Ala Ala Ala Ile Leu Leu Ala
        275                 280                 285

Arg Arg Ser Lys Ala Glu Glu Leu Gly Leu Pro Ile Leu Gly Val Leu
    290                 295                 300
```

-continued

Arg Ser Tyr Ala Val Val Gly Val Pro Pro Asp Ile Met Gly Ile Gly
305                 310                 315                 320

Pro Ala Tyr Ala Ile Pro Val Ala Leu Gln Lys Ala Gly Leu Thr Val
            325                 330                 335

Ser Asp Val Asp Ile Phe Glu Ile Asn Glu Ala Phe Ser Gln Ala
        340                 345                 350

Ala Tyr Cys Val Glu Lys Leu Arg Leu Pro Pro Glu Lys Val Asn Pro
            355                 360                 365

Leu Gly Gly Ala Val Ala Leu Gly His Pro Leu Gly Cys Thr Gly Ala
        370                 375                 380

Arg Gln Val Ile Thr Leu Leu Asn Glu Leu Lys Arg Arg Gly Lys Arg
385                 390                 395                 400

Ala Tyr Gly Val Val Ser Met Cys Ile Gly Thr Gly Met Gly Ala Ala
            405                 410                 415

Ala Val Phe Glu Tyr Pro Gly Asn
            420

<210> SEQ ID NO 3
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      ACAA1 protein"

<400> SEQUENCE: 3
gagcttctct cggcagtcat                                            20

<210> SEQ ID NO 4
<211> LENGTH: 19
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      ACAA1 protein"

<400> SEQUENCE: 4
ctcagaaact gggcgattc                                             19

<210> SEQ ID NO 5
<211> LENGTH: 18
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      ACAA1 protein"

<400> SEQUENCE: 5
gcaatcatgg cccgaatc                                              18

<210> SEQ ID NO 6
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding ACAA1 protein"

<400> SEQUENCE: 6
ccccgacgaa cactgtctat                                          20

<210> SEQ ID NO 7
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      ACAA1 protein"

<400> SEQUENCE: 7
gtgcctttgt ccactgtcaa                                          20

<210> SEQ ID NO 8
<211> LENGTH: 18
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      ACAA1 protein"

<400> SEQUENCE: 8
acaggccatg ccaatgtc                                            18

<210> SEQ ID NO 9
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      ACAA1 protein"

<400> SEQUENCE: 9
tcacgggaga agcaggatac                                          20

<210> SEQ ID NO 10
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      ACAA1 protein"

<400> SEQUENCE: 10
ctcttggtgc ccttgtcatc                                          20

<210> SEQ ID NO 11
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      ACAA1 protein"

<400> SEQUENCE: 11
ggctgacagt gagtgacgtg                                          20

<210> SEQ ID NO 12
<211> LENGTH: 19
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      ACAA1 protein"

<400> SEQUENCE: 12 aggggggttca ccttctcag                                          19

<210> SEQ ID NO 13
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      ACAA1 protein"

<400> SEQUENCE: 13
gtggcatcag aaatgggtct                                          20

<210> SEQ ID NO 14
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      ACAA1 protein"

<400> SEQUENCE: 14
ctctggcctt ctccttctcc                                          20

<210> SEQ ID NO 15
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      ACAA1 protein"

<400> SEQUENCE: 15
attacttcgc gcttgatgga                                          20

<210> SEQ ID NO 16
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      ACAA1 protein"

<400> SEQUENCE: 16
agggcaaagg tatcctgctt                                          20

<210> SEQ ID NO 17

```
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      ACAA1 protein"

<400> SEQUENCE: 17
gcctgccttc aagaaagatg                                                 20

<210> SEQ ID NO 18
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      ACAA1 protein"

<400> SEQUENCE: 18
taagacctca ggaccccaag                                                 20

<210> SEQ ID NO 19
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      ACAA1 protein"

<400> SEQUENCE: 19
tggggtcctg aggtcttatg                                                 20

<210> SEQ ID NO 20
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      ACAA1 protein"

<400> SEQUENCE: 20
tctcgaagat gtccacgtca                                                 20

<210> SEQ ID NO 21
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      ACAA1 protein"

<400> SEQUENCE: 21
gtggcatcag aaatgggtct                                                 20

<210> SEQ ID NO 22
<211> LENGTH: 20
<212> TYPE: DNA
<213> ORGANISM: Artificial Sequence
<220> FEATURE:
```

```
<221> NAME/KEY: Source
<223> OTHER INFORMATION: /note="Description of Artificial Sequence:
      Reverse primer for amplifying the nucleotide sequence encoding
      ACAA1 protein"

<400> SEQUENCE: 22
agggcaaagg tatcctgctt                                                    20

<210> SEQ ID NO 23
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      ACAA1 protein"

<400> SEQUENCE: 23
tgacccagga tgagggtatc                                                    20

<210> SEQ ID NO 24
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      ACAA1 protein"

<400> SEQUENCE: 24
tctcgaagat gtccacgtca                                                    20

<210> SEQ ID NO 25
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      ACAA1 protein"

<400> SEQUENCE: 25
ggagactgtg cctttgtcca                                                    20

<210> SEQ ID NO 26
<211> LENGTH: 19
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      ACAA1 protein"

<400> SEQUENCE: 26
ctctgtcagc cagggacat                                                     19

<210> SEQ ID NO 27
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding ACAA1 protein"
```

<400> SEQUENCE: 27
cggttctcaa ggacgtgaat                                                20

<210> SEQ ID NO 28
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding ACAA1 protein"

<400> SEQUENCE: 28
agtgacatcc cggagactgt                                                20

<210> SEQ ID NO 29
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding ACAA1 protein"

<400> SEQUENCE: 29
gtggcatcag aaatgggtct                                                20

<210> SEQ ID NO 30
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding ACAA1 protein"

<400> SEQUENCE: 30
agctgagatt gtgcctgtga                                                20

<210> SEQ ID NO 31
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding ACAA1 protein"

<400> SEQUENCE: 31
atcaatgagg cctttgcaag                                                20

<210> SEQ ID NO 32
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding ACAA1 protein"

<400> SEQUENCE: 32
acagagggaa ccctggaaat                                                20

<210> SEQ ID NO 33
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding ACAA1 protein"

<400> SEQUENCE: 33
gattgcctga ttcctatggg                                            20

<210> SEQ ID NO 34
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding ACAA1 protein"

<400> SEQUENCE: 34
gtccaaggca gaagagttgg                                            20

<210> SEQ ID NO 35
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding ACAA1 protein"

<400> SEQUENCE: 35
atgccatccc agtagctttg                                            20

<210> SEQ ID NO 36
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding ACAA1 protein"

<400> SEQUENCE: 36
gcctgtggga taacctctga                                            20

<210> SEQ ID NO 37
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding ACAA1 protein"

<400> SEQUENCE: 37
aaactgaagc ctgccttcaa                                            20

<210> SEQ ID NO 38
<211> LENGTH: 20

```
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding ACAA1 protein"

<400> SEQUENCE: 38
atagacagtg ttcgtcgggg                                                   20

<210> SEQ ID NO 39
<211> LENGTH: 60
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding ACAA1 protein"

<400> SEQUENCE: 39
gctacgcaga cagtcctgct gctctagcag caaggcagta acaccacaaa agcaaaacca      60

<210> SEQ ID NO 40
<211> LENGTH: 1749
<212> TYPE: DNA
<213> ORGANISM: Homo Sapiens

<400> SEQUENCE: 40
ggcgcttccg caggaagaag gaagcggcgc cgccatcgcc tcccggcgct ccctccccga      60
ctcctaagtc cttcggccgc caccatgtcc gcctcggctg tcttcattct ggacgttaag     120
ggcaagccat tgatcagccg caactacaag ggcgatgtgg ccatgagcaa gattgagcac     180
ttcatgcctt tgctggtaca gcgggaggag gaaggcgccc tggccccgct gctgagccac     240
ggccaggtcc acttcctatg gatcaaaaac agcaacctct acttggtggc caccacatcg     300
aagaatgcca atgcctccct ggtgtactcc ttcctgtata agacaataga ggtattctgc     360
gaatacttca aggagctgga ggaggagagc atccgggaca ctttgtcat  cgtctacgag     420 ttgctggacg agctcatgga ctttggcttc ccgcagacca ccgacagcaa gatcctgcag     480
gagtacatca ctcagcagag caacaagctg agacgggca  agtcacgggt gccacccact     540
gtcaccaacg ctgtgtcctg gcgctccgag ggtatcaagt ataagaagaa cgaggtcttc     600
attgatgtca tagagtctgt caacctgctg gtcaatgcca acggcagcgt ccttctgagc     660
gaaatcgtcg gtaccatcaa gctcaaggtg tttctgtcag gaatgccaga gctgcggctg     720
ggcctcaatg accgcgtgct cttcgagctc actggccgca gcaagaacaa atcagtagag     780
ctggaggatg taaaattcca ccagtgcgtg cggctctctc gctttgacaa cgaccgcacc     840
atctccttca tcccgcctga tggtgacttt gagctcatgt cataccgcct cagcacccag     900
gtcaagccac tgatctggat tgagtctgtc attgagaagt tctcccacag ccgcgtggag     960
atcatggtca aggccaaggg gcagtttaag aaacagtcag tggccaacgg tgtggagata    1020
tctgtgcctg tacccagcga tgccgactcc cccagattca agaccagtgt gggcagcgcc    1080
aagtatgtgc cggagagaaa cgtcgtgatt tggagtatta agtctttccc gggggggcaag    1140 gagtacttga tgcgagccca ctttggcctc cccagtgtgg aaaaggaaga ggtggagggc    1200
cggcccccca tcggggtcaa gtttgagatc ccctacttca ccgtctctgg gatccaggtc    1260
cgatacatga agatcattga gaaagtggt  taccaggccc tgccctgggt tcgctacatc    1320
```

-continued

```
acccagagtg gcgattacca acttcgtacc agctagaagg gagaagagat gggggcttga   1380
acacggggct tccttacagc cccggatgca gattttagag ggagggcagg tgcgggctgt   1440
gtgtgtctgt gtgagggcag gtcctggact tggcagtttc ttgctcccag cacccgcccc   1500
ttcctcacct cttccttatt ccataggctg ggagagaaac tctctgcttc cctcgccctt   1560
ggagctttcc ccatccccct gatttatat gaagaaatag aagaggggct tgaagtcccc   1620
ctcgcgagtg ccttcttgca attacctgcc ttagcgggtg ttgcgggtcc ctccttcaca   1680
gccgctgagc ccagaggtcc cgctggcccc tcctctgaat tttaggatgt cattaaaaag   1740
atgaatcta                                                           1749
```

```
<210> SEQ ID NO 41
<211> LENGTH: 423
<212> TYPE: PRT
<213> ORGANISM: Homo Sapiens

<400> SEQUENCE: 41

Met Ser Ala Ser Ala Val Phe Ile Leu Asp Val Lys Gly Lys Pro Leu
1               5                   10                  15

Ile Ser Arg Asn Tyr Lys Gly Asp Val Ala Met Ser Lys Ile Glu His
            20                  25                  30

Phe Met Pro Leu Leu Val Gln Arg Glu Glu Glu Gly Ala Leu Ala Pro
        35                  40                  45

Leu Leu Ser His Gly Gln Val His Phe Leu Trp Ile Lys His Ser Asn
    50                  55                  60

Leu Tyr Leu Val Ala Thr Thr Ser Lys Asn Ala Asn Ala Ser Leu Val
65                  70                  75                  80

Tyr Ser Phe Leu Tyr Lys Thr Ile Glu Val Phe Cys Glu Tyr Phe Lys
                85                  90                  95

Glu Leu Glu Glu Glu Ser Ile Arg Asp Asn Phe Val Ile Val Tyr Glu
            100                 105                 110

Leu Leu Asp Glu Leu Met Asp Phe Gly Phe Pro Gln Thr Thr Asp Ser
        115                 120                 125

Lys Ile Leu Gln Glu Tyr Ile Thr Gln Gln Ser Asn Lys Leu Glu Thr
    130                 135                 140

Gly Lys Ser Arg Val Pro Pro Thr Val Thr Asn Ala Val Ser Trp Arg
145                 150                 155                 160

Ser Glu Gly Ile Lys Tyr Lys Asn Glu Val Phe Ile Asp Val Ile
                165                 170                 175

Glu Ser Val Asn Leu Leu Val Asn Ala Asn Gly Ser Val Leu Leu Ser
            180                 185                 190

Glu Ile Val Gly Thr Ile Lys Leu Lys Val Phe Leu Ser Gly Met Pro
        195                 200                 205

Glu Leu Arg Leu Gly Leu Asn Asp Arg Val Leu Phe Glu Leu Thr Gly
    210                 215                 220

Arg Ser Lys Asn Lys Ser Val Glu Leu Glu Asp Val Lys Phe His Gln
225                 230                 235                 240

Cys Val Arg Leu Ser Arg Phe Asp Asn Asp Arg Thr Ile Ser Phe Ile
                245                 250                 255

Pro Pro Asp Gly Asp Phe Glu Leu Met Ser Tyr Arg Leu Ser Thr Gln
            260                 265                 270

Val Lys Pro Leu Ile Trp Ile Glu Ser Val Ile Glu Lys Phe Ser His
        275                 280                 285

Ser Arg Val Glu Ile Met Val Lys Ala Lys Gly Gln Phe Lys Lys Gln
```

-continued

```
                290                 295                 300
Ser Val Ala Asn Gly Val Glu Ile Ser Val Pro Val Pro Ser Asp Ala
305                 310                 315                 320

Asp Ser Pro Arg Phe Lys Thr Ser Val Gly Ser Ala Lys Tyr Val Pro
                325                 330                 335

Glu Arg Asn Val Val Ile Trp Ser Ile Lys Ser Phe Pro Gly Gly Lys
                340                 345                 350

Glu Tyr Leu Met Arg Ala His Phe Gly Leu Pro Ser Val Glu Lys Glu
            355                 360                 365

Glu Val Glu Gly Arg Pro Pro Ile Gly Val Lys Phe Glu Ile Pro Tyr
        370                 375                 380

Phe Thr Val Ser Gly Ile Gln Val Arg Tyr Met Lys Ile Ile Glu Lys
385                 390                 395                 400

Ser Gly Tyr Gln Ala Leu Pro Trp Val Arg Tyr Ile Thr Gln Ser Gly
                405                 410                 415

Asp Tyr Gln Leu Arg Thr Ser
            420

<210> SEQ ID NO 42
<211> LENGTH: 23
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      AP1M2 protein"

<400> SEQUENCE: 42
cgccaccatg tccgcctcgg ctg                                          23

<210> SEQ ID NO 43
<211> LENGTH: 22
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      AP1M2 protein"

<400> SEQUENCE: 43
gctcaatctt gctcatggcc ac                                           22

<210> SEQ ID NO 44
<211> LENGTH: 21
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      AP1M2 protein"

<400> SEQUENCE: 44
caggtccact tcctatggat c                                            21

<210> SEQ ID NO 45
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
```

Reverse primer for amplifying the nucleotide sequence encoding AP1M2 protein"

<400> SEQUENCE: 45
caaagttgtc ccggatgctc                     20

<210> SEQ ID NO 46
<211> LENGTH: 18
<212> TYPE: DNA
<213> ORGANISM: Artificial Sequence
<220> FEATURE:
<221> NAME/KEY: Source
<223> OTHER INFORMATION: /note="Description of Artificial Sequence: Forward primer for amplifying the nucleotide sequence encoding AP1M2 protein"

<400> SEQUENCE: 46
cgctccgagg gtatcaag                       18

<210> SEQ ID NO 47
<211> LENGTH: 19
<212> TYPE: DNA
<213> ORGANISM: Artificial Sequence
<220> FEATURE:
<221> NAME/KEY: Source
<223> OTHER INFORMATION: /note="Description of Artificial Sequence: Reverse primer for amplifying the nucleotide sequence encoding AP1M2 protein"

<400> SEQUENCE: 47
cttgctgcgg ccagtgagc                      19

<210> SEQ ID NO 48
<211> LENGTH: 22
<212> TYPE: DNA
<213> ORGANISM: Artificial Sequence
<220> FEATURE:
<221> NAME/KEY: Source
<223> OTHER INFORMATION: /note="Description of Artificial Sequence: Forward primer for amplifying the nucleotide sequence encoding AP1M2 protein"

<400> SEQUENCE: 48
gactttgagc tcatgtcata cc                  22

<210> SEQ ID NO 49
<211> LENGTH: 22
<212> TYPE: DNA
<213> ORGANISM: Artificial Sequence
<220> FEATURE:
<221> NAME/KEY: Source
<223> OTHER INFORMATION: /note="Description of Artificial Sequence: Reverse primer for amplifying the nucleotide sequence encoding AP1M2 protein"

<400> SEQUENCE: 49
cttaatactc caaatcacga cg                  22

<210> SEQ ID NO 50
<211> LENGTH: 19
<212> TYPE: DNA
<213> ORGANISM: Artificial Sequence
<220> FEATURE:
<221> NAME/KEY: Source
<223> OTHER INFORMATION: /note="Description of Artificial Sequence: Forward primer for amplifying the nucleotide sequence encoding AP1M2 protein"

<400> SEQUENCE: 50

```
gtttgagatc ccctacttc                                                      19

<210> SEQ ID NO 51
<211> LENGTH: 24
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      AP1M2 protein"

<400> SEQUENCE: 51
gcctggtaac cacttttctc aatg                                                24

<210> SEQ ID NO 52
<211> LENGTH: 19
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      AP1M2 protein"

<400> SEQUENCE: 52
ctgggttcgc tacatcacc                                                      19

<210> SEQ ID NO 53
<211> LENGTH: 15
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      AP1M2 protein"

<400> SEQUENCE: 53
gccccgtgtt caagc                                                          15

<210> SEQ ID NO 54
<211> LENGTH: 19
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      AP1M2 protein"

<400> SEQUENCE: 54
catgcctttg ctggtacag                                                      19

<210> SEQ ID NO 55
<211> LENGTH: 21
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      AP1M2 protein"

<400> SEQUENCE: 55
gagtacacca gggaggcatt g                                                   21
```

```
<210> SEQ ID NO 56
<211> LENGTH: 19
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      AP1M2 protein"

<400> SEQUENCE: 56
ctccctggtg tactccttc                                              19

<210> SEQ ID NO 57
<211> LENGTH: 22
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      AP1M2 protein"

<400> SEQUENCE: 57
gctgtcggtg gtctgcggga ag                                          22

<210> SEQ ID NO 58
<211> LENGTH: 19
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      AP1M2 protein"

<400> SEQUENCE: 58
cagcaagatc ctgcaggag                                              19

<210> SEQ ID NO 59
<211> LENGTH: 19
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      AP1M2 protein"

<400> SEQUENCE: 59
caggttgaca gactctatg                                              19

<210> SEQ ID NO 60
<211> LENGTH: 60
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding AP1M2 protein"

<400> SEQUENCE: 60
atgaagaaat agaagagggg cttgaagtcc tcctcgcgag tgccttcttg caattacctg    60

<210> SEQ ID NO 61
<211> LENGTH: 58
<212> TYPE: DNA
<213> ORGANISM: Artificial Sequence
```

```
<220> FEATURE:
<221> NAME/KEY: Source
<223> OTHER INFORMATION: /note="Description of Artificial Sequence:
      Probe for detecting a nucleotide molecule having a nucleic acid
      sequence encoding AP1M2 protein"

<400> SEQUENCE: 61
ccaggtccac ttcctatgga tcaaacacag caacctctac ttggtggcca ccacatcg        58

<210> SEQ ID NO 62
<211> LENGTH: 43
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding AP1M2 protein"

<400> SEQUENCE: 62
gacaatagag gtattctgcg aatacttcaa ggagctggag gag                        43

<210> SEQ ID NO 63
<211> LENGTH: 54
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding AP1M2 protein"

<400> SEQUENCE: 63
caatgaccgc gtgctcttcg agctcactgg ccgcagcaag aacaaatcag taga            54

<210> SEQ ID NO 64
<211> LENGTH: 56
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding AP1M2 protein"

<400> SEQUENCE: 64
tttcccgggg ggcaaggagt acttgatgcg agcccacttt ggcctcccca gtgtgg          56

<210> SEQ ID NO 65
<211> LENGTH: 5132
<212> TYPE: DNA
<213> ORGANISM: Homo Sapiens

<400> SEQUENCE: 65
gagggagctc cgaggacgag ggggagggcc ggagctgcgc gtgctgcttt gcccgagccc       60
gagcccgagc ccgagcccga gcccgagccc gagcccgaac gcaagcctgg gagcgcggag      120
cccggctagg gactcctcct atttatggag caggcaccca acatggctga gccccggggc      180
cccgtagacc atggagtcca gattcgcttc atcacagagc cagtgagtgg tgcagagatg      240
ggcactctac gtcgaggtgg acgacgccca gctaaggatg caagagccag tacctacggg      300
gttgctgtgc gtgtgcaggg aatcgctggg cagcccttttg tggtgctcaa cagtggggag      360
aaaggcggtg actcctttgg ggtccaaatc aaggggggcca atgaccaagg ggcctcagga      420
gctctgagct cagatttgga actccctgag aaccccctact ctcaggtcaa gggatttcct      480
```

-continued

```
gcccctcgc agagcagcac atctgatgag gagcctgggg cctactggaa tggaaagcta    540
ctccgttccc actcccaggc ctcactggca ggccctggcc cagtggatcc tagtaacaga    600
agcaacagca tgctggagct agccccgaaa gtggcttccc caggtagcac cattgacact    660
gctcccctgt cttcagtgga ctcactcatc aacaagtttg acagtcaact ggaggccag    720 gcccggggtc ggactggccg ccgaacacgg atgctacccc ctgaacagcg caaacggagc    780
aagagcctgg acagccgcct cccacgggac acctttgagg aacggagcg ccagtccacc    840 aaccactgga cctctagcac aaaatatgac aaccatgtgg gcacttcgaa gcagccagcc    900
cagagccaga acctgagtcc tctcagtggc tttagccgtt ctcgtcagac tcaggactgg    960
gtccttcaga gttttgagga gccgcggagg agtgcacagg accccaccat gctgcagttc   1020
aaatcaactc cagacctcct tcgagaccag caggaggcag ccccaccagg cagtgtggac   1080
catatgaagg ccaccatcta tggcatcctg agggagggaa gctcagaaag tgaaacctct   1140
gtgaggagga aggttagttt ggtgctggag aagatgcagc ctctagtgat ggtttcttct   1200
ggttctacta aggccgtggc agggcagggt gagcttaccc gaaaagtgga ggagctacag   1260
cgaaagctgg atgaagaggt gaagaagcgg cagaagctag agccatccca agttgggctg   1320
gagcggcagc tggaggagaa aacagaagag tgcagccgac tgcaggagct gctggagagg   1380
aggaaggggg aggcccagca gagcaacaag gagctccaga acatgaagcg cctcttggac   1440
cagggtgaag atttacgaca tgggctggag acccaggtga tggagctgca gaacaagctg   1500
aaacatgtcc agggtcctga gcctgctaag gaggtgttac tgaaggacct gttagagacc   1560
cgggaacttc tggaagaggt cttggagggg aaacagcgag tagaggagca gctgaggctg   1620
cgggagcggg agttgacagc cctgaagggg gccctgaaag aggaggtagc ctcccgtgac   1680
caggaggtgg aacatgtccg gcagcagtac cagcgagaca cagagcagct ccgcaggagc   1740
atgcaagatg caacccagga ccatgcagtg ctggaggccg agaggcagaa gatgtcagcc   1800
cttgtgcgag ggctgcagag ggagctggag gagacttcag aggagacagg gcattggcag   1860
agtatgttcc agaagaacaa ggaggatctt agagccacca agcaggaact cctgcagctg   1920
cgaatggaga aggaggagat ggaagaggag cttggagaga agatagaggt cttgcagagg   1980
gaattagagc aggcccgagc tagtgctgga gatactcgcc aggttgaggt gctcaagaag   2040
gagctgctcc ggacacagga ggagcttaag gaactgcagg cagaacggca gagccaggag   2100
gtggctgggc gacaccggga ccgggagttg agaagcagc tggcggtcct gagggtcgag   2160
gctgatcgag gtcgggagct ggaagaacag aacctccagc tacaaaagac cctccagcaa   2220
ctgcgacagg actgtgaaga ggcttccaag gctaagatgg tggccgaggc agaggcaaca   2280
gtgctggggc agcggcgggc cgcagtggag acgacgcttc gggagaccca ggaggaaaat   2340
gacgaattcc gccggcgcat cctgggtttg gagcagcagc tgaaggagac tcgaggtctg   2400
gtggatggtg gggaagcggt ggaggcacga ctacgggaca gctgcagcg gctgaggca   2460 gagaaacagc agctggagga ggccctgaat gcgtcccagg aagaggaggg gagtctggca   2520
gcagccaagc gggcactgga ggcacgccta gaggaggctc agcgggggct ggcccgcctg   2580
gggcaggagc agcagacact gaaccggacc tggaggagg aagggaagca gcgggaggtg   2640
ctccggcgag gcaaggctga gctggaggag cagaagcgtt gctggacag gactgtggac   2700 cgactgaaca aggagttgga gaagatcggg gaggactcta gcaagccct gcagcagctc   2760 caggcccagc tggaggatta taaggaaaag gcccggcggg aggtggcaga tgcccagcgc   2820
caggccaagg attgggccag tgaggctgag aagacctctg gaggactgag ccgacttcag   2880
```

```
gatgagatcc agaggctgcg gcaggccctg caggcatccc aggctgagcg ggacacagcc    2940
cggctggaca aagagctact ggcccagcga ctgcaggggc tggagcaaga ggcagagaac    3000
aagaagcgtt cccaggacga cagggcccgg cagctgaagg gtctcgagga aaaagtctca    3060
cggctggaaa cagagttaga tgaggagaag aacaccgtgg agctgctaac agatcgggtg    3120
aatcgtggcc gggaccaggt ggatcagctg aggacagagc tcatgcagga aaggtctgct    3180
cggcaggacc tggagtgtga caaaatctcc ttggagagac agaacaagga cctgaagacc    3240
cggttggcca gctcagaagg cttccagaag cctagtgcca gcctctctca gcttgagtcc    3300
cagaatcagt tgttgcagga gcggctacag gctgaagaga gggagaagac agttctgcag    3360
tctaccaatc gaaaactgga gcggaaagtt aagaactat ccatccagat tgaagacgag     3420
cggcagcatg tcaatgacca gaaagaccag ctaagcctga gggtgaaggc tttgaagcgt    3480
caggtggatg aagcagaaga ggaaattgag cgactggacg gcctgaggaa gaaggcccag    3540
cgtgaggtgg aggagcagca tgaggtcaat gaacagctcc aggcccggat caagtctctg    3600
gagaaggact cctggcgcaa agcttcccgc tcagctgctg agtcagctct caaaaacgaa    3660
gggctgagct cagatgagga attcgacagt gtctacgatc cctcgtccat tgcatcactg    3720
cttacggaga gcaacctaca gaccagctcc tgttagctcg tggtcctcaa ggactcagaa    3780
accaggctcg aggcctatcc cagcaagtgc tgctctgctc tgcccaccct gggttctgca    3840
ttcctatggg tgacccaatt attcagacct aagacaggga ggggtcagag tgatggtgat    3900
aaaaaaaaaa aatcatcagc aataagctga tagatggact ttccactgta ggagtggaca    3960
tttcaagcca actgagcctt ttcctcaagt gccgacacct ccctcatctc tcttatagtg    4020
gaaggatggt cagcattagg ctgatgggga ctgagaagga taggaaggga tagaaattgc    4080
catgtgtata aagctttatt ctttagccct taaccctaag gctcagggaa atacccctatg   4140 ttattgtgct ccctggattc ctgcaactca ttttccttcc actctggagc agggtgaggg    4200
gaatgttatg ggtaacagac atgcaggcat ggctctaccc atttctttgc acaagtatgg    4260
ggcccatgtg gtagtcccca tacccctcca gttcctatat ttttgtcttc ttcctttccc    4320
ctctttgcca ttcctacctt gcattttttcc tgtcagtgcc ttagccaagg caaggagata    4380
aggatgctct tcttgctttt tatatctgca cattcatacc tctccaaaga ccagcttttc    4440
cccagccagg gccctcagcc ttccctgctg ccccagtgat tgattgagag agctgttggg    4500
gtttctctgc caatgacccc tgggagaggg actttggtag ggtcatgata aagtggcggg    4560
ggtctggtcc tgctcagggt tttcatcctt cctcctctcc ctcctctgtg actgtggata    4620
tggttataag gtggttgcac ctgggagccc tgacaactgg ctgcacaaat tccaaaagta    4680
aaggtgtcag tccctgtggc cttccttggg gcttctctga ccacatgtgc ccaacttcaa    4740
taagagaacc aagggaccct cattttctga ggtgcttggc tctgattcag ggctttgcaa    4800
ggggttagaa gctgactgta aaaatgggaa gaggcaacgg aagacattta tttctccttt    4860
ggattttggg gagaaccaag ccctggtagg gaagaggtaa gggggatgat tcacctccat    4920
atttcctaag caggttgtat agggagccgg tggcaggagg aaggctgttt tcacaaatga    4980
cttgtaatgt cgtgattaaa aaaattccta tattcttctg caaatcaaac gttctttccc    5040
aatccaatcc agccttggtt ttattttaaa ttaaatatta aaattacaca tttatattga    5100
aaaaaaaaaa aaaaaaaaaa aaaaaaaaaa aa                                  5132
```

<210> SEQ ID NO 66

```
<211> LENGTH: 1203
<212> TYPE: PRT
<213> ORGANISM: Homo Sapiens

<400> SEQUENCE: 66

Met Glu Gln Ala Pro Asn Met Ala Glu Pro Arg Gly Pro Val Asp His
1               5                   10                  15

Gly Val Gln Ile Arg Phe Ile Thr Glu Pro Val Ser Gly Ala Glu Met
            20                  25                  30

Gly Thr Leu Arg Arg Gly Arg Arg Pro Ala Lys Asp Ala Arg Ala
        35                  40                  45

Ser Thr Tyr Gly Val Ala Val Arg Val Gln Gly Ile Ala Gly Gln Pro
    50                  55                  60

Phe Val Val Leu Asn Ser Gly Glu Lys Gly Gly Asp Ser Phe Gly Val
65                  70                  75                  80

Gln Ile Lys Gly Ala Asn Asp Gln Gly Ala Ser Gly Ala Leu Ser Ser
                85                  90                  95

Asp Leu Glu Leu Pro Glu Asn Pro Tyr Ser Gln Val Lys Gly Phe Pro
            100                 105                 110

Ala Pro Ser Gln Ser Ser Thr Ser Asp Glu Glu Pro Gly Ala Tyr Trp
        115                 120                 125

Asn Gly Lys Leu Leu Arg Ser His Ser Gln Ala Ser Leu Ala Gly Pro
    130                 135                 140

Gly Pro Val Asp Pro Ser Asn Arg Ser Asn Ser Met Leu Glu Leu Ala
145                 150                 155                 160

Pro Lys Val Ala Ser Pro Gly Ser Thr Ile Asp Thr Ala Pro Leu Ser
                165                 170                 175

Ser Val Asp Ser Leu Ile Asn Lys Phe Asp Ser Gln Leu Gly Gly Gln
            180                 185                 190

Ala Arg Gly Arg Thr Gly Arg Arg Thr Arg Met Leu Pro Pro Glu Gln
        195                 200                 205

Arg Lys Arg Ser Lys Ser Leu Asp Ser Arg Leu Pro Arg Asp Thr Phe
    210                 215                 220

Glu Glu Arg Glu Arg Gln Ser Thr Asn His Trp Thr Ser Ser Thr Lys
225                 230                 235                 240

Tyr Asp Asn His Val Gly Thr Ser Lys Gln Pro Ala Gln Ser Gln Asn
                245                 250                 255

Leu Ser Pro Leu Ser Gly Phe Ser Arg Ser Arg Gln Thr Gln Asp Trp
            260                 265                 270

Val Leu Gln Ser Phe Glu Glu Pro Arg Arg Ser Ala Gln Asp Pro Thr
        275                 280                 285

Met Leu Gln Phe Lys Ser Thr Pro Asp Leu Leu Arg Asp Gln Gln Glu
    290                 295                 300

Ala Ala Pro Pro Gly Ser Val Asp His Met Lys Ala Thr Ile Tyr Gly
305                 310                 315                 320

Ile Leu Arg Glu Gly Ser Glu Ser Glu Thr Ser Val Arg Arg Lys
                325                 330                 335

Val Ser Leu Val Leu Glu Lys Met Gln Pro Leu Val Met Val Ser Ser
            340                 345                 350

Gly Ser Thr Lys Ala Val Ala Gly Gln Gly Glu Leu Thr Arg Lys Val
        355                 360                 365

Glu Glu Leu Gln Arg Lys Leu Asp Glu Val Lys Lys Arg Gln Lys
    370                 375                 380

Leu Glu Pro Ser Gln Val Gly Leu Glu Arg Gln Leu Glu Glu Lys Thr
```

```
                385                 390                 395                 400
        Glu Glu Cys Ser Arg Leu Gln Glu Leu Leu Glu Arg Arg Lys Gly Glu
                        405                 410                 415

Ala Gln Gln Ser Asn Lys Glu Leu Gln Asn Met Lys Arg Leu Leu Asp
                        420                 425                 430

Gln Gly Glu Asp Leu Arg His Gly Leu Glu Thr Gln Val Met Glu Leu
                        435                 440                 445

Gln Asn Lys Leu Lys His Val Gln Gly Pro Glu Pro Ala Lys Glu Val
                        450                 455                 460

Leu Leu Lys Asp Leu Leu Glu Thr Arg Glu Leu Leu Glu Glu Val Leu
        465                 470                 475                 480

Glu Gly Lys Gln Arg Val Glu Gln Leu Arg Leu Arg Glu Arg Glu
                        485                 490                 495

Leu Thr Ala Leu Lys Gly Ala Leu Lys Glu Val Ala Ser Arg Asp
                        500                 505                 510

Gln Glu Val Glu His Val Arg Gln Gln Tyr Gln Arg Asp Thr Glu Gln
                        515                 520                 525

Leu Arg Arg Ser Met Gln Asp Ala Thr Gln Asp His Ala Val Leu Glu
                530                 535                 540

Ala Glu Arg Gln Lys Met Ser Ala Leu Val Arg Gly Leu Gln Arg Glu
        545                 550                 555                 560

Leu Glu Glu Thr Ser Glu Glu Thr Gly His Trp Gln Ser Met Phe Gln
                        565                 570                 575

Lys Asn Lys Glu Asp Leu Arg Ala Thr Lys Gln Glu Leu Leu Gln Leu
                        580                 585                 590

Arg Met Glu Lys Glu Met Glu Glu Leu Gly Glu Lys Ile Glu
                        595                 600                 605

Val Leu Gln Arg Glu Leu Glu Gln Ala Arg Ala Ser Ala Gly Asp Thr
                        610                 615                 620

Arg Gln Val Glu Val Leu Lys Lys Glu Leu Leu Arg Thr Gln Glu Glu
        625                 630                 635                 640

Leu Lys Glu Leu Gln Ala Glu Arg Gln Ser Gln Glu Val Ala Gly Arg
                        645                 650                 655

His Arg Asp Arg Glu Leu Glu Lys Gln Leu Ala Val Leu Arg Val Glu
                        660                 665                 670

Ala Asp Arg Gly Arg Glu Leu Glu Glu Gln Asn Leu Gln Leu Gln Lys
                        675                 680                 685

Thr Leu Gln Gln Leu Arg Gln Asp Cys Glu Glu Ala Ser Lys Ala Lys
                        690                 695                 700

Met Val Ala Glu Ala Glu Ala Thr Val Leu Gly Gln Arg Arg Ala Ala
        705                 710                 715                 720

Val Glu Thr Thr Leu Arg Glu Thr Gln Glu Glu Asn Asp Glu Phe Arg
                        725                 730                 735

Arg Arg Ile Leu Gly Leu Glu Gln Gln Leu Lys Glu Thr Arg Gly Leu
                        740                 745                 750

Val Asp Gly Gly Glu Ala Val Glu Ala Arg Leu Arg Asp Lys Leu Gln
                        755                 760                 765

Arg Leu Glu Ala Glu Lys Gln Gln Leu Glu Glu Ala Leu Asn Ala Ser
                        770                 775                 780

Gln Glu Glu Glu Gly Ser Leu Ala Ala Ala Lys Arg Ala Leu Glu Ala
        785                 790                 795                 800

Arg Leu Glu Glu Ala Gln Arg Gly Leu Ala Arg Leu Gly Gln Glu Gln
                        805                 810                 815
```

Gln Thr Leu Asn Arg Ala Leu Glu Glu Gly Lys Gln Arg Glu Val
                820                 825                 830

Leu Arg Arg Gly Lys Ala Glu Leu Glu Gln Lys Arg Leu Leu Asp
                835                 840                 845

Arg Thr Val Asp Arg Leu Asn Lys Glu Leu Glu Lys Ile Gly Glu Asp
850                 855                 860

Ser Lys Gln Ala Leu Gln Gln Leu Gln Ala Gln Leu Glu Asp Tyr Lys
865                 870                 875                 880

Glu Lys Ala Arg Arg Glu Val Ala Asp Ala Gln Arg Gln Ala Lys Asp
                885                 890                 895

Trp Ala Ser Glu Ala Glu Lys Thr Ser Gly Gly Leu Ser Arg Leu Gln
                900                 905                 910

Asp Glu Ile Gln Arg Leu Arg Gln Ala Leu Gln Ala Ser Gln Ala Glu
                915                 920                 925

Arg Asp Thr Ala Arg Leu Asp Lys Glu Leu Leu Ala Gln Arg Leu Gln
930                 935                 940

Gly Leu Glu Gln Glu Ala Glu Asn Lys Lys Arg Ser Gln Asp Asp Arg
945                 950                 955                 960

Ala Arg Gln Leu Lys Gly Leu Glu Glu Lys Val Ser Arg Leu Glu Thr
                965                 970                 975

Glu Leu Asp Glu Glu Lys Asn Thr Val Glu Leu Leu Thr Asp Arg Val
                980                 985                 990

Asn Arg Gly Arg Asp Gln Val Asp Gln Leu Arg Thr Glu Leu Met Gln
                995                 1000                1005

Glu Arg Ser Ala Arg Gln Asp Leu Glu Cys Asp Lys Ile Ser Leu
        1010                1015                1020

Glu Arg Gln Asn Lys Asp Leu Lys Thr Arg Leu Ala Ser Ser Glu
        1025                1030                1035

Gly Phe Gln Lys Pro Ser Ala Ser Leu Ser Gln Leu Glu Ser Gln
        1040                1045                1050

Asn Gln Leu Leu Gln Glu Arg Leu Gln Ala Glu Glu Arg Glu Lys
        1055                1060                1065

Thr Val Leu Gln Ser Thr Asn Arg Lys Leu Glu Arg Lys Val Lys
        1070                1075                1080

Glu Leu Ser Ile Gln Ile Glu Asp Glu Arg Gln His Val Asn Asp
        1085                1090                1095

Gln Lys Asp Gln Leu Ser Leu Arg Val Lys Ala Leu Lys Arg Gln
        1100                1105                1110

Val Asp Glu Ala Glu Glu Glu Ile Glu Arg Leu Asp Gly Leu Arg
        1115                1120                1125

Lys Lys Ala Gln Arg Glu Val Glu Glu Gln His Glu Val Asn Glu
        1130                1135                1140

Gln Leu Gln Ala Arg Ile Lys Ser Leu Glu Lys Asp Ser Trp Arg
        1145                1150                1155

Lys Ala Ser Arg Ser Ala Ala Glu Ser Ala Leu Lys Asn Glu Gly
        1160                1165                1170

Leu Ser Ser Asp Glu Glu Phe Asp Ser Val Tyr Asp Pro Ser Ser
        1175                1180                1185

Ile Ala Ser Leu Leu Thr Glu Ser Asn Leu Gln Thr Ser Ser Cys
        1190                1195                1200

<210> SEQ ID NO 67
<211> LENGTH: 19

```
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding CGN
      protein"

<400> SEQUENCE: 67
gctttagccg ttctcgtca                                                    19

<210> SEQ ID NO 68
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding CGN
      protein"

<400> SEQUENCE: 68
ctggtctcga aggaggtctg                                                   20

<210> SEQ ID NO 69
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding CGN
      protein"

<400> SEQUENCE: 69
cagacctcct tcgagaccag                                                   20

<210> SEQ ID NO 70
<211> LENGTH: 21
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding CGN
      protein"

<400> SEQUENCE: 70
ttcctcctca cagaggtttc a                                                 21

<210> SEQ ID NO 71
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding CGN
      protein"

<400> SEQUENCE: 71
tacagcgaaa gctggatgaa                                                   20

<210> SEQ ID NO 72
<211> LENGTH: 20
<212> TYPE: DNA
<213> ORGANISM: Artificial Sequence
<220> FEATURE:
<221> NAME/KEY: Source
```

<223> OTHER INFORMATION: /note="Description of Artificial Sequence:
Reverse primer for amplifying the nucleotide sequence encoding CGN
protein"

<400> SEQUENCE: 72
agtcggctgc actcttctgt				20

<210> SEQ ID NO 73
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
Forward primer for amplifying the nucleotide sequence encoding CGN
protein"

<400> SEQUENCE: 73
tgcagaacaa gctgaaacat				20

<210> SEQ ID NO 74
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
Reverse primer for amplifying the nucleotide sequence encoding CGN
protein"

<400> SEQUENCE: 74
gctgctcctc tactcgctgt				20

<210> SEQ ID NO 75
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
Forward primer for amplifying the nucleotide sequence encoding CGN
protein"

<400> SEQUENCE: 75
gggcattggc agagtatgtt				20

<210> SEQ ID NO 76
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
Reverse primer for amplifying the nucleotide sequence encoding CGN
protein"

<400> SEQUENCE: 76
ttccatctcc tccttctcca				20

<210> SEQ ID NO 77
<211> LENGTH: 19
<212> TYPE: DNA
<213> ORGANISM: Artificial Sequence
<220> FEATURE:
<221> NAME/KEY: Source
<223> OTHER INFORMATION: /note="Description of Artificial Sequence:
Forward primer for amplifying the nucleotide sequence encoding CGN
protein"

```
<400> SEQUENCE: 77
cagcaactgc gacaggact                                                19

<210> SEQ ID NO 78
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding CGN
      protein"

<400> SEQUENCE: 78
cattttcctc ctgggtctcc                                               20

<210> SEQ ID NO 79
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding CGN
      protein"

<400> SEQUENCE: 79
ctgagctgga ggagcagaag                                               20

<210> SEQ ID NO 80
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding CGN
      protein"

<400> SEQUENCE: 80
tgcagggctt gcttagagtc                                               20

<210> SEQ ID NO 81
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding CGN
      protein"

<400> SEQUENCE: 81
tggagcaaga ggcagagaac                                               20

<210> SEQ ID NO 82
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding CGN
      protein"

<400> SEQUENCE: 82
actctgtttc cagccgtgag                                               20
```

<210> SEQ ID NO 83
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding CGN protein"

<400> SEQUENCE: 83
caggactggg tccttcagag                                                  20

<210> SEQ ID NO 84
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding CGN protein"

<400> SEQUENCE: 84
caggcagtgt ggaccatatg                                                  20

<210> SEQ ID NO 85
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding CGN protein"

<400> SEQUENCE: 85
gctagagcca tcccaagttg                                                  20

<210> SEQ ID NO 86
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding CGN protein"

<400> SEQUENCE: 86
tgagcctgct aaggaggtgt                                                  20

<210> SEQ ID NO 87
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding CGN protein"

<400> SEQUENCE: 87
tagagccacc aagcaggaac                                                  20

<210> SEQ ID NO 88
<211> LENGTH: 20
<212> TYPE: DNA

```
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding CGN protein"

<400> SEQUENCE: 88
ttccaaggct aagatggtgg                                                 20

<210> SEQ ID NO 89
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding CGN protein"

<400> SEQUENCE: 89
gacaggactg tggaccgact                                                 20

<210> SEQ ID NO 90
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding CGN protein"

<400> SEQUENCE: 90
tgaagggtct cgaggaaaaa                                                 20

<210> SEQ ID NO 91
<211> LENGTH: 60
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding CGN protein"

<400> SEQUENCE: 91
gggaagaggt aaggggatg attcacctcc atatttccta agcaggttgt atagggagcc      60

<210> SEQ ID NO 92
<211> LENGTH: 4838
<212> TYPE: DNA
<213> ORGANISM: Homo Sapiens

<400> SEQUENCE: 92
gtcttcccct cgtgggccct gagcgggact gcagccagcc ccctggggcg ccagctttga     60
ggcccccgac agctgctctc gggagccgcc tcccgacacc cgagcccgc cggcgcctcc    120 cgctcccggc tcccggctcc tggctccctc cgcctccccc gccctcgcc ccgccgccaa    180 gaggccccgc tcccgggtcg gacgcctggg tctgccggga agagcgatga gaggtgtctg    240
aaggtggcta ttcactgagc gatggggttg gacttgaagg aatgccaaga gatgctgccc    300 ccacccccctt aggcccgagg gatcaggagc tatgggacca gaggccctgt catctttact    360
gctgctgctc ttggtggcaa gtggagatgc tgacatgaag ggacattttg atcctgccaa    420
gtgccgctat gccctgggca tgcaggaccg gaccatccca gacagtgaca tctctgcttc    480
```

```
cagctcctgg tcagattcca ctgccgcccg ccacagcagg ttggagagca gtgacgggga    540
tggggcctgg tgccccgcag ggtcggtgtt tcccaaggag gaggagtact tgcaggtgga    600
tctacaacga ctgcacctgg tggctctggt gggcacccag ggacggcatg ccggggggcct   660 gggcaaggag ttctcccgga gctaccggct gcgttactcc cggatggtc gccgctggat    720 gggctggaag gaccgctggg gtcaggaggt gatctcaggc aatgaggacc ctgagggagt    780
ggtgctgaag gaccttgggc ccccatggt tgcccgactg gttcgcttct accccgggc     840 tgaccgggtc atgagcgtct gtctgcgggt agagctctat ggctgcctct ggagggatgg   900
actcctgtct tacaccgccc ctgtggggca gacaatgtat ttatctgagg ccgtgtacct   960
caacgactcc acctatgacg gacataccgt gggcggactg cagtatgggg gtctgggcca  1020
gctggcagat ggtgtggtgg ggctggatga ctttaggaag agtcaggagc tgcgggtctg  1080
gccaggctat gactatgtgg gatggagcaa ccacagcttc tccagtggct atgtggagat   1140
ggagtttgag tttgaccggc tgagggcctt ccaggctatg caggtccact gtaacaacat   1200
gcacacgctg ggagcccgtc tgcctggcgg ggtggaatgt cgcttccggc gtggccctgc   1260
catggcctgg gagggggagc ccatgcgcca aacctaggg ggcaacctgg gggaccccag    1320
agcccgggct gtctcagtgc cccttggcgg ccgtgtggct cgctttctgc agtgccgctt   1380
cctctttgcg gggccctggt tactcttcag cgaaatctcc ttcatctctg atgtggtgaa   1440
caattcctct ccggcactgg gaggcacctt cccgccagcc cctggtggc cgcctggccc    1500 acctcccacc aacttcagca gcttggagct ggagcccaga ggccagcagc ccgtggccaa   1560
ggccgagggg agcccgaccg ccatcctcat cggctgcctg gtggccatca tcctgctcct   1620
gctgctcatc attgccctca tgctctggcg gctgcactgg cgcaggctcc tcagcaaggc   1680
tgaacggagg gtgttggaag aggagctgac ggttcacctc tctgtccctg ggacactat    1740 cctcatcaac aaccgcccag gtcctagaga gccaccccg taccaggagc cccggcctcg    1800
tgggaatccg ccccactccg ctccctgtgt ccccaatggc tctgcctaca gtggggacta   1860
tatggagcct gagaagccag gcgcccccgct tctgcccccca cctcccagga cagcgtccc    1920 ccattatgcc gaggctgaca ttgttaccct gcagggcgtc accgggggca cacctatcc    1980 ccattatgcc gaggctgaca ttgttaccct gcagggcgtc accgggggca cacctatgc    2040 tgtgcctgca ctgccccccag gggcagtcgg ggatgggccc cccagagtgg attccctgc    2100 tgtgcctgca ctgccccccag gggcagtcgg ggatgggccc cccagagtgg attccctcg    2160 atctcgactc cgcttcaagg agaagcttgg cgagggccag tttggggagg tgcacctgcg   2220
atctcgactc cgcttcaagg agaagcttgg cgagggccag tttggggagg tgcacctgtg   2280
tgaggtcgac agccctcaag atctggttag tcttgatttc ccccttaatg tgcgtaagtg   2340
tgaggtcgac agccctcaag atctggttag tcttgatttc ccccttaatg tgcgtaaggg   2400 acacccttttg ctggtagctg tcaagatctt acgccagat gccaccaaga atgccagggg   2460 acacccttttg ctggtagctg tcaagatctt acggccagat gccaccaaga atgccaggaa   2520
tgatttcctg aaagaggtga agatcatgtc gaggctcaag gacccaaaca tcattcggaa   2580
tgatttcctg aaagaggtga agatcatgtc gaggctcaag gacccaaaca tcattcggct   2640
gctgggcgtg tgtgtgcagg acgacccccct ctgcatgatt actgactaca tggagaacct   2700
gctgggcgtg tgtgtgcagg acgacccccct ctgcatgatt actgactaca tggagaacgg   2760
cgacctcaac cagttcctca gtgcccacca gctggaggac aaggcagccg aggggggccgg   2820
```

```
cgacctcaac cagttcctca gtgcccacca gctggaggac aaggcagccg agggggcccc    2880
tggggacggg caggctgcgc aggggcccac catcagctac ccaatgctgc tgcatgtgcc    2940
tggggacggg caggctgcgc aggggcccac catcagctac ccaatgctgc tgcatgtggc    3000
agcccagatc gcctccggca tgcgctatct ggccacactc aactttgtac atcgggacgc    3060
agcccagatc gcctccggca tgcgctatct ggccacactc aactttgtac atcgggacct    3120
ggccacgcgg aactgcctag ttggggaaaa tttcaccatc aaaatcgcag actttggcct    3180
ggccacgcgg aactgcctag ttggggaaaa tttcaccatc aaaatcgcag actttggcat    3240
gagccggaac ctctatgctg gggactatta ccgtgtgcag ggccgggcag tgctgcccat    3300
gagccggaac ctctatgctg gggactatta ccgtgtgcag ggccgggcag tgctgcccat    3360
ccgctggatg gcctgggagt gcatcctcat ggggaagttc acgactgcga gtgacgtgat    3420
ccgctggatg gcctgggagt gcatcctcat ggggaagttc acgactgcga gtgacgtgtg    3480
ggcctttggt gtgaccctgt gggaggtgct gatgctctgt agggcccagc cctttgggtg    3540
ggcctttggt gtgaccctgt gggaggtgct gatgctctgt agggcccagc cctttgggca    3600
gctcaccgac gagcaggtca tcgagaacgc gggggagttc ttccgggacc agggccggca    3660
gctcaccgac gagcaggtca tcgagaacgc gggggagttc ttccgggacc agggccggca    3720
ggtgtacctg tcccggccgc ctgcctgccc gcagggccta tatgagctga tgcttcggca    3780
ggtgtacctg tcccggccgc ctgcctgccc gcagggccta tatgagctga tgcttcggtg    3840
ctggagccgg gagtctgagc agcgaccacc cttttcccag ctgcatcggt tcctggcatg    3900
ctggagccgg gagtctgagc agcgaccacc cttttcccag ctgcatcggt tcctggcaga    3960
ggatgcactc aacacggtgt gaatcacaca tccagctgcc cctccctcag ggagcgatcc    4020
aggggaagcc agtgacacta aaacaagagg acacaatggc acctctgccc ttcccctccc    4080
gacagcccat cacctctaat agaggcagtg agactgcagg tgggctgggc ccacccaggg    4140
agctgatgcc ccttctcccc ttcctggaca cactctcatg tccccttcct gttcttcctt    4200
cctagaagcc cctgtcgccc acccagctgg tcctgtggat gggatcctct ccaccctcct    4260
ctagccatcc cttggggaag ggtgggagaa aatataggat agacactgga catggcccat    4320
tggagcacct gggccccact ggacaacact gattcctgga gaggtggctg cgcccccagc    4380
ttctctctcc ctgtcacaca ctggaccccca ctggctgaga atctgggggt gaggaggaca    4440
agaaggagag gaaaatgttt ccttgtgcct gctcctgtac ttgtcctcag cttgggcttc    4500
ttcctcctcc atcacctgaa acactggacc tgggggtagc cccgcccagc ccctcagtca    4560
cccccacttc ccacttgcag tcttgtagct agaacttctc taagcctata cgtttctgtg    4620
gagtaaatat tgggattggg gggaaagagg gagcaacggc ccatagcctt ggggttggac    4680
atctctagtg tagctgccac attgattttt ctataatcac ttggggtttg tacatttttg    4740
gggggagaga cacagatttt tacactaata tatggaccta gcttgaggca attttaatcc    4800
cctgcactag gcaggtaata ataaaggttg agttttcc                           4838
```

<210> SEQ ID NO 93
<211> LENGTH: 876
<212> TYPE: PRT
<213> ORGANISM: Homo Sapiens

<400> SEQUENCE: 93

```
Met Gly Pro Glu Ala Leu Ser Ser Leu Leu Leu Leu Leu Leu Val Ala
1               5                   10                  15
```

-continued

```
Ser Gly Asp Ala Asp Met Lys Gly His Phe Asp Pro Ala Lys Cys Arg
             20                  25                  30
Tyr Ala Leu Gly Met Gln Asp Arg Thr Ile Pro Asp Ser Asp Ile Ser
         35                  40                  45
Ala Ser Ser Ser Trp Ser Asp Ser Thr Ala Ala Arg His Ser Arg Leu
 50                  55                  60
Glu Ser Ser Asp Gly Asp Gly Ala Trp Cys Pro Ala Gly Ser Val Phe
 65                  70                  75                  80
Pro Lys Glu Glu Glu Tyr Leu Gln Val Asp Leu Gln Arg Leu His Leu
                 85                  90                  95
Val Ala Leu Val Gly Thr Gln Gly Arg His Ala Gly Leu Gly Lys
             100                 105                 110
Glu Phe Ser Arg Ser Tyr Arg Leu Arg Tyr Ser Arg Asp Gly Arg Arg
             115                 120                 125
Trp Met Gly Trp Lys Asp Arg Trp Gly Gln Glu Val Ile Ser Gly Asn
         130                 135                 140
Glu Asp Pro Glu Gly Val Val Leu Lys Asp Leu Gly Pro Pro Met Val
145                 150                 155                 160
Ala Arg Leu Val Arg Phe Tyr Pro Arg Ala Asp Arg Val Met Ser Val
                 165                 170                 175
Cys Leu Arg Val Glu Leu Tyr Gly Cys Leu Trp Arg Asp Gly Leu Leu
             180                 185                 190
Ser Tyr Thr Ala Pro Val Gly Gln Thr Met Tyr Leu Ser Glu Ala Val
         195                 200                 205
Tyr Leu Asn Asp Ser Thr Tyr Asp Gly His Thr Val Gly Gly Leu Gln
 210                 215                 220
Tyr Gly Gly Leu Gly Gln Leu Ala Asp Gly Val Val Gly Leu Asp Asp
225                 230                 235                 240
Phe Arg Lys Ser Gln Glu Leu Arg Val Trp Pro Gly Tyr Asp Tyr Val
                 245                 250                 255
Gly Trp Ser Asn His Ser Phe Ser Ser Gly Tyr Val Glu Met Glu Phe
             260                 265                 270
Glu Phe Asp Arg Leu Arg Ala Phe Gln Ala Met Gln Val His Cys Asn
         275                 280                 285
Asn Met His Thr Leu Gly Ala Arg Leu Pro Gly Gly Val Glu Cys Arg
 290                 295                 300
Phe Arg Arg Gly Pro Ala Met Ala Trp Glu Gly Glu Pro Met Arg His
305                 310                 315                 320
Asn Leu Gly Gly Asn Leu Gly Asp Pro Arg Ala Arg Ala Val Ser Val
                 325                 330                 335
Pro Leu Gly Gly Arg Val Ala Arg Phe Leu Gln Cys Arg Phe Leu Phe
             340                 345                 350
Ala Gly Pro Trp Leu Leu Phe Ser Glu Ile Ser Phe Ile Ser Asp Val
         355                 360                 365
Val Asn Asn Ser Ser Pro Ala Leu Gly Gly Thr Phe Pro Pro Ala Pro
 370                 375                 380
Trp Trp Pro Pro Gly Pro Pro Thr Asn Phe Ser Ser Leu Glu Leu
385                 390                 395                 400
Glu Pro Arg Gly Gln Gln Pro Val Ala Lys Ala Glu Gly Ser Pro Thr
                 405                 410                 415
Ala Ile Leu Ile Gly Cys Leu Val Ala Ile Leu Leu Leu Leu Leu
             420                 425                 430
Ile Ile Ala Leu Met Leu Trp Arg Leu His Trp Arg Arg Leu Leu Ser
```

-continued

```
                435                 440                 445
Lys Ala Glu Arg Arg Val Leu Glu Glu Glu Leu Thr Val His Leu Ser
450                 455                 460
Val Pro Gly Asp Thr Ile Leu Ile Asn Asn Arg Pro Gly Pro Arg Glu
465                 470                 475                 480
Pro Pro Pro Tyr Gln Glu Pro Arg Pro Arg Gly Asn Pro Pro His Ser
                    485                 490                 495
Ala Pro Cys Val Pro Asn Gly Ser Ala Tyr Ser Gly Asp Tyr Met Glu
                500                 505                 510
Pro Glu Lys Pro Gly Ala Pro Leu Leu Pro Pro Pro Gln Asn Ser
            515                 520                 525
Val Pro His Tyr Ala Glu Ala Asp Ile Val Thr Leu Gln Gly Val Thr
530                 535                 540
Gly Gly Asn Thr Tyr Ala Val Pro Ala Leu Pro Pro Gly Ala Val Gly
545                 550                 555                 560
Asp Gly Pro Pro Arg Val Asp Phe Pro Arg Ser Arg Leu Arg Phe Lys
                565                 570                 575
Glu Lys Leu Gly Glu Gly Gln Phe Gly Glu Val His Leu Cys Glu Val
            580                 585                 590
Asp Ser Pro Gln Asp Leu Val Ser Leu Asp Phe Pro Leu Asn Val Arg
        595                 600                 605
Lys Gly His Pro Leu Leu Val Ala Val Lys Ile Leu Arg Pro Asp Ala
    610                 615                 620
Thr Lys Asn Ala Arg Asn Asp Phe Leu Lys Glu Val Lys Ile Met Ser
625                 630                 635                 640
Arg Leu Lys Asp Pro Asn Ile Ile Arg Leu Leu Gly Val Cys Val Gln
                645                 650                 655
Asp Asp Pro Leu Cys Met Ile Thr Asp Tyr Met Glu Asn Gly Asp Leu
            660                 665                 670
Asn Gln Phe Leu Ser Ala His Gln Leu Glu Asp Lys Ala Ala Glu Gly
        675                 680                 685
Ala Pro Gly Asp Gly Gln Ala Ala Gln Gly Pro Thr Ile Ser Tyr Pro
    690                 695                 700
Met Leu Leu His Val Ala Ala Gln Ile Ala Ser Gly Met Arg Tyr Leu
705                 710                 715                 720
Ala Thr Leu Asn Phe Val His Arg Asp Leu Ala Thr Arg Asn Cys Leu
                725                 730                 735
Val Gly Glu Asn Phe Thr Ile Lys Ile Ala Asp Phe Gly Met Ser Arg
            740                 745                 750
Asn Leu Tyr Ala Gly Asp Tyr Tyr Arg Val Gln Gly Arg Ala Val Leu
        755                 760                 765
Pro Ile Arg Trp Met Ala Trp Glu Cys Ile Leu Met Gly Lys Phe Thr
    770                 775                 780
Thr Ala Ser Asp Val Trp Ala Phe Gly Val Thr Leu Trp Glu Val Leu
785                 790                 795                 800
Met Leu Cys Arg Ala Gln Pro Phe Gly Gln Leu Thr Asp Glu Gln Val
                805                 810                 815
Ile Glu Asn Ala Gly Glu Phe Phe Arg Asp Gln Gly Arg Gln Val Tyr
            820                 825                 830
Leu Ser Arg Pro Pro Ala Cys Pro Gln Gly Leu Tyr Glu Leu Met Leu
        835                 840                 845
Arg Cys Trp Ser Arg Glu Ser Glu Gln Arg Pro Pro Phe Ser Gln Leu
    850                 855                 860
```

```
His Arg Phe Leu Ala Glu Asp Ala Leu Asn Thr Val
865                 870                 875
```

```
<210> SEQ ID NO 94
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      DDR1 protein"

<400> SEQUENCE: 94
catctctgct tccagctcct                                            20

<210> SEQ ID NO 95
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      DDR1 protein"

<400> SEQUENCE: 95
tactcctcct ccttgggaaa                                            20

<210> SEQ ID NO 96
<211> LENGTH: 19
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      DDR1 protein"

<400> SEQUENCE: 96
agctaccggc tgcgttact                                             19

<210> SEQ ID NO 97
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      DDR1 protein"

<400> SEQUENCE: 97
cttcagcacc actccctcag                                            20

<210> SEQ ID NO 98
<211> LENGTH: 19
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      DDR1 protein"

<400> SEQUENCE: 98
cgtctgtctg cgggtagag                                             19
```

```
<210> SEQ ID NO 99
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      DDR1 protein"

<400> SEQUENCE: 99
ccgtcatagg tggagtcgtt                                              20

<210> SEQ ID NO 100
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      DDR1 protein"

<400> SEQUENCE: 100
caacgactcc acctatgacg                                              20

<210> SEQ ID NO 101
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      DDR1 protein"

<400> SEQUENCE: 101
tgctccatcc cacatagtca                                              20

<210> SEQ ID NO 102
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      DDR1 protein"

<400> SEQUENCE: 102
tgactatgtg ggatggagca                                              20

<210> SEQ ID NO 103
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      DDR1 protein"

<400> SEQUENCE: 103
ccagcgtgtg catgttgtta                                              20

<210> SEQ ID NO 104
<211> LENGTH: 18
<212> TYPE: DNA
```

```
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      DDR1 protein"

<400> SEQUENCE: 104
tgtctcagtg ccccttgg                                                     18

<210> SEQ ID NO 105
<211> LENGTH: 19
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      DDR1 protein"

<400> SEQUENCE: 105
gtgccggaga ggaattgtt                                                    19

<210> SEQ ID NO 106
<211> LENGTH: 19
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      DDR1 protein"

<400> SEQUENCE: 106
acctcccacc aacttcagc                                                    19

<210> SEQ ID NO 107
<211> LENGTH: 19
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      DDR1 protein"

<400> SEQUENCE: 107
cagcaggagc aggatgatg                                                    19

<210> SEQ ID NO 108
<211> LENGTH: 19
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      DDR1 protein"

<400> SEQUENCE: 108
catcatcctg ctcctgctg                                                    19

<210> SEQ ID NO 109
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
```

Reverse primer for amplifying the nucleotide sequence encoding
DDR1 protein"

<400> SEQUENCE: 109
ccagggacag agaggtgaac                                                    20

<210> SEQ ID NO 110
<211> LENGTH: 18
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      DDR1 protein"

<400> SEQUENCE: 110
accgcccagg tcctagag                                                      18

<210> SEQ ID NO 111
<211> LENGTH: 19
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      DDR1 protein"

<400> SEQUENCE: 111
cggtaggctg gattggaga                                                     19

<210> SEQ ID NO 112
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      DDR1 protein"

<400> SEQUENCE: 112
caccctttgc tggtagctgt                                                    20

<210> SEQ ID NO 113
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      DDR1 protein"

<400> SEQUENCE: 113
cgaatgatgt ttgggtcctt                                                    20

<210> SEQ ID NO 114
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding DDR1 protein"

<400> SEQUENCE: 114

```
acagcaggtt ggagagcagt                                                  20

<210> SEQ ID NO 115
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding DDR1 protein"

<400> SEQUENCE: 115
gtcaggaggt gatctcaggc                                                  20

<210> SEQ ID NO 116
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding DDR1 protein"

<400> SEQUENCE: 116
ctctatggct gcctctggag                                                  20

<210> SEQ ID NO 117
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding DDR1 protein"

<400> SEQUENCE: 117
gtggggctgg atgactttag                                                  20

<210> SEQ ID NO 118
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding DDR1 protein"

<400> SEQUENCE: 118
agtttgagtt tgaccggctg                                                  20

<210> SEQ ID NO 119
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding DDR1 protein"

<400> SEQUENCE: 119
ccctggttac tcttcagcga                                                  20
```

```
<210> SEQ ID NO 120
<211> LENGTH: 18
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding DDR1 protein"

<400> SEQUENCE: 120
cttggagctg gagcccag                                              18

<210> SEQ ID NO 121
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding DDR1 protein"

<400> SEQUENCE: 121
agggtgttgg aagaggagct                                            20

<210> SEQ ID NO 122
<211> LENGTH: 19
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding DDR1 protein"

<400> SEQUENCE: 122
actctgctcc ctgtgtccc                                             19

<210> SEQ ID NO 123
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding DDR1 protein"

<400> SEQUENCE: 123
gccaggaatg atttcctgaa                                            20

<210> SEQ ID NO 124
<211> LENGTH: 60
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding DDR1 protein"

<400> SEQUENCE: 124
attgggattg gggggaaaga gggagcaacg gcccatagcc ttggggttgg acatctctag   60

<210> SEQ ID NO 125
<211> LENGTH: 3156
<212> TYPE: DNA
<213> ORGANISM: Homo Sapiens
```

<400> SEQUENCE: 125

```
actccgcaac ctgtcgctca ggttcctcct ctcccggccc cgccccggcc cggccccgcc    60
gagcgtccca cccgcccgcg ggagacctgg cgccccggcc gaggcgcgaa cagacggacg   120
caccggcgag cgccgagggg acaggccgag cgcggggcgc cggaggcagg tgtgggacag   180
gcactggcct cagaccgggg ccacactgag gtctgccctt ctcccgctgg ccgccaccca   240
agacaccatg agccagtccg gggccgtgag ctgctgcccg ggtgccacca atggcagcct   300
gggccggtcc gacggtgtgg ccaagatgag ccccaaggac ctgtttgagc agaggaagaa   360
gtattccaac tccaacgtca tcatgcacga gacctcgcag taccacgtcc agcacctggc   420
cacattcatc atggacaaga gcgaagccat cacgtctgtg gacgacgcca tccggaagct   480
ggtgcagctg agctccaagg agaagatctg gacccaggat gctgctgcag gtgaacga    540
ccagtcgctg cggctgctgg acatcgagtc acaggaggag ctggaagact cccgctgcc   600
cacggtgcag cgcagccaga cggtcctcaa ccagctgcgc tacccgtctg tgctgctgct   660
cgtgtgccag gactcggagc agagcaagcc ggatgtccac ttcttccact gcgatgaggt   720
ggaggcagag ctggtgcacg aggacatcga gagcgcgttg gccgactgcc ggctgggcaa   780
gaagatgcgg ccgcagaccc tgaagggaca ccaggagaag attcggcagc ggcagtccat   840
cctgcctcct ccccagggcc cggcgcccat cccctttccag caccgcggcg gggattcccc   900
ggaggccaag aatcgcgtgg gcccgcaggt gccactcagc gagccaggtt ccgccgtcg   960
ggagtcgcag gaggagccgc gggccgtgct ggctcagaag atagagaagg agacgcaaat  1020
cctcaactgc gccctggacg acatcgagtg gtttgtggcc cggctgcaga aggcagccga  1080
ggctttcaag cagctgaacc agcggaaaaa ggggaagaag aagggcaaga aggcgccagc  1140
agagggcgtc ctcacactgc gggcacggcc cccctcgag ggcgagttca tcgactgctt   1200
ccagaaaatc aagctggcga ttaacttgct ggcaaagctg cagaagcaca tccagaaccc  1260
cagcgccgcg gagctcgtgc acttcctctt cgggcctctg gacctgatcg tcaacacctg  1320
cagtggccca gacatcgcac gctccgtctc ctgcccactg ctctcccgag atgccgtgga  1380
cttcctgcgc ggccacctgg tccctaagga gatgtcgctg tgggagtcac tgggagagag  1440
ctggatgcgg cccccgttcc gagtggccgc ggagccacag gtgcccctct acgtgcccaa  1500
gttccacagc ggctgggagc tcctgtggga tgtgctgcag gaggcccct gggaggtgga   1560
ggggctggcg tctgccccca tcgaggaggt gagtccagtg agccgacagt ccataagaaa  1620
ctcccagaag cacagcccca cttcagagcc cacccccccg ggggatgccc taccaccagt  1680
cagctcccca catactcaca ggggctacca gccaacacca gccatggcca agtacgtcaa  1740
gatcctgtat gacttcacag cccgaaatgc caacgagcta tcggtgctca aggatgaggt  1800
cctagaggtg ctggaggacg gccggcagtg gtggaagctg cgcagccgca gcggccaggc  1860
ggggtacgtg ccctgcaaca tcctaggcga ggcgcgaccg gaggacgccg cgccccgtt   1920
cgagcaggcc ggtcagaagt actggggccc cgccagcccg acccacaagc tacccccaag  1980
cttccccgggg aacaaagacg agctcatgca gcacatggac gaggtcaacg acagctcat  2040
ccggaaaatc agcaacatca gggcgcagcc acagaggcac ttccgcgtgg agcgcagcca  2100
gcccgtgagc cagccgctca cctacgagtc gggtccggac gaggtccgcg cctggctgga  2160
agccaaggcc ttcagcccgc ggatcgtgga gaacctgggc atcctgaccg gccgcagct   2220
cttctccctc aacaaggagg agctgaagaa agtgtgcggc gaggagggcg tccgcgtgta  2280
```

-continued

```
cagccagctc accatgcaga aggccttcct ggagaagcag caaagtgggt cggagctgga   2340
agaactcatg aacaagtttc attccatgaa tcagaggagg ggggaggaca gctaggccca   2400
gctgccttgg gctggggcct gcggagggga agcccaccca caatgcatgg agtattattt   2460
ttatatgtgt atgtattttg tatcaaggac acggaggggg tgtggtgctg gctagaggtc   2520
cctgcccctg tctggaggca caacgcccat ccttaggcca aacagtaccc aaggcctcag   2580
cccacaccaa gactaatctc agccaaacct gctgcttggt ggtgccagcc ccttgtccac   2640
cttctcttga ggccacagaa ctccctgggg ctggggcctc tttctctggc ctcccctgtg   2700
cacctggggg gtcctggccc ctgtgatgct cccccatccc cacccacttc tacatccatc   2760 cacacccag ggtgagctgg agctccaggc tggccaggct gaacctcgca cacacgcaga   2820
gttctgctcc ctgaggggg cccggagggg gctccagcag gaggccgtgg gtgccattcg   2880
ggggaaagtg ggggaacgac acacacttca cctgcaaggg ccgacaacgc aggggacacc   2940
gtgccggctt cagacactcc cagcgcccac tcttacaggc ccaggactgg agctttctct   3000
ggccaagttt caggccaatg atccccgcat ggtgttgggg gtgctggtgt gtcttggtgc   3060
ctggacttga gtctcaccct acagatgaga ggtggctgag gcaccagggc taagcaatta   3120
aaccagttaa gtctcccagg aaaaaaaaaa aaaaaa                             3156
```

<210> SEQ ID NO 126
<211> LENGTH: 715
<212> TYPE: PRT
<213> ORGANISM: Homo Sapiens

<400> SEQUENCE: 126

```
Met Ser Gln Ser Gly Ala Val Ser Cys Cys Pro Gly Ala Thr Asn Gly
1               5                   10                  15

Ser Leu Gly Arg Ser Asp Gly Val Ala Lys Met Ser Pro Lys Asp Leu
            20                  25                  30

Phe Glu Gln Arg Lys Lys Tyr Ser Asn Ser Asn Val Ile Met His Glu
        35                  40                  45

Thr Ser Gln Tyr His Val Gln His Leu Ala Thr Phe Ile Met Asp Lys
    50                  55                  60

Ser Glu Ala Ile Thr Ser Val Asp Asp Ala Ile Arg Lys Leu Val Gln
65                  70                  75                  80

Leu Ser Ser Lys Glu Lys Ile Trp Thr Gln Glu Met Leu Leu Gln Val
                85                  90                  95

Asn Asp Gln Ser Leu Arg Leu Leu Asp Ile Glu Ser Gln Glu Glu Leu
            100                 105                 110

Glu Asp Phe Pro Leu Pro Thr Val Gln Arg Ser Gln Thr Val Leu Asn
        115                 120                 125

Gln Leu Arg Tyr Pro Ser Val Leu Leu Leu Val Cys Gln Asp Ser Glu
    130                 135                 140

Gln Ser Lys Pro Asp Val His Phe Phe His Cys Asp Glu Val Glu Ala
145                 150                 155                 160

Glu Leu Val His Glu Asp Ile Glu Ser Ala Leu Ala Asp Cys Arg Leu
                165                 170                 175

Gly Lys Lys Met Arg Pro Gln Thr Leu Lys Gly His Gln Glu Lys Ile
            180                 185                 190

Arg Gln Arg Gln Ser Ile Leu Pro Pro Gln Gly Pro Ala Pro Ile
        195                 200                 205

Pro Phe Gln His Arg Gly Gly Asp Ser Pro Glu Ala Lys Asn Arg Val
    210                 215                 220
```

-continued

```
Gly Pro Gln Val Pro Leu Ser Glu Pro Gly Phe Arg Arg Arg Glu Ser
225                 230                 235                 240

Gln Glu Glu Pro Arg Ala Val Leu Ala Gln Lys Ile Glu Lys Glu Thr
            245                 250                 255

Gln Ile Leu Asn Cys Ala Leu Asp Asp Ile Glu Trp Phe Val Ala Arg
        260                 265                 270

Leu Gln Lys Ala Ala Glu Ala Phe Lys Gln Leu Asn Gln Arg Lys Lys
    275                 280                 285

Gly Lys Lys Lys Gly Lys Lys Ala Pro Ala Glu Gly Val Leu Thr Leu
290                 295                 300

Arg Ala Arg Pro Pro Ser Glu Gly Glu Phe Ile Asp Cys Phe Gln Lys
305                 310                 315                 320

Ile Lys Leu Ala Ile Asn Leu Leu Ala Lys Leu Gln Lys His Ile Gln
                325                 330                 335

Asn Pro Ser Ala Ala Glu Leu Val His Phe Leu Phe Gly Pro Leu Asp
            340                 345                 350

Leu Ile Val Asn Thr Cys Ser Gly Pro Asp Ile Ala Arg Ser Val Ser
        355                 360                 365

Cys Pro Leu Leu Ser Arg Asp Ala Val Asp Phe Leu Arg Gly His Leu
370                 375                 380

Val Pro Lys Glu Met Ser Leu Trp Glu Ser Leu Gly Glu Ser Trp Met
385                 390                 395                 400

Arg Pro Arg Ser Glu Trp Pro Arg Glu Pro Gln Val Pro Leu Tyr Val
                405                 410                 415

Pro Lys Phe His Ser Gly Trp Glu Pro Val Asp Val Leu Gln Glu
            420                 425                 430

Ala Pro Trp Glu Val Glu Gly Leu Ala Ser Ala Pro Ile Glu Glu Val
            435                 440                 445

Ser Pro Val Ser Arg Gln Ser Ile Arg Asn Ser Gln Lys His Ser Pro
            450                 455                 460

Thr Ser Glu Pro Thr Pro Pro Gly Asp Ala Leu Pro Pro Val Ser Ser
465                 470                 475                 480

Pro His Thr His Arg Gly Tyr Gln Pro Thr Pro Ala Met Ala Lys Tyr
                485                 490                 495

Val Lys Ile Leu Tyr Asp Phe Thr Ala Arg Asn Ala Asn Glu Leu Ser
            500                 505                 510

Val Leu Lys Asp Glu Val Leu Glu Val Leu Glu Asp Gly Arg Gln Trp
        515                 520                 525

Trp Lys Leu Arg Ser Arg Ser Gly Gln Ala Gly Tyr Val Pro Cys Asn
    530                 535                 540

Ile Leu Gly Glu Ala Arg Pro Glu Asp Ala Gly Ala Pro Phe Glu Gln
545                 550                 555                 560

Ala Gly Gln Lys Tyr Trp Gly Pro Ala Ser Pro Thr His Lys Leu Pro
                565                 570                 575

Pro Ser Phe Pro Gly Asn Lys Asp Glu Leu Met Gln His Met Asp Glu
            580                 585                 590

Val Asn Asp Glu Leu Ile Arg Lys Ile Ser Asn Ile Arg Ala Gln Pro
        595                 600                 605

Gln Arg His Phe Arg Val Glu Arg Ser Gln Pro Val Ser Gln Pro Leu
    610                 615                 620

Thr Tyr Glu Ser Gly Pro Asp Gly Val Arg Ala Trp Leu Glu Ala Lys
625                 630                 635                 640
```

-continued

Ala Phe Ser Pro Arg Ile Val Glu Asn Leu Gly Ile Leu Thr Gly Pro
            645                 650                 655

Gln Leu Phe Ser Leu Asn Lys Glu Glu Leu Lys Lys Val Cys Gly Glu
        660                 665                 670

Glu Gly Val Arg Val Tyr Ser Gln Leu Thr Met Gln Lys Ala Phe Leu
    675                 680                 685

Glu Lys Gln Gln Ser Gly Ser Glu Leu Glu Glu Leu Met Asn Lys Phe
690                 695                 700

His Ser Met Asn Gln Arg Arg Gly Glu Asp Ser
705                 710                 715

<210> SEQ ID NO 127
<211> LENGTH: 18
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      EPS8L2 protein"

<400> SEQUENCE: 127
gagacctggc gccccggc                                                 18

<210> SEQ ID NO 128
<211> LENGTH: 18
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      EPS8L2 protein"

<400> SEQUENCE: 128
gtggccccgg tctgaggc                                                 18

<210> SEQ ID NO 129
<211> LENGTH: 19
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      EPS8L2 protein"

<400> SEQUENCE: 129
gagccagtcc ggggccgtg                                                19

<210> SEQ ID NO 130
<211> LENGTH: 18
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      EPS8L2 protein"

<400> SEQUENCE: 130
cttggggctc atcttggc                                                 18

<210> SEQ ID NO 131
<211> LENGTH: 21
<212> TYPE: DNA

```
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      EPS8L2 protein"

<400> SEQUENCE: 131
cgacggtgtg gccaagatga g                                           21

<210> SEQ ID NO 132
<211> LENGTH: 17
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      EPS8L2 protein"

<400> SEQUENCE: 132
cgtggtactg cgaggtc                                                17

<210> SEQ ID NO 133
<211> LENGTH: 19
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      EPS8L2 protein"

<400> SEQUENCE: 133
ctccaacgtc atcatgcac                                              19

<210> SEQ ID NO 134
<211> LENGTH: 19
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      EPS8L2 protein"

<400> SEQUENCE: 134
gatggcgtcg tccacagac                                              19

<210> SEQ ID NO 135
<211> LENGTH: 19
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      EPS8L2 protein"

<400> SEQUENCE: 135
cagtcgctgc ggctgctgg                                              19

<210> SEQ ID NO 136
<211> LENGTH: 19
<212> TYPE: DNA
<213> ORGANISM: Artificial Sequence
<220> FEATURE:
<221> NAME/KEY: Source
<223> OTHER INFORMATION: /note="Description of Artificial Sequence:
```

-continued

Reverse primer for amplifying the nucleotide sequence encoding EPS8L2 protein"

<400> SEQUENCE: 136
ggaccgtctg gctgcgctg                                               19

<210> SEQ ID NO 137
<211> LENGTH: 21
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      EPS8L2 protein"

<400> SEQUENCE: 137
gatgtccact tcttccactg c                                            21

<210> SEQ ID NO 138
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      EPS8L2 protein"

<400> SEQUENCE: 138
ccgaatcttc tcctggtgtc                                              20

<210> SEQ ID NO 139
<211> LENGTH: 21
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      EPS8L2 protein"

<400> SEQUENCE: 139
gaggccaaga atcgcgtggg c                                            21

<210> SEQ ID NO 140
<211> LENGTH: 19
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      EPS8L2 protein"

<400> SEQUENCE: 140
gtccagggcg cagttgagg                                               19

<210> SEQ ID NO 141
<211> LENGTH: 19
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      EPS8L2 protein"

<400> SEQUENCE: 141
cgactgcttc cagaaaatc    19

<210> SEQ ID NO 142
<211> LENGTH: 19
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      EPS8L2 protein"

<400> SEQUENCE: 142
cgaagaggaa gtgcacgag    19

<210> SEQ ID NO 143
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      EPS8L2 protein"

<400> SEQUENCE: 143
gatgtcgctg tgggagtcac    20

<210> SEQ ID NO 144
<211> LENGTH: 18
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      EPS8L2 protein"

<400> SEQUENCE: 144
gaggggcacc tgtggctc    18

<210> SEQ ID NO 145
<211> LENGTH: 18
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      EPS8L2 protein"

<400> SEQUENCE: 145
ggtggagggg ctggcgtc    18

<210> SEQ ID NO 146
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      EPS8L2 protein"

<400> SEQUENCE: 146
ggctctgaag tggggctgtg    20

```
<210> SEQ ID NO 147
<211> LENGTH: 60
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding EPS8L2 protein"

<400> SEQUENCE: 147
gcttcccggg gaacaaagac gagctcatgc agcacatgga cgaggtcaac gacgagctca       60

<210> SEQ ID NO 148
<211> LENGTH: 48
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding EPS8L2 protein"

<400> SEQUENCE: 148
gcagagctgg tgcacgagga catcgagagc gcgttggccg actgccgg                     48

<210> SEQ ID NO 149
<211> LENGTH: 51
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding EPS8L2 protein"

<400> SEQUENCE: 149
gccgtcggga gtcgcaggag gagccgcggg ccgtgctggc tcagaagata g                 51

<210> SEQ ID NO 150
<211> LENGTH: 43
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding EPS8L2 protein"

<400> SEQUENCE: 150
gctcgtgtgc caggactcgg agcagagcaa gccggatgtc cac                          43

<210> SEQ ID NO 151
<211> LENGTH: 48
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding EPS8L2 protein"

<400> SEQUENCE: 151
gtacagccag ctcaccatgc agaaggcctt cctggagaag cagcaaag                     48

<210> SEQ ID NO 152
<211> LENGTH: 2767
<212> TYPE: DNA
<213> ORGANISM: Homo Sapiens
```

<400> SEQUENCE: 152

```
ataaaccctg agatatgagg gttgggcgag acatccgagc ctgtttcgtt ccgtgttggg      60
accaggaata accctgactt ctgagctttc ataaccccag gatcctccag aaaatttgcg     120
gcgcgctgag ggaaaacctt gctgaagctg tacattggaa tgcgtttaca gtcattgtaa     180
tggaagcaaa atacatgaag gaaaaactgt tatttgtatc cctgcttatt gcacctgacg     240
actagttgca gatggttttg tttacctaag aaaacttgtg atataaatga aaaaaacacc     300
tgttttccta gagtcattgg ttacaaatat gcttcgtcta agagctattt gtccattctc     360
ctggagagtg tttcaatttc gacccatcag ttgtgaacca ctaattattc agatgaataa     420
gtgtacagat gaggagcaaa tgtttggttt tattgaaaga acaaagcca tactttcaga      480
aaagcaagtg ggatgtgcat ttgatatgct ttggaagctt caaaagcaga agaccagcct     540
gttaaaaaat gctgagtatg tcagagacca tcctcaattt cttactcttc ataatttagc     600
tacaaataaa ttcaaattaa tgaatgacga taccctggtg aatgtgttat acgtcacaca     660
acagtttgct ggtgaggccc atgacccgct agttgaagca ctagttacag aagcatggag     720
aaggctagaa aggtttgata ttaaactgct ctcagaattt tcctcttgcc tagcagatca     780
gcatttgtat tttagtccat taatgggaaa aatagctgat attgttcata ggaacttgga     840
aaccacacag gacttaagtt ccttgtctgt cttgatggtc aacatatctt ctttaatatc     900
acgacatttt caacaacaac tggtgaacaa aacagaactt cttttgaca ccatagattc      960
ttctgaggtc aacgttgcaa aaagcatagc aaagtttctt cgaaatgtta gatatcgtta    1020
tcaaccacta ttagaaagat gtaataacgt atttttaagt aatgtggacc accttgattt    1080
ggattccatc agtaaaatac ttagtgtata caaatttcta caatttaata gttttgaatt    1140
tattataatg gctaaaaaga agctaactga aatgattcct ctgtgtaatc atcctgctag    1200
ctttgtaaaa ttgtttgtag cattgggacc cattgcagga cctgaagaaa agaaacaact    1260
taaatcaact atgttattga tgtcagagga cctaactggc gagcaagccc tggcagtgtt    1320
gggagcaatg ggagatatgg aaagcagaaa ctcatgtctg attaaaagag ttacttcagt    1380
tctgcataaa catttggatg gctataaacc attagagttg ttgaagataa ctcaagaatt    1440
aacttttctg catttccaaa ggaaggagtt ttttgcgaaa cttagagaat tactgcttag    1500
ttatttgaaa aatagtttca taccaactga ggtgtctgtt ctggtccgtg ctatttccct    1560
gctcccttct cctcacttgg acgaagtggg gatatcccga attgaagccg ttttaccaca    1620
gtgtgaccta aataacctga gtagttttgc cacatctgtt ttaagatgga ttcagcatga    1680
tcacatgtat ttggataata tgactgcgaa acaactgaaa ctacttcaaa aattagatca    1740
ctatggtcgt cagagactac aacacagcaa cagtttggat ctgttacgga aggaacttaa    1800
atctctcaaa ggaaacacgt ttcctgagtc acttcttgaa gaaatgattg ctactttaca    1860
gcatttcatg gatgatatta attacataaa tgttggggag attgcatctt ttatttctag    1920
tactgattac ctcagtactt tgctactaga taggatagcc tcagtggctg ttcagcagat    1980
tgaaagatc catccttta caatccctgc tattattcgt ccattcagcg tattgaacta      2040
tgatccacct caaagggatg aattttggg aacttgcgtg caacatctta attcttactt     2100
aggtatattg gatccttta tattagtgtt tcttggtttc ctttggcca cacttgaata      2160
ttttccagaa gatctgctaa aggcaatttt taacatcaaa ttcttagcta gattggattc    2220
tcaacttgaa agtattggtg gcatggatgg aacacaacag cagattttta aaatgttagc    2280
```

-continued

```
agaggtacta ggaggaatca attgtgtaaa agcctcggtt cttacgcctt attaccacaa    2340
agtagatttt gagtgtatct tggataaaag aaaaaaacct cttccgtatg gaagccataa    2400
tatagcattg ggacaactac cagaaatgcc ctgggaatca aatatcgaaa tagttggatc    2460
aaggctgcca ccaggggctg aaaggattgc tttggaattt ttggattcaa aagcactttg    2520
tagaaatatc cctcacatga aggaaaatc tgctatgaaa aaacgacatt tggaaattct     2580
ggggtatcgt gtaattcaga tttcccagtt tgaatggaac tctatggcac tgtcaacaaa    2640
ggatgctcgg atggactacc tgagagaatg tatatttgga gaagtcaagt catgtttgta    2700
gtttttattt aaaatgaatg ttatcgtgtg ttacatttgg acctatttta ataaagtggc    2760
ctgtctc                                                              2767
```

<210> SEQ ID NO 153
<211> LENGTH: 804
<212> TYPE: PRT
<213> ORGANISM: Homo Sapiens

<400> SEQUENCE: 153

```
Met Lys Lys Thr Pro Val Phe Leu Glu Ser Leu Val Thr Asn Met Leu
1               5                   10                  15

Arg Leu Arg Ala Ile Cys Pro Phe Ser Trp Arg Val Phe Gln Phe Arg
            20                  25                  30

Pro Ile Ser Cys Glu Pro Leu Ile Ile Gln Met Asn Lys Cys Thr Asp
        35                  40                  45

Glu Glu Gln Met Phe Gly Phe Ile Glu Arg Asn Lys Ala Ile Leu Ser
    50                  55                  60

Glu Lys Gln Val Gly Cys Ala Phe Asp Met Leu Trp Lys Leu Gln Lys
65                  70                  75                  80

Gln Lys Thr Ser Leu Leu Lys Asn Ala Glu Tyr Val Arg Asp His Pro
                85                  90                  95

Gln Phe Leu Thr Leu His Asn Leu Ala Thr Asn Lys Phe Lys Leu Met
            100                 105                 110

Asn Asp Asp Thr Leu Val Asn Val Leu Tyr Val Thr Gln Gln Phe Ala
        115                 120                 125

Gly Glu Ala His Asp Pro Leu Val Glu Ala Leu Val Thr Glu Ala Trp
    130                 135                 140

Arg Arg Leu Glu Arg Phe Asp Ile Lys Leu Leu Ser Glu Phe Ser Ser
145                 150                 155                 160

Cys Leu Ala Asp Gln His Leu Tyr Phe Ser Pro Leu Met Gly Lys Ile
                165                 170                 175

Ala Asp Ile Val His Arg Asn Leu Glu Thr Thr Gln Asp Leu Ser Ser
            180                 185                 190

Leu Ser Val Leu Met Val Asn Ile Ser Ser Leu Ile Ser Arg His Phe
        195                 200                 205

Gln Gln Gln Leu Val Asn Lys Thr Glu Leu Leu Phe Asp Thr Ile Asp
    210                 215                 220

Ser Ser Glu Val Asn Val Ala Lys Ser Ile Ala Lys Phe Leu Arg Asn
225                 230                 235                 240

Val Arg Tyr Arg Tyr Gln Pro Leu Leu Glu Arg Cys Asn Asn Val Phe
                245                 250                 255

Leu Ser Asn Val Asp His Leu Asp Leu Asp Ser Ile Ser Lys Ile Leu
            260                 265                 270

Ser Val Tyr Lys Phe Leu Gln Phe Asn Ser Phe Glu Phe Ile Ile Met
        275                 280                 285
```

```
Ala Lys Lys Lys Leu Thr Glu Met Ile Pro Leu Cys Asn His Pro Ala
    290                 295                 300
Ser Phe Val Lys Leu Phe Val Ala Leu Gly Pro Ile Ala Gly Pro Glu
305                 310                 315                 320
Glu Lys Lys Gln Leu Lys Ser Thr Met Leu Leu Met Ser Glu Asp Leu
                325                 330                 335
Thr Gly Glu Gln Ala Leu Ala Val Leu Gly Ala Met Gly Asp Met Glu
            340                 345                 350
Ser Arg Asn Ser Cys Leu Ile Lys Arg Val Thr Ser Val Leu His Lys
        355                 360                 365
His Leu Asp Gly Tyr Lys Pro Leu Glu Leu Leu Lys Ile Thr Gln Glu
    370                 375                 380
Leu Thr Phe Leu His Phe Gln Arg Lys Glu Phe Phe Ala Lys Leu Arg
385                 390                 395                 400
Glu Leu Leu Leu Ser Tyr Leu Lys Asn Ser Phe Ile Pro Thr Glu Val
                405                 410                 415
Ser Val Leu Val Arg Ala Ile Ser Leu Leu Pro Ser Pro His Leu Asp
            420                 425                 430
Glu Val Gly Ile Ser Arg Ile Glu Ala Val Leu Pro Gln Cys Asp Leu
        435                 440                 445
Asn Asn Leu Ser Ser Phe Ala Thr Ser Val Leu Arg Trp Ile Gln His
    450                 455                 460
Asp His Met Tyr Leu Asp Asn Met Thr Ala Lys Gln Leu Lys Leu Leu
465                 470                 475                 480
Gln Lys Leu Asp His Tyr Gly Arg Gln Arg Leu Gln His Ser Asn Ser
                485                 490                 495
Leu Asp Leu Leu Arg Lys Glu Leu Lys Ser Leu Lys Gly Asn Thr Phe
            500                 505                 510
Pro Glu Ser Leu Leu Glu Glu Met Ile Ala Thr Leu Gln His Phe Met
        515                 520                 525
Asp Asp Ile Asn Tyr Ile Asn Val Gly Glu Ile Ala Ser Phe Ile Ser
    530                 535                 540
Ser Thr Asp Tyr Leu Ser Thr Leu Leu Leu Asp Arg Ile Ala Ser Val
545                 550                 555                 560
Ala Val Gln Gln Ile Glu Lys Ile His Pro Phe Thr Ile Pro Ala Ile
                565                 570                 575
Ile Arg Pro Phe Ser Val Leu Asn Tyr Asp Pro Pro Gln Arg Asp Glu
            580                 585                 590
Phe Leu Gly Thr Cys Val Gln His Leu Asn Ser Tyr Leu Gly Ile Leu
        595                 600                 605
Asp Pro Phe Ile Leu Val Phe Leu Gly Phe Ser Leu Ala Thr Leu Glu
    610                 615                 620
Tyr Phe Pro Glu Asp Leu Leu Lys Ala Ile Phe Asn Ile Lys Phe Leu
625                 630                 635                 640
Ala Arg Leu Asp Ser Gln Leu Glu Ser Ile Gly Gly Met Asp Gly Thr
                645                 650                 655
Gln Gln Gln Ile Phe Lys Met Leu Ala Glu Val Leu Gly Gly Ile Asn
            660                 665                 670
Cys Val Lys Ala Ser Val Leu Thr Pro Tyr Tyr His Lys Val Asp Phe
        675                 680                 685
Glu Cys Ile Leu Asp Lys Arg Lys Lys Pro Leu Pro Tyr Gly Ser His
    690                 695                 700
```

```
Asn Ile Ala Leu Gly Gln Leu Pro Glu Met Pro Trp Glu Ser Asn Ile
705                 710                 715                 720

Glu Ile Val Gly Ser Arg Leu Pro Pro Gly Ala Glu Arg Ile Ala Leu
            725                 730                 735

Glu Phe Leu Asp Ser Lys Ala Leu Cys Arg Asn Ile Pro His Met Lys
        740                 745                 750

Gly Lys Ser Ala Met Lys Lys Arg His Leu Glu Ile Leu Gly Tyr Arg
        755                 760                 765

Val Ile Gln Ile Ser Gln Phe Glu Trp Asn Ser Met Ala Leu Ser Thr
    770                 775                 780

Lys Asp Ala Arg Met Asp Tyr Leu Arg Glu Cys Ile Phe Gly Glu Val
785                 790                 795                 800

Lys Ser Cys Leu

<210> SEQ ID NO 154
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      FASTKD1 protein"

<400> SEQUENCE: 154
tgaatgacga taccctggtg                                              20

<210> SEQ ID NO 155
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      FASTKD1 protein"

<400> SEQUENCE: 155
agccttctcc atgcttctgt                                              20

<210> SEQ ID NO 156
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      FASTKD1 protein"

<400> SEQUENCE: 156
ccatgacccg ctagttgaag                                              20

<210> SEQ ID NO 157
<211> LENGTH: 21
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      FASTKD1 protein"

<400> SEQUENCE: 157
tgatctgcta ggcaagagga a                                            21
```

<210> SEQ ID NO 158
<211> LENGTH: 21
<212> TYPE: DNA
<213> ORGANISM: Artificial Sequence
<220> FEATURE:
<221> NAME/KEY: Source
<223> OTHER INFORMATION: /note="Description of Artificial Sequence:
    Forward primer for amplifying the nucleotide sequence encoding
    FASTKD1 protein"

<400> SEQUENCE: 158
ttcctcttgc ctagcagatc a                                         21

<210> SEQ ID NO 159
<211> LENGTH: 21
<212> TYPE: DNA
<213> ORGANISM: Artificial Sequence
<220> FEATURE:
<221> NAME/KEY: Source
<223> OTHER INFORMATION: /note="Description of Artificial Sequence:
    Reverse primer for amplifying the nucleotide sequence encoding
    FASTKD1 protein"

<400> SEQUENCE: 159
tgttgaccat caagacagac a                                         21

<210> SEQ ID NO 160
<211> LENGTH: 22
<212> TYPE: DNA
<213> ORGANISM: Artificial Sequence
<220> FEATURE:
<221> NAME/KEY: Source
<223> OTHER INFORMATION: /note="Description of Artificial Sequence:
    Forward primer for amplifying the nucleotide sequence encoding
    FASTKD1 protein"

<400> SEQUENCE: 160
tcctctgtgt aatcatcctg ct                                        22

<210> SEQ ID NO 161
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
    Reverse primer for amplifying the nucleotide sequence encoding
    FASTKD1 protein"

<400> SEQUENCE: 161
ctcgccagtt aggtcctctg                                           20

<210> SEQ ID NO 162
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
    Forward primer for amplifying the nucleotide sequence encoding
    FASTKD1 protein"

<400> SEQUENCE: 162
ggagcaatgg gagatatgga                                           20

<210> SEQ ID NO 163
<211> LENGTH: 21

```
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      FASTKD1 protein"

<400> SEQUENCE: 163
ttcctttgga aatgcagaaa a                                          21

<210> SEQ ID NO 164
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      FASTKD1 protein"

<400> SEQUENCE: 164
tgcatttcca aaggaaggag                                            20

<210> SEQ ID NO 165
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      FASTKD1 protein"

<400> SEQUENCE: 165
caagtgagga gaagggagca                                            20

<210> SEQ ID NO 166
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      FASTKD1 protein"

<400> SEQUENCE: 166
aaatgttggg gagattgcat                                            20

<210> SEQ ID NO 167
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      FASTKD1 protein"

<400> SEQUENCE: 167
tcaatacgct gaatggacga                                            20

<210> SEQ ID NO 168
<211> LENGTH: 20
<212> TYPE: DNA
<213> ORGANISM: Artificial Sequence
<220> FEATURE:
<221> NAME/KEY: Source
```

```
<223> OTHER INFORMATION: /note="Description of Artificial Sequence:
      Forward primer for amplifying the nucleotide sequence encoding
      FASTKD1 protein"

<400> SEQUENCE: 168
gatccacctc aaagggatga                                              20

<210> SEQ ID NO 169
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      FASTKD1 protein"

<400> SEQUENCE: 169
ggccaaagag aaaccaagaa                                              20

<210> SEQ ID NO 170
<211> LENGTH: 22
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      FASTKD1 protein"

<400> SEQUENCE: 170
gtgtttcttg gtttctcttt gg                                           22

<210> SEQ ID NO 171
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      FASTKD1 protein"

<400> SEQUENCE: 171
ctgttgtgtt ccatccatgc                                              20

<210> SEQ ID NO 172
<211> LENGTH: 21
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      FASTKD1 protein"

<400> SEQUENCE: 172
gcattgggac aactaccaga a                                            21

<210> SEQ ID NO 173
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      FASTKD1 protein"
```

```
<400> SEQUENCE: 173
gtatgggagc gcaaaagaag                                              20

<210> SEQ ID NO 174
<211> LENGTH: 23
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      FASTKD1 protein"

<400> SEQUENCE: 174
tgtgttgctt catatttgta ccc                                          23

<210> SEQ ID NO 175
<211> LENGTH: 24
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      FASTKD1 protein"

<400> SEQUENCE: 175
catagcagat tttcctttca tgtg                                         24

<210> SEQ ID NO 176
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      FASTKD1 protein"

<400> SEQUENCE: 176
tgaccgcttc tgtcaacaat                                              20

<210> SEQ ID NO 177
<211> LENGTH: 21
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      FASTKD1 protein"

<400> SEQUENCE: 177
tgaatccaaa aattccaaag c                                            21

<210> SEQ ID NO 178
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding FASTKD1 protein"

<400> SEQUENCE: 178
gacccgctag ttgaagcact                                              20
```

```
<210> SEQ ID NO 179
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding FASTKD1 protein"

<400> SEQUENCE: 179
acagaagcat ggagaaggct                                              20

<210> SEQ ID NO 180
<211> LENGTH: 21
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding FASTKD1 protein"

<400> SEQUENCE: 180
gaacttggaa accacacagg a                                            21

<210> SEQ ID NO 181
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding FASTKD1 protein"

<400> SEQUENCE: 181
ttgtagcatt gggacccatt                                              20

<210> SEQ ID NO 182
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding FASTKD1 protein"

<400> SEQUENCE: 182
tgcataaaca tttggatggc                                              20

<210> SEQ ID NO 183
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding FASTKD1 protein"

<400> SEQUENCE: 183
ttctggtccg tgctatttcc                                              20

<210> SEQ ID NO 184
<211> LENGTH: 20
<212> TYPE: DNA
```

-continued

```
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding FASTKD1 protein"

<400> SEQUENCE: 184
gtggctgttc agcagattga                                           20

<210> SEQ ID NO 185
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding FASTKD1 protein"

<400> SEQUENCE: 185
gaacttgcgt gcaacatctt                                           20

<210> SEQ ID NO 186
<211> LENGTH: 21
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding FASTKD1 protein"

<400> SEQUENCE: 186
ccagaagatc tgctaaaggc a                                         21

<210> SEQ ID NO 187
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding FASTKD1 protein"

<400> SEQUENCE: 187
tgccctggga atcaaatatc                                           20

<210> SEQ ID NO 188
<211> LENGTH: 21
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding FASTKD1 protein"

<400> SEQUENCE: 188
ggattgcttt ggaatttttg g                                         21

<210> SEQ ID NO 189
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
```

Probe for detecting a nucleotide molecule having a nucleic acid sequence encoding FASTKD1 protein"

<400> SEQUENCE: 189
atggatggaa cacaacagca                                                    20

<210> SEQ ID NO 190
<211> LENGTH: 57
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding FASTKD1 protein"

<400> SEQUENCE: 190
tgaatggaac tctatggcac tgtcaacaaa ggatgctcgg atggactacc tgagaga         57

<210> SEQ ID NO 191
<211> LENGTH: 3263
<212> TYPE: DNA
<213> ORGANISM: Homo Sapiens

<400> SEQUENCE: 191
gagagagctg agagccagga ctcagtgctg agcttggtgt cccaccgcca caaggaggca        60
gggaagaaac ccactagtcc cagctcctgg ggtggcacag acattgcaac tggccctgcc       120
tgtgggtcct aggggcccgtt ggctaccagg aggctaagaa cactgctcat gaatgacagt      180
gagccctgaa agctctgggg gtgtcaccca gtcccacaag cctgcatccc ctgcagtgga       240
gatgggctca gctcctggac gtgccacaga cagaaagcat aacatacact cgccaggaag       300
agcctttgcc tgactcaggg cagctcagag tgtggggcag aaggtgacca gccagctcag       360
ggcaggagat gcagagcaca gccaattacc tgtggcacac agatgacctg ctggggcagg       420
gggccactgc cagtgtgtac aaggcccgca acaagaaatc cggagagctg gttgctgtga       480
aggtcttcaa cactaccagc tacctgcggc cccgcgaggt gcaggtgagg gagtttgagg       540
tcctgcggaa gctgaaccac cagaacatcg tcaagctctt tgcggtggag agacgggcg        600 gaagccggca gaaggtactg gtgatggagt actgctccag tgggagcctg ctgagtgtgc       660
tggagagccc tgaaatgcc tttgggctgc ctgaggatga gttcctggtg gtgctgcgct        720
gtgtggtggc cggcatgaac cacctgcggg agaacggcat tgtgcatcgc gacatcaagc       780
cggggaacat catgcgcctc gtaggggagg aggggcagag catctacaag ctgacagact       840
tcggcgctgc ccgggagctg gatgatgatg agaagttcgt ctcggtctat gggactgagg       900
agtacctgca tcccgacatg tatgagcggg cggtgcttcg aaagcccccag caaaaagcgt       960 tcggggtgac tgtggatctc tggagcattg gagtgacctt gtaccatgca gccactggca      1020
gcctgccctt catcccctt ggtgggccac ggcggaacaa ggagatcatg taccggatca        1080
ccacggagaa gccggctggg gccattgcag gtgcccagag gcgggagaac gggcccctgg      1140
agtggagcta caccctcccc atcacctgcc agctgtcact ggggctgcag agccagctgg      1200
tgcccatcct ggccaacatc ctggaggtgg agcaggccaa gtgctggggc ttcgaccagt      1260
tctttgcgga gaccagtgac atcctgcagc gagttgtcgt ccatgtcttc tccctgtccc      1320
aggcagtcct gcaccacatc tatatccatg cccacaacac gatagccatt ttccaggagg     1380
ccgtgcacaa gcagaccagt gtggccccccc gacaccagga gtacctcttt gagggtcacc    1440
tctgtgtcct cgagcccagc gtctcagcac agcacatcgc ccacacgacg gcaagcagcc    1500

```
ccctgaccct cttcagcaca gccatcccta aggggctggc cttcagggac cctgctctgg    1560
acgtccccaa gttcgtcccc aaagtggacc tgcaggcgga ttacaacact gccaagggcg    1620
tgttgggcgc cggctaccag gccctgcggc tggcacgggc cctgctggat gggcaggagc    1680
taatgtttcg ggggctgcac tgggtcatgg aggtgctcca ggccacatgc agacggactc    1740
tggaagtggc aaggacatcc ctcctctacc tcagcagcag cctgggaact gagaggttca    1800
gcagcgtggc tggaacgcct gagatccagg aactgaaggc ggctgcagaa ctgaggtcca    1860
ggctgcggac tctagcggag gtcctctcca gatgctccca aaatatcacg agacccagg     1920
agagcctgag cagcctgaac cgggagctgg tgaagagccg ggatcaggta catgaggaca    1980
gaagcatcca gcagattcag tgctgtttgg acaagatgaa cttcatctac aaacagttca    2040
agaagtctag gatgaggcca gggcttggct acaacgagga gcagattcac aagctggata    2100
aggtgaattt cagtcattta gccaaaagac tcctgcaggt gttccaggag gagtgcgtgc    2160
agaagtatca agcgtcctta gtcacacacg gcaagaggat gagggtggtg cacgagacca    2220
ggaaccacct gcgcctggtt ggctgttctg tggctgcctg taacacagaa gcccaggggg    2280
tccaggagag tctcagcaag ctcctggaag agctatctca ccagctcctt caggaccgag    2340
caaagggggc tcaggcctcg ccgcctccca tagctcctta ccccagccct acacgaaagg    2400
acctgcttct ccacatgcaa gagctctgcg aggggatgaa gctgctggca tctgacctcc    2460
tggacaacaa ccgcatcatc gaacggctaa atagagtccc agcacctcct gatgtctgag    2520
ctccatgggg cacatgaggc atcctgaagc attagaatga ttccaacact gctcttctgc    2580
accatgagac caacccaggg caagatccca tcccatcaca tcagcctacc tcctcctgg    2640
ctgctggcca ggatgtcgcc agcattacct tccactgcct ttctccctgg aagcagcac    2700
agctgagact gggcaccagg ccacctctgt tgggaccac aggaaagagt gtggcagcaa    2760
ctgcctggct gacctttcta tcttctctag gctcaggtac tgctcctcca tgcccatggc    2820
tgggccgtgg ggagaagaag ctctcatacg ccttcccact ccctctggtt tataggactt    2880
cactccctag ccaacaggag aggaggcctc ctggggtttc cccagggcag taggtcaaac    2940
gacctcatca cagtcttcct tcctcttcaa gcgtttcatg ttgaacacag ctctctccgc    3000
tcccttgtga tttctgaggg tcaccactgc cagcctcagg caacatagag agcctcctgt    3060
tctttctatg cttggtctga ctgagcctaa agttgagaaa atgggtggcc aaggccagtg    3120
ccagtgtctt ggggccccctt tggctctccc tcactctctg aggctccagc tggtcctggg    3180
acatgcagcc aggactgtga gtctgggcag gtccaaggcc tgcaccttca agaagtggaa    3240
taaatgtggc ctttgcttct gtt                                            3263
```

<210> SEQ ID NO 192
<211> LENGTH: 716
<212> TYPE: PRT
<213> ORGANISM: Homo Sapiens

<400> SEQUENCE: 192

```
Met Gln Ser Thr Ala Asn Tyr Leu Trp His Thr Asp Asp Leu Leu Gly
1               5                   10                  15

Gln Gly Ala Thr Ala Ser Val Tyr Lys Ala Arg Asn Lys Lys Ser Gly
            20                  25                  30

Glu Leu Val Ala Val Lys Val Phe Asn Thr Thr Ser Tyr Leu Arg Pro
        35                  40                  45

Arg Glu Val Gln Val Arg Glu Phe Glu Val Leu Arg Lys Leu Asn His
```

```
            50                  55                  60
Gln Asn Ile Val Lys Leu Phe Ala Val Glu Glu Thr Gly Gly Ser Arg
 65                  70                  75                  80
Gln Lys Val Leu Val Met Glu Tyr Cys Ser Ser Gly Ser Leu Leu Ser
                     85                  90                  95
Val Leu Glu Ser Pro Glu Asn Ala Phe Gly Leu Pro Glu Asp Glu Phe
                    100                 105                 110
Leu Val Val Leu Arg Cys Val Val Ala Gly Met Asn His Leu Arg Glu
                    115                 120                 125
Asn Gly Ile Val His Arg Asp Ile Lys Pro Gly Asn Ile Met Arg Leu
                    130                 135                 140
Val Gly Glu Glu Gly Gln Ser Ile Tyr Lys Leu Thr Asp Phe Gly Ala
145                 150                 155                 160
Ala Arg Glu Leu Asp Asp Glu Lys Phe Val Ser Val Tyr Gly Thr
                    165                 170                 175
Glu Glu Tyr Leu His Pro Asp Met Tyr Glu Arg Ala Val Leu Arg Lys
                    180                 185                 190
Pro Gln Gln Lys Ala Phe Gly Val Thr Val Asp Leu Trp Ser Ile Gly
                    195                 200                 205
Val Thr Leu Tyr His Ala Ala Thr Gly Ser Leu Pro Phe Ile Pro Phe
                    210                 215                 220
Gly Gly Pro Arg Arg Asn Lys Glu Ile Met Tyr Arg Ile Thr Thr Glu
225                 230                 235                 240
Lys Pro Ala Gly Ala Ile Ala Gly Ala Gln Arg Arg Glu Asn Gly Pro
                    245                 250                 255
Leu Glu Trp Ser Tyr Thr Leu Pro Ile Thr Cys Gln Leu Ser Leu Gly
                    260                 265                 270
Leu Gln Ser Gln Leu Val Pro Ile Leu Ala Asn Ile Leu Glu Val Glu
                    275                 280                 285
Gln Ala Lys Cys Trp Gly Phe Asp Gln Phe Phe Ala Glu Thr Ser Asp
                    290                 295                 300
Ile Leu Gln Arg Val Val Val His Val Phe Ser Leu Ser Gln Ala Val
305                 310                 315                 320
Leu His His Ile Tyr Ile His Ala His Asn Thr Ile Ala Ile Phe Gln
                    325                 330                 335
Glu Ala Val His Lys Gln Thr Ser Val Ala Pro Arg His Gln Glu Tyr
                    340                 345                 350
Leu Phe Glu Gly His Leu Cys Val Leu Glu Pro Ser Val Ser Ala Gln
                    355                 360                 365
His Ile Ala His Thr Thr Ala Ser Ser Pro Leu Thr Leu Phe Ser Thr
                    370                 375                 380
Ala Ile Pro Lys Gly Leu Ala Phe Arg Asp Pro Ala Leu Asp Val Pro
385                 390                 395                 400
Lys Phe Val Pro Lys Val Asp Leu Gln Ala Asp Tyr Asn Thr Ala Lys
                    405                 410                 415
Gly Val Leu Gly Ala Gly Tyr Gln Ala Leu Arg Leu Ala Arg Ala Leu
                    420                 425                 430
Leu Asp Gly Gln Glu Leu Met Phe Arg Gly Leu His Trp Val Met Glu
                    435                 440                 445
Val Leu Gln Ala Thr Cys Arg Arg Thr Leu Glu Val Ala Arg Thr Ser
                    450                 455                 460
Leu Leu Tyr Leu Ser Ser Ser Leu Gly Thr Glu Arg Phe Ser Ser Val
465                 470                 475                 480
```

Ala Gly Thr Pro Glu Ile Gln Glu Leu Lys Ala Ala Ala Glu Leu Arg
                485                 490                 495

Ser Arg Leu Arg Thr Leu Ala Glu Val Leu Ser Arg Cys Ser Gln Asn
            500                 505                 510

Ile Thr Glu Thr Gln Glu Ser Leu Ser Ser Leu Asn Arg Glu Leu Val
        515                 520                 525

Lys Ser Arg Asp Gln Val His Glu Asp Arg Ser Ile Gln Gln Ile Gln
    530                 535                 540

Cys Cys Leu Asp Lys Met Asn Phe Ile Tyr Lys Gln Phe Lys Lys Ser
545                 550                 555                 560

Arg Met Arg Pro Gly Leu Gly Tyr Asn Glu Glu Gln Ile His Lys Leu
                565                 570                 575

Asp Lys Val Asn Phe Ser His Leu Ala Lys Arg Leu Leu Gln Val Phe
            580                 585                 590

Gln Glu Glu Cys Val Gln Lys Tyr Gln Ala Ser Leu Val Thr His Gly
        595                 600                 605

Lys Arg Met Arg Val Val His Glu Thr Arg Asn His Leu Arg Leu Val
    610                 615                 620

Gly Cys Ser Val Ala Ala Cys Asn Thr Glu Ala Gln Gly Val Gln Glu
625                 630                 635                 640

Ser Leu Ser Lys Leu Leu Glu Glu Leu Ser His Gln Leu Leu Gln Asp
                645                 650                 655

Arg Ala Lys Gly Ala Gln Ala Ser Pro Pro Ile Ala Pro Tyr Pro
            660                 665                 670

Ser Pro Thr Arg Lys Asp Leu Leu His Met Gln Glu Leu Cys Glu
        675                 680                 685

Gly Met Lys Leu Leu Ala Ser Asp Leu Leu Asp Asn Asn Arg Ile Ile
    690                 695                 700

Glu Arg Leu Asn Arg Val Pro Ala Pro Pro Asp Val
705                 710                 715

<210> SEQ ID NO 193
<211> LENGTH: 23
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      IKBKE protein"

<400> SEQUENCE: 193
gtgccacaga cagaaagcat aac                                            23

<210> SEQ ID NO 194
<211> LENGTH: 18
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      IKBKE protein"

<400> SEQUENCE: 194
ggctgtgctc tgcatctc                                                  18

<210> SEQ ID NO 195
<211> LENGTH: 18

```
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      IKBKE protein"

<400> SEQUENCE: 195
ggggccactg ccagtgtg                                                    18

<210> SEQ ID NO 196
<211> LENGTH: 23
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      IKBKE protein"

<400> SEQUENCE: 196
gcaggtagct ggtagtgttg aag                                              23

<210> SEQ ID NO 197
<211> LENGTH: 21
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      IKBKE protein"

<400> SEQUENCE: 197
gaggtcctgc ggaagctgaa c                                                21

<210> SEQ ID NO 198
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      IKBKE protein"

<400> SEQUENCE: 198
cactcagcag gctcccactg                                                  20

<210> SEQ ID NO 199
<211> LENGTH: 21
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      IKBKE protein"

<400> SEQUENCE: 199
cctgaggatg agttcctggt g                                                21

<210> SEQ ID NO 200
<211> LENGTH: 22
<212> TYPE: DNA
<213> ORGANISM: Artificial Sequence
<220> FEATURE:
<221> NAME/KEY: Source
```

```
<223> OTHER INFORMATION: /note="Description of Artificial Sequence:
      Reverse primer for amplifying the nucleotide sequence encoding
      IKBKE protein"

<400> SEQUENCE: 200
gtcgcgatgc acaatgccgt tc                                              22

<210> SEQ ID NO 201
<211> LENGTH: 24
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      IKBKE protein"

<400> SEQUENCE: 201
ggatgatgat gagaagttcg tctc                                            24

<210> SEQ ID NO 202
<211> LENGTH: 19
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      IKBKE protein"

<400> SEQUENCE: 202
gaacgctttt tgctggggc                                                  19

<210> SEQ ID NO 203
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      IKBKE protein"

<400> SEQUENCE: 203
catccccttt ggtgggccac                                                 20

<210> SEQ ID NO 204
<211> LENGTH: 18
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      IKBKE protein"

<400> SEQUENCE: 204
ccgttctccc gcctctgg                                                   18

<210> SEQ ID NO 205
<211> LENGTH: 19
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      IKBKE protein"
```

```
<400> SEQUENCE: 205
cctggagtgg agctacacc                                                    19

<210> SEQ ID NO 206
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      IKBKE protein"

<400> SEQUENCE: 206
cacttggcct gctccacctc                                                   20

<210> SEQ ID NO 207
<211> LENGTH: 19
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      IKBKE protein"

<400> SEQUENCE: 207
gtcccaggca gtcctgcac                                                    19

<210> SEQ ID NO 208
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      IKBKE protein"

<400> SEQUENCE: 208
gacgctgggc tcgaggacac                                                   20

<210> SEQ ID NO 209
<211> LENGTH: 22
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      IKBKE protein"

<400> SEQUENCE: 209
gaccctcttc agcacagcca tc                                                22

<210> SEQ ID NO 210
<211> LENGTH: 18
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      IKBKE protein"

<400> SEQUENCE: 210
gccgcagggc ctggtagc                                                     18
```

<210> SEQ ID NO 211
<211> LENGTH: 21
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      IKBKE protein"

<400> SEQUENCE: 211
gatccaggaa ctgaaggcgg c                                           21

<210> SEQ ID NO 212
<211> LENGTH: 19
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      IKBKE protein"

<400> SEQUENCE: 212
cctgatcccg gctcttcac                                              19

<210> SEQ ID NO 213
<211> LENGTH: 60
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding IKBKE protein"

<400> SEQUENCE: 213
ctcctgttct ttctatgctt ggtctgactg agcctaaagt tgagaaaatg ggtggccaag    60

<210> SEQ ID NO 214
<211> LENGTH: 35
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding IKBKE protein"

<400> SEQUENCE: 214
catcacctgc cagctgtcac tggggctgca gagcc                            35

<210> SEQ ID NO 215
<211> LENGTH: 35
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding IKBKE protein"

<400> SEQUENCE: 215
ctatatccat gcccacaaca cgatagccat tttcc                            35

<210> SEQ ID NO 216
<211> LENGTH: 40
<212> TYPE: DNA

```
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding IKBKE protein"

<400> SEQUENCE: 216
ggacgtcccc aagttcgtcc ccaaagtgga cctgcaggcg                              40

<210> SEQ ID NO 217
<211> LENGTH: 43
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding IKBKE protein"

<400> SEQUENCE: 217
ggtccaggag agtctcagca agctcctgga agagctatct cac                          43

<210> SEQ ID NO 218
<211> LENGTH: 1578
<212> TYPE: DNA
<213> ORGANISM: Homo Sapiens

<400> SEQUENCE: 218
aaggtgagcg actgcaggca aacccggcga cagcgcagct cgcgtcgacc ctggctcctc        60
tgcctgcccc ctcaggcccc cgcctccttc aggatgacgc tggacgtggg gccggaggat       120
gagctgcccg actgggccgc cgccaaagag ttttaccaga agtacgaccc taaggacgtc       180
atcggcagag gagtgagctc tgtggtccgc cgttgtgttc atcgagctac tggccacgag       240
tttgcggtga agattatgga agtgacagct gagcggctga gtcctgagca gctggaggag       300
gtgcgggaag ccacacggcg agagacacac atccttcgcc aggtcgccgg ccaccccac        360 atcatcaccc tcatcgattc ctacgagtct tctagcttca tgttcctggt gtttgacctg       420
atgcggaagg gagagctgtt tgactatctc acagagaagg tggccctctc tgaaaaggaa       480
accaggtcca tcatgcggtc tctgctggaa gcagtgagct ttctccatgc caacaacatt       540
gtgcatcgag atctgaagcc cgagaatatt ctcctagatg acaatatgca gatccgactt       600
tcagatttcg ggttctcctg ccacttggaa cctggcgaga gcttcgaga gttgtgtggg        660 accccagggt atctagcgcc agagatcctt aaatgctcca tggatgaaac ccacccaggc       720
tatggcaagg aggtcgacct ctgggcctgt ggggtgatct tgttcacact cctggctggc       780
tcgccaccct tctggcaccg gcggcagatc ctgatgttac gcatgatcat ggagggccag       840
taccagttca gttcccccga gtgggatgac cgttccagca ctgtcaaaga cctgatctcc       900
aggctgctgc aggtggatcc tgaggcacgc ctgacagctg agcaggccct acagcacccc       960
ttctttgagc gttgtgaagg cagccaaccc tggaacctca ccccccgcca gcggttccgg      1020
gtggcagtgt ggacagtgct ggctgctgga cgagtggccc taagcaccca tcgtgtacgg      1080
ccactgacca agaatgcact gttgagggac cctatgcgc tgcggtcagt gcggcacctc      1140
atcgacaact gtgccttccg gctctacggg cactgggtaa agaaggggga gcagcagaac      1200
cgggcggctc tctttcagca ccggcccct gggccttttc ccatcatggg ccctgaagag       1260
gagggagact ctgctgctat aactgaggat gaggccgtgc ttgtgctggg ctaggacctc      1320
aaccccaggg attcccagga agcagaactc tccagaagaa gggttttgat cattccagct      1380
```

```
cctctgggct ctggcctctg gcctcaggcc cactaatgat cctgctaccc tcttgaagac    1440
cagcccggta cctctctccc cactggccag gactctgaga tcagagctgg ggtggaaggg    1500
agccattctg aacgccacgc ctggcccggt cagtgctgca tgcactgcat atgaaataaa    1560
atctgctaca cgccaggg                                                  1578
```

<210> SEQ ID NO 219
<211> LENGTH: 406
<212> TYPE: PRT
<213> ORGANISM: Homo Sapiens

<400> SEQUENCE: 219

```
Met Thr Leu Asp Val Gly Pro Glu Asp Glu Leu Pro Asp Trp Ala Ala
1               5                   10                  15

Ala Lys Glu Phe Tyr Gln Lys Tyr Asp Pro Lys Asp Val Ile Gly Arg
            20                  25                  30

Gly Val Ser Ser Val Val Arg Arg Cys Val His Arg Ala Thr Gly His
        35                  40                  45

Glu Phe Ala Val Lys Ile Met Glu Val Thr Ala Glu Arg Leu Ser Pro
    50                  55                  60

Glu Gln Leu Glu Glu Val Arg Glu Ala Thr Arg Arg Glu Thr His Ile
65                  70                  75                  80

Leu Arg Gln Val Ala Gly His Pro His Ile Ile Thr Leu Ile Asp Ser
                85                  90                  95

Tyr Glu Ser Ser Ser Phe Met Phe Leu Val Phe Asp Leu Met Arg Lys
            100                 105                 110

Gly Glu Leu Phe Asp Tyr Leu Thr Glu Lys Val Ala Leu Ser Glu Lys
        115                 120                 125

Glu Thr Arg Ser Ile Met Arg Ser Leu Leu Glu Ala Val Ser Phe Leu
    130                 135                 140

His Ala Asn Asn Ile Val His Arg Asp Leu Lys Pro Glu Asn Ile Leu
145                 150                 155                 160

Leu Asp Asp Asn Met Gln Ile Arg Leu Ser Asp Phe Gly Phe Ser Cys
                165                 170                 175

His Leu Glu Pro Gly Glu Lys Leu Arg Glu Leu Cys Gly Thr Pro Gly
            180                 185                 190

Tyr Leu Ala Pro Glu Ile Leu Lys Cys Ser Met Asp Glu Thr His Pro
        195                 200                 205

Gly Tyr Gly Lys Glu Val Asp Leu Trp Ala Cys Gly Val Ile Leu Phe
    210                 215                 220

Thr Leu Leu Ala Gly Ser Pro Pro Phe Trp His Arg Arg Gln Ile Leu
225                 230                 235                 240

Met Leu Arg Met Ile Met Glu Gly Gln Tyr Gln Phe Ser Ser Pro Glu
                245                 250                 255

Trp Asp Asp Arg Ser Ser Thr Val Lys Asp Leu Ile Ser Arg Leu Leu
            260                 265                 270

Gln Val Asp Pro Glu Ala Arg Leu Thr Ala Glu Gln Ala Leu Gln His
        275                 280                 285

Pro Phe Phe Glu Arg Cys Glu Gly Ser Gln Pro Trp Asn Leu Thr Pro
    290                 295                 300

Arg Gln Arg Phe Arg Val Ala Val Trp Thr Val Leu Ala Ala Gly Arg
305                 310                 315                 320

Val Ala Leu Ser Thr His Arg Val Arg Pro Leu Thr Lys Asn Ala Leu
                325                 330                 335
```

```
Leu Arg Asp Pro Tyr Ala Leu Arg Ser Val Arg His Leu Ile Asp Asn
            340                 345                 350

Cys Ala Phe Arg Leu Tyr Gly His Trp Val Lys Lys Gly Glu Gln Gln
        355                 360                 365

Asn Arg Ala Ala Leu Phe Gln His Arg Pro Pro Gly Pro Phe Pro Ile
    370                 375                 380

Met Gly Pro Glu Glu Glu Gly Asp Ser Ala Ala Ile Thr Glu Asp Glu
385                 390                 395                 400

Ala Val Leu Val Leu Gly
                405

<210> SEQ ID NO 220
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      PHKG2 protein"

<400> SEQUENCE: 220
ccgccaaaga gttttaccag                                                    20

<210> SEQ ID NO 221
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      PHKG2 protein"

<400> SEQUENCE: 221
tccataatct tcaccgcaaa                                                    20

<210> SEQ ID NO 222
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      PHKG2 protein"

<400> SEQUENCE: 222
ggcgagagac acacatcctt                                                    20

<210> SEQ ID NO 223
<211> LENGTH: 21
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      PHKG2 protein"

<400> SEQUENCE: 223
caaacaccag gaacatgaag c                                                  21

<210> SEQ ID NO 224
<211> LENGTH: 21
```

```
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      PHKG2 protein"

<400> SEQUENCE: 224
gcttcatgtt cctggtgttt g                                          21

<210> SEQ ID NO 225
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      PHKG2 protein"

<400> SEQUENCE: 225
ttttcagaga gggccacctt                                            20

<210> SEQ ID NO 226
<211> LENGTH: 21
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      PHKG2 protein"

<400> SEQUENCE: 226
ggaagggaga gctgtttgac t                                          21

<210> SEQ ID NO 227
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      PHKG2 protein"

<400> SEQUENCE: 227
tgttgttggc atggagaaag                                            20

<210> SEQ ID NO 228
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      PHKG2 protein"

<400> SEQUENCE: 228
tcagatttcg ggttctcctg                                            20

<210> SEQ ID NO 229
<211> LENGTH: 20
<212> TYPE: DNA
<213> ORGANISM: Artificial Sequence
<220> FEATURE:
<221> NAME/KEY: Source
```

```
<223> OTHER INFORMATION: /note="Description of Artificial Sequence:
      Reverse primer for amplifying the nucleotide sequence encoding
      PHKG2 protein"

<400> SEQUENCE: 229
atagcctggg tgggtttcat                                              20

<210> SEQ ID NO 230
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      PHKG2 protein"

<400> SEQUENCE: 230
atgaaaccca cccaggctat                                              20

<210> SEQ ID NO 231
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      PHKG2 protein"

<400> SEQUENCE: 231
tgcgtaacat caggatctgc                                              20

<210> SEQ ID NO 232
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      PHKG2 protein"

<400> SEQUENCE: 232
cgttccagca ctgtcaaaga                                              20

<210> SEQ ID NO 233
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      PHKG2 protein"

<400> SEQUENCE: 233
ccttcacaac gctcaaagaa                                              20

<210> SEQ ID NO 234
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      PHKG2 protein"
```

```
<400> SEQUENCE: 234
accccttctt tgagcgttgt                                               20

<210> SEQ ID NO 235
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      PHKG2 protein"

<400> SEQUENCE: 235
cgtacacgat gggtgcttag                                               20

<210> SEQ ID NO 236
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding PHKG2 protein"

<400> SEQUENCE: 236
ccgttgtgtt catcgagcta                                               20

<210> SEQ ID NO 237
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding PHKG2 protein"

<400> SEQUENCE: 237
catcaccctc atcgattcct                                               20

<210> SEQ ID NO 238
<211> LENGTH: 21
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding PHKG2 protein"

<400> SEQUENCE: 238
ggaagggaga gctgtttgac t                                             21

<210> SEQ ID NO 239
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding PHKG2 protein"

<400> SEQUENCE: 239
aggaaaccag gtccatcatg                                               20
```

<210> SEQ ID NO 240
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
     Probe for detecting a nucleotide molecule having a nucleic acid
     sequence encoding PHKG2 protein"

<400> SEQUENCE: 240
cagggtatct agcgccagag                                               20

<210> SEQ ID NO 241
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
     Probe for detecting a nucleotide molecule having a nucleic acid
     sequence encoding PHKG2 protein"

<400> SEQUENCE: 241
cctgtggggt gatcttgttc                                               20

<210> SEQ ID NO 242
<211> LENGTH: 19
<212> TYPE: DNA
<213> ORGANISM: Artificial Sequence
<220> FEATURE:
<221> NAME/KEY: Source
<223> OTHER INFORMATION: /note="Description of Artificial Sequence:
     Probe for detecting a nucleotide molecule having a nucleic acid
     sequence encoding PHKG2 protein"

<400> SEQUENCE: 242
acagctgagc aggccctac                                                19

<210> SEQ ID NO 243
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
     Probe for detecting a nucleotide molecule having a nucleic acid
     sequence encoding PHKG2 protein"

<400> SEQUENCE: 243
gttgtggcag tgtggacagt                                               20

<210> SEQ ID NO 244
<211> LENGTH: 60
<212> TYPE: DNA
<213> ORGANISM: Artificial Sequence
<220> FEATURE:
<221> NAME/KEY: Source
<223> OTHER INFORMATION: /note="Description of Artificial Sequence:
     Probe for detecting a nucleotide molecule having a nucleic acid
     sequence encoding PHKG2 protein"

<400> SEQUENCE: 244
ctcaacccca gggattccca ggaagcagaa ctctccagaa gaagggtttt gatcattcca   60

<210> SEQ ID NO 245
<211> LENGTH: 2578
<212> TYPE: DNA

<213> ORGANISM: Homo Sapiens

<400> SEQUENCE: 245

```
gagcctcgaa gtccgccggc caatcgaagg cgggccccag cggcgcgtgc gcgccgcggc        60
cagcgcgcgc gggcggggggg gcaggcgcgc cccggaccca ggatttataa aggcgaggcc       120
gggaccggcg cgcgctctcg tcgcccccgc tgtcccggcg gcgccaaccg aagcgccccg       180
cctgatccgt gtccgacatg ctgcgccgcg ctctgctgtg cctggccgtg gccgccctgg       240
tgcgcgccga cgcccccgag gaggaggacc acgtcctggt gctgcggaaa agcaacttcg       300
cggaggcgct ggcggcccac aagtacctgc tggtggagtt ctatgcccct tggtgtggcc       360
actgcaaggc tctggcccct gagtatgcca aagccgctgg gaagctgaag gcagaaggtt       420
ccgagatcag gttggccaag gtggacgcca cggaggagtc tgacctggcc cagcagtacg       480
gcgtgcgcgg ctatcccacc atcaagttct tcaggaatgg agacacggct tcccccaagg       540
aatatacagc tggcagagag gctgatgaca tcgtgaactg gctgaagaag cgcacgggcc       600
cggctgccac caccctgcct gacggcgcag ctgcagagtc cttggtggag tccagcgagg       660
tggctgtcat cggcttcttc aaggacgtgg agtcggactc tgccaagcag ttttgcagg       720
cagcagaggc catcgatgac ataccatttg ggatcacttc caacagtgac gtgttctcca       780
aataccagct cgacaaagat ggggttgtcc tctttaagaa gtttgatgaa ggccggaaca       840
actttgaagg ggaggtcacc aaggagaacc tgctggactt tatcaaacac aaccagctgc       900
cccttgtcat cgagttcacc gagcagacag ccccgaagat ttttggaggt gaaatcaaga       960
ctcacatcct gctgttcttg cccaagagtg tgtctgacta tgacggcaaa ctgagcaact      1020
tcaaaacagc agccgagagc ttcaagggca agatcctgtt catcttcatc gacagcgacc      1080
acaccgacaa ccagcgcatc ctcgagttct ttggcctgaa gaaggaagag tgcccggccg      1140
tgcgcctcat caccctggag gaggagatga ccaagtacaa gcccgaatcg gaggagctga      1200
cggcagagag gatcacagag ttctgccacc gcttcctgga gggcaaaatc aagcccacc      1260
tgatgagcca ggagctgccg gaggactggg acaagcagcc tgtcaaggtg cttgttggga      1320
agaactttga gacgtggct tttgatgaga aaaaaaacgt ctttgtggag ttctatgccc      1380
catggtgtgg tcactgcaaa cagttggctc ccatttggga taaactggga gagacgtaca      1440
aggaccatga aacatcgtc atcgccaaga tggactcgac tgccaacgag gtggaggccg      1500
tcaaagtgca cagcttcccc acactcaagt tctttcctgc cagtgccgac aggacggtca      1560
ttgattacaa cggggaacgc acgctggatg gttttaagaa attcctggag agcgtggcc      1620
aggatggggc aggggatgat gacgatctcg aggacctgga agaagcagag gagccagaca      1680
tggaggaaga cgatgatcag aaagctgtga agatgaact gtaatacgca aagccagacc      1740
cgggcgctgc cgagacccct cggggggctgc acacccagca gcagcgcacg cctccgaagc      1800
ctgcggcctc gcttgaagga gggcgtcgcc ggaaacccag ggaacctctc tgaagtgaca      1860
cctcaccccct acacaccgtc cgttcacccc cgtctcttcc ttctgctttt cggttttgg      1920
aaagggatcc atctccaggc agcccacccct ggtgggctt gtttcctgaa accatgatgt      1980
acttttcat acatgagtct gtccagagtg cttgctaccg tgttcggagt ctcgctgcct      2040
ccctcccgcg ggaggtttct cctcttttg aaaattccgt ctgtgggatt tttagacatt      2100
tttcgacatc agggtatttg ttccaccttg gccaggcctc ctcggagaag cttgtccccc      2160
gtgtgggagg gacggagccg gactggacat ggtcactcag taccgcctgc agtgtcgcca      2220
tgactgatca tggctcttgc atttttgggt aaatggagac ttccggatcc tgtcagggtg      2280
```

```
tcccccatgc ctggaagagg agctggtggc tgccagccct ggggcccggc acaggcctgg    2340
gccttcccct tccctcaagc cagggctcct cctcctgtcg tgggctcatt gtgaccactg    2400
gcctctctac agcacggcct gtggcctgtt caaggcagaa ccacgaccct tgactcccgg    2460
gtggggaggt ggccaaggat gctggagctg aatcagacgc tgacagttct tcaggcattt    2520
ctatttcaca atcgaattga acacattggc caaataaagt tgaaatttta ccacctgt     2578
```

```
<210> SEQ ID NO 246
<211> LENGTH: 508
<212> TYPE: PRT
<213> ORGANISM: Homo Sapiens

<400> SEQUENCE: 246
```

Met Leu Arg Arg Ala Leu Leu Cys Leu Ala Val Ala Ala Leu Val Arg
1               5                   10                  15

Ala Asp Ala Pro Glu Glu Glu Asp His Val Leu Val Leu Arg Lys Ser
            20                  25                  30

Asn Phe Ala Glu Ala Leu Ala Ala His Lys Tyr Leu Leu Val Glu Phe
        35                  40                  45

Tyr Ala Pro Trp Cys Gly His Cys Lys Ala Leu Ala Pro Glu Tyr Ala
    50                  55                  60

Lys Ala Ala Gly Lys Leu Lys Ala Glu Gly Ser Glu Ile Arg Leu Ala
65                  70                  75                  80

Lys Val Asp Ala Thr Glu Glu Ser Asp Leu Ala Gln Gln Tyr Gly Val
                85                  90                  95

Arg Gly Tyr Pro Thr Ile Lys Phe Phe Arg Asn Gly Asp Thr Ala Ser
            100                 105                 110

Pro Lys Glu Tyr Thr Ala Gly Arg Glu Ala Asp Asp Ile Val Asn Trp
        115                 120                 125

Leu Lys Lys Arg Thr Gly Pro Ala Ala Thr Thr Leu Pro Asp Gly Ala
    130                 135                 140

Ala Ala Glu Ser Leu Val Glu Ser Ser Glu Val Ala Val Ile Gly Phe
145                 150                 155                 160

Phe Lys Asp Val Glu Ser Asp Ser Ala Lys Gln Phe Leu Gln Ala Ala
                165                 170                 175

Glu Ala Ile Asp Asp Ile Pro Phe Gly Ile Thr Ser Asn Ser Asp Val
            180                 185                 190

Phe Ser Lys Tyr Gln Leu Asp Lys Asp Gly Val Val Leu Phe Lys Lys
        195                 200                 205

Phe Asp Glu Gly Arg Asn Asn Phe Glu Gly Glu Val Thr Lys Glu Asn
    210                 215                 220

Leu Leu Asp Phe Ile Lys His Asn Gln Leu Pro Leu Val Ile Glu Phe
225                 230                 235                 240

Thr Glu Gln Thr Ala Pro Lys Ile Phe Gly Gly Glu Ile Lys Thr His
                245                 250                 255

Ile Leu Leu Phe Leu Pro Lys Ser Val Ser Asp Tyr Asp Gly Lys Leu
            260                 265                 270

Ser Asn Phe Lys Thr Ala Ala Glu Ser Phe Lys Gly Lys Ile Leu Phe
        275                 280                 285

Ile Phe Ile Asp Ser Asp His Thr Asp Asn Gln Arg Ile Leu Glu Phe
    290                 295                 300

Phe Gly Leu Lys Lys Glu Glu Cys Pro Ala Val Arg Leu Ile Thr Leu
305                 310                 315                 320

```
Glu Glu Glu Met Thr Lys Tyr Lys Pro Glu Ser Glu Glu Leu Thr Ala
            325                 330                 335

Glu Arg Ile Thr Glu Phe Cys His Arg Phe Leu Glu Gly Lys Ile Lys
        340                 345                 350

Pro His Leu Met Ser Gln Glu Leu Pro Glu Asp Trp Asp Lys Gln Pro
            355                 360                 365

Val Lys Val Leu Val Gly Lys Asn Phe Glu Asp Val Ala Phe Asp Glu
    370                 375                 380

Lys Lys Asn Val Phe Val Glu Phe Tyr Ala Pro Trp Cys Gly His Cys
385                 390                 395                 400

Lys Gln Leu Ala Pro Ile Trp Asp Lys Leu Gly Glu Thr Tyr Lys Asp
                405                 410                 415

His Glu Asn Ile Val Ile Ala Lys Met Asp Ser Thr Ala Asn Glu Val
            420                 425                 430

Glu Ala Val Lys Val His Ser Phe Pro Thr Leu Lys Phe Phe Pro Ala
        435                 440                 445

Ser Ala Asp Arg Thr Val Ile Asp Tyr Asn Gly Glu Arg Thr Leu Asp
    450                 455                 460

Gly Phe Lys Lys Phe Leu Glu Ser Gly Gly Gln Asp Gly Ala Gly Asp
465                 470                 475                 480

Asp Asp Asp Leu Glu Asp Leu Glu Glu Ala Glu Glu Pro Asp Met Glu
                485                 490                 495

Glu Asp Asp Asp Gln Lys Ala Val Lys Asp Glu Leu
            500                 505

<210> SEQ ID NO 247
<211> LENGTH: 19
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      P4HB protein"

<400> SEQUENCE: 247
gctgcggaaa agcaacttc                                                    19

<210> SEQ ID NO 248
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      P4HB protein"

<400> SEQUENCE: 248
ctgatctcgg aaccttctgc                                                   20

<210> SEQ ID NO 249
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      P4HB protein"

<400> SEQUENCE: 249
```
ggctatccca ccatcaagtt                                              20

<210> SEQ ID NO 250
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      P4HB protein"

<400> SEQUENCE: 250
tcttcagcca gttcacgatg                                              20

<210> SEQ ID NO 251
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      P4HB protein"

<400> SEQUENCE: 251
gcagagtcct tggtggagtc                                              20

<210> SEQ ID NO 252
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      P4HB protein"

<400> SEQUENCE: 252
tggaagtgat cccaaatggt                                              20

<210> SEQ ID NO 253
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      P4HB protein"

<400> SEQUENCE: 253
accatttggg atcacttcca                                              20

<210> SEQ ID NO 254
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      P4HB protein"

<400> SEQUENCE: 254
ggtgacctcc ccttcaaagt                                              20

<210> SEQ ID NO 255

-continued

```
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      P4HB protein"

<400> SEQUENCE: 255
ccccttgtca tcgagttcac                                                  20

<210> SEQ ID NO 256
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      P4HB protein"

<400> SEQUENCE: 256
tgctcagttt gccgtcatag                                                  20

<210> SEQ ID NO 257
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      P4HB protein"

<400> SEQUENCE: 257
tcacatcctg ctgttcttgc                                                  20

<210> SEQ ID NO 258
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      P4HB protein"

<400> SEQUENCE: 258
gtcgctgtcg atgaagatga                                                  20

<210> SEQ ID NO 259
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      P4HB protein"

<400> SEQUENCE: 259
gacggcagag aggatcacag                                                  20

<210> SEQ ID NO 260
<211> LENGTH: 20
<212> TYPE: DNA
<213> ORGANISM: Artificial Sequence
<220> FEATURE:
```

```
<221> NAME/KEY: Source
<223> OTHER INFORMATION: /note="Description of Artificial Sequence:
      Reverse primer for amplifying the nucleotide sequence encoding
      P4HB protein"

<400> SEQUENCE: 260
ttcttcccaa caagcacctt                                              20

<210> SEQ ID NO 261
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      P4HB protein"

<400> SEQUENCE: 261
agcctgtcaa ggtgcttgtt                                              20

<210> SEQ ID NO 262
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      P4HB protein"

<400> SEQUENCE: 262
caaatgggag ccaactgttt                                              20

<210> SEQ ID NO 263
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      P4HB protein"

<400> SEQUENCE: 263
acagcttccc cacactcaag                                              20

<210> SEQ ID NO 264
<211> LENGTH: 19
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      P4HB protein"

<400> SEQUENCE: 264
caccgctctc caggaattt                                               19

<210> SEQ ID NO 265
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      P4HB protein"
```

-continued

<400> SEQUENCE: 265
gcacgctgga tggttttaag                                        20

<210> SEQ ID NO 266
<211> LENGTH: 21
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      P4HB protein"

<400> SEQUENCE: 266
tcatcgtctt cctccatgtc t                                      21

<210> SEQ ID NO 267
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding P4HB protein"

<400> SEQUENCE: 267
cacaagtacc tgctggtgga                                        20

<210> SEQ ID NO 268
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding P4HB protein"

<400> SEQUENCE: 268
ggcttccccc aaggaatata                                        20

<210> SEQ ID NO 269
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding P4HB protein"

<400> SEQUENCE: 269
gcttcttcaa ggacgtggag                                        20

<210> SEQ ID NO 270
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding P4HB protein"

<400> SEQUENCE: 270
ctcgacaaag atggggttgt                                        20

<210> SEQ ID NO 271
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
Probe for detecting a nucleotide molecule having a nucleic acid
sequence encoding P4HB protein"

<400> SEQUENCE: 271
tcacatcctg ctgttcttgc                                              20

<210> SEQ ID NO 272
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
Probe for detecting a nucleotide molecule having a nucleic acid
sequence encoding P4HB protein"

<400> SEQUENCE: 272
ctatgacggc aaactgagca                                              20

<210> SEQ ID NO 273
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
Probe for detecting a nucleotide molecule having a nucleic acid
sequence encoding P4HB protein"

<400> SEQUENCE: 273
aaaatcaagc cccacctgat                                              20

<210> SEQ ID NO 274
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
Probe for detecting a nucleotide molecule having a nucleic acid
sequence encoding P4HB protein"

<400> SEQUENCE: 274
tgaagacgtg gcttttgatg                                              20

<210> SEQ ID NO 275
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
Probe for detecting a nucleotide molecule having a nucleic acid
sequence encoding P4HB protein"

<400> SEQUENCE: 275
ggtcattgat tacaacgggg                                              20

<210> SEQ ID NO 276
<211> LENGTH: 20

<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding P4HB protein"

<400> SEQUENCE: 276
atgacgatct cgaggacctg                                              20

<210> SEQ ID NO 277
<211> LENGTH: 60
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding P4HB protein"

<400> SEQUENCE: 277
ggcatttcta tttcacaatc gaattgaaca cattggccaa ataaagttga aattttcccc   60

<210> SEQ ID NO 278
<211> LENGTH: 2026
<212> TYPE: DNA
<213> ORGANISM: Homo Sapiens

<400> SEQUENCE: 278
aagtgctggg atgacaggtg tgagccaccg ccccccggccc ctcgcccgcc ttttgaagga   60
gcctttcgtc ctcaagggcg aggccactcc cccccgcga gttccatgcc ccctagaggg   120
tcatcgttcc cgacggggag gtggcgcccc cccccgggcc ccgggccccg accgccgtg   180 ctgcctcctt ccgggccctc ctccgcgatg acggcgccgc cagcaggcca ggcggactgg   240
gcggggctcc gagcggggac tgggacccag accgactagg ggactgggag cgggcggcgc   300
ggccatggcg ggctgctgcg ccgcgctggc ggccttcctg ttcgagtacg acacgccgcg   360
catcgtgctc atccgcagcc gcaaagtggg gctcatgaac cgcgccgtgc aactgctcat   420
cctggcctac gtcatcgggt gggtgttttgt gtgggaaaag ggctaccagg aaaactgactc   480 cgtggtcagc tccgttacga ccaaggtcaa gggcgtggct gtgaccaaca cttctaaact   540
tggattccgg atctgggatg tggcggatta tgtgatacca gctcaggagg aaaactcccct   600 cttcgtcatg accaacgtga tcctcaccat gaaccagaca cagggcctgt gccccgagat   660
tccagatgcg accactgtgt gtaaatcaga tgccagctgt actgccggct ctgccggcac   720
ccacagcaac ggagtctcaa caggcaggtg cgtagctttc aacgggtctg tcaagacgtg   780
tgaggtggcg gcctggtgcc cggtggagga tgacacacac gtgccacaac ctgctttttt   840
aaaggctgca gaaaacttca ctcttttggt taagaacaac atctggtatc caaatttaa   900 tttcagcaag aggaatatcc ttcccaacat caccactact tacctcaagt cgtgcattta   960
tgatgctaaa acagatccct tctgccccat attccgtctt ggcaaaatag tggagaacgc  1020
aggacacagt ttccaggaca tggccgtgga gggaggcatc atgggcatcc aggtcaactg  1080
ggactgcaac ctggacagag ccgcctccct ctgcttgccc aggtactcct tccgccgcct  1140
cgatacacgg gacgttgagc acaacgtatc tcctggctac aatttcaggt tgccaagta  1200 ctacagagac ctggctggca acgagcagcg cacgctcatc aaggcctatg catccgcttt  1260
cgacatcatt gtgtttggga aggcagggaa atttgacatc atccccacta tgatcaacat  1320

-continued

```
cggctctggc ctggcactgc taggcatggc gaccgtgctg tgtgacatca tagtcctcta    1380
ctgcatgaag aaaagactct actatcggga aagaaatat aaatatgtgg aagattacga    1440
gcagggtctt gctagtgagc tggaccagtg aggcctaccc cacacctggg ctctccacag    1500
ccccatcaaa gaacagagag gaggaggagg gagaaatggc caccacatca ccccagagaa    1560
atttctggaa tctgattgag tctccactcc acaagcactc agggttcccc agcagctcct    1620
gtgtgttgtg tgcaggatct gtttgcccac tcggcccagg aggtcagcag tctgttcttg    1680
gctgggtcaa ctctgctttt cccgcaacct ggggttgtcg ggggagcgct ggcccgacgc    1740
agtggcactg ctgtggcttt cagggctgga gctggctttg ctcagaagcc tcctgtctcc    1800
agctctctcc aggacaggcc cagtcctctg aggcacggcg gctctgttca agcactttat    1860
gcggcagggg aggccgcctg gctgcagtca ctagacttgt agcaggcctg ggctgcaggc    1920
ttccccccga ccattccctg cagccatgcg gcagagctgg catttctcct cagagaagcg    1980
ctgtgctaag gtgatcgagg accagacatt aaagcgtgat tttctt                  2026
```

<210> SEQ ID NO 279
<211> LENGTH: 388
<212> TYPE: PRT
<213> ORGANISM: Homo Sapiens

<400> SEQUENCE: 279

```
Met Ala Gly Cys Cys Ala Ala Leu Ala Ala Phe Leu Phe Glu Tyr Asp
 1               5                  10                  15

Thr Pro Arg Ile Val Leu Ile Arg Ser Arg Lys Val Gly Leu Met Asn
            20                  25                  30

Arg Ala Val Gln Leu Leu Ile Leu Ala Tyr Val Ile Gly Trp Val Phe
        35                  40                  45

Val Trp Glu Lys Gly Tyr Gln Glu Thr Asp Ser Val Val Ser Ser Val
    50                  55                  60

Thr Thr Lys Val Lys Gly Val Ala Val Thr Asn Thr Ser Lys Leu Gly
65                  70                  75                  80

Phe Arg Ile Trp Asp Val Ala Asp Tyr Val Ile Pro Ala Gln Glu Glu
                85                  90                  95

Asn Ser Leu Phe Val Met Thr Asn Val Ile Leu Thr Met Asn Gln Thr
            100                 105                 110

Gln Gly Leu Cys Pro Glu Ile Pro Asp Ala Thr Thr Val Cys Lys Ser
        115                 120                 125

Asp Ala Ser Cys Thr Ala Gly Ser Ala Gly Thr His Ser Asn Gly Val
    130                 135                 140

Ser Thr Gly Arg Cys Val Ala Phe Asn Gly Ser Val Lys Thr Cys Glu
145                 150                 155                 160

Val Ala Ala Trp Cys Pro Val Glu Asp Asp Thr His Val Pro Gln Pro
                165                 170                 175

Ala Phe Leu Lys Ala Ala Glu Asn Phe Thr Leu Leu Val Lys Asn Asn
            180                 185                 190

Ile Trp Tyr Pro Lys Phe Asn Phe Ser Lys Arg Asn Ile Leu Pro Asn
        195                 200                 205

Ile Thr Thr Thr Tyr Leu Lys Ser Cys Ile Tyr Asp Ala Lys Thr Asp
    210                 215                 220

Pro Phe Cys Pro Ile Phe Arg Leu Gly Lys Ile Val Glu Asn Ala Gly
225                 230                 235                 240

His Ser Phe Gln Asp Met Ala Val Glu Gly Gly Ile Met Gly Ile Gln
                245                 250                 255
```

```
Val Asn Trp Asp Cys Asn Leu Asp Arg Ala Ala Ser Leu Cys Leu Pro
        260                 265                 270

Arg Tyr Ser Phe Arg Arg Leu Asp Thr Arg Asp Val Glu His Asn Val
            275                 280                 285

Ser Pro Gly Tyr Asn Phe Arg Phe Ala Lys Tyr Tyr Arg Asp Leu Ala
        290                 295                 300

Gly Asn Glu Gln Arg Thr Leu Ile Lys Ala Tyr Gly Ile Arg Phe Asp
305                 310                 315                 320

Ile Ile Val Phe Gly Lys Ala Gly Lys Phe Asp Ile Ile Pro Thr Met
                325                 330                 335

Ile Asn Ile Gly Ser Gly Leu Ala Leu Leu Gly Met Ala Thr Val Leu
            340                 345                 350

Cys Asp Ile Ile Val Leu Tyr Cys Met Lys Lys Arg Leu Tyr Tyr Arg
        355                 360                 365

Glu Lys Lys Tyr Lys Tyr Val Glu Asp Tyr Glu Gln Gly Leu Ala Ser
    370                 375                 380

Glu Leu Asp Gln
385

<210> SEQ ID NO 280
<211> LENGTH: 361
<212> TYPE: PRT
<213> ORGANISM: Homo Sapiens

<400> SEQUENCE: 280

Met Ala Gly Cys Cys Ala Ala Leu Ala Ala Phe Leu Phe Glu Tyr Asp
1               5                   10                  15

Thr Pro Arg Ile Val Leu Ile Arg Ser Arg Lys Val Gly Leu Met Asn
            20                  25                  30

Arg Ala Val Gln Leu Leu Ile Leu Ala Tyr Val Ile Gly Trp Val Phe
        35                  40                  45

Val Trp Glu Lys Gly Tyr Gln Glu Thr Asp Ser Val Val Ser Ser Val
    50                  55                  60

Thr Thr Lys Val Lys Gly Val Ala Val Thr Asn Thr Ser Lys Leu Gly
65                  70                  75                  80

Phe Arg Ile Trp Asp Val Ala Asp Tyr Val Ile Pro Ala Gln Glu Glu
                85                  90                  95

Asn Ser Leu Phe Val Met Thr Asn Val Ile Leu Thr Met Asn Gln Thr
            100                 105                 110

Gln Gly Leu Cys Pro Glu Ile Pro Asp Ala Thr Thr Val Cys Lys Ser
        115                 120                 125

Asp Ala Ser Cys Thr Ala Gly Ser Ala Gly Thr His Ser Asn Val Val
    130                 135                 140

Cys Thr Leu Ile Pro Ala Phe Leu Lys Ala Ala Glu Asn Phe Thr Leu
145                 150                 155                 160

Leu Val Lys Asn Asn Ile Trp Tyr Pro Lys Phe Asn Phe Ser Lys Arg
                165                 170                 175

Asn Ile Leu Pro Asn Ile Thr Thr Thr Tyr Leu Lys Ser Cys Ile Tyr
            180                 185                 190

Asp Ala Lys Thr Asp Pro Phe Cys Pro Ile Phe Arg Leu Gly Lys Ile
        195                 200                 205

Val Glu Asn Ala Gly His Ser Phe Gln Asp Met Ala Val Glu Gly Gly
    210                 215                 220

Ile Met Gly Ile Gln Val Asn Trp Asp Cys Asn Leu Asp Arg Ala Ala
```

```
            225                 230                 235                 240
Ser Leu Cys Leu Pro Arg Tyr Ser Phe Arg Arg Leu Asp Thr Arg Asp
                245                 250                 255

Val Glu His Asn Val Ser Pro Gly Tyr Asn Phe Arg Phe Ala Lys Tyr
            260                 265                 270

Tyr Arg Asp Leu Ala Gly Asn Glu Gln Arg Thr Leu Ile Lys Ala Tyr
        275                 280                 285

Gly Ile Arg Phe Asp Ile Ile Val Phe Gly Lys Ala Gly Lys Phe Asp
    290                 295                 300

Ile Ile Pro Thr Met Ile Asn Ile Gly Ser Gly Leu Ala Leu Leu Gly
305                 310                 315                 320

Met Ala Thr Val Leu Cys Asp Ile Ile Val Leu Tyr Cys Met Lys Lys
                325                 330                 335

Arg Leu Tyr Tyr Arg Glu Lys Lys Tyr Lys Tyr Val Glu Asp Tyr Glu
            340                 345                 350

Gln Gly Leu Ala Ser Glu Leu Asp Gln
        355                 360

<210> SEQ ID NO 281
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      P2RX4 protein"

<400> SEQUENCE: 281
aactgctcat cctggcctac                                                  20

<210> SEQ ID NO 282
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      P2RX4 protein"

<400> SEQUENCE: 282
gtcgtaacgg agctgaccac                                                  20

<210> SEQ ID NO 283
<211> LENGTH: 19
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      P2RX4 protein"

<400> SEQUENCE: 283
ggatgtggcg gattatgtg                                                   19

<210> SEQ ID NO 284
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
```

Reverse primer for amplifying the nucleotide sequence encoding
P2RX4 protein"

<400> SEQUENCE: 284
cctgtgtctg gttcatggtg                                      20

<210> SEQ ID NO 285
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      P2RX4 protein"

<400> SEQUENCE: 285
agattccaga tgcgaccact                                      20

<210> SEQ ID NO 286
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      P2RX4 protein"

<400> SEQUENCE: 286
cagacccgtt gaaagctacg                                      20

<210> SEQ ID NO 287
<211> LENGTH: 21
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      P2RX4 protein"

<400> SEQUENCE: 287
tctgtcaaga cgtgtgaggt g                                    21

<210> SEQ ID NO 288
<211> LENGTH: 22
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      P2RX4 protein"

<400> SEQUENCE: 288
ccaaaagagt gaagtttct gc                                    22

<210> SEQ ID NO 289
<211> LENGTH: 23
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      P2RX4 protein"

<400> SEQUENCE: 289

-continued

```
ttttggttaa gaacaacatc tgg                                          23

<210> SEQ ID NO 290
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      P2RX4 protein"

<400> SEQUENCE: 290
atatggggca gaagggatct                                              20

<210> SEQ ID NO 291
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      P2RX4 protein"

<400> SEQUENCE: 291
cgcttcgaca tcattgtgtt                                              20

<210> SEQ ID NO 292
<211> LENGTH: 19
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      P2RX4 protein"

<400> SEQUENCE: 292
tagcagtgcc aggccagag                                               19

<210> SEQ ID NO 293
<211> LENGTH: 24
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      P2RX4 protein"

<400> SEQUENCE: 293
gaaaagactc tactatcggg agaa                                         24

<210> SEQ ID NO 294
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      P2RX4 protein"

<400> SEQUENCE: 294
ctgttctttg atggggctgt                                              20
```

```
<210> SEQ ID NO 295
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding P2RX4 protein"

<400> SEQUENCE: 295
ttgtgtggga aaagggctac                                              20

<210> SEQ ID NO 296
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding P2RX4 protein"

<400> SEQUENCE: 296
ttcgtcatga ccaacgtgat                                              20

<210> SEQ ID NO 297
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding P2RX4 protein"

<400> SEQUENCE: 297
tcagatgcca gctgtactgc                                              20

<210> SEQ ID NO 298
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding P2RX4 protein"

<400> SEQUENCE: 298
gtggaggatg acacacacgt                                              20

<210> SEQ ID NO 299
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding P2RX4 protein"

<400> SEQUENCE: 299
tccttcccaa catcaccact                                              20

<210> SEQ ID NO 300
<211> LENGTH: 20
<212> TYPE: DNA
<213> ORGANISM: Artificial Sequence
```

```
<220> FEATURE:
<221> NAME/KEY: Source
<223> OTHER INFORMATION: /note="Description of Artificial Sequence:
      Probe for detecting a nucleotide molecule having a nucleic acid
      sequence encoding P2RX4 protein"

<400> SEQUENCE: 300
gaaggcaggg aaatttgaca                                                   20

<210> SEQ ID NO 301
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding P2RX4 protein"

<400> SEQUENCE: 301
gggtcttgct agtgagctgg                                                   20

<210> SEQ ID NO 302
<211> LENGTH: 60
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding P2RX4 protein"

<400> SEQUENCE: 302
ctcctcagag aagcgctgtg ctaaggtgat cgaggaccag acattaaagc gtgattttct       60

<210> SEQ ID NO 303
<211> LENGTH: 14
<212> TYPE: PRT
<213> ORGANISM: Artificial Sequence
<220> FEATURE:
<221> NAME/KEY: Source
<223> OTHER INFORMATION: /note="Description of Artificial Sequence:
      Synthetic peptide representing the C Terminus of the sequence
      according to NP_002551.2"

<400> SEQUENCE: 303

Tyr Arg Glu Lys Lys Tyr Lys Tyr Val Glu Asp Tyr Glu Gln
1               5                   10

<210> SEQ ID NO 304
<211> LENGTH: 3502
<212> TYPE: DNA
<213> ORGANISM: Homo Sapiens

<400> SEQUENCE: 304
gcaggcttct tcggtgcccg agagggagcg ggtgcccaag ggggtggtcc ctgtggcagg       60
tcccggggtg ggggcgcggc gctccgggaa gagccttccg caggtccccg ccccgtcacg      120
tgggcgccgg ccccggccgc tgcggtcggt ccgctggttg gtcgggcgct tggtccggca      180
gttggtcggt gggccagtgg cccgtcgctc gcttctgggc tctcatgttt gaaggtggga      240
gggacacggg agcggcccgc acacctgagc cgcccggaga ggagcctcgg ccccgtaccc      300
agtaagaaga ggaggaggcc aggcaggcaa aaggagtcat ggcttctgat gctagtcatg      360
cgctggaagc tgccctggag caaatggacg ggatcattgc aggcactaaa acaggtgcag      420
atcttagtga tggtacttgt gagcctggac tggcttcccc ggcctcctac atgaacccct      480
```

```
tcccggtgct ccatctcatc gaggacttga ggctggcctt ggagatgctg gagcttcctc    540
aggagagagc agccctcctg agccagatcc ctggcccaac agctgcctac ataaaggaat    600
ggtttgaaga gagcttgtcc caggtaaacc accacagtgc tgctagtaat gaaacctacc    660
aggaacgctt ggcacgtcta aaggggata aggagtccct catattgcag gtgagtgtcc     720
tcacagacca agtagaagcc cagggagaaa agattcgaga cctggaagtg tgtctggaag    780
gacaccaggt gaaactcaat gctgctgaag agatgcttca acaggagctg ctaagccgca    840
catctcttga gacccagaag ctcgatctga tgactgaagt gtctgagctg aagctcaagc    900
tggttggcat ggagaaggag cagagagagc aggaggagaa gcagagaaaa gcagaggagt    960
tactgcaaga gctcaggcac ctcaaaatca agtggaaga gttggaaaat gaaaggaatc    1020
agtatgaatg gaagctaaag gccactaagg ctgaagtcgc ccagctgcaa gaacaggtgg    1080
ccctgaaaga tgcagaaatt gagcgtctgc acagccagct ctcccggaca gcagctctcc    1140
acagtgagag tcacacagag agagaccaag aaattcaacg tctgaaaatg gggatggaaa    1200
ctttgctgct tgccaatgaa gataaggacc gtcggataga ggagcttacg gggctgttaa    1260
accagtaccg gaaggtaaag gagattgtga tggtcactca agggccttcg gagagaactc    1320
tctcaatcaa tgaagaagaa ccggagggag gtttcagcaa gtggaacgct acaaataagg    1380
accctgaaga attatttaaa caagagatgc ctccaagatg tagctctcct acagtggggc    1440
cacctccatt gccacagaaa tcactggaaa ccagggctca gaaaaagctc tcttgtagtc    1500
tagaagactt gagaagtgaa tctgtggata agtgtatgga tgggaaccag cccttcccgg    1560
tgttagaacc caaggacagc cctttcttgg cggagcacaa atatcccact ttacctggga    1620
agctttcagg agccacgccc aatggagagg ctgccaaatc tcctcccacc atctgccagc    1680
ctgacgccac ggggagcagc ctgctgaggc tgagagacac agaaagtggc tgggacgaca    1740
ctgctgtggt caatgacctc tcatccacat catcgggcac tgaatcaggt cctcagtctc    1800
ctctgacacc agatggtaaa cggaatccca aaggcattaa gaagttctgg ggaaaaatcc    1860
gaagaactca gtcaggaaat ttctacactg cacgctgggg gatggcagag tttcgacgag    1920
gtgggctccg ggcaaccgca gggccaagac tctctaggac cagggactcc aagggacaga    1980
aaagtgacgc caatgccccc tttgcccagt ggagcacaga gcgtgtgtgt gcatggctgg    2040
aggactttgg cctggctcag tatgtgatct ttgccaggca gtgggtatct tctggccaca    2100
ccttattgac agccaccccT caggacatgg aaaaggagct aggaattaag cacccactcc    2160
acaggaagaa gcttgtttta gcagtgaaag ccatcaacac caaacaggag gagaagtctg    2220
cactgctaga ccacatttgg gtgacaaggt ggcttgatga tattggctta ccccagtaca    2280
aagaccagtt tcatgaatct agagttgaca gacgaatgct gcaataccta actgtgaacg    2340
atttactctt cttaaaagtc accagccaac tacatcatct cagcatcaaa tgtgccattc    2400
acgtgctgca tgtcaacaag ttcaaccccc actgcctgca ccgcggcca gctgatgaga    2460 gtaacctttc tccttcagaa gttgtacagt ggtccaacca cagggtgatg gagtggttac    2520
gatctgtgga cctggcagag tatgcaccca atcttcgagg gagtggagtc catggaggcc    2580
tcattatcct ggagccacgc ttcactgggg acacctggcc tatgcttctc aacatccccc    2640
cacaaaagac gctcctcagg cgccacctga ccaccaagtt caatgccttg attggtccgg    2700
aggctgaaca ggagaagcga gagaaaatgg cctcaccagc ttacacacca ctgaccacca    2760
cagccaaagt ccggccaagg aaactaggat tttcacactt cggaaacata agaaaaaaga    2820
```

```
agttcgatga atcgacggac tacatttgcc caatggagcc cagtgacggt gtcagtgata    2880
gtcacagggt ctacagtggc taccggggcc tcagcccct tgatgcccct gaactggatg    2940
ggctggacca ggtgggacag attagctgat gcccttgtca cctgccctct gtgcaccctg   3000
agagctcaca gtaacactgt gtgtgtcacc atataactgc acctcacccc cgcacgtgtg   3060
catgactcgc agagaatatt ccagcaattg tgtaccctg ggccagtctc tttgaaccct    3120
gagggtggcc aggatctgga gctgcatctc taagggcca ggctttgggg accattgcca   3180
aaggtggact caggaggaaa gacacttaaa gacacttta catgtctagt aattcttgat    3240
gttcatcttc agcaccagtg gaaacacatg aacttcgatg caggtccaga gaccatggac   3300
actcccacga ggctcagctc tcaggcaccc cctacacttc agttgaggga aaagctcaag   3360
tgccttaggc ccgtggacca cagtcttggc tgagatcaaa gggatgagca acagggactt   3420
ctgccacagt gacaatggaa ttgtgttgtg ccttacttca gaggtggtct cttctttctt   3480
gtaataaaag caatatttat gc                                            3502
```

<210> SEQ ID NO 305
<211> LENGTH: 876
<212> TYPE: PRT
<213> ORGANISM: Homo Sapiens

<400> SEQUENCE: 305

Met Ala Ser Asp Ala Ser His Ala Leu Glu Ala Leu Glu Gln Met
1               5                   10                  15

Asp Gly Ile Ile Ala Gly Thr Lys Thr Gly Ala Asp Leu Ser Asp Gly
            20                  25                  30

Thr Cys Glu Pro Gly Leu Ala Ser Pro Ala Ser Tyr Met Asn Pro Phe
        35                  40                  45

Pro Val Leu His Leu Ile Glu Asp Leu Arg Leu Ala Leu Glu Met Leu
    50                  55                  60

Glu Leu Pro Gln Glu Arg Ala Ala Leu Leu Ser Gln Ile Pro Gly Pro
65                  70                  75                  80

Thr Ala Ala Tyr Ile Lys Glu Trp Phe Glu Ser Leu Ser Gln Val
                85                  90                  95

Asn His His Ser Ala Ala Ser Asn Glu Thr Tyr Gln Glu Arg Leu Ala
            100                 105                 110

Arg Leu Glu Gly Asp Lys Glu Ser Leu Ile Leu Gln Val Ser Val Leu
        115                 120                 125

Thr Asp Gln Val Glu Ala Gln Gly Glu Lys Ile Arg Asp Leu Glu Val
    130                 135                 140

Cys Leu Glu Gly His Gln Val Lys Leu Asn Ala Ala Glu Glu Met Leu
145                 150                 155                 160

Gln Gln Glu Leu Leu Ser Arg Thr Ser Leu Glu Thr Gln Lys Leu Asp
                165                 170                 175

Leu Met Thr Glu Val Ser Glu Leu Lys Leu Lys Leu Val Gly Met Glu
            180                 185                 190

Lys Glu Gln Arg Glu Gln Glu Glu Lys Gln Arg Lys Ala Glu Glu Leu
        195                 200                 205

Leu Gln Glu Leu Arg His Leu Lys Ile Lys Val Glu Glu Leu Glu Asn
    210                 215                 220

Glu Arg Asn Gln Tyr Glu Trp Lys Leu Lys Ala Thr Lys Ala Glu Val
225                 230                 235                 240

Ala Gln Leu Gln Glu Gln Val Ala Leu Lys Asp Ala Glu Ile Glu Arg
                245                 250                 255

-continued

```
Leu His Ser Gln Leu Ser Arg Thr Ala Ala Leu His Ser Glu Ser His
            260                 265                 270
Thr Glu Arg Asp Gln Glu Ile Gln Arg Leu Lys Met Gly Met Glu Thr
        275                 280                 285
Leu Leu Leu Ala Asn Glu Asp Lys Asp Arg Arg Ile Glu Glu Leu Thr
290                 295                 300
Gly Leu Leu Asn Gln Tyr Arg Lys Val Lys Glu Ile Val Met Val Thr
305                 310                 315                 320
Gln Gly Pro Ser Glu Arg Thr Leu Ser Ile Asn Glu Glu Pro Glu
                325                 330                 335
Gly Gly Phe Ser Lys Trp Asn Ala Thr Asn Lys Asp Pro Glu Glu Leu
            340                 345                 350
Phe Lys Gln Glu Met Pro Pro Arg Cys Ser Ser Pro Thr Val Gly Pro
        355                 360                 365
Pro Pro Leu Pro Gln Lys Ser Leu Glu Thr Arg Ala Gln Lys Lys Leu
    370                 375                 380
Ser Cys Ser Leu Glu Asp Leu Arg Ser Glu Ser Val Asp Lys Cys Met
385                 390                 395                 400
Asp Gly Asn Gln Pro Phe Pro Val Leu Glu Pro Lys Asp Ser Pro Phe
                405                 410                 415
Leu Ala Glu His Lys Tyr Pro Thr Leu Pro Gly Lys Leu Ser Gly Ala
            420                 425                 430
Thr Pro Asn Gly Glu Ala Ala Lys Ser Pro Pro Thr Ile Cys Gln Pro
        435                 440                 445
Asp Ala Thr Gly Ser Ser Leu Arg Leu Arg Asp Thr Glu Ser Gly
    450                 455                 460
Trp Asp Asp Thr Ala Val Val Asn Asp Leu Ser Ser Thr Ser Ser Gly
465                 470                 475                 480
Thr Glu Ser Gly Pro Gln Ser Pro Leu Thr Pro Asp Gly Lys Arg Asn
                485                 490                 495
Pro Lys Gly Ile Lys Lys Phe Trp Gly Lys Ile Arg Arg Thr Gln Ser
            500                 505                 510
Gly Asn Phe Tyr Thr Asp Thr Leu Gly Met Ala Glu Phe Arg Arg Gly
        515                 520                 525
Gly Leu Arg Ala Thr Ala Gly Pro Arg Leu Ser Arg Thr Arg Asp Ser
    530                 535                 540
Lys Gly Gln Lys Ser Asp Ala Asn Ala Pro Phe Ala Gln Trp Ser Thr
545                 550                 555                 560
Glu Arg Val Cys Ala Trp Leu Glu Asp Phe Gly Leu Ala Gln Tyr Val
                565                 570                 575
Ile Phe Ala Arg Gln Trp Val Ser Ser Gly His Thr Leu Leu Thr Ala
            580                 585                 590
Thr Pro Gln Asp Met Glu Lys Glu Leu Gly Ile Lys His Pro Leu His
        595                 600                 605
Arg Lys Lys Leu Val Leu Ala Val Lys Ala Ile Asn Thr Lys Gln Glu
    610                 615                 620
Glu Lys Ser Ala Leu Leu Asp His Ile Trp Val Thr Arg Trp Leu Asp
625                 630                 635                 640
Asp Ile Gly Leu Pro Gln Tyr Lys Asp Gln Phe His Glu Ser Arg Val
                645                 650                 655
Asp Arg Arg Met Leu Gln Tyr Leu Thr Val Asn Asp Leu Leu Phe Leu
            660                 665                 670
```

-continued

```
Lys Val Thr Ser Gln Leu His His Leu Ser Ile Lys Cys Ala Ile His
            675                 680                 685
Val Leu His Val Asn Lys Phe Asn Pro His Cys Leu His Arg Arg Pro
690                 695                 700
Ala Asp Glu Ser Asn Leu Ser Pro Ser Glu Val Val Gln Trp Ser Asn
705                 710                 715                 720
His Arg Val Met Glu Trp Leu Arg Ser Val Asp Leu Ala Glu Tyr Ala
                725                 730                 735
Pro Asn Leu Arg Gly Ser Gly Val His Gly Gly Leu Ile Ile Leu Glu
                740                 745                 750
Pro Arg Phe Thr Gly Asp Thr Leu Ala Met Leu Leu Asn Ile Pro Pro
                755                 760                 765
Gln Lys Thr Leu Leu Arg Arg His Leu Thr Thr Lys Phe Asn Ala Leu
            770                 775                 780
Ile Gly Pro Glu Ala Glu Gln Glu Lys Arg Glu Lys Met Ala Ser Pro
785                 790                 795                 800
Ala Tyr Thr Pro Leu Thr Thr Thr Ala Lys Val Arg Pro Arg Lys Leu
                805                 810                 815
Gly Phe Ser His Phe Gly Asn Ile Arg Lys Lys Lys Phe Asp Glu Ser
                820                 825                 830
Thr Asp Tyr Ile Cys Pro Met Glu Pro Ser Asp Gly Val Ser Asp Ser
                835                 840                 845
His Arg Val Tyr Ser Gly Tyr Arg Gly Leu Ser Pro Leu Asp Ala Pro
            850                 855                 860
Glu Leu Asp Gly Leu Asp Gln Val Gly Gln Ile Ser
865                 870                 875

<210> SEQ ID NO 306
<211> LENGTH: 19
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      PPFIBP2 protein"

<400> SEQUENCE: 306
gctagtcatg cgctggaag                                                   19

<210> SEQ ID NO 307
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      PPFIBP2 protein"

<400> SEQUENCE: 307
gaagctccag catctccaag                                                  20

<210> SEQ ID NO 308
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      PPFIBP2 protein"
```

<400> SEQUENCE: 308
cccaggtaaa ccaccacagt                                              20

<210> SEQ ID NO 309
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      PPFIBP2 protein"

<400> SEQUENCE: 309
ctggtgtcct tccagacaca                                              20

<210> SEQ ID NO 310
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      PPFIBP2 protein"

<400> SEQUENCE: 310
tgtgtctgga aggacaccag                                              20

<210> SEQ ID NO 311
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      PPFIBP2 protein"

<400> SEQUENCE: 311
tcctcctgct ctctctgctc                                              20

<210> SEQ ID NO 312
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      PPFIBP2 protein"

<400> SEQUENCE: 312
aagagctcag gcacctcaaa                                              20

<210> SEQ ID NO 313
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      PPFIBP2 protein"

<400> SEQUENCE: 313
ctcactgtgg agagctgctg                                              20

<210> SEQ ID NO 314
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
Forward primer for amplifying the nucleotide sequence encoding
PPFIBP2 protein"

<400> SEQUENCE: 314
aaactttgct gcttgccaat                                               20

<210> SEQ ID NO 315
<211> LENGTH: 22
<212> TYPE: DNA
<213> ORGANISM: Artificial Sequence
<220> FEATURE:
<221> NAME/KEY: Source
<223> OTHER INFORMATION: /note="Description of Artificial Sequence:
Reverse primer for amplifying the nucleotide sequence encoding
PPFIBP2 protein"

<400> SEQUENCE: 315
ttgagtgacc atcacaatct cc                                            22

<210> SEQ ID NO 316
<211> LENGTH: 24
<212> TYPE: DNA
<213> ORGANISM: Artificial Sequence
<220> FEATURE:
<221> NAME/KEY: Source
<223> OTHER INFORMATION: /note="Description of Artificial Sequence:
Forward primer for amplifying the nucleotide sequence encoding
PPFIBP2 protein"

<400> SEQUENCE: 316
tctctcaatc aatgaagaag aacc                                          24

<210> SEQ ID NO 317
<211> LENGTH: 21
<212> TYPE: DNA
<213> ORGANISM: Artificial Sequence
<220> FEATURE:
<221> NAME/KEY: Source
<223> OTHER INFORMATION: /note="Description of Artificial Sequence:
Reverse primer for amplifying the nucleotide sequence encoding
PPFIBP2 protein"

<400> SEQUENCE: 317
tccagtgatt tctgtggcaa t                                             21

<210> SEQ ID NO 318
<211> LENGTH: 21
<212> TYPE: DNA
<213> ORGANISM: Artificial Sequence
<220> FEATURE:
<221> NAME/KEY: Source
<223> OTHER INFORMATION: /note="Description of Artificial Sequence:
Forward primer for amplifying the nucleotide sequence encoding
PPFIBP2 protein"

<400> SEQUENCE: 318
gcctccaaga tgtagctctc c                                             21

<210> SEQ ID NO 319
<211> LENGTH: 23

```
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      PPFIBP2 protein"

<400> SEQUENCE: 319
tccacagatt cacttctcaa gtc                                            23

<210> SEQ ID NO 320
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      PPFIBP2 protein"

<400> SEQUENCE: 320
cggagcacaa atatcccact                                                20

<210> SEQ ID NO 321
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      PPFIBP2 protein"

<400> SEQUENCE: 321
ctttgggatt ccgtttacca                                                20

<210> SEQ ID NO 322
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      PPFIBP2 protein"

<400> SEQUENCE: 322
tggtaaacgg aatcccaaag                                                20

<210> SEQ ID NO 323
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      PPFIBP2 protein"

<400> SEQUENCE: 323
ttggagtccc tggtcctaga                                                20

<210> SEQ ID NO 324
<211> LENGTH: 20
<212> TYPE: DNA
<213> ORGANISM: Artificial Sequence
<220> FEATURE:
<221> NAME/KEY: Source
```

```
<223> OTHER INFORMATION: /note="Description of Artificial Sequence:
      Forward primer for amplifying the nucleotide sequence encoding
      PPFIBP2 protein"

<400> SEQUENCE: 324
tctaggacca gggactccaa                                                   20

<210> SEQ ID NO 325
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      PPFIBP2 protein"

<400> SEQUENCE: 325
gggtggctgt caataaggtg                                                   20

<210> SEQ ID NO 326
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding PPFIBP2 protein"

<400> SEQUENCE: 326
caggcactaa aacaggtgca                                                   20

<210> SEQ ID NO 327
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding PPFIBP2 protein"

<400> SEQUENCE: 327 agggataag gagtccctca                                                    20

<210> SEQ ID NO 328
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding PPFIBP2 protein"

<400> SEQUENCE: 328
ttgagaccca gaagctcgat                                                   20

<210> SEQ ID NO 329
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding PPFIBP2 protein"
```

```
<400> SEQUENCE: 329
gaaattgagc gtctgcacag                                                 20

<210> SEQ ID NO 330
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding PPFIBP2 protein"

<400> SEQUENCE: 330
ttacggggct gttaaaccag                                                 20

<210> SEQ ID NO 331
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding PPFIBP2 protein"

<400> SEQUENCE: 331
cagcaagtgg aacgctacaa                                                 20

<210> SEQ ID NO 332
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding PPFIBP2 protein"

<400> SEQUENCE: 332
tgccacagaa atcactggaa                                                 20

<210> SEQ ID NO 333
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding PPFIBP2 protein"

<400> SEQUENCE: 333
acacagaaag tggctgggac                                                 20

<210> SEQ ID NO 334
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding PPFIBP2 protein"

<400> SEQUENCE: 334
ttctacactg acacgctggg                                                 20
```

<210> SEQ ID NO 335
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence: Probe for detecting a nucleotide molecule having a nucleic acid sequence encoding PPFIBP2 protein"

<400> SEQUENCE: 335
ggcctggctc agtatgtgat                                                   20

<210> SEQ ID NO 336
<211> LENGTH: 60
<212> TYPE: DNA
<213> ORGANISM: Artificial Sequence
<220> FEATURE:
<221> NAME/KEY: Source
<223> OTHER INFORMATION: /note="Description of Artificial Sequence: Probe for detecting a nucleotide molecule having a nucleic acid sequence encoding PPFIBP2 protein"

<400> SEQUENCE: 336
agatcaaagg gatgagcaac agggacttct gccacagtga caatggaatt gtgttgtgcc       60

<210> SEQ ID NO 337
<211> LENGTH: 2326
<212> TYPE: DNA
<213> ORGANISM: Homo Sapiens

<400> SEQUENCE: 337
gtgaaaagag gactctcagg ggctcacagg ggctctcact gctggttggc cctgccctcc       60
cttccccctc agcagggtgc ccggaagctg gaaccttgtt atctgggtaa ttagtttcag      120
accctgcact gaggccggcc aggtctcggg gctgcctccc ataggttgtg caccctgacc      180
ccgagaggga ggcgaggcgc tgcttgtcga cagctagagg ctggcctggg gagcaggttt      240
ggggtgccct cccacactgc cctccctgcc ccggcccatg ccccccaggg ctgcctgggc      300
ctggttattg tgtggggcct cctgacccag ccaagggcac gaagctctgg gaaggggatg      360
cccccgaggg tgccagtcca gctagctgcc ccaccccctca ggcccagcct ggcccccaag      420
ctccccactc tggtgccccg agcagccctg tgggcaagca gccgccgcca tggccgagca      480
cctggagctg ctggcagaga tgcccatggt gggcaggatg agcacacagg agcggctgaa      540
gcatgcccag aagcggcgcg cccagcaggt gaagatgtgg gccaggctg agaaggaggc      600 ccagggcaag aagggtcctg gggagcgtcc ccggaaggag gcagccagcc aagggctcct      660
gaagcaggtc ctcttccctc ccagtgttgt ccttctggag gccgctgccc gaaatgacct      720
ggaagaagtc cgccagttcc ttgggagtgg ggtcagccct gacttggcca acgaggacgg      780
cctgacggcc ctgcaccagt gctgcattga tgatttccga gagatggtgc agcagctcct      840
ggaggctggg gccaacatca atgcctgtga cagtgagtgc tggacgcctc tgcatgctgc      900
ggccacctgc ggccacctgc acctggtgga gctgctcatc gccagtggcg ccaatctcct      960
ggcggtcaac accgacggga acatgcccta tgacctgtgt gatgatgagc agacgctgga     1020
ctgcctggag actgccatgg ccgaccgtgg catcacccag acagcatcg aggccgcccg     1080 ggccgtgcca gaactgcgca tgctggacga catccggagc cggctgcagg ccggggcaga     1140
cctccatgcc cccctggacc acgggggccac gctgctgcac gtcgcagccg ccaacggggt     1200
cagcgaggcg gctgccctgc tgctggaaca ccgagccagc ctgagcgcta aggaccaaga     1260

-continued

```
cggctgggag ccgctgcacg ccgcggccta ctggggccag gtgccctgg tggagctgct   1320
cgtggcgcac ggggccgacc tgaacgcaaa gtccctgatg gacgagacgc cccttgatgt   1380
gtgcggggac gaggaggtgc gggccaagct gctggagctg aagcacaagc acgacgccct   1440
cctgcgcgcc cagagccgcc agcgctcctt gctgcgccgc cgcacctcca cgccggcag    1500
ccgcgggaag gtggtgaggc gggtgagcct aacccagcgc accgacctgt accgcaagca   1560
gcacgcccag gaggccatcg tgtggcaaca gccgccgccc accagccgg agccgcccga    1620
ggacaacgat gaccgccaga caggcgcaga gctcaggccg ccgccccgg aggaggacaa    1680
ccccgaagtg gtcaggccgc acaatggccg agtaggggc tccccagtgc ggcatctata    1740
ctccaagcga ctagaccgga gtgtctccta ccagctgagc cccctggaca gcaccacccc   1800
ccacaccctg gtccacgaca aggcccacca ccctggct gacctgaagc gccagcgagc     1860
tgctgccaag ctgcagcgac ccccacctga ggggcccgag agccctgaga cagctgagcc   1920
tggcctgcct ggtgacacgg tgaccccca gcctgactgt ggcttcaggg caggcgggga    1980
cccacccctg ctcaagctca cagccccggc ggtggaggct cccgtggaga ggaggccgtg   2040
ctgcctgctc atgtgaggct gttgctcagc atgcaggggc cctgtcgcgg cacagccca    2100
aggctgcctc cccacggtgc gtgccctggt gctgcgggtg cagcacggaa accccggctt   2160
ctactgtaca ggacactggc ccctctcagg tcagaagaca tgcctggagg gatgtctggc   2220
tgcaaagact atttttatcc tgcaactctt gataaagggc tgttttgcca tggaaaaaaa   2280
aaaaaaaaaa aaaaaaaaaa aaaaaaaaaa aaaaaaaaaa aaaaaa                  2326
```

<210> SEQ ID NO 338
<211> LENGTH: 528
<212> TYPE: PRT
<213> ORGANISM: Homo Sapiens

<400> SEQUENCE: 338

```
Met Ala Glu His Leu Glu Leu Leu Ala Glu Met Pro Met Val Gly Arg
1               5                   10                  15

Met Ser Thr Gln Glu Arg Leu Lys His Ala Gln Lys Arg Arg Ala Gln
            20                  25                  30

Gln Val Lys Met Trp Ala Gln Ala Glu Lys Glu Ala Gln Gly Lys Lys
        35                  40                  45

Gly Pro Gly Glu Arg Pro Arg Lys Glu Ala Ala Ser Gln Gly Leu Leu
    50                  55                  60

Lys Gln Val Leu Phe Pro Pro Ser Val Leu Leu Glu Ala Ala Ala
65                  70                  75                  80

Arg Asn Asp Leu Glu Glu Val Arg Gln Phe Leu Gly Ser Gly Val Ser
                85                  90                  95

Pro Asp Leu Ala Asn Glu Asp Gly Leu Thr Ala Leu His Gln Cys Cys
            100                 105                 110

Ile Asp Asp Phe Arg Glu Met Val Gln Gln Leu Leu Glu Ala Gly Ala
        115                 120                 125

Asn Ile Asn Ala Cys Asp Ser Glu Cys Trp Thr Pro Leu His Ala Ala
    130                 135                 140

Ala Thr Cys Gly His Leu His Leu Val Glu Leu Ile Ala Ser Gly
145                 150                 155                 160

Ala Asn Leu Leu Ala Val Asn Thr Asp Gly Asn Met Pro Tyr Asp Leu
                165                 170                 175

Cys Asp Asp Glu Gln Thr Leu Asp Cys Leu Glu Thr Ala Met Ala Asp
```

```
            180             185             190
Arg Gly Ile Thr Gln Asp Ser Ile Glu Ala Ala Arg Ala Val Pro Glu
            195             200             205

Leu Arg Met Leu Asp Asp Ile Arg Ser Arg Leu Gln Ala Gly Ala Asp
210             215             220

Leu His Ala Pro Leu Asp His Gly Ala Thr Leu Leu His Val Ala Ala
225             230             235             240

Ala Asn Gly Phe Ser Glu Ala Ala Leu Leu Leu Glu His Arg Ala
            245             250             255

Ser Leu Ser Ala Lys Asp Gln Asp Gly Trp Glu Pro Leu His Ala Ala
            260             265             270

Ala Tyr Trp Gly Gln Val Pro Leu Val Glu Leu Leu Val Ala His Gly
            275             280             285

Ala Asp Leu Asn Ala Lys Ser Leu Met Asp Glu Thr Pro Leu Asp Val
            290             295             300

Cys Gly Asp Glu Glu Val Arg Ala Lys Leu Leu Glu Leu Lys His Lys
305             310             315             320

His Asp Ala Leu Leu Arg Ala Gln Ser Arg Gln Arg Ser Leu Leu Arg
            325             330             335

Arg Arg Thr Ser Ser Ala Gly Ser Arg Gly Lys Val Val Arg Arg Val
            340             345             350

Ser Leu Thr Gln Arg Thr Asp Leu Tyr Arg Lys Gln His Ala Gln Glu
            355             360             365

Ala Ile Val Trp Gln Gln Pro Pro Thr Ser Pro Glu Pro Pro Glu
            370             375             380

Asp Asn Asp Asp Arg Gln Thr Gly Ala Glu Leu Arg Pro Pro Pro
385             390             395             400

Glu Glu Asp Asn Pro Glu Val Val Arg Pro His Asn Gly Arg Val Gly
            405             410             415

Gly Ser Pro Val Arg His Leu Tyr Ser Lys Arg Leu Asp Arg Ser Val
            420             425             430

Ser Tyr Gln Leu Ser Pro Leu Asp Ser Thr Thr Pro His Thr Leu Val
            435             440             445

His Asp Lys Ala His His Thr Leu Ala Asp Leu Lys Arg Gln Arg Ala
            450             455             460

Ala Ala Lys Leu Gln Arg Pro Pro Glu Gly Pro Glu Ser Pro Glu
465             470             475             480

Thr Ala Glu Pro Gly Leu Pro Gly Asp Thr Val Thr Pro Gln Pro Asp
            485             490             495

Cys Gly Phe Arg Ala Gly Gly Asp Pro Pro Leu Leu Lys Leu Thr Ala
            500             505             510

Pro Ala Val Glu Ala Pro Val Glu Arg Arg Pro Cys Cys Leu Leu Met
            515             520             525

<210> SEQ ID NO 339
<211> LENGTH: 21
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      PPP1R16A protein"

<400> SEQUENCE: 339
gtgttgtcct tctggaggcc g                                         21
```

```
<210> SEQ ID NO 340
<211> LENGTH: 21
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      PPP1R16A protein"

<400> SEQUENCE: 340
gccgtcaggc cgtcctcgtt g                                         21

<210> SEQ ID NO 341
<211> LENGTH: 19
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      PPP1R16A protein"

<400> SEQUENCE: 341
gctgcccgaa atgacctgg                                            19

<210> SEQ ID NO 342
<211> LENGTH: 19
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      PPP1R16A protein"

<400> SEQUENCE: 342
cggaaatcat caatgcagc                                            19

<210> SEQ ID NO 343
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      PPP1R16A protein"

<400> SEQUENCE: 343
gacgcctctg catgctgcgg                                           20

<210> SEQ ID NO 344
<211> LENGTH: 21
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      PPP1R16A protein"

<400> SEQUENCE: 344
cacaggtcat agggcatgtt c                                         21

<210> SEQ ID NO 345
<211> LENGTH: 20
```

```
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      PPP1R16A protein"

<400> SEQUENCE: 345
gatgagcaga cgctggactg                                               20

<210> SEQ ID NO 346
<211> LENGTH: 18
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      PPP1R16A protein"

<400> SEQUENCE: 346
ctccggatgt cgtccagc                                                 18

<210> SEQ ID NO 347
<211> LENGTH: 18
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      PPP1R16A protein"

<400> SEQUENCE: 347
caggccgggg cagacctc                                                 18

<210> SEQ ID NO 348
<211> LENGTH: 21
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      PPP1R16A protein"

<400> SEQUENCE: 348
ggctcggtgt tccagcagca g                                             21

<210> SEQ ID NO 349
<211> LENGTH: 17
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      PPP1R16A protein"

<400> SEQUENCE: 349
gggagccgct gcacgcc                                                  17

<210> SEQ ID NO 350
<211> LENGTH: 18
<212> TYPE: DNA
<213> ORGANISM: Artificial Sequence
<220> FEATURE:
<221> NAME/KEY: Source
```

```
<223> OTHER INFORMATION: /note="Description of Artificial Sequence:
      Reverse primer for amplifying the nucleotide sequence encoding
      PPP1R16A protein"

<400> SEQUENCE: 350
cccgcacctc ctcgtccc                                                 18

<210> SEQ ID NO 351
<211> LENGTH: 18
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      PPP1R16A protein"

<400> SEQUENCE: 351
ctgcgcgccc agagccgc                                                 18

<210> SEQ ID NO 352
<211> LENGTH: 18
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      PPP1R16A protein"

<400> SEQUENCE: 352
gcgtgctgct tgcggtac                                                 18

<210> SEQ ID NO 353
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      PPP1R16A protein"

<400> SEQUENCE: 353
gccagacagg cgcagagctc                                               20

<210> SEQ ID NO 354
<211> LENGTH: 18
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      PPP1R16A protein"

<400> SEQUENCE: 354
ctactcggcc attgtgcg                                                 18

<210> SEQ ID NO 355
<211> LENGTH: 81
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding PPP1R16A protein"
```

<400> SEQUENCE: 355
tctactgtac aggacactgg cccctctcag gtcagaagac atgcctggag ggatgtctgg    60
ctgcaaagac tatttttatc c    81

<210> SEQ ID NO 356
<211> LENGTH: 37
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding PPP1R16A protein"

<400> SEQUENCE: 356
ctgacggccc tgcaccagtg ctgcattgat gatttcc    37

<210> SEQ ID NO 357
<211> LENGTH: 31
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding PPP1R16A protein"

<400> SEQUENCE: 357
gactgccatg gccgaccgtg gcatcaccca g    31

<210> SEQ ID NO 358
<211> LENGTH: 30
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding PPP1R16A protein"

<400> SEQUENCE: 358
gctcgtggcg cacggggccg acctgaacgc    30

<210> SEQ ID NO 359
<211> LENGTH: 29
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding PPP1R16A protein"

<400> SEQUENCE: 359
gcgccggcag ccgcgggaag gtggtgagg    29

<210> SEQ ID NO 360
<211> LENGTH: 1539
<212> TYPE: DNA
<213> ORGANISM: Homo Sapiens

<400> SEQUENCE: 360
gaattcgggg ggaggggggca gtgtcctccg agccaggaca ggcatgttgt tgggactggc    60
ggccatggag ctgaaggtgt gggtggatgg catccagcgt gtggtctgtg ggtctcaga   120 gcagaccacc tgccaggaag tggtcatcgc actagcccaa gcaataggcc agactggccg   180

```
ctttgtgctt gtgcagcggc ttcgggagaa ggagcggcag ttgctgccac aagagtgtcc      240
agtgggcgcc caggccacct gcggacagtt tgccagcgat gtccagtttg tcctgaggcg      300
cacagggccc agcctagctg ggaggccctc ctcagacagc tgtccacccc cggaacgctg      360
cctaattcgt gccagcctcc ctgtaaagcc acgggctgcg ctgggctgtg agccccgcaa      420
aacactgacc cccgagccag ccccagcct ctcacgccct gggcctgcgg ccctgtgac       480
acccacacca ggctgctgca cagacctgcg gggcctggag ctcagggtgc agaggaatgc      540
tgaggagctg ggccatgagg ccttctggga gcaagagctg cgccgggagc aggcccggga      600
gcgagaggga caggcacgcc tgcaggcact aagtgcggcc actgctgagc atgccgcccg      660
gctgcaggcc ctggacgctc aggcccgtgc cctggaggct gagctgcagc tggcagcgga      720
ggcccctggg ccccctcac ctatggcatc tgccactgag cgcctgcacc aggacctggc      780
tgttcaggag cggcagagtg cggaggtgca gggcagcctg gctctggtga gccgggccct      840
ggaggcagca gagcgagcct tgcaggctca ggctcaggag ctggaggagc tgaaccgaga      900
gctccgtcag tgcaacctgc agcagttcat ccagcagacc ggggctgcgc tgccaccgcc      960
cccacgcct gacaggggcc ctcctggcac tcagggccct ctgcctccag ccagagagga     1020
gtccctcctg ggcgctccct ctgagtccca tgctggtgcc cagcctaggc cccgaggtgg     1080
ccccccatgac gcagaactcc tggaggtagc agcagctcct gccccagagt ggtgtcctct     1140
ggcagcccag ccccaggctc tgtgacagcc tagtgagggc tgcaagacca tcctgcccgg     1200
accacagaag gagagttggc ggtcacagag ggctcctctg ccaggcagtg ggaagccctg     1260
ggtttggcct caggagctgg gggtgcagtg ggggactgcc ctagtccttg ccaggtcgcc     1320
cagcaccctg gagaagcatg gggcgtagcc agctcggaac ttgccaggcc caaaggcca     1380
cgactgcctg ttggggacag gagatgcatg gacagtgtgc tcaagctgtg gcatgtgct    1440
tgcctgcggg agaggtcctt cactgtgtgt acacagcaag agcatgtgtg tgccacttcc     1500
cctaccccaa cgtgaaaacc tcaataaact gcccgaagc                            1539
```

<210> SEQ ID NO 361
<211> LENGTH: 373
<212> TYPE: PRT
<213> ORGANISM: Homo Sapiens

<400> SEQUENCE: 361

Met Leu Leu Gly Leu Ala Ala Met Glu Leu Lys Val Trp Val Asp Gly
1               5                   10                  15

Ile Gln Arg Val Val Cys Gly Val Ser Glu Gln Thr Thr Cys Gln Glu
                20                  25                  30

Val Val Ile Ala Leu Ala Gln Ala Ile Gly Gln Thr Gly Arg Phe Val
            35                  40                  45

Leu Val Gln Arg Leu Arg Glu Lys Glu Arg Gln Leu Leu Pro Gln Glu
        50                  55                  60

Cys Pro Val Gly Ala Gln Ala Thr Cys Gly Gln Phe Ala Ser Asp Val
65                  70                  75                  80

Gln Phe Val Leu Arg Arg Thr Gly Pro Ser Leu Ala Gly Arg Pro Ser
                85                  90                  95

Ser Asp Ser Cys Pro Pro Glu Arg Cys Leu Ile Arg Ala Ser Leu
                100                 105                 110

Pro Val Lys Pro Arg Ala Ala Leu Gly Cys Glu Pro Arg Lys Thr Leu
        115                 120                 125

```
Thr Pro Glu Pro Ala Pro Ser Leu Ser Arg Pro Gly Pro Ala Ala Pro
    130                 135                 140

Val Thr Pro Thr Pro Gly Cys Cys Thr Asp Leu Arg Gly Leu Glu Leu
145                 150                 155                 160

Arg Val Gln Arg Asn Ala Glu Glu Leu Gly His Glu Ala Phe Trp Glu
                165                 170                 175

Gln Glu Leu Arg Arg Glu Gln Ala Arg Glu Arg Glu Gly Gln Ala Arg
            180                 185                 190

Leu Gln Ala Leu Ser Ala Ala Thr Ala Glu His Ala Ala Arg Leu Gln
            195                 200                 205

Ala Leu Asp Ala Gln Ala Arg Ala Leu Glu Ala Glu Leu Gln Leu Ala
        210                 215                 220

Ala Glu Ala Pro Gly Pro Pro Ser Pro Met Ala Ser Ala Thr Glu Arg
225                 230                 235                 240

Leu His Gln Asp Leu Ala Val Gln Glu Arg Gln Ser Ala Glu Val Gln
                245                 250                 255

Gly Ser Leu Ala Leu Val Ser Arg Ala Leu Glu Ala Ala Glu Arg Ala
            260                 265                 270

Leu Gln Ala Gln Ala Gln Glu Leu Glu Glu Leu Asn Arg Glu Leu Arg
            275                 280                 285

Gln Cys Asn Leu Gln Gln Phe Ile Gln Gln Thr Gly Ala Ala Leu Pro
        290                 295                 300

Pro Pro Pro Arg Pro Asp Arg Gly Pro Pro Gly Thr Gln Gly Pro Leu
305                 310                 315                 320

Pro Pro Ala Arg Glu Glu Ser Leu Leu Gly Ala Pro Ser Glu Ser His
                325                 330                 335

Ala Gly Ala Gln Pro Arg Pro Arg Gly Gly Pro His Asp Ala Glu Leu
            340                 345                 350

Leu Glu Val Ala Ala Ala Pro Ala Pro Glu Trp Cys Pro Leu Ala Ala
            355                 360                 365

Gln Pro Gln Ala Leu
    370

<210> SEQ ID NO 362
<211> LENGTH: 19
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      RASSF7 protein"

<400> SEQUENCE: 362
ctgccaggaa gtggtcatc                                               19

<210> SEQ ID NO 363
<211> LENGTH: 17
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      RASSF7 protein"

<400> SEQUENCE: 363
gccgctgcac aagcaca                                                 17
```

<210> SEQ ID NO 364
<211> LENGTH: 16
<212> TYPE: DNA
<213> ORGANISM: Artificial Sequence
<220> FEATURE:
<221> NAME/KEY: Source
<223> OTHER INFORMATION: /note="Description of Artificial Sequence:
    Forward primer for amplifying the nucleotide sequence encoding
    RASSF7 protein"

<400> SEQUENCE: 364
catggagctg aaggtg                                                    16

<210> SEQ ID NO 365
<211> LENGTH: 17
<212> TYPE: DNA
<213> ORGANISM: Artificial Sequence
<220> FEATURE:
<221> NAME/KEY: Source
<223> OTHER INFORMATION: /note="Description of Artificial Sequence:
    Reverse primer for amplifying the nucleotide sequence encoding
    RASSF7 protein"

<400> SEQUENCE: 365
ctcaggacaa actggac                                                   17

<210> SEQ ID NO 366
<211> LENGTH: 16
<212> TYPE: DNA
<213> ORGANISM: Artificial Sequence
<220> FEATURE:
<221> NAME/KEY: Source
<223> OTHER INFORMATION: /note="Description of Artificial Sequence:
    Forward primer for amplifying the nucleotide sequence encoding
    RASSF7 protein"

<400> SEQUENCE: 366
gccactgagc gcctgc                                                    16

<210> SEQ ID NO 367
<211> LENGTH: 17
<212> TYPE: DNA
<213> ORGANISM: Artificial Sequence
<220> FEATURE:
<221> NAME/KEY: Source
<223> OTHER INFORMATION: /note="Description of Artificial Sequence:
    Reverse primer for amplifying the nucleotide sequence encoding
    RASSF7 protein"

<400> SEQUENCE: 367
gtctgctgga tgaactg                                                   17

<210> SEQ ID NO 368
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
    Forward primer for amplifying the nucleotide sequence encoding
    RASSF7 protein"

<400> SEQUENCE: 368
cagcagagcg agccttgcag                                                20

<210> SEQ ID NO 369
<211> LENGTH: 17
<212> TYPE: DNA
<213> ORGANISM: Artificial Sequence

```
<220> FEATURE:
<221> NAME/KEY: Source
<223> OTHER INFORMATION: /note="Description of Artificial Sequence:
      Reverse primer for amplifying the nucleotide sequence encoding
      RASSF7 protein"

<400> SEQUENCE: 369
ctgagtgcca ggagggc                                                    17

<210> SEQ ID NO 370
<211> LENGTH: 18
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      RASSF7 protein"

<400> SEQUENCE: 370
cacggcctga cagggggcc                                                  18

<210> SEQ ID NO 371
<211> LENGTH: 15
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      RASSF7 protein"

<400> SEQUENCE: 371
gcctaggctg ggcac                                                      15

<210> SEQ ID NO 372
<211> LENGTH: 18
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      RASSF7 protein"

<400> SEQUENCE: 372
ctctgagtcc catgctgg                                                   18

<210> SEQ ID NO 373
<211> LENGTH: 16
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      RASSF7 protein"

<400> SEQUENCE: 373
gacaccactc tggggc                                                     16

<210> SEQ ID NO 374
<211> LENGTH: 16
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
```

RASSF7 protein"

<400> SEQUENCE: 374
tgcccagcct aggccc                                             16

<210> SEQ ID NO 375
<211> LENGTH: 17
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      RASSF7 protein"

<400> SEQUENCE: 375
gccagaggac accactc                                            17

<210> SEQ ID NO 376
<211> LENGTH: 50
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding RASSF7 protein"

<400> SEQUENCE: 376
gagaggtcct tcactgtgtg tacacagcaa gagcatgtgt gtgccacttc         50

<210> SEQ ID NO 377
<211> LENGTH: 51
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding RASSF7 protein"

<400> SEQUENCE: 377
agtgtcctcc gagccaggac aggcatgttg ttgggactgg cggccatgga g       51

<210> SEQ ID NO 378
<211> LENGTH: 55
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding RASSF7 protein"

<400> SEQUENCE: 378
gagccgggcc ctggaggcag cagagcgagc cttgcaggct caggctcagg agctg   55

<210> SEQ ID NO 379
<211> LENGTH: 57
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding RASSF7 protein"

<400> SEQUENCE: 379

```
cggcctgaca ggggcccctcc tggcactcag ggccctctgc ctccagccag agaggag      57
```

<210> SEQ ID NO 380
<211> LENGTH: 60
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding RASSF7 protein"

<400> SEQUENCE: 380

```
gaggagctgg gccatgaggc cttctgggag caagagctgc gccgggagca ggcccgggag    60
```

<210> SEQ ID NO 381
<211> LENGTH: 14
<212> TYPE: PRT
<213> ORGANISM: Artificial Sequence
<220> FEATURE:
<221> NAME/KEY: Source
<223> OTHER INFORMATION: /note="Description of Artificial Sequence:
      Epitope of RASSF7"

<400> SEQUENCE: 381

Cys Thr Asp Leu Arg Gly Leu Glu Leu Arg Val Gln Arg Asn
1               5                   10

<210> SEQ ID NO 382
<211> LENGTH: 1237
<212> TYPE: DNA
<213> ORGANISM: Homo Sapiens

<400> SEQUENCE: 382

```
cgattcaggg gagggagcaa ctggagcctc aggccctcca gagtagtctg cctgaccacc    60
ctggagccca cagaagccca ggacgtctcc cgcgaagcct ccccgtgtgt ggctgaggat   120
ggctgagcag cagggccggg agcttgaggc tgagtgcccc gtctgctgga acccttcaa   180
caacacgttc catacccca aaatgctgga ttgctgccac tccttctgcg tggaatgtct   240
ggcccacctc agccttgtga ctccagcccg gcgccgcctg ctgtgcccac tctgtcgcca   300
gcccacagtg ctggcctcag gcagcctgt cactgacttg cccacggaca ctgccatgct   360
cgccctgctc cgcctggagc cccaccatgt catcctggaa ggccatcagc tgtgcctcaa   420
ggaccagccc aagagccgct acttcctgcg ccagcctcaa gtctacacgc tggaccttgg   480
ccccagcct gggggccaga ctgggccgcc ccagacacg gcctctgcca ccgtgtctac   540
gcccatcctc atccccagcc accactcttt gagggagtgt ttccgcaacc ctcagttccg   600
catctttgcc tacctgatgg ccgtcatcct cagtgtcact ctgttgctca tattctccat   660
cttttggacc aagcagttcc tttggggtgt ggggtgagtg ctgttcccag acaagaaacc   720
aaaccttttt cggttgctgc tgggtatggt gactacggag cctcatttgg tattgtcttc   780
cttttgtagtg ttgtttatt tacaatccag ggattgttca ggccatgtgt ttgcttctgg   840
gaacaatttt aaaaaaaaac aaaaaaacga aaagcttgaa ggactgggag atgtggagcg   900
acctccgggt gtgagtgtgg cgtcatgaa gggcagagaa gcggttctga ccacagagct   960
ccacagcaag ttgtgccaaa gggctgcaca gtggtatcca ggaacctgac tagcccaaat  1020
agcaagttgc atttctcact ggagctgctt caaaatcagt gcattttt ttgagttgct  1080
ctttactat gggttgctaa aaaaaaaaaa aaaattggga agtgagcttc aattctgtgg  1140
gtaaatgtgt gtttgtttct ctttgaatgt cttgccactg gttgcagtaa aagtgttctg  1200
```
tattcattaa aaaaaaaaaa aaaaaaaaaa aaaaaaa         1237

<210> SEQ ID NO 383
<211> LENGTH: 192
<212> TYPE: PRT
<213> ORGANISM: Homo Sapiens

<400> SEQUENCE: 383

Met Ala Glu Gln Gln Gly Arg Glu Leu Glu Ala Glu Cys Pro Val Cys
1               5                   10                  15

Trp Asn Pro Phe Asn Asn Thr Phe His Thr Pro Lys Met Leu Asp Cys
            20                  25                  30

Cys His Ser Phe Cys Val Glu Cys Leu Ala His Leu Ser Leu Val Thr
        35                  40                  45

Pro Ala Arg Arg Arg Leu Leu Cys Pro Leu Cys Arg Gln Pro Thr Val
    50                  55                  60

Leu Ala Ser Gly Gln Pro Val Thr Asp Leu Pro Thr Asp Thr Ala Met
65                  70                  75                  80

Leu Ala Leu Leu Arg Leu Glu Pro His His Val Ile Leu Glu Gly His
                85                  90                  95

Gln Leu Cys Leu Lys Asp Gln Pro Lys Ser Arg Tyr Phe Leu Arg Gln
            100                 105                 110

Pro Gln Val Tyr Thr Leu Asp Leu Gly Pro Gln Pro Gly Gly Gln Thr
        115                 120                 125

Gly Pro Pro Pro Asp Thr Ala Ser Ala Thr Val Ser Thr Pro Ile Leu
    130                 135                 140

Ile Pro Ser His His Ser Leu Arg Glu Cys Phe Arg Asn Pro Gln Phe
145                 150                 155                 160

Arg Ile Phe Ala Tyr Leu Met Ala Val Ile Leu Ser Val Thr Leu Leu
                165                 170                 175

Leu Ile Phe Ser Ile Phe Trp Thr Lys Gln Phe Leu Trp Gly Val Gly
            180                 185                 190

<210> SEQ ID NO 384
<211> LENGTH: 17
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      RNF183 protein"

<400> SEQUENCE: 384
gagaagctgg gctggag         17

<210> SEQ ID NO 385
<211> LENGTH: 16
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      RNF183 protein"

<400> SEQUENCE: 385
cagccacaca cggga         16

<210> SEQ ID NO 386

```
<211> LENGTH: 22
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      RNF183 protein"

<400> SEQUENCE: 386
cagctgtgtg ctaagaacaa ag                                            22

<210> SEQ ID NO 387
<211> LENGTH: 19
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      RNF183 protein"

<400> SEQUENCE: 387
gccctgctgc tcagccatc                                                19

<210> SEQ ID NO 388
<211> LENGTH: 18
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      RNF183 protein"

<400> SEQUENCE: 388
gcagaaggca gcgaggac                                                 18

<210> SEQ ID NO 389
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      RNF183 protein"

<400> SEQUENCE: 389
ggcagcaatc cagcattttg                                               20

<210> SEQ ID NO 390
<211> LENGTH: 19
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      RNF183 protein"

<400> SEQUENCE: 390
ctgcgtggaa tgtctggcc                                                19

<210> SEQ ID NO 391
<211> LENGTH: 19
<212> TYPE: DNA
<213> ORGANISM: Artificial Sequence
<220> FEATURE:
```

```
<221> NAME/KEY: Source
<223> OTHER INFORMATION: /note="Description of Artificial Sequence:
      Reverse primer for amplifying the nucleotide sequence encoding
      RNF183 protein"

<400> SEQUENCE: 391
caagtcagtg acaggctgc                                                    19

<210> SEQ ID NO 392
<211> LENGTH: 19
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      RNF183 protein"

<400> SEQUENCE: 392
gtctacacgc tggaccttg                                                    19

<210> SEQ ID NO 393
<211> LENGTH: 19
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      RNF183 protein"

<400> SEQUENCE: 393
gatgcggaac tgagggttg                                                    19

<210> SEQ ID NO 394
<211> LENGTH: 19
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      RNF183 protein"

<400> SEQUENCE: 394
ctacctgatg gccgtcatc                                                    19

<210> SEQ ID NO 395
<211> LENGTH: 19
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      RNF183 protein"

<400> SEQUENCE: 395
ccagcagcaa ccgaaaaag                                                    19

<210> SEQ ID NO 396
<211> LENGTH: 18
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      RNF183 protein"
```

```
<400> SEQUENCE: 396
catgcgtgca gggctgca                                                18

<210> SEQ ID NO 397
<211> LENGTH: 17
<212> TYPE: DNA
<213> ORGANISM: Artificial Sequence
<220> FEATURE:
<221> NAME/KEY: Source
<223> OTHER INFORMATION: Reverse primer for amplifying the nucleotide
      sequence encoding RNF183 protein

<400> SEQUENCE: 397
gtgctgctct cccaggg                                                 17

<210> SEQ ID NO 398
<211> LENGTH: 19
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      RNF183 protein"

<400> SEQUENCE: 398
ccgtggaatc gattcccag                                               19

<210> SEQ ID NO 399
<211> LENGTH: 23
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      RNF183 protein"

<400> SEQUENCE: 399
ctgtttctca tatgggtcat tcg                                          23

<210> SEQ ID NO 400
<211> LENGTH: 41
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding RNF183 protein"

<400> SEQUENCE: 400
atggctgagc agcagggccg ggagcttgag gctgagtgcc c                      41

<210> SEQ ID NO 401
<211> LENGTH: 32
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding RNF183 protein"

<400> SEQUENCE: 401
gcccacggac actgccatgc tcgccctgct cc                                32
```

<210> SEQ ID NO 402
<211> LENGTH: 37
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding RNF183 protein"

<400> SEQUENCE: 402
ggaccagccc aagagccgct acttcctgcg ccagcct                           37

<210> SEQ ID NO 403
<211> LENGTH: 32
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding RNF183 protein"

<400> SEQUENCE: 403
cgctggacct tggcccccag cctgggggcc ag                                32

<210> SEQ ID NO 404
<211> LENGTH: 28
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding RNF183 protein"

<400> SEQUENCE: 404
gttcctttgg ggtgtggggt gagtgctg                                     28

<210> SEQ ID NO 405
<211> LENGTH: 60
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding RNF183 protein"

<400> SEQUENCE: 405
cagtggtatc caggaacctg actagcccaa atagcaagtt gcatttctca ctggagctgc  60

<210> SEQ ID NO 406
<211> LENGTH: 1413
<212> TYPE: DNA
<213> ORGANISM: Homo Sapiens

<400> SEQUENCE: 406
gcttccggcg gaagcggcct caacaaggga aactttattg ttcccgtggg gcagtcgagg  60
atgtcggtga attacgcggc ggggctgtcg ccgtacgcgg acaagggcaa gtgcggcctc 120
ccggagatct tcgacccccc ggaggagctg gagcggaagg tgtgggaact ggcgaggctg 180
gtctggcagt cttccagtgt ggtgttccac acgggtgccg gcatcagcac tgcctctggc 240
atccccgact tcaggacaa actggcagag ctccacggga acatgtttgt ggaagaatgt 300
gccaagtgta agacgcagta cgtccgagac acagtcgtgg gcaccatggg cctgaaggcc 360

```
acgggccggc tctgcaccgt ggctaaggca aggggggctgc gagcctgcag gggagagctg     420
agggacacca tcctagactg ggaggactcc ctgcccgacc gggacctggc actcgccgat     480
gaggccagca gatccggccc agcgggaacc tgccgctggc taccaagcgc cggggaggcc     540
gcctggtcat cgtcaacctg cagcccacca agcacgaccg ccatgctgac ctccgcatcc     600
atggctacgt tgacgaggtc atgacccggc tcatgaagca cctggggctg agatccccg      660
cctgggacgg ccccgtgtg ctggagaggg cgctgccacc cctgccccgc cgcccacccc     720
ccaagctgga gcccaaggag gaatctccca cccggatcaa cggctctatc ccgccggcc     780
ccaagcagga gccctgcgcc cagcacaacg gctcagagcc cgccagcccc aaacgggagc     840
ggcccaccag ccctgccccc cacagacccc ccaaaagggt gaaggccaag gcggtcccca     900
gctgaccagg gtgcttgggg agggtggggc ttttttgtaga aactgtggat tcttttttctc    960
tcgtggtctc actttgttac ttgtttctgt ccccgggagc tcagggctc tgagagctgt     1020
gctccaggcc aggggttaca cctgccctcc gtggtccctc cctgggctcc aggggcctct     1080
ggtgcggttc cgggaagaag ccacaccccca gaggtgacag gtgagcccct gccacacccc   1140
agcctctgac ttgctgtgtt gtccagaggt gaggctgggc cctccctggt ctccagctta    1200
aacaggagtg aactccctct gtccccaggg cctcccttct gggcccccta cagcccaccc    1260
tacccctcct ccatgggccc tgcaggaggg gagacccacc ttgaagtggg ggatcagtag    1320
aggcttgcac tgcctttggg gctggaggga gacgtgggtc caccaggctt ctggaaaagt   1380
cctcaatgca ataaaaacaa tttctttctt gca                                 1413
```

<210> SEQ ID NO 407
<211> LENGTH: 187
<212> TYPE: PRT
<213> ORGANISM: Homo Sapiens

<400> SEQUENCE: 407

Met Ser Val Asn Tyr Ala Ala Gly Leu Ser Pro Tyr Ala Asp Lys Gly
1               5                   10                  15

Lys Cys Gly Leu Pro Glu Ile Phe Asp Pro Pro Glu Glu Leu Glu Arg
            20                  25                  30

Lys Val Trp Glu Leu Ala Arg Leu Val Trp Gln Ser Ser Val Val
        35                  40                  45

Phe His Thr Gly Ala Gly Ile Ser Thr Ala Ser Gly Ile Pro Asp Phe
    50                  55                  60

Arg Asp Lys Leu Ala Glu Leu His Gly Asn Met Phe Val Glu Glu Cys
65                  70                  75                  80

Ala Lys Cys Lys Thr Gln Tyr Val Arg Asp Thr Val Val Gly Thr Met
                85                  90                  95

Gly Leu Lys Ala Thr Gly Arg Leu Cys Thr Val Ala Lys Ala Arg Gly
            100                 105                 110

Leu Arg Ala Cys Arg Gly Glu Leu Arg Asp Thr Ile Leu Asp Trp Glu
        115                 120                 125

Asp Ser Leu Pro Asp Arg Asp Leu Ala Leu Ala Asp Glu Ala Ser Arg
    130                 135                 140

Ser Gly Pro Ala Gly Thr Cys Arg Trp Leu Pro Ser Ala Gly Glu Ala
145                 150                 155                 160

Ala Trp Ser Ser Ser Thr Cys Ser Pro Pro Ser Thr Thr Ala Met Leu
                165                 170                 175

Thr Ser Ala Ser Met Ala Thr Leu Thr Arg Ser
            180                 185

<210> SEQ ID NO 408
<211> LENGTH: 20
<212> TYPE: DNA
<213> ORGANISM: Artificial Sequence
<220> FEATURE:
<221> NAME/KEY: Source
<223> OTHER INFORMATION: Forward primer for amplifying the nucleotide sequence encoding SIRT6 protein

<400> SEQUENCE: 408
ttgtggaaga atgtgccaag                                              20

<210> SEQ ID NO 409
<211> LENGTH: 19
<212> TYPE: DNA
<213> ORGANISM: Artificial Sequence
<220> FEATURE:
<221> NAME/KEY: Source
<223> OTHER INFORMATION: /note="Description of Artificial Sequence: Reverse primer for amplifying the nucleotide sequence encoding SIRT6 protein"

<400> SEQUENCE: 409
ccttagccac ggtgcagag                                               19

<210> SEQ ID NO 410
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence: Forward primer for amplifying the nucleotide sequence encoding SIRT6 protein"

<400> SEQUENCE: 410
tcttccagtg tggtgttcca                                              20

<210> SEQ ID NO 411
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence: Reverse primer for amplifying the nucleotide sequence encoding SIRT6 protein"

<400> SEQUENCE: 411
ttggcacatt cttccacaaa                                              20

<210> SEQ ID NO 412
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence: Forward primer for amplifying the nucleotide sequence encoding SIRT6 protein"

<400> SEQUENCE: 412
agctgaggga caccatccta                                              20

<210> SEQ ID NO 413
<211> LENGTH: 19

```
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      SIRT6 protein"

<400> SEQUENCE: 413
gcaggttgac gatgaccag                                                    19

<210> SEQ ID NO 414
<211> LENGTH: 18
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      SIRT6 protein"

<400> SEQUENCE: 414
gcttcctggt cagccaga                                                     18

<210> SEQ ID NO 415
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      SIRT6 protein"

<400> SEQUENCE: 415
atgtacccag cgtgatggac                                                   20

<210> SEQ ID NO 416
<211> LENGTH: 18
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      SIRT6 protein"

<400> SEQUENCE: 416
gcttcctggt cagccaga                                                     18

<210> SEQ ID NO 417
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      SIRT6 protein"

<400> SEQUENCE: 417
ctaggatggt gtccctcagc                                                   20

<210> SEQ ID NO 418
<211> LENGTH: 20
<212> TYPE: DNA
<213> ORGANISM: Artificial Sequence
<220> FEATURE:
<221> NAME/KEY: Source
```

```
<223> OTHER INFORMATION: /note="Description of Artificial Sequence:
      Forward primer for amplifying the nucleotide sequence encoding
      SIRT6 protein"

<400> SEQUENCE: 418
gagagctgag ggacaccatc                                              20

<210> SEQ ID NO 419
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      SIRT6 protein"

<400> SEQUENCE: 419
gtacccagcg tgatggacag                                              20

<210> SEQ ID NO 420
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      SIRT6 protein"

<400> SEQUENCE: 420
aggatgtcgg tgaattacgc                                              20

<210> SEQ ID NO 421
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      SIRT6 protein"

<400> SEQUENCE: 421
aaaggtggtg tcgaacttgg                                              20

<210> SEQ ID NO 422
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding SIRT6 protein"

<400> SEQUENCE: 422
tgtaagacgc agtacgtccg                                              20

<210> SEQ ID NO 423
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding SIRT6 protein"
```

```
<400> SEQUENCE: 423
gacttcaggg acaaactggc                                              20

<210> SEQ ID NO 424
<211> LENGTH: 18
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding SIRT6 protein"

<400> SEQUENCE: 424
actgggagga ctccctgc                                                18

<210> SEQ ID NO 425
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding SIRT6 protein"

<400> SEQUENCE: 425
tgtaagacgc agtacgtccg                                              20

<210> SEQ ID NO 426
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding SIRT6 protein"

<400> SEQUENCE: 426
tgtaagacgc agtacgtccg                                              20

<210> SEQ ID NO 427
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding SIRT6 protein"

<400> SEQUENCE: 427
tagactggga ggactccctg                                              20

<210> SEQ ID NO 428
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding SIRT6 protein"

<400> SEQUENCE: 428
gagtctggac catggaggag                                              20
```

<210> SEQ ID NO 429
<211> LENGTH: 50
<212> TYPE: DNA
<213> ORGANISM: Artificial Sequence
<220> FEATURE:
<221> NAME/KEY: Source
<223> OTHER INFORMATION: /note="Description of Artificial Sequence:
    Probe for detecting a nucleotide molecule having a nucleic acid
    sequence encoding SIRT6 protein"

<400> SEQUENCE: 429

| | | |
|---|---|---|
| gaagtgggggg atcagtagag gcttgcactg cctttggggc tggagggaga | | 50 |

<210> SEQ ID NO 430
<211> LENGTH: 2859
<212> TYPE: DNA
<213> ORGANISM: Homo Sapiens

<400> SEQUENCE: 430

| | | |
|---|---|---|
| atgaacctgt gtggcctcat gcccatcttc cccgctcccc tcgaccaggt ggctgacatg | | 60 |
| gaggagctga ccatctggga acagcacacg gccacactgt ccaaggaccc ccgccggggc | | 120 |
| tttggcattg cgatctctgg aggccgagac cggcccggtg gatccatggt tgtatctgac | | 180 |
| gtggtacctg gagggccggc ggagggcagg ctacagacag gcgaccacat cgtcatggtg | | 240 |
| aacggggttt ccatggagaa tgccacctcc gcgtttgcca ttcagatact caagacctgc | | 300 |
| accaagatgg ccaacatcac agtgaaacgt ccccggagga tccacctgcc cgccaccaaa | | 360 |
| gccagcccct ccagcccagg cgccaggac tcggatgaag acgatgggcc ccagcgggtg | | 420 |
| gaggaggtgg accagggccg gggctatgac ggcgactcat ccagtggctc cggccgctcc | | 480 |
| tgggacgagc gctcccgccg gccgaggcct ggtcgccggg gccgggccgg cagccatggg | | 540 |
| cgtaggagcc caggtggtgg ctctgaggcc aacgggctgg ccctggtgtc cggctttaag | | 600 |
| cggctgccac ggcaggacgt gcagatgaag cctgtgaagt cagtgctggt gaagaggaga | | 660 |
| gacagcgaag agtttggcgt caagctgggc agtcagatct tcatcaagca cattacagat | | 720 |
| tcgggcctgg ctgccggca ccgtgggctg caggaaggag atctcattct acagatcaac | | 780 |
| ggggtgtcta gccagaacct gtcactgaac gacacccggc gactgattga agtcagaa | | 840 |
| gggaagctaa gcctgctggt gctgagagat cgtgggcagt tcctggtgaa cattccgcct | | 900 |
| gctgtcagtg acagcgacag ctcgccattg aggaaggcg tgaccatggc tgatgagatg | | 960 |
| tcctctcccc ctgcagacat ctcggacctc gcctcggagc tatcgcaggc accaccatcc | | 1020 |
| cacatcccac caccacccg gcatgctcag cggagcccg aggccagcca gaccgactct | | 1080 |
| cccgtggaga gtccccggct tcggcgggaa agttcagtag attccagaac catctcggaa | | 1140 |
| ccagatgagc aacggtcaga gttgcccagg gaaagcagct atgacatcta cagagtgccc | | 1200 |
| agcagtcaga gcatggagga tcgtgggtac agccccgaca cgcgtgtggt ccgcttcctc | | 1260 |
| aagggcaaga gcatcgggct gcggctggca ggggcaatg acgtgggcat cttcgtgtcc | | 1320 |
| ggggtgcagg cgggcagccc ggccgacggg cagggcatcc aggagggaga tcagattctg | | 1380 |
| caggtgaatg acgtgccatt ccagaacctg acacgggagg aggcagtgca gttcctgctg | | 1440 |
| gggctgccac caggcgagga gatggagctg gtgacgcaga ggaagcagga catttttctgg | | 1500 |
| aaaatggtgc agtcccgcgt gggtgactcc ttctacatcc gcactcactt tgagctggag | | 1560 |
| cccagtccac cgtctggcct gggcttcacc cgtggcgacg tcttccacgt gctggacacg | | 1620 |
| ctgcaccccg gccccgggca gagccacgca cgaggaggcc actggctggc ggtgcgcatg | | 1680 |

-continued

```
ggtcgtgacc tgcgggagca agagcgggc atcattccca accagagcag ggcggagcag    1740
ctggccagcc tggaagctgc ccagagggcc gtgggagtcg ggcccggctc ctccgcgggc    1800
tccaatgctc gggccgagtt ctggcggctg cggggtcttc gtcgaggagc aagaagacc    1860 actcagcgga gccgtgagga cctctcagct ctgacccgac agggccgcta cccgccctac    1920
gaacgagtgg tgttgcgaga agccagtttc aagcgcccgg tagtgatcct gggacccgtg    1980
gccgacattg ctatgcagaa gttgactgct gagatgcctg accagtttga aatcgcagag    2040
actgtgtcca ggaccgacag cccctccaag atcatcaaac tagacaccgt gcgggtgatt    2100
gcagaaaaag acaagcatgc gctcctggat gtgacccct ccgccatcga gcgcctcaac    2160
tatgtgcagt actacccat tgtggtcttc ttcatcccg agagccggcc ggccctcaag    2220
gcactgcgcc agtggctggc gcctgcctcc cgccgcagca cccgtcgcct ctacgcacaa    2280
gcccagaagc tgcgaaaaca cagcagccac ctcttcacag ccaccatccc tctgaatggc    2340
acgagtgaca cctggtacca ggagctcaag gccatcattc gagagcagca gacgcggccc    2400
atctggacgg cggaagatca gctggatggc tccttggagg acaacctaga cctccctcac    2460
cacggcctgg ccgacagctc cgctgacctc agctgcgaca gccgcgttaa cagcgactac    2520
gagacggacg gcgagggcgg cgcgtacacg gatggcgagg gctacacaga cggcgagggg    2580
gggccctaca cggatgtgga tgatgagccc ccggctccag ccctggcccg gtcctcggag    2640
cccgtgcagg cagatgagtc ccagagcccg agggatcgtg ggagaatctc ggctcatcag    2700
ggggcccagg tggacagccg ccaccccag ggacagtggc gacaggacag catgcgaacc    2760
tatgaacggg aagccctgaa gaaaaagttt atgcgagtac atgatgcgga gtcctccgat    2820
gaagacggct atgactgggg tccggccact gacctgtga                         2859
```

<210> SEQ ID NO 431  
<211> LENGTH: 952  
<212> TYPE: PRT  
<213> ORGANISM: Homo Sapiens

<400> SEQUENCE: 431

```
Met Asn Leu Cys Gly Leu Met Pro Ile Phe Pro Ala Pro Leu Asp Gln
1               5                   10                  15

Val Ala Asp Met Glu Glu Leu Thr Ile Trp Glu Gln His Thr Ala Thr
            20                  25                  30

Leu Ser Lys Asp Pro Arg Arg Gly Phe Gly Ile Ala Ile Ser Gly Gly
        35                  40                  45

Arg Asp Arg Pro Gly Gly Ser Met Val Val Ser Asp Val Val Pro Gly
    50                  55                  60

Gly Pro Ala Glu Gly Arg Leu Gln Thr Gly Asp His Ile Val Met Val
65                  70                  75                  80

Asn Gly Val Ser Met Glu Asn Ala Thr Ser Ala Phe Ala Ile Gln Ile
                85                  90                  95

Leu Lys Thr Cys Thr Lys Met Ala Asn Ile Thr Val Lys Arg Pro Arg
            100                 105                 110

Arg Ile His Leu Pro Ala Thr Lys Ala Ser Pro Ser Pro Gly Arg
        115                 120                 125

Gln Asp Ser Asp Glu Asp Gly Pro Gln Arg Val Glu Glu Val Asp
    130                 135                 140

Gln Gly Arg Gly Tyr Asp Gly Asp Ser Ser Gly Ser Gly Arg Ser
145                 150                 155                 160

Trp Asp Glu Arg Ser Arg Arg Pro Arg Pro Gly Arg Arg Gly Arg Ala
```

```
                165                 170                 175
Gly Ser His Gly Arg Ser Pro Gly Gly Ser Glu Ala Asn Gly
            180                 185                 190
Leu Ala Leu Val Ser Gly Phe Lys Arg Leu Pro Arg Gln Asp Val Gln
            195                 200                 205
Met Lys Pro Val Lys Ser Val Leu Val Lys Arg Arg Asp Ser Glu Glu
    210                 215                 220
Phe Gly Val Lys Leu Gly Ser Gln Ile Phe Ile Lys His Ile Thr Asp
225                 230                 235                 240
Ser Gly Leu Ala Ala Arg His Arg Gly Leu Gln Glu Gly Asp Leu Ile
                245                 250                 255
Leu Gln Ile Asn Gly Val Ser Ser Gln Asn Leu Ser Leu Asn Asp Thr
            260                 265                 270
Arg Arg Leu Ile Glu Lys Ser Glu Gly Lys Leu Ser Leu Leu Val Leu
        275                 280                 285
Arg Asp Arg Gly Gln Phe Leu Val Asn Ile Pro Pro Ala Val Ser Asp
    290                 295                 300
Ser Asp Ser Ser Pro Leu Glu Glu Gly Val Thr Met Ala Asp Glu Met
305                 310                 315                 320
Ser Ser Pro Pro Ala Asp Ile Ser Asp Leu Ala Ser Glu Leu Ser Gln
                325                 330                 335
Ala Pro Pro Ser His Ile Pro Pro Pro Arg His Ala Gln Arg Ser
            340                 345                 350
Pro Glu Ala Ser Gln Thr Asp Ser Pro Val Glu Ser Pro Arg Leu Arg
        355                 360                 365
Arg Glu Ser Ser Val Asp Ser Arg Thr Ile Ser Glu Pro Asp Glu Gln
    370                 375                 380
Arg Ser Glu Leu Pro Arg Glu Ser Ser Tyr Asp Ile Tyr Arg Val Pro
385                 390                 395                 400
Ser Ser Gln Ser Met Glu Asp Arg Gly Tyr Ser Pro Asp Thr Arg Val
                405                 410                 415
Val Arg Phe Leu Lys Gly Lys Ser Ile Gly Leu Arg Leu Ala Gly Gly
            420                 425                 430
Asn Asp Val Gly Ile Phe Val Ser Gly Val Gln Ala Gly Ser Pro Ala
        435                 440                 445
Asp Gly Gln Gly Ile Gln Glu Gly Asp Gln Ile Leu Gln Val Asn Asp
    450                 455                 460
Val Pro Phe Gln Asn Leu Thr Arg Glu Glu Ala Val Gln Phe Leu Leu
465                 470                 475                 480
Gly Leu Pro Pro Gly Glu Glu Met Glu Leu Val Thr Gln Arg Lys Gln
                485                 490                 495
Asp Ile Phe Trp Lys Met Val Gln Ser Arg Val Gly Asp Ser Phe Tyr
            500                 505                 510
Ile Arg Thr His Phe Glu Leu Glu Pro Ser Pro Pro Ser Gly Leu Gly
        515                 520                 525
Phe Thr Arg Gly Asp Val Phe His Val Leu Asp Thr Leu His Pro Gly
    530                 535                 540
Pro Gly Gln Ser His Ala Arg Gly Gly His Trp Leu Ala Val Arg Met
545                 550                 555                 560
Gly Arg Asp Leu Arg Glu Gln Glu Arg Gly Ile Ile Pro Asn Gln Ser
                565                 570                 575
Arg Ala Glu Gln Leu Ala Ser Leu Glu Ala Ala Gln Arg Ala Val Gly
            580                 585                 590
```

```
Val Gly Pro Gly Ser Ser Ala Gly Ser Asn Ala Arg Ala Glu Phe Trp
        595                 600                 605

Arg Leu Arg Gly Leu Arg Arg Gly Ala Lys Lys Thr Thr Gln Arg Ser
610                 615                 620

Arg Glu Asp Leu Ser Ala Leu Thr Arg Gln Gly Arg Tyr Pro Pro Tyr
625                 630                 635                 640

Glu Arg Val Val Leu Arg Glu Ala Ser Phe Lys Arg Pro Val Val Ile
            645                 650                 655

Leu Gly Pro Val Ala Asp Ile Ala Met Gln Lys Leu Thr Ala Glu Met
                660                 665                 670

Pro Asp Gln Phe Glu Ile Ala Glu Thr Val Ser Arg Thr Asp Ser Pro
            675                 680                 685

Ser Lys Ile Ile Lys Leu Asp Thr Val Arg Val Ile Ala Glu Lys Asp
        690                 695                 700

Lys His Ala Leu Leu Asp Val Thr Pro Ser Ala Ile Glu Arg Leu Asn
705                 710                 715                 720

Tyr Val Gln Tyr Tyr Pro Ile Val Val Phe Ile Pro Glu Ser Arg
                    725                 730                 735

Pro Ala Leu Lys Ala Leu Arg Gln Trp Leu Ala Pro Ala Ser Arg Arg
                740                 745                 750

Ser Thr Arg Arg Leu Tyr Ala Gln Ala Gln Lys Leu Arg Lys His Ser
        755                 760                 765

Ser His Leu Phe Thr Ala Thr Ile Pro Leu Asn Gly Thr Ser Asp Thr
770                 775                 780

Trp Tyr Gln Glu Leu Lys Ala Ile Ile Arg Glu Gln Thr Arg Pro
785                 790                 795                 800

Ile Trp Thr Ala Glu Asp Gln Leu Asp Gly Ser Leu Glu Asp Asn Leu
                805                 810                 815

Asp Leu Pro His His Gly Leu Ala Asp Ser Ser Ala Asp Leu Ser Cys
                820                 825                 830

Asp Ser Arg Val Asn Ser Asp Tyr Glu Thr Asp Gly Glu Gly Gly Ala
        835                 840                 845

Tyr Thr Asp Gly Glu Gly Tyr Thr Asp Gly Gly Pro Tyr Thr
        850                 855                 860

Asp Val Asp Asp Glu Pro Pro Ala Pro Ala Leu Ala Arg Ser Ser Glu
865                 870                 875                 880

Pro Val Gln Ala Asp Glu Ser Gln Ser Pro Arg Asp Arg Gly Arg Ile
                885                 890                 895

Ser Ala His Gln Gly Ala Gln Val Ser Arg His Pro Gln Gly Gln
                900                 905                 910

Trp Arg Gln Asp Ser Met Arg Thr Tyr Glu Arg Glu Ala Leu Lys Lys
        915                 920                 925

Lys Phe Met Arg Val His Asp Ala Glu Ser Ser Asp Glu Asp Gly Tyr
930                 935                 940

Asp Trp Gly Pro Ala Thr Asp Leu
945                 950
```

<210> SEQ ID NO 432
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
     Forward primer for amplifying the nucleotide sequence encoding TJP3 protein"

<400> SEQUENCE: 432
ccctcgacca ggtggctgac                                                    20

<210> SEQ ID NO 433
<211> LENGTH: 19
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      TJP3 protein"

<400> SEQUENCE: 433
cctccagaga tcgcaatgc                                                     19

<210> SEQ ID NO 434
<211> LENGTH: 19
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      TJP3 protein"

<400> SEQUENCE: 434
gtatctgacg tggtacctg                                                     19

<210> SEQ ID NO 435
<211> LENGTH: 22
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      TJP3 protein"

<400> SEQUENCE: 435
ggcaaacgcg gaggtggcat tc                                                 22

<210> SEQ ID NO 436
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      TJP3 protein"

<400> SEQUENCE: 436
cggggtttcc atggagaatg                                                    20

<210> SEQ ID NO 437
<211> LENGTH: 19
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      TJP3 protein"

<400> SEQUENCE: 437
gcgggcaggt ggatcctcc                    19

<210> SEQ ID NO 438
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      TJP3 protein"

<400> SEQUENCE: 438
gcaggacgtg cagatgaagc                    20

<210> SEQ ID NO 439
<211> LENGTH: 21
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      TJP3 protein"

<400> SEQUENCE: 439
cccgaatctg taatgtgctt g                  21

<210> SEQ ID NO 440
<211> LENGTH: 21
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      TJP3 protein"

<400> SEQUENCE: 440
gtgggctgca ggaaggagat c                  21

<210> SEQ ID NO 441
<211> LENGTH: 22
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      TJP3 protein"

<400> SEQUENCE: 441
gaactgccca cgatctctca gc                 22

<210> SEQ ID NO 442
<211> LENGTH: 19
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      TJP3 protein"

<400> SEQUENCE: 442
gatcgtgggc agttcctgg                     19

<210> SEQ ID NO 443

```
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      TJP3 protein"

<400> SEQUENCE: 443
gatgtctgca gggggagagg                                                    20

<210> SEQ ID NO 444
<211> LENGTH: 19
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      TJP3 protein"

<400> SEQUENCE: 444 cacccccggca tgctcagcg                                                    19

<210> SEQ ID NO 445
<211> LENGTH: 19
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      TJP3 protein"

<400> SEQUENCE: 445
ccgagatggt tctggaatc                                                     19

<210> SEQ ID NO 446
<211> LENGTH: 19
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      TJP3 protein"

<400> SEQUENCE: 446
gagtccccgg cttcggcgg                                                     19

<210> SEQ ID NO 447
<211> LENGTH: 21
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      TJP3 protein"

<400> SEQUENCE: 447
cgatcctcca tgctctgact g                                                  21

<210> SEQ ID NO 448
<211> LENGTH: 18
<212> TYPE: DNA
<213> ORGANISM: Artificial Sequence
<220> FEATURE:
```

```
<221> NAME/KEY: Source
<223> OTHER INFORMATION: /note="Description of Artificial Sequence:
      Forward primer for amplifying the nucleotide sequence encoding
      TJP3 protein"

<400> SEQUENCE: 448
gtgcaggcgg gcagcccg                                                   18

<210> SEQ ID NO 449
<211> LENGTH: 19
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      TJP3 protein"

<400> SEQUENCE: 449
gtcctgcttc ctctgcgtc                                                  19

<210> SEQ ID NO 450
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      TJP3 protein"

<400> SEQUENCE: 450
cgagagcagc agacgcggcc                                                 20

<210> SEQ ID NO 451
<211> LENGTH: 19
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      TJP3 protein"

<400> SEQUENCE: 451
gaggtcagcg gagctgtcg                                                  19

<210> SEQ ID NO 452
<211> LENGTH: 60
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding TJP3 protein"

<400> SEQUENCE: 452
cagggacagt ggcgacagga cagcatgcga acctatgaac gggaagccct gaagaaaaag     60

<210> SEQ ID NO 453
<211> LENGTH: 42
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding TJP3 protein"
```

-continued

<400> SEQUENCE: 453
gaacagcaca cggccacact gtccaaggac ccccgccggg gc    42

<210> SEQ ID NO 454
<211> LENGTH: 54
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding TJP3 protein"

<400> SEQUENCE: 454
accaagatgg ccaacatcac agtgaaacgt ccccggagga tccacctgcc cgcc    54

<210> SEQ ID NO 455
<211> LENGTH: 54
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding TJP3 protein"

<400> SEQUENCE: 455
cagtgacagc gacagctcgc cattggagga aggcgtgacc atggctgatg agat    54

<210> SEQ ID NO 456
<211> LENGTH: 54
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding TJP3 protein"

<400> SEQUENCE: 456
cgagtggtgt tgcgagaagc cagtttcaag cgcccggtag tgatcctggg accc    54

<210> SEQ ID NO 457
<211> LENGTH: 85
<212> TYPE: PRT
<213> ORGANISM: Artificial Sequence
<220> FEATURE:
<221> NAME/KEY: Source
<223> OTHER INFORMATION: /note="Description of Artificial Sequence:
      Partial recombinant amino acid sequence of TJP3"

<400> SEQUENCE: 457

Asp Glu Pro Pro Ala Pro Ala Leu Ala Arg Ser Ser Glu Pro Val Gln
1               5                   10                  15

Ala Asp Glu Ser Gln Ser Pro Arg Asp Arg Gly Arg Ile Ser Ala His
            20                  25                  30

Gln Gly Ala Gln Val Asp Ser Arg His Pro Gln Gly Gln Trp Arg Gln
        35                  40                  45

Asp Ser Met Arg Thr Tyr Glu Arg Glu Ala Leu Lys Lys Lys Phe Met
    50                  55                  60

Arg Val His Asp Ala Glu Ser Ser Asp Glu Asp Gly Tyr Asp Trp Gly
65                  70                  75                  80

Pro Ala Thr Asp Leu
            85

<210> SEQ ID NO 458
<211> LENGTH: 1938
<212> TYPE: DNA
<213> ORGANISM: Homo Sapiens

<400> SEQUENCE: 458

```
ggggcgcttc ctggggccgc gcgtccaggg agctgtgccg tccgcccgtc cgtctgcccg      60
caggcattgc ccgagccagc cgagccgcca gagccgcggg ccgcggggt gtcgcgggcc     120
caaccccagg atgctcccct gcgcctcctg cctacccggg tctctactgc tctgggcgct     180
gctactgttg ctcttgggat cagcttctcc tcaggattct gaagagcccg acagctacac     240
ggaatgcaca gatggctatg agtgggaccc agacagccag cactgccggg atgtcaacga     300
gtgtctgacc atccctgagg cctgcaaggg gaaatgaag tgcatcaacc actacgggg      360
ctacttgtgc ctgccccgct ccgctgccgt catcaacgac ctacacggcg agggaccccc     420
gccaccagtg cctcccgctc aacaccccaa ccctgccca ccaggctatg agcccgacga     480
tcaggacagc tgtgtggatg tggacgagtg tgcccaggcc ctgacgact gtcgcccag      540
ccaggactgc cataacttgc ctggctccta tcagtgcacc tgccctgatg gttaccgcaa     600
gatcgggccc gagtgtgtgg acatagacga gtgccgctac cgctactgcc agcaccgctg     660
cgtgaacctg cctggctcct ccgctgcca gtgcgagccg gcttccagc tgggcctaa      720
caaccgctcc tgtgttgatg tgaacgagtg tgacatgggg gccccatgcg agcagcgctg     780
cttcaactcc tatgggacct tcctgtgtcg ctgccaccag ggctatgagc tgcatcggga     840
tggcttctcc tgcagtgata ttgatgagtg tagctactcc agctacctct gtcagtaccg     900
ctgcgtcaac gagccaggcc gtttctcctg ccactgccca cagggttacc agctgctggc     960
cacacgcctc tgccaagaca ttgatgagtg tgagtctggt gcgcaccagt gctccgaggc    1020
ccaaacctgt gtcaacttcc atgggggcta ccgctgcgtg acaccaacc gctgcgtgga    1080
gccctacatc caggtctctg agaaccgctg tctctgcccg gcctccaacc ctctatgtcg    1140
agagcagcct tcatccattg tgcaccgcta catgaccatc acctcggagc ggagcgtgcc    1200
cgctgacgtg ttccagatcc aggcgacctc cgtctacccc ggtgcctaca atgccttca    1260
gatccgtgct ggaaactcgc aggggactt ttacattagg caaatcaaca acgtcagcgc    1320
catgctggtc ctcgcccggc cggtgacggg ccccgggag tacgtgctgg acctggagat    1380
ggtcaccatg aattccctca tgagctaccg ggccagctct gtactgaggc tcaccgtctt    1440
tgtagggcc tacaccttct gaggagcagg agggagccac cctccctgca gctaccctag    1500
ctgaggagcc tgttgtgagg ggcagaatga gaaaggcaat aaagggagaa agaaagtcct    1560
ggtggctgag gtgggcgggt cacactgcag gaagcctcag gctggggcag ggtggcactt    1620
gggggggcag gccaagttca cctaaatggg ggtctctata tgttcaggcc caggggcccc    1680
cattgacagg agctgggagc tctgcaccac gagcttcagt caccccgaga ggagaggag     1740
taacgaggag ggcggactcc aggccccggc ccagagattt ggacttggct ggcttgcagg    1800
ggtcctaaga aactccactc tggacagcgc caggaggccc tgggttccat tcctaactct    1860
gcctcaaact gtacatttgg ataagcccta gtagttccct gggcctgttt ttctataaaa    1920
cgaggcaact ggactgtt                                                 1938
```

<210> SEQ ID NO 459
<211> LENGTH: 443
<212> TYPE: PRT

<213> ORGANISM: Homo Sapiens

<400> SEQUENCE: 459

```
Met Leu Pro Cys Ala Ser Cys Leu Pro Gly Ser Leu Leu Leu Trp Ala
1               5                   10                  15

Leu Leu Leu Leu Leu Leu Gly Ser Ala Ser Pro Gln Asp Ser Glu Glu
            20                  25                  30

Pro Asp Ser Tyr Thr Glu Cys Thr Asp Gly Tyr Glu Trp Asp Pro Asp
        35                  40                  45

Ser Gln His Cys Arg Asp Val Asn Glu Cys Leu Thr Ile Pro Glu Ala
    50                  55                  60

Cys Lys Gly Glu Met Lys Cys Ile Asn His Tyr Gly Gly Tyr Leu Cys
65                  70                  75                  80

Leu Pro Arg Ser Ala Ala Val Ile Asn Asp Leu His Gly Glu Gly Pro
                85                  90                  95

Pro Pro Pro Val Pro Pro Ala Gln His Pro Asn Pro Cys Pro Pro Gly
            100                 105                 110

Tyr Glu Pro Asp Asp Gln Asp Ser Cys Val Asp Val Asp Glu Cys Ala
        115                 120                 125

Gln Ala Leu His Asp Cys Arg Pro Ser Gln Asp Cys His Asn Leu Pro
    130                 135                 140

Gly Ser Tyr Gln Cys Thr Cys Pro Asp Gly Tyr Arg Lys Ile Gly Pro
145                 150                 155                 160

Glu Cys Val Asp Ile Asp Glu Cys Arg Tyr Arg Tyr Cys Gln His Arg
                165                 170                 175

Cys Val Asn Leu Pro Gly Ser Phe Arg Cys Gln Cys Glu Pro Gly Phe
            180                 185                 190

Gln Leu Gly Pro Asn Asn Arg Ser Cys Val Asp Val Asn Glu Cys Asp
        195                 200                 205

Met Gly Ala Pro Cys Glu Gln Arg Cys Phe Asn Ser Tyr Gly Thr Phe
    210                 215                 220

Leu Cys Arg Cys His Gln Gly Tyr Glu Leu His Arg Asp Gly Phe Ser
225                 230                 235                 240

Cys Ser Asp Ile Asp Glu Cys Ser Tyr Ser Tyr Leu Cys Gln Tyr
                245                 250                 255

Arg Cys Val Asn Glu Pro Gly Arg Phe Ser Cys His Cys Pro Gln Gly
            260                 265                 270

Tyr Gln Leu Leu Ala Thr Arg Leu Cys Gln Asp Ile Asp Glu Cys Glu
        275                 280                 285

Ser Gly Ala His Gln Cys Ser Glu Ala Gln Thr Cys Val Asn Phe His
    290                 295                 300

Gly Gly Tyr Arg Cys Val Asp Thr Asn Arg Cys Val Glu Pro Tyr Ile
305                 310                 315                 320

Gln Val Ser Glu Asn Arg Cys Leu Cys Pro Ala Ser Asn Pro Leu Cys
                325                 330                 335

Arg Glu Gln Pro Ser Ser Ile Val His Arg Tyr Met Thr Ile Thr Ser
            340                 345                 350

Glu Arg Ser Val Pro Ala Asp Val Phe Gln Ile Gln Ala Thr Ser Val
        355                 360                 365

Tyr Pro Gly Ala Tyr Asn Ala Phe Gln Ile Arg Ala Gly Asn Ser Gln
    370                 375                 380

Gly Asp Phe Tyr Ile Arg Gln Ile Asn Asn Val Ser Ala Met Leu Val
385                 390                 395                 400
```

```
Leu Ala Arg Pro Val Thr Gly Pro Arg Glu Tyr Val Leu Asp Leu Glu
            405                 410                 415

Met Val Thr Met Asn Ser Leu Met Ser Tyr Arg Ala Ser Ser Val Leu
        420                 425                 430

Arg Leu Thr Val Phe Val Gly Ala Tyr Thr Phe
        435                 440
```

<210> SEQ ID NO 460
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      EFEMP2 protein"

<400> SEQUENCE: 460
tgctcttggg atcagcttct                                                 20

<210> SEQ ID NO 461
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      EFEMP2 protein"

<400> SEQUENCE: 461
cctcagggat ggtcagacac                                                 20

<210> SEQ ID NO 462
<211> LENGTH: 18
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      EFEMP2  protein"

<400> SEQUENCE: 462
tgcccaccag gctatgag                                                   18

<210> SEQ ID NO 463
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      EFEMP2 protein"

<400> SEQUENCE: 463
caggcaagtt atggcagtcc                                                 20

<210> SEQ ID NO 464
<211> LENGTH: 20
<212> TYPE: DNA
<213> ORGANISM: Artificial sequence
<220> FEATURE:
<221> NAME/KEY: Source
<223> OTHER INFORMATION: /note="Description of Artificial Sequence:
      Forward primer for amplifying the nucleotide sequence encoding
      EFEMP2 protein"

```
<400> SEQUENCE: 464
aacttgcctg gctcctatca                                              20

<210> SEQ ID NO 465
<211> LENGTH: 19
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      EFEMP2 protein"

<400> SEQUENCE: 465
gtgctggcag tagcggtag                                               19

<210> SEQ ID NO 466
<211> LENGTH: 18
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      EFEMP2 protein"

<400> SEQUENCE: 466
ggcctaacaa ccgctcct                                                18

<210> SEQ ID NO 467
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      EFEMP2 protein"

<400> SEQUENCE: 467
cgacacagga aggtcccata                                              20

<210> SEQ ID NO 468
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      EFEMP2 protein"

<400> SEQUENCE: 468
tatgggacct tcctgtgtcg                                              20

<210> SEQ ID NO 469
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      EFEMP2 protein"

<400> SEQUENCE: 469
gatgcagcgg tactgacaga                                              20
```

<210> SEQ ID NO 470
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      EFEMP2 protein"

<400> SEQUENCE: 470
gtcagtaccg ctgcatcaac                                              20

<210> SEQ ID NO 471
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      EFEMP2 protein"

<400> SEQUENCE: 471
cgcaccagac tcacactcat                                              20

<210> SEQ ID NO 472
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      EFEMP2 protein"

<400> SEQUENCE: 472
gtggagccct acatccaggt                                              20

<210> SEQ ID NO 473
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      EFEMP2 protein"

<400> SEQUENCE: 473
tccgaggtga tggtcatgta                                              20

<210> SEQ ID NO 474
<211> LENGTH: 50
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding EFEMP2 protein"

<400> SEQUENCE: 474
ttcatccatt gtgcaccgct acatgaccat cacctcggag cggagcgtgc              50

<210> SEQ ID NO 475
<211> LENGTH: 20

```
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding EFEMP2 protein"

<400> SEQUENCE: 475
gaagagcccg acagctacac                                               20

<210> SEQ ID NO 476
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding EFEMP2 protein"

<400> SEQUENCE: 476
caggcaagtt atggcagtcc                                               20

<210> SEQ ID NO 477
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding EFEMP2 protein"

<400> SEQUENCE: 477
cctgatggtt accgcaagat                                               20

<210> SEQ ID NO 478
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding EFEMP2 protein"

<400> SEQUENCE: 478
gtgaacgagt gtgacatggg                                               20

<210> SEQ ID NO 479
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding EFEMP2 protein"

<400> SEQUENCE: 479
atggcttctc ctgcagtgat                                               20

<210> SEQ ID NO 480
<211> LENGTH: 19
<212> TYPE: DNA
<213> ORGANISM: Artificial Sequence
<220> FEATURE:
<221> NAME/KEY: Source
```

<223> OTHER INFORMATION: /note="Description of Artificial Sequence:
      Probe for detecting a nucleotide molecule having a nucleic acid
      sequence encoding EFEMP2 protein"

<400> SEQUENCE: 480
acgcctctgc caagacatt                                              19

<210> SEQ ID NO 481
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding EFEMP2 protein"

<400> SEQUENCE: 481
atgtcgagag cagccttcat                                             20

<210> SEQ ID NO 482
<211> LENGTH: 2210
<212> TYPE: DNA
<213> ORGANISM: Homo Sapiens

<400> SEQUENCE: 482
agccgcggcc tcaactaaaa gtggccattg acctttcaag ctttcgagca gtgatgcaat      60
agaatagtat ttcaaagaaa aatgcttatc gaaattttgg atccggtttt cccgtgattg     120
ttaagggttt cttttaaaaa gtaggtcaca tttcaagtag gtcatatttc gggggcgggt     180
gcgcagacaa ggagatgagt ttccactaag gccaggggc ctccaacggg gttggaggtg     240
agaatcccag gtagggtaga ggtgccgaga tccttccgaa tcccagcccg ggggcgtcag     300
ccctgcaggg aatggcagag acactctccg gactgaggga accgaggcca gtcaccaagc     360
cccttccggg cgcgcaggcg atcagtgggt gaccgcggct gcgagggact ttgtcatccg     420
tcctccagga tctggggaga aagagcccca tcccttctct ctctgccacc atttcggaca     480
ccccgcaggg actcgttttg ggattcgcac tgacttcaag gaaggacgcg aacccttctc     540
tgaccccagc tcgggcggcc acctgtcttt gccgcggtga cccttctctc atgaccctgc     600
ggtgccttga gccctccggg aatggcgggg aagggacgcg gagccagtgg gggaccgcgg     660
ggtcggcgga ggagccatcc ccgcaggcgg cgcgtctggc gaaggccctg cgggagctcg     720
gtcagacagg atggtactgg ggaagtatga ctgttaatga agccaaagag aaattaaaag     780
aggcaccaga aggaactttc ttgattagag atagctcgca ttcagactac ctactaacaa     840
tatctgttaa aacatcagct ggaccaacta atcttcgaat cgaataccaa gacggaaaat     900
tcagattgga ctctatcata tgtgtcaaat ccaagcttaa acaatttgac agtgtggttc     960
atctgatcga ctactatgtt cagatgtgca aggataagcg acaggtcca gaagccccc     1020 ggaacggcac tgttcacctt tatctgacca aaccgctcta cacgtcagca ccatctctgc    1080
agcatctctg taggctcacc attaacaaat gtaccggtgc catctgggga ctgcctttac    1140
caacaagact aaaagattac ttggaagaat ataaattcca ggtataaatg tttctctttt    1200
tttaaacatg tctcacatag agtatctccg aatgcagcta tgtaaaagag aaccaaaact    1260
tgagtgctct ggataactat atggaatgct ttctaagaac agctgaagct aatctaattt    1320
aaatttaaca gcttgaagag gtagctaggt gtttaaagtt cctccagata cttttacctg    1380
agtgatgctt cccttcctaa ggctgaccaa gacctgttga tccttttaga ttaaaaataa    1440

```
aatgtcgcat gtaaaggctg aagtcgcgtt ttatcagaat gccttgcctt cttaggttct   1500
tttccattat gtcaaaggtc caggctccag taggagagaa agaactcctc ataggaatac   1560
tgaagaagtg ggaaggaacc aagctgacac aggcctcact gcaatttgat atgcctgctg   1620
atcagagtct cttgggcatt ttatattttg cattctgatg tacctaggag ttttgttaaa   1680
cagatgatgt atgtgagtat ttatcccatt ttatgcaatt aaccaaatca accaaaaaaa   1740
gtgaccatga agtcctgtat ttgtcttttt actacatgta ggaactctca tgtgaatgag   1800
tactgtagta atccattcta tgggagcctt atttcagaaa tatttcaaac tggtgcaaat   1860
ggaaaagact ttctcttttc ctttaaagct aaagacaaga atatcatgct atacaggtgc   1920
aactcaatcc ccgttaataa aaaccaatgt aggtataggc attctaccct ttgaaatagc   1980
tgtgtcccaa cctgttgcca ttgattttt ggaaatggct ttagaaatat ccaagttgtc    2040
cttgaattgt ctaaccatgg acataaacag ttgtctccct tctactgtgt agaatacttt   2100
gacttaattt tcttccagat acaggggat acctgcctgt ttttcaaagt gtttatttac    2160
tgctgttact atttgattag aatgtattaa ataaaaaaaa cctgatttct             2210
```

<210> SEQ ID NO 483
<211> LENGTH: 198
<212> TYPE: PRT
<213> ORGANISM: Homo Sapiens

<400> SEQUENCE: 483

```
Met Thr Leu Arg Cys Leu Glu Pro Ser Gly Asn Gly Glu Gly Thr
1               5                   10                  15

Arg Ser Gln Trp Gly Thr Ala Gly Ser Ala Glu Pro Ser Pro Gln
            20                  25                  30

Ala Ala Arg Leu Ala Lys Ala Leu Arg Glu Leu Gly Gln Thr Gly Trp
        35                  40                  45

Tyr Trp Gly Ser Met Thr Val Asn Glu Ala Lys Glu Lys Leu Lys Glu
    50                  55                  60

Ala Pro Glu Gly Thr Phe Leu Ile Arg Asp Ser Ser His Ser Asp Tyr
65                  70                  75                  80

Leu Leu Thr Ile Ser Val Lys Thr Ser Ala Gly Pro Thr Asn Leu Arg
                85                  90                  95

Ile Glu Tyr Gln Asp Gly Lys Phe Arg Leu Asp Ser Ile Ile Cys Val
            100                 105                 110

Lys Ser Lys Leu Lys Gln Phe Asp Ser Val Val His Leu Ile Asp Tyr
        115                 120                 125

Tyr Val Gln Met Cys Lys Asp Lys Arg Thr Gly Pro Glu Ala Pro Arg
    130                 135                 140

Asn Gly Thr Val His Leu Tyr Leu Thr Lys Pro Leu Tyr Thr Ser Ala
145                 150                 155                 160

Pro Ser Leu Gln His Leu Cys Arg Leu Thr Ile Asn Lys Cys Thr Gly
                165                 170                 175

Ala Ile Trp Gly Leu Pro Leu Pro Thr Arg Leu Lys Asp Tyr Leu Glu
            180                 185                 190

Glu Tyr Lys Phe Gln Val
        195
```

<210> SEQ ID NO 484
<211> LENGTH: 18
<212> TYPE: DNA
<213> ORGANISM: Artificial Sequence
<220> FEATURE:

```
<221> NAME/KEY: Source
<223> OTHER INFORMATION: /note="Description of Artificial Sequence:
      Forward primer for amplifying the nucleotide sequence encoding
      SOCS2 protein"

<400> SEQUENCE: 484
agtcaccaag ccccttcc                                                    18

<210> SEQ ID NO 485
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      SOCS2 protein"

<400> SEQUENCE: 485
gctctttctc cccagatcct                                                  20

<210> SEQ ID NO 486
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding
      SOCS2 protein"

<400> SEQUENCE: 486
gggactgcct ttaccaacaa                                                  20

<210> SEQ ID NO 487
<211> LENGTH: 22
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding
      SOCS2 protein"

<400> SEQUENCE: 487
tttacatagc tgcattcgga ga                                               22

<210> SEQ ID NO 488
<211> LENGTH: 60
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding SOCS2 protein"

<400> SEQUENCE: 488
agtgtggttc atctgatcga ctactatgtt cagatgtgca aggataagcg gacaggtcca     60

<210> SEQ ID NO 489
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding SOCS2 protein"
```

<400> SEQUENCE: 489
gactttgtca tccgtcctcc                                                  20

<210> SEQ ID NO 490
<211> LENGTH: 25
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding SOCS2 protein"

<400> SEQUENCE: 490
acttggaaga atataaattc caggt                                            25

<210> SEQ ID NO 491
<211> LENGTH: 2287
<212> TYPE: DNA
<213> ORGANISM: Homo Sapiens

<400> SEQUENCE: 491
gaatctacaa taagacaaat ttcaaatcaa gttgctccac tatactgcat aagcagttta      60
gaatcttaag cagatgcaaa aagaataaag caaatgggag gaaaaaaaag gccgataaag     120
tttctggcta caatacaaga gacatatcat taccatgtga tctaatgtgg gtgtcagccg     180
gattgtgttc attgagggaa accttatttt ttaactgtgc tatggagtag aagcaggagg     240 tttttcaacct agtcacagag cagcacctac ccctcctcc tttccacacc tgcaaactct      300
tttacttggg ctgaatattt agtgtaatta catctcagct ttgagggctc ctgtggcaaa     360
ttcccggatt aaaaggttcc ctggttgtga aaatacatga gataaatcat gaaggccact     420
atcatcctcc ttctgcttgc acaagtttcc tgggctggac cgtttcaaca gagaggctta     480
tttgacttta tgctagaaga tgaggcttct gggataggcc cagaagttcc tgatgaccgc     540
gacttcgagc cctccctagg cccagtgtgc cccttccgct gtcaatgcca tcttcgagtg     600
gtccagtgtt ctgatttggg tctggacaaa gtgccaaagg atcttccccc tgacacaact     660
ctgctagacc tgcaaaacaa caaaataacc gaaatcaaag atggagactt taagaacctg    720
aagaaccttc acgcattgat tcttgtcaac aataaaatta gcaaagttag tcctggagca    780
tttacccctt tggtgaagtt ggaacgactt tatctgtcca agaatcagct gaaggaattg    840
ccagaaaaaa tgcccaaaac tcttcaggag ctgcgtgccc atgagaatga gatcaccaaa    900
gtgcgaaaag ttactttcaa tggactgaac cagatgattg tcatagaact gggcaccaat    960
ccgctgaaga gctcaggaat tgaaaatggg gctttccagg aatgaagaa gctctcctac    1020 atccgcattg ctgataccaa tatcaccagc attcctcaag gtcttcctcc ttcccttacg    1080
gaattacatc ttgatggcaa caaaatcagc agagttgatg cagctagcct gaaaggactg    1140
aataatttgg ctaagttggg attgagtttc aacagcatct ctgctgttga caatggctct    1200
ctggccaaca cgcctcatct gagggagctt cacttggaca caacaagct taccagagta    1260 cctggtgggc tggcagagca taagtacatc caggttgtct accttcataa caacaatatc    1320
tctgtagttg gatcaagtga cttctgccca cctggacaca caccaaaaa ggcttcttat    1380 tcgggtgtga gtcttttcag caacccggtc cagtactggg agatacagcc atccaccttc    1440
agatgtgtct acgtgcgctc tgccattcaa ctcggaaact ataagtaatt ctcaagaaag    1500 cccctcatttt tataacctgg caaaatcttg ttaatgtcat tgctaaaaaa taaataaaag    1560

```
ctagatactg gaaacctaac tgcaatgtgg atgttttacc cacatgactt attatgcata   1620
aagccaaatt tccagtttaa gtaattgcct acaataaaaa gaaattttgc ctgccatttt   1680
cagaatcatc ttttgaagct ttctgttgat gttaactgag ctactagaga tattcttatt   1740
tcactaaatg taaaatttgg agtaaatata tatgtcaata tttagtaaag cttttctttt   1800
ttaatttcca ggaaaaaata aaaagagtat gagtcttctg taattcattg agcagttagc   1860
tcatttgaga taaagtcaaa tgccaaacac tagctctgta ttaatcccca tcattactgg   1920
taaagcctca tttgaatgtg tgaattcaat acaggctatg taaaatttt actaatgtca    1980 ttattttgaa aaaataaatt taaaaataca ttcaaaatta ctattgtata caagcttaat   2040
tgttaatatt ccctaaacac aattttatga agggagaaga cattggtttg ttgacaataa   2100
cagtacatct tttcaagttc tcagctattt cttctacctc tccctatctt acatttgagt   2160
atggtaactt atgtcatcta tgttgaatgt aagcttataa agcacaaagc atacatttcc   2220
tgactggtct agagaactga tgtttcaatt taccccctctg ctaaataaat attaaaacta  2280
tcatgtg                                                            2287
```

```
<210> SEQ ID NO 492
<211> LENGTH: 359
<212> TYPE: PRT
<213> ORGANISM: Homo Sapiens

<400> SEQUENCE: 492

Met Lys Ala Thr Ile Ile Leu Leu Leu Ala Gln Val Ser Trp Ala
1               5                   10                  15

Gly Pro Phe Gln Gln Arg Gly Leu Phe Asp Phe Met Leu Glu Asp Glu
            20                  25                  30

Ala Ser Gly Ile Gly Pro Glu Val Pro Asp Asp Arg Asp Phe Glu Pro
        35                  40                  45

Ser Leu Gly Pro Val Cys Pro Phe Arg Cys Gln Cys His Leu Arg Val
    50                  55                  60

Val Gln Cys Ser Asp Leu Gly Leu Asp Lys Val Pro Lys Asp Leu Pro
65                  70                  75                  80

Pro Asp Thr Thr Leu Leu Asp Leu Gln Asn Asn Lys Ile Thr Glu Ile
                85                  90                  95

Lys Asp Gly Asp Phe Lys Asn Leu Lys Asn Leu His Ala Leu Ile Leu
            100                 105                 110

Val Asn Asn Lys Ile Ser Lys Val Ser Pro Gly Ala Phe Thr Pro Leu
        115                 120                 125

Val Lys Leu Glu Arg Leu Tyr Leu Ser Lys Asn Gln Leu Lys Glu Leu
    130                 135                 140

Pro Glu Lys Met Pro Lys Thr Leu Gln Glu Leu Arg Ala His Glu Asn
145                 150                 155                 160

Glu Ile Thr Lys Val Arg Lys Val Thr Phe Asn Gly Leu Asn Gln Met
                165                 170                 175

Ile Val Ile Glu Leu Gly Thr Asn Pro Leu Lys Ser Ser Gly Ile Glu
            180                 185                 190

Asn Gly Ala Phe Gln Gly Met Lys Lys Leu Ser Tyr Ile Arg Ile Ala
        195                 200                 205

Asp Thr Asn Ile Thr Ser Ile Pro Gln Gly Leu Pro Pro Ser Leu Thr
    210                 215                 220

Glu Leu His Leu Asp Gly Asn Lys Ile Ser Arg Val Asp Ala Ala Ser
225                 230                 235                 240
```

Leu Lys Gly Leu Asn Asn Leu Ala Lys Leu Gly Leu Ser Phe Asn Ser
                245                 250                 255

Ile Ser Ala Val Asp Asn Gly Ser Leu Ala Asn Thr Pro His Leu Arg
            260                 265                 270

Glu Leu His Leu Asp Asn Asn Lys Leu Thr Arg Val Pro Gly Gly Leu
        275                 280                 285

Ala Glu His Lys Tyr Ile Gln Val Val Tyr Leu His Asn Asn Asn Ile
    290                 295                 300

Ser Val Val Gly Ser Ser Asp Phe Cys Pro Pro Gly His Asn Thr Lys
305                 310                 315                 320

Lys Ala Ser Tyr Ser Gly Val Ser Leu Phe Ser Asn Pro Val Gln Tyr
                325                 330                 335

Trp Glu Ile Gln Pro Ser Thr Phe Arg Cys Val Tyr Val Arg Ser Ala
            340                 345                 350

Ile Gln Leu Gly Asn Tyr Lys
        355

<210> SEQ ID NO 493
<211> LENGTH: 19
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding DCN
      protein"

<400> SEQUENCE: 493
agctttgagg gctcctgtg                                              19

<210> SEQ ID NO 494
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding DCN
      protein"

<400> SEQUENCE: 494
gcaagcagaa ggaggatgat                                             20

<210> SEQ ID NO 495
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding DCN
      protein"

<400> SEQUENCE: 495
aatgccatct tcgagtggtc                                             20

<210> SEQ ID NO 496
<211> LENGTH: 21
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding DCN protein"

<400> SEQUENCE: 496
tgcaggtcta gcagagttgt g                                              21

<210> SEQ ID NO 497
<211> LENGTH: 21
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding DCN
      protein"

<400> SEQUENCE: 497
aaccgaaatc aaagatggag a                                              21

<210> SEQ ID NO 498
<211> LENGTH: 19
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding DCN
      protein"

<400> SEQUENCE: 498
gtccaggtgg gcagaagtc                                                 19

<210> SEQ ID NO 499
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding DCN
      protein"

<400> SEQUENCE: 499
aatgccatct tcgagtggtc                                                20

<210> SEQ ID NO 500
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding DCN
      protein"

<400> SEQUENCE: 500
ctgctgattt tgttgccatc                                                20

<210> SEQ ID NO 501
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding DCN
      protein"

<400> SEQUENCE: 501
tggcaacaaa atcagcagag                                              20

<210> SEQ ID NO 502
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding DCN
      protein"

<400> SEQUENCE: 502
gccattgtca acagcagaga                                              20

<210> SEQ ID NO 503
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding DCN
      protein"

<400> SEQUENCE: 503
gggctggcag agcataagta                                              20

<210> SEQ ID NO 504
<211> LENGTH: 19
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding DCN
      protein"

<400> SEQUENCE: 504
gtccaggtgg gcagaagtc                                               19

<210> SEQ ID NO 505
<211> LENGTH: 21
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding DCN
      protein"

<400> SEQUENCE: 505
aaccgaaatc aaagatggag a                                            21

<210> SEQ ID NO 506
<211> LENGTH: 21
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding DCN
      protein"

<400> SEQUENCE: 506
ccaaaggtgt aaatgctcca g                                            21

<210> SEQ ID NO 507

```
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding DCN
      protein"

<400> SEQUENCE: 507
gagatcacca aagtgcgaaa                                               20

<210> SEQ ID NO 508
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding DCN
      protein"

<400> SEQUENCE: 508
aaagccccat tttcaattcc                                               20

<210> SEQ ID NO 509
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Forward primer for amplifying the nucleotide sequence encoding DCN
      protein"

<400> SEQUENCE: 509
aatgccatct tcgagtggtc                                               20

<210> SEQ ID NO 510
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Reverse primer for amplifying the nucleotide sequence encoding DCN
      protein"

<400> SEQUENCE: 510
aaagccccat tttcaattcc                                               20

<210> SEQ ID NO 511
<211> LENGTH: 58
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding DCN protein"

<400> SEQUENCE: 511
tttaactgtg ctatggagta gaagcaggag gttttcaacc tagtcacaga gcagcacc    58

<210> SEQ ID NO 512
<211> LENGTH: 20
<212> TYPE: DNA
<213> ORGANISM: Artificial Sequence
<220> FEATURE:
```

<221> NAME/KEY: Source
<223> OTHER INFORMATION: /note="Description of Artificial Sequence:
      Probe for detecting a nucleotide molecule having a nucleic acid
      sequence encoding DCN protein"

<400> SEQUENCE: 512
ttcccggatt aaaaggttcc                                              20

<210> SEQ ID NO 513
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding DCN protein"

<400> SEQUENCE: 513
aagtgccaaa ggatcttccc                                              20

<210> SEQ ID NO 514
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding DCN protein"

<400> SEQUENCE: 514
cctgaagaac cttcacgttg                                              20

<210> SEQ ID NO 515
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding DCN protein"

<400> SEQUENCE: 515
tcctccttcc cttacggaat                                              20

<210> SEQ ID NO 516
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding DCN protein"

<400> SEQUENCE: 516
atgcagctag cctgaaagga                                              20

<210> SEQ ID NO 517
<211> LENGTH: 21
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding DCN protein"

```
<400> SEQUENCE: 517
catccaggtt gtctaccttc a                                              21

<210> SEQ ID NO 518
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding DCN protein"

<400> SEQUENCE: 518
tgaagaacct tcacgcattg                                                20

<210> SEQ ID NO 519
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding DCN protein"

<400> SEQUENCE: 519
tgtcatagaa ctgggcacca                                                20

<210> SEQ ID NO 520
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Probe for detecting a nucleotide molecule having a nucleic acid
      sequence encoding DCN protein"

<400> SEQUENCE: 520
gttctgattt ggaactgggc                                                20

<210> SEQ ID NO 521
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding ACAA1"

<400> SEQUENCE: 521
tcacgggaga agcaggatac                                                20

<210> SEQ ID NO 522
<211> LENGTH: 18
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding ACAA1"

<400> SEQUENCE: 522
cttgctctgg gctcttgc                                                  18
```

```
<210> SEQ ID NO 523
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding ACAA1"

<400> SEQUENCE: 523
ccagagattg cctgattcct                                              20

<210> SEQ ID NO 524
<211> LENGTH: 19
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding ACAA1"

<400> SEQUENCE: 524
cctgcttctc ccgtgaaat                                               19

<210> SEQ ID NO 525
<211> LENGTH: 19
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding ACAA1"

<400> SEQUENCE: 525
agctggggga catctgtgt                                               19

<210> SEQ ID NO 526
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding ACAA1"

<400> SEQUENCE: 526
cactcagaaa ctgggcgatt                                              20

<210> SEQ ID NO 527
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding AP1M2"

<400> SEQUENCE: 527
cacatcgaag aatgccaatg                                              20

<210> SEQ ID NO 528
<211> LENGTH: 21
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding AP1M2"
```

<400> SEQUENCE: 528
gctccttgaa gtattcgcag a                                          21

<210> SEQ ID NO 529
<211> LENGTH: 19
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding AP1M2"

<400> SEQUENCE: 529
tgctcttcga gctcactgg                                             19

<210> SEQ ID NO 530
<211> LENGTH: 19
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding AP1M2"

<400> SEQUENCE: 530
cacgcactgg tggaatttt                                             19

<210> SEQ ID NO 531
<211> LENGTH: 21
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding AP1M2"

<400> SEQUENCE: 531
gttcgctaca tcacccagag t                                          21

<210> SEQ ID NO 532
<211> LENGTH: 19
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding AP1M2"

<400> SEQUENCE: 532
gtaaggaagc cccgtgttc                                             19

<210> SEQ ID NO 533
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding CGN"

<400> SEQUENCE: 533
gagcttaccc gaaaagtgga                                            20

<210> SEQ ID NO 534
<211> LENGTH: 20
<212> TYPE: DNA
<213> ORGANISM: Artificial Sequence

```
<220> FEATURE:
<221> NAME/KEY: Source
<223> OTHER INFORMATION: /note="Description of Artificial Sequence:
      Primer amplifying the nucleotide sequence encoding CGN"

<400> SEQUENCE: 534
tctagcttct gccgcttctt                                                     20

<210> SEQ ID NO 535
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding CGN"

<400> SEQUENCE: 535
ggagatactc gccaggttga                                                     20

<210> SEQ ID NO 536
<211> LENGTH: 21
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding CGN"

<400> SEQUENCE: 536
ccttaagctc ctcctgtgtc c                                                   21

<210> SEQ ID NO 537
<211> LENGTH: 22
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding CGN"

<400> SEQUENCE: 537
cctctgtgag gaggaaggtt ag                                                  22

<210> SEQ ID NO 538
<211> LENGTH: 26
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding CGN"

<400> SEQUENCE: 538
ttagtagaac cagaagaaac catcac                                              26

<210> SEQ ID NO 539
<211> LENGTH: 18
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding DDR1"

<400> SEQUENCE: 539
tagagagcca cccccgta                                                       18
```

<210> SEQ ID NO 540
<211> LENGTH: 22
<212> TYPE: DNA
<213> ORGANISM: Artificial Sequence
<220> FEATURE:
<221> NAME/KEY: Source
<223> OTHER INFORMATION: /note="Description of Artificial Sequence:
    Primer amplifying the nucleotide sequence encoding DDR1"

<400> SEQUENCE: 540
ccatatagtc cccactgtag gc                                              22

<210> SEQ ID NO 541
<211> LENGTH: 19
<212> TYPE: DNA
<213> ORGANISM: Artificial Sequence
<220> FEATURE:
<221> NAME/KEY: Source
<223> OTHER INFORMATION: /note="Description of Artificial Sequence:
    Primer amplifying the nucleotide sequence encoding DDR1"

<400> SEQUENCE: 541
ccactctgct ccctgtgtc                                                  19

<210> SEQ ID NO 542
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
    Primer amplifying the nucleotide sequence encoding DDR1"

<400> SEQUENCE: 542
ctggcttctc aggctccata                                                 20

<210> SEQ ID NO 543
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
    Primer amplifying the nucleotide sequence encoding DDR1"

<400> SEQUENCE: 543
tggggactat taccgtgtgc                                                 20

<210> SEQ ID NO 544
<211> LENGTH: 18
<212> TYPE: DNA
<213> ORGANISM: Artificial Sequence
<220> FEATURE:
<221> NAME/KEY: Source
<223> OTHER INFORMATION: /note="Description of Artificial Sequence:
    Primer amplifying the nucleotide sequence encoding DDR1"

<400> SEQUENCE: 544
acgtcactcg cagtcgtg                                                   18

<210> SEQ ID NO 545
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
    Primer amplifying the nucleotide sequence encoding EPS8L2"

```
<400> SEQUENCE: 545
gcagctcttc tccctcaaca                                              20

<210> SEQ ID NO 546
<211> LENGTH: 19
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding EPS8L2"

<400> SEQUENCE: 546
cccactttgc tgcttctcc                                               19

<210> SEQ ID NO 547
<211> LENGTH: 19
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding EPS8L2"

<400> SEQUENCE: 547
caagatgagc cccaaggac                                               19

<210> SEQ ID NO 548
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding EPS8L2"

<400> SEQUENCE: 548
tgatgacgtt ggagttggaa                                              20

<210> SEQ ID NO 549
<211> LENGTH: 22
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding EPS8L2"

<400> SEQUENCE: 549
caaggatgag gtcctagagg tg                                           22

<210> SEQ ID NO 550
<211> LENGTH: 18
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding EPS8L2"

<400> SEQUENCE: 550
gatgttgcag ggcacgta                                                18

<210> SEQ ID NO 551
<211> LENGTH: 20
<212> TYPE: DNA
```

```
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding FASTKD1"

<400> SEQUENCE: 551
tggaaattct ggggtatcgt                                                    20

<210> SEQ ID NO 552
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding FASTKD1"

<400> SEQUENCE: 552
gcatcctttg ttgacagtgc                                                    20

<210> SEQ ID NO 553
<211> LENGTH: 24
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding FASTKD1"

<400> SEQUENCE: 553
cctgggaatc aaatatcgaa atag                                               24

<210> SEQ ID NO 554
<211> LENGTH: 21
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding FASTKD1"

<400> SEQUENCE: 554
ccaaaaattc caaagcaatc c                                                  21

<210> SEQ ID NO 555
<211> LENGTH: 25
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding FASTKD1"

<400> SEQUENCE: 555
aagaattaac ttttctgcat ttcca                                              25

<210> SEQ ID NO 556
<211> LENGTH: 22
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding FASTKD1"

<400> SEQUENCE: 556
cagaacagac acctcagttg gt                                                 22
```

```
<210> SEQ ID NO 557
<211> LENGTH: 18
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding GMIP"

<400> SEQUENCE: 557
aaccctggcc atggagac                                                 18

<210> SEQ ID NO 558
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding GMIP"

<400> SEQUENCE: 558
ccgccacttc tcaatctcag                                               20

<210> SEQ ID NO 559
<211> LENGTH: 18
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding GMIP"

<400> SEQUENCE: 559
cccagcacca cagtaccc                                                 18

<210> SEQ ID NO 560
<211> LENGTH: 21
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding GMIP"

<400> SEQUENCE: 560
ctctgtggag ttggaatctc g                                             21

<210> SEQ ID NO 561
<211> LENGTH: 18
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding GMIP"

<400> SEQUENCE: 561
ctggtggccc atctgttc                                                 18

<210> SEQ ID NO 562
<211> LENGTH: 21
<212> TYPE: DNA
<213> ORGANISM: Artificial Sequence
<220> FEATURE:
<221> NAME/KEY: Source
<223> OTHER INFORMATION: /note="Description of Artificial Sequence:
```

Primer amplifying the nucleotide sequence encoding GMIP"

<400> SEQUENCE: 562
ggttgttggc agacatcttg t					21

<210> SEQ ID NO 563
<211> LENGTH: 25
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding IKBKE"

<400> SEQUENCE: 563
acagttcaag aagtctagga tgagg				25

<210> SEQ ID NO 564
<211> LENGTH: 23
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding IKBKE"

<400> SEQUENCE: 564
tggctaaatg actgaaattc acc				23

<210> SEQ ID NO 565
<211> LENGTH: 21
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding IKBKE"

<400> SEQUENCE: 565
ggacatccct cctctacctc a					21

<210> SEQ ID NO 566
<211> LENGTH: 18
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding IKBKE"

<400> SEQUENCE: 566
ggatctcagg cgttccag					18

<210> SEQ ID NO 567
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding IKBKE"

<400> SEQUENCE: 567
ctgcctgagg atgagttcct					20

<210> SEQ ID NO 568
<211> LENGTH: 19

```
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding IKBKE"

<400> SEQUENCE: 568
gatgcacaat gccgttctc                                                    19

<210> SEQ ID NO 569
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding P2RX4"

<400> SEQUENCE: 569
ccgttacgac caaggtcaag                                                   20

<210> SEQ ID NO 570
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding P2RX4"

<400> SEQUENCE: 570
tgacgaagag ggagttttcc                                                   20

<210> SEQ ID NO 571
<211> LENGTH: 21
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding P2RX4"

<400> SEQUENCE: 571
tctgtcaaga cgtgtgaggt g                                                 21

<210> SEQ ID NO 572
<211> LENGTH: 23
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding P2RX4"

<400> SEQUENCE: 572
agtgaagttt tctgcagcct tta                                               23

<210> SEQ ID NO 573
<211> LENGTH: 21
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding P2RX4"

<400> SEQUENCE: 573
```

```
tctcctggct acaatttcag g                                              21
```

<210> SEQ ID NO 574
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding P2RX4"

<400> SEQUENCE: 574

```
atgccatagg ccttgatgag                                                20
```

<210> SEQ ID NO 575
<211> LENGTH: 21
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding P4HB"

<400> SEQUENCE: 575

```
gcttccccca aggaatatac a                                              21
```

<210> SEQ ID NO 576
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding P4HB"

<400> SEQUENCE: 576

```
tcttcagcca gttcacgatg                                                20
```

<210> SEQ ID NO 577
<211> LENGTH: 18
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding P4HB"

<400> SEQUENCE: 577

```
gcagggqatg atgacgat                                                  18
```

<210> SEQ ID NO 578
<211> LENGTH: 19
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding P4HB"

<400> SEQUENCE: 578

```
cgtcttcctc catgtctgg                                                 19
```

<210> SEQ ID NO 579
<211> LENGTH: 19
<212> TYPE: DNA
<213> ORGANISM: Artificial Sequence
<220> FEATURE:
<221> NAME/KEY: Source
<223> OTHER INFORMATION: /note="Description of Artificial Sequence:
     Primer amplifying the nucleotide sequence encoding P4HB"

<400> SEQUENCE: 579
ctggagggca aaatcaagc                                                19

<210> SEQ ID NO 580
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
     Primer amplifying the nucleotide sequence encoding P4HB"

<400> SEQUENCE: 580
ttcttcccaa caagcacctt                                               20

<210> SEQ ID NO 581
<211> LENGTH: 22
<212> TYPE: DNA
<213> ORGANISM: Artificial Sequence
<220> FEATURE:
<221> NAME/KEY: Source
<223> OTHER INFORMATION: /note="Description of Artificial Sequence:
     Primer amplifying the nucleotide sequence encoding PHKG2"

<400> SEQUENCE: 581
gcagatccga ctttcagatt tc                                            22

<210> SEQ ID NO 582
<211> LENGTH: 19
<212> TYPE: DNA
<213> ORGANISM: Artificial Sequence
<220> FEATURE:
<221> NAME/KEY: Source
<223> OTHER INFORMATION: /note="Description of Artificial Sequence:
     Primer amplifying the nucleotide sequence encoding PHKG2"

<400> SEQUENCE: 582
ggggtcccac acaactctc                                                19

<210> SEQ ID NO 583
<211> LENGTH: 21
<212> TYPE: DNA
<213> ORGANISM: Artificial Sequence
<220> FEATURE:
<221> NAME/KEY: Source
<223> OTHER INFORMATION: /note="Description of Artificial Sequence:
     Primer amplifying the nucleotide sequence encoding PHKG2"

<400> SEQUENCE: 583
ttccagcact gtcaaagacc t                                             21

<210> SEQ ID NO 584
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
     Primer amplifying the nucleotide sequence encoding PHKG2"

<400> SEQUENCE: 584
aaagaagggg tgctgtaggg                                               20

<210> SEQ ID NO 585

```
<211> LENGTH: 19
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding PHKG2"

<400> SEQUENCE: 585
aggctatggc aaggaggtc                                                   19

<210> SEQ ID NO 586
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding PHKG2"

<400> SEQUENCE: 586
tgcgtaacat caggatctgc                                                  20

<210> SEQ ID NO 587
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding PPFIBP2"

<400> SEQUENCE: 587 agggggataag gagtccctca                                                 20

<210> SEQ ID NO 588
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding PPFIBP2"

<400> SEQUENCE: 588
ctggtgtcct tccagacaca                                                  20

<210> SEQ ID NO 589
<211> LENGTH: 21
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding PPFIBP2"

<400> SEQUENCE: 589
gaatggaagc taaaggccac t                                                21

<210> SEQ ID NO 590
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding PPFIBP2"

<400> SEQUENCE: 590
```
atctttcagg gccacctgtt                     20

<210> SEQ ID NO 591
<211> LENGTH: 21
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding PPFIBP2"

<400> SEQUENCE: 591
aatcttcgag ggagtggagt c                   21

<210> SEQ ID NO 592
<211> LENGTH: 18
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding PPFIBP2"

<400> SEQUENCE: 592
cagggtgtcc ccagtgaa                       18

<210> SEQ ID NO 593
<211> LENGTH: 19
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding PPPIR16A"

<400> SEQUENCE: 593
ccctcccagt gttgtcctt                      19

<210> SEQ ID NO 594
<211> LENGTH: 18
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding PPPIR16A"

<400> SEQUENCE: 594
ccccactccc aaggaact                       18

<210> SEQ ID NO 595
<211> LENGTH: 18
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding PPPIR16A"

<400> SEQUENCE: 595
gagtgctgga cgcctctg                       18

<210> SEQ ID NO 596
<211> LENGTH: 18
<212> TYPE: DNA
<213> ORGANISM: Artificial Sequence
<220> FEATURE:

```
<221> NAME/KEY: Source
<223> OTHER INFORMATION: /note="Description of Artificial Sequence:
      Primer amplifying the nucleotide sequence encoding PPPIR16A"

<400> SEQUENCE: 596
ttgaccgcca ggagattg                                                   18

<210> SEQ ID NO 597
<211> LENGTH: 21
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding PPPIR16A"

<400> SEQUENCE: 597
atgccctatg acctgtgtga t                                               21

<210> SEQ ID NO 598
<211> LENGTH: 19
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding PPPIR16A"

<400> SEQUENCE: 598
gatgctgtcc tgggtgatg                                                  19

<210> SEQ ID NO 599
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding RASSF7"

<400> SEQUENCE: 599
cactagccca agcaataggc                                                 20

<210> SEQ ID NO 600
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding RASSF7"

<400> SEQUENCE: 600
cactcttgtg gcagcaactg                                                 20

<210> SEQ ID NO 601
<211> LENGTH: 18
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding RASSF7"

<400> SEQUENCE: 601
cagcctggct ctggtgag                                                   18
```

```
<210> SEQ ID NO 602
<211> LENGTH: 19
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding RASSF7"

<400> SEQUENCE: 602
ggagctctcg gttcagctc                                              19

<210> SEQ ID NO 603
<211> LENGTH: 18
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding RASSF7"

<400> SEQUENCE: 603
tctgcctcca gccagaga                                               18

<210> SEQ ID NO 604
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding RASSF7"

<400> SEQUENCE: 604
ctccaggagt tctgcgtcat                                             20

<210> SEQ ID NO 605
<211> LENGTH: 21
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding RNF183"

<400> SEQUENCE: 605
tccagagtag tctgcctgac c                                           21

<210> SEQ ID NO 606
<211> LENGTH: 18
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding RNF183"

<400> SEQUENCE: 606
catcctcagc cacacacg                                               18

<210> SEQ ID NO 607
<211> LENGTH: 21
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding RNF183"
```

-continued

<400> SEQUENCE: 607
tccagagtag tctgcctgac c                                              21

<210> SEQ ID NO 608
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding RNF183"

<400> SEQUENCE: 608
tgttgttgaa ggggttccag                                                20

<210> SEQ ID NO 609
<211> LENGTH: 18
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding RNF183"

<400> SEQUENCE: 609
tctgccaccg tgtctacg                                                  18

<210> SEQ ID NO 610
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding RNF183"

<400> SEQUENCE: 610
cggaaacact ccctcaaaga                                                20

<210> SEQ ID NO 611
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding SIRT6"

<400> SEQUENCE: 611
agctgaggga caccatccta                                                20

<210> SEQ ID NO 612
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding SIRT6"

<400> SEQUENCE: 612
atgtacccag cgtgatggac                                                20

<210> SEQ ID NO 613
<211> LENGTH: 20
<212> TYPE: DNA
<213> ORGANISM: Artificial Sequence

```
<220> FEATURE:
<221> NAME/KEY: Source
<223> OTHER INFORMATION: /note="Description of Artificial Sequence:
      Primer amplifying the nucleotide sequence encoding SIRT6"

<400> SEQUENCE: 613
aggatgtcgg tgaattacgc                                                    20

<210> SEQ ID NO 614
<211> LENGTH: 18
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding SIRT6"

<400> SEQUENCE: 614
agaccagcct cgccagtt                                                      18

<210> SEQ ID NO 615
<211> LENGTH: 18
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding SIRT6"

<400> SEQUENCE: 615
ggtcagccag aacgtgga                                                      18

<210> SEQ ID NO 616
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding SIRT6"

<400> SEQUENCE: 616
gtggagctct gccagtttgt                                                    20

<210> SEQ ID NO 617
<211> LENGTH: 18
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding TJP3"

<400> SEQUENCE: 617
gtgggcatct tcgtgtcc                                                      18

<210> SEQ ID NO 618
<211> LENGTH: 19
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding TJP3"

<400> SEQUENCE: 618
gaatggcacg tcattcacc                                                     19
```

<210> SEQ ID NO 619
<211> LENGTH: 18
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding TJP3"

<400> SEQUENCE: 619
atctggacgg cggaagat                                                18

<210> SEQ ID NO 620
<211> LENGTH: 21
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding TJP3"

<400> SEQUENCE: 620
ggtgagggag gtctaggttg t                                            21

<210> SEQ ID NO 621
<211> LENGTH: 23
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding TJP3"

<400> SEQUENCE: 621
tcatcaagca cattacagat tcg                                          23

<210> SEQ ID NO 622
<211> LENGTH: 19
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding TJP3"

<400> SEQUENCE: 622
ggctagacac cccgttgat                                               19

<210> SEQ ID NO 623
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding EFEMP2"

<400> SEQUENCE: 623
actcgcaggg ggacttttac                                              20

<210> SEQ ID NO 624
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding EFEMP2"

```
<400> SEQUENCE: 624
catgagggaa ttcatggtga                                              20

<210> SEQ ID NO 625
<211> LENGTH: 18
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding EFEMP2"

<400> SEQUENCE: 625
atcgggatgg cttctcct                                                18

<210> SEQ ID NO 626
<211> LENGTH: 19
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding EFEMP2"

<400> SEQUENCE: 626
tgatgcagcg gtactgaca                                               19

<210> SEQ ID NO 627
<211> LENGTH: 19
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding EFEMP2"

<400> SEQUENCE: 627
agtaccgctg catcaacga                                               19

<210> SEQ ID NO 628
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding EFEMP2"

<400> SEQUENCE: 628
cgcaccagac tcacactcat                                              20

<210> SEQ ID NO 629
<211> LENGTH: 18
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding SOCS2"

<400> SEQUENCE: 629
ggagctcggt cagacagg                                                18

<210> SEQ ID NO 630
<211> LENGTH: 25
<212> TYPE: DNA
```

```
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding SOCS2"

<400> SEQUENCE: 630
ctaatcaaga aagttccttc tggtg                                          25

<210> SEQ ID NO 631
<211> LENGTH: 18
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding SOCS2"

<400> SEQUENCE: 631
cagtcaccaa gccccttc                                                  18

<210> SEQ ID NO 632
<211> LENGTH: 19
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding SOCS2"

<400> SEQUENCE: 632
aagggatggg gctctttct                                                 19

<210> SEQ ID NO 633
<211> LENGTH: 18
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding SOCS2"

<400> SEQUENCE: 633
ggagctcggt cagacagg                                                  18

<210> SEQ ID NO 634
<211> LENGTH: 21
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding SOCS2"

<400> SEQUENCE: 634
gttccttctg gtgcctcttt t                                              21

<210> SEQ ID NO 635
<211> LENGTH: 25
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding DCN"

<400> SEQUENCE: 635
ggagacttta agaacctgaa gaacc                                          25
```

-continued

```
<210> SEQ ID NO 636
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding DCN"

<400> SEQUENCE: 636
cgttccaact tcaccaaagg                                             20

<210> SEQ ID NO 637
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding DCN"

<400> SEQUENCE: 637
ctgtcaatgc catcttcgag                                             20

<210> SEQ ID NO 638
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding DCN"

<400> SEQUENCE: 638
gatcctttgg cactttgtcc                                             20

<210> SEQ ID NO 639
<211> LENGTH: 23
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding DCN"

<400> SEQUENCE: 639
caatatcacc agcattcctc aag                                         23

<210> SEQ ID NO 640
<211> LENGTH: 20
<212> TYPE: DNA
<213> ORGANISM: Artificial Sequence
<220> FEATURE:
<221> NAME/KEY: Source
<223> OTHER INFORMATION: /note="Description of Artificial Sequence:
      Primer amplifying the nucleotide sequence encoding DCN"

<400> SEQUENCE: 640
ctgctgattt tgttgccatc                                             20
```

MARKERS FOR ENDOMETRIAL CANCER

FIELD OF THE INVENTION

The invention relates to the detection diagnosis, and prognosis of uterine cancer. The invention relates to the surprising finding that biomarkers corresponding to ACAA1, AP1M2, CGN, DDR1, EPS8L2, FASTKD1, GMIP, IKBKE, P2RX4, P4HB, PHKG2, PPFIBP2, PPP1R16A, RASSF7, RNF183, SIRT6, TJP3, EFEMP2, SOCS2, and DCN are differentially expressed in control samples as compared to samples from patients having endometrial cancer and are therefore useful for detecting endometrial cancer. In particular these biomarkers having excellent sensitivity, specificity, and/or the ability to separate affected from non affected individuals. Furthermore, the inventors found that the differential expression of these biomarkers in primary endometrial cancer tumor tissue is correlated to their expression level in uterine fluid samples as compared to control values. Thus these biomarkers are robust in that they are found to be differentially expressed in several different types of samples from affected and individuals.

BACKGROUND OF THE INVENTION

Each year in Europe there are about 150,000 new cases of endometrial cancer and about 46,000 women die from the disease (Ferlay et al. (2007) *Ann. Onc.* 18:581-592). In the United States, about 41,000 new case of endometrial carcinoma are diagnosed per year and 7,300 women die each year (see American Cancer Society statistics available on the internet). The incidence and death rate from endometrial cancer are increasing.

Endometrial cancer (EC) is the most frequent invasive tumors of the female genital tract and the fourth most common in women in western countries (Jemal et al. (2008) *CA Cancer J Clin* 58:71-96). New methods for the diagnosis, prognosis, and classification of endometrial cancer are needed to combat this deadly disease.

Often endometrial cancer is detected early, in its initial stages, by presentation of disease-related symptoms. Unfortunately, 20% of patients present with myometrial invasion and/or lymph node affectation, which are main indicators related to poor prognosis, decrease in survival rate, and more advanced disease. The primary therapeutic modality for endometrial cancer is surgical treatment.

Common symptoms of uterine cancer (e.g., endometrial cancer) include unusual vaginal bleeding or discharge, trouble urinating, pelvic pain, and pain during intercourse. Uterine cancer usually occurs after menopause. Other risk factors for endometrial cancer include being obese, taking estrogen-alone hormone replacement therapy, treatment with tamixofen and having a genetic predisposition to cancer (e.g., Lynch Syndrome). The standard treatment for endometrial cancer varies depending on the stage of the disease. Treatment usually involves surgery to remove the uterus which is called a hysterectomy, although other options include hormone therapy and radiotherapy.

Methods routinely used in the clinic for diagnosing endometrial cancer include biopsy followed by cytological analysis and/or trans-vaginal ultrasound. The diagnosis of endometrial carcinoma is usually done by pathology examination of an endometrial aspirate (20-30%), and by biopsy-guided hysteroscopy (70-80%). The rate of success of diagnosis with hysteroscopy is over 90%, with false positives in the case of precursor lesions of the endometrial adenocarcinoma (hyperplasias); endometrial polyps, that present a non-negligible degree of malignancy (0-4.8%) and must be removed although asymptomatic or benign appearance; or in the case of diffuse forms of endometrial adenocarcinomas that are difficult to differentiate from an endometrial hyperplasia. Thus, there is a need for a less invasive diagnostic test based on molecular markers. Such a less invasive test based on molecular markers would allow for more routine screening of uterine cancer. A diagnostic test based of molecular markers obtained in a less invasive manner and that has sensitivity and specificity comparable to that of the endometrial biopsy can preclude unnecessary hysteroscopy.

Endometrial carcinomas can be classified into low grade (type I) and high-grade (type 2). Type I endometrioid endometrial cancer (sometimes called estrogen dependent), which represent approximately 80% of new cases, are low grade tumors associated with estrogen stimulation, usually developed in peri- or post-menopausal women and are usually preceded by endometrial hyperplasia with or without atypia. Type II non-endometrioid endometrial cancer usually affects older women, are less differentiated and of worse prognosis, not associated with estrogen stimulation, and are related to atrophic endometrium or, occasionally, with endometrial polyps.

Type I cancers are typically known to have alterations in PTEN, KRAS2, DNA mismatch repair defects, CTNNB1, and have near diploid karyotype. Type II cancers typically have TP53 mutations and ErBB2 overexpression and are mostly non-diploid. Sugiyama et al. ((2003) *Clin. Can. Res.* 9:5589-5600) reported that certain genes are selectively up or down regulated in type I versus type II endometrial cancers. For example, they found that MLH1 was down-regulated in type I cancers as well as other genes related to DNA damage signaling and repair like $O^6$-methyl-guanine DNA methyltransferase, DNA polymerase α catalytic subunit, and Ku (p70/p80) antigen. VEGF-C was found to be upregulated in type I cancers at the protein and mRNA level as compared to type II cancers. KRAS was found to be upregulated in type II cancers. STAT1 was upregulated in type I cancers and STAT2 was upregulated in type II cancers. Konecny et al. ((2009) *British Journal of Cancer* 100, 89-95) report that the rate HER2 gene amplification as measured by fluorescence in situ hybridization was greater in type II cancers whereas EGFR expression as measured by IHC techniques was significantly lower in type II cancers. Deng et al. ((2005) *Clin. Can. Res.* vol. 11, no 23:8258-8264) report that EIG121 is a marker for type I estrogen associated cancers.

Uterine cancers are also classified histologically according to cell-type. The most common cell-type is referred to endometrioid and represents around 80% of the newly diagnosed cases. Other less common uterine cancers are referred to as serous and clear cell carcinomas. Most of the type I cancers are of the endometrioid cell-type whereas the type II cancers are more likely to be non-endometrioid uterine cancers. Type II cancers are more likely to metastasize and have a poorer prognosis than type I cancers. Type I cancers typically have a better prognosis and respond better to therapy.

A number of studies have examined gene-expression profiles for classifying uterine cancers. Sugiyama et al. ((2003) *Clin. Canc. Res.* 9:5589-5600) report that between the type I and II cancers 45 gene were highly expressed in type I cancers and 24 highly expressed in type I cancers. Risinger et al. ((2003) *Canc. Res.* 63:6-11) report that microarray analysis of different histologic subtypes of endometrial cancer have distinct gene expression profiles. They found that 191 genes exhibited greater than 2-fold difference in expression between endometrioid and non-endometrioid endometrial cancers.

A number of endometrial cancer biomarkers for endometrial cancer have been identified. Elevated levels of CA 125, CA 15-3, and CA 19-9 are associated with shorter survival time. CA 125 correlates with tumor size and stage and is an independent predictor of the extrauterine spread.

Serum markers for the detection of uterine cancer have been reported in the literature. Yurkovetsky et al. ((2007) *Gyn. Onc.* 107:58-65) identified that prolactin is a serum biomarker with sensitivity and specificity for endometrial cancer. They found serum CA 125, CA 15-3, and CEA, are higher in patients with Stage III disease as compared to stage I. A five-biomarker panel of prolactin, GH, eotaxin, E-selectin, and TSH discriminated endometrial cancer from ovarian and breast cancer.

Another important issue for clinicians for diagnosis of endometrial cancer relates to synchronous cancers. Guirguis et al. (*Gyn. Onc.* (2008) 108:370-376) have reported that 10% of ovarian cancer patients have a tumor in the endometrium and 5-25% of patients with endometrial cancer also have a tumor in the ovary. Determining the primary site of a cancer has important treatment implications. Stage III endometrial carcinoma is treated with surgery followed by chemotherapy and/or radiation; while dual primary stage I ovarian and endometrial cancers have a better prognosis and may not require adjuvant therapy.

Current methods of diagnosing endometrial cancer often create discomfort to the patient and sometimes rely on subjective interpretation of visual images. There is a need for less invasive methods of screening for endometrial cancer which are less subjective in interpretation. In addition there is a need for new markers that are useful for the early detection of endometrial cancer. Current methods for detecting endometrial cancer include the dilation and curettage method which is considered the gold standard, but this method is invasive, can cause significant discomfort, and may require a trained pathologist for interpretation, and therefore is not suitable as a general screening tool. Another less invasive method for diagnosing endometrial cancer involves transvaginal ultrasound which measures the thickness of the endometrium. In a study of patients having post-menopausal bleeding, using a cutoff of 4 mm, it was found that transvaginal ultrasound had 100% sensitivity and 60% specificity (Gull et al. (2003) *Am. J. Obstet. Gynecol.* 188 (2):401-408). In women without vaginal bleeding, the sensitivity of the endometrial thickness measurement was 17% for a threshold 6 mm and 33% for a threshold of 5 mm (Fleischer et al. (2001) *Am. J. Obstet. Gynecol.* 184:70-75). TVS has a high rate of false positives since other conditions besides endometrial cancer can produce a thicker endometrium. One potential problem with the use of TVS in pre- and peri-menopausal women is that the thickness of the endometrium varies as a function of the phase of the menstrual cycle. Furthermore, women taking tamoxifen also have thicker endometrium. Therefore there is a need for techniques and markers that can complement and/or improve the ability of TVS in the diagnosis of endometrial cancer.

Clearly there is room for improvement in the tools currently available for screening for endometrial cancer.

BRIEF SUMMARY OF THE INVENTION

The invention relates to the surprising finding that biomarkers corresponding to ACAA1, AP1M2, CGN, DDR1, EPS8L2, FASTKD1, GMIP, IKBKE, P2RX4, P4HB, PHKG2, PPFIBP2, PPP1R16A, RASSF7, RNF183, SIRT6, TJP3, EFEMP2, SOCS2, and DCN are differentially expressed in control samples as compared to samples from patients having endometrial cancer and are therefore useful for detecting endometrial cancer. In particular these biomarkers having excellent sensitivity, specificity, and/or the ability to separate affected from non affected individuals. Furthermore, the inventors found that the differential expression of these biomarkers in primary endometrial cancer tumor tissue is correlated to their expression level in uterine fluid samples as compared to control values. Thus, these biomarkers are robust in that they are found to be differentially expressed in several different types of samples from affected individuals as compared to non-affected individuals.

Therefore, the present invention relates to an in vitro diagnostic method for the diagnosis of endometrial cancer or an increased likelihood of endometrial comprising detecting the level of (1) from 1 to 17 biomarker(s) chosen from ACAA1, AP1M2, CGN, DDR1, EPS8L2, FASTKD1, GMIP, IKBKE, P2RX4, P4HB, PHKG2, PPFIBP2, PPP1R16A, RASSF7, RNF183, SIRT6, and TJP3 in a sample from a patient wherein an increased level of said from 1 to 17 biomarkers compared to a control value indicates a diagnosis of endometrial cancer or increased likelihood of endometrial cancer and/or (2) detecting the level of from 1 to 3 biomarkers chosen from EFEMP2, SOCS2, and DCN, wherein a decreased level of EFEMP2, SOCS2, and/or DCN compared to a control value indicates a diagnosis of endometrial cancer or increased likelihood of endometrial cancer.

Accordingly, the present invention relates to an in vitro diagnostic method for the diagnosis of endometrial cancer comprising (1) detecting the level of from 1 to 17 biomarker(s) chosen from P4HB, GMIP, IKBKE, FASTKD1, DDR1, SIRT6, PHKG2, ACAA1, AP1M2, EPS8L2, P2RX4, PPFIBP2, PPP1R16A, CGN, RASSF7, RNF183, and TJP3 in a sample from a patient wherein an increased level of said from 1 to 17 biomarkers compared to a control value indicates the existence of endometrial cancer and/or (2) detecting the level of from 1 to 3 biomarkers chosen from EFEMP2, SOCS2, and DCN, wherein a decreased level of EFEMP2, SOCS2, and/or DCN compared to a control value indicates the existence of endometrial cancer.

The biomarkers of Table 1 were found to be differential expressed between endometrial cancer samples and normal samples as determined by microarray studies (see Table 1 in the Detailed Description of the Invention). The inventors have found that individually each of the biomarkers of Table 1 have predictive value for the diagnosis of endometrial cancer. Furthermore, the levels of combinations of markers of Table 1 have additional predictive value for the diagnosis of endometrial cancer (See Example 5). For example, the inventors have surprisingly found that sub-groups of the biomarkers of Table 1 having from 2-20 biomarkers in various combinations to give fingerprint patterns have excellent predictive value for diagnosis or detection of endometrial cancer. Generally, if more than one of the biomarkers of Table 1 are differentially expressed in a sample, this increases the likelihood that the individual has endometrial cancer. Moreover, the inventors have also found that addition of other biomarkers besides those listed in Table 1, to the fingerprint pattern also can increase predictive value, and can be useful for classifying endometrial cancers, for differential diagnosis of diseases other than endometrial cancer, and for endometrial cancer prognosis. Table 1 lists the ENSEMBL accession numbers for the genes, mRNA, and proteins corresponding to the biomarkers of the invention. Some of the biomarkers have alternative transcripts. The invention relates to determining the differential expression of any of these alternative transcripts (or protein isoforms) as long as it expression is correlated with the absence or presence of endometrial cancer. Preferred transcripts (or protein isoforms) for detecting endometrial cancer are those which were detected with the array probes as indicated in the Examples.

The inventors have also found that the markers of Table 1 can be detected in uterine fluid samples and that the level of expression of these markers are correlated in primary tumor and uterine fluid (e.g., obtained by a uterine wash or aspiration).

The invention therefore provides methods for determining the level of from 1 to 20 of the biomarkers listed in Table 1 in a test sample. The method can comprise providing or obtaining a test sample from the patient; determining the level of from 1 to 20 of the biomarkers of Table 1 in the sample; and comparing the level of the biomarker(s) in the test sample(s) to a control value (e.g., control sample, control value, or control score). A higher level of biomarker(s) which was found to be overexpressed in endometrial cancer as shown in Table 1 in the test sample obtained from the patient compared to the control value (e.g., control sample, control value, and/or control score) indicates endometrial cancer, an increased likelihood of endometrial cancer, and/or a precancerous condition (e.g., endometrial hyperplasia). A lower level of biomarker(s) which was found to be underexpressed in endometrial cancer as shown in Table 1 in the test sample obtained from the patient compared to level in the control value (e.g., control sample, control value, and/or control score) indicates endometrial cancer, an increased likelihood of endometrial cancer, and/or a precancerous condition (e.g., endometrial hyperlasia). The level of the biomarker(s) can be determined using appropriate assays, including RT-PCR, quantitative PCR, multiplex PCR, Northern hybridization, microarray analysis, two-hybrid assays such as GAL4 DNA binding domain based assays, antibody based assays, EIA, blot assays, sandwich assays, and the like. The level of the biomarkers of Table 1 can be determined in body fluids and tissues for the diagnosis of endometrial cancer. The level of the biomarkers of Table 1 can be determined in tumor tissue obtained by biopsy for example. The level of the biomarkers of Table 1 can be determined in samples obtained from uterine aspirates and/or fluid. The level of the biomarkers of Table 1 can be determined in blood, serum, or plasma.

The biomarkers of Table 1 include ACAA1, AP1M2, CGN, DDR1, EPS8L2, FASTKD1, GMIP, IKBKE, P2RX4, P4HB, PHKG2, PPFIBP2, PPP1R16A, RASSF7, RNF183, SIRT6, and TJP3, which were found to be upregulated in endometrial cancer and DCN, SOCS2, and EFEMP2 which were found to be down regulated in endometrial cancer in these studies. In one embodiment, the biomarkers for use in the method of the invention for detecting endometrial cancer or an increased likelihood of endometrial cancer include from 1 to 17 of the upregulated biomarkers listed in Table 1 and from 1 to 3 of the downregulated markers listed in Table 1.

In one embodiment, the invention provides a method for diagnosing endometrial cancer comprising obtaining a sample from an individual and determining the level of one or more biomarkers chosen from ACAA1, AP1M2, CGN, DDR1, EPS8L2, FASTKD1, GMIP, IKBKE, P2RX4, P4HB, PHKG2, PPFIBP2, PPP1R16A, RASSF7, RNF183, SIRT6, TJP3, EFEMP2, SOCS2, and DCN wherein if said markers are differentially expressed compared to a control value, then the individual is diagnosed with endometrial cancer and/or an increased likelihood of endometrial cancer. According to one aspect of this embodiment, the sample is chosen from a tissue sample and a fluid sample. In one aspect, the fluid sample is a uterine fluid sample or uterine aspirate. According to one aspect of this embodiment, the level of mRNA corresponding to the biomarker is determined. According to one aspect of this embodiment, the level of protein corresponding to the biomarker is determined.

Accordingly, the present invention relates to an in vitro diagnostic method for the diagnosis of endometrial cancer comprising
(1) detecting the level of one or more biomarker(s) chosen from P4HB, GMIP, IKBKE, FASTKD1, DDR1, SIRT6, PHKG2, ACAA1, AP1M2, EPS8L2, P2RX4, PPFIBP2, PPP1R16A, CGN, RASSF7, RNF183, and TJP3 in a sample from a patient wherein an increased level of said one or more biomarkers compared to a control value indicates the existence of endometrial cancer and/or
(2) detecting the level of one or more biomarkers chosen from EFEMP2, SOCS2, and DCN, wherein a decreased level of EFEMP2, SOCS2, and/or DCN compared to a control value indicates the existence of endometrial cancer.

In a further embodiment, the present invention relates to an in vitro diagnostic method for the diagnosis of endometrial cancer comprising
(1) detecting the level of from 1 to 17 biomarker(s) chosen from P4HB, GMIP, IKBKE, FASTKD1, DDR1, SIRT6, PHKG2, ACAA1, AP1M2, EPS8L2, P2RX4, PPFIBP2, PPP1R16A, CGN, RASSF7, RNF183, and TJP3 in a sample from a patient wherein an increased level of said from 1 to 17 biomarkers compared to a control value indicates the existence of endometrial cancer and/or
(2) detecting the level of from 1 to 3 biomarkers chosen from EFEMP2, SOCS2, and DCN, wherein a decreased level of EFEMP2, SOCS2, and/or DCN compared to a control value indicates the existence of endometrial cancer.

In one embodiment, the in vitro diagnostic method comprises detecting the level of P4HB. In another embodiment, the in vitro diagnostic method comprises detecting the level of EFEMP2. In a further embodiment the in vitro method comprises detecting the level of IKBKE. In a further embodiment the in vitro diagnostic method comprises detecting the level of GMIP.

In accordance with the in vitro diagnostic method of the invention, the level of one or more of GMIP, IKBKE, or EFEMP2 may be detected in addition to P4HB. The in vitro diagnostic method may further comprise detecting the level of one or more of P4HB, IKBKE, or GMIP in addition to EFEMP2. The in vitro diagnostic method may further comprise detecting the level of one or more of GMIP, EFEMP2, or P4HB in addition to IKBKE. It is also envisaged that the in vitro diagnostic method may further comprise detecting the level of FASTKD1, DDR1, SIRT6, and/or PHKG2. The in vitro diagnostic method may further comprise detecting the level of from 1 to 12 biomarkers chosen from ACAA1, AP1M2, EPS8L2, P2RX4, PPFIBP2, PPP1R16A, CGN, RASSF7, RNF183, TJP3, SOCS2, and DCN.

In one embodiment, the patient has a risk factor for endometrial cancer or is being screened for endometrial cancer. Further, the sample from the patient may be (obtained) from a patient with abnormal uterine bleeding. In other words, the patient may suffer from abnormal uterine bleeding. The sample from said patient may also be (obtained) from a patient having an endometrium with increased thickness. The patient may, accordingly, have an endometrium with increased thickness.

The sample from the patient may be (obtained) from a pre-menopausal, peri-menopausal, or post-menopausal patient. Accordingly, the patient is a pre-menopausal, peri-menopausal, or post-menopausal patient. In one embodiment, the patient is pre-menopausal. In another embodiment, the patient is peri-menopausal. In a further embodiment, the patient is post-menopausal.

The sample may be a tissue sample, blood and/or serum, and/or uterine fluid. In one embodiment, the sample is a uterine fluid sample. The uterine fluid sample may be obtained by aspiration.

In one embodiment, the level of the biomarkers is determined with an antibody in accordance with the present invention. The level of the biomarker(s) may also be determined by RT-PCR.

The following markers may be detected in accordance with the in vitro diagnostic method of the present invention: P4HB, IKBKE, EFEMP2, SOCS2, FASTKD1, GMIP, DDR1, SIRT6, PHKG2, EPS8L2, PPP1R16A, P2RX4, RASSF7, and/or TJP3. Also the following markers may be detected in accordance with the in vitro diagnostic method of the present invention: P4HB, IKBKE, SOCS2, GMIP, DDR1, SIRT6, PHKG2, EPS8L2, PPP1R16A, P2RX4, RASSF7, and/or TJP3.

The markers to be detected may be P2RX4, P4HB, PHKG2, PPFIBP2, and/or SOCS2. The markers to be detected may also be P4HB, RASSF7, RNF183 and/or IKBKE.

In one embodiment, the in vitro diagnostic method comprises the detection of from 2 to 20 markers.

Preferably, the combination of the following markers is detected: P4HB, EFEMP2, SIRT6, GMIP, FASTKD1 and DDR1. Also preferred is the detection of a combination of the following markers: P4HB, EFEMP2, SIRT6, GMIP, FASTKD1 and PHKG2. Also preferred is the detection of a combination of the following markers: P4HB, EFEMP2, SIRT6, ACAA1, AP1M2, EPS8L2, IKBKE, P2RX4, PPFIBP2 and PPP1R16A.

The following marker combinations are also preferably detected in accordance with the present invention:
GMIP, IKBKE, PFHB, EFEMP2;
DDR1, FASTKD1, GMIP, IKBKE, P4HB, PHKG2, SIRT6, EFEMP2;
P4HB, EFEMP2, IKBKE, GMIP, FASTKD1.

In context of the present invention combinations of markers which include a combination with P4HB (i.e. set of markers including P4HB) are particularly preferred.

Also envisaged herein is the detection of the following combination of markers:
DDR1, FASTKD1, GMIP, IKBKE, P4HB, PHKG2, SIRT6, EFEMP2; SOCS2;
P4HB, SOCS2;
GMIP, IKBKE, P4HB, SOCS2;
GMIP, IKBKE, P4HB, SOCS2, FASTKD1;
GMIP, IKBKE, P4HB, SOCS2, DDR1;
GMIP, IKBKE, P4HB, SOCS2, PHKG2;
GMIP, IKBKE, P4HB, SOCS2, SIRT6;
GMIP, IKBKE, P4HB, SOCS2, ACAA1;
GMIP, IKBKE, P4HB, SOCS2, AP1M2;
GMIP, IKBKE, P4HB, SOCS2, EFEMP2;
GMIP, IKBKE, P4HB, SOCS2, EPS8L2;
GMIP, IKBKE, P4HB, SOCS2, P2RX4;
GMIP, IKBKE, P4HB, SOCS2, PPFIB2;
GMIP, IKBKE, P4HB, SOCS2, PPP1R16A;
GMIP, IKBKE, P4HB, SOCS2, ACAA1, FASTKD1;
GMIP, IKBKE, P4HB, SOCS2, FASTKD1, PHKG2;
GMIP, IKBKE, P4HB, SOCS2, FASTKD1, SIRT6;
GMIP, IKBKE, P4HB, SOCS2;

One or more additional biomarkers may be detected in accordance with the herein disclosed in vitro diagnostic method. The one or more additional biomarkers may be chosen from differential diagnosis biomarkers, prognostic biomarkers, biomarkers useful for detecting endometrial cancer, biomarkers for classify endometrial cancer and auxiliary biomarkers for detecting endometrial cancer. In one embodiment, the one or more additional biomarkers are chosen from differential diagnosis biomarkers.

The one or more auxiliary biomarkers may be chosen from prognostic markers. The one or more auxiliary biomarkers may be chosen from endometrial cancer classification markers.

In a further embodiment, the present invention relates to a nucleic acid chosen from
IKBKE mRNA, cDNA, or a complement thereof;
P4HB mRNA, cDNA, or a complement thereof;
SOCS2 mRNA, cDNA, or a complement thereof;
GMIP mRNA, cDNA, or a complement thereof;
DDR1 mRNA, cDNA, or a complement thereof;
EPS8L2 mRNA, cDNA, or a complement thereof; and
PPP1R16A mRNA, cDNA, or a complement thereof,
for use in diagnosing endometrial cancer.

The invention also relates to a nucleic acid chosen from
Primers for IKBKE;
Primers for P4HB;
Primers for SOCS2;
Primers for GMIP;
Primers for DDR1;
Primers for EPS8L2; and
Primers for PPP1R16A;
for use in diagnosing endometrial cancer.

In one embodiment, the invention relates to a nucleic acid chosen from
probe for IKBKE;
probe for P4HB;
probe for SOCS2;
probe for GMIP;
probe for DDR1;
probe for EPS8L2; and
probe for PPP1R16A,
for use in diagnosing endometrial cancer.

Also a kit comprising two or more of the herein described probes for use in diagnosing endometrial cancer is envisaged in context of the present invention. Further, a kit comprising primers for two or more herein disclosed primers/primer pairs for use in diagnosing endometrial cancer is envisaged in context of the present invention.

In a further embodiment, the present invention relates to an antibody chosen from an antibody to IKBKE;
an antibody to P4HB;
an antibody to SOCS2;
an antibody to GMIP;
an antibody to DDR1;
an antibody to EPS8L2; and
an antibody to PPP1R16A,
for use in diagnosing endometrial cancer.

Accordingly, a kit comprising antibodies to two or more herein disclosed antibodies for use in diagnosing endometrial cancer is envisaged. The invention further relates to a kit for obtaining uterine fluid for use in diagnosing endometrial cancer by assessing the levels of from 1-20 biomarkers as defined and described herein.

The in vitro diagnostic method of the present invention may comprise determining/detecting the level of 2 biomarkers, 3 biomarkers, 4 biomarkers, 5 biomarkers, 7 biomarkers, 10 biomarkers, 15 biomarkers or 20 biomarkers.

In one embodiment, the present invention relates to an in vitro diagnostic method for diagnosing endometrial cancer comprising obtaining a uterine fluid aspirate sample from a patient having a symptom or risk factor for endometrial cancer and determining the level of from 1 to 100 biomarkers markers that are differentially expressed in endometrial cancer as compared to control values representative of individuals not affected by endometrial cancer, wherein (1) if the levels of 1 to 100 biomarkers are upregulated in the endometrial aspirate sample in the patient and in the control value then the patient has an increased likelihood of having endometrial cancer and wherein (2) if the level of the 1 to 100 biomarkers are downregulated in the aspirate sample and then the patient has an increased likelihood of having endometrial cancer.

The present invention further relates to a nucleic acid chosen from
ACAA1 mRNA, cDNA, or a complement thereof;
AP1M2 mRNA, cDNA, or a complement thereof;
CGN mRNA, cDNA, or a complement thereof;
FASTKD1 mRNA, cDNA, or a complement thereof;
P2RX4 mRNA, cDNA, or a complement thereof;
RASSF7 mRNA, cDNA, or a complement thereof;
RNF183 mRNA, cDNA, or a complement thereof;
PHKG2 mRNA, cDNA, or a complement thereof;
PPFIBP2 mRNA, cDNA, or a complement thereof,
SIRT6 mRNA, cDNA, or a complement thereof,
TJP3 mRNA, cDNA, or a complement thereof;
EFEMP2 mRNA, cDNA, or a complement thereof; and
DCN mRNA, cDNA, or a complement thereof,
for use in diagnosing endometrial cancer.

Also subject of the present invention is a nucleic acid chosen from
Primers for ACAA1;
Primers for AP1M2;
Primers for CGN;
Primers for FASTKD1;
Primers for P2RX4;
Primers for RASSSF7;
Primers for RNF183;
Primers for SIRT6;
Primers for PPFIBP2;
Primers for PHKG2;
Primers for TJP3;
Primers for EFEMP2; and
Primers for DCN;
for use in diagnosing endometrial cancer.

In a further embodiment, the present invention relates to a nucleic acid chosen from
probe for ACAA1;
probe for AP1M2;
probe for CGN;
probe for FASTKD1;
probe for P2RX4;
probe for RASSF7;
probe for RNF183;
probe for SIRT6;
probe for PPFIBP2;
probe for PKHG2;
probe for TJP3;
probe for EFEMP2; and
probe for DCN,
for use in diagnosing endometrial cancer.

In another embodiment, the invention relates to an antibody chosen from
an antibody to ACAA1;
an antibody to AP1M2;
an antibody to CGN;
an antibody to FASTKD1;
an antibody to P2RX4;
an antibody to RASSF7;
an antibody to RNF183;
an antibody to SIRT6;
an antibody to PPFIBP2;
an antibody to PKHG2;
an antibody to TJP3;
an antibody to EFEMP2; and
an antibody to DCN,
for use in diagnosing endometrial cancer.

The antibody/antibodies, nucleic acid(s), probes, primer(s)/primer pair(s), and/or kit(s) described and defined herein are useful in the in diagnosis of endometrial cancer in accordance with the present invention. Therefore the antibody/antibodies, nucleic acid(s), probes, primer(s)/primer pair(s), and/or kit(s) described and defined herein are for use in diagnosing endometrial cancer. Similarly, also the use of the antibody/antibodies, nucleic acid(s), probes, primer(s)/primer pair(s), and/or kit(s) for the preparation of a diagnostic composition for diagnosing endometrial cancer is envisaged. Also a diagnostic composition for use in diagnosing endometrial cancer and comprising the herein described and defined antibody/antibodies, nucleic acid(s), probes, primer(s)/primer pair(s), and/or kit(s) is envisaged in context of the present invention.

Diagnosing endometrial cancer may, in this context, comprise or relate to a diagnostic method practised on the human or animal body which comprises or includes the features relating to
(i) the diagnosis for curative purposes stricto sensu representing the deductive medical or veterinary decision phase as a purely intellectual exercise,
(ii) the preceding steps which are constitutive for making that diagnosis, and
(iii) the specific interactions with the human or animal body which occur when carrying those out among these preceding steps which are of a technical nature.

In a further embodiment, the present invention relates to an in vitro diagnostic method for diagnosing endometrial cancer comprising providing or obtaining a uterine fluid sample from a human patient having a symptom or risk factor for a gynecological cancer and determining the level of RNA expression of from 2 to 9 biomarkers chosen from P4HB, EFEMP2, GMIP, IKBKE, DDR1, FASTKD1, SIRT6, PKHG2, and SOCS2 by quantitative PCR wherein an increased level of from 1 to 7 biomarkers chosen from P4HB, GMIP, IKBKE, DDR1, FASTKD1, SIRT6, and PKHG2 and/or a decreased level of EFEMP2 or SOCS2 as compared to control indicates the existence of endometrial cancer. Preferably, the gynecological cancer is endometrial cancer.

In one embodiment, the expression level of 2 to 8 biomarkers chosen from P4HB, EFEMP2, GMIP, IKBKE, DDR1, FASTKD1, SIRT6, and PKHG2 may be determined. The 2 to 8 biomarkers may also be chosen from P4HB, GMIP, IKBKE, DDR1, FASTKD1, SIRT6, PKHG2, and SOCS2.

The detection of the level may comprise contacting said one or more biomarkers with primers and reagents capable of amplifying specifically said one or more biomarkers and detecting the level of said amplified one or more biomarkers with a probe or probes that hybridize to said amplified biomarker. The probe hybrids specifically to said amplified biomarker.

The following combinations of biomarkers may, in particular, be detected in accordance with the method of the present invention: P4HB and EFEMP2; P4HB and IKBKE; P4HB and GMIP; EFEMP2 and IKBKE; EFEMP2 and P4HB; P4HB, GMIP, and IKBKE; P4HB, GMIP, and IKBKE.

Also the following combination of markers may be detected in accordance with the present method, wherein said combination comprises IKBKE and P4HB; IKBKE and SOCS2; P4HB and SOCS2; GMIP and IKBKE; GMIP and P4HB; GMIP and SOCS2; GMIP, SOCS2, and IKBKE; GMIP, SOCS2, and P4HB; GMIP, IKBKE, and P4HB; IKBKE, P4HB, and SOCS2; GMIP, IKBKE, P4HB, and SOCS2; GMIP, SOCS2, IKBKE, and EPS8L2; GMIP, SOCS2, P4HB, and EPS8L2; GMIP, IKBKE, P4HB, and EPS8L2; IKBKE, P4HB, SOCS2, and EPS8L2; GMIP, IKBKE, P4HB, SOCS2, and DDR1; GMIP, IKBKE, P4HB, SOCS2, EPS8L2, and PPP1R16A; GMIP, IKBKE, P4HB, SOCS2, PHKG2, and RASSF7; GMIP, IKBKE, P4HB, SOCS2, EPS8L2, and DDR1; GMIP, IKBKE, P4HB, SOCS2, EPS8L2, PPP1R16A, and DDR1; DDR1, EPS8L2, GMIP, IKBKE, P2RX4, P4HB, PHKG2, PPP1R16A, RASSF7, SIRT6, TJP3, and SOCS2; or DDR1, EPS8L2, GMIP, IKBKE, P2RX4, P4HB, PHKG2, PPP1R16A, RASSF7, SIRT6, TJP3, RNF183 and SOCS2.

Further, the following combination of markers may be detected in accordance with the present method, wherein said combination comprises GMIP, IKBKE, P4HB, SOCS2 and FASTKD1; GMIP, IKBKE, P4HB, SOCS2 and DDR1; GMIP, IKBKE, P4HB, SOCS2 and PHKG2; GMIP, IKBKE, P4HB, SOCS2 and SIRT6; GMIP, IKBKE, P4HB, SOCS2 and ACAA1; GMIP, IKBKE, P4HB, SOCS2 and EFEMP2; GMIP, IKBKE, P4HB, SOCS2 and EPS8L2; GMIP, IKBKE, P4HB, SOCS2 and P2RX4; GMIP, IKBKE, P4HB, SOCS2 and PPFIBP2; GMIP, IKBKE, P4HB, SOCS2 and PPP1R16A; GMIP, IKBKE, P4HB, SOCS2, ACAA1 and FASTKD1; GMIP, IKBKE, P4HB, SOCS2, PHKG2 and FASTKD1; GMIP, IKBKE, P4HB, SOCS2, SIRT6 and FASTKD1; ACAA1, AP1M2, EPS8L2, IKBKE, P2RX4, P4HB, PPFIBP2, PPP1R16A, SIRT6, and EFEMP2; GMIP, IKBKE, P4HB, and EFEMP2; DDR1, FASTKD1, PHKG2, SIRT6, SOCS2, GMIP, IKBKE, P4HB, and EFEMP2; DDR1, FASTKD1, PHKG2, SIRT6, GMIP, IKBKE, P4HB, and EFEMP2; or P4HB, EFEMP2, IKBKE, GMIP, and FASTKD1.

Further, the following combination of markers may be detected in accordance with the present method, wherein said combination comprises GMIP, IKBKE, P4HB, EFEMP2 and FASTKD1; GMIP, IKBKE, P4HB, EFEMP2 and DDR1; GMIP, IKBKE, P4HB, EFEMP2 and PHKG2; GMIP, IKBKE, P4HB, EFEMP2 and SIRT6; GMIP, IKBKE, P4HB, EFEMP2 and ACAA1; GMIP, IKBKE, P4HB, SOCS2 and EFEMP2; GMIP, IKBKE, P4HB, EFEMP2 and EPS8L2; GMIP, IKBKE, P4HB, EFEMP2 and P2RX4; GMIP, IKBKE, P4HB, EFEMP2 and PPFIBP2; GMIP, IKBKE, P4HB, EFEMP2 and PPP1R16A; GMIP, IKBKE, P4HB, EFEMP2, ACAA1 and FASTKD1; GMIP, IKBKE, P4HB, EFEMP2, PHKG2 and FASTKD1; or GMIP, IKBKE, P4HB, EFEMP2, SIRT6 and FASTKD1.

The methods of the present invention may further comprise providing a uterine fluid sample obtained from a patient with a pipelle device or syringe wherein the patient has a risk factor or symptom of endometrial cancer; contacting said sample with an agent capable of preserving, preventing, or lessening the degradation of RNA in said uterine fluid sample; determining in said sample the expression level of mRNA corresponding to from 1 to 20 herein described markers (preferably 2 to 8 markers) and one or more endogenous genes using quantitative PCR; normalizing the expression level of from 1 to 20 (preferably 2 to 8 markers) herein described biomarkers with the one or more endogenous genes; comparing the normalized level of the from 1 to 20 (preferably 2 to 8 markers) biomarkers to a control value wherein differential expression of from 1 to 20 (preferably 2 to 8 markers) of the biomarkers indicates endometrial cancer or an increased likelihood of endometrial cancer.

The present invention relates further to an in vitro diagnostic method comprising providing a uterine fluid sample obtained from a patient with a pipelle device or syringe wherein the patient has a risk factor or symptom of endometrial cancer; contacting said sample with an agent capable of preserving, preventing, or lessening the degradation of RNA in said uterine fluid sample; determining in said sample the expression level of mRNA corresponding to from 1 to 20 herein described markers (preferably 2 to 8 markers) and one or more endogenous genes using quantitative PCR; normalizing the expression level of from 1 to 20 (preferably 2 to 8 markers) herein described biomarkers with the one or more endogenous genes; comparing the normalized level of the from 1 to 20 (preferably 2 to 8 markers) biomarkers to a control value wherein differential expression of from 1 to 20 (preferably 2 to 8 markers) of the biomarkers indicates endometrial cancer or an increased likelihood of endometrial cancer.

The one or more endogenous genes may be chosen from POLR2A, B2M, PFN1, HMBS, G6PD, and PABPN1.

In one embodiment, the invention provides a method for diagnosing endometrial cancer comprising obtaining a sample from an individual and determining the level of from 1-17 biomarkers chosen from ACAA1, AP1M2, CGN, DDR1, EPS8L2, FASTKD1, GMIP, IKBKE, P2RX4, P4HB, PHKG2, PPFIBP2, PPP1R16A, RASSF7, RNF183, SIRT6, TJP3, and/or from 1 to 3 biomarkers chosen from EFEMP2, SOCS2, and DCN wherein if said markers are differentially expressed compared to a control value, then the individual is diagnosed with endometrial cancer and/or an increased likelihood of endometrial cancer. In a specific aspect of this embodiment, when the level of from 1 to 17 biomarkers chosen from ACAA1, AP1M2, CGN, DDR1, EPS8L2, FASTKD1, GMIP, IKBKE, P2RX4, P4HB, PHKG2, PPFIBP2, PPP1R16A, RASSF7, RNF183, SIRT6, TJP3, are increased relative to a control value and/or the level from 1 to 3 biomarkers chosen from EFEMP2, SOCS2, and DCN are decreased relative to control value then this indicates endometrial cancer or an increased chance of having endometrial cancer. According to one aspect of this embodiment, the sample is chosen from a tissue sample and a fluid sample. In one aspect, the fluid sample is a uterine fluid sample or uterine aspirate. According to one aspect of this embodiment, the level of mRNA corresponding to the biomarker is determined. According to another aspect of this embodiment, the level of protein corresponding to the biomarker is determined.

Amongst the biomarkers of Table 1, the levels of CGN, P4HB, PPP1R16A, IKBKE, RASSF7, RNF183, and TJP3, were found to have the highest mean level of overexpression in the RT-PCR studies as compared to their expression in normal samples (e.g., not having endometrial cancer). Thus, given that the RT-PCR experiments demonstrated a high level of overexpression in a statistically significant manner (all p-values are less than 0.0001 for the sample set studied) for these markers, they represent preferred markers for diagnosis of endometrial cancer and/or an increased likelihood of having endometrial cancer. Therefore, the levels of CGN, P4HB, PPP1R16A, IKBKE, RASSF7, RNF183, and TJP3 are excellent predictors of endometrial cancer and/or an increased likelihood of having endometrial cancer. The levels of these markers are less likely to give a false positive as compared to other markers whose expression levels are not as high and/or as significant. In one embodiment, the invention provides a method for diagnosing endometrial cancer comprising obtaining a sample from an individual and determining the level of one or more biomarkers chosen from CGN, P4HB, PPP1R16A, IKBKE, RASSF7, RNF183, and TJP3 wherein if one or more of said markers are differentially expressed compared to a control value, then the individual is diagnosed with endometrial cancer and/or an increased likelihood of cancer. Fingerprint patterns/expression profiles having from 1-7 biomarkers chosen from CGN, P4HB, PPP1R16A, IKBKE, RASSF7, RNF183, and TJP3 and from 1-13 biomarkers chosen from ACAA1, AP1M2, DDR1, EPS8L2, FASTKD1, GMIP, P2RX4, PHKG2, PPFIBP2, SIRT6, EFEMP2, SOCS2, and DCN, are one example of a set preferred profiles for diagnosing and/or predicting an increased likelihood of endometrial cancer. Specific examples of such profiles are described below. According to one aspect of this embodiment, the sample is chosen from a tissue sample and a fluid sample. In one aspect, the fluid sample is a uterine fluid sample or uterine aspirate. According to one aspect of this embodiment, the level of mRNA corresponding to the biomarker is determined. According to one aspect of this embodiment, the level of protein corresponding to the biomarker is determined.

Amongst the biomarkers of Table 1, the level of some biomarkers were found to be able to differentiate samples from patients having cancer as compared to normal samples (or control) and samples from patients in the secretory phase of the menstrual cycle. Therefore, the levels of ACAA1, DDR1, EPS8L2, GMIP, IKBKE, P2RX4, P4HB, PHKG2, PPFIBP2, RASSF7, SIRT6, TJP3, SOCS2, and DCN are excellent predictors of endometrial cancer in pre- and postmenopausal women and in peri-menopausal women, the levels of these markers are less likely to give a false positive as compared to other markers who expression level varies as a function of cycle. In one embodiment, the invention provides a method for diagnosing endometrial cancer comprising obtaining a sample from an individual and determining the level of one or more biomarkers chosen from ACAA1, DDR1, EPS8L2, GMIP, IKBKE, LSR, P2RX4, P4HB, PHKG2, PPFIBP2, RASSF7, SIRT6, TJP3, SOCS2, and DCN wherein if one or more of said markers are differentially expressed compared to a control value, then the individual is diagnosed with endometrial cancer and/or an increased likelihood of endometrial cancer. Fingerprint patterns/expression profiles having from 1-15 markers chosen from ACAA1, DDR1, EPS8L2, GMIP, IKBKE, P2RX4, P4HB, PHKG2, PPFIBP2, PPP1R16A, RASSF7, SIRT6, TJP3, SOCS2, and DCN and from 1 to 5 markers chosen from AP1M2, CGN, FASTKD1, RNF183, and EFEMP2 are one example of a set preferred profiles for diagnosing and/or predicting an increased likelihood of endometrial cancer since the expression level of at least one of the markers in the profile does not vary as a function of menstrual cycle phase. Specific examples of such profiles are described below. According to one aspect of this embodiment, the sample is chosen from a tissue sample and a fluid sample. In one aspect, the fluid sample is a uterine fluid sample or uterine aspirate. According to one aspect of this embodiment, the level of mRNA corresponding to the biomarker is determined. According to one aspect of this embodiment, the level of protein corresponding to the biomarker is determined.

In one embodiment, the invention provides a method for diagnosing endometrial cancer comprising obtaining a sample from an individual and determining the level of one or more biomarkers chosen from IKBKE, P4HB, SOCS2, GMIP, DDR1, EPS8L2, PPP1R16A, P2RX4, PHKG2, RASSF7, SIRT6, TJP3, AP1M2, RNF183, and DCN wherein if one or more of said markers are differentially expressed compared to a control value, then the individual is diagnosed with endometrial and/or an increased likelihood of endometrial cancer. According to one aspect of this embodiment, the sample is chosen from a tissue sample and a fluid sample. In one aspect, the fluid sample is a uterine fluid sample or uterine aspirate. According to one aspect of this embodiment, the level of mRNA corresponding to the biomarker is determined. According to one aspect of this embodiment, the level of protein corresponding to the biomarker is determined.

In one embodiment, the invention provides a method for diagnosing endometrial cancer comprising obtaining a sample from an individual and determining the level of one or more biomarkers chosen from IKBKE, P4HB, SOCS2, GMIP, DDR1, EPS8L2, PPP1R16A, P2RX4, PHKG2, RASSF7, SIRT6, and TJP3, wherein if one or more of said markers are differentially expressed compared to a control value, then the individual is diagnosed with endometrial cancer and/or an increased likelihood of endometrial cancer. According to one aspect of this embodiment, the sample is chosen from a tissue sample and a fluid sample. In one aspect, the fluid sample is a uterine fluid sample or uterine aspirate. According to one aspect of this embodiment, the level of mRNA corresponding to the biomarker is determined. According to one aspect of this embodiment, the level of protein corresponding to the biomarker is determined.

In one embodiment of the invention, preferred biomarkers for diagnosing endometrial cancer and/or diagnosing an increased likelihood of endometrial cancer are IKBKE, P4HB, SOCS2, GMIP, DDR1, EPS8L2, and PPP1R16A. In one aspect, the level of the biomarker in primary tumor is determined. In one aspect, the level of the biomarker in blood, plasma, or serum is determined. In one aspect, the level of the biomarker uterine fluid is determined. Thus, the method according to this embodiment, comprise obtaining a sample and determining the level of from 1 to 7 biomarkers chosen from IKBKE, P4HB, SOCS2, GMIP, DDR1, EPS8L2, and PPP1R16A wherein differential expression of one or more of these biomarkers as compared to a control value indicates endometrial cancer and/or an increased risk of having endometrial cancer. In one aspect of this invention, the protein level of the biomarker is determined and/or estimated. In another aspect, the mRNA expression level is determined and/or estimated.

In one embodiment of the invention, preferred biomarkers for diagnosing endometrial cancer and/or an increased likelihood of endometrial cancer include GMIP, IKBKE, P4HB, RASSF7, DDR1, RNF183, EFEMP2 and SOCS2. GMIP, IKBKE, P4HB, RASSF7, DDR1, RNF183, EFEMP2 and SOCS2 were found to have excellent AUROC values and therefore are unexpectedly good classifiers in the sample set studied. In one aspect, the level of the biomarker in primary tumor is determined. In one aspect, the level of the biomarker in blood, plasma, or serum is determined. In one aspect, the level of the biomarker uterine fluid is determined. Thus, the method according to this embodiment, comprise obtaining a sample and determining the level of from 1 to 8 biomarkers chosen from GMIP, IKBKE, P4HB, RASSF7, DDR1, RNF183, EFEMP2 and SOCS2 wherein differential expression of one or more of these biomarkers as compared to a control value indicates endometrial cancer and/or an increased risk of having endometrial cancer. In one aspect of this invention, the protein level of the biomarker is determined and/or estimated. In another aspect, the mRNA expression level is determined and/or estimated.

In one embodiment of the invention, preferred biomarkers for diagnosing endometrial cancer and/or diagnosing an increased likelihood of endometrial cancer include P2RX4, P4HB, PHKG2, PPFIBP2 and SOCS2. As a result of these studies it was found that P2RX4, P4HB, PHKG2, PPFIBP2 and SOCS2 have excellent specificity for endometrial cancer diagnosis. In one aspect, the level of the biomarker in primary tumor is determined. In one aspect, the level of the biomarker in blood, plasma, or serum is determined. In one aspect, the level of the biomarker uterine fluid is determined. Thus, the method according to this embodiment, comprise obtaining a sample and determining the level of from 1 to 5 biomarkers chosen from P2RX4, P4HB, PHKG2, PPFIBP2 and SOCS2 wherein differential expression of one or more of these biomarkers as compared to a control value indicates endometrial cancer and/or an increased risk of having endometrial cancer. In one aspect of this invention, the protein level of the biomarker is determined and/or estimated. In another aspect, the mRNA expression level is determined and/or estimated.

In one embodiment of the invention, preferred biomarkers for diagnosing endometrial cancer and/or diagnosing an increased likelihood of endometrial cancer include IKBKE, P4HB, RASSF7, and RNF183. As a result of these studies it was found that IKBKE, P4HB, RASSF7, and RNF183 have excellent sensitivity for endometrial cancer diagnosis. In one aspect, the level of the biomarker in primary tumor is determined. In one aspect, the level of the biomarker in blood, plasma, or serum is determined. In one aspect, the level of the biomarker uterine fluid is determined. Thus, the method according to this embodiment, comprise obtaining a sample and determining the level of from 1 to 4 biomarkers chosen from IKBKE, P4HB, RASSF7, and RNF183 wherein differential expression of one or more of these biomarkers as compared to a control value indicates endometrial cancer and/or an increased risk of having endometrial cancer. In one aspect of this invention, the protein level of the biomarker is determined and/or estimated. In another aspect, the mRNA expression level is determined and/or estimated.

In one embodiment, the invention provides a method for diagnosing endometrial cancer comprising obtaining a sample from an individual and determining the level of from 2 to 7 biomarkers chosen from GMIP, IKBKE, P4HB, SOCS2, EPS8L2, PPP1R16A, and TJP3 wherein if said markers are differentially expressed compared to a control value, then the individual is diagnosed with endometrial cancer and/or an increased likelihood of endometrial cancer. As result of the studies disclosed herein, it was surprisingly found that combinations (e.g., profiles and/or fingerprint patterns) of biomarkers chosen from GMIP, IKBKE, P4HB, SOCS2, EPS8L2, PPP1R16A, and TJP3 have excellent sensitivity and specificity for endometrial cancer and the AUROC values for various combinations of these markers are indicative of the ability of these markers to separate patients having endometrial cancer from those not having endometrial cancer.

According to one aspect of this embodiment, the sample is chosen from a tissue sample and a fluid sample. In one aspect, the fluid sample is a uterine fluid sample or uterine aspirate. According to one aspect of this embodiment, the level of mRNA corresponding to the biomarker is determined. According to one aspect of this embodiment, the level of protein corresponding to the biomarker is determined.

In one embodiment, the invention provides a method for diagnosing endometrial cancer comprising obtaining a sample from an individual and determining the level of from 2 to 9 biomarkers chosen from GMIP, IKBKE, P4HB, SOCS2, EFEMP2, PHKG2, SIRT6, DDR1, and FASTKD1 wherein if said markers are differentially expressed compared to a control value, then the individual is diagnosed with endometrial cancer and/or an increased likelihood of endometrial cancer. As result of the studies disclosed herein, it was surprisingly found that combinations (e.g., profiles and/or fingerprint patterns) of biomarkers chosen from GMIP, IKBKE, P4HB, SOCS2, EFEMP2, PHKG2, SIRT6, DDR1, and FASTKD1 have excellent sensitivity and specificity for endometrial cancer and the AUROC values for various combinations of these markers are indicative of the ability of these markers to separate patients having endometrial cancer from those not having endometrial cancer. According to one aspect of this embodiment, the sample is chosen from a tissue sample and a fluid sample. In one aspect, the fluid sample is a uterine fluid sample or uterine aspirate. According to one aspect of this embodiment, the level of mRNA corresponding to the biomarker is determined. According to one aspect of this embodiment, the level of protein corresponding to the biomarker is determined. In one specific aspect of this embodiment, the in vitro diagnostic method comprises providing a uterine fluid sample obtained from a patient with a pipelle device or syringe wherein the patient has a risk factor or symptom of endometrial cancer; contacting said sample with an agent capable of preserving, preventing, or lessening the degradation of RNA in said uterine fluid sample; determining in said sample the expression level of mRNA corresponding to said from 2 to 9 markers and one or more endogenous genes using quantitative PCR; normalizing the expression level of said from 2 to 9 biomarkers with the one or more endogenous genes; comparing the normalized level of the from 2 to 9 biomarkers to a control value wherein differential expression of from 2 to 9 of the biomarkers indicates endometrial cancer or an increased likelihood of endometrial cancer. In one specific aspect of this method, said one or more endogenous genes are chosen from POLR2A, B2M, PFN1, HMBS, G6PD, and PABPN1.

In one embodiment, the invention provides a method for diagnosing endometrial cancer comprising obtaining a sample from an individual and determining the level of from 2 to 8 biomarkers chosen from GMIP, IKBKE, P4HB, EFEMP2, PHKG2, SIRT6, DDR1, and FASTKD1 wherein if said markers are differentially expressed compared to a control value, then the individual is diagnosed with endometrial cancer and/or an increased likelihood of endometrial cancer. As result of the studies disclosed herein, it was surprisingly found that combinations (e.g., profiles and/or fingerprint patterns) of biomarkers chosen from GMIP, IKBKE, P4HB, EFEMP2, PHKG2, SIRT6, DDR1, and FASTKD1 have excellent sensitivity and specificity for endometrial cancer and the AUROC values for various combinations of these markers are indicative of the ability of these markers to separate patients having endometrial cancer from those not having endometrial cancer. According to one aspect of this embodiment, the sample is chosen from a tissue sample and a fluid sample. In one aspect, the fluid sample is a uterine fluid sample or uterine aspirate. According to one aspect of this embodiment, the level of mRNA corresponding to the biomarker is determined. According to one aspect of this embodiment, the level of protein corresponding to the biomarker is determined. According to one aspect of this embodiment, the level of 2 to 8 biomarkers are determined by quantitative PCR. In one specific aspect of this embodiment, the in vitro diagnostic method comprises providing a uterine fluid sample obtained from a patient with a pipelle device or syringe wherein the patient has a risk factor or symptom of endometrial cancer; contacting said sample with an agent capable of preserving, preventing, or lessening the degradation of RNA in said uterine fluid sample; determining in said sample the expression level of mRNA corresponding to said from 2 to 9 markers and one or more endogenous genes using quantitative PCR; normalizing the expression level of said from 2 to 8 biomarkers with the one or more endogenous genes; comparing the normalized level of the from 2 to 8 biomarkers to a control value wherein differential expression of from 2 to 8 of the biomarkers indicates endometrial cancer or an increased likelihood of endometrial cancer. In one specific aspect of this method, said one or more endogenous genes are chosen from POLR2A, B2M, PFN1, HMBS, G6PD, and PABPN1.

In one embodiment, the invention provides a method for diagnosing endometrial cancer comprising obtaining a sample from an individual and determining the level of from 2 to 8 biomarkers chosen from GMIP, IKBKE, P4HB, SOCS2, PHKG2, SIRT6, DDR1, and FASTKD1 wherein if said markers are differentially expressed compared to a control value, then the individual is diagnosed with endometrial cancer and/or an increased likelihood of endometrial cancer. As result of the studies disclosed herein, it was surprisingly found that combinations (e.g., profiles and/or fingerprint patterns) of biomarkers chosen from GMIP, IKBKE, P4HB, SOCS2, PHKG2, SIRT6, DDR1, and FASTKD1 have excellent sensitivity and specificity for endometrial cancer and the AUROC values for various combinations of these markers are indicative of the ability of these markers to separate patients having endometrial cancer from those not having endometrial cancer. According to one aspect of this embodiment, the sample is chosen from a tissue sample and a fluid sample. In one aspect, the fluid sample is a uterine fluid sample or uterine aspirate. According to one aspect of this embodiment, the level of mRNA corresponding to the biomarker is determined. According to one aspect of this embodiment, the level of protein corresponding to the biomarker is determined. According to one aspect of this embodiment, the level of 2 to 8 biomarkers are determined by quantitative PCR. In one specific aspect of this embodiment, the in vitro diagnostic method comprises providing a uterine fluid sample obtained from a patient with a pipelle device or syringe wherein the patient has a risk factor or symptom of endometrial cancer; contacting said sample with an agent capable of preserving, preventing, or lessening the degradation of RNA in said uterine fluid sample; determining in said sample the expression level of mRNA corresponding to said from 2 to 8 markers and one or more endogenous genes using quantitative PCR; normalizing the expression level of said from 2 to 8 biomarkers with the one or more endogenous genes; comparing the normalized level of the from 2 to 8 biomarkers to a control value wherein differential expression of from 2 to 8 of the biomarkers indicates endometrial cancer or an increased likelihood of endometrial cancer. In one specific aspect of this method, said one or more endogenous genes are chosen from POLR2A, B2M, PFN1, HMBS, G6PD, and PABPN1.

In one embodiment, the present invention provides a method for characterizing a sample obtained from a patient for prognostic, diagnostic and/or pharmacogenomic uses. Characterization of a sample obtained from a patient by determining the levels of one or more of the biomarkers of Table 1 can be used to provide information regarding diagnosis of endometrial cancer, disease progression, diagnosis of endometrial cancer type (and/or subtype), and selection of an appropriate therapeutic treatment. According to the method of the invention, a sample is obtained from an individual. The individual can be a healthy person, an individual diagnosed with cancer, an individual suspected of having cancer, an individual displaying one or more symptoms of cancer and/or an individual desiring screening for cancer. The method comprises the step of determining the level of the biomarker(s) of Table 1 in a sample obtained from a patient. Alternative methods for determining the biomarkers at the RNA and/or protein (IHC, mRNA expression analysis, etc) can be used in these methods. Detection of increased levels of from 1 to 17 the biomarkers of Table 1 that were found to be upregulated in endometrial cancer and/or detection of decreased levels of from 1 to 3 biomarkers that were found to be downregulated in endometrial cancer, compared to a control value, indicates that the patient has increased likelihood of having endometrial cancer.

In one embodiment, the invention provides a method for diagnosing a gynecological cancer comprising the use of diagnostic reagents for assaying for or detecting from 1 to 20 of the biomarkers listed in Table 1. In a more specific aspect of this embodiment, the diagnostic reagents are used for detecting the level of from 1 to 20 of the biomarkers listed in Table 1, for the diagnosis of endometrial cancer. In a more specific aspect of this embodiment, the diagnostic reagents are used for detecting the level of from 1 to 20 of the biomarkers listed in Table 1, for the detection of endometrial cancer. In one aspect of this embodiment, the level of the mRNA corresponding to from 1 to 20 biomarkers is determined. In one aspect of this embodiment, the level of the mRNA corresponding to from 2 to 17 biomarkers is determined. In one aspect of this embodiment, the level of the mRNA corresponding to from 3 to 15 biomarkers is determined. In one aspect of this embodiment, the level of a protein or polypeptide corresponding to from 1 to 20 biomarkers is determined. In one aspect of this embodiment, the level of a protein or polypeptide corresponding to from 2 to 17 biomarkers is determined. In one aspect of this embodiment, the level of a protein or polypeptide corresponding to from 3 to 15 biomarkers is determined. In one aspect of this embodiment, the sample that is analyzed is a tumor sample. In one aspect of this embodiment, the sample is analyzed is a uterine fluid sample. In one aspect of this embodiment, the sample that is analyzed is a serum, blood, or plasma sample. In one aspect, the sample is that is used is obtained by using a soft, straw-like device (pipelle) that is used to suction off a small sample of lining from the uterus (e.g., uterine fluid). In one aspect, the sample is obtained by using a sharp-edged tool called a curette by scraping a small sample and collecting it with a syringe or suction (e.g., dilation and curettage). In one aspect, the sample is obtained by using an electronic suction device (e.g., Vabra aspiration). In one aspect, the sample is obtained by using a spray of liquid (jet irrigation) to wash off some of the tissue that lines the uterus. In some aspects, a brush may be used to remove some of the lining before the washing is done. In one aspect, a blood, serum, or plasma sample is analyzed for from 1 to 20 of the biomarkers of the invention.

In microarray studies, GMIP was found to be overexpressed in samples from patients having endometrial cancer as compared to normal values (non-affected). In RT-PCR studies this result was confirmed and a p-value of less than 0.0001 was obtained for aspirate samples from non-affected individuals versus aspirates from individuals having endometrial cancer comparisons. The expression of GMIP was also found to be correlated in primary tumor and uterine fluid. Thus, GMIP is an excellent biomarker for diagnosing endometrial cancer and/or an increased likelihood of endometrial cancer. Furthermore, fingerprint patterns/profiles having GMIP are expected to be useful for diagnosing endometrial cancer and/or an increased likelihood of endometrial cancer. In one embodiment, the invention provides a method for diagnosing endometrial cancer and/or an increased likelihood of endometrial cancer comprising obtaining a sample from an individual and determining the level of GMIP and from 2 to 19 other biomarkers chosen from Table 1 wherein if said markers are differentially expressed compared to a control value, then the individual is diagnosed with endometrial cancer and/or an increased likelihood of endometrial cancer. For example, GMIP alone has AUROC value in Table 6 of 0.88 IKBKE alone has an AUROC value of 0.90, when these two markers are combined together in a profile the AUROC value 0.92 with a substantial increase in specificity (increased AUROC value indicate increased ability to separate the population). According to one aspect of this embodiment, the sample is chosen from a tissue sample and a fluid sample. In one aspect, the fluid sample is a uterine fluid sample or uterine aspirate. According to one aspect of this embodiment, the level of mRNA corresponding to the biomarker is determined. According to one aspect of this embodiment, the level of protein corresponding to the biomarker is determined.

In microarray studies, IKBKE was found to be overexpressed in samples from patients having endometrial cancer as compared to normal values (non-affected). In RT-PCR studies this result was confirmed and a p-value of less than 0.0001 was obtained for aspirate samples from non-affected individuals versus aspirates from individuals having endometrial cancer comparisons. The expression of IKBKE was also found to be correlated in primary tumor and uterine fluid. Thus, IKBKE is an excellent biomarker for diagnosing endometrial cancer and/or an increased likelihood of endometrial cancer. Furthermore, fingerprint patterns/profiles having IKBKE are expected to be useful for diagnosing endometrial cancer and/or an increased likelihood of endometrial cancer. In one embodiment, the invention provides a method for diagnosing endometrial cancer and/or an increased likelihood of endometrial cancer comprising obtaining a sample from an individual and determining the level of IKBKE and from 2 to 19 biomarkers chosen from Table 1 wherein if said markers are differentially expressed compared to a control value, then the individual is diagnosed with endometrial cancer and/or an increased likelihood of endometrial cancer. For example, IKBKE alone has AUROC value in Table 6 of 0.90, P4HB alone has an AUROC value of 0.97, when these two markers are combined together in a profile the AUROC value 0.98 with a substantial increase in specificity to 100% (increased AUROC value indicate increased ability to separate the population). According to one aspect of this embodiment, the sample is chosen from a tissue sample and a fluid sample. In one aspect, the fluid sample is a uterine fluid sample or uterine aspirate. According to one aspect of this embodiment, the level of mRNA corresponding to the biomarker is determined. According to one aspect of this embodiment, the level of protein corresponding to the biomarker is determined.

In microarray studies, EPS8L2 was found to be overexpressed in samples from patients having endometrial cancer as compared to normal values (non-affected). In RT-PCR studies this result was confirmed and a p-value of less than 0.002 was obtained for aspirate samples from non-affected individuals versus aspirates from individuals having endometrial cancer comparisons. The expression of EPS8L2 was also found to be correlated in primary tumor and uterine fluid. Thus, EPS8L2 is an excellent biomarker for diagnosing endometrial cancer and/or an increased likelihood of endometrial cancer. Furthermore, fingerprint patterns/profiles having EPS8L2 are expected to be useful for diagnosing endometrial cancer and/or an increased likelihood of endometrial cancer. In one embodiment, the invention provides a method for diagnosing endometrial cancer and/or an increased likelihood of endometrial cancer comprising obtaining a sample from an individual and determining the level of EPS8L2 and from 2 to 19 other biomarkers chosen from Table 1 wherein if said markers are differentially expressed compared to a control value, then the individual is diagnosed with endometrial cancer and/or an increased likelihood of endometrial cancer. For example, when EPS8L2 is combined with GMIP, IKBKE, P4HB, SOCS2, and DDR1 the AUROC value is 1 and the sensitivity is nearly 96% and the specificity is 100% (see Table 11). According to one aspect of this embodiment, the sample is chosen from a tissue sample and a fluid sample. In one aspect, the fluid sample is a uterine fluid sample or uterine aspirate. According to one aspect of this embodiment, the level of mRNA corresponding to the biomarker is determined. According to one aspect of this embodiment, the level of protein corresponding to the biomarker is determined.

In microarray studies, SOCS2 was found to be underexpressed in samples from patients having endometrial cancer as compared to normal values (non-affected). In RT-PCR studies this result was confirmed and a p-value of less than 0.0001 was obtained for aspirate samples from non-affected individuals versus aspirates from individuals having endometrial cancer comparisons. The expression of SOCS2 was also found to be correlated in primary tumor and uterine fluid. Thus, SOCS2 is an excellent biomarker for diagnosing endometrial cancer and/or an increased likelihood of endometrial cancer. Furthermore, fingerprint patterns/profiles having SOCS2 are expected to be useful for diagnosing endometrial cancer and/or an increased likelihood of endometrial cancer. In one embodiment, the invention provides a method for diagnosing endometrial cancer and/or an increased likelihood of endometrial cancer comprising obtaining a sample from an individual and determining the level of SOCS2 and from 2 to 19 other biomarkers chosen from Table 1 wherein if said markers are differentially expressed compared to a control value, then the individual is diagnosed with endometrial cancer and/or an increased likelihood of endometrial cancer. For example, SOCS2 alone has AUROC value in Table 6 of 0.93, GMIP alone has an AUROC value of 0.88, when these two markers are combined together in a profile the AUROC value 0.999 with a substantial increase in sensitivity to 100% (increased AUROC value indicate increased ability to separate the population). According to one aspect of this embodiment, the sample is chosen from a tissue sample and a fluid sample. In one aspect, the fluid sample is a uterine fluid sample or uterine aspirate. According to one aspect of this embodiment, the level of mRNA corresponding to the biomarker is determined. According to one aspect of this embodiment, the level of protein corresponding to the biomarker is determined.

In microarray studies, EPS8L2 was found to be overexpressed in samples from patients having endometrial cancer as compared to normal values (non-affected). In RT-PCR studies this result was confirmed and a p-value of less than 0.002 was obtained for aspirate samples from non-affected individuals versus aspirates from individuals having endometrial cancer comparisons. The expression of EPS8L2 was also found to be correlated in primary tumor and uterine fluid. Thus, EPS8L2 is an excellent biomarker for diagnosing endometrial cancer and/or an increased likelihood of endometrial cancer. Furthermore, fingerprint patterns/profiles having EPS8L2 are expected to be useful for diagnosing endometrial cancer and/or an increased likelihood of endometrial cancer. In one embodiment, the invention provides a method for diagnosing endometrial cancer and/or an increased likelihood of endometrial cancer comprising obtaining a sample from an individual and determining the level of EPS8L2 and from 2 to 19 other biomarkers chosen from Table 1 wherein if said markers are differentially expressed compared to a control value, then the individual is diagnosed with endometrial cancer and/or an increased likelihood of endometrial cancer. For example, when EPS8L2 is combined with GMIP, IKBKE, P4HB, SOCS2, and DDR1 the AUROC value is 1 and the sensitivity is nearly 96% and the specificity is 100% (see Table 11). According to one aspect of this embodiment, the sample is chosen from a tissue sample and a fluid sample. In one aspect, the fluid sample is a uterine fluid sample or uterine aspirate. According to one aspect of this embodiment, the level of mRNA corresponding to the biomarker is determined. According to one aspect of this embodiment, the level of protein corresponding to the biomarker is determined.

In microarray studies, RASSF7 was found to be overexpressed in samples from patients having endometrial cancer as compared to normal values (non-affected). In RT-PCR studies this result was confirmed and a p-value of less than 0.0005 was obtained for aspirate samples from non-affected individuals versus aspirates from individuals having endometrial cancer comparisons. The expression of RASSF7 was also found to be correlated in primary tumor and uterine fluid. Thus, RASSF7 is an excellent biomarker for diagnosing endometrial cancer and/or an increased likelihood of endometrial cancer. Furthermore, fingerprint patterns/profiles having RASSF7 are expected to be useful for diagnosing endometrial cancer and/or an increased likelihood of endometrial cancer. In one embodiment, the invention provides a method for diagnosing endometrial cancer and/or an increased likelihood of endometrial cancer comprising obtaining a sample from an individual and determining the level of RASSF7 and from 2 to 19 other biomarkers chosen from Table 1 wherein if said markers are differentially expressed compared to a control value, then the individual is diagnosed with endometrial cancer and/or an increased likelihood of endometrial cancer. For example, when RASSF7 is combined with DDR1, EPS8L2, GMIP, IKBKE, P2RX4, P4HB, PHKG2, PPP1R16A, SIRT6, TJP3 and SOCS2 the AUROC value is 1 and the sensitivity is 100% and the specificity is 100% (see Table 11). According to one aspect of this embodiment, the sample is chosen from a tissue sample and a fluid sample. In one aspect, the fluid sample is a uterine fluid sample or uterine aspirate. According to one aspect of this embodiment, the level of mRNA corresponding to the biomarker is determined. According to one aspect of this embodiment, the level of protein corresponding to the biomarker is determined.

In microarray studies, DDR1 was found to be overexpressed in samples from patients having endometrial cancer as compared to normal values (non-affected). In RT-PCR studies this result was confirmed and a p-value of less than 0.02 was obtained for aspirate samples from non-affected individuals versus aspirates from individuals having endometrial cancer comparisons. The expression of DDR1 was also found to be correlated in primary tumor and uterine fluid. Thus, DDR1 is an excellent biomarker for diagnosing endometrial cancer and/or an increased likelihood of endometrial cancer. Furthermore, fingerprint patterns/profiles having DDR1 are expected to be useful for diagnosing endometrial cancer and/or an increased likelihood of endometrial cancer. In one embodiment, the invention provides a method for diagnosing endometrial cancer and/or an increased likelihood of endometrial cancer comprising obtaining a sample from an individual and determining the level of DDR1 and from 2 to 19 other biomarkers chosen from Table 1 wherein if said markers are differentially expressed compared to a control value, then the individual is diagnosed with endometrial cancer and/or an increased likelihood of endometrial cancer. For example, when DDR1 is combined with EPS8L2, GMIP, IKBKE, P2RX4, P4HB, PHKG2, PPP1R16A, SIRT6, TJP3, SOCS2, and RNF183 the AUROC value is 1 and the sensitivity is 100% and the specificity is 100% (see Table 11). According to one aspect of this embodiment, the sample is chosen from a tissue sample and a fluid sample. In one aspect, the fluid sample is a uterine fluid sample or uterine aspirate. According to one aspect of this embodiment, the level of mRNA corresponding to the biomarker is determined. According to one aspect of this embodiment, the level of protein corresponding to the biomarker is determined.

In microarray studies, PPP1R16A was found to be overexpressed in samples from patients having endometrial cancer as compared to normal values (non-affected). In RT-PCR studies this result was confirmed and a p-value of less than 0.0001 was obtained for aspirate samples from non-affected individuals versus aspirates from individuals having endometrial cancer comparisons. The expression of PPP1R16A was also found to be correlated in primary tumor and uterine fluid. Thus, PPP1R16A is an excellent biomarker for diagnosing endometrial cancer and/or an increased likelihood of endometrial cancer. Furthermore, fingerprint patterns/profiles having PPP1R16A are expected to be useful for diagnosing endometrial cancer and/or an increased likelihood of endometrial cancer. In one embodiment, the invention provides a method for diagnosing endometrial cancer and/or an increased likelihood of endometrial cancer comprising obtaining a sample from an individual and determining the level of PPP1R16A and from 2 to 19 other biomarkers chosen from Table 1 wherein if said markers are differentially expressed compared to a control value, then the individual is diagnosed with endometrial cancer and/or an increased likelihood of endometrial cancer. For example, when PPP1R16A is combined with GMIP, IKBKE, P4HB, SOCS2, and EPS8L2 the AUROC value is nearly 1 and the sensitivity is nearly 92% and the specificity is 100% (see Table 11). According to one aspect of this embodiment, the sample is chosen from a tissue sample and a fluid sample. In one aspect, the fluid sample is a uterine fluid sample or uterine aspirate. According to one aspect of this embodiment, the level of mRNA corresponding to the biomarker is determined. According to one aspect of this embodiment, the level of protein corresponding to the biomarker is determined.

In microarray studies, PHKG2 was found to be overexpressed in samples from patients having endometrial cancer as compared to normal values (non-affected). In RT-PCR studies this result was confirmed and a p-value of less than 0.0001 was obtained for aspirate samples from non-affected individuals versus aspirates from individuals having endometrial cancer comparisons. The expression of PHKG2 was also found to be correlated in primary tumor and uterine fluid. Thus, PHKG2 is an excellent biomarker for diagnosing endometrial cancer and/or an increased likelihood of endometrial cancer. Furthermore, fingerprint patterns/profiles having PHKG2 are expected to be useful for diagnosing endometrial cancer and/or an increased likelihood of endometrial cancer. In one embodiment, the invention provides a method for diagnosing endometrial cancer and/or an increased likelihood of endometrial cancer comprising obtaining a sample from an individual and determining the level of PHKG2 and from 2 to 19 other biomarkers chosen from Table 1 wherein if said markers are differentially expressed compared to a control value, then the individual is diagnosed with endometrial cancer and/or an increased likelihood of endometrial cancer. For example, when PHKG2 is combined with DDR1, EPS8L2, GMIP, IKBKE, P2RX4, P4HB, PPP1R16A, SIRT6, TJP3, SOCS2, and RNF183 the AUROC value is 1 and the sensitivity is 100% and the specificity is 100% (see Table 11). According to one aspect of this embodiment, the sample is chosen from a tissue sample and a fluid sample. In one aspect, the fluid sample is a uterine fluid sample or uterine aspirate. According to one aspect of this embodiment, the level of mRNA corresponding to the biomarker is determined. According to one aspect of this embodiment, the level of protein corresponding to the biomarker is determined.

In microarray studies, P2RX4 was found to be overexpressed in samples from patients having endometrial cancer as compared to normal values (non-affected). In RT-PCR studies this result was confirmed and a p-value of less than 0.0005 was obtained for aspirate samples from non-affected individuals versus aspirates from individuals having endometrial cancer comparisons. The expression of P2RX4 was also found to be correlated in primary tumor and uterine fluid. Thus, P2RX4 is an excellent biomarker for diagnosing endometrial cancer and/or an increased likelihood of endometrial cancer. Furthermore, fingerprint patterns/profiles having P2RX4 are expected to be useful for diagnosing endometrial cancer and/or an increased likelihood of endometrial cancer. In one embodiment, the invention provides a method for diagnosing endometrial cancer and/or an increased likelihood of endometrial cancer comprising obtaining a sample from an individual and determining the level of P2RX4 and from 2 to 19 other biomarkers chosen from Table 1 wherein if said markers are differentially expressed compared to a control value, then the individual is diagnosed with endometrial cancer and/or an increased likelihood of endometrial cancer. For example, when P2RX4 is combined with DDR1, EPS8L2, GMIP, IKBKE, P4HB, PHKG2, PPP1R16A, SIRT6, TJP3, SOCS2, and RNF183 the AUROC value is 1 and the sensitivity is 100% and the specificity is 100% (see Table 11). According to one aspect of this embodiment, the sample is chosen from a tissue sample and a fluid sample. In one aspect, the fluid sample is a uterine fluid sample or uterine aspirate. According to one aspect of this embodiment, the level of mRNA corresponding to the biomarker is determined. According to one aspect of this embodiment, the level of protein corresponding to the biomarker is determined.

In microarray studies, ACAA1 was found to be overexpressed in samples from patients having endometrial cancer as compared to normal values (non-affected). In RT-PCR studies this result was confirmed and a p-value of less than 0.0001 was obtained for aspirate samples from non-affected individuals versus aspirates from individuals having endometrial cancer comparisons. The expression of ACAA1 was also found to be correlated in primary tumor and uterine fluid. Thus, ACAA1 is an excellent biomarker for diagnosing endometrial cancer and/or an increased likelihood of endometrial cancer. Furthermore, fingerprint patterns/profiles having ACAA1 are expected to be useful for diagnosing endometrial cancer and/or an increased likelihood of endometrial cancer. In one embodiment, the invention provides a method for diagnosing endometrial cancer and/or an increased likelihood of endometrial cancer comprising obtaining a sample from an individual and determining the level of ACAA1 and from 2 to 19 other biomarkers chosen from Table 1 wherein if said markers are differentially expressed compared to a control value, then the individual is diagnosed with endometrial cancer and/or an increased likelihood of endometrial cancer. According to one aspect of this embodiment, the sample is chosen from a tissue sample and a fluid sample. In one aspect, the fluid sample is a uterine fluid sample or uterine aspirate. According to one aspect of this embodiment, the level of mRNA corresponding to the biomarker is determined. According to one aspect of this embodiment, the level of protein corresponding to the biomarker is determined.

In microarray studies, AP1M2 was found to be overexpressed in samples from patients having endometrial cancer as compared to normal values (non-affected). In RT-PCR studies this result was confirmed and a p-value of less than 0.0001 was obtained for aspirate samples from non-affected individuals versus aspirates from individuals having endometrial cancer comparisons. The expression of AP1M2 was also found to be correlated in primary tumor and uterine fluid. Thus, AP1M2 is an excellent biomarker for diagnosing endometrial cancer and/or an increased likelihood of endometrial cancer. Furthermore, fingerprint patterns/profiles having AP1M2 are expected to be useful for diagnosing endometrial cancer and/or an increased likelihood of endometrial cancer. In one embodiment, the invention provides a method for diagnosing endometrial cancer and/or an increased likelihood of endometrial cancer comprising obtaining a sample from an individual and determining the level of AP1M2 and from 2 to 19 other biomarkers chosen from Table 1 wherein if said markers are differentially expressed compared to a control value, then the individual is diagnosed with endometrial cancer and/or an increased likelihood of endometrial cancer. According to one aspect of this embodiment, the sample is chosen from a tissue sample and a fluid sample. In one aspect, the fluid sample is a uterine fluid sample or uterine aspirate. According to one aspect of this embodiment, the level of mRNA corresponding to the biomarker is determined.

In microarray studies, CGN was found to be overexpressed in samples from patients having endometrial cancer as compared to normal values (non-affected). In RT-PCR studies this result was confirmed and a p-value of less than 0.0001 was obtained for aspirate samples from non-affected individuals versus aspirates from individuals having endometrial cancer comparisons. The expression of CGN was also found to be correlated in primary tumor and uterine fluid. Thus, CGN is an excellent biomarker for diagnosing endometrial cancer and/or an increased likelihood of endometrial cancer. Furthermore, fingerprint patterns/profiles having CGN are expected to be useful for diagnosing endometrial cancer and/or an increased likelihood of endometrial cancer. In one embodiment, the invention provides a method for diagnosing endometrial cancer and/or an increased likelihood of endometrial cancer comprising obtaining a sample from an individual and determining the level of CGN and from 2 to 19 other biomarkers chosen from Table 1 wherein if said markers are differentially expressed compared to a control value, then the individual is diagnosed with endometrial cancer and/or an increased likelihood of endometrial cancer. According to one aspect of this embodiment, the sample is chosen from a tissue sample and a fluid sample. In one aspect, the fluid sample is a uterine fluid sample or uterine aspirate. According to one aspect of this embodiment, the level of mRNA corresponding to the biomarker is determined.

In microarray studies, FASTKD1 was found to be overexpressed in samples from patients having endometrial cancer as compared to normal values (non-affected). In RT-PCR studies this result was confirmed and a p-value of less than 0.0001 was obtained for aspirate samples from non-affected individuals versus aspirates from individuals having endometrial cancer comparisons. The expression of FASTKD1 was also found to be correlated in primary tumor and uterine fluid. Thus, FASTKD1 is an excellent biomarker for diagnosing endometrial cancer and/or an increased likelihood of endometrial cancer. Furthermore, fingerprint patterns/profiles having FASTKD1 are expected to be useful for diagnosing endometrial cancer and/or an increased likelihood of endometrial cancer. In one embodiment, the invention provides a method for diagnosing endometrial cancer and/or an increased likelihood of endometrial cancer comprising obtaining a sample from an individual and determining the level of FASTKD1 and from 2 to 19 other biomarkers chosen from Table 1 wherein if said markers are differentially expressed compared to a control value, then the individual is diagnosed with endometrial cancer and/or an increased likelihood of endometrial cancer. According to one aspect of this embodiment, the sample is chosen from a tissue sample and a fluid sample. In one aspect, the fluid sample is a uterine fluid sample or uterine aspirate. According to one aspect of this embodiment, the level of mRNA corresponding to the biomarker is determined.

In microarray studies, PPFIBP2 was found to be overexpressed in samples from patients having endometrial cancer as compared to normal values (non-affected). In RT-PCR studies this result was confirmed and a p-value of less than 0.02 was obtained for aspirate samples from non-affected individuals versus aspirates from individuals having endometrial cancer comparisons. The expression of PPFIBP2 was also found to be correlated in primary tumor and uterine fluid. Thus, PPFIBP2 is an excellent biomarker for diagnosing endometrial cancer and/or an increased likelihood of endometrial cancer. Furthermore, fingerprint patterns/profiles having PPFIBP2 are expected to be useful for diagnosing endometrial cancer and/or an increased likelihood of endometrial cancer. In one embodiment, the invention provides a method for diagnosing endometrial cancer and/or an increased likelihood of endometrial cancer comprising obtaining a sample from an individual and determining the level of PPFIBP2 and from 2 to 19 other biomarkers chosen from Table 1 wherein if said markers are differentially expressed compared to a control value, then the individual is diagnosed with endometrial cancer and/or an increased likelihood of endometrial cancer. According to one aspect of this embodiment, the sample is chosen from a tissue sample and a fluid sample. In one aspect, the fluid sample is a uterine fluid sample or uterine aspirate. According to one aspect of this embodiment, the level of mRNA corresponding to the biomarker is determined.

In microarray studies, RNF183 was found to be overexpressed in samples from patients having endometrial cancer as compared to normal values (non-affected). In RT-PCR studies this result was confirmed and a p-value of less than 0.0001 was obtained for aspirate samples from non-affected individuals versus aspirates from individuals having endometrial cancer comparisons. The expression of RNF183 was also found to be correlated in primary tumor and uterine fluid. Thus, RNF183 is an excellent biomarker for diagnosing endometrial cancer and/or an increased likelihood of endometrial cancer. Furthermore, fingerprint patterns/profiles having RNF183 are expected to be useful for diagnosing endometrial cancer and/or an increased likelihood of endometrial cancer. In one embodiment, the invention provides a method for diagnosing endometrial cancer and/or an increased likelihood of endometrial cancer comprising obtaining a sample from an individual and determining the level of RNF183 and from 2 to 19 other biomarkers chosen from Table 1 wherein if said markers are differentially expressed compared to a control value, then the individual is diagnosed with endometrial cancer and/or an increased likelihood of endometrial cancer. For example, when RNF183 is combined with DDR1, EPS8L2, GMIP, IKBKE, P2RX4, P4HB, PHKG2, PPP1R16A, SIRT6, TJP3, and SOCS2 the AUROC value is 1 and the sensitivity is 100% and the specificity is 100% (see Table 11). According to one aspect of this embodiment, the sample is chosen from a tissue sample and a fluid sample. In one aspect, the fluid sample is a uterine fluid sample or uterine aspirate. According to one aspect of this embodiment, the level of mRNA corresponding to the biomarker is determined.

In microarray studies, SIRT6 was found to be overexpressed in samples from patients having endometrial cancer as compared to normal values (non-affected). In RT-PCR studies this result was confirmed and a p-value of less than 0.0001 was obtained for aspirate samples from non-affected individuals versus aspirates from individuals having endometrial cancer comparisons. The expression of SIRT6 was also found to be correlated in primary tumor and uterine fluid. Thus, SIRT6 is an excellent biomarker for diagnosing endometrial cancer and/or an increased likelihood of endometrial cancer. Furthermore, fingerprint patterns/profiles having SIRT6 are expected to be useful for diagnosing endometrial cancer and/or an increased likelihood of endometrial cancer. In one embodiment, the invention provides a method for diagnosing endometrial cancer and/or an increased likelihood of endometrial cancer comprising obtaining a sample from an individual and determining the level of SIRT6 and from 2 to 19 other biomarkers chosen from Table 1 wherein if said markers are differentially expressed compared to a control value, then the individual is diagnosed with endometrial cancer and/or an increased likelihood of endometrial cancer. For example, when SIRT6 is combined with DDR1, EPS8L2, GMIP, IKBKE, P2RX4, P4HB, PHKG2, PPP1R16A, TJP3, SOCS2, and RNF183 the AUROC value is 1 and the sensitivity is 100% and the specificity is 100% (see Table 11). According to one aspect of this embodiment, the sample is chosen from a tissue sample and a fluid sample. In one aspect, the fluid sample is a uterine fluid sample or uterine aspirate. According to one aspect of this embodiment, the level of mRNA corresponding to the biomarker is determined.

In microarray studies, TJP3 was found to be overexpressed in samples from patients having endometrial cancer as compared to normal values (non-affected). In RT-PCR studies this result was confirmed and a p-value of less than 0.0001 was obtained for aspirate samples from non-affected individuals versus aspirates from individuals having endometrial cancer comparisons. The expression of TJP3 was also found to be correlated in primary tumor and uterine fluid. Thus, TJP3 is an excellent biomarker for diagnosing endometrial cancer and/or an increased likelihood of endometrial cancer. Furthermore, fingerprint patterns/profiles having TJP3 are expected to be useful for diagnosing endometrial cancer and/or an increased likelihood of endometrial cancer. In one embodiment, the invention provides a method for diagnosing endometrial cancer and/or an increased likelihood of endometrial cancer comprising obtaining a sample from an individual and determining the level of TJP3 and from 2 to 19 other biomarkers chosen from Table 1 wherein if said markers are differentially expressed compared to a control value, then the individual is diagnosed with endometrial cancer and/or an increased likelihood of endometrial cancer. For example, when TJP3 is combined with DDR1, EPS8L2, GMIP, IKBKE, P2RX4, P4HB, PHKG2, PPP1R16A, SIRT6, SOCS2, and RNF183 the AUROC value is 1 and the sensitivity is 100% and the specificity is 100% (see Table 11). According to one aspect of this embodiment, the sample is chosen from a tissue sample and a fluid sample. In one aspect, the fluid sample is a uterine fluid sample or uterine aspirate. According to one aspect of this embodiment, the level of mRNA corresponding to the biomarker is determined.

In microarray studies, EFEMP2 was found to be overexpressed in samples from patients having endometrial cancer as compared to normal values (non-affected). In RT-PCR studies this result was confirmed and a p-value of less than 0.0001 was obtained for aspirate samples from non-affected individuals versus aspirates from individuals having endometrial cancer comparisons. The expression of EFEMP2 was also found to be correlated in primary tumor and uterine fluid. Thus, EFEMP2 is an excellent biomarker for diagnosing endometrial cancer and/or an increased likelihood of endometrial cancer. Furthermore, fingerprint patterns/profiles having EFEMP2 are expected to be useful for diagnosing endometrial cancer and/or an increased likelihood of endometrial cancer. In one embodiment, the invention provides a method for diagnosing endometrial cancer and/or an increased likelihood of endometrial cancer comprising obtaining a sample from an individual and determining the level of EFEMP2 and from 2 to 19 other biomarkers chosen from Table 1 wherein if said markers are differentially expressed compared to a control value, then the individual is diagnosed with endometrial cancer and/or an increased likelihood of endometrial cancer. According to one aspect of this embodiment, the sample is chosen from a tissue sample and a fluid sample. In one aspect, the fluid sample is a uterine fluid sample or uterine aspirate. According to one aspect of this embodiment, the level of mRNA corresponding to the biomarker is determined.

In microarray studies, DCN was found to be overexpressed in samples from patients having endometrial cancer as compared to normal values (non-affected). In RT-PCR studies this result was confirmed and a p-value of less than 0.005 was obtained for aspirate samples from non-affected individuals versus aspirates from individuals having endometrial cancer comparisons. The expression of DCN was also found to be correlated in primary tumor and uterine fluid. Thus, DCN is an excellent biomarker for diagnosing endometrial cancer and/or an increased likelihood of endometrial cancer. Furthermore, fingerprint patterns/profiles having DCN are expected to be useful for diagnosing endometrial cancer and/or an increased likelihood of endometrial cancer. In one embodiment, the invention provides a method for diagnosing endometrial cancer and/or an increased likelihood of endometrial cancer comprising obtaining a sample from an individual and determining the level of DCN, and from 2 to 19 other biomarkers chosen from Table 1 wherein if said markers are differentially expressed compared to a control value, then the individual is diagnosed with endometrial cancer and/or an increased likelihood of endometrial cancer. According to one aspect of this embodiment, the sample is chosen from a tissue sample and a fluid sample. In one aspect, the fluid sample is a uterine fluid sample or uterine aspirate. According to one aspect of this embodiment, the level of mRNA corresponding to the biomarker is determined.

In one embodiment, the invention provide an in vitro diagnostic method for the diagnosis of endometrial cancer or an increased likelihood of endometrial comprising detecting the level of (1) from 1 to 17 biomarker(s) chosen from ACAA1, AP1M2, CGN, DDR1, EPS8L2, FASTKD1, GMIP, IKBKE, P2RX4, P4HB, PHKG2, PPFIBP2, PPP1R16A, RASSF7, RNF183, SIRT6, and TJP3 in a sample from a patient wherein an increased level of said from 1 to 17 biomarkers compared to a control value indicates a diagnosis of endometrial cancer or increased likelihood of endometrial cancer and/or (2) detecting the level of from 1 to 3 biomarkers chosen from EFEMP2, SOCS2, and DCN, wherein a decreased level of EFEMP2, SOCS2, and/or DCN compared to a control value indicates a diagnosis of endometrial cancer or increased likelihood of endometrial cancer. In one preferred aspect, the method of diagnosing endometrial cancer or an increased likelihood of endometrial cancer involves using one or more upregulated biomarkers and one or more down-regulated biomarkers according to Table 1.

In one aspect of this embodiment, the patient has a risk factor for endometrial cancer or is being screened for endometrial cancer.

In one aspect of this embodiment, the sample from said patient is obtained from a patient with abnormal uterine bleeding.

In one aspect of this embodiment, the sample is from said patient is obtained from a patient having an endometrium with increased thickness.

In one aspect of this embodiment, the sample from said patient is obtained from a pre-menopausal, peri-menopausal, or post-menopausal patient.

In one aspect of this embodiment, the patient is pre-menopausal.

In one aspect of this embodiment, the patient is peri-menopausal.

In one aspect of this embodiment, the patient is post-menopausal.

In one aspect of this embodiment, the sample is chosen from a tissue sample, blood and/or serum, and uterine fluid.

In one aspect of this embodiment, the sample is a uterine fluid sample.

In one aspect of this embodiment, the uterine fluid sample is obtained by aspiration.

In one aspect of this embodiment, the level of the biomarker(s) is determined with an antibody.

In one aspect of this embodiment, the level of the biomarker(s) is determined by RT-PCR. In one specific aspect, the level of the biomarker is determined by quantitative RT-PCR.

In one aspect of this embodiment, the markers are chosen from IKBKE, P4HB, SOCS2, GMIP, DDR1, EPS8L2, PPP1R16A, P2RX4, PHKG2, RASSF7, SIRT6, and TJP3.

In one aspect of this embodiment, the marker(s) is chosen from P2RX4, P4HB, PHKG2, PPFIBP2, and SOCS2.

In one aspect of this embodiment, the markers are chosen from P4HB, RASSF7, RNF183, and IKBKE.

In one aspect of this embodiment, from 2 to 20 markers are detected.

In one aspect of this embodiment, one or more additional auxiliary biomarkers are detected.

In one aspect of this embodiment, the one or more auxiliary biomarkers are chosen from differential diagnosis biomarkers, prognostic biomarkers, biomarkers useful for detecting endometrial cancer, biomarkers for classify endometrial cancer and additional biomarkers for detecting endometrial cancer.

In one aspect of this embodiment, the one or more auxiliary biomarkers are chosen from differential diagnosis biomarkers.

In one aspect of this embodiment, the one or more auxiliary biomarkers are chosen from prognostic markers.

In one aspect of this embodiment, the one or more auxiliary biomarkers are chosen from endometrial cancer classification markers.

In one aspect of this embodiment, the invention provides a nucleic acid chosen from IKBKE mRNA, cDNA, or a complement thereof; P4HB mRNA, cDNA, or a complement thereof; SOCS2 mRNA, cDNA, or a complement thereof; GMIP mRNA, cDNA, or a complement thereof; DDR1 mRNA, cDNA, or a complement thereof; EPS8L2 mRNA, cDNA, or a complement thereof; and PPP1R16A mRNA, cDNA, complement thereof, for use for diagnosing endometrial cancer or an increased likelihood of having endometrial cancer.

In one aspect of this embodiment, the invention provides a nucleic acid chosen from ACAA1 mRNA, cDNA, or a complement thereof; AP1M2 mRNA, cDNA, or a complement thereof; CGN mRNA, cDNA, or a complement thereof; P2RX4 mRNA, cDNA, or a complement thereof; PPFIBP2 mRNA, cDNA, or a complement thereof; RASSF7 mRNA, cDNA, or a complement thereof; TJP3 mRNA, cDNA, or a complement thereof; DCN mRNA, cDNA, or a complement thereof; and RNF183 mRNA, cDNA, or a complement thereof, for use for diagnosing endometrial cancer or an increased likelihood of having endometrial cancer.

In one aspect of this embodiment, the invention provides a nucleic acid chosen from EFEMP2 mRNA, cDNA, or a complement thereof; PHKG2 mRNA, cDNA, or a complement thereof; SIRT6 mRNA, cDNA, or a complement thereof; and FASTKD1 mRNA, cDNA, or a complement thereof, for use for diagnosing endometrial cancer or an increased likelihood of having endometrial cancer.

In one aspect of this embodiment, the invention provides primers chosen from primers for IKBKE; primers for P4HB; primers for SOCS2; primers for GMIP; primers for DDR1; primers for EPS8L2; and primers for PPP1R16A; for use for diagnosing endometrial cancer and/or an increased likelihood of having endometrial cancer.

In one aspect of this embodiment, the invention provides primers chosen from primers for ACAA1; primers for AP1M2; primers for CGN; primers for P2RX4; primers for PPFIBP2; primers for RASSF7; primers for RNF183; primers for TJP3; and primers for DCN; for use for diagnosing endometrial cancer and/or an increased likelihood of having endometrial cancer.

In one aspect of this embodiment, the invention provides primers chosen from primers for EFEMP2; primers for SIRT6; primers for PHKG2; and primers for FASTKD1; for use for diagnosing endometrial cancer and/or an increased likelihood of having endometrial cancer.

In one aspect of this embodiment, the invention provides a nucleic acid chosen from probe for IKBKE; probe for P4HB; probe for SOCS2; probe for GMIP; probe for DDR1; probe for EPS8L2; and probe for PPP1R16A, for diagnosing endometrial cancer and/or an increased likelihood of having endometrial cancer.

In one aspect of this embodiment, the invention provides a nucleic acid chosen from probe for ACAA1; probe for AP1M2; probe for CGN; probe for P2RX4; probe for PPFIBP2; probe for RASSF7; probe for RNF183; probe for TJP3; and probe for DCN, for diagnosing endometrial cancer and/or an increased likelihood of having endometrial cancer.

In one aspect of this embodiment, the invention provides a nucleic acid chosen from probe for EFEMP2; probe for FASTKD1; probe for SIRT6; probe for GMIP; and probe for PHKG2, for diagnosing endometrial cancer and/or an increased likelihood of having endometrial cancer.

In one aspect of this embodiment, the invention provides a kit comprising two or more probes to the 1-20 biomarkers of the invention, for diagnosing endometrial cancer and/or an increased likelihood of cancer.

In one aspect of this embodiment, the invention provides a kit comprising primers for two or more of the 1-20 biomarkers of the invention for diagnosing endometrial cancer and/or an increased likelihood of cancer.

In one aspect of this embodiment, the invention provides an antibody chosen from an antibody to IKBKE; an antibody to P4HB; an antibody to SOCS2; an antibody to GMIP; an antibody to DDR1; an antibody to EPS8L2; and an antibody to PPP1R16A, for diagnosing endometrial cancer and/or an increased likelihood of having endometrial cancer.

In one aspect of this embodiment, the invention provides an antibody chosen from an antibody to ACAA1; an antibody to AP1M2; an antibody to CGN; an antibody to P2RX4; an antibody to PPFIBP2; an antibody to RASSF7; an antibody to RNF183; an antibody to TJP3; and an antibody to DCN, for diagnosing endometrial cancer and/or an increased likelihood of having endometrial cancer.

In one aspect of this embodiment, the invention provides an antibody chosen from an antibody to EFEMP2; an antibody to FASTKD1; an antibody to SIRT6; an antibody to GMIP; and an antibody to PHKG2; for diagnosing endometrial cancer and/or an increased likelihood of having endometrial cancer.

In one aspect of this embodiment, the invention provides a kit comprising antibodies to two or more biomarkers of Table 1 for diagnosing endometrial cancer and/or an increased likelihood of cancer.

In aspect of this embodiment, the invention provides a kit for obtaining uterine fluid for diagnosing endometrial cancer and/or an increased likelihood of endometrial cancer by assessing the levels of from 1-20 biomarkers of Table 1.

In one aspect of this embodiment, the in vitro diagnostic method comprises determining the level of 2 biomarkers of the invention. In one aspect of this embodiment, the in vitro diagnostic method comprises determining the level of 3 biomarkers of the invention. In one aspect of this embodiment, the in vitro diagnostic method comprises determining the level of 4 biomarkers of the invention. In one aspect of this embodiment, the in vitro diagnostic method comprises determining the level of 5 biomarkers of the invention. In one aspect of this embodiment, the in vitro diagnostic method comprises determining the level of 5 biomarkers of the invention. In one aspect of this embodiment, the in vitro diagnostic method comprises determining the level of 7 biomarkers of the invention. In one aspect of this embodiment, the in vitro diagnostic method comprises determining the level of 10 biomarkers of the invention. In one aspect of this embodiment, the in vitro diagnostic method comprises determining the level of 15 biomarkers of the invention. In one aspect of this embodiment, the in vitro diagnostic method comprises determining the level of 20 biomarkers of the invention.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. In case of conflict, the present specification, including definitions, will control. In addition, the materials, methods, and examples are illustrative only and not intended to be limiting.

Other features and advantages of the invention will be apparent from the following detailed description, and from the claims.

BRIEF DESCRIPTION OF THE DRAWINGS

FIGS. 2A and 2B is a box and whiskers plots represent the relative amount of RNA (RQ) present in the aspirate samples from patients having endometrial cancer as compared with the control samples for each gene as determined by RT-PCR. 30 tumor samples and 24 controls were considered in the plots. Boxes represent the interquartile range for each gene and the whiskers go from percentile 10 to 90 of the RQ values for each gene. The bar in the boxes represents the median RQ. The white boxes represent the values for the tumour samples of each gene and the shaded boxes the values for the control samples. See Example 4 for details.

FIG. 3 shows an example of the expression level of RNF183 as determined by RT-PCR in aspirates obtained from patients having endometrial cancer (RNF183_T), normals in secretory phase (RNF183_S), normals not having endometrial cancer (RNF183_N), and all normals together (RNF183_Nt).

FIG. 4 shows an example of the expression level of AP1M2 as determined by RT-PCR in aspirates obtained from patients having endometrial cancer (AP1M2_T), normals in secretory phase (AP1M2_S), normals not having endometrial cancer (AP1M2_N), and all normals together (AP1M2_Nt).

FIG. 5 shows an example of the expression level of CGN as determined by RT-PCR in aspirates obtained from patients having endometrial cancer (CGN_T), normals in secretory phase (CGN_S), normals not having endometrial cancer (CGN_N), and all normals together (CGN_Nt).

FIG. 6 shows an example of the expression level of FASTKD1 as determined by RT-PCR in aspirates obtained from patients having endometrial cancer (FASTKD1_T), normals in secretory phase (FASTKD1_S), normals not having endometrial cancer (FASTKD1_N), and all normals together (FASTKD1_Nt).

FIG. 7 shows an example of the expression level of IKBKE as determined by RT-PCR in aspirates obtained from patients having endometrial cancer (IKBKE_T), normals in secretory phase (IKBKE_S), normals not having endometrial cancer (IKBKE_N), and all normals together (IKBKE_Nt).

FIG. 8 shows an example of the expression level of P4HB as determined by RT-PCR in aspirates obtained from patients having endometrial cancer (P4HB_T), normals in secretory phase (P4HB_S), normals not having endometrial cancer (P4HB_N), and all normals together (P4HB_Nt).

FIG. 9 shows an example of the expression level of SOCS2 as determined by RT-PCR in aspirates obtained from patients having endometrial cancer (SOCS2_T), normals in secretory phase (SOCS2_S), normals not having endometrial cancer (SOCS2_N), and all normals together (SOCS2_Nt).

DETAILED DESCRIPTION OF THE INVENTION

Figure 1:
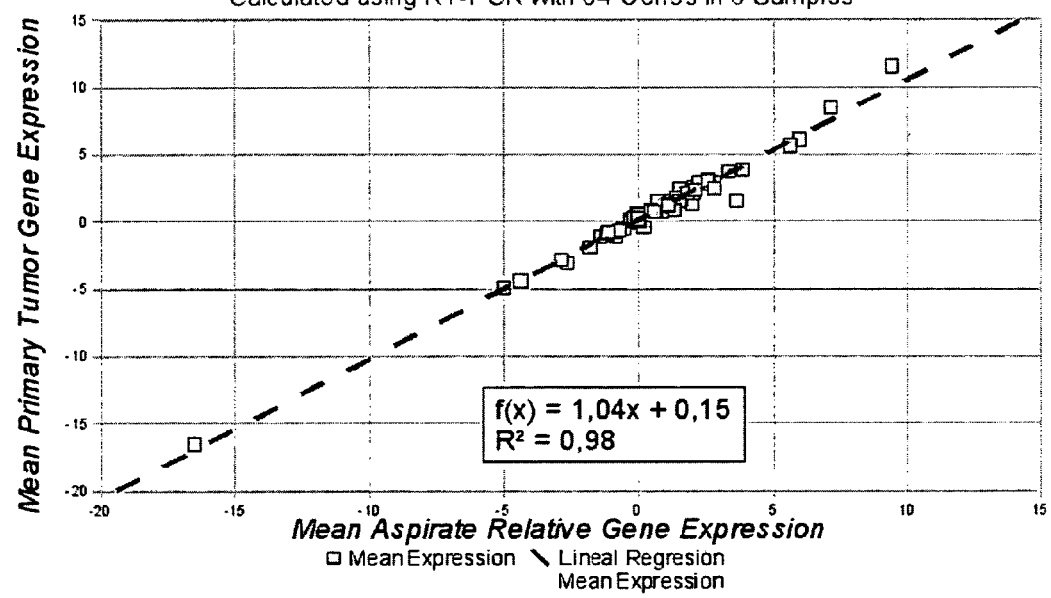
FIG. 1 shows correlation of the expression level of biomarkers in primary tumor and in uterine fluid for the biomarkers including those of the invention. See Example 3 for details.

The present invention is based on the finding of the association of alterations in the mRNA expression levels of the biomarkers listed in Table 1 in samples from patients having endometrial cancer as compared to control values (e.g., normal tissue (non-affected) or value). These biomarkers therefore represent endometrial cancer biomarkers. Additionally, the inventors surprisingly found that samples obtained from uterine fluid of endometrial cancer patients display expression profiles for the biomarkers listed in Table 1 that were generally correlated to the expression profiles from the primary tumor. Furthermore, a number of the markers found by the inventors are expected to be found on cell surfaces and/or in blood as blood based markers (or in other body fluids like uterine fluid). As shown in Example 6, the upregulated biomarkers of Table 1 were shown to be overexpressed at the protein level in primary tissue as compared to normal non-affected tissue. For example, the protein level of P4HB by western blot analysis, revealed that this biomarker is overexpressed at a protein level as well. FIG. 11 through FIG. 16 show overexpression, at the protein level, of AP1M2, IKBKE, EPS8L2, DDR1, CGN, and TJP3. Furthermore, P4HB, PPP1R16A and EPS8L2 presented a specific cytoplasmatic expression within the tumoral cells in all carcinoma histological types and grades, and an absence or faint cytoplasmatic staining within the normal epithelial glands as determined by tissue microarray (TMA) immunohistochemistry (IHC).

These studies provide endometrial cancer diagnostic biomarkers with excellent predictive value, alone or in combinations, that may be detected using methods which are less invasive as compared to the current standard of care. Furthermore, the inventors have identified specific subsets of biomarkers that are capable of distinguishing, in endometrial aspirates samples, endometrial cancer affected patients from different sub-groups of non-affected patients.

Several of the studies used to identify (expression microarray) and validate (RT-PCR) the biomarkers of the invention are described briefly below and in more detail in the Example section.

More specifically, the inventors performed gene expression analysis on expression microarrays to detect genes that are differentially expressed in endometrial cancer as compared to normal tissues. The gene expression microarray studies disclosed herein revealed that a number of genes in endometrial cancer samples were overexpressed as compared to normal endometrial tissue. It was found that ACAA1, AP1M2, CGN, DDR1, EPS8L2, FASTKD1, GMIP, IKBKE, P2RX4, P4HB, PHKG2, PPFIBP2, PPP1R16A, RASSF7, RNF183, SIRT6, and TJP3, were overexpressed in endometrial cancer samples and EFEMP2, SOCS2, and DCN were underexpressed, as compared to their respective levels in normal endometrial tissue using a microarray experimental strategy. These results are summarized in Table 1 which has the common abbreviation for the gene, the ENSMBL accession numbers (corresponding to the gene, transcript(s), and protein related to the biomarkers of the invention), the fold change values and the p-values for statistical significance.

TABLE 1

Differential expression of endometrial cancer biomarkers in primary tumor as compared to control values (obtained from a pool of unaffected tissue, see Example 1).

| | | | | Array data | |
|---|---|---|---|---|---|
| Name | gene | Transcrip | Protein | Fold change | p-value |
| RASSF7 | ENSG00000099849 | ENST00000397583 | ENSP00000380713 | 1.94 | 0.07 |
| | | ENST00000397582 | ENSP00000380712 | | |
| CGN | ENSG00000143375 | ENST00000271636 | ENSP00000271636 | 1.79 | 0.22 |
| AP1M2 | ENSG00000129354 | ENST00000250244 | ENSP00000250244 | 1.71 | 0.11 |
| PHKG2 | ENSG00000156873 | ENST00000328273 | ENSP00000329968 | 1.34 | 0.09 |
| PPP1R16A | ENSG00000160972 | ENST00000292539 | ENSP00000292539 | 1.44 | 0.10 |
| DDR1 | ENSG00000137332 | ENST00000259875 | ENSP00000259875 | 1.93 | 0.13 |
| | | ENST00000400414 | ENSP00000383265 | | |
| | | ENST00000400411 | ENSP00000383262 | | |
| | | ENST00000383377 | ENSP00000372868 | | |
| | | ENST00000400410 | ENSP00000383261 | | |
| P4HB | ENSG00000185624 | ENST00000331483 | ENSP00000327801 | 1.90 | 0.13 |
| RNF183 | ENSG00000165188 | ENST00000297894 | ENSP00000297894 | 1.73 | 0.19 |
| IKBKE | ENSG00000143466 | ENST00000367120 | ENSP00000356087 | 1.37 | 0.17 |
| EPS8L2 | ENSG00000177106 | ENST00000318562 | ENSP00000320828 | 1.34 | 0.20 |
| TJP3 | ENSG00000105289 | ENST00000262968 | ENSP00000262968 | 1.57 | 0.17 |
| | | ENST00000382008 | ENSP00000371438 | | |
| SIRT6 | ENSG00000077463 | ENST00000269860 | ENSP00000269860 | 1.27 | 0.15 |
| | | ENST00000305232 | ENSP00000305310 | | |
| | | ENST00000337491 | ENSP00000337332 | | |
| | | ENST00000381935 | ENSP00000371360 | | |
| GMIP | ENSG00000089639 | ENST00000203556 | ENSP00000203556 | 1.42 | 0.05 |
| ACAA1 | ENSG00000060971 | ENST00000333167 | ENSP00000333664 | 1.26 | 0.11 |
| | | ENST00000301810 | ENSP00000301810 | | |
| | | ENST00000358122 | ENSP00000350838 | | |
| FASTKD1 | ENSG00000138399 | ENST00000260971 | ENSP00000260971 | 1.71 | 0.06 |
| | | ENST00000361619 | ENSP00000354598 | | |
| | | ENST00000361819 | ENSP00000354821 | | |
| DCN | ENSG00000011465 | ENST00000052754 | ENSP00000052754 | −2.55 | 0.06 |
| | | ENST00000228329 | ENSP00000228329 | | |
| | | ENST00000303320 | ENSP00000302031 | | |
| | | ENST00000350856 | ENSP00000308451 | | |
| SOCS2 | ENSG00000120833 | ENST00000340600 | ENSP00000339428 | −1.69 | 0.06 |
| | | ENST00000393123 | ENSP00000376831 | | |
| EFEMP2 | ENSG00000172638 | ENST00000307998 | ENSP00000309953 | −1.22 | 0.08 |
| P2RX4 | ENSG00000135124 | ENST00000337233 | ENSP00000336607 | 1.70 | 0.12 |
| | | ENST00000359949 | ENSP00000353032 | | |
| PPFIBP2 | ENSG00000166387 | ENST00000299492 | ENSP00000299492 | 1.52 | 0.11 |

As shown in FIG. 1, it was found that the markers of Table 1 were also found to be differentially expressed in samples obtained from uterine fluid in patients having endometrial cancer. Markers which were not highly correlated fall off or further away from the correlation line in FIG. 1.

The overexpression of ACAA1, AP1M2, CGN, DDR1, EPS8L2, FASTKD1, GMIP, IKBKE, P2RX4, P4HB, PHKG2, PPFIBP2, PPP1R16A, RASSF7, RNF183, SIRT6, and TJP3, and the underexpression of DCN, SOCS2, and EFEMP2 in endometrial cancer was validated by RT-PCR using an independent set of samples. The samples used in this study were obtained from uterine fluid of individuals having endometrial cancer and from patients not having endometrial cancer. These results are summarized in Table 2 and illustrated in FIG. 2A and FIG. 2B. These results demonstrate that these markers displayed statistically significant differential expression in endometrial cancer samples in samples from individuals having endometrial cancer as compared to normal individuals and/or samples (e.g., control value).

TABLE 2

Differential expression of biomarkers in aspirate samples from patients having endometrial cancer compared to aspirates from patients not having endometrial cancer.

|          | Mean RQ | SEM   | p value  |
|----------|---------|-------|----------|
| ACAA1    | 1.472   | 0.476 | <0.0001  |
| AP1M2    | 1.688   | 0.422 | <0.0001  |
| CGN      | 2.348   | 1.312 | <0.0001  |
| DCN      | 0.246   | 0.196 | 0.002    |
| DDR1     | 1.515   | 0.534 | 0.0167   |
| EFEMP2   | 0.414   | 0.289 | <0.0001  |
| EPS8L2   | 1.646   | 0.559 | 0.0016   |
| FASTKD1  | 1.693   | 0.662 | <0.0001  |
| GMIP     | 1.338   | 0.491 | <0.0001  |
| IKBKE    | 2.877   | 1.617 | <0.0001  |
| P2RX4    | 1.544   | 0.504 | 0.0002   |
| P4HB     | 1.998   | 0.647 | <0.0001  |
| PHKG2    | 1.557   | 0.378 | <0.0001  |
| PPFIBP2  | 1.540   | 0.725 | 0.0094   |
| PPP1R16A | 1.915   | 0.789 | <0.0001  |
| RASSF7   | 1.848   | 0.770 | 0.0001   |
| RNF183   | 3.648   | 2.368 | <0.0001  |
| SIRT6    | 1.611   | 0.550 | <0.0001  |
| SOCS2    | 0.265   | 0.177 | <0.0001  |
| TJP3     | 2.088   | 0.928 | <0.0001  |

The p-values were calculated using a non-parametic Mann-Whitney test. Mean RQ refers to relative quantity, and SEM refers to standard error of the mean.

The finding of the correlation of expression levels of these biomarkers in primary tissue and uterine fluid was surprising given the heterogeneity of uterine fluid and the findings in the initial microarrays studies. It is believed that this is the first time that that the levels of biomarkers in primary endometrial cancer were shown to be correlated in a statistically significant manner to those found in uterine fluid and therefore this provides a less invasive and more standardized method of screening for endometrial cancer and/or an increased risk of endometrial cancer. The invention therefore provides a method for diagnosing endometrial cancer and/or an increased likelihood of endometrial cancer by obtaining a uterine fluid sample and determining the level of biomarkers differentially expressed in endometrial cancer as compared to control value. In one aspect, the uterine fluid sample is obtained by aspiration. In one aspect, the uterine fluid sample is obtained gently washing and/or rinse the uterine cavity. In one aspect, the level of mRNA is determined. In one aspect, the level of protein is determined. In one aspect, the biomarkers are chosen from the 20 listed in Table 1.

Surprisingly, the p-values for the individual biomarkers in Table 1 as determined in the microarray studies with one sample set were significantly improved upon when the same biomarkers were analyzed by a different technique (quantitative RT-PCR) using a different set of samples, obtained from the patient by a different method. In general the p-values were over 100 fold improved compared to the microarray studies.

The inventors have found that individually each of the biomarkers of Table 1 have predictive value for the diagnosis of endometrial cancer. Furthermore, combinations of these biomarkers have additional predictive value for the diagnosis of endometrial cancer. For example, the inventors have surprisingly found that numerous sub-groups of the biomarkers of Table 1 having from 2-20 biomarkers in various combinations give fingerprint patterns having excellent predictive value for diagnosis or detection of endometrial cancer. Additionally, the inventors have also contemplate that addition of other biomarkers besides those listed in Table 1, to the fingerprint pattern also can increase predictive value, and can be useful for classifying endometrial cancers, for differential diagnosis of diseases other than endometrial cancer, and for endometrial cancer prognosis.

In one embodiment, the present invention provides a method for characterizing a sample obtained from a patient for prognostic, diagnostic and/or pharmacogenomic uses. Characterization of the a sample obtained from a patient according to the levels one or more of the biomarkers of Table 1 can be used to provide information regarding disease progression, diagnosis of endometrial cancer type (and/or subtype), and selection of an appropriate therapeutic treatment. According to the method of the invention, a sample is obtained from an individual. The individual can be a healthy person, an individual diagnosed with cancer, an individual suspected of having cancer, an individual displaying one or more symptoms of cancer and/or an individual desiring screening for cancer. The method comprises the step of determining the level of the biomarker(s) of Table 1 in a sample obtained for a patient. Alternative methods for determining the biomarkers (IHC, mRNA expression analysis, etc) can be used in these methods.

In one embodiment, the invention provides a method for diagnosing endometrial cancer and/or an increased likelihood of having endometrial cancer which comprises obtaining a sample from an individual and determining the level of from 1 to 20 biomarkers of Table 1 in the sample. If the level of from 1 to 17 of the upregulated biomarkers are increased relative to control value and/or the level of from 1 to 3 of the downregulated markers are decreased compared to control value, then the patient has an increased likelihood of having endometrial cancer.

In one embodiment, the invention provides a method for diagnosing endometrial cancer which comprises obtaining a sample from a patient having a symptom of endometrial cancer and determining the level of from 1 to 20 biomarkers of Table 1 in the sample. In one aspect of this embodiment, the symptom of endometrial cancer is chosen from vaginal bleeding and/or spotting in postmenopausal women, abnormal uterine bleeding, abnormal menstrual periods, bleeding between normal periods in premenopausal women in women older than 40, extremely long, heavy, or frequent episodes of bleeding, anemia caused by chronic loss of blood, lower abdominal pain or pelvic cramping, thin white or clear vaginal discharge in postmenopausal women, and suspect symptoms in peri-menopausal. Thus, in one aspect of this embodiment, the invention relates to a method for diagnosing endometrial cancer comprising obtaining or providing a sample from an individual having vaginal bleeding and/or spotting in postmenopausal women, abnormal uterine bleeding, abnormal menstrual periods, bleeding between normal periods in premenopausal women in women older than 40, extremely long, heavy, or frequent episodes of bleeding, anemia caused by chronic loss of blood, lower abdominal pain or pelvic cramping, thin white or clear vaginal discharge in postmenopausal women, or suspect symptoms in peri-menopausal and determining the level of from 1-17 biomarkers chosen from ACAA1, AP1M2, CGN, DDR1, EPS8L2, FASTKD1, GMIP, IKBKE, P2RX4, P4HB, PHKG2, PPFIBP2, PPP1R16A, RASSF7, RNF183, SIRT6, TJP3, and/or from 1 to 3 biomarkers chosen from EFEMP2, SOCS2, and DCN wherein if said markers are differentially expressed compared to a control value, then the individual is diagnosed with endometrial cancer and/or an increased likelihood of endometrial cancer. In a specific aspect of this embodiment, when the level of from 1 to 17 biomarkers chosen from ACAA1, AP1M2, CGN, DDR1, EPS8L2, FASTKD1, GMIP, IKBKE, P2RX4, P4HB, PHKG2, PPFIBP2, PPP1R16A, RASSF7, RNF183, SIRT6, TJP3, are increased relative to a control value and/or the level from 1 to 3 biomarkers chosen from EFEMP2, SOCS2, and DCN are decreased relative to control value then this indicates endometrial cancer or an increased chance of having endometrial cancer. According to one aspect of this embodiment, the levels of the one or more biomarkers for detecting endometrial cancer are normalized to one or more endogenous biomarkers or genes. According to one aspect of this embodiment, the sample is chosen from a tissue sample and a fluid sample. In one aspect, the fluid sample is a uterine fluid sample or uterine aspirate. According to one aspect of this embodiment, the level of mRNA corresponding to the biomarker is determined. According to another aspect of this embodiment, the level of protein corresponding to the biomarker is determined.

In one embodiment, the invention provides a method for diagnosing endometrial cancer which comprises obtaining a sample from a patient having a risk factor for endometrial cancer and determining the level of from 1 to 20 biomarkers of Table 1 in the sample. In one aspect of this embodiment, the risk factor for endometrial cancer is chosen from high levels of estrogen, endometrial hyperplasia, obesity, hypertension, polycystic ovary syndrome, nulliparity, infertility, early menarche, late menopause, endometrial polyps or other benign growths of the uterine lining, diabetes, tamoxifen exposure, hyperplasia, high intake of animal fat, pelvic radiation therapy, breast cancer, ovarian cancer, heavy daily alcohol consumption, family history of cancer, family history of HNPCC, and being an HNPCC mutation carrier. In one aspect of this embodiment, the biomarkers are selected for distinguishing patients having tumor from those in secretory phase of the menstrual cycle. Thus, in one aspect of this embodiment, the invention relates to a method for diagnosing endometrial cancer comprising obtaining or providing a sample from an individual having a risk factor for cancer which is high levels of estrogen, endometrial hyperplasia, obesity, hypertension, polycystic ovary syndrome, nulliparity, infertility, early menarche, late menopause, endometrial polyps or other benign growths of the uterine lining, diabetes, tamoxifen exposure, hyperplasia, high intake of animal fat, pelvic radiation therapy, breast cancer, ovarian cancer, heavy daily alcohol consumption, family history of cancer, family history of HNPCC, or being an HNPCC mutation carrier which is and determining the level of from 1-17 biomarkers chosen from ACAA1, AP1M2, CGN, DDR1, EPS8L2, FASTKD1, GMIP, IKBKE, P2RX4, P4HB, PHKG2, PPFIBP2, PPP1R16A, RASSF7, RNF183, SIRT6, TJP3, and/or from 1 to 3 biomarkers chosen from EFEMP2, SOCS2, and DCN wherein if said markers are differentially expressed compared to a control value, then the individual is diagnosed with endometrial cancer and/or an increased likelihood of endometrial cancer. In a specific aspect of this embodiment, when the level of from 1 to 17 biomarkers chosen from ACAA1, AP1M2, CGN, DDR1, EPS8L2, FASTKD1, GMIP, IKBKE, P2RX4, P4HB, PHKG2, PPFIBP2, PPP1R16A, RASSF7, RNF183, SIRT6, TJP3, are increased relative to a control value and/or the level from 1 to 3 biomarkers chosen from EFEMP2, SOCS2, and DCN are decreased relative to control value then this indicates endometrial cancer or an increased chance of having endometrial cancer. According to one aspect of this embodiment, the levels of the one or more biomarkers for detecting endometrial cancer are normalized to one or more endogenous biomarkers or genes. According to one aspect of this embodiment, the sample is chosen from a tissue sample and a fluid sample. In one aspect, the fluid sample is a uterine fluid sample or uterine aspirate. According to one aspect of this embodiment, the level of mRNA corresponding to the biomarker is determined. According to another aspect of this embodiment, the level of protein corresponding to the biomarker is determined. In a preferred aspect of this embodiment, the method involves determining the level of from 1-17 upregulated biomarkers of Table 1 and from 1-3 downregulated markers of Table 1 by quantitative PCR in a uterine fluid sample.

In one embodiment, the invention provides a method for diagnosing endometrial cancer which comprises obtaining a sample from a patient having an endometrium with an increased thickness. In one aspect of this embodiment, the thickness of the endometrium is measured by transvaginal ultrasound. "Increased thickness" refers a thickness above a value common employed in the art to identify patients that warrant further work-up or investigation. The method of this embodiment involves determining the level determining the level of from 1 to 20 biomarkers of Table 1 in a sample obtained from a patient having an endometrium of increased thickness. According to an aspect of this embodiment, the sample is a uterine fluid sample. In another aspect of this embodiment, the level of from 1-20 mRNA biomarkers is determined. In another aspect of this embodiment, the level of from 1-20 protein biomarkers is determined. In one aspect of this embodiment, the biomarkers are chosen from those that are capable of distinguishing samples from endometrial cancer affected patients and from those patients having another condition that increases the thickness of the endometrium. Conditions that increases the thickness of the endometrium but are not necessarily present in endometrial cancer patients include, but are not limited to, tamoxifen exposure, exposure to hormones, phase of menstrual cycle (in general the endometrium thickness increase in going from proliferative to secretory phase). Some preferred biomarkers which performed well in separating samples from patients affected with endometrial cancer from non-endometrial cancer affected patients in the secretory phase are shown in Table 9 in the Examples. Thus, in one aspect of this embodiment, the invention relates to a method for diagnosing endometrial cancer comprising obtaining or providing a sample from an individual having increased endometrial thickness and determining the level of from 1-17 biomarkers chosen from ACAA1, AP1M2, CGN, DDR1, EPS8L2, FASTKD1, GMIP, IKBKE, P2RX4, P4HB, PHKG2, PPFIBP2, PPP1R16A, RASSF7, RNF183, SIRT6, TJP3, and/or from 1 to 3 biomarkers chosen from EFEMP2, SOCS2, and DCN wherein if said markers are differentially expressed compared to a control value, then the individual is diagnosed with endometrial cancer and/or an increased likelihood of endometrial cancer. In a specific aspect of this embodiment, when the level of from 1 to 17 biomarkers chosen from ACAA1, AP1M2, CGN, DDR1, EPS8L2, FASTKD1, GMIP, IKBKE, P2RX4, P4HB, PHKG2, PPFIBP2, PPP1R16A, RASSF7, RNF183, SIRT6, TJP3, are increased relative to a control value and/or the level from 1 to 3 biomarkers chosen from EFEMP2, SOCS2, and DCN are decreased relative to control value then this indicates endometrial cancer or an increased chance of having endometrial cancer. According to one aspect of this embodiment, the levels of the one or more biomarkers for detecting endometrial cancer are normalized to one or more endogenous biomarkers or genes. According to one aspect of this embodiment, the sample is chosen from a tissue sample and a fluid sample. In one aspect, the fluid sample is a uterine fluid sample or uterine aspirate. According to one aspect of this embodiment, the level of mRNA corresponding to the biomarker is determined. According to another aspect of this embodiment, the level of protein corresponding to the biomarker is determined. In a preferred aspect of this embodiment, the method involves determining the level of from 1-17 upregulated biomarkers of Table 1 and from 1-3 downregulated markers of Table 1 by quantitative PCR in a uterine fluid sample.

Profiles, Fingerprint Patterns, and Combinations

The initial microarray studies disclosed herein demonstrated that each of the biomarkers of Table 1, as independent biomarkers, have predictive value for diagnosing endometrial cancer. Furthermore, it was found that combinations of markers (e.g., profiles or fingerprint patterns) have increased predictive value for endometrial cancer. Thus, in addition to using these markers as individual markers, they can be used in combinations of 2 to 20 biomarkers for diagnosing endometrial cancer. In some embodiments additional markers can be included in the profile or fingerprint pattern for differential diagnostic purposes (exclude or confirm a disease or conditions other than endometrial cancer (e.g., endometrial hyperplasia, endometriosis, ovarian cancer, fibroids, etc.)), classification of type of endometrial cancer (e.g., type I versus type II), classification of cell type of endometrial cancer, and prognosis.

In one embodiment, the invention provides for profiles and/or fingerprint patterns having 2, 3, 4, 5, 6, 7, 8, 9, 10, 11, 12, 13, 14, 15, 16, 17, 18, 19, or 20, of the biomarkers of Table 1. In one aspect of this embodiment, the level of mRNA corresponding to the biomarkers in the profile is determined for use in diagnosis endometrial cancer and/or an increased likelihood of endometrial cancer. In one aspect of this embodiment, the level of protein corresponding to the biomarkers in the profile is determined for use in diagnosis endometrial cancer and/or an increased likelihood of endometrial cancer. In one aspect of this embodiment, the level of the biomarkers is determined in a sample obtained from uterine fluid. In one aspect of this embodiment, the level of the biomarkers is determined in a sample obtained from serum, blood, or plasma.

In one embodiment, the invention provides a method for diagnosing endometrial cancer comprising determining the level of an ACAA1 biomarker in combination with the level of one or more biomarkers. In a specific aspect of this embodiment the one or more biomarkers are chosen from differential diagnosis biomarkers, prognostic biomarkers, biomarkers useful for detecting endometrial cancer, biomarkers for classify endometrial cancer and auxiliary biomarkers for detecting endometrial cancer. In one aspect of this embodiment, the one or more biomarkers are chosen from differential diagnosis biomarkers, biomarkers useful for detecting endometrial cancer, and biomarkers useful for classifying endometrial cancer. In one aspect of this embodiment, the one or more biomarkers useful for detecting endometrial cancer are chosen from AP1M2, CGN, DDR1, EPS8L2, FASTKD1, GMIP, IKBKE, P2RX4, P4HB, PHKG2, PPFIBP2, PPP1R16A, RASSF7, RNF183, SIRT6, TJP3, EFEMP2, SOCS2, and DCN. Combinations or subcombinations including ACAA1 are ACAA1 and AP1M2; ACAA1 and CGN; ACAA1 and DDR1; ACAA1 and EPS8L2; ACAA1 and FASTKD1; ACAA1 and GMIP; ACAA1 and IKBKE; ACAA1 and P2RX4; ACAA1 and P4HB; ACAA1 and PHKG2; ACAA1 and PPFIBP2; ACAA1 and PPP1R16A; ACAA1 and RASSF7; ACAA1 and RNF183; ACAA1 and SIRT6; ACAA1 and TJP3; ACAA1 and EFEMP2; ACAA1 and SOCS2; or ACAA1 and DCN. In one aspect of this embodiment, the level(s) of gene expression of the biomarker is determined. In another aspect of this embodiment, the level(s) of protein expression is determined. In one aspect of this embodiment, a tumor or suspected sample is analyzed. In another aspect a fluid sample is analyzed. In another aspect of this embodiment, a sample obtained from uterine fluid is analyzed. In yet another aspect of this embodiment, a serum or blood samples is analyzed. In one aspect, the sample that is analyzed is obtained from a cell.

In one embodiment, the invention provides a method for diagnosing endometrial cancer comprising determining the level of an AP1M2 biomarker in combination with the level of one or more biomarkers. In a specific aspect of this embodiment the one or more biomarkers are chosen from differential diagnosis biomarkers, prognostic biomarkers, biomarkers useful for detecting endometrial cancer, biomarkers for classify endometrial cancer and auxiliary biomarkers for detecting endometrial cancer. In one aspect of this embodiment, the one or more biomarkers are chosen from differential diagnosis biomarkers, biomarkers useful for detecting endometrial cancer, and biomarkers useful for classifying endometrial cancer. In one aspect of this embodiment, the one or more biomarkers useful for detecting endometrial cancer are chosen from ACAA1, CGN, DDR1, EPS8L2, FASTKD1, GMIP, IKBKE, P2RX4, P4HB, PHKG2, PPFIBP2, PPP1R16A, RASSF7, RNF183, SIRT6, TJP3, EFEMP2, SOCS2, and DCN. Combinations or subcombinations including AP1M2 are AP1M2 and ACAA1; AP1M2 and CGN; AP1M2 and DDR1; AP1M2 and EPS8L2; AP1M2 and FASTKD1; AP1M2 and GMIP; AP1M2 and IKBKE; AP1M2 and P2RX4; AP1M2 and P4HB; AP1M2 and PHKG2; AP1M2 and PPFIBP2; AP1M2 and PPP1R16A; AP1M2 and RASSF7; AP1M2 and RNF183; AP1M2 and SIRT6; AP1M2 and TJP3; AP1M2 and EFEMP2; AP1M2 and SOCS2; or AP1M2 and DCN. In one aspect of this embodiment, the level(s) of gene expression of the biomarker is determined. In another aspect of this embodiment, the level(s) of protein expression is determined. In one aspect of this embodiment, a tumor or suspected sample is analyzed. In another aspect a fluid sample is analyzed. In another aspect of this embodiment, a sample obtained from uterine fluid is analyzed. In yet another aspect of this embodiment, a serum or blood samples is analyzed. In one aspect, the sample that is analyzed is obtained from a cell.

In one embodiment, the invention provides a method for diagnosing endometrial cancer comprising determining the level of a CGN biomarker in combination with the level of one or more biomarkers. In a specific aspect of this embodiment the one or more biomarkers are chosen from differential diagnosis biomarkers, prognostic biomarkers, biomarkers useful for detecting endometrial cancer, biomarkers for classify endometrial cancer and auxiliary biomarkers for detecting endometrial cancer. In one aspect of this embodiment, the one or more biomarkers are chosen from differential diagnosis biomarkers, biomarkers useful for detecting endometrial cancer, and biomarkers useful for classifying endometrial cancer. In one aspect of this embodiment, the one or more biomarkers useful for detecting endometrial cancer are chosen from ACAA1, AP1M2, DDR1, EPS8L2, FASTKD1, GMIP, IKBKE, P2RX4, P4HB, PHKG2, PPFIBP2, PPP1R16A, RASSF7, RNF183, SIRT6, TJP3, EFEMP2, SOCS2, and DCN. Combinations or subcombinations including CGN are CGN and AP1M2; ACAA1 and CGN; CGN and DDR1; CGN and EPS8L2; CGN and FASTKD1; CGN and GMIP; CGN and IKBKE; CGN and P2RX4; CGN and P4HB; CGN and PHKG2; CGN and PPFIBP2; CGN and PPP1R16A; CGN and RASSF7; CGN and RNF183; CGN and SIRT6; CGN and TJP3; CGN and EFEMP2; CGN and SOCS2; or CGN and DCN. In one aspect of this embodiment, the level(s) of gene expression of the biomarker is determined. In another aspect of this embodiment, the level(s) of protein expression is determined. In one aspect of this embodiment, a tumor or suspected sample is analyzed. In another aspect a fluid sample is analyzed. In another aspect of this embodiment, a sample obtained from uterine fluid is analyzed. In yet another aspect of this embodiment, a serum or blood samples is analyzed. In one aspect, the sample that is analyzed is obtained from a cell.

In one embodiment, the invention provides a method for diagnosing endometrial cancer comprising determining the level of a DDR1 biomarker in combination with the level of one or more biomarkers. In a specific aspect of this embodiment the one or more biomarkers are chosen from differential diagnosis biomarkers, prognostic biomarkers, biomarkers useful for detecting endometrial cancer, biomarkers for classify endometrial cancer and auxiliary biomarkers for detecting endometrial cancer. In one aspect of this embodiment, the one or more biomarkers are chosen from differential diagnosis biomarkers, biomarkers useful for detecting endometrial cancer, and biomarkers useful for classifying endometrial cancer. In one aspect of this embodiment, the one or more biomarkers useful for detecting endometrial cancer are chosen from ACAA1, AP1M2, CGN, EPS8L2, FASTKD1, GMIP, IKBKE, P2RX4, P4HB, PHKG2, PPFIBP2, PPP1R16A, RASSF7, RNF183, SIRT6, TJP3, EFEMP2, SOCS2, and DCN. A preferred combination or subcombination useful for detecting endometrial cancer or an increased likelihood of endometrial cancer is DDR1 and P4HB; DDR1 and GMIP; DDR1 and IKBKE; DDR1 and EFEMP2; DDR1 and SOCS2; DDR1, P4HB, and GMIP; DDR1, P4HB, GMIP, and IKBKE; DDR1, P4HB, GMIP, IKBKE and EFEMP2; or DDR1, GMIP, IKBKE, P4HB, and SOCS2. In one aspect of this embodiment, the level(s) of gene expression of the biomarker is determined. In another aspect of this embodiment, the level(s) of protein expression is determined. In one aspect of this embodiment, a tumor or suspected sample is analyzed. In another aspect a fluid sample is analyzed. In another aspect of this embodiment, a sample obtained from uterine fluid is analyzed. In yet another aspect of this embodiment, a serum or blood samples is analyzed. In one aspect, the sample that is analyzed is obtained from a cell.

In one embodiment, the invention provides a method for diagnosing endometrial cancer comprising determining the level of an EPS8L2 biomarker in combination with the level of one or more biomarkers. In a specific aspect of this embodiment the one or more biomarkers are chosen from differential diagnosis biomarkers, prognostic biomarkers, biomarkers useful for detecting endometrial cancer, biomarkers for classify endometrial cancer and auxiliary biomarkers for detecting endometrial cancer. In one aspect of this embodiment, the one or more biomarkers are chosen from differential diagnosis biomarkers, biomarkers useful for detecting endometrial cancer, and biomarkers useful for classifying endometrial cancer. In one aspect of this embodiment, the one or more biomarkers useful for detecting endometrial cancer are chosen from ACAA1, AP1M2, CGN, DDR1, FASTKD1, GMIP, IKBKE, P2RX4, P4HB, PHKG2, PPFIBP2, PPP1R16A, RASSF7, RNF183, SIRT6, TJP3, EFEMP2, SOCS2, and DCN. Combinations or subcombinations including EPS8L2 are EPS8L2 and AP1M2; EPS8L2 and CGN; EPS8L2 and DDR1; EPS8L2 and EPS8L2; EPS8L2 and FASTKD1; EPS8L2 and GMIP; EPS8L2 and IKBKE; EPS8L2 and P2RX4; EPS8L2 and P4HB; EPS8L2 and PHKG2; EPS8L2 and PPFIBP2; EPS8L2 and PPP1R16A; EPS8L2 and RASSF7; EPS8L2 and RNF183; EPS8L2 and SIRT6; EPS8L2 and TJP3; EPS8L2 and EFEMP2; EPS8L2 and SOCS2; EPS8L2 and ACAA1; or EPS8L2 and DCN. In one aspect of this embodiment, the level(s) of gene expression of the biomarker is determined. In another aspect of this embodiment, the level(s) of protein expression is determined. In one aspect of this embodiment, a tumor or suspected sample is analyzed. In another aspect a fluid sample is analyzed. In another aspect of this embodiment, a sample obtained from uterine fluid is analyzed. In yet another aspect of this embodiment, a serum or blood samples is analyzed. In one aspect, the sample that is analyzed is obtained from a cell.

In one embodiment, the invention provides a method for diagnosing endometrial cancer comprising determining the level of a FASTKD1 biomarker in combination with the level of one or more biomarkers. In a specific aspect of this embodiment the one or more biomarkers are chosen from differential diagnosis biomarkers, prognostic biomarkers, biomarkers useful for detecting endometrial cancer, biomarkers for classify endometrial cancer and auxiliary biomarkers for detecting endometrial cancer. In one aspect of this embodiment, the one or more biomarkers are chosen from differential diagnosis biomarkers, biomarkers useful for detecting endometrial cancer, and biomarkers useful for classifying endometrial cancer. In one aspect of this embodiment, the one or more biomarkers useful for detecting endometrial cancer are chosen from ACAA1, AP1M2, CGN, DDR1, EPS8L2, GMIP, IKBKE, P2RX4, P4HB, PHKG2, PPFIBP2, PPP1R16A, RASSF7, RNF183, SIRT6, TJP3, EFEMP2, SOCS2, and DCN. A preferred combination or subcombination useful for detecting endometrial cancer or an increased likelihood of endometrial cancer is FASTD1 and P4HB; FASTKD1 and GMIP; FASTKD1 and IKBKE; FASTKD1 and EFEMP2; FASTKD1 and SOCS2; FASTD1 and DDR1; FASTKD1 and SIRT6; FASTKD1 and PHKG2; FASTKD1, P4HB, and GMIP; FASTKD1, P4HB and IKBKE; FASTKD1, P4HB, and EFEMP2; FASTKD1, P4HB, EFEMP2, IKBKE, and GMIP; FASTKD1, P4HB, EFEMP2, SIRT6, DDR1, and GMIP; or FASTKD1, P4HB, EFEMP2, SIRT6, PHKG2, and GMIP. In one aspect of this embodiment, the level(s) of gene expression of the biomarker is determined. In another aspect of this embodiment, the level(s) of protein expression is determined. In one aspect of this embodiment, a tumor or suspected sample is analyzed. In another aspect a fluid sample is analyzed. In another aspect of this embodiment, a sample obtained from uterine fluid is analyzed. In yet another aspect of this embodiment, a serum or blood samples is analyzed. In one aspect, the sample that is analyzed is obtained from a cell.

In one embodiment, the invention provides a method for diagnosing endometrial cancer comprising determining the level of a GMIP biomarker in combination with the level of one or more biomarkers. In a specific aspect of this embodiment the one or more biomarkers are chosen from differential diagnosis biomarkers, prognostic biomarkers, biomarkers useful for detecting endometrial cancer, biomarkers for classify endometrial cancer and auxiliary biomarkers for detecting endometrial cancer. In one aspect of this embodiment, the one or more biomarkers are chosen from differential diagnosis biomarkers, biomarkers useful for detecting endometrial cancer, and biomarkers useful for classifying endometrial cancer. In one aspect of this embodiment, the one or more biomarkers useful for detecting endometrial cancer are chosen from ACAA1, AP1M2, CGN, DDR1, EPS8L2, FASTKD1, IKBKE, P2RX4, P4HB, PHKG2, PPFIBP2, PPP1R16A, RASSF7, RNF183, SIRT6, TJP3, EFEMP2, SOCS2, and DCN. A preferred combination or subcombination useful for detecting endometrial cancer or an increased likelihood of endometrial cancer is GMIP and P4HB; FASTKD1 and GMIP; GMIP and IKBKE; GMIP and EFEMP2; GMIP and SOCS2; GMIP and DDR1; GMIP and SIRT6; GMIP and PHKG2; GMIP, P4HB, and IKBKE;

GMIP, SOCS2, and IKBKE; GMIP, SOCS2, and P4HB; GMIP, IKBKE, P4HB, and EFEMP2; GMIP, IKBKE, P4HB, and SOCS2; GMIP, P4HB, EFEMP2, IKBKE, and FASTKD1; GMIP, P4HB, EFEMP2, SIRT6, DDR1, and FASTKD1; or GMIP, P4HB, EFEMP2, SIRT6, PHKG2, and FASTKD1. In one aspect of this embodiment, the level(s) of gene expression of the biomarker is determined. In another aspect of this embodiment, the level(s) of protein expression is determined. In one aspect of this embodiment, a tumor or suspected sample is analyzed. In another aspect a fluid sample is analyzed. In another aspect of this embodiment, a sample obtained from uterine fluid is analyzed. In yet another aspect of this embodiment, a serum or blood samples is analyzed. In one aspect, the sample that is analyzed is obtained from a cell.

In one embodiment, the invention provides a method for diagnosing endometrial cancer comprising determining the level of an IKBKE biomarker in combination with the level of one or more biomarkers. In a specific aspect of this embodiment the one or more biomarkers are chosen from differential diagnosis biomarkers, prognostic biomarkers, biomarkers useful for detecting endometrial cancer, biomarkers for classify endometrial cancer and auxiliary biomarkers for detecting endometrial cancer. In one aspect of this embodiment, the one or more biomarkers are chosen from differential diagnosis biomarkers, biomarkers useful for detecting endometrial cancer, and biomarkers useful for classifying endometrial cancer. In one aspect of this embodiment, the one or more biomarkers useful for detecting endometrial cancer are chosen from ACAA1, AP1M2, CGN, DDR1, EPS8L2, FASTKD1, GMIP, P2RX4, P4HB, PHKG2, PPFIBP2, PPP1R16A, RASSF7, RNF183, SIRT6, TJP3, EFEMP2, SOCS2, and DCN. A preferred combination or subcombination useful for detecting endometrial cancer or an increased likelihood of endometrial cancer is IKBKE and P4HB; IKBKE and GMIP; IKBKE and FASTKD1; IKBKE and EFEMP2; IKBKE and SOCS2; IKBKE and DDR1; IKBKE and SIRT6; IKBKE and PHKG2; IKBKE, P4HB, and GMIP; IKBKE, P4HB, and EFEMP2; IKBKE, GMIP, and EFEMP2; IKBKE, P4HB, and SOCS2; IKBKE, GMIP, P4HB, and SOCS2; IKBKE, GMIP, P4HB, and EFEMP2; IKBKE, P4HB, EFEMP2, GMIP, and FASTKD1; or IKBKE, DDR1, GMIP, P4HB, PHKG2, SIRT6, and EFEMP2. In one aspect of this embodiment, the level(s) of gene expression of the biomarker is determined. In another aspect of this embodiment, the level(s) of protein expression is determined. In one aspect of this embodiment, a tumor or suspected sample is analyzed. In another aspect a fluid sample is analyzed. In another aspect of this embodiment, a sample obtained from uterine fluid is analyzed. In yet another aspect of this embodiment, a serum or blood samples is analyzed. In one aspect, the sample that is analyzed is obtained from a cell.

In one embodiment, the invention provides a method for diagnosing endometrial cancer comprising determining the level of a P2RX4 biomarker in combination with the level of one or more biomarkers. In a specific aspect of this embodiment the one or more biomarkers are chosen from differential diagnosis biomarkers, prognostic biomarkers, biomarkers useful for detecting endometrial cancer, biomarkers for classify endometrial cancer and auxiliary biomarkers for detecting endometrial cancer. In one aspect of this embodiment, the one or more biomarkers are chosen from differential diagnosis biomarkers, biomarkers useful for detecting endometrial cancer, and biomarkers useful for classifying endometrial cancer. In one aspect of this embodiment, the one or more biomarkers useful for detecting endometrial cancer are chosen from ACAA1, AP1M2, CGN, DDR1, EPS8L2, FASTKD1, GMIP, IKBKE, P4HB, PHKG2, PPFIBP2, PPP1R16A, RASSF7, RNF183, SIRT6, TJP3, EFEMP2, SOCS2, and DCN. Combinations or subcombinations including P2RX4 are P2RX4 and AP1M2; P2RX4 and CGN; P2RX4 and DDR1; P2RX4 and EPS8L2; P2RX4 and FASTKD1; P2RX4 and GMIP; P2RX4 and IKBKE; P2RX4 and P4HB; P2RX4 and PHKG2; P2RX4 and PPFIBP2; P2RX4 and PPP1R16A; P2RX4 and RASSF7; P2RX4 and RNF183; P2RX4 and SIRT6; P2RX4 and TJP3; P2RX4 and EFEMP2; P2RX4 and SOCS2; P2RX4 and ACAA1; or P2RX4 and DCN. In one aspect of this embodiment, the level(s) of gene expression of the biomarker is determined. In another aspect of this embodiment, the level(s) of protein expression is determined. In one aspect of this embodiment, a tumor or suspected sample is analyzed. In another aspect a fluid sample is analyzed. In another aspect of this embodiment, a sample obtained from uterine fluid is analyzed. In yet another aspect of this embodiment, a serum or blood samples is analyzed. In one aspect, the sample that is analyzed is obtained from a cell.

In one embodiment, the invention provides a method for diagnosing endometrial cancer comprising determining the level of a P4HB biomarker in combination with the level of one or more biomarkers. In a specific aspect of this embodiment the one or more biomarkers are chosen from differential diagnosis biomarkers, prognostic biomarkers, biomarkers useful for detecting endometrial cancer, biomarkers for classify endometrial cancer and auxiliary biomarkers for detecting endometrial cancer. In one aspect of this embodiment, the one or more biomarkers are chosen from differential diagnosis biomarkers, biomarkers useful for detecting endometrial cancer, and biomarkers useful for classifying endometrial cancer. In one aspect of this embodiment, the one or more biomarkers useful for detecting endometrial cancer are chosen from ACAA1, AP1M2, CGN, DDR1, EPS8L2, FASTKD1, GMIP, IKBKE, P2RX4, PHKG2, PPFIBP2, PPP1R16A, RASSF7, RNF183, SIRT6, TJP3, EFEMP2, SOCS2, and DCN. A preferred combination or subcombination useful for detecting endometrial cancer or an increased likelihood of endometrial cancer is FASTD1 and P4HB; P4HB and GMIP; P4HB and IKBKE; P4HB and EFEMP2; P4HB and SOCS2; P4HB and DDR1; P4HB and SIRT6; P4HB and PHKG2; P4HB, GMIP, and IKBKE; P4HB, GMIP, and SOCS2; P4HB, GMIP, and EFEMP2; P4HB, IKBKE, GMIP, and SOCS2; P4HB, IKBKE, GMIP, and EFEMP2; P4HB, EFEMP2, IKBKE, GMIP, and FASTKD1; P4HB, EFEMP2, SIRT6, GMIP, DDR1, and FASTKD1; P4HB, EFEMP2, SIRT6, GMIP, PHKG2, and FASTKD1; or DDR1, FASTKD1, GMIP, IKBKE, P4HB, PHKG2, SIRT6, and EFEMP2. In one aspect of this embodiment, the level(s) of gene expression of the biomarker is determined. In another aspect of this embodiment, the level(s) of protein expression is determined. In one aspect of this embodiment, a tumor or suspected sample is analyzed. In another aspect a fluid sample is analyzed. In another aspect of this embodiment, a sample obtained from uterine fluid is analyzed. In yet another aspect of this embodiment, a serum or blood samples is analyzed. In one aspect, the sample that is analyzed is obtained from a cell.

In one embodiment, the invention provides a method for diagnosing endometrial cancer comprising determining the level of a PHKG2 biomarker in combination with the level of one or more biomarkers. In a specific aspect of this embodiment the one or more biomarkers are chosen from differential diagnosis biomarkers, prognostic biomarkers, biomarkers useful for detecting endometrial cancer, biomarkers for classify endometrial cancer and auxiliary biomarkers for detecting endometrial cancer. In one aspect of this embodiment, the one or more biomarkers are chosen from differential diagnosis biomarkers, biomarkers useful for detecting endometrial cancer, and biomarkers useful for classifying endometrial cancer. In one aspect of this embodiment, the one or more biomarkers useful for detecting endometrial cancer are chosen from ACAA1, AP1M2, CGN, DDR1, EPS8L2, FASTKD1, GMIP, IKBKE, P2RX4, P4HB, PPFIBP2, PPP1R16A, RASSF7, RNF183, SIRT6, TJP3, EFEMP2, SOCS2, and DCN. A preferred combination or subcombination useful for detecting endometrial cancer or an increased likelihood of endometrial cancer is PHKG2 and P4HB; PHKG2 and GMIP; PHKG2 and IKBKE; PHKG2 and EFEMP2; PHKG2 and SOCS2; PHKG2 and DDR1; PHKG2 and SIRT6; FASTKD1 and PHKG2; PHKG2, P4HB, and EFEMP2; PHKG2, P4HB, GMIP; PHKG2, P4HB, IKBKE, and EFEMP2; PHKG2, P4HB, IKBKE, and SOCS2; P4HB, EFEMP2, SIRT6, GMIP, PHKG2, and FASTKD1; or DDR1, FASTKD1, GMIP, IKBKE, P4HB, PHKG2, SIRT6, and EFEMP2 In one aspect of this embodiment, the level(s) of gene expression of the biomarker is determined. In another aspect of this embodiment, the level(s) of protein expression is determined. In one aspect of this embodiment, a tumor or suspected sample is analyzed. In another aspect a fluid sample is analyzed. In another aspect of this embodiment, a sample obtained from uterine fluid is analyzed. In yet another aspect of this embodiment, a serum or blood samples is analyzed. In one aspect, the sample that is analyzed is obtained from a cell.

In one embodiment, the invention provides a method for diagnosing endometrial cancer comprising determining the level of a PPFIBP2 biomarker in combination with the level of one or more biomarkers. In a specific aspect of this embodiment the one or more biomarkers are chosen from differential diagnosis biomarkers, prognostic biomarkers, biomarkers useful for detecting endometrial cancer, biomarkers for classify endometrial cancer and auxiliary biomarkers for detecting endometrial cancer. In one aspect of this embodiment, the one or more biomarkers are chosen from differential diagnosis biomarkers, biomarkers useful for detecting endometrial cancer, and biomarkers useful for classifying endometrial cancer. In one aspect of this embodiment, the one or more biomarkers useful for detecting endometrial cancer are chosen from ACAA1, AP1M2, CGN, DDR1, EPS8L2, FASTKD1, GMIP, IKBKE, P2RX4, P4HB, PHKG2, PPP1R16A, RASSF7, RNF183, SIRT6, TJP3, EFEMP2, SOCS2, and DCN. Combinations or subcombinations including PPFIBP2 are PPFIBP2 and AP1M2; PPFIBP2 and CGN; PPFIBP2 and DDR1; PPFIBP2 and EPS8L2; PPFIBP2 and FASTKD1; PPFIBP2 and GMIP; PPFIBP2 and IKBKE; PPFIBP2 and P2RX4; PPFIBP2 and P4HB; PPFIBP2 and PHKG2; PPFIBP2 and PPP1R16A; PPFIBP2 and RASSF7; PPFIBP2 and RNF183; PPFIBP2 and SIRT6; PPFIBP2 and TJP3; PPFIBP2 and EFEMP2; PPFIBP2 and SOCS2; PPFIBP2 and ACAA1; or PPFIBP2 and DCN. In one aspect of this embodiment, the level(s) of gene expression of the biomarker is determined. In another aspect of this embodiment, the level(s) of protein expression is determined. In one aspect of this embodiment, a tumor or suspected sample is analyzed. In another aspect a fluid sample is analyzed. In another aspect of this embodiment, a sample obtained from uterine fluid is analyzed. In yet another aspect of this embodiment, a serum or blood samples is analyzed. In one aspect, the sample that is analyzed is obtained from a cell.

In one embodiment, the invention provides a method for diagnosing endometrial cancer comprising determining the level of a PPP1R16A biomarker in combination with the level of one or more biomarkers. In a specific aspect of this embodiment the one or more biomarkers are chosen from differential diagnosis biomarkers, prognostic biomarkers, biomarkers useful for detecting endometrial cancer, biomarkers for classify endometrial cancer and auxiliary biomarkers for detecting endometrial cancer. In one aspect of this embodiment, the one or more biomarkers are chosen from differential diagnosis biomarkers, biomarkers useful for detecting endometrial cancer, and biomarkers useful for classifying endometrial cancer. In one aspect of this embodiment, the one or more biomarkers useful for detecting endometrial cancer are chosen from ACAA1, AP1M2, CGN, DDR1, EPS8L2, FASTKD1, GMIP, IKBKE, P2RX4, P4HB, PHKG2, PPFIBP2, RASSF7, RNF183, SIRT6, TJP3, EFEMP2, SOCS2, and DCN. Combinations or subcombinations including PPP1R16A are PPP1R16A and AP1M2; PPP1R16A and CGN; PPP1R16A and DDR1; PPP1R16A and EPS8L2; PPP1R16A and FASTKD1; PPP1R16A and GMIP; PPP1R16A and IKBKE; PPP1R16A and P2RX4; PPP1R16A and P4HB; PPP1R16A and PHKG2; PPFIBP2 and PPP1R16A; PPP1R16A and RASSF7; PPP1R16A and RNF183; PPP1R16A and SIRT6; PPP1R16A and TJP3; PPP1R16A and EFEMP2; PPP1R16A and SOCS2; PPP1R16A and ACAA1; or PPP1R16A and DCN. In one aspect of this embodiment, the level(s) of gene expression of the biomarker is determined. In another aspect of this embodiment, the level(s) of protein expression is determined. In one aspect of this embodiment, a tumor or suspected sample is analyzed. In another aspect a fluid sample is analyzed. In another aspect of this embodiment, a sample obtained from uterine fluid is analyzed. In yet another aspect of this embodiment, a serum or blood samples is analyzed. In one aspect, the sample that is analyzed is obtained from a cell.

In one embodiment, the invention provides a method for diagnosing endometrial cancer comprising determining the level of a RASSF7 biomarker in combination with the level of one or more biomarkers. In a specific aspect of this embodiment the one or more biomarkers are chosen from differential diagnosis biomarkers, prognostic biomarkers, biomarkers useful for detecting endometrial cancer, biomarkers for classify endometrial cancer and auxiliary biomarkers for detecting endometrial cancer. In one aspect of this embodiment, the one or more biomarkers are chosen from differential diagnosis biomarkers, biomarkers useful for detecting endometrial cancer, and biomarkers useful for classifying endometrial cancer. In one aspect of this embodiment, the one or more biomarkers useful for detecting endometrial cancer are chosen from ACAA1, AP1M2, CGN, DDR1, EPS8L2, FASTKD1, GMIP, IKBKE, P2RX4, P4HB, PHKG2, PPFIBP2, PPP1R16A, RNF183, SIRT6, TJP3, EFEMP2, SOCS2, and DCN. Combinations or subcombinations including RASSF7 are RASSF7 and AP1M2; RASSF7 and CGN; RASSF7 and DDR1; RASSF7 and EPS8L2; RASSF7 and FASTKD1; RASSF7 and GMIP; RASSF7 and IKBKE; RASSF7 and P2RX4; RASSF7 and P4HB; RASSF7 and PHKG2; RASSF7 and PPP1R16A; RASSF7 and RNF183; RASSF7 and SIRT6; RASSF7 and TJP3; RASSF7 and EFEMP2; RASSF7 and SOCS2; RASSF7 and ACAA1; or RASSF7 and DCN. In one aspect of this embodiment, the level(s) of gene expression of the biomarker is determined. In another aspect of this embodiment, the level(s) of protein expression is determined. In one aspect of this embodiment, a tumor or suspected sample is analyzed. In another aspect a fluid sample is analyzed. In another aspect of this embodiment, a sample obtained from uterine fluid is analyzed. In yet another aspect of this embodiment, a serum or blood samples is analyzed. In one aspect, the sample that is analyzed is obtained from a cell.

In one embodiment, the invention provides a method for diagnosing endometrial cancer comprising determining the level of a RNF183 biomarker in combination with the level of one or more biomarkers. In a specific aspect of this embodiment the one or more biomarkers are chosen from differential diagnosis biomarkers, prognostic biomarkers, biomarkers useful for detecting endometrial cancer, biomarkers for classify endometrial cancer and auxiliary biomarkers for detecting endometrial cancer. In one aspect of this embodiment, the one or more biomarkers are chosen from differential diagnosis biomarkers, biomarkers useful for detecting endometrial cancer, and biomarkers useful for classifying endometrial cancer. In one aspect of this embodiment, the one or more biomarkers useful for detecting endometrial cancer are chosen from ACAA1, AP1M2, CGN, DDR1, EPS8L2, FASTKD1, GMIP, IKBKE, P2RX4, P4HB, PHKG2, PPFIBP2, PPP1R16A, RASSF7, SIRT6, TJP3, EFEMP2, SOCS2, and DCN. Combinations or subcombinations including RNF183 are RNF183 and AP1M2; RNF183 and CGN; RNF183 and DDR1; RNF183 and EPS8L2; RNF183 and FASTKD1; RNF183 and GMIP; RNF183 and IKBKE; RNF183 and P2RX4; RNF183 and P4HB; RNF183 and PHKG2; RNF183 and PPP1R16A; RASSF7 and RNF183; RNF183 and SIRT6; RNF183 and TJP3; RNF183 and EFEMP2; RNF183 and SOCS2; RNF183 and ACAA1; or RNF183 and DCN. In one aspect of this embodiment, the level(s) of gene expression of the biomarker is determined. In another aspect of this embodiment, the level(s) of protein expression is determined. In one aspect of this embodiment, a tumor or suspected sample is analyzed. In another aspect a fluid sample is analyzed. In another aspect of this embodiment, a sample obtained from uterine fluid is analyzed. In yet another aspect of this embodiment, a serum or blood samples is analyzed. In one aspect, the sample that is analyzed is obtained from a cell.

In one embodiment, the invention provides a method for diagnosing endometrial cancer comprising determining the level of a SIRT6 biomarker in combination with the level of one or more biomarkers. In a specific aspect of this embodiment the one or more biomarkers are chosen from differential diagnosis biomarkers, prognostic biomarkers, biomarkers useful for detecting endometrial cancer, biomarkers for classify endometrial cancer and auxiliary biomarkers for detecting endometrial cancer. In one aspect of this embodiment, the one or more biomarkers are chosen from differential diagnosis biomarkers, biomarkers useful for detecting endometrial cancer, and biomarkers useful for classifying endometrial cancer. In one aspect of this embodiment, the one or more biomarkers useful for detecting endometrial cancer are chosen from ACAA1, AP1M2, CGN, DDR1, EPS8L2, FASTKD1, GMIP, IKBKE, P2RX4, P4HB, PHKG2, PPFIBP2, PPP1R16A, RASSF7, RNF183, SIRT6, TJP3, EFEMP2, SOCS2, and DCN. A preferred combination or subcombination useful for detecting endometrial cancer or an increased likelihood of endometrial cancer is SIRT6 and P4HB; SIRT6 and GMIP; SIRT6 and IKBKE; SIRT6 and EFEMP2; SIRT6 and SOCS2; SIRT6 and DDR1; FASTKD1 and SIRT6; SIRT6 and PHKG2; SIRT6, P4HB, and EFEMP2; SIRT6, P4HB, and IKBKE; SIRT6, IKBKE, and EFEMP2; SIRT6, P4HB, and SOCS2; SIRT6, P4HB, IKBKE, and GMIP; SIRT6, P4HB, EFEMP2, GMIP, DDR1, and FASTKD1; SIRT6, P4HB, EFEMP2, GMIP, PHKG2, and FASTKD1; or SIRT6, P4HB, EFEMP2, GMIP, IKBKE, PHKG2, DDR1, and FASTKD1. In one aspect of this embodiment, the level(s) of gene expression of the biomarker is determined. In another aspect of this embodiment, the level(s) of protein expression is determined. In one aspect of this embodiment, a tumor or suspected sample is analyzed. In another aspect a fluid sample is analyzed. In another aspect of this embodiment, a sample obtained from uterine fluid is analyzed. In yet another aspect of this embodiment, a serum or blood samples is analyzed. In one aspect, the sample that is analyzed is obtained from a cell.

In one embodiment, the invention provides a method for diagnosing endometrial cancer comprising determining the level of a TJP3 biomarker in combination with the level of one or more biomarkers. In a specific aspect of this embodiment the one or more biomarkers are chosen from differential diagnosis biomarkers, prognostic biomarkers, biomarkers useful for detecting endometrial cancer, biomarkers for classify endometrial cancer and auxiliary biomarkers for detecting endometrial cancer. In one aspect of this embodiment, the one or more biomarkers are chosen from differential diagnosis biomarkers, biomarkers useful for detecting endometrial cancer, and biomarkers useful for classifying endometrial cancer. In one aspect of this embodiment, the one or more biomarkers useful for detecting endometrial cancer are chosen from ACAA1, AP1M2, CGN, DDR1, EPS8L2, FASTKD1, GMIP, IKBKE, P2RX4, P4HB, PHKG2, PPFIBP2, PPP1R16A, RASSF7, RNF183, SIRT6, EFEMP2, SOCS2, and DCN. Combinations or subcombinations including TJP3 are TJP3 and AP1M2; TJP3 and CGN; TJP3 and DDR1; TJP3 and EPS8L2; TJP3 and FASTKD1; TJP3 and GMIP; TJP3 and IKBKE; TJP3 and P2RX4; TJP3 and P4HB; TJP3 and PHKG2; TJP3 and PPP1R16A; TJP3 and RNF183; TJP3 and SIRT6; TJP3 and RASSF7; TJP3 and EFEMP2; TJP3 and SOCS2; TJP3 and ACAA1; or TJP3 and DCN. In one aspect of this embodiment, the level(s) of gene expression of the biomarker is determined. In another aspect of this embodiment, the level(s) of protein expression is determined. In one aspect of this embodiment, a tumor or suspected sample is analyzed. In another aspect a fluid sample is analyzed. In another aspect of this embodiment, a sample obtained from uterine fluid is analyzed. In yet another aspect of this embodiment, a serum or blood samples is analyzed. In one aspect, the sample that is analyzed is obtained from a cell.

In one embodiment, the invention provides a method for diagnosing endometrial cancer comprising determining the level of an EFEMP2 biomarker in combination with the level of one or more biomarkers. In a specific aspect of this embodiment the one or more biomarkers are chosen from differential diagnosis biomarkers, prognostic biomarkers, biomarkers useful for detecting endometrial cancer, biomarkers for classify endometrial cancer and auxiliary biomarkers for detecting endometrial cancer. In one aspect of this embodiment, the one or more biomarkers are chosen from differential diagnosis biomarkers, biomarkers useful for detecting endometrial cancer, and biomarkers useful for classifying endometrial cancer. In one aspect of this embodiment, the one or more biomarkers useful for detecting endometrial cancer are chosen from ACAA1, AP1M2, CGN, DDR1, EPS8L2, FASTKD1, GMIP, IKBKE, P2RX4, P4HB, PHKG2, PPFIBP2, PPP1R16A, RASSF7, RNF183, SIRT6, TJP3, SOCS2, and DCN. A preferred combination or subcombination useful for detecting endometrial cancer or an increased likelihood of endometrial cancer is EFEMP2 and P4HB; EFEMP2 and GMIP; EFEMP2 and IKBKE; FASTKD1 and EFEMP2; EFEMP2 and SOCS2; EFEMP2 and DDR1; EFEMP2 and SIRT6; EFEMP2 and PHKG2; EFEMP2, P4HB, and IKBKE; EFEMP2, IKBKE, and GMIP; EFEMP2, IKBKE, and FASTKD1; EFEMP2, GMIP, and DDR1; EFEMP2, SIRT6, and FASTKD1; EFEMP2, IKBKE, GMIP, and P4HB; EFEMP2, P4HB, IKBKE, GMIP, and FASTKD1; EFEMP2, P4HB, SIRT6, DDR1, GMIP, and FASTKD1; EFEMP2, P4HB, SIRT6, PHKG2, GMIP, and FASTKD1; or EFEMP2, P4HB, IKBKE, GMIP, DDR1, PHKG2, SIRT6, and FASTKD1; In one aspect of this embodiment, the level(s) of gene expression of the biomarker is determined. In another aspect of this embodiment, the level(s) of protein expression is determined. In one aspect of this embodiment, a tumor or suspected sample is analyzed. In another aspect a fluid sample is analyzed. In another aspect of this embodiment, a sample obtained from uterine fluid is analyzed. In yet another aspect of this embodiment, a serum or blood samples is analyzed. In one aspect, the sample that is analyzed is obtained from a cell.

In one embodiment, the invention provides a method for diagnosing endometrial cancer comprising determining the level of a SOCS2 biomarker in combination with the level of one or more biomarkers. In a specific aspect of this embodiment the one or more biomarkers are chosen from differential diagnosis biomarkers, prognostic biomarkers, biomarkers useful for detecting endometrial cancer, biomarkers for classify endometrial cancer and auxiliary biomarkers for detecting endometrial cancer. In one aspect of this embodiment, the one or more biomarkers are chosen from differential diagnosis biomarkers, biomarkers useful for detecting endometrial cancer, and biomarkers useful for classifying endometrial cancer. In one aspect of this embodiment, the one or more biomarkers useful for detecting endometrial cancer are chosen from ACAA1, AP1M2, CGN, DDR1, EPS8L2, FASTKD1, GMIP, IKBKE, P2RX4, P4HB, PHKG2, PPFIBP2, PPP1R16A, RASSF7, RNF183, SIRT6, TJP3, EFEMP2, and DCN. A preferred combination or subcombination useful for detecting endometrial cancer or an increased likelihood of endometrial cancer is SOCS2 and P4HB; SOCS2 and GMIP; SOCS2 and IKBKE; SOCS2 and EFEMP2; FASTKD1 and SOCS2; SOCS2 and DDR1; SOCS2 and SIRT6; SOCS21 and PHKG2; SOCS2, P4HB, and IKBKE; SOCS2, GMIP, and P4HB; SOCS2, P4HB, and IKBKE; GMIP, P4HB, IKBKE, and SOCS2; SOCS2, GMIP, IKBKE, P4HB, and DDR1; or SOCS2, DDR1, FASTKD1, GMIP, IKBKE, P4HB, PHKG2, SIRT6, and EFEMP2. In one aspect of this embodiment, the level(s) of gene expression of the biomarker is determined. In another aspect of this embodiment, the level(s) of protein expression is determined. In one aspect of this embodiment, a tumor or suspected sample is analyzed. In another aspect a fluid sample is analyzed. In another aspect of this embodiment, a sample obtained from uterine fluid is analyzed. In yet another aspect of this embodiment, a serum or blood samples is analyzed. In one aspect, the sample that is analyzed is obtained from a cell.

In one embodiment, the invention provides a method for diagnosing endometrial cancer comprising determining the level of a DCN biomarker in combination with the level of one or more biomarkers. In a specific aspect of this embodiment the one or more biomarkers are chosen from differential diagnosis biomarkers, prognostic biomarkers, biomarkers useful for detecting endometrial cancer, biomarkers for classify endometrial cancer and auxiliary biomarkers for detecting endometrial cancer. In one aspect of this embodiment, the one or more biomarkers are chosen from differential diagnosis biomarkers, biomarkers useful for detecting endometrial cancer, and biomarkers useful for classifying endometrial cancer. In one aspect of this embodiment, the one or more biomarkers useful for detecting endometrial cancer are chosen from ACAA1, AP1M2, CGN, DDR1, EPS8L2, FASTKD1, GMIP, IKBKE, P2RX4, P4HB, PHKG2, PPFIBP2, PPP1R16A, RASSF7, RNF183, SIRT6, TJP3, EFEMP2, and SOCS2. Combinations or subcombinations including DCN are DCN and AP1M2; DCN and CGN; DCN and DDR1; DCN and EPS8L2; DCN and FASTKD1; DCN and GMIP; DCN and IKBKE; DCN and P2RX4; DCN and P4HB; DCN and PHKG2; DCN and PPP1R16A; DCN and RNF183; DCN and SIRT6; DCN and RASSF7; DCN and EFEMP2; DCN and SOCS2; or DCN and ACAA1. In one aspect of this embodiment, the level(s) of gene expression of the biomarker is determined. In another aspect of this embodiment, the level(s) of protein expression is determined. In one aspect of this embodiment, a tumor or suspected sample is analyzed. In another aspect a fluid sample is analyzed. In another aspect of this embodiment, a sample obtained from uterine fluid is analyzed. In yet another aspect of this embodiment, a serum or blood samples is analyzed. In one aspect, the sample that is analyzed is obtained from a cell.

In a preferred aspect of the in vitro diagnostic method of the invention the levels of a combination of markers is detected where said combination comprises IKBKE and P4HB; IKBKE and SOCS2; P4HB and SOCS2; GMIP and IKBKE; GMIP and P4HB; GMIP and SOCS2; GMIP, SOCS2, and IKBKE; GMIP, SOCS2, and P4HB; GMIP, IKBKE, and P4HB; IKBKE, P4HB, and SOCS2; GMIP, IKBKE, P4HB, and SOCS2; GMIP, SOCS2, IKBKE, and EPS8L2; GMIP, SOCS2, P4HB, and EPS8L2; GMIP, IKBKE, P4HB, and EPS8L2; IKBKE, P4HB, SOCS2, and EPS8L2; GMIP, IKBKE, P4HB, SOCS2, and DDR1; GMIP, IKBKE, P4HB, SOCS2, EPS8L2, and PPP1R16A; GMIP, IKBKE, P4HB, SOCS2, PHKG2, and RASSF7; GMIP, IKBKE, P4HB, SOCS2, EPS8L2, and DDR1; GMIP, IKBKE, P4HB, SOCS2, EPS8L2, PPP1R16A, and DDR1; DDR1, EPS8L2, GMIP, IKBKE, P2RX4, P4HB, PHKG2, PPP1R16A, RASSF7, SIRT6, TJP3, and SOCS2; or DDR1, EPS8L2, GMIP, IKBKE, P2RX4, P4HB, PHKG2, PPP1R16A, RASSF7, SIRT6, TJP3, RNF183 and SOCS2.

In another preferred aspect of the in vitro diagnostic method of the invention a the levels of a combination of markers is detected where said combination comprises GMIP, IKBKE, P4HB, SOCS2 and FASTKD1; GMIP, IKBKE, P4HB, SOCS2 and DDR1; GMIP, IKBKE, P4HB, SOCS2 and PHKG2; GMIP, IKBKE, P4HB, SOCS2 and SIRT6; GMIP, IKBKE, P4HB, SOCS2 and ACAA1; GMIP, IKBKE, P4HB, SOCS2 and EFEMP2; GMIP, IKBKE, P4HB, SOCS2 and EPS8L2; GMIP, IKBKE, P4HB, SOCS2 and P2RX4; GMIP, IKBKE, P4HB, SOCS2 and PPFIBP2; GMIP, IKBKE, P4HB, SOCS2 and PPP1R16A; GMIP, IKBKE, P4HB, SOCS2, ACAA1 and FASTKD1; GMIP, IKBKE, P4HB, SOCS2, PHKG2 and FASTKD1; GMIP, IKBKE, P4HB, SOCS2, SIRT6 and FASTKD1; ACAA1, AP1M2, EPS8L2, IKBKE, P2RX4, P4HB, PPFIBP2, PPP1R16A, SIRT6, and EFEMP2; GMIP, IKBKE, P4HB, and EFEMP2; DDR1, FASTKD1, PHKG2, SIRT6, SOCS2, GMIP, IKBKE, P4HB, and EFEMP2; DDR1, FASTKD1, PHKG2, SIRT6, GMIP, IKBKE, P4HB, and EFEMP2; or P4HB, EFEMP2, IKBKE, GMIP, and FASTKD1.

In yet another preferred aspect of the in vitro diagnostic method of the invention the levels of a combination of markers is detected where said combination comprises GMIP, IKBKE, P4HB, EFEMP2 and FASTKD1; GMIP, IKBKE, P4HB, EFEMP2 and DDR1; GMIP, IKBKE, P4HB, EFEMP2 and PHKG2; GMIP, IKBKE, P4HB, EFEMP2 and SIRT6; GMIP, IKBKE, P4HB, EFEMP2 and ACAA1; GMIP, IKBKE, P4HB, SOCS2 and EFEMP2; GMIP, IKBKE, P4HB, EFEMP2 and EPS8L2; GMIP, IKBKE, P4HB, EFEMP2 and P2RX4; GMIP, IKBKE, P4HB, EFEMP2 and PPFIBP2; GMIP, IKBKE, P4HB, EFEMP2 and PPP1R16A; GMIP, IKBKE, P4HB, EFEMP2, ACAA1 and FASTKD1; GMIP, IKBKE, P4HB, EFEMP2, PHKG2 and FASTKD1; or GMIP, IKBKE, P4HB, EFEMP2, SIRT6 and FASTKD1.

Auxiliary Biomarkers

"Auxiliary biomarkers" refer to biomarkers that can be used in conjunction with the one or more biomarkers of Table 1. The auxiliary biomarkers can be used in the methods of the invention to provide further characterization of a disease or condition a patient may have.

Differential diagnosis biomarkers are useful for distinguishing between diseases that may present with similar clinical symptoms. For example, a patient may have symptoms of endometrial cancer (e.g., vaginal bleeding and/or pelvic pain) but these symptoms can also be caused by different diseases (e.g., ovarian cancer). Therefore, the differential diagnosis biomarkers provide information for characterization a disease. Examples of diseases that may present similar symptoms as endometrial cancer include uterine fibroids, endometriosis, endometrial hyperplasia, uterine sarcoma—another type of uterus cancer, uterine leiomyomas, endometrial polyp (type of polyp), cervical cancer, atrophic endometrium, adenomyosis, atrophic vaginitis, ovarian tumour, leiomyosarcoma, and endometrial proliferation.

According to the inventors' finding that the level of biomarkers in primary endometrial cancer tissue can be correlated to their levels in uterine fluid, it is contemplated that uterine fluid samples can be used for differential diagnosis of conditions other than endometrial cancer. Thus, in one aspect, the invention provides a method for the differential diagnosis of endometrial cancer by obtaining a uterine fluid sample from a patient and determining the level of one or more biomarkers that are capable of distinguishing endometrial cancer from non-endometrial cancer. Differential diagnosis biomarkers for endometriosis are useful for distinguishing endometriosis from endometrial cancer. Differential diagnosis biomarkers for ovarian cancer are useful for distinguishing ovarian cancer from endometrial cancer. Examples of biomarkers useful for distinguishing endometrial cancer from ovarian cancer include, but are not limited to, those described in Yurkovetsky et al. (*Gyn. Onc.* (2007) 107:58-65) where they reported a five-biomarker panel of prolactin, GH, eotaxin, E-selectin, and TSH for discriminating endometrial cancer from ovarian and breast cancer.

A number of endometrial cancer biomarkers have been identified. CA 125 correlates with tumor size and stage and is an independent predictor of the extrauterine spread. Serum markers for the detection of uterine cancer have been reported in the literature.

Prognosis biomarkers: Elevated levels of CA 125, CA 15-3, and CA 19-9 are associated with shorter survival time. They found serum CA 125 CA 15-3 and CEA are higher in patients with Stage III disease as compared to stage I. Another group of prognostic markers include estrogen receptor, progesterone receptor, and HER2.

Biomarkers for classifying endometrial cancer include those for estimating stage of the cancer, cell-type, and/or type of endometrial cancer (e.g., type I versus type II). Examples of biomarkers for classifying endometrial cancer include, but are not limited to, those described in Sugiyama et al. (2003) *Clin. Can. Res.* 9:5589-5600. Genes showing higher expression in type I as compared to type II include MMP11, RHOG, and platelet-derived growth factor B subunit precursor, STAT2, octamer-binding transcription factor 1, and GATA-6, growth factor VEGF-C precursor, caspase (caspase 1/IL-1 β converting enzyme). Genes showing higher expression in type II as compared to type I included PIRIN, EGR1, STAT1, IFN regulatory factor 1, and KRAS. Konecny et al. ((2009) *British Journal of Cancer* 100, 89-95) report that the rate HER2 gene amplification as measured by fluorescence in situ hybridization was greater in type II cancers whereas EGFR expression as measured by IHC techniques was significantly lower in type II cancers. Deng et al. ((2005) *Clin. Can. Res.* vol. 11, no 23:8258-8264) report that EIG121 is a marker for type I estrogen associated cancers. Markers for classifying endometrial cancer can also be used to distinguish different histological types of endometrial cancer like serous and endometrioid cancers. Risinger et al. ((2003) *Canc. Res.* 63:6-11) identified biomarkers that could distinguish papillary serous cancers from endometrioid cancers. For example AGR2, TFF3, DUSP6, IGF2, FOLR1, and UCHL1 were found to be differentially expressed between papillary serous and endometrioid cancers as found by microarray and validated by RT-PCR. AGR2, TFF3, DUSP6 were found to be upregulated in endometrioid type cancers whereas IGF2, FOLR1 and UCHL1 were found to be upregulated in papillary serous cancers.

According to the inventor's finding that the level of biomarkers in primary endometrial cancer tissue can be correlated to their levels in uterine fluid, it is contemplated that uterine fluid samples can be used to classify the type of endometrial cancer. Classifying the type of endometrial cancer can refer to distinguishing type I and type II cancers. Classifying the type of endometrial cancer can also refer to determining the histological type and/or sub-type of endometrial cancer. Thus, in one aspect, the invention provides a method for classifying an endometrial cancer by obtaining a uterine fluid sample from a patient and determining the level of one or more biomarkers that are capable of classifying an endometrial cancer.

"Auxiliary biomarkers for detecting endometrial cancer" refer to biomarkers that can be used in addition to the biomarkers of Table 1 for the diagnosis of endometrial cancer and/or an increased risk of having endometrial cancer: Yurkovetsky et al. (*Gyn. Onc.* (2007) 107:58-65) identified that prolactin is a serum biomarker with sensitivity and specificity for endometrial cancer. Yurkovetsky et al. found that prolactin, GH, eotaxin, E-selectin, and TSH were useful markers for diagnosing endometrial cancer.

In some aspects of these embodiments, one or more auxiliary biomarkers are examined for alterations in a sample from a patient suspected of having endometrial cancer. In a specific aspect, the auxiliary biomarkers are chosen from serum biomarkers. In a more specific aspect the serum biomarkers are one or more proteins chosen from CA 125, CA 15-3, CA 19-9, CEA, AFP, CA 72-4, VEGF, bFGF, IGFBPI, HGF, ErbB2, EGFR, TGF α, Fas, FasL, Cyfra 21-1, MMP-1, MMP-2, MMP-3, MMP-7, MMP-8, MMP-9, MMP-12, MMP-13, tPAI, sICAM, sVCAM, sE-selectin, adiponectin, resistin, IL-6, IL-8, TNF α, TNFR I, G-CSF, CD40L, IL-2R, IP-10, MCP-1, MIP-1α, MIP-1β, MIF, eotaxin, RANTES, FSH, LH, TSH, ACTH, Prolactin, GH, βHCG, hK8, hK10, active PAI-1, ULBP-1, ULBP-2, ULBP-3, MICA, angiostatin, SCC, serum amyloid A, TTR, S100, mesothelin, and myeloperoxidase (MPO). In a more specific aspect, the serum biomarkers are chosen from prolactin, GH, eotaxin, e-selectin and FSH. In an even more specific aspect, the serum biomarker is prolactin. In some aspects, the auxiliary biomarker(s) can be examined in uterine aspirates (e.g., mRNA level and/or protein levels).

Samples

The invention, in some embodiments, relates to characterizing one or more biomarkers of Table 1, from a sample from a patient suspected of having endometrial cancer or desiring screening for cancer. Examples of such samples that can be used in the invention are fluid, tissue samples, and/or cells. Depending on the specific marker, the methods used for characterizing the biomarkers of the invention can include e.g., examining the DNA copy number of the gene corresponding to the biomarker, detecting the protein related to the biomarker, determining the mRNA expression levels of the biomarker, etc. The invention is useful for a number of applications including diagnosis, prognosis, staging, predicting response to therapy. The inventors have found evidence of differential expression of the biomarkers of Table 1 in a number of different samples including mRNA in primary tumor, protein in primary tumor, and mRNA in aspirates, and protein in aspirates. The biomarkers of Table 1 include those that are overexpressed in samples from endometrial cancer patients as compared to normal levels. Additionally some of the biomarkers of Table 1 are underexpressed in samples from endometrial cancer patients as compared to normal levels The invention, in some embodiments, relates to characterizing one or more of the biomarkers of Table 1, from a patient sample (e.g., tumor, cancer cell, sample suspected of being cancer, body fluid (e.g., uterine fluid), blood, serum, plasma, and vaginal blood/discharge) and/or from a "normal" cell, from an individual (or alternatively a control value can be used in lieu of the normal value from the cell).

In one aspect, the sample to be analyzed is obtained from a patient that has risk factors for endometrial cancer. Risk factors for endometrial cancer include, but are not limited to, having Lynch Syndrome, being genetically related to a person having Lynch Syndrome, obese, taking estrogen-alone hormone replacement therapy, and prior treatment with tamixofen.

In one aspect of this embodiment, the sample is analyzed is a uterine fluid sample. In one aspect, the sample is that is used is obtained by using a soft, straw-like device (pipelle) to suction off a small sample of lining from the uterus. In one aspect, the sample is obtained by using a sharp-edged tool called a curette by scraping a small sample and collect it with a syringe or suction (e.g., dilation and curettage). In one aspect, the sample is obtained by using an electronic suction device (e.g., Vabra aspiration). In one aspect, the sample is obtained by using a spray of liquid (jet irrigation) to wash off some of the tissue that lines the uterus. In some aspects, a brush may be used to remove some of the lining before the washing is done.

In one embodiment, the sample for analyzing the biomarkers is obtained using a syringe or pipelle type device. In one embodiment, the device for collection of the uterine fluid sample from an internal cavity (e.g., uterus) of a patient, comprises a barrel having an opening at one end thereof, a plunger operable axially within the barrel, the barrel and the plunger defining a fluid chamber having a volume which varies on axial movement of the plunger within the barrel, and a hollow, elongate tube extending from the fluid chamber through the opening in the barrel, the tube being in operative engagement with the plunger for axial movement to extend and retract the tube within respect to the barrel on axial movement of the plunger, and the tube being in fluid communication with the fluid chamber to provide a fluid flow path to and from the fluid chamber through the hollow tube. In one aspect of this embodiment, after the sample is obtained using the device, it is stored in an agent that preserves the integrity of the biomarkers of interest. For example, when the biomarker being analyzed is a nucleic acid like RNA, the sample can be stored in an agent that prevents degradation of RNA molecules in the sample, or if the biomarker is a protein the sample can be stored e.g., in an agent that preserves protein. Example of agents that prevent degradation of RNA molecules in a sample are RNase inhibitors (e.g., RNEASY™ from Qiagen, SUPERase•In™ from Ambion or ScriptGuard™ RNase Inhibitor from epicenter biotechnologies) or molecules that precipitate RNA out of biological solutions (e.g., triphenylmethane dyes (e.g., methyl green, crystal violet, and pararosaniline), cresyl violet, polyamines, and cobalt ions). Example of agents that prevent the degradation of protein is protease inhibitors (e.g., PMSF (phenylmethanesulfonyl fluoride, Complete protease inhibitor cocktail from Roche, or Pepstatin) or agents that fix tissues (formalin).

Thus the invention provides in one embodiment, an in vitro diagnostic method for endometrial cancer comprising obtaining a uterine fluid aspirate sample from a patient having a symptom or risk factor for endometrial cancer and determining the level of from 1 to 100 biomarkers markers that are differentially expressed in endometrial cancer as compared to control values representative of individuals not affected by endometrial cancer, wherein (1) if the levels of 1-100 biomarkers are upregulated in the endometrial aspirate sample in the patient and in the control value then the patient has an increased likelihood of having endometrial cancer and wherein (2) if the level of the 1-100 biomarkers are downregulated in the aspirate sample and then the patient has an increased likelihood of having endometrial cancer. The biomarkers of this aspect can be any biomarkers that are differentially represented in endometrial cancer patient samples compared to samples from patients not affected with endometrial cancer and are useful for diagnosis of endometrial cancer or an increased likelihood of endometrial cancer. Preferred biomarkers are the 1-20 described herein in Table 1.

Methods of Detecting Biomarkers

The invention relates to the identification of biomarkers that are useful for diagnosing endometrial cancer. The invention provides methods for detecting one or more of the biomarkers of Table 1 for diagnosing endometrial cancer. The method of the invention can be used to detect one or more proteins corresponding to the biomarkers of Table 1 for diagnosing endometrial cancer. The method of the invention can be used to detect one or more mRNA corresponding to the biomarkers of Table 1 for diagnosing endometrial cancer. The biomarkers can be detected in a sample obtained from a patient e.g., a sample obtained from uterine tissue, uterine fluid, or blood.

In some embodiments, the method of the invention involves obtaining a sample and determining the level of 1, 2, 3, 4, 5, 6, 7, 8, 9, 10, 11, 12, 13, 14, 15, 16, 17, 18, 19, or 20, of the biomarkers of Table 1 in the sample. In a specific aspect, the method involves determining the level of 2 or more biomarkers listed in Table 1. In a specific aspect, the method involves determining the level of 3 or more biomarkers listed in Table 1. In a specific aspect, the method involves determining the level of 4 or more biomarkers listed in Table 1. In a specific aspect, the method involves determining the level of 5 or more biomarkers listed in Table 1. In a specific aspect, the method involves determining the level of 6 or more biomarkers listed in Table 1. In a specific aspect, the method involves determining the level of 7 or more biomarkers listed in Table 1. In a specific aspect, the method involves determining the level of 8 or more biomarkers listed in Table 1. In a specific aspect, the method involves determining the level of 9 or more biomarkers listed in Table 1. In a specific aspect, the method involves determining the level of 10 or more biomarkers listed in Table 1. In a specific aspect, the method involves determining the level of 11 or more biomarkers listed in Table 1. In a specific aspect, the method involves determining the level of 12 or more biomarkers listed in Table 1. In a specific aspect, the method involves determining the level of 13 or more biomarkers listed in Table 1. In a specific aspect, the method involves determining the level of 14 or more biomarkers listed in Table 1. In a specific aspect, the method involves determining the level of 15 or more biomarkers listed in Table 1. In a specific aspect, the method involves determining the level of 20 of the biomarkers listed in Table 1. In a specific aspect, the method involves determining the level of from 2 to 20 of the biomarkers listed in Table 1. In a specific aspect, the method involves determining the level of from 3 to 20 of the biomarkers listed in Table 1. In a specific aspect, the method involves determining the level of from 3 to 17 of the biomarkers listed in Table 1. In a specific aspect, the method involves determining the level of from 4 to 17 of the biomarkers listed in Table 1. In a specific aspect, the method involves determining the level of from 5 to 17 of the biomarkers listed in Table 1. In a specific aspect, the method involves determining the level of from 10 to 17 of the biomarkers listed in Table 1. In one aspect of this embodiment, the method involves determining the level of less than 500 different biomarkers. In one aspect of this embodiment, the method involves determining the level of less than 250 different biomarkers. In one aspect of this embodiment, the method involves determining the level of less than 100 different biomarkers. In one aspect of this embodiment, the method involves determining the level of less than 50 different biomarkers. Increased levels of one or more biomarkers of Table 1 that are overexpressed and/or decreased eels of one or more biomarkers of Table 1 that are underexpressed indicate that there is an increased likelihood of endometrial cancer. It is understood that in some aspects of this embodiment, the biomarkers analyzed include more than those listed in Table 1.

In some aspects of these embodiments, the method involves obtaining a sample and determining the level of mRNA of 1, 2, 3, 4, 5, 6, 7, 8, 9, 10, 11, 12, 13, 14, 15, 16, 17, 18, 19, or 20, of the biomarkers of Table 1 in the sample. In a specific aspect, the method involves determining the level of mRNA of 2 or more biomarkers listed in Table 1. In a specific aspect, the method involves determining the level of mRNA of 3 or more biomarkers listed in Table 1. In a specific aspect, the method involves determining the level of mRNA of 4 or more biomarkers listed in Table 1. In a specific aspect, the method involves determining the level of mRNA of 5 or more biomarkers listed in Table 1. In a specific aspect, the method involves determining the level of mRNA of 6 or more biomarkers listed in Table 1. In a specific aspect, the method involves determining the level of mRNA of 7 or more biomarkers listed in Table 1. In a specific aspect, the method involves determining the level of mRNA of 8 or more biomarkers listed in Table 1. In a specific aspect, the method involves determining the level of mRNA of 9 or more biomarkers listed in Table 1. In a specific aspect, the method involves determining the level of mRNA of 10 or more biomarkers listed in Table 1. In a specific aspect, the method involves determining the level of mRNA of 11 or more biomarkers listed in Table 1. In a specific aspect, the method involves determining the level of mRNA of 12 or more biomarkers listed in Table 1. In a specific aspect, the method involves determining the level of mRNA of 13 or more biomarkers listed in Table 1. In a specific aspect, the method involves determining the level of mRNA of 14 or more biomarkers listed in Table 1. In a specific aspect, the method involves determining the level of mRNA of 15 or more biomarkers listed in Table 1. In a specific aspect, the method involves determining the level of mRNA of 20 of the biomarkers listed in Table 1. In a specific aspect, the method involves determining the level of mRNA of from 2 to 20 of the biomarkers listed in Table 1. In a specific aspect, the method involves determining the level of mRNA of from 3 to 20 of the biomarkers listed in Table 1. In a specific aspect, the method involves determining the level of mRNA of from 3 to 17 of the biomarkers listed in Table 1. In a specific aspect, the method involves determining the level of mRNA of from 4 to 17 of the biomarkers listed in Table 1. In a specific aspect, the method involves determining the level of mRNA of from 5 to 17 of the biomarkers listed in Table 1. In a specific aspect, the method involves determining the level of mRNA of from 10 to 20 of the biomarkers listed in Table 1. In one aspect of this embodiment, the method involves determining the level of mRNA of less than 500 different biomarkers. In one aspect of this embodiment, the method involves determining the level of mRNA of less than 250 different biomarkers. In one aspect of this embodiment, the method involves determining the level of mRNA of less than 100 different biomarkers. In one aspect of this embodiment, the method involves determining the level of mRNA of less than 50 different biomarkers. Increased levels of one or more mRNAs corresponding to the biomarkers of Table 1 that are overexpressed and/or decreased levels of one or more biomarkers of Table 1 that are underexpressed indicate that there is an increased likelihood of endometrial cancer. It is understood that in some aspects of this embodiment, the biomarkers analyzed include more than those listed in Table 1.

In some aspects of these embodiments, the method involves obtaining a sample and determining the protein level of 1, 2, 3, 4, 5, 6, 7, 8, 9, 10, 11, 12, 13, 14, 15, 16, 17, 18, 19, or 20, of the biomarkers of Table 1 in the sample. In a specific aspect, the method involves determining the protein level of 2 or more biomarkers listed in Table 1. In a specific aspect, the method involves determining the protein level of 3 or more biomarkers listed in Table 1. In a specific aspect, the method involves determining the protein level of 4 or more biomarkers listed in Table 1. In a specific aspect, the method involves determining the protein level of 5 or more biomarkers listed in Table 1. In a specific aspect, the method involves determining the protein level of 6 or more biomarkers listed in Table 1. In a specific aspect, the method involves determining the protein level of 7 or more biomarkers listed in Table 1. In a specific aspect, the method involves determining the protein level of 8 or more biomarkers listed in Table 1. In a specific aspect, the method involves determining the protein level of 9 or more biomarkers listed in Table 1. In a specific aspect, the method involves determining the protein level of 10 or more biomarkers listed in Table 1. In a specific aspect, the method involves determining the protein level of 11 or more biomarkers listed in Table 1. In a specific aspect, the method involves determining the protein level of 12 or more biomarkers listed in Table 1. In a specific aspect, the method involves determining the protein level of 13 or more biomarkers listed in Table 1. In a specific aspect, the method involves determining the protein level of 14 or more biomarkers listed in Table 1. In a specific aspect, the method involves determining the protein level of 15 or more biomarkers listed in Table 1. In a specific aspect, the method involves determining the protein level of 20 of the biomarkers listed in Table 1. In a specific aspect, the method involves determining the protein level of from 2 to 20 of the biomarkers listed in Table 1. In a specific aspect, the method involves determining the protein level of from 3 to 20 of the biomarkers listed in Table 1. In a specific aspect, the method involves determining the protein level of from 3 to 17 of the biomarkers listed in Table 1. In a specific aspect, the method involves determining the protein level of from 4 to 17 of the biomarkers listed in Table 1. In a specific aspect, the method involves determining the protein level of from 5 to 17 of the biomarkers listed in Table 1. In a specific aspect, the method involves determining the protein level of from 10 to 17 of the biomarkers listed in Table 1. In one aspect of this embodiment, the method involves determining the protein level of less than 500 different biomarkers. In one aspect of this embodiment, the method involves determining the protein level of less than 250 different biomarkers. In one aspect of this embodiment, the method involves determining the protein level of less than 100 different biomarkers. In one aspect of this embodiment, the method involves determining the protein level of less than 50 different biomarkers. In one aspect of this embodiment, the method involves determining the protein level of from 1 to 10 different biomarkers. Increased levels of one or more proteins corresponding to the biomarkers of Table 1 indicate that there is an increased likelihood of endometrial cancer. It is understood that in some aspects of this embodiment, the biomarkers analyzed include more than those listed in Table 1.

In one embodiment, the invention provides a method for detecting one or more protein biomarkers in serum, blood, and/or plasma. In a specific aspect of this embodiment, the one or more biomarkers are chosen from ACAA1, AP1M2, CGN, DDR1, EPS8L2, FASTKD1, GMIP, IKBKE, P2RX4, P4HB, PHKG2, PPFIBP2, PPP1R16A, RASSF7, RNF183, SIRT6, TJP3, EFEMP2, SOCS2, and DCN. In a more specific aspect, the one or more biomarkers are chosen from IKBKE, P4HB, SOCS2, GMIP, DDR1, EPS8L2, PPP1R16A, P2RX4, PHKG2, RASSF7, SIRT6, TJP3, AP1M2, RNF183, and DCN. In another specific aspect of this embodiment, the method comprises detecting the level of IKBKE. In another specific aspect of this embodiment, the method comprises detecting the level of P4HB. In another specific aspect of this embodiment, the method comprises detecting the level of SOCS2. In another specific aspect of this embodiment, the method comprises detecting the level of GMIP. In another specific aspect of this embodiment, the method comprises detecting the level of AP1M2. In another specific aspect of this embodiment, the method comprises detecting the level of EPS8L2. In another specific aspect of this embodiment, the method comprises detecting the level of DDR1. In another specific aspect of this embodiment, the method comprises detecting the level of CGN. In another specific aspect of this embodiment, the method comprises detecting the level of TJP3.

In some aspects of these embodiments, the method involves determining the level of 1, 2, 3, 4, 5, 6, 7, 8, 9, 10, 11, 12, 13, 14, 15, 16, 17, 18, 19, 20, 21, 22, 23, 24, 25, 30, 35, 40, or 50 or more of biomarkers in addition to one or more of those listed in Table 1. These markers can be those whose expression levels are known to be altered in patients having endometrial cancer. Alternatively, the additional biomarkers can be used for differential diagnosis of other diseases (e.g., endometriosis, ovarian cancer, and fibroids), for classifying the type of cancer, prognostic information and/or for providing information for selecting a therapy. In a specific aspect of this embodiment, the additional biomarkers are analyzed in uterine fluid samples.

In a specific aspect of the invention, the one or more biomarkers listed in Table 1 are detected on an array having different probes on the array which are oligonucleotides having from about 5 to 200 bases in length. In another specific aspect, each of the different probes on the array is an oligonucleotide having from about 15 to 200, 15 to 150, 15 to 100, 15 to 75, 15 to 60, or 20 to 55 bases in length. In one aspect, the array has probes to 2 or more biomarkers listed in Table 1. In one aspect, the array has probes to 3 or more biomarkers listed in Table 1. In one aspect, the array has probes to 4 or more biomarkers listed in Table 1. In one aspect, the array has probes to 5 or more biomarkers listed in Table 1. In one aspect, the array has probes to 6 or more biomarkers listed in Table 1. In one aspect, the array has probes to 7 or more biomarkers listed in Table 1. In one aspect, the array has probes to less than 1000 different genes. In one aspect, the array has probes to less than 500 different genes. In one aspect, the array has probes to less than 100 different genes.

In some aspects of these embodiments, the copy number of the one or more biomarkers listed in Table 1 is determined. In another aspect of this embodiment, the copy number profile of 1, 2, 3, 4, 5, 6, 7, 8, 9, 10, 11, 12, 13, 14, 15, 16, 17, 18, 19, or 20 of the biomarkers of Table 1 (or loci corresponding to the biomarker) are determined for detecting endometrial cancer.

In one aspect, the invention provides primers that can hybridize to a nucleic acid corresponding to a biomarker listed in Table 1 and be used to amplify a nucleic acid or fragment thereof corresponding to said biomarker for diagnosing endometrial cancer according to the methods of the invention. In a more specific aspect, the primers are designed to amplify one or more exons of the biomarker. In another aspect, the primers are designed to amplify a fragment of one or more exons of the biomarker. In one aspect, the primers are suitable for RT-PCR analysis. In one aspect, the method of the invention involves the use of primers to amplify a nucleic acid corresponding to a biomarker of Table 1, and detecting the amplification product with a probe to the amplification product. In another aspect, the method of the invention involves the use of primers to amplify a nucleic acid corresponding to a biomarker of Table 1, and detecting the amplification product with a dye that allows for quantification of the amplification product.

In one aspect, the invention provides probes to the biomarkers of Table 1 for detecting a nucleic acid or fragment thereof corresponding to the biomarker. The probes can be used in the methods of the invention e.g., for diagnosing endometrial cancer. In a specific aspect, the probe is for the biomarker mRNA or a nucleic acid, is obtained from the mRNA corresponding to the biomarker. In a specific aspect, the probe corresponds to two contiguous exons of the biomarker of Table 1, (or fragments of two or more contiguous exons). In a specific aspect, the probe corresponds to an exon of the biomarker or a fragment thereof. In a specific aspect, the probe corresponds to at least a portion of the promoter region of the biomarker and at least a portion of exon 1 of the biomarker.

In one aspect of the invention, a multiplex PCR assay is used to assess the levels of from 2 to 20 of the biomarkers of Table 1 to detect the presence or absence of endometrial cancer. In a more specific aspect, the levels of from 3 to 20 biomarkers of Table 1 are assessed by multiplex PCR. In a more specific aspect, the levels of from 4 to 20 biomarkers of Table 1 are assessed by multiplex PCR. In a more specific aspect, the levels of from 5 to 20 biomarkers of Table 1 are assessed by multiplex PCR. In a more specific aspect, the levels of from 6 to 20 biomarkers of Table 1 are assessed by multiplex PCR. In a more specific aspect, the levels of from 7 to 20 biomarkers of Table 1 are assessed by multiplex PCR. In a more specific aspect, the levels of from 8 to 20 or more biomarkers of Table 1 are assessed by multiplex PCR. In a more specific aspect, the levels of from 9 to 20 biomarkers of Table 1 are assessed by multiplex PCR. In a more specific aspect, the levels of from 10 to 20 or more biomarkers of Table 1 are assessed by multiplex PCR. In a more specific aspect, the levels of from 15 to 20 biomarkers of Table 1 are assessed by multiplex PCR. In a more specific aspect, the levels of from 20 of the biomarkers of Table 1 are assessed by multiplex PCR.

Quantitative PCR

In some embodiments, the invention relies on quantitative PCR to determine the level of one or more biomarkers of Table 1. In a specific aspect the quantitative PCR method is quantitative RT-PCR. The methods can be semi-quantitative or fully quantitative.

The methods of the invention for detecting the biomarkers of the invention can comprise competitive quantitative PCR or real-time quantitative PCR which both estimate target gene concentration in a sample by comparison with standard curves constructed from amplifications of serial dilutions of standard DNA. Quantitative PCR or real-time quantitative PCR differ substantially in how the standard curves are generated. In competitive QPCR, an internal competitor DNA is added at a known concentration to both serially diluted standard samples and unknown (e.g., obtained from a patient) samples. After coamplification, ratios of the internal competitor and target PCR products are calculated for both standard dilutions and unknown samples, and a standard curve is constructed that plots competitor-target PCR product ratios against the initial target DNA concentration of the standard dilutions. Given equal amplification efficiency of competitor and target DNA, the concentration of the latter in patient samples can be extrapolated from this standard curve.

In real-time QPCR, the accumulation of amplification product is measured continuously in both standard dilutions of target DNA and samples containing unknown amounts of target DNA. A standard curve is constructed by correlating initial template concentration in the standard samples with the number of PCR cycles ($C_t$) necessary to produce a specific threshold concentration of product. In the test samples, target PCR product accumulation is measured after the same $C_t$, which allows interpolation of target DNA concentration from the standard curve. Although real-time QPCR permits more rapid and facile measurement of target DNA during routine analyses, competitive QPCR remains an important alternative for target quantification in environmental samples. The coamplification of a known amount of competitor DNA with target DNA is an intuitive way to correct for sample-to-sample variation of amplification efficiency due to the presence of inhibitory substrates and large amounts of background DNA that are obviously absent from the standard dilutions.

Another type of QPCR is applied quantitatively PCR. Often termed "relative quantitative PCR," this method determines the relative concentrations of specific nucleic acids. In the context of the present invention, RT-PCR is performed on mRNA species isolated from patients. By determining that the concentration of a specific mRNA species, it can be determined if the gene encoding the specific mRNA species is differentially expressed.

In one embodiment, the invention provides a method comprising, obtaining a test sample from cells, tissue, or fluid of a patient; detecting the level of one or more of the biomarkers of Table 1 and comparing the level of the biomarker(s) in the sample to the level expected for a normal sample (or control value).

In one embodiment, the invention provides a method comprising, obtaining a suspected tumor sample from a patient; detecting the level of one or more biomarkers listed in Table 1 and comparing the level of biomarker(s) in the sample to the level expected for a normal unaffected sample (or control value).

In one embodiment, the invention provides a method comprising, obtaining a sample from a patient comprising a cell; detecting the level of one or more of the biomarkers of Table 1 in said cell and comparing the level of the biomarker(s) in the cell to the level expected for a normal unaffected cell (or control value).

In one embodiment, the invention provides a method comprising, obtaining a test sample from a fluid of a patient; detecting the level of one or more of the biomarkers of Table 1 and comparing the level of the biomarker(s) in the sample to the level expected for a normal unaffected sample. In one aspect of this embodiment, the fluid is uterine fluid obtained by aspiration. In one aspect of this embodiment, the fluid is uterine fluid obtained by aspiration with a CORNIER™ pipelle. In one aspect of this embodiment, the fluid is uterine fluid. In another aspect of this embodiment, the fluid is vaginal discharge. In one embodiment, the invention provides a method comprising, obtaining a test sample from a blood or serum sample from a patient; and detecting the level of one or more of the biomarkers of Table 1 and comparing the level of the biomarker(s) in the sample to the level expected for a normal unaffected sample.

In one embodiment, the invention provides a method comprising, obtaining a test sample from the urine of a patient; detecting the level of one or more of the biomarkers of Table 1 and comparing the level of the biomarkers in the urine to the level expected for a control value.

In one embodiment, the invention provides a method comprising, obtaining a test sample from the uterus of a patient using a brush; and detecting the level of one or more of the biomarkers of Table 1 and comparing the level of the biomarkers in the sample to the level expected for a normal sample.

The presence of increased levels of one or more of the biomarkers of Table 1 can indicate endometrial cancer or a precancerous condition in the tissue e.g., endometrial hyperplasia. In one aspect of this embodiment, the method involves identifying a patient in need of analysis of one or more biomarkers of Table 1.

In another aspect of this embodiment, the present invention provides methods for diagnosing or predicting a endometrial cancer. The method of this aspect can comprise (1) obtaining a test sample from cells, tissue, and/or fluid (2) obtaining a control sample from cells, tissue, or fluid that is normal, or obtaining a normal control value, and (3) detecting or measuring in both the test sample and the control sample the level of one or more mRNA transcripts corresponding to one or more of the biomarkers of Table 1. If the level of the one or more transcripts is higher in the test sample than that in the control sample, this indicates endometrial cancer (and/or and increased risk of having endometrial cancer) or a precancerous condition in the test sample cells or tissue. In another aspect the control sample may be obtained from a different individual or be a normalized value based on baseline data obtained from a population. In one aspect of this embodiment, the method involves identifying a patient in need of analysis of one or more of the biomarkers of Table 1. In one aspect, the patient in need of analysis of one or more of the biomarkers of Table 1 is one that is at risk of having endometrial cancer, is suspected of having endometrial cancer, or and/or is undergoing screening.

In yet another aspect of this embodiment, the method comprises, obtaining a test sample from cells, tissue, or fluid; detecting the number of DNA copies of one or more of the biomarkers of Table 1 ((e.g., per cell) in the sample; and comparing the number of DNA copies detected (for example, quantitatively and/or qualitatively) in the sample to a control sample or a known value (or a control value), thereby determining whether the copy number of the biomarker(s) is amplified in the test sample. In one aspect of this embodiment, the method involves identifying a patient in need of analysis of one or more of the biomarkers of Table 1. In one aspect, the patient in need of analysis of one or more of the biomarkers of Table 1 is one that is at risk of having endometrial cancer, is suspected of having endometrial cancer, or and/or is undergoing screening.

In yet another aspect of this embodiment, the method comprises (1) obtaining a test sample from cells, tissue, or fluid;

contacting the sample with an antibody to a protein or fragment thereof corresponding to one or more of the biomarkers of Table 1, and detecting in the test sample, the level of the biomarker(s), wherein an increased level the biomarker(s), as compared to a control value indicates the patient may have a precancerous or a cancerous condition. In another aspect, the control value may be obtained from a different individual or be a normalized value based on baseline data obtained from a population. Alternatively, a given level of a biomarker, representative of the endometrial cancer-free population, that has been previously established based on measurements from normal, endometrial cancer-free patients, can be used as a control value. A control data point from a reference database, based on data obtained from control samples representative of an endometrial cancer-free population, also can be used as a control value. In one aspect of this embodiment, the method involves identifying a patient in need of analysis of one or more of the biomarkers of Table 1. In one aspect, the patient in need of analysis of the biomarker(s) is one that is at risk of having endometrial cancer, is suspected of having endometrial cancer, or and/or is undergoing screening.

In some embodiments, the method of the invention involves comparing the expression of a biomarker of the invention to an endogenous biomarker. For example, the expression level of one or more of the biomarkers listed in Table 1 are normalized to the level of expression of an endogenous biomarker. Thus, in one specific aspect, the endogenous biomarker is chosen from POLR2A, B2M, PFN1, HMBS, G6PD, and PABPN1. The ENSMBL reference numbers are given below for these endogenous biomarkers.

| Name | Gene | Transcript | Protein |
|---|---|---|---|
| POLR2A | ENSG00000181222 | ENST00000322644 | ENSP00000314949 |
| B2M | ENSG00000166710 | ENST00000349264 | ENSP00000340858 |
| PFN1 | ENSG00000108518 | ENST00000225655 | ENSP00000225655 |
| HMBS | ENSG00000149397 | ENST00000278715 | ENSP00000278715 |
| G6PD | ENSG00000160211 | ENST00000393562 | ENSP00000377192 |
| PABPN1 | ENSG00000100836 | ENST00000216727 | ENSP00000216727 |

Diagnostic and Prognostic Reagents

The invention provides reagents for detecting the biomarkers of the invention (e.g., those in Table 1). The reagents are useful for detecting protein and nucleic acid levels of the biomarkers of Table 1 for detecting and/or diagnosing endometrial cancer. The reagents below can be used for detecting combinations of the biomarkers to diagnose endometrial cancer. Specific examples of nucleic acids, probes, primers, etc. related to each of the individual biomarkers are given in the Examples.

In one embodiment, the invention provides an ACAA1 nucleic acid for detecting endometrial cancer. In a related aspect, the invention provides primers for amplifying an ACAA1 nucleic acid for detecting endometrial cancer. In another related aspect the invention provides a probe that can hybridize to an ACAA1 nucleic acid for detecting endometrial cancer.

In another related aspect, the invention provides an antibody that binds immunologically to an ACAA1 protein for detecting endometrial cancer. In a related aspect the invention provides an ACAA1 polypeptide for generating an antibody. In yet another related aspect, the invention provides an ACAA1 polypeptide for generating an immune response against the marker.

In one embodiment, the invention provides an AP1M2 nucleic acid for detecting endometrial cancer. In a related aspect, the invention provides primers for amplifying an AP1M2 nucleic acid for detecting endometrial cancer. In another related aspect the invention provides a probe that can hybridize to an AP1M2 nucleic acid for detecting endometrial cancer.

In another related aspect, the invention provides an antibody that binds immunologically to an AP1M2 protein for detecting endometrial cancer. In a related aspect the invention provides an AP1M2 polypeptide for generating an antibody. In yet another related aspect, the invention provides an AP1M2 polypeptide for generating an immune response against the marker.

In one embodiment, the invention provides a CGN nucleic acid for detecting endometrial cancer. In a related aspect, the invention provides primers for amplifying a CGN nucleic acid for detecting endometrial cancer. In another related aspect the invention provides a probe that can hybridize to a CGN nucleic acid for detecting endometrial cancer.

In another related aspect, the invention provides an antibody that binds immunologically to a CGN protein for detecting endometrial cancer. In a related aspect the invention provides a CGN polypeptide for generating an antibody. In yet another related aspect, the invention provides a CGN polypeptide for generating an immune response against the marker.

In one embodiment, the invention provides a DDR1 nucleic acid for detecting endometrial cancer. In a related aspect, the invention provides primers for amplifying a DDR1 nucleic acid for detecting endometrial cancer. In another related aspect the invention provides a probe that can hybridize to a DDR1 nucleic acid for detecting endometrial cancer.

In another related aspect, the invention provides an antibody that binds immunologically to a DDR1 protein for detecting endometrial cancer. In a related aspect the invention provides a DDR1 polypeptide for generating an antibody. In yet another related aspect, the invention provides a DDR1 polypeptide for generating an immune response against the marker.

In one embodiment, the invention provides an EPS8L2 nucleic acid for detecting endometrial cancer. In a related aspect, the invention provides primers for amplifying an EPS8L2 nucleic acid for detecting endometrial cancer. In another related aspect the invention provides a probe that can hybridize to an EPS8L2 nucleic acid for detecting endometrial cancer.

In another related aspect, the invention provides an antibody that binds immunologically to an EPS8L2 protein for detecting endometrial cancer. In a related aspect the invention provides an EPS8L2 polypeptide for generating an antibody. In yet another related aspect, the invention provides an EPS8L2 polypeptide for generating an immune response against the marker.

In one embodiment, the invention provides a FASTKD1 nucleic acid for detecting endometrial cancer. In a related aspect, the invention provides primers for amplifying a FASTKD1 nucleic acid for detecting endometrial cancer. In another related aspect the invention provides a probe that can hybridize to a FASTKD1 nucleic acid for detecting endometrial cancer.

In another related aspect, the invention provides an antibody that binds immunologically to a FASTKD1 protein for detecting endometrial cancer. In a related aspect the invention provides a FASTKD1 polypeptide for generating an antibody. In yet another related aspect, the invention provides a FASTKD1 polypeptide for generating an immune response against the marker.

In one embodiment, the invention provides a GMIP nucleic acid for detecting endometrial cancer. In a related aspect, the invention provides primers for amplifying a GMIP nucleic acid for detecting endometrial cancer. In another related aspect the invention provides a probe that can hybridize to a GMIP nucleic acid for detecting endometrial cancer.

In another related aspect, the invention provides an antibody that binds immunologically to a GMIP protein for detecting endometrial cancer. In a related aspect the invention provides a GMIP polypeptide for generating an antibody. In yet another related aspect, the invention provides a GMIP polypeptide for generating an immune response against the marker.

In one embodiment, the invention provides an IKBKE nucleic acid for detecting endometrial cancer. In a related aspect, the invention provides primers for amplifying an IKBKE nucleic acid for detecting endometrial cancer. In another related aspect the invention provides a probe that can hybridize to an IKBKE nucleic acid for detecting endometrial cancer.

In another related aspect, the invention provides an antibody that binds immunologically to an IKBKE protein for detecting endometrial cancer. In a related aspect the invention provides an IKBKE polypeptide for generating an antibody. In yet another related aspect, the invention provides an IKBKE polypeptide for generating an immune response against the marker.

In one embodiment, the invention provides a P2RX4 nucleic acid for detecting endometrial cancer. In a related aspect, the invention provides primers for amplifying a P2RX4 nucleic acid for detecting endometrial cancer. In another related aspect the invention provides a probe that can hybridize to a P2RX4 nucleic acid for detecting endometrial cancer.

In another related aspect, the invention provides an antibody that binds immunologically to a P2RX4 protein for detecting endometrial cancer. In a related aspect the invention provides a P2RX4 polypeptide for generating an antibody. In yet another related aspect, the invention provides a P2RX4 polypeptide for generating an immune response against the marker.

In one embodiment, the invention provides a P4HB nucleic acid for detecting endometrial cancer. In a related aspect, the invention provides primers for amplifying a P4HB nucleic acid for detecting endometrial cancer. In another related aspect the invention provides a probe that can hybridize to a P4HB nucleic acid for detecting endometrial cancer.

In another related aspect, the invention provides an antibody that binds immunologically to a P4HB protein for detecting endometrial cancer. In a related aspect the invention provides a P4HB polypeptide for generating an antibody. In yet another related aspect, the invention provides a P4HB polypeptide for generating an immune response against the marker.

In one embodiment, the invention provides a PHKG2 nucleic acid for detecting endometrial cancer. In a related aspect, the invention provides primers for amplifying a PHKG2 nucleic acid for detecting endometrial cancer. In another related aspect the invention provides a probe that can hybridize to a PHKG2 nucleic acid for detecting endometrial cancer.

In another related aspect, the invention provides an antibody that binds immunologically to a PHKG2 protein for detecting endometrial cancer. In a related aspect the invention provides a PHKG2 polypeptide for generating an antibody. In yet another related aspect, the invention provides a PHKG2 polypeptide for generating an immune response against the marker.

In one embodiment, the invention provides a PPFIBP2 nucleic acid for detecting endometrial cancer. In a related aspect, the invention provides primers for amplifying a PPFIBP2 nucleic acid for detecting endometrial cancer. In another related aspect the invention provides a probe that can hybridize to a PPFIBP2 nucleic acid for detecting endometrial cancer.

In another related aspect, the invention provides an antibody that binds immunologically to a PPFIBP2 protein for detecting endometrial cancer. In a related aspect the invention provides a PPFIBP2 polypeptide for generating an antibody. In yet another related aspect, the invention provides a PPFIBP2 polypeptide for generating an immune response against the marker.

In one embodiment, the invention provides a PPP1R16A nucleic acid for detecting endometrial cancer. In a related aspect, the invention provides primers for amplifying a PPP1R16A nucleic acid for detecting endometrial cancer. In another related aspect the invention provides a probe that can hybridize to a PPP1R16A nucleic acid for detecting endometrial cancer.

In another related aspect, the invention provides an antibody that binds immunologically to a PPP1R16A protein for detecting endometrial cancer. In a related aspect the invention provides a PPP1R16A polypeptide for generating an antibody. In yet another related aspect, the invention provides a PPP1R16A polypeptide for generating an immune response against the marker.

In one embodiment, the invention provides a RASSF7 nucleic acid for detecting endometrial cancer. In a related aspect, the invention provides primers for amplifying a RASSF7 nucleic acid for detecting endometrial cancer. In another related aspect the invention provides a probe that can hybridize to a RASSF7 nucleic acid for detecting endometrial cancer.

In another related aspect, the invention provides an antibody that binds immunologically to a RASSF7 protein for detecting endometrial cancer. In a related aspect the invention provides a RASSF7 polypeptide for generating an antibody. In yet another related aspect, the invention provides a RASSF7 polypeptide for generating an immune response against the marker.

In one embodiment, the invention provides a RNF183 nucleic acid for detecting endometrial cancer. In a related aspect, the invention provides primers for amplifying a RNF183 nucleic acid for detecting endometrial cancer. In another related aspect the invention provides a probe that can hybridize to a RNF183 nucleic acid for detecting endometrial cancer.

In another related aspect, the invention provides an antibody that binds immunologically to a RNF183 protein for detecting endometrial cancer. In a related aspect the invention provides a RNF183 polypeptide for generating an antibody.

In yet another related aspect, the invention provides a RNF183 polypeptide for generating an immune response against the marker.

In one embodiment, the invention provides a SIRT6 nucleic acid for detecting endometrial cancer. In a related aspect, the invention provides primers for amplifying a SIRT6 nucleic acid for detecting endometrial cancer. In another related aspect the invention provides a probe that can hybridize to a SIRT6 nucleic acid for detecting endometrial cancer.

In another related aspect, the invention provides an antibody that binds immunologically to a SIRT6 protein for detecting endometrial cancer. In a related aspect the invention provides a SIRT6 polypeptide for generating an antibody. In yet another related aspect, the invention provides a SIRT6 polypeptide for generating an immune response against the marker.

In one embodiment, the invention provides a TJP3 nucleic acid for detecting endometrial cancer. In a related aspect, the invention provides primers for amplifying a TJP3 nucleic acid for detecting endometrial cancer. In another related aspect the invention provides a probe that can hybridize to a TJP3 nucleic acid for detecting endometrial cancer.

In another related aspect, the invention provides an antibody that binds immunologically to a TJP3 protein for detecting endometrial cancer. In a related aspect the invention provides a TJP3 polypeptide for generating an antibody. In yet another related aspect, the invention provides a TJP3 polypeptide for generating an immune response against the marker.

In one embodiment, the invention provides an EFEMP2 nucleic acid for detecting endometrial cancer. In a related aspect, the invention provides primers for amplifying an EFEMP2 nucleic acid for detecting endometrial cancer. In another related aspect the invention provides a probe that can hybridize to an EFEMP2 nucleic acid for detecting endometrial cancer.

In another related aspect, the invention provides an antibody that binds immunologically to an EFEMP2 protein for detecting endometrial cancer. In a related aspect the invention provides an EFEMP2 polypeptide for generating an antibody. In yet another related aspect, the invention provides an EFEMP2 polypeptide for generating an immune response against the marker.

In one embodiment, the invention provides a SOCS2 nucleic acid for detecting endometrial cancer. In a related aspect, the invention provides primers for amplifying a SOCS2 nucleic acid for detecting endometrial cancer. In another related aspect the invention provides a probe that can hybridize to a SOCS2 nucleic acid for detecting endometrial cancer.

In another related aspect, the invention provides an antibody that binds immunologically to a SOCS2 protein for detecting endometrial cancer. In a related aspect the invention provides a SOCS2 polypeptide for generating an antibody. In yet another related aspect, the invention provides a SOCS2 polypeptide for generating an immune response against the marker.

In one embodiment, the invention provides a DCN nucleic acid for detecting endometrial cancer. In a related aspect, the invention provides primers for amplifying a DCN nucleic acid for detecting endometrial cancer. In another related aspect the invention provides a probe that can hybridize to a DCN nucleic acid for detecting endometrial cancer.

In another related aspect, the invention provides an antibody that binds immunologically to a DCN protein for detecting endometrial cancer. In a related aspect the invention provides a DCN polypeptide for generating an antibody. In yet another related aspect, the invention provides a DCN polypeptide for generating an immune response against the marker.

Kits

The invention also provides kits for detecting one or more of the biomarkers of Table 1. In one embodiment, the kit is useful for detecting and/or diagnosing a gynecological cancer. In another embodiment, the kit is useful for detecting and/or diagnosing endometrial cancer. In one aspect, the kit contains reagents for detecting CGN. In one aspect, the kit contains means for detecting CGN. In one aspect, the kit contains reagents for detecting AP1M2. In one aspect, the kit contains means for detecting AP1M2. In one aspect, the kit contains reagents for detecting EPS8L2. In one aspect, the kit contains means for detecting EPS8L2. In one aspect, the kit contains reagents for detecting IKBKE. In one aspect, the kit contains means for detecting IKBKE. In one aspect, the kit contains reagents for detecting PPP1R16A. In one aspect, the kit contains means for detecting PPP1R16A. In one aspect, the kit contains reagents for detecting RASSF7. In one aspect, the kit contains means for detecting RASSF7. In one aspect, the kit contains reagents for detecting TJP3. In one aspect, the kit contains means for detecting TJP3. In one aspect, the kit contains reagents for detecting P2RX4. In one aspect, the kit contains means for detecting P2RX4. In one aspect, the kit contains reagents for detecting RNF183. In one aspect, the kit contains means for detecting RNF183. In one aspect, the kit contains reagents for detecting GMIP. In one aspect, the kit contains means for detecting GMIP. In one aspect, the kit contains reagents for detecting PHKG2. In one aspect, the kit contains means for detecting PHKG2. In one aspect, the kit contains reagents for detecting P4HB. In one aspect, the kit contains means for detecting P4HB. In one aspect, the kit contains reagents for detecting PPFIBP2. In one aspect, the kit contains means for detecting PPFIBP2. In one aspect, the kit contains reagents for detecting FASTKD1. In one aspect, the kit contains means for detecting FASTKD1. In one aspect, the kit contains reagents for detecting DDR1. In one aspect, the kit contains means for detecting DDR1. In one aspect, the kit contains reagents for detecting SIRT6. In one aspect, the kit contains means for detecting SIRT6. In one aspect, the kit contains reagents for detecting ACAA1. In one aspect, the kit contains means for detecting ACAA1. In one aspect, the kit contains reagents for detecting DCN. In one aspect, the kit contains means for detecting DCN. In one aspect, the kit contains reagents for detecting SOCS2. In one aspect, the kit contains means for detecting SOCS2. In one aspect, the kit contains reagents for detecting EFEMP2. In one aspect, the kit contains means for detecting EFEMP2.

In one aspect, the kit contains reagents for detecting from 2 to 20 of the biomarkers of Table 1. In one aspect, the kit contains means for detecting from 2 to 20 of the biomarkers of Table 1. In one aspect, the kit contains reagents for detecting from 3 to 20 of the biomarkers of Table 1. In one aspect, the kit contains means for detecting from 3 to 20 of the biomarkers of Table 1. In one aspect, the kit contains reagents for detecting from 4 to 20 of the biomarkers of Table 1. In one aspect, the kit contains means for detecting from 4 to 20 of the biomarkers of Table 1. In one aspect, the kit contains reagents for detecting from 5 to 20 of the biomarkers of Table 1. In one aspect, the kit contains means for detecting from 5 to 20 of the biomarkers of Table 1. In one aspect, the kit contains reagents for detecting from 6 to 20 of the biomarkers of Table 1. In one aspect, the kit contains means for detecting from 6 to 20 of the biomarkers of Table 1. In one aspect, the kit contains reagents for detecting from 7 to 20 of the biomarkers of Table 1. In one aspect, the kit contains means for detecting from 7 to 20 of the biomarkers of Table 1. In one aspect, the kit contains reagents for detecting from 8 to 20 of the biomarkers of Table 1. In one aspect, the kit contains means for detecting from 8 to 20 of the biomarkers of Table 1. In one aspect, the kit contains reagents for detecting from 9 to 20 of the biomarkers of Table 1. In one aspect, the kit contains means for detecting from 9 to 20 of the biomarkers of Table 1. In one aspect, the kit contains means for detecting from 10 to 20 of the biomarkers of Table 1. In one aspect, the kit contains means for detecting from 10 to 20 of the biomarkers of Table 1. In one aspect, the kit contains means for detecting from 15 to 20 of the biomarkers of Table 1. In one aspect, the kit comprises reagents for the RT-PCR evaluation of from 1 to 20 of the biomarkers of Table 1. In one aspect, the kit comprises means for the RT-PCR evaluation of from 1 to 20 of the biomarkers of Table 1. In one aspect, the kit comprises reagents for microarray evaluation of from 1 to 20 of the biomarkers of Table 1. In one aspect, the kit comprises means for microarray evaluation of from 1 to 20 of the biomarkers of Table 1. In one aspect, the kit comprises reagents for antibody-based evaluation of from 1 to 20 of the biomarkers of Table 1. In one aspect, the kit comprises means for antibody-based evaluation of from 1 to 20 of the biomarkers of Table 1. In one aspect, the kit has reagents for detecting different biomarkers in addition to one or more of those listed in Table 1. In one aspect, the kit has means for detecting different biomarkers in addition to the 1 to 20 of those listed in Table 1. In one aspect, the kit has reagents for multiplex PCR of from 2 to 20 markers of Table 1. In one aspect, the kit has means for multiplex PCR of from 2 to 20 markers of Table 1.

In some aspects, the kit has a device for obtaining a sample for analysis. In one aspect the device is a pipelle. In another aspect, the device is as described in U.S. Pat. No. 7,207,951, Issued Apr. 24, 2007, which is incorporated by herein reference in its entirety. In another aspect, the device is curettage. In another aspect, the device is a brush. One example of a brush device is the tao brush In some aspects, the kit has an agent to stabilizing the samples obtained from the patient. For example, in a specific aspect, the agent is a buffer for stabilizing the sample obtained from the patient comprises an RNA preserving solution. In another aspect, the agent is useful for stabilizing blood or serum samples.

Diagnostic Antibodies to the Biomarkers of Table 1

Diagnostic antibodies to one or more of the biomarkers of Table 1 (also referred to as a target protein) for diagnostic uses can be obtained in any number of ways. Furthermore, antibodies to some of the biomarkers of Table 1 are commercially available or described in the literature. These known antibodies can be used in the methods of the invention and/or as the basis of engineering new antibodies. Phage display techniques can be used to generate antibodies to one or more of the biomarkers of Table 1. Standard hybridoma technologies can be used to generate antibodies to one or more of the biomarkers of Table 1. Antibodies to some of the biomarkers of Table 1 are known in the art see the examples. In some aspects, the antibody to one or more of the biomarkers of Table 1 is derived from an animal source (e.g., mouse, rat, or rabbit).

Polyclonal Antibodies

The target protein antibodies may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant t will be injected in the mammal by multiple subcutaneous or intraperitoneal injections. The immunizing agent may include the target protein polypeptide (or fragment thereof) or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and M PL-TDM adjuvant (monophosphoryl Lipid A, synthetic trehalose dicorynomycolate). The immunization protocol may be selected by one skilled in the art without undue experimentation.

Monoclonal Antibodies

The target protein antibodies may, alternatively, be monoclonal antibodies. Monoclonal antibodies may be prepared using hybridoma methods, such as those described by Kohler and Milstein (1975) *Nature* 256:495. In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the target protein polypeptide (or fragment thereof) or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, Monoclonal Antibodies: Principles and Practice, Academic Press, (1986) pp. 59-103). Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies (Kozbor (1984) *J. Immunol.* 133:3001; Brodeur et al., Monoclonal Antibody Production Techniques and Applications, Marcel Dekker, Inc., New York, (1987) pp. 51-63).

The culture medium in which the hybridoma cells are cultured can then be assayed for the presence of monoclonal antibodies directed against target protein. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard (1980) Anal. Biochem. 107:220.

After the desired hybridoma cells are identified, the clones may be subcloned by limiting dilution procedures and grown by standard methods [Monoclonal Antibodies: Principles and Practice, Academic Press, (1986) pp. 59-103]. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences [U.S. Pat. No. 4,816,567; Morrison et al., supra] or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

Phage Display

Antibodies to the biomarkers of the invention can also be made by using combinatorial libraries to screen for synthetic antibody clones with the desired activity or activities. In principle, synthetic antibody clones are selected by screening phage libraries containing phage that display various fragments of antibody variable region (Fv) fused to phage coat protein. Such phage libraries are panned by affinity chromatography against the desired antigen. Clones expressing Fv fragments capable of binding to the desired antigen are adsorbed to the antigen and thus separated from the non-binding clones in the library. The binding clones are then eluted from the antigen, and can be further enriched by additional cycles of antigen adsorption/elution. Antibodies to the biomarkers of the invention can be obtained by designing a suitable antigen screening procedure to select for the phage clone of interest followed by construction of a full length antibody clone using the Fv sequences from the phage clone of interest and suitable constant region (Fc) sequences described in Kabat et al., Sequences of Proteins of Immunological Interest, Fifth Edition, NIH Publication 91-3242, Bethesda Md. (1991), vols. 1-3.

Antibody Conjugates

The antibodies (and fragments thereof) of the invention can be conjugated to molecules for diagnostic purposes. For example, an antibody to a biomarker of Table 1 can be conjugated to a detectable label (e.g., for imaging purposes) for diagnosing or detecting endometrial cancer. Suitable detectable markers include, but are not limited to, a radioisotope, a nanoparticle, a fluorescent compound, a bioluminescent compound, chemiluminescent compound, a metal chelator or an enzyme. Techniques for conjugating diagnostic agents to antibodies are well known (Holmes et al. (2001) Curr Protoc Cytom. May; Chapter 4: Unit 4.2; Kumar et al (2008) ACS Nano. March; 2 (3):449-56; Rosenthal et al. (2006) *Laryngoscope* September; 116 (9):1636-41). Additionally kits for conjugating agents to diagnostic antibodies are commercially available.

Data and Information

In one aspect of the invention, the present invention relates to methods for comparing and compiling data wherein the data is stored in electronic or paper format. Electronic format can be selected from the group consisting of electronic mail, disk, compact disk (CD), digital versatile disk (DVD), memory card, memory chip, ROM or RAM, magnetic optical disk, tape, video, video clip, microfilm, internet, shared network, shared server and the like; wherein data is displayed, transmitted or analyzed via electronic transmission, video display, telecommunication, or by using any of the above stored formats; wherein data is compared and compiled at the site of sampling specimens or at a location where the data is transported following a process as described above. The data of this embodiment is information regarding the results of the analysis of the biomarkers of Table 1.

The biomarkers, reagents, targets, assays, tests, inquiries and methodologies described herein can be employed in a variety of contexts, including diagnostic discovery, diagnostic development, safety and efficacy monitoring, comparative studies, marketing and the like. The information provided by the invention can be communicated to regulators, physicians and other healthcare providers, manufacturers, owners, investors, patients, and/or the general public. This information and the like can be used in exploratory research, pre-clinical and clinical settings, labeling, production, advertising, and sales, for example.

DEFINITIONS

As used herein an "ACAA1 biomarker" refers to an "ACAA1 nucleic acid" or an "ACAA1 protein" that can be specifically detected. An ACAA1 nucleic acid can be a RNA molecule, DNA molecule, or other nucleic acid that corresponds to the human ACAA1 gene or a fragment thereof. For example, an ACAA1 nucleic acid can be a cDNA, or fragment thereof, corresponding to an ACAA1 mRNA molecule. An ACAA1 protein refers to a protein (or fragment thereof) encoded or expressed by the ACAA1 gene. Examples of ACAA1 biomarkers are given in the examples as well as some reagents useful for detecting ACAA1 biomarkers, nucleic acids, and proteins.

As used herein an "AP1M2 biomarker" refers to an "AP1M2 nucleic acid" or an "AP1M2 protein" that can be specifically detected. An AP1M2 nucleic acid can be a RNA molecule, DNA molecule, or other nucleic acid that corresponds to the human AP1M2 gene or a fragment thereof. For example, an AP1M2 nucleic acid can be a cDNA, or fragment thereof, corresponding to an AP1M2 mRNA molecule. An AP1M2 protein refers to a protein (or fragment thereof) encoded or expressed by the AP1M2 gene. Examples of AP1M2 biomarkers are given in the examples as well as some reagents useful for detecting AP1M2 biomarkers, nucleic acids, and proteins.

As used herein a "CGN biomarker" refers to a "CGN nucleic acid" or a "CGN protein" that can be specifically detected. A CGN nucleic acid can be a RNA molecule, DNA molecule, or other nucleic acid that corresponds to the human CGN gene or a fragment thereof. For example, a CGN nucleic acid can be a cDNA, or fragment thereof, corresponding to a CGN mRNA molecule. A CGN protein refers to a protein (or fragment thereof) encoded or expressed by the CGN gene. Examples of CGN biomarkers are given in the examples as well as some reagents useful for detecting CGN biomarkers, nucleic acids, and proteins.

As used herein a "DDR1 biomarker" refers to a "DDR1 nucleic acid" or a "DDR1 protein" that can be specifically detected. A DDR1 nucleic acid can be a RNA molecule, DNA molecule, or other nucleic acid that corresponds to the human DDR1 gene or a fragment thereof. For example, a DDR1 nucleic acid can be a cDNA, or fragment thereof, corresponding to a DDR1 mRNA molecule. A DDR1 protein refers to a protein (or fragment thereof) encoded or expressed by the DDR1 gene. Examples of DDR1 biomarkers are given in the examples as well as some reagents useful for detecting DDR1 biomarkers, nucleic acids, and proteins.

As used herein an "EPS8L2 biomarker" refers to an "EPS8L2 nucleic acid" or an "EPS8L2 protein" that can be specifically detected. An EPS8L2 nucleic acid can be a RNA molecule, DNA molecule, or other nucleic acid that corresponds to the human EPS8L2 gene or a fragment thereof. For example, an EPS8L2 nucleic acid can be a cDNA, or fragment thereof, corresponding to an EPS8L2 mRNA molecule. An EPS8L2 protein refers to a protein (or fragment thereof) encoded or expressed by the EPS8L2 gene. Examples of EPS8L2 biomarkers are given in the examples as well as some reagents useful for detecting EPS8L2 biomarkers, nucleic acids, and proteins.

As used herein a "FASTKD1 biomarker" refers to a "FASTKD1 nucleic acid" or an "FASTKD1 protein" that can be specifically detected. A FASTKD1 nucleic acid can be a RNA molecule, DNA molecule, or other nucleic acid that corresponds to the human FASTKD1 gene or a fragment thereof. For example, a FASTKD1 nucleic acid can be a cDNA, or fragment thereof, corresponding to an FASTKD1 mRNA molecule. A FASTKD1 protein refers to a protein (or fragment thereof) encoded or expressed by the FASTKD1 gene. Examples of FASTKD1 biomarkers are given in the examples as well as some reagents useful for detecting FASTKD1 biomarkers, nucleic acids, and proteins.

As used herein a "GMIP biomarker" refers to an "GMIP nucleic acid" or an "GMIP protein" that can be specifically detected. An GMIP nucleic acid can be a RNA molecule, DNA molecule, or other nucleic acid that corresponds to the human GMIP gene or a fragment thereof. For example, a GMIP nucleic acid can be a cDNA, or fragment thereof, corresponding to a GMIP mRNA molecule. A GMIP protein refers to a protein (or fragment thereof) encoded or expressed by the GMIP gene. Examples of GMIP biomarkers are given in the examples as well as some reagents useful for detecting GMIP biomarkers, nucleic acids, and proteins.

As used herein an "IKBKE biomarker" refers to an "IKBKE nucleic acid" or an "IKBKE protein" that can be specifically detected. An IKBKE nucleic acid can be a RNA molecule, DNA molecule, or other nucleic acid that corresponds to the human IKBKE gene or a fragment thereof. For example, an IKBKE nucleic acid can be a cDNA, or fragment thereof, corresponding to an IKBKE mRNA molecule. An IKBKE protein refers to a protein (or fragment thereof) encoded or expressed by the IKBKE gene. Examples of IKBKE biomarkers are given in the examples as well as some reagents useful for detecting IKBKE biomarkers, nucleic acids, and proteins.

As used herein a "P2RX4 biomarker" refers to a "P2RX4 nucleic acid" or an "P2RX4 protein" that can be specifically detected. A P2RX4 nucleic acid can be a RNA molecule, DNA molecule, or other nucleic acid that corresponds to the human P2RX4 gene or a fragment thereof. For example, a P2RX4 nucleic acid can be a cDNA, or fragment thereof, corresponding to a P2RX4 mRNA molecule. A P2RX4 protein refers to a protein (or fragment thereof) encoded or expressed by the P2RX4 gene. Examples of P2RX4 biomarkers are given in the examples as well as some reagents useful for detecting P2RX4 biomarkers, nucleic acids, and proteins.

As used herein a "P4HB biomarker" refers to a "P4HB nucleic acid" or a "P4HB protein" that can be specifically detected. A P4HB nucleic acid can be a RNA molecule, DNA molecule, or other nucleic acid that corresponds to the human P4HB gene or a fragment thereof. For example, a P4HB nucleic acid can be a cDNA, or fragment thereof, corresponding to a P4HB mRNA molecule. A P4HB protein refers to a protein (or fragment thereof) encoded or expressed by the P4HB gene. Examples of P4HB biomarkers are given in the examples as well as some reagents useful for detecting P4HB biomarkers, nucleic acids, and proteins.

As used herein a "PHKG2 biomarker" refers to a "PHKG2 nucleic acid" or an "PHKG2 protein" that can be specifically detected. A PHKG2 nucleic acid can be a RNA molecule, DNA molecule, or other nucleic acid that corresponds to the human AP1M2 gene or a fragment thereof. For example, a PHKG2 nucleic acid can be a cDNA, or fragment thereof, corresponding to a PHKG2 mRNA molecule. A PHKG2 protein refers to a protein (or fragment thereof) encoded or expressed by the PHKG2 gene. Examples of PHKG2 biomarkers are given in the examples as well as some reagents useful for detecting PHKG2 biomarkers, nucleic acids, and proteins.

As used herein a "PPFIBP2 biomarker" refers to a "PPFIBP2 biomarker nucleic acid" or a "PPFIBP2 biomarker protein" that can be specifically detected. A PPFIBP2 biomarker nucleic acid can be a RNA molecule, DNA molecule, or other nucleic acid that corresponds to the human PPFIBP2 biomarker gene or a fragment thereof. For example, a PPFIBP2 biomarker nucleic acid can be a cDNA, or fragment thereof, corresponding to an PPFIBP2 biomarker mRNA molecule. A PPFIBP2 biomarker protein refers to a protein (or fragment thereof) encoded or expressed by the PPFIBP2 biomarker gene. Examples of PPFIBP2 biomarker biomarkers are given in the examples as well as some reagents useful for detecting PPFIBP2 biomarker biomarkers, nucleic acids, and proteins.

As used herein a "PPP1R16A biomarker" refers to a "PPP1R16A nucleic acid" or a "PPP1R16A protein" that can be specifically detected. A PPP1R16A nucleic acid can be a RNA molecule, DNA molecule, or other nucleic acid that corresponds to the human PPP1R16A gene or a fragment thereof. For example, a PPP1R16A nucleic acid can be a cDNA, or fragment thereof, corresponding to a PPP1R16A mRNA molecule. A PPP1R16A protein refers to a protein (or fragment thereof) encoded or expressed by the PPP1R16A gene. Examples of PPP1R16A biomarkers are given in the examples as well as some reagents useful for detecting PPP1R16A biomarkers, nucleic acids, and proteins.

As used herein a "TJP3 biomarker" refers to a "TJP3 nucleic acid" or a "TJP3 protein" that can be specifically detected. A TJP3 nucleic acid can be a RNA molecule, DNA molecule, or other nucleic acid that corresponds to the human TJP3 gene or a fragment thereof. For example, a TJP3 nucleic acid can be a cDNA, or fragment thereof, corresponding to a TJP3 mRNA molecule. A TJP3 protein refers to a protein (or fragment thereof) encoded or expressed by the TJP3 gene. Examples of TJP3 biomarkers are given in the examples as well as some reagents useful for detecting TJP3 biomarkers, nucleic acids, and proteins.

As used herein an "RASSF7 biomarker" refers to an "RASSF7 nucleic acid" or an "RASSF7 protein" that can be specifically detected. An RASSF7 nucleic acid can be a RNA molecule, DNA molecule, or other nucleic acid that corresponds to the human RASSF7 gene or a fragment thereof. For example, an RASSF7 nucleic acid can be a cDNA, or fragment thereof, corresponding to an RASSF7 mRNA molecule. An RASSF7 protein refers to a protein (or fragment thereof) encoded or expressed by the RASSF7 gene. Examples of RASSF7 biomarkers are given in the examples as well as some reagents useful for detecting RASSF7 biomarkers, nucleic acids, and proteins.

As used herein a "RNF183 biomarker" refers to a "RNF183 nucleic acid" or a "RNF183 protein" that can be specifically detected. A RNF183 nucleic acid can be a RNA molecule, DNA molecule, or other nucleic acid that corresponds to the human RNF183 gene or a fragment thereof. For example, a RNF183 nucleic acid can be a cDNA, or fragment thereof, corresponding to a RNF183 mRNA molecule. A RNF183 protein refers to a protein (or fragment thereof) encoded or expressed by the RNF183 gene. Examples of RNF183 biomarkers are given in the examples as well as some reagents useful for detecting RNF183 biomarkers, nucleic acids, and proteins.

As used herein a "SIRT6 biomarker" refers to a "SIRT6 nucleic acid" or a "SIRT6 protein" that can be specifically detected. A SIRT6 nucleic acid can be a RNA molecule, DNA molecule, or other nucleic acid that corresponds to the human SIRT6 gene or a fragment thereof. For example, a SIRT6 nucleic acid can be a cDNA, or fragment thereof, corresponding to a SIRT6 mRNA molecule. A SIRT6 protein refers to a protein (or fragment thereof) encoded or expressed by the SIRT6 gene. Examples of SIRT6 biomarkers are given in the examples as well as some reagents useful for detecting SIRT6 biomarkers, nucleic acids, and proteins.

As used herein a "DCN biomarker" refers to a "DCN nucleic acid" or a "DCN protein" that can be specifically detected. A DCN nucleic acid can be a RNA molecule, DNA molecule, or other nucleic acid that corresponds to the human DCN gene or a fragment thereof. For example, a DCN nucleic acid can be a cDNA, or fragment thereof, corresponding to a DCN mRNA molecule. A DCN protein refers to a protein (or fragment thereof) encoded or expressed by the DCN gene. Examples of LSR biomarkers are given in the examples as well as some reagents useful for detecting DCN biomarkers, nucleic acids, and proteins.

As used herein a "SOCS2 biomarker" refers to a "SOCS2 nucleic acid" or a "SOCS2 protein" that can be specifically detected. A SOCS2 nucleic acid can be a RNA molecule, DNA molecule, or other nucleic acid that corresponds to the human SOCS2 gene or a fragment thereof. For example, a SOCS2 nucleic acid can be a cDNA, or fragment thereof, corresponding to a SOCS2 mRNA molecule. A SOCS2 protein refers to a protein (or fragment thereof) encoded or expressed by the SOCS2 gene. Examples of SOCS2 biomarkers are given in the examples as well as some reagents useful for detecting SOCS2 biomarkers, nucleic acids, and proteins.

As used herein an "EFEMP2 biomarker" refers to an "EFEMP2 nucleic acid" or an "EFEMP2 protein" that can be specifically detected. An EFEMP2 nucleic acid can be a RNA molecule, DNA molecule, or other nucleic acid that corresponds to the human EFEMP2 gene or a fragment thereof. For example, an EFEMP2 nucleic acid can be a cDNA, or fragment thereof, corresponding to an EFEMP2 mRNA molecule. An EFEMP2 protein refers to a protein (or fragment thereof) encoded or expressed by the EFEMP2 gene. Examples of EFEMP2 biomarkers are given in the examples as well as some reagents useful for detecting EFEMP2 biomarkers, nucleic acids, and proteins.

As used herein, the term "sensitivity" refers to the proportion of reference test positive (diseased) subjects who test positive with the screening test.

As used herein, the term "specificity" refers to the proportion of reference test negative (healthy) subjects who test negative with the screening test.

As used herein, the term "secretory phase" refers to a phase of the menstrual cycle that is distinguishable from the other phases of the menstrual cycle using standard procedures in the art, e.g., pathological examination of tissue obtained from endometrium or uterus. Secretory phase is associated with bleeding (menstruation).

As used herein, the term "ROC" or "receiver operator characteristic" refers to a graphical plot of sensitivity vs. (1-specificity) or in other words a plot of true positive rate versus fraction of false positives. The area under the ROC, or AUROC, curve can range from 0 to 1. An area under the ROC curve of 1 is a perfect test or separation of groups while an area under the ROC of 0.5 indicates that the classifier is essentially unable to separate the groups and is therefore not useful.

A "cancer" in an animal refers to the presence of cells possessing characteristics typical of cancer-causing cells, for example, uncontrolled proliferation, loss of specialized functions, immortality, significant metastatic potential, significant increase in anti-apoptotic activity, rapid growth and proliferation rate, and certain characteristic morphology and cellular markers.

The phrase "detecting a cancer" or "diagnosing a cancer" refers to determining the presence or absence of cancer or a precancerous condition in an animal. "Detecting a cancer" also can refer to obtaining evidence regarding the likelihood of the presence of precancerous or cancerous cells in the animal or assessing the predisposition of a patient to the development of a cancer. Detecting a cancer can be accomplished using the methods of this invention alone, in combination with other methods, or in light of other information regarding the state of health of the animal.

A "tumor," as used herein, refers to all neoplastic cell growth and proliferation, whether malignant or benign, and all precancerous and cancerous cells and tissues.

The term "precancerous" refers to cells or tissues having characteristics relating to changes that may lead to malignancy or cancer.

In general, a "gene" is a region on the genome that is capable of being transcribed to an RNA that either has a regulatory function, a catalytic function, and/or encodes a protein. An eukaryotic gene typically has introns and exons, which may organize to produce different RNA splice variants that encode alternative versions of a mature protein. The skilled artisan will appreciate that the present invention encompasses all encoding transcripts that may be found, including splice variants, allelic variants and transcripts that occur because of alternative promoter sites or alternative poly-adenylation sites of the biomarkers as listed in Table 1. A "full-length" gene or RNA therefore encompasses any naturally occurring splice variants, allelic variants, other alternative transcripts, splice variants generated by recombinant technologies which bear the same function as the naturally occurring variants, and the resulting RNA molecules. A "fragment" of a gene, including an oncogene, can be any portion from the gene, which may or may not represent a functional domain, for example, a catalytic domain, a DNA binding domain, etc. A fragment may preferably include nucleotide sequences that encode for at least 25 contiguous amino acids, and preferably at least about 30, 40, 50, 60, 65, 70, 75 or more contiguous amino acids or any integer thereabout or therebetween. In some aspects of the invention, the skilled artisan recognizes that the term gene is used interchangeably with the term "locus", which refers more generically to a region of genomic DNA regardless if it codes for RNA, protein, or a regulatory element.

A "differentially expressed gene transcript", as used herein, refers to a gene, transcript that is found at a different level in different cell or tissue types of an organism having a tumor or cancer, compared to the level or state of the gene transcript found in the cells of the same tissue in a healthy organism, or in the cells of the same tissue in the same organism. Multiple copies of gene transcripts may be found in an organism having the tumor or cancer, while fewer copies of the same gene transcript are found in a healthy organism or healthy cells of the same tissue in the same organism, or vice-versa for underexpressed genes. In general, differentially expressed transcripts are those which when measured in an affected sample or sample from an affected patient have a detectably different level of expression as compared to a control value which is representative of a non-affected sample or sample from a non-affected patient. Examples of differential expression include a change of 10% or more, 20% or more 30% or more, 40% or more, or 50% or more in affected as compared to non-affected.

As used herein the term "polypeptide" means a sequence of amino acids joined together by peptide bonds. The amino acid sequence of the polypeptide can determined by the sequence of the DNA bases which encode the amino acids of the polypeptide chain. The polypeptides described herein include, but are not limited to, complete proteins, fragments of complete proteins, epitopes of proteins etc. As used herein the term polypeptide, peptide, and protein refer to molecule having two or more amino acid residues (natural or unnatural) joined together by one or more peptide bonds.

A "differentially expressed gene," can be a target, fingerprint, or pathway gene. For example, a "fingerprint gene", as used herein, refers to a differentially expressed gene whose expression pattern can be used as a prognostic or diagnostic marker for the evaluation of tumors and cancers, or which can be used to identify compounds useful for the treatment of tumors and cancers, for example, endometrial cancer. Fingerprint genes can be one or more genes (or corresponding biomarkers e.g., protein) corresponding to the biomarkers of Table 1.

A "fingerprint pattern", as used herein, refers to a pattern generated when the expression pattern of a series (which can range from two up to all the fingerprint genes that exist for a given state) of fingerprint genes is determined. A fingerprint pattern also may be referred to as n "profile". A fingerprint pattern or expression profile having from 1 to 20 of the biomarkers of Table 1 can be used in the same diagnostic, prognostic, and methods of the invention.

"Pathway genes", as used herein, are genes that encode proteins or polypeptides that interact with other gene products involved in tumors and cancers. Pathway genes also can exhibit target gene and/or fingerprint gene characteristics.

A "detectable" RNA expression level, as used herein, means a level that is detectable by standard techniques currently known in the art or those that become standard at some future time, and include for example, differential display, RT (reverse transcriptase)-coupled polymerase chain reaction (PCR), Northern Blot, and/or RNase protection analyses.

The nucleic acid molecules of the invention, for example, those corresponding to one or more biomarkers of Table 1, and its subsequences/alternative transcripts, can be inserted into a vector, as described below, which will facilitate expression of the insert. The nucleic acid molecules and the polypeptides they encode can be used directly as diagnostic agents, or can be used (directly in the case of the polypeptide or indirectly in the case of a nucleic acid molecule) to generate antibodies that, in turn, are clinically useful as a diagnostic agent. Accordingly, vectors containing the nucleic acids of the invention, cells transfected with these vectors, the polypeptides expressed, and antibodies generated against either the entire polypeptide or an antigenic fragment thereof, are among the aspects of the invention.

An "isolated DNA molecule" is a fragment of DNA that has been separated from the chromosomal or genomic DNA of an organism. Isolation also is defined to connote a degree of separation from original source or surroundings.

"Complementary DNA" (cDNA), often referred to as "copy DNA", is a single-stranded DNA molecule that is formed from an mRNA template by the enzyme reverse transcriptase. Those skilled in the art also use the term "cDNA" to refer to a double-stranded DNA molecule that comprises such a single-stranded DNA molecule and its complement DNA strand.

The term "expression" refers to the biosynthesis of a gene product.

A "cloning vector" is a nucleic acid molecule, for example, a plasmid, cosmid or bacteriophage that has the capability of replicating autonomously in a host cell. Cloning vectors typically contain (i) one or a small number of restriction endonuclease recognition sites at which foreign DNA sequences can be inserted in a determinable fashion without loss of an essential biological function of the vector, and (ii) a marker gene that is suitable for use in the identification and selection of cells transformed or transfected with the cloning vector. Marker genes include, but are not limited to, genes that provide tetracycline resistance or ampicillin resistance.

An "expression vector" is a nucleic acid construct, generated recombinantly or synthetically, bearing a series of specified nucleic acid elements that enable transcription of a particular gene in a host cell. Typically, gene expression is placed under the control of certain regulatory elements, including constitutive or inducible promoters, tissue-preferred regulatory elements, and enhancers.

A "recombinant host" may be any prokaryotic or eukaryotic cell that contains either a cloning vector or expression vector. This term also includes those prokaryotic or eukaryotic cells that have been genetically engineered to contain the cloned gene(s) in the chromosome or genome of the host cell.

The term "operably linked" is used to describe the connection between regulatory elements and a gene or its coding region. That is, gene expression is typically placed under the control of certain regulatory elements, including constitutive or inducible promoters, tissue-specific regulatory elements, and enhancers. Such a gene or coding region is said to be "operably linked to" or "operatively linked to" or "operably associated with" the regulatory elements, meaning that the gene or coding region is controlled or influenced by the regulatory element.

"Sequence homology" is used to describe the sequence relationships between two or more nucleic acids, polynucleotides, proteins, or polypeptides, and is understood in the context of and in conjunction with the terms including: (a) reference sequence, (b) comparison window, (c) sequence identity, (d) percentage of sequence identity, and (e) substantial identity or "homologous."

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence can be chosen from at least about 16 amino acids, at least about 20 amino acids, at least about 25 amino acids, and about 35 amino acids, about 50 amino acids, or about 100 amino acids. For nucleic acids, the length of the reference nucleic acid sequence can be chosen from at least about 50 nucleotides, at least about 60 nucleotides, at least about 75 nucleotides, and about 100 nucleotides or about 300 nucleotides or any integer thereabout or there between.

A "comparison window" includes reference to a contiguous and specified segment of a polynucleotide sequence, wherein the polynucleotide sequence may be compared to a reference sequence and wherein the portion of the polynucleotide sequence in the comparison window may comprise additions, substitutions, or deletions (i.e., gaps) compared to the reference sequence (which does not comprise additions, substitutions, or deletions) for optimal alignment of the two sequences. Generally, the comparison window is at least 20 contiguous nucleotides in length, and optionally can be 30, 40, 50, 100, or longer. Those of skill in the art understand that to avoid a misleadingly high similarity to a reference sequence due to inclusion of gaps in the polynucleotide sequence a gap penalty is typically introduced and is subtracted from the number of matches.

Methods of alignment of sequences for comparison are well-known in the art. Optimal alignment of sequences for comparison may be conducted by the local homology algorithm of Smith and Waterman (1981) *Adv. Appl. Math.*, 2: 482; by the homology alignment algorithm of Needleman and Wunsch (1970) *J. Mol. Biol.*, 48: 443; by the search for similarity method of Pearson and Lipman (1988) *Proc. Natl. Acad. Sci. USA*, 8: 2444; by computerized implementations of these algorithms, including, but not limited to: CLUSTAL in the PC/Gene program by Intelligenetics, Mountain View, Calif., GAP, BESTFIT, BLAST, FASTA, and TFASTA in the Wisconsin Genetics Software Package, Genetics Computer Group (GCG), 7 Science Dr., Madison, Wis., USA; the CLUSTAL program is well described by Higgins and Sharp (1988) *Gene* 73: 237-244; Corpet et al. (1988) *Nucleic Acids Research*, 16:881-90; Huang, et al., Computer Applications in the Biosciences, 8:1-6, 1992; and Pearson, et al. (1994) Methods in Molecular Biology, 24:7-331. The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, Current Protocols in Molecular Biology, Chapter 19, Ausubel, et al., Eds., Greene Publishing and Wiley-Interscience, New York, 1995. New versions of the above programs or new programs altogether will undoubtedly become available in the future, and can be used with the present invention.

Unless otherwise stated, sequence identity/similarity values provided herein refer to the value obtained using the BLAST 2.0 suite of programs, or their successors, using default parameters. Altschul et al. (1997) *Nucleic Acids Res,* 2:3389-3402. It is to be understood that default settings of these parameters can be readily changed as needed in the future.

As those ordinary skilled in the art will understand, BLAST searches assume that proteins can be modeled as random sequences. However, many real proteins comprise regions of nonrandom sequences which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, (1993) *Comput. Chem.* 17:149-163) and XNU (Clayerie and States (1993) *Comput. Chem.,* 17:191-1) low-complexity filters can be employed alone or in combination.

"Sequence identity" or "identity" in the context of two nucleic acid or polypeptide sequences includes reference to the residues in the two sequences which are the same when aligned for maximum correspondence over a specified comparison window, and can take into consideration additions, deletions and substitutions. When percentage of sequence identity is used in reference to proteins it is recognized that residue positions which are not identical often differ by conservative amino acid substitutions, where amino acid residues are substituted for other amino acid residues with similar chemical properties (for example, charge or hydrophobicity) and therefore do not deleteriously change the functional properties of the molecule. Where sequences differ in conservative substitutions, the percent sequence identity may be adjusted upwards to correct for the conservative nature of the substitution. Sequences which differ by such conservative substitutions are said to have sequence similarity. Approaches for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, for example, according to the algorithm of Meyers and Miller (1988) *Computer Applic. Biol. Sci.,* 4: 11-17 for example, as implemented in the program PC/GENE (Intelligenetics, Mountain View, Calif., USA).

"Percentage of sequence identity" means the value determined by comparing two optimally aligned sequences over a comparison window, wherein the portion of the polynucleotide sequence in the comparison window may comprise additions, substitutions, or deletions (i.e., gaps) as compared to the reference sequence (which does not comprise additions, substitutions, or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" or "homologous" in their various grammatical forms in the context of polynucleotides means that a polynucleotide comprises a sequence that has a desired identity, for example, at least 60% identity, preferably at least 70% sequence identity, more preferably at least 80%, still more preferably at least 90% and even more preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes n normally means sequence identity of at least 60%, more preferably at least 70%, 80%, 90%, and even more preferably at least 95%.

Another indication that nucleotide sequences are substantially identical is if two molecules hybridize to each other under stringent conditions. However, nucleic acids which do not hybridize to each other under stringent conditions are still substantially identical if the polypeptides which they encode are substantially identical. This may occur, for example, when a copy of a nucleic acid is created using the maximum codon degeneracy permitted by the genetic code. One indication that two nucleic acid sequences are substantially identical is that the polypeptide which the first nucleic acid encodes is immunologically cross reactive with the polypeptide encoded by the second nucleic acid, although such cross-reactivity is not required for two polypeptides to be deemed substantially identical.

The term "substantial identity" or "homologous" in their various grammatical forms in the context of peptides indicates that a peptide comprises a sequence that has a desired identity, for example, at least 60% identity, preferably at least 70% sequence identity to a reference sequence, more preferably 80%, still more preferably 85%, even more preferably at least 90% or 95% sequence identity to the reference sequence over a specified comparison window. Preferably, optimal alignment is conducted using the homology alignment algorithm of Needleman and Wunsch (1970) *J. Mol. Biol.*, 48:443. An indication that two peptide sequences are substantially identical is that one peptide is immunologically reactive with antibodies raised against the second peptide, although such cross-reactivity is not required for two polypeptides to be deemed substantially identical. Thus, a peptide is substantially identical to a second peptide, for example, where the two peptides differ only by a conservative substitution. Peptides which are "substantially similar" share sequences as noted above except that residue positions which are not identical may differ by conservative amino acid changes. Conservative substitutions typically include, but are not limited to, substitutions within the following groups: glycine and alanine; valine, isoleucine, and leucine; aspartic acid and glutamic acid; asparagine and glutamine; serine and threonine; lysine and arginine; and phenylalanine and tyrosine, and others as known to the skilled person.

"Biological subject" as used herein refers to a target biological object obtained, reached, or collected in vivo, ex-vivo, or in situ, that contains or is suspected of containing nucleic acids or polypeptides corresponding to a biomarker of Table 1.

"Biological sample" as used herein refers to a sample obtained from a biological subject, including sample of biological tissue or fluid origin, obtained, reached, or collected in vivo, ex-vivo, or in situ, that contains or is suspected of containing nucleic acids or polypeptides corresponding to a biomarker of Table 1. A biological sample also includes samples from a region of a biological subject containing precancerous or cancer cells or tissues. Such samples can be, but are not limited to, organs, tissues, fractions and cells isolated from mammals including, humans such as a patient. Biological samples also may include sections of the biological sample including tissues, for example, frozen sections taken for histologic purposes. A biological sample, as described herein, can be: a "control" or a "control sample" or a "test sample". A biological sample can be obtained from the uterus using commonly employed clinical practices (e.g., aspiration, brush, curettage, or hysteroscopy).

A "control" or "control value" refers to a representative of healthy, endometrial cancer-free biological subject or information obtained from a different individual or a normalized value, which can be based on baseline data obtained from a population or other acceptable sources. A control also can refer to a given level of a biomarker of Table 1, representative of the endometrial cancer-free population, that has been previously established based on measurements from normal, endometrial cancer-free individuals. A control also can be a reference data point in a database based on data obtained from control samples representative of a cancer-free population. Further, a control can be established by a specific age, sex, ethnicity or other demographic parameters. In some contexts, the control is implicit in the particular measurement. A control value or control can also refer to a "control score". Control scores can be values obtained from the determination of the expression level of one or more biomarkers of the invention. For example, different programs and algorithms are commercially available for generating formulas that yield a score value based on the measurement of the levels of one or more biomarkers, that can indicate whether an individual is likely to have a condition or not. In another example, a score over or below a certain threshold that may indicate an increased (or decreased) likelihood of having the disease. A control score value can be based on a single marker or a combination of markers.

A "control sample" refers to a sample of biological material representative of healthy, cancer-free animals or a normal biological subject obtained from a cancer-free population. The level of a biomarker of Table 1, in a control sample is desirably typical of the general population of normal, cancer-free animals of the same species. This sample either can be collected from an animal for the purpose of being used in the methods described in the present invention or it can be any biological material representative of normal, cancer-free animals suitable for use in the methods of this invention. A control sample also can be obtained from normal tissue from the animal that has cancer or is suspected of having cancer.

A "test sample" as used herein refers to a biological sample, including sample of biological tissue or fluid origin, obtained, reached, or collected in vivo, ex-vivo, or in situ, that contains or is suspected of containing nucleic acids or polypeptides corresponding to a biomarker of Table 1. A test sample also includes biological samples containing precancerous or cancer cells or tissues. A test sample also may include sections of the biological sample including tissues, for example, frozen sections taken for histologic purposes.

"Providing a biological subject, a biological sample, or a test sample" means to obtain a biological subject in vivo, ex-vivo, or in situ, including tissue or cell sample for use in the methods described in the present invention. Most often, this will be done by removing a sample of cells from an animal, but also can be accomplished in vivo, ex-vivo, or in situ, or by using previously isolated cells (for example, isolated from another person, at another time, and/or for another purpose). The sample can also be obtained from sources such as blood, serum, and uterine fluid.

"Data" includes, but is not limited to, information obtained that relates to "biological sample", "test sample", "control sample", and/or "control", as described above, wherein the information is applied in generating a test level for diagnostics, prevention, monitoring or therapeutic use. The present invention relates to methods for comparing and compiling data wherein the data is stored in electronic or paper formats. Electronic format can be selected from the group consisting of electronic mail, disk, compact disk (CD), digital versatile disk (DVD), memory card, memory chip, ROM or RAM, magnetic optical disk; tape, video, video clip, microfilm, internet, shared network, shared server and the like; wherein data is displayed, transmitted or analyzed via electronic transmission, video display, telecommunication, or by using any of the above stored formats; wherein data is compared and compiled at the site of sampling specimens or at a location where the data is transported following a process as: described above.

"Overexpression" of a gene or an "increased," or "elevated," level of a ribonucleotide or protein refers to a level of the gene, ribonucleotide or polypeptide that, in comparison with a control level/value of gene, ribonucleotides or polypeptide, is detectably higher. Comparison may be carried out by statistical analyses on numeric measurements of the expression; or, it may be done through visual examination of experimental results by qualified researchers. Examples of overexpression include a change of 10% or more, 20% or more 30% or more, 40% or more, or 50% or more in affected as compared to non-affected.

"Underexpression" of a gene or a "decreased," or "lower," level of a ribonucleotide or protein refers to a level of the gene, ribonucleotide or polypeptide that, in comparison with a control level of gene, ribonucleotides or polypeptide, is detectably lower. Comparison may be carried out by statistical analyses on numeric measurements of the expression; or, it may be done through visual examination of experimental results by qualified researchers. Examples of underexpression include a change of 10% or more, 20% or more 30% or more, 40% or more, or 50% or more in affected as compared to non-affected.

A level of ribonucleotide or polypeptide, that is "expected" in a control sample refers to a level that represents a typical, cancer-free sample, and from which an elevated, or diagnostic, presence of the polypeptide or polynucleotide, can be distinguished. Preferably, an "expected" level will be controlled for such factors as the age, sex, medical history, etc. of the mammal, as well as for the particular biological subject being tested.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified. Various levels of purity may be applied as needed according to this invention in the different methodologies set forth herein; the customary purity standards known in the art may be used if no standard is otherwise specified.

An "isolated nucleic acid molecule" can refer to a nucleic acid molecule, depending upon the circumstance, that is separated from the 5' and 3' coding sequences of genes or gene fragments contiguous in the naturally occurring genome of an organism. The term "isolated nucleic acid molecule" also includes nucleic acid molecules which are not naturally occurring, for example, nucleic acid molecules created-by recombinant DNA techniques.

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral methyl phosphonates, 2-O-methyl ribonucleotides, and peptide-nucleic acids (PNAs).

Unless otherwise indicated, a particular nucleic acid sequence also implicitly encompasses conservatively, modified variants thereof (for example, degenerate codon substitutions) and complementary sequences, as well as the sequence explicitly indicated. Specifically, degenerate codon substitutions may be achieved by generating sequences in which the third position of one or more selected (or all) codons is substituted with suitable mixed base and/or deoxyinosine residues (Batzer et al. (1991) *Nucleic Acid Res,* 19:081; Ohtsuka et al. (1985) *J. Biol. Chem.,* 260:2600-2608; Rossolini et al. (1994) *Mol. Cell Probes,* 8:91-98). The term nucleic acid can be used interchangeably with gene, cDNA, mRNA, oligonucleotide, and polynucleotide.

A "label" or a "detectable moiety" is a composition that when linked with the nucleic acid or protein molecule of interest renders the latter detectable, via spectroscopic, photochemical, biochemical, immunochemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens. A "labeled nucleic acid or oligonucleotide probe" is one that is bound, either covalently, through a linker or a chemical bond, or noncovalently, through ionic bonds, van der Waals forces, electrostatic attractions, hydrophobic interactions, or hydrogen bonds, to a label such that the presence of the nucleic acid or probe may be detected by detecting the presence of the label bound to the nucleic acid or probe.

As used herein a "nucleic acid or oligonucleotide probe" is defined as a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (7-deazaguanosine, inosine, etc.). In addition, the bases in a probe may be joined by a linkage other than a phosphodiester bond, so long as it does not unduly interfere with hybridization. It will be understood by one of skill in the art that probes may bind target sequences lacking complete complementarity with the probe sequence depending upon the stringency of the hybridization conditions. The probes are preferably directly labeled with isotopes, for example, chromophores, lumiphores, chromogens, or indirectly labeled with biotin to which a streptavidin complex may later bind. By assaying for the presence or absence of the probe, one can detect the presence or absence of a target gene of interest.

The phrase "selectively (or specifically) hybridizes to" refers to the binding, duplexing, or hybridizing of a molecule only to a particular nucleotide sequence under stringent hybridization conditions when that sequence is present in a complex mixture (for example, total cellular or library DNA or RNA).

The phrase "stringent hybridization conditions" refers to conditions under which a probe will hybridize to its target complementary sequence, typically in a complex mixture of nucleic acids, but to no other sequences. Stringent conditions are sequence-dependent and circumstance-dependent; for example, longer sequences can hybridize with specificity at higher temperatures. An extensive guide to the hybridization of nucleic acids is found in Tijssen (1993) Techniques in Biochemistry and Molecular Biology-Hybridization with Nucleic Probes, "Overview of principles of hybridization and the strategy of nucleic acid assays". In the context of the present invention, as used herein, the term "hybridizes under stringent conditions" is intended to describe conditions for hybridization and washing under which nucleotide sequences at least 60% homologous to each other typically remain hybridized to each other. Preferably, the conditions are such that sequences at least about 65%, more preferably at least about 70%, and even more preferably at least about 75% or more homologous to each other typically remain hybridized to each other.

Generally, stringent conditions are selected to be about 5 to 10 C lower than the thermal melting point (Tm) for the specific sequence at a defined ionic strength pH. The Tm is the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30 C for short probes (for example, 10 to 50 nucleotides) and at least about 60 C for long probes (for example, greater than 50 nucleotides). Stringent conditions also may be achieved with the addition of destabilizing agents, for example, formamide. For selective or specific hybridization, a positive signal is at least two times background, preferably 10 times background hybridization.

Exemplary stringent hybridization conditions can be as following, for example: 50% formamide, 5×SSC and 1% SDS, incubating at 42 C, or 5×SSC and 1% SDS, incubating at 65 C., with wash in 0.2×SSC and 0.1% SDS at 65 C. Alternative conditions include, for example, conditions at least as stringent as hybridization at 68 C for 20 hours, followed by washing in 2×SSC, 0.1% SDS, twice for 30 minutes at 55 C and three times for 15 minutes at 60 C. Another alternative set of conditions is hybridization in 6×SSC at about 45 C, followed by one or more washes in 0.2×SSC, 0.1% SDS at 50-65 C. For PCR, a temperature of about 36 C is typical for low stringency amplification, although annealing temperatures may vary between about 32 C and 48 C depending on primer length. For high stringency PCR amplification, a temperature of about 62 C is typical, although high stringency annealing temperatures can range from about 50 C to about 65 C, depending on the primer length and specificity. Typical cycle conditions for both high and low stringency amplifications include a denaturation phase of 90 C to 95 C for 30 sec. to 2 min., an annealing phase lasting 30 sec. to 2 min., and an extension phase of about 72 C for 1 to 2 min.

Nucleic acids that do not hybridize to each other under stringent conditions can still be substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37 C, and a wash in 1×SSC at 45 C. A positive hybridization is at least twice background. Those of ordinary skill will readily recognize that alternative hybridization and wash conditions can be utilized to provide conditions of similar stringency.

The term "target gene" or "target biomarker" or "target nucleic acid" or "target protein" can refer to a target nucleic acid (DNA and RNA) or protein (or polypeptide), (e.g., corresponding to the biomarkers in Table 1) and can include their polymorphic variants, alleles, mutants, and interspecies homologs that have (i) substantial nucleotide sequence homology (for example, at least 60% identity, preferably at least 70% sequence identity, more preferably at least 80%, still more preferably at least 90% and even more preferably at least 95%) with the nucleotide sequence indicated in ENSEMBL™ database for the indicated ID number; or (ii) at least 65% sequence homology with the amino acid sequence as indicated in the ENSEMBL™ record; or (iii) substantial nucleotide sequence homology (for example, at least 60% identity, preferably at least 70% sequence identity, more preferably at least 80%, still more preferably at least 90% and even more preferably at least 95%) with the nucleotide sequence as set forth in the ENSEMBL™ record with substantial sequence homology with the encoded amino acid sequence. As used in herein, and unless otherwise specified, these terms refer the entire gene sequence, mRNA sequence, and/or protein sequence as well as fragments of these sequences. In a more specific definition, these terms refer to the minimal amount of nucleic acid or amino acid sequence that can be used to identify biomarker in a specific manner. The skilled artisan recognizes that the target genes/biomarker can have numerous splice forms and variants. When referring to a specific target gene or locus by a reference number (e.g., ENTREZ™ gene ID or ENSEMBL™), all splices forms and variant which are included in the various embodiments of the invention. The target gene/biomarker can also comprise a regulatory element. These sequences are representative of one particular individual in the population of humans. Humans vary from one to another in their gene sequences. These variations are very minimal, sometimes occurring at a frequency of about 1 to 10 nucleotides per gene. Different forms of any particular gene exist within the human population. These different forms are called allelic variants. Allelic variants often do not change the amino acid sequence of the encoded protein; such variants are termed synonymous. Even if they do change the encoded amino acid (non-synonymous), the function of the protein is not typically affected. Such changes are evolutionarily or functionally neutral. When a gene ID (e.g., GENBANK™ or ENSEMBL™) is referred to in the present application all allelic variants are intended to be encompassed by the term. The gene ID sequences given for a biomarker are provided merely as representative examples of a wild-type human sequence. The invention is not limited to a single allelic form of the amplified genes or regions (and proteins they encode).

EXAMPLES

The following examples are included to demonstrate preferred embodiments of the invention. It should be appreciated by those of skill in the art that the techniques disclosed in the examples which follow represent techniques used by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Identification of Endometrial Cancer Biomarkers

In order to identify biomarkers for predicting and/or diagnosing endometrial cancer, gene expression levels from fifty-six endometrial primary tumors in several differentiation stages were compared with 10 normal (i.e., not having endometrial cancer) endometrial tissues by DNA microarray technique. This technique allows us to check the expression of the whole genome in a particular type of cell, tissue, organ, or in this case, check the differential gene expression between endometrial cancer and healthy endometrial tissue. A microarray chip contains small DNA sequences arranged in a regular pattern with specific addresses for probes for typically thousands of genes.

The amount of specific mRNAs in a sample can be estimated by it hybridization signal on the array.

Sample Description

Tumor samples were obtained from patients who underwent surgery and control tissue was obtained from non affected regions of endometrial tissue from the same patients. During preparation of the specimens, care was taken to macroscopically dissect the cancer away from any adjacent myometrium.

Ten control samples (nine of them were paired with their corresponding tumor samples and the tenth was an atrophic endometrium) were used and the basic characteristics of the other test samples are summarized in Table 3 below.

TABLE 3

Affected Samples used in Microarray studies

| Samples | Sample Diagnosis | Tumor Grade | FIGO stage |
|---|---|---|---|
| 1 | Endometroid carcinoma | G1 | Ia |
| 2 | Endometroid carcinoma | G1 | Ib |
| 3 | Endometroid carcinoma | G1 | Ib |
| 4 | Endometroid carcinoma | G1 | Ib |
| 5 | Endometroid carcinoma | G1 | Ia |
| 6 | Endometroid carcinoma | G1 | Ia |
| 7 | Endometroid carcinoma | G1 | Ia |
| 8 | Endometroid carcinoma | G2 | Ib |
| 9 | Endometroid carcinoma | G2 | IIb |
| 10 | Endometroid carcinoma | G2 | IIIa |
| 11 | Endometroid carcinoma | G2 | Ib |
| 12 | Endometroid carcinoma | G2 | Ic |
| 13 | Endometroid carcinoma | G2 | Ia |

TABLE 3-continued

Affected Samples used in Microarray studies

| Samples | Sample Diagnosis | Tumor Grade | FIGO stage |
|---|---|---|---|
| 14 | Endometroid carcinoma | G2 | Ic |
| 15 | Endometroid carcinoma | G2 | Ic |
| 16 | Endometroid carcinoma | G2 | Ib |
| 17 | Endometroid carcinoma | G2 | IIb |
| 18 | Endometroid carcinoma | G2 | IIb |
| 19 | Endometroid carcinoma | G2 | Ib |
| 20 | Endometroid carcinoma | G2 | Ic |
| 21 | Endometroid carcinoma | G2 | IVb |
| 22 | Endometroid carcinoma | G2 | IIb |
| 23 | Endometroid carcinoma | G2 | Ic |
| 24 | Endometroid carcinoma | G2 | IIb |
| 25 | Endometroid carcinoma | G2 | Ib |
| 26 | Endometroid carcinoma | G2 | Ic |
| 27 | Endometroid carcinoma | G2 | Ib |
| 28 | Endometroid carcinoma | G2 | Ib |
| 29 | Endometroid carcinoma | G2 | IIb |
| 30 | Endometroid carcinoma | G2 | Ib |
| 31 | Endometroid carcinoma | G3 | Ic |
| 32 | Endometroid carcinoma | G3 | IIIa |
| 33 | Endometroid carcinoma | G3 | IIb |
| 34 | Endometroid carcinoma | G3 | IIb |
| 35 | Endometroid carcinoma | G3 | Ib |
| 36 | Endometroid carcinoma | G3 | IIa |
| 37 | Endometroid carcinoma | G3 | IIa |
| 38 | Endometroid carcinoma | G3 | Ic |
| 40 | ATIPIC HIPERPLASIA | | |
| 41 | ATIPIC HIPERPLASIA | | |
| 42 | ATIPIC HIPERPLASIA | | |
| 43 | Serous carcinoma | G3 | IIIc |
| 44 | Serous carcinoma | G3 | IIIc |
| 45 | Serous carcinoma | G3 | Ib |
| 46 | Serous carcinoma | G3 | Ib |
| 47 | Serous carcinoma | G3 | IIIa |
| 48 | Clara cell type | G3 | IIIc |
| 49 | Undifferenciated | G3 | IIb |
| 50 | Undifferenciated | G3 | IIIa |
| 51 | Villoglandular | G3 | Ib |
| 52 | Villoglandular | G2 | Ib |
| 53 | Adeno-squamous | G2 | Ib |
| 54 | Adeno-squamous | G2 | IIb |
| 55 | Adeno-squamous | G3 | Ic |
| 56 | Mucinous type | G3 | IIIa |

Total RNA was extracted with the RNEASY™ mini kit (Qiagen, Hilden, Germany), following the instructions provided by the manufacturer. Quantity and quality of the obtained RNA was measured with a NANODROP™ (Nandrop ND-1000, Agilent 2100 Bioanalyzer) and low quality RNA was discarded from the array hybridization process.

Microarray Design

Microarrays for Gene Expression were designed by the Tethys algorithm using the ENSEMBL™ database. For sequences where we did not find high quality probes, we complemented the design with Oryzon Optimized Agilent probes. DNA microarray synthesis was outsourced to Agilent.

The Whole Genome Gene Expression Array contains:
20148 Oryzon High Quality probes from ENSEMBL™ Database.
5698 Oryzon Tm optimized Agilent probes.
The total number of probes was 25846.

aRNA Labeling

Cy3 and Cy5 labeled aRNA was produced using the MESSAGEAMPLIFICATION™ kit by Ambion (Ref: 1819 for 96x kit or Ref: 1751 for 20x kit). These kits are used with some modifications introduced by Oryzon genomics. RNA labeling was performed essentially using the Eberwine protocol (Van Gelder, 1992) commercialized by Ambion with the MESSAGEAMPLIFICATION™ Kit (Ambion/Applied Biosystems) with minor modifications. 500 ng of total RNA was reverse transcribed in presence of oligo(dT)$_{24}$, second-strand synthesis was generated and transcription of this dsDNA was prepared using CTP_Cy3 or CTP_Cy5 (PERKINELMER™). Amplified cRNA was quantified by Nanodrop ND-1000 and cRNA quality was controlled with the Agilent RNA Bionalyzer 2100.

Microarray Hybridization

Microarray hybridization was performed at 60° C. and 17 hours hybridization time according to Agilent indications, using Agilent gaskets (G2534-60002), Agilent hybridization chambers (G2534A) and in an Agilent DNA Hybridization Oven (G2545A). Oryzon hybridization controls are also used in hybridization process. Controls for the hybridization process corresponding to 3 cDNA clones of maize (Xet, Zm42, Exp) were included in all analysis. Exp is used as the negative spike control and was not amplified nor labeled. For Xet and Zm42 PCR fragments were generated by PCR amplification from the vector with universal primers and cRNA was generated using in vitro transcription systems (T7 or T3 MEGASCRIPT™ kit; Ambion) with CTP_Cy3 or CTP_Cy5 (PERKINELMER™). Both of the positive spike controls Xet and Zm42 were with both the Cy5 and Cy3 fluorofor.

Data Acquisition

Initial Raw Data were obtained using an Agilent DNA Microarray Scanner (G2505B) and Agilent acquisition software (Feature Extraction Software). The extraction protocol performed does not use background subtraction, computation of dye biases and ratio correction.

Data Analysis

A large number of controls were included in the microarray designs to monitor scanner and array performance and to control spatial homogeneity and correct deviations. This way, the overall error on the microarray data measurements can be estimated by the spreading analysis of the data from the controls.

The mean fold change or M values can be ranked based on their probability of being different from 0, according to the absolute value of the regularized t-statistic (Baldi and Long, 2001) which uses a Bayesian framework to derive a modified and improved t-student statistics. To make Fold Change based selection, the mean M distribution was used. This distribution is adjusted to a normal distribution and an iterative process is used to define the mean M numbers that are outside the distribution. The cut-off is chosen as n times the Standard deviations ($\sigma$) from the mean. This method generates a robust mean and standard deviation and allows to dynamically adjusting the cut-off value to the noise distribution of the data. Typically, values with mean FC>3$\sigma$ or mean FC<−3$\sigma$ of the sample data distribution were selected.

An indirect analysis comparison where the expression levels of particular biomarkers in tumor samples were compared to a reference RNA pool obtained from a group of over 20 cell lines (melanoma, lung cancer, ovarian cancer, colon cancer, and several non-cancer cell lines). The expression level of particular genes in the normal samples (controls) were compared to the same reference pool and final expression fold changes between tumor and normal endometrial tissue were generated in silico eliminating the reference pool.

Candidate genes were selected as biomarkers for endometrial cancer based on fold overexpression, p-value, and other factors. Table 1 in the Detailed Description of the Invention shows 17 overexpressed, genes and 3 genes underexpressed identified using these procedures. The overexpression of these genes was validated by RT-PCR as described in the next examples.

The results from the microarray studies are summarized in Table 1 in the Detailed Description of the Invention, which shows the common abbreviation used for the gene, the ENSEMBL™ gene, transcript and protein accession numbers along with the fold overexpression and calculated p-values.

Example 2

Uterine Fluid Sample Preparation

Endometrial aspirates were collected with the help of a Cornier CORNIER™ pipelle, after complete informed consent was obtained from all patients. The aspirate (uterine fluid) was immediately transferred to an EPPENDORF™ tube containing 500 microliters of a RNA preserving solution (RNALATER™, Ambion). The sample was centrifuged and the pellet containing a representative population of cells from the uterine cavity was further processed for RNA extraction (Qiagen). Quality tests (Bioanalyzer) were performed before the analysis of gene expression by TAQMAN™ technology for the selected markers of endometrial carcinoma.

Example 3

Correlation of Biomarkers in Primary Tumor and in Uterine Fluid

The levels of biomarkers from primary tumor sample and uterine fluid sample obtained by the procedure of Example 2 were compared as by RT-PCR following the general RT-PCR protocol as described in Example 4. The biomarkers in this study included ACAA1, AP1M2, CGN, DDR1, EPS8L2, FASTKD1, GMIP, IKBKE, P2RX4, P4HB, PHKG2, PPFIBP2, PPP1R16A, RASSF7, RNF183, SIRT6, TJP3, EFEMP2, SOCS2, and DCN whose expression level was found to be surprisingly correlated between the primary tumor and endometrial aspirates (uterine fluid). See FIG. 1. As can be seen in FIG. 1, the expression level of a number of biomarkers of endometrial cancer are correlated in uterine fluid and primary tumor. In particular, it was found that there was a high level of correlation of expression of biomarkers corresponding to ACAA1, AP1M2, CGN, DDR1, EPS8L2, FASTKD1, GMIP, IKBKE, P2RX4, P4HB, PHKG2, PPFIBP2, PPP1R16A, RASSF7, RNF183, SIRT6, TJP3, EFEMP2, SOCS2, and DCN in tumor sample and in samples obtained from uterine fluid. Thus, the inventors have surprisingly finding of a group of genes that can be used to diagnosis or predict an increased likelihood of endometrial cancer based on their expression levels in samples obtained from uterine fluid. Furthermore, the inventors have shown that uterine fluid can be used to assess biomarkers for endometrial cancer. For example, prognostic biomarkers for endometrial cancer, biomarkers for staging endometrial cancer, biomarkers for determining the type of endometrial cancer (e.g., Type 1 vs. Type II) or type (endometrioid, clear cell, serrous, etc.), auxiliary diagnostic biomarkers, differential diagnosis biomarkers, can be assayed in uterine fluid to characterize the cancer.

Example 4

Confirmation of Overexpression of Biomarkers by Quantitative RT-PCR

Once array data were obtained, a group of upregulated and downregulated genes in tumor samples compared with normal tissue were selected in-part based on their p-values and standard deviations. These candidates were selected to determine their expression levels by an independent technique using a different set of tumor samples.

Microfluidic Cards (MFC) from Applied Biosystems were used to perform RT-PCR with RNA isolated from tumor and normal endometrial tissue samples. In this case both types of tissues, healthy and carcinogenic were obtained from the same patient by microdissection procedures. These studies confirmed the microarray results for most of the markers of Table 1. Another set of RT-PCR studies were performed using aspirates obtained from endometrial cancer patients (confirmed) and aspirates from non-affected individuals. These studies using aspirates samples are described in more detail below.

Aspirate samples were obtained following a procedure similar to that described in Example 2. The description of patient characteristics for the affected and non-affected samples are given in Table 4 and Table 5 below.

Briefly, wells of the Microfluidic Card contain Applied Biosystems fluorogenic 5' nuclease assays that detect the real-time amplification of the array selected targets. Relative levels of gene expression are determined from the fluorescence data generated during PCR using the ABI PRISM® 7900HT Sequence Detection System (7900HT SDS) Relative Quantification software.

Data analysis was made using the comparative ΔΔCt method of relative quantification. Differentially expressed genes were confirmed by thorough statistical analysis using a modified T-test.

The samples used for the study described in this Example included:

Samples from 30 patients having endometrial cancer: 25 endometroid adenocarcinomas with 9 in G3, 9 in G2 and 7 in G1. And 5 tumor samples from different type II carcinomas (4 in G3 and 1 in G2)

Samples from 24 patients not having endometrial cancer ("controls" or "normals"). These were a heterogeneous mix of samples some of them from patients with other non-tumoral pathologies liked polyps: 4 samples from patients with atrophic endometriod, 4 normal samples, two from patients having polyps from post-menopausical women and 11 samples from pre-menopausical women (7 of them in secretory phase and 4 in proliferative phase of the cycle). See Tables below for a summary of samples.

TABLE 4

Affected Samples for RT-PCR Studies

| Aspirates from women with a tumor | Sample Diagnosis | Tumor Grade | FIGO stage |
|---|---|---|---|
| 1 | Endometroid carcinoma | G1 | IIb |
| 2 | Endometroid carcinoma | G1 | Ia |
| 3 | Endometroid carcinoma | G1 | Ib |
| 4 | Endometroid carcinoma | G1 | Ib |
| 5 | Endometroid carcinoma | G1 | Ia |
| 6 | Endometroid carcinoma | G1 | Ia |
| 7 | Endometroid carcinoma | G1 | Ib |
| 8 | Endometroid carcinoma | G2 | IIb |
| 9 | Endometroid carcinoma | G2 | Ib |
| 10 | Endometroid carcinoma | G2 | Ib |
| 11 | Endometroid carcinoma | G2 | Ib |
| 12 | Endometroid carcinoma | G2 | Ib |
| 13 | Endometroid carcinoma | G2 | Ia |
| 14 | Endometroid carcinoma | G2 | Ia |
| 15 | Endometroid carcinoma | G2 | Ib |
| 16 | Endometroid carcinoma | G2 | Ib |
| 17 | Endometroid carcinoma | G3 | IIb |

TABLE 4-continued

Affected Samples for RT-PCR Studies

| Aspirates from women with a tumor | Sample Diagnosis | Tumor Grade | FIGO stage |
|---|---|---|---|
| 18 | Endometroid carcinoma | G3 | Ic |
| 19 | Endometroid carcinoma | G3 | Ic |
| 20 | Endometroid carcinoma | G3 | Ib |
| 21 | Endometroid carcinoma | G3 | Ic |
| 22 | Endometroid carcinoma | G3 | Ib |
| 23 | Endometroid carcinoma | G3 | Ib |
| 24 | Endometroid carcinoma | G3 | Ib |
| 25 | Endometroid carcinoma | G3 | Ic |
| 26 | Clara Cell type | G3 | IIb |
| 27 | Clara Cell type | G3 | IIIc |
| 28 | Adeno-squamous | G3 | IIIa |
| 29 | Undifferenciated | G3 | IIIc |
| 30 | squamo-transitional | G2 | Ib |

TABLE 5

Non-Affected Samples for RT-PCR Studies
Control aspirates 7 pre-menopausic in secretory phase
6 pre-menopausic in proliferative phase
11 aspirates from postmenopausical women Experimental Procedures RNA samples were isolated from aspirate samples following the procedure above described and a quality control was performed previously to final sample selection. Aspirate samples were collected as described in Example 2.

RT-PCR was performed following Applied Biosystem standard protocol for the 7900HT system. The protocol consisted in a two-step method where the first step is the generation of cDNA from the RNA samples using a High Capacity cDNA Kit and the second step is the amplification of cDNA, once loaded in the MFC, by the ABI PRISM® 7900 HT system.

RT-PCR data were collected for a set of 20 genes identified in Example 1 and quantified relative to POLR2A levels. The RQ values for the aspirates corresponding to the 30 tumor samples and the 24 samples that were not endometrial cancer (normals) are illustrated in a box and whiskers plot, see FIGS. 2A and 2B. Table 2 in the Detailed Description of the Invention gives a summary of the mean RQ values, standard error of the mean and p-values calculated for these markers in this sample set. As can be seen, the p-values obtained using the control sample set in the microarray studies (Table 1) were significantly improved in a different sample set using different techniques (microarray versus RT-PCR) and different sources of sample (aspirates versus primary tumor). In most cases the p-value improved over 100-fold for the biomarkers. This is related in part to the robust nature of the microarray experimental design and robust selection of markers based on the Inventors' criteria.

The next table shows the sensitivity and specificity for each individual gene on the patent application and the area under de ROC (AUROC) curve for each gene when comparing the RQ values from the 30 tumour samples and the 24 control samples. A support vector machine (SVM) program was used to calculate the data. As can be seen in the table below, the markers identified in these studies have excellent sensitivity and/or specificity for predicting an increased likelihood and/or diagnosis of endometrial cancer. Furthermore, the AUROC values for these biomarkers indicate that these markers are very useful for diagnosis of endometrial cancer.

TABLE 6

Sensitivity, Specificity and AUROC values for the biomarkers of the invention determined from aspirates samples in affected (endometrial cancer) and non-affected individuals.

| GENE | sensitivity | specificity | AUROC |
|---|---|---|---|
| ACAA1 | 66.67% | 90.00% | 0.81 |
| AP1M2 | 58.33% | 86.67% | 0.83 |
| CGN | 79.17% | 76.67% | 0.81 |
| DDR1 | 79.17% | 90.00% | 0.89 |
| EPS8L2 | 70.83% | 86.67% | 0.81 |
| FASTKD1 | 70.83% | 76.67% | 0.84 |
| GMIP | 75.00% | 83.33% | 0.88 |
| IKBKE | 83.33% | 73.33% | 0.90 |
| P2RX4 | 62.50% | 96.67% | 0.82 |
| P4HB | 91.67% | 96.67% | 0.97 |
| PHKG2 | 70.83% | 93.33% | 0.84 |
| PPFIBP2 | 58.33% | 96.67% | 0.78 |
| PPP1R16A | 75.00% | 80.00% | 0.85 |
| RASSF7 | 100.00% | 60.00% | 0.89 |
| RNF183 | 95.83% | 73.33% | 0.88 |
| SIRT6 | 79.17% | 73.33% | 0.84 |
| TJP3 | 79.17% | 76.67% | 0.82 |
| EFEMP2 | 66.67% | 83.33% | 0.88 |
| SOCS2 | 79.17% | 93.33% | 0.93 |
| DCN | 66.67% | 90.00% | 0.85 |

Control samples were a heterogeneous group with pre and post-menopausal women. At the same time, aspirates from pre-menopausal women could be divided in two categories depending of the uterine endometrial cycle phase they were when the sample was taken: proliferative or secretory. The characterization of secretory versus proliferative phase patients was accomplished by a pathologist using standard techniques.

Some of the genes tested could give a false positive result for endometrial cancer if the aspirate was taken from pre-menopausal women in secretory phase. In order to check which genes could give false positives depending of the cycle phase or which others could distinguish between tumour samples and secretory phase, we performed a statistical analysis comparing tumours with different control groups.

- tumors versus control samples (all the control samples: 24 samples)
- tumors versus control samples minus the ones in secretory phase: 17 samples
- tumors samples versus control samples in secretory phase: 7 samples
- tumors samples versus control samples from postmenopausal women: 11 samples The area ROC for each comparison was calculated using the GraphPad Prism program and anova test was applied to see if the differences among these groups were significant.

In the Tables below the following abbreviations are used for p-values:
***$p<0.0001$
**$p<0.001$
*$p<0.01$
ns (not significant).

As it is shown on the tables there are genes, like P4HB or SOCS2, which separate the tumour samples from the control independently of the nature of the control samples (post-menopausical, pre-menopausical in secretory or in proliferative). Other genes like P2RX4 or PPFIBP2, could distinguish between a tumour sample (affected) and a sample in secretory phase better as compared to controls from postmenopausal women.

This observation opens the possibility of using different algorithms and/or different set of genes depending if the test is interrogating pre-menopausical or post-menopausical women. Furthermore, a primary modality for screening for endometrial problems is the trans-vaginal ultrasound which is used to estimate endometrial thickness where patients having a thicker endometrium (over a certain threshold) are likely to have endometrial cancer or another disease or condition. Endometrium thickness also varies as a function of the phase of the menstrual with individuals in secretory phase having a thicker endometrium as compared to individuals in proliferative phase. Thus, these finding indicate that the methods and biomarkers of the invention can be used to aid and improve the ability of transvaginal ultrasound to identify endometrial cancer.

TABLE 7

Summary of Data for RT-PCR Studies comparing the expression levels of biomarkers in aspirates (30) from patients affected with endometrial cancer and aspirates obtained from individuals all patients non affected with endometrial cancer (24).

| Comparison por 30T/24Crtl | ROC 30Tvs24Ctrl | Anova |
|---|---|---|
| P4HB | 0.974 | *** |
| SOCS2 | 0.955 | *** |
| IKBKE | 0.897 | *** |
| RNF183 | 0.883 | *** |
| EFEMP2 | 0.881 | *** |
| PHKG2 | 0.875 | *** |
| DCN | 0.854 | *** |
| PPP1R16A | 0.846 | *** |
| AP1M2 | 0.843 | *** |
| FASTKD1 | 0.838 | *** |
| SIRT6 | 0.836 | *** |
| CGN | 0.829 | *** |
| GMIP | 0.824 | *** |
| TJP3 | 0.824 | *** |
| RASSF7 | 0.817 | *** |
| ACAA1 | 0.817 | *** |
| EPS8L2 | 0.813 | *** |
| P2RX4 | 0.807 | *** |
| DDR1 | 0.769 | ** |
| PPFIBP2 | 0.745 | * |

Table 7 shows that the 20 biomarkers capable of distinguishing aspirates from endometrial cancer affected patients from aspirate from all control non-affected patients with high ROC values and/or excellent statistical significance.

TABLE 8

Summary of Data for RT-PCR Studies comparing the expression levels of biomarkers in aspirates (30) from patients affected with endometrial cancer and aspirates obtained from individuals patients non-affected with endometrial cancer and that were not in secretory phase (17)

| comparison 30T/17 Ctrl | ROC 30T vs 17Ctrl | Anova |
|---|---|---|
| P4HB | 0.963 | *** |
| SOCS2 | 0.936 | *** |
| RNF183 | 0.904 | *** |
| EFEMP2 | 0.900 | *** |
| FASTKD1 | 0.863 | *** |
| AP1M2 | 0.859 | *** |
| IKBKE | 0.858 | *** |
| PHKG2 | 0.845 | *** |
| CGN | 0.832 | *** |
| SIRT6 | 0.828 | ** |
| PPP1R16A | 0.817 | ** |
| DCN | 0.801 | ** |
| TJP3 | 0.8 | ** |
| GMIP | 0.798 | *** |
| RASSF7 | 0.798 | ** |

TABLE 8-continued

Summary of Data for RT-PCR Studies comparing the expression levels of biomarkers in aspirates (30) from patients affected with endometrial cancer and aspirates obtained from individuals patients non-affected with endometrial cancer and that were not in secretory phase (17)

| comparison 30T/17 Ctrl | ROC 30T vs 17Ctrl | Anova |
|---|---|---|
| ACAA1 | 0.784 | ** |
| EPS8L2 | 0.767 | ** |
| P2RX4 | 0.728 | * |
| DDR1 | 0.680 | ns |
| PPFIBP2 | 0.644 | ns |

Table 8 shows the rankings of 20 biomarkers of the invention capable of distinguishing aspirates from endometrial cancer affected patients from aspirates from all control non-affected patients excluding patients in the secretory phase. Table 7 shows the biomarkers of the invention have high ROC values and/or excellent statistical significance for separating these populations.

TABLE 9

Summary of Data for RT-PCR studies comparing the expression levels of biomarkers in aspirates (30) from patients affected with endometrial cancer and aspirates obtained from individuals patients non affected with endometrial cancer and that were in secretory phase (7)

| comparison 30T/7 Sec | ROC 30T vs 7 Sec | Anova |
|---|---|---|
| P4HB | 1 | ** |
| SOCS2 | 1.000 | *** |
| P2RX4 | 1 | *** |
| IKBKE | 0.991 | *** |
| PPFIBP2 | 0.991 | ** |
| DDR1 | 0.986 | ** |
| DCN | 0.981 | ** |
| PHKG2 | 0.948 | ** |
| EPS8L2 | 0.924 | * |
| PPP1R16A | 0.917 | ** |
| GMIP | 0.9 | * |
| ACAA1 | 0.895 | * |
| TJP3 | 0.881 | * |
| RASSF7 | 0.864 | * |
| SIRT6 | 0.857 | * |
| EFEMP2 | 0.833 | ns |
| RNF183 | 0.831 | ns |
| CGN | 0.82 | ns |
| AP1M2 | 0.805 | ns |
| FASTKD1 | 0.779 | ns |

As can be seen in the Table 9 preferred markers capable of distinguishing aspirates from endometrial cancer affected patients from aspirates from non-endometrial cancer affected patients in secretory phase include P4HB, SOCS2 P2RX4, IKBKE, PPFIB2, DDR1 and DCN which have high ROC values and/or excellent statistical significance.

As seen from the data in Tables 7 & 9 above examples of genes capable of differentiating between aspirates from patients having tumor and aspirates from all non-affected patients (including secretory phase) and/or between aspirates from patients having tumor and aspirates from non-affected patients in secretory phase include P4HB, SOCS2, and IKBKE which have high statistical significance and ROC values.

TABLE 10

Summary of Data for RT-PCR Studies comparing the expression levels of biomarkers in aspirates (30) from patients affected with endometrial cancer and aspirates obtained from post-menopausal patients non affected with endometrial cancer (11).

| Ranking por 30T/11N | ROC 30Tvs11crtl postm | Anova |
|---|---|---|
| PHKG2 | 0.9476 | * |
| P4HB | 0.9424 | *** |
| EFEMP2 | 0.903 | *** |
| RNF183 | 0.8909 | *** |
| SOCS2 | 0.8667 | * |
| FASTKD1 | 0.8439 | ** |
| GMIP | 0.8394 | ** |
| SIRT6 | 0.8364 | ** |
| AP1M2 | 0.8182 | * |
| IKBKE | 0.7955 | ns |
| CGN | 0.7864 | * |
| PPP1R16A | 0.7652 | ns |
| TJP3 | 0.7515 | ns |
| RASSF7 | 0.7515 | ns |
| ACAA1 | 0.7242 | ns |
| DCN | 0.7167 | ns |
| EPS8L2 | 0.697 | ns |
| P2RX4 | 0.6303 | ns |
| DDR1 | 0.5879 | ns |
| PPFIBP2 | 0.5318 | ns |

As can be seen in the Table 10 preferred markers capable of distinguishing aspirates from endometrial cancer affected patients from aspirate from post menopausal non endometrial cancer affected patients include PHKG2, P4HB, EFEMP2, RNF183, and SOCS2 which have high ROC values and/or excellent statistical significance.

Figure 2B:
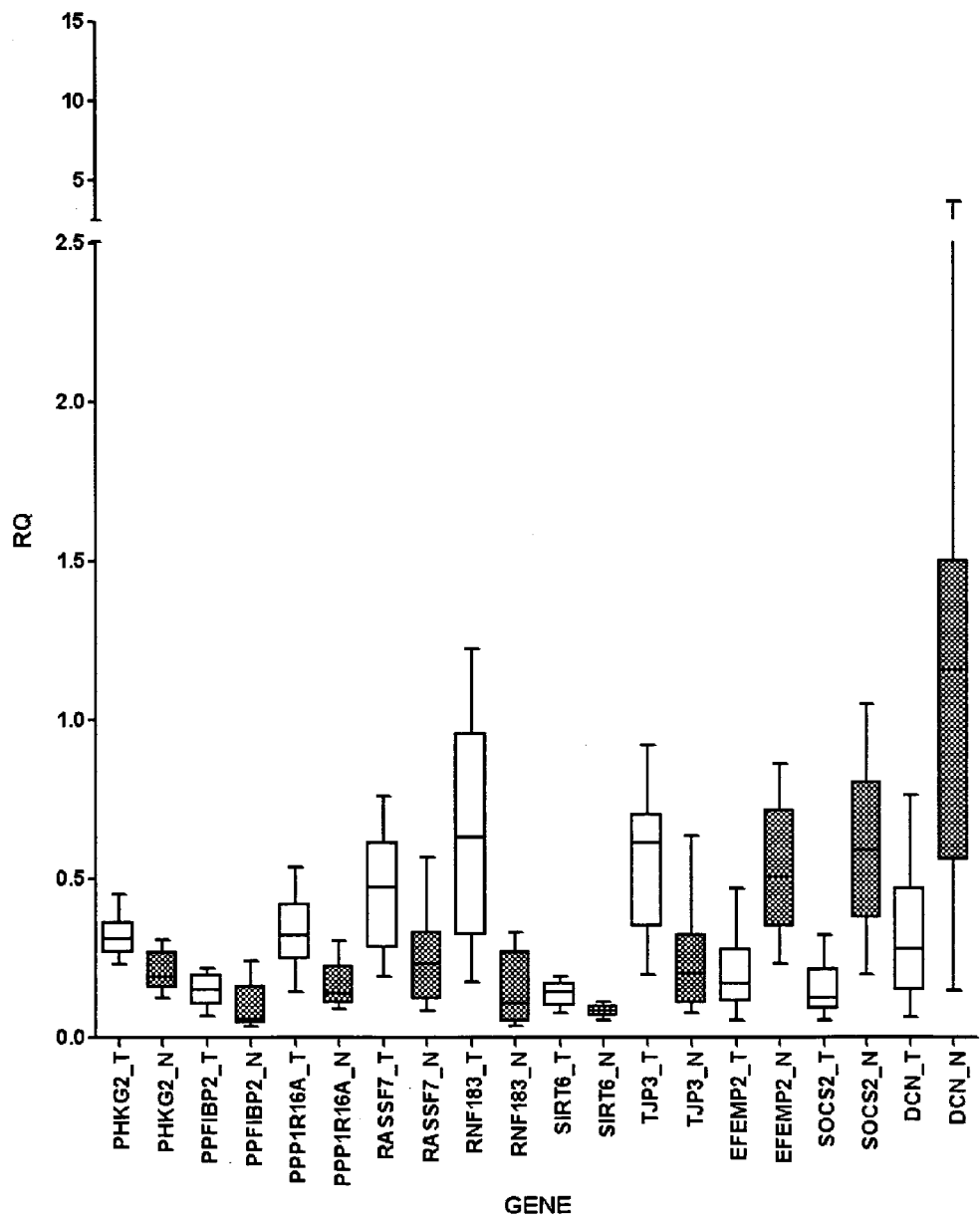

In reference to FIGS. 2A and 2B (box and whisker plot), RQ: relative quantity, it is the relative amount of RNA for a specific gene present on the tumours samples referred to the amount present on the control sample for the same gene.

To calculate the RQ the Ct values of each gene were normalise respect to the Ct of the endogenous gene to get the delta Ct. The formula $2^{-(deltaCt)}$ was used to calculate de RQ.

A number of endogenous genes can be used as a control for normalization as well as other controls for normalization. In one example a preferred endogenous gene has the following characteristics: it is a gene constitutively expressed in the same tissue under different circumstances like for example cancer development. So it could be used to normalize differences in the amount of cDNA when loading the samples or variations due to experimental reasons for the qRT-PCR.

We have tested four different housekeeping genes as possible endogenous genes for normalization purposes: 18S, B2M, PFN-1 and POLR2A. Finally, POLR2A was the most stable gene from all of them and all the calculations and statistics were done using it as endogenous. Its expression level is similar to the genes questioned in our test and different as compared to 18 S whose expression is quiet high compared to the genes selected for the test. It is contemplated that endogenous biomarkers such as POLR2A, B2M, PFN1, HMBS, G6PD, or PABPN1 or another stable gene can be used for normalization purposes in the methods of the invention if they so require.

Example 5

Profiles for Diagnosing Endometrial Cancer

A support vector machine based algorithm was used to identify combinations of markers of Table 1 that are useful for predicting endometrial cancer and/or an increased likelihood of having endometrial cancer. In particular, the publically available program DTREG program was used to analyze the data (see the www at DTREG.COM).

Support vector machine algorithm can be used for many applications including identifying gene expression profiles for separating populations having different phenotypic characteristics. The idea behind the algorithm is a multidimensional representation of the data, e.g., each marker is plotted on a different dimension and a plane is sought though this multidimensional representation of the data that can separate the phenotypes. The plan through the "middle" is referred to as the separating hyperplane and represents a solution: answers (e.g., expression level over a given threshold value) that fall on one side of the line fall into one category (e.g., cancer) and answers (e.g., expression level over a given threshold value) that follow on the other side of the line correspond to the other category (e.g., no cancer). A number of separating hyper plane can be possible for each dataset. The question becomes which is the best separating hyperplane. In support vector machine theory, the best solution is referred to as the maximum margin hyperplane. This maximum margin hyperplane is the one that separates the two groups and adopts the maximal distance from any one of the given expression profiles.

Although individual genes show a high sensitivity and specificity, these parameters are even higher when combined several genes. Some examples of the sensitivity, specificity and AUROC genes combined two to two, three to three, four to four, five to five, six to six, seven to seven and all of them together. See the Table below for a summary of the data.

were obtained from samples from uterine fluid and indicate that combinations of biomarkers detected in uterine fluid can be useful for diagnosing and/or characterizing endometrial cancer. Furthermore, these results were obtained in samples from pre and post menopausal women and therefore represents a set of markers that can be examined across these types of patients. It is noted that different programs and algorithms can be used to generate profiles or fingerprint patterns. The invention is intended to encompass profiles and/or fingerprint patterns using programs and algorithms other than DTREG as used herein. The profiles identified in Table 11 are non-limiting examples used to illustrate that combinations of the biomarkers of Table 1 have excellent sensitivity and specificity for endometrial cancer.

Additional Combinations

The values of sensitivity and specificity although fully define the validity of a diagnostic test have the disadvantage of not providing relevant information when making a clinical decision to a particular test result. However, they have the advantage of been intrinsic properties to the test and define its validity irrespective of the prevalence of the disease in the population to which it applies.

Sensitivity

It is the probability of classifying correctly an individual patient or the probability that a individual with cancer obtains a positive result when applying the diagnostic test Specificity It is the probability of classifying correctly a healthy individual or the probability that a healthy individual obtaining a

TABLE 11

Data Summarizing Predictive Values for Combinations

| combinations | sensitivity | specificity | AUROC |
|---|---|---|---|
| IKBKE + P4HB | 91.67% | 100.00% | 0.978 |
| IKBKE + SOCS2 | 79.17% | 96.67% | 0.951 |
| P4HB + SOCS2 | 91.67% | 100.00% | 1 |
| GMIP + IKBKE | 79.17% | 90.00% | 0.915 |
| GMIP + P4HB | 95.83% | 96.67% | 0.982 |
| GMIP + SOCS2 | 100.00% | 86.67% | 0.999 |
| GMIP + SOCS2 + IKBKE | 95.83% | 100.00% | 1 |
| GMIP + SOCS2 + P4HB | 91.67% | 100.00% | 0.983 |
| GMIP + IKBKE + P4HB | 91.67% | 100.00% | 0.978 |
| IKBKE + P4HB + SOCS2 | 91.67% | 100.00% | 0.981 |
| GMIP + IKBKE + P4HB + SOCS2 | 100.00% | 100.00% | 1 |
| GMIP + SOCS2 + IKBKE + EPS8L2 | 91.67% | 100.00% | 0.993 |
| GMIP + SOCS2 + P4HB + EPS8L2 | 91.67% | 100.00% | 0.976 |
| GMIP + IKBKE + P4HB + EPS8L2 | 91.67% | 100.00% | 0.976 |
| IKBKE + P4HB + SOCS2 + EPS8L2 | 87.50% | 100.00% | 0.981 |
| GMIP + IKBKE + P4HB + SOCS2 + DDR1 | 91.67% | 100.00% | 1 |
| GMIP + IKBKE + P4HB + SOCS2 + EPS8L2 + PPP1R16A | 91.67% | 100.00% | 0.999 |
| GMIP + IKBKE + P4HB + SOCS2 + PHKG2 + RASSF7 | 95.83% | 100.00% | 1 |
| GMIP + IKBKE + P4HB + SOCS2 + DDR1 + EPS8L2 | 95.83% | 100.00% | 1 |
| GMIP + IKBKE + P4HB + SOCS2 + EPS8L2 + PPP1R16A + DDR1 | 95.83% | 100.00% | 1 |
| DDR1 + EPS8L2 + GMIP + IKBKE + P2RX4 + P4HB + PHKG2 + PPP1R16A + RASSF7 + SIRT6 + TJP3 + SOCS2 | 100.00% | 100.00% | 1 |
| DDR1 + EPS8L2 + GMIP + IKBKE + P2RX4 + P4HB + PHKG2 + PPP1R16A + RASSF7 + SIRT6 + TJP3 + SOCS2 + RNF183 | 100.00% | 100.00% | 1 |
| ALL TOGETHER: 20 GENES | 100.00% | 100.00% | 1 |

As can be seen in the Table above very high sensitivity and specificities were obtained for combinations of the biomarkers of the invention and the AUROC values are very high. Thus, these results show that combinations of 2 or more markers chosen from ACAA1, AP1M2, CGN, DDR1, EPS8L2, FASTKD1, GMIP, IKBKE, P2RX4, P4HB, PHKG2, PPFIBP2, PPP1R16A, RASSF7, RNF183, SIRT6, TJP3, EFEMP2, SOCS2, and DCN give unexpectedly good sensitivity and specificity for predicting an increased likelihood and/or diagnosing endometrial cancer. These results negative result when applying the diagnostic test Sensitivity and specificity can, therefore, to assess the validity of a diagnostic test. However, these concepts are not much help in clinical practice. When a patient undergoes a diagnostic test, the doctor has no a priori information about their diagnosis so the question arises to the next one: given a positive (or negative) on the test? What is the probability that the individual tested has the disease (or not)? These probabilities are known as positive predictive value and negative predictive value of a particular test. Positive predictive value is the probability of having the disease if the individual has a positive result when applying the diagnostic test. Negative predictive value is the probability that an individual who has obtained a negative result on the test, is actually healthy.

Clinicians prefer diagnostic tests with high negative predictive value as they can not allow people with cancer get a wrong diagnosis. For this reason we have prioritized these combinations which give us the highest negative predictive values.

The follow values in Table 12 were calculated using the indicated markers as determined by RT-PCR in uterine fluid samples.

Figure 17:
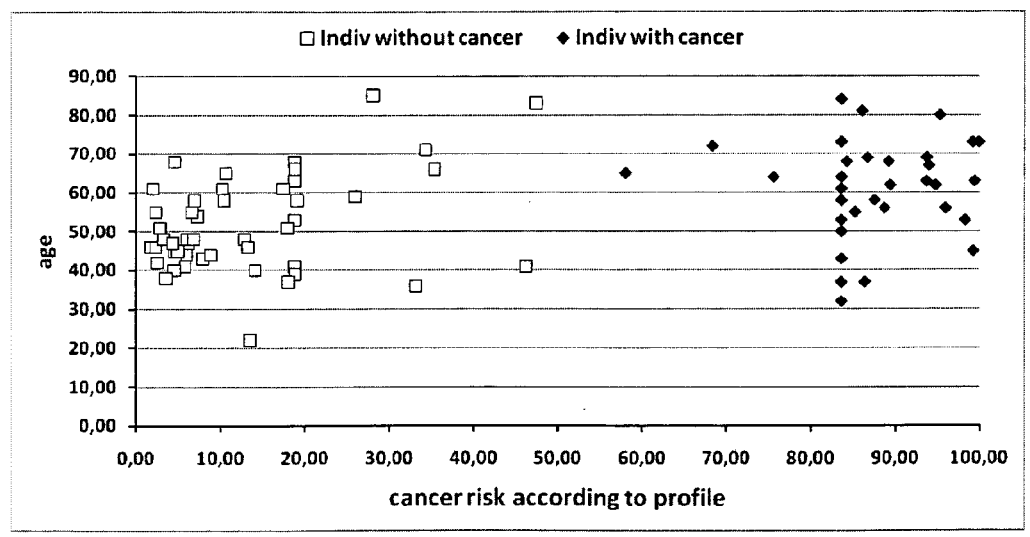
FIG. 17 shows the calculated risk of cancer using 48 non-tumor samples and 33 tumor samples using the ACAA1, AP1M2, EPS8L2, IKBKE, P2RX4, P4HB, PPFIBP2, PPP1R16A, SIRT6, EFEMP2. See Example 5.

ACAA1, AP1M2, EPS8L2, IKBKE, P2RX4, P4HB, PPFIBP2, PPP1R16A, SIRT6, and EFEMP2 the result is shown in FIG. 17.

Figure 18:
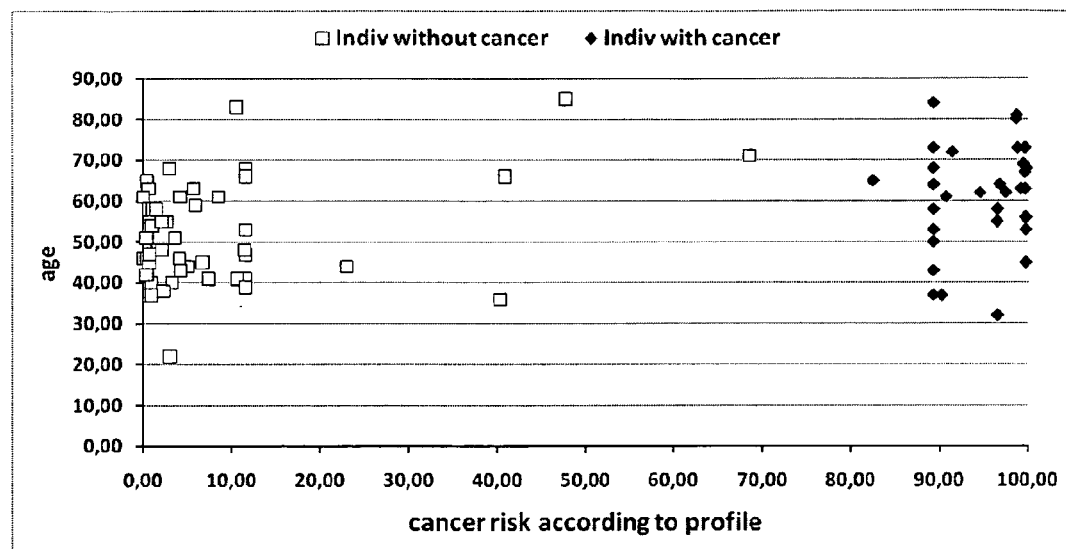
FIG. 18 shows the calculated risk of cancer using 48 non-tumor samples and 33 tumor samples using the FASTKD1, GMIP, P4HB, EFEMP2, SIRT6, and PHKG2. See Example 5.

FIG. 18 shows the calculated risk of cancer for the 48 non-tumor and 33 tumor samples using FASTKD1, GMIP, P4HB, EFEMP2, DDR1, and SIRT6.

Figure 19:
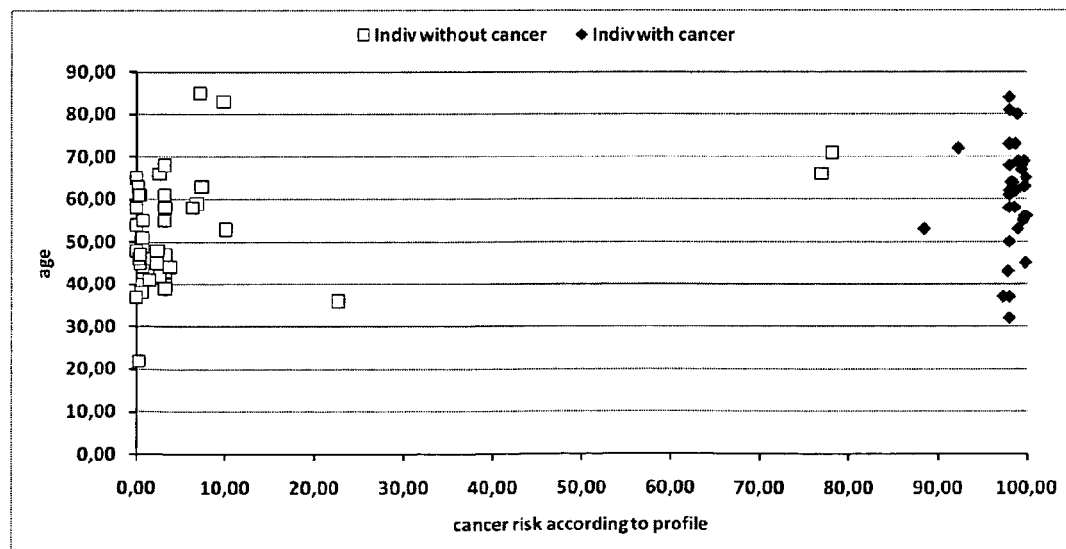
FIG. 19 shows the calculated risk of cancer using 48 non-tumor samples and 33 tumor samples using the FASTKD1, GMIP, P4HB, EFEMP2, DDR1, and SIRT6. See Example 5.

FIG. 19 shows the calculated risk of cancer for the 48 non-tumor and 33 tumor samples using FASTKD1, GMIP, P4HB, EFEMP2, PHKG2, and SIRT6.

As shown on FIG. 17, the first combination is able to classify all the samples correctly but the percentage of some healthy samples of having cancer are very close to 50%: some

TABLE 12

| combinations | DTREG-SVM | | | | |
|---|---|---|---|---|---|
| | sensitivity | specificity | AUROC | NPV | PPV |
| P4HB + SOCS2 | 91.67% | 100.00% | 1 | 93.75% | 100.00% |
| GMIP + IKBKE + P4HB + SOCS2 | 100.00% | 100.00% | 1 | 100.00% | 100.00% |
| GMIP + IKBKE + P4HB + SOCS2 + FASTKD1 | 100.00% | 100.00% | 1 | 100.00% | 100.00% |
| GMIP + IKBKE + P4HB + SOCS2 + DDR1 | 95.83% | 100.00% | 1 | 96.77% | 100.00% |
| GMIP + IKBKE + P4HB + SOCS2 + PHKG2 | 91.67% | 100.00% | 1 | 93.75% | 100.00% |
| GMIP + IKBKE + P4HB + SOCS2 + SIRT6 | 91.67% | 100.00% | 1 | 93.75% | 100.00% |
| GMIP + IKBKE + P4HB + SOCS2 + ACAA1 | 100.00% | 100.00% | 1 | 100.00% | 100.00% |
| GMIP + IKBKE + P4HB + SOCS2 + AP1M2 | 91.67% | 96.67% | 0.979 | 93.55% | 95.65% |
| GMIP + IKBKE + P4HB + SOCS2 + EFEMP2 | 91.67% | 100.00% | 1 | 93.75% | 100.00% |
| GMIP + IKBKE + P4HB + SOCS2 + EPS8L2 | 91.67% | 100.00% | 1 | 93.75% | 100.00% |
| GMIP + IKBKE + P4HB + SOCS2 + P2RX4 | 83.33% | 96.67% | 0.964 | 87.88% | 95.24% |
| GMIP + IKBKE + P4HB + SOCS2 + PPFIBP2 | 91.67% | 96.67% | 0.979 | 93.55% | 95.65% |
| GMIP + IKBKE + P4HB + SOCS2 + PPP1R16A | 95.83% | 100.00% | 1 | 96.77% | 100.00% |
| GMIP + IKBKE + P4HB + SOCS2 + ACAA1 + FASTKD1 | 100.00% | 100.00% | 1 | 100.00% | 100.00% |
| GMIP + IKBKE + P4HB + SOCS2 + FASTKD1 + PHKG2 | 100.00% | 100.00% | 1 | 100.00% | 100.00% |
| GMIP + IKBKE + P4HB + SOCS2 + FASTKD1 + SIRT6 | 100.00% | 100.00% | 1 | 100.00% | 100.00% |
| ACAA1 + AP1M2 + EPS8L2 + IKBKE + P2RX4 + P4HB + PPFIBP2 + PPP1R16A + SIRT6 + EFEMP2 | 100.00% | 100.00% | 1 | 100.00% | 100.00% |
| GMIP + IKBKE + P4HB + EFEMP2 | 100.00% | 93.33% | 0.999 | 100.00% | 92.31% |
| DDR1 + FASTKD1 + GMIP + IKBKE + P4HB + PHKG2 + SIRT6 + EFEMP2 + SOCS2 | 100.00% | 100.00% | 1 | 100.00% | 100.00% |
| DDR1 + FASTKD1 + GMIP + IKBKE + P4HB + PHKG2 + SIRT6 + EFEMP2 | 100.00% | 100.00% | 1 | 100.00% | 100.00% |
| P4HB + EFEMP2 + IKBKE + GMIP + FASTKD1 | 100.00% | 100.00% | 1 | 100.00% | 100.00% |

The combinations shown in FIG. 18 (P4HB, EFEMP2, SIRT6, DDR1, GMIP, and FASTKD1) and FIG. 19 (P4HB, EFEMP2, SIRT6, PHKG2, GMIP, and FASTKD1), and the combination of all 20 markers have sensitivities, specificities, NPVs, and PPVs of 100% and AUROCs of 1.

Maximizing Negative Predictive Value: New samples: three new cancer samples and 24 no tumor samples giving a total amount of samples in the following analysis (33T and 48 non tumor) with the additional sample having the following characteristics:

| Aspirates from women with a tumor | Sample Diagnosis | Tumor Grade | FIGO stage |
|---|---|---|---|
| 31 | Endometroid carcinoma | G1 | IA |
| 32 | Endometroid carcinoma | G2 | IB |
| 33 | Endometroid/ squamo-transitional | G3 | IA |
| Control aspirates | | | |
| 4 pre-menopausic in secretory phase | | | |
| 5 pre-menopausic in proliferative phase | | | |
| 4 pre-menopausic (unknown cycle phase) | | | |
| 11 aspirates from postmenopausical women | | | |

The calculated the risk of cancer for 48 non tumor and 33 tumor samples using the following combination of genes cancer samples are too close to be misclassified when using this combination. In summary, the risk of misclassifying cancer patients with a false diagnosis. Although the combinations in FIG. 18 and FIG. 19 misclassify one and two healthy patients samples respectively, both of them classify correctly all the cancer patients and they do it with a higher percentage of risk of cancer than the previous combination. For that reason these combinations are valuable from a clinical point of view.

Example 6

Detection of Protein Corresponding to the Biomarkers of Table 1

Detection of protein corresponding to the Biomarkers of Table 1 can be accomplished by any number of means available to the skill artisan. According to this method samples from controls (or a control value is established) and affected individuals are obtained (e.g., serum, tissue, and uterine fluid) and probe for with antibodies selective or specific to the particular biomarker. One method for detecting the proteins is by western blot analysis and is exemplified as in the case of P4HB.

Western blot analysis from human samples from normal endometrial tissue and tumour endometrial cancer tissues in order to test the protein level of P4HB (aprox. 60 kDa) in these samples.

Figure 10:
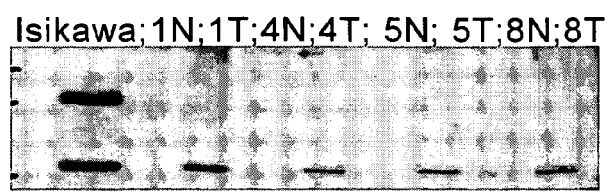
FIG. 10 shows a western blot of endometrial cancer tissue with antibody against a Biomarker of the invention: P4HB. The samples tested include four normal tissues (N) and four tumor tissues (T). Normal and tumors tissues were obtained from the same patient. As a positive control: total protein extract from the endometrial tumour cell line Isikawa. See Example 6.
Figure 11:
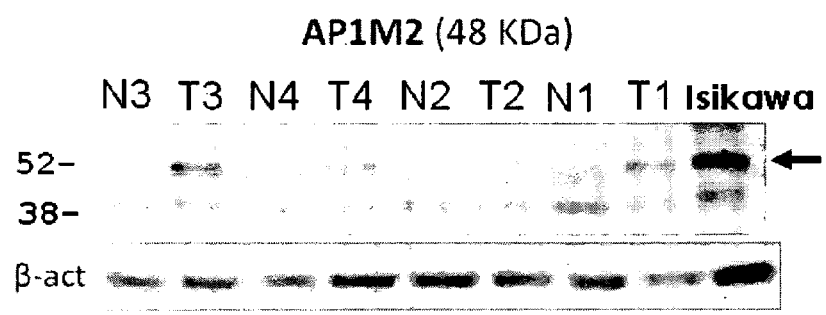
FIG. 11 shows a western blot of endometrial cancer tissue with antibody against a Biomarker of the invention: AP1M2. The samples tested include four normal tissues (N) and four tumor tissues (T) from 4 different patients. Matched normal and tumors tissues were obtained from the same patient. As a positive control: total protein extract from the endometrial tumor cell line Isikawa. See Example 6.
Figure 12:
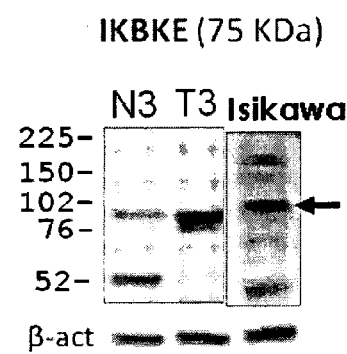
FIG. 12 shows a western blot of endometrial cancer tissue with antibody against a Biomarker of the invention: IKBKE. The samples tested include a normal tissue (N) and a tumor tissue (T). Matched normal and tumors tissue were obtained from the same patient. As a positive control: total protein extract from the endometrial tumor cell line Isikawa. See Example 6.
Figure 13:
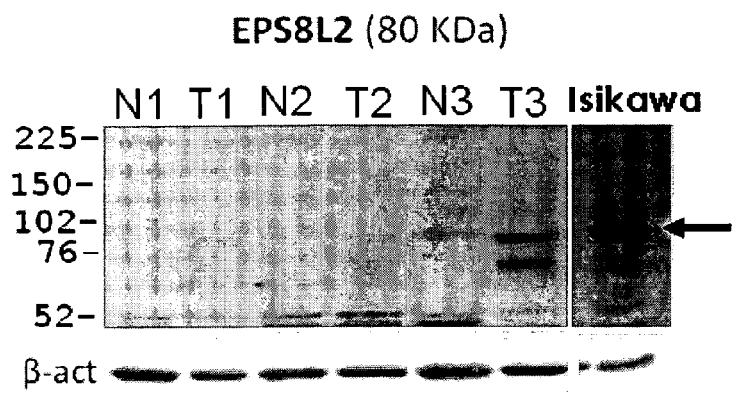
FIG. 13 shows a western blot of endometrial cancer tissue with antibody against a Biomarker of the invention: EPS8L2. The samples tested include 3 normal tissues (N) and 3 tumor tissues (T) from 3 different patients. As a positive control: total protein extract from the endometrial tumor cell line. Matched normal and tumors tissues were obtained from the same patient. See example 6.
Figure 14:
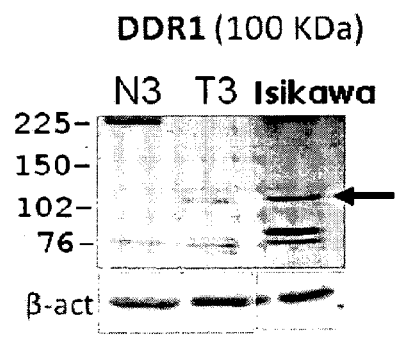
FIG. 14 shows a western blot of endometrial cancer tissue with antibody against a Biomarker of the invention: DDR1. The samples tested include a normal tissue (N) and a tumor tissue (T). Matched normal and tumors tissue were obtained from the same patient. As a positive control: total protein extract from the endometrial tumor cell line Isikawa. See Example 6.
Figure 15:
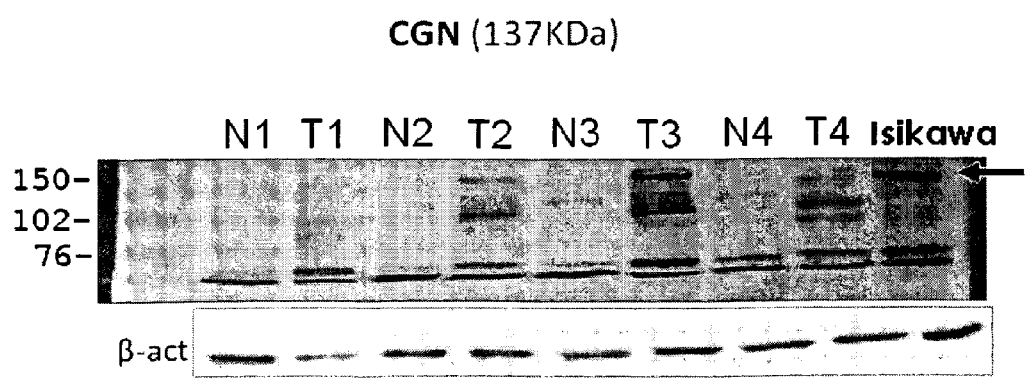
FIG. 15 shows a western blot of endometrial cancer tissue with antibody against a Biomarker of the invention: CGN. The samples tested include four normal tissues (N) and four tumor tissues (T) from four different patients. Matched normal and tumors tissues were obtained from the same patient. As a positive control: total protein extract from the endometrial tumor cell line Isikawa. See Example 6.
Figure 16:
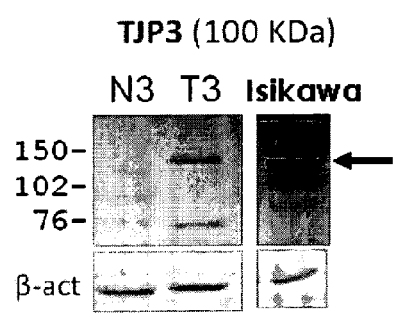
FIG. 16 shows a western blot of endometrial cancer tissue with antibody against a Biomarker of the invention: TJP3. The samples tested include a normal tissue (N) and a tumor tissue (T). Matched normal and tumors tissue were obtained from the same patient. As a positive control: total protein extract from the endometrial tumor cell line Isikawa. See Example 6.

Gels were loaded with 40 ug of total protein extracts from each sample. As can be seen in FIG. 10, tumor samples stained much more strongly for P4HB as compared to normal tissue.

The samples tested include four normal tissues (N) and four tumour tissues (T). Normal and tumours tissues were obtained from the same patient. As a positive control: total protein extract from the endometrial tumour cell line Isikawa. The Antibody used: LS-C38385 from LifeSpan.

The results confirm to protein level the results obtained in the array and the TaqMan experiments.

Western blot analysis was performed for AP1M2, IKBKE, EPS8L2, DDR1, CGN, and TJP3. See FIG. 10 through FIG. 16. These results confirm at the protein level the results obtained in the array and the TAQMAN™ experiments for these biomarkers.

For immunohistochemistry validation, tissue microarrays were constructed. In order to cover the complete range from normal tissue to different types and grades of endometrial carcinomas, representative areas from 70 paraffin-embedded carcinomas (56 endometrioid, 6 serous papillary, 1 mucinous, 4 clear cell carcinomas, 3 carcinosarcomas), and 11 non-neoplastic endometria (4 atrophic, 3 proliferative, 1 secretory endometrial and 3 hyperplasias), were carefully selected and marked on individual paraffin blocks. Two tissue cores of 1 mm in diameter were obtained from each paraffin block and were precisely arrayed in a new paraffin block. Sections of 5 µm were obtained from all tissue microarray paraffin blocks. The protocol was approved by the Institutional Review Board at Hospital Vall D'Hebron, and informed consent was obtained from all of the patients. P4HB, PPP1R16A and EPS8L2 were detected by the indirect immunoperoxidase assay with citrate buffer pH 7.3 for antigen retrieval. Sections were incubated with a primary antibodies against P4HB (LS-C38385) and PPP1R16A (H00084988-M06) for 1 h at room temperature using a dilution 1:500 and 1:100, respectively, and EPS8L2 (H00064787-B01) overnight at 1:100 dilution. Thereafter sections were incubated with peroxidase conjugated goat anti-mouse immunoglobulin (EnVision Dual System, DAKO, Glostrup, Denmark). Endogenous peroxidase activity was quenched with 3% H2O2. Sections were washed, and reactions were developed with diaminobenzidine, followed by counterstaining with haematoxylin. Semiquantitative evaluation of the proteins was performed by three independent investigators, scoring the intensity of the stained and the percentage of positive cells.

TMA immunohistochemistry confirmed the differential expression of the three proteins at the tumoral glands when compared to the normal endometrial glands. P4HB, PPP1R16A and EPS8L2 presented a specific cytoplasmatic expression within the tumoral cells in all carcinoma histological types and grades, and an absence or faint cytoplasmatic stain within the normal epithelial glands. These results confirm at the protein level the results obtained for these proteins in the microarray and quantitative PCR experiments described herein.

Example 7

ACAA1

ACAA1 was found to be overexpressed in endometrial cancer primary tissue as compared to normal endometrial tissue by the microarray experiment described in Example 1. Further studies using RT-PCR demonstrated that ACAA1 was overexpressed in primary endometrial cancer tissue as compared to normal endometrial tissue and it was surprisingly found that ACAA1 was overexpressed in samples obtained from uterine fluid (e.g., aspirates) from patients having endometrial cancer by the methods described in Examples 2-4. Example 5 shows that ACAA1 can be combined with other biomarkers to give excellent predictive power for diagnosis of endometrial cancer.

The sequence of an mRNA corresponding to ACAA1 is given in ENSEMBL accession no. ENST00000333167 and has a sequence as in SEQ ID NO:1

```
  1 ATGTGGTTCTGCGCGTGTGCGGACGGCTGTCTGTTAACTCCGCGGTCAGTTCCCGGACTG
 61 GTGGCTGGTCTGCAGGGTTGACCTGCGCAATGCAGAGGCTGCAGGTAGTGCTGGGCCACC
121 TGAGGGGTCCGGCCGATTCCGGCTGGATGCCGCAGGCCGCGCCTTGCCTGAGCGGTGCCC
181 CGCAGGCCTCGGCCGCGGACGTGGTGGTGGTGCACGGGCGGCGCACGGCCATCTGCCGGG
241 CGGGCCGCGGCGGCTTCAAGGACACCACCCCCGACGAGCTTCTCTCGGCAGTCATGACCG
301 CGGTTCTCAAGGACGTGAATCTGAGGCCGGAACAGCTGGGGGACATCTGTGTCGGAAATG
361 TGCTGCAGCCTGGGGCCGGGGCAATCATGGCCCGAATCGCCCAGTTTCTGAGTGACATCC
421 CGGAGACTGTGCCTTTGTCCACTGTCAATAGACAGTGTTCGTCGGGGCTACAGGCAGTGG
481 CCAGCATAGCAGGTGGCATCAGAAATGGGTCTTATGACATTGGCATGGCCTGTGGGGTGG
541 AGTCCATGTCCCTGGCTGACAGAGGGAACCCTGGAAATATTACTTCGCGCTTGATGGAGA
601 AGGAGAAGGCCAGAGATTGCCTGATTCCTATGGGGATAACCTCTGAGAATGTGGCTGAGC
661 GGTTTGGCATTTCACGGGAGAAGCAGGATACCTTTGCCCTGGCTTCCCAGCAGAAGGCAG
721 CAAGAGCCCAGAGCAAGGGCTGTTTCCAAGCTGAGATTGTGCCTGTGACCACCACGGTCC
781 ATGATGACAAGGGCACCAAGAGGAGCATCACTGTGACCCAGGATGAGGGTATCCGCCCCA
841 GCACCACCATGGAGGGCCTGGCCAAACTGAAGCCTGCCTTCAAGAAAGATGGTTCTACCA
901 CAGCTGGAAACTCTAGCCAGGTGAGTGATGGGGCAGCTGCCATCCTGCTGGCCCGGAGGT
961 CCAAGGCAGAAGAGTTGGGCCTTCCCATCCTTGGGGTCCTGAGGTCTTATGCAGTGGTTG
```

-continued

```
1021 GGGTCCCACCTGACATCATGGGCATTGGACCTGCCTATGCCATCCCAGTAGCTTTGCAAA
1081 AAGCAGGGCTGACAGTGAGTGACGTGGACATCTTCGAGATCAATGAGGCCTTTGCAAGCC
1141 AGGCTGCCTACTGTGTGGAGAAGCTACGACTCCCCCCTGAGAAGGTGAACCCCCTGGGGG
1201 GTGCAGTGGCCTTAGGGCACCCACTGGGCTGCACTGGGGCACGACAGGTCATCACGCTGC
1261 TCAATGAGCTGAAGCGCCGTGGGAAGAGGGCATACGGAGTGGTGTCCATGTGCATCGGGA
1321 CTGGAATGGGAGCCGCTGCCGTCTTTGAATACCCTGGGAACTGAGTGAGGTCCCAGGCTG
1381 GAGGCGCTACGCAGACAGTCCTGCTGCTCTAGCAGCAAGGCAGTAACACCACAAAAGCAA
1441 AACCACATGGGAAAACTCAGCACTGGTGGTGGTGGCAGTGGACAGATCAAGGCACTTCAA
1501 CTCATTTGGAAAATGTGAACACTGATGACATGGTATAGGAGTGGGTGGGGTGTTGAGCCA
1561 CCCATCAGACCCTCTTTAGCTGTGCAAGATAAAAGCAGCCTGGGTCACCCAGGCCACAAG
1621 GCCATGGTTAATTCTTAAGGCAAGGCAAATCCATGGATGAGAAGTGCAATGGGCATAGTA
1681 AAAGTGCATGAATTT
```

The corresponding amino acid sequence is given in ENSEMBL accession no. ENSP00000333664 and has a sequence as in SEQ ID NO:2

```
  1 MQRLQVVLGHLRGPADSGWMPQAAPCLSGAPQASAADVVVVHGRRTAICRAGRGGFKDTT
 61 PDELLSAVMTAVLKDVNLRPEQLGDICVGNVLQPGAGAIMARIAQFLSDIPETVPLSTVN
121 RQCSSGLQAVASIAGGIRNGSYDIGMACGVESMSLADRGNPGNITSRLMEKEKARDCLIP
181 MGITSENVAERFGISREKQDTFALASQQKAARAQSKGCFQAEIVPVTTTVHDDKGTKRSI
241 TVTQDEGIRPSTTMEGLAKLKPAFKKDGSTTAGNSSQVSDGAAAILLARRSKAEELGLPI
301 LGVLRSYAVVGVPPDIMGIGPAYAIPVALQKAGLTVSDVDIFEINEAFASQAAYCVEKLR
361 LPPEKVNPLGGAVALGHPLGCTGARQVITLLNELKRRGKRAYGVVSMCIGTGMGAAAVFE
421 YPGN
```

Primers for amplifying the sequence ACAA1 can be designed using primer design software such as Oligo Calc and/or Primer 3.
Examples of primer pairs for amplifying ACAA1 include those in

```
Forward
                              SEQ ID NO: 3
GAGCTTCTCTCGGCAGTCAT

Reverse
                              SEQ ID NO: 4
CTCAGAAACTGGGCGATTC

Forward
                              SEQ ID NO: 5
GCAATCATGGCCCGAATC

Reverse
                              SEQ ID NO: 6
CCCCGACGAACACTGTCTAT

Forward
                              SEQ ID NO: 7
GTGCCTTTGTCCACTGTCAA

Reverse
                              SEQ ID NO: 8
ACAGGCCATGCCAATGTC
```

-continued
```
Forward
                              SEQ ID NO: 9
TCACGGGAGAAGCAGGATAC Reverse
                              SEQ ID NO: 10
CTCTTGGTGCCCTTGTCATC Forward
                              SEQ ID NO: 11
GGCTGACAGTGAGTGACGTG Reverse
                              SEQ ID NO: 12
AGGGGGTTCACCTTCTCAG Forward
                              SEQ ID NO: 13
GTGGCATCAGAAATGGGTCT Reverse
                              SEQ ID NO: 14
CTCTGGCCTTCTCCTTCTCC Forward
                              SEQ ID NO: 15
ATTACTTCGCGCTTGATGGA Reverse
                              SEQ ID NO: 16
AGGGCAAAGGTATCCTGCTT
```

-continued

Forward
SEQ ID NO: 17
GCCTGCCTTCAAGAAAGATG

Reverse
SEQ ID NO: 18
TAAGACCTCAGGACCCCAAG

Forward
SEQ ID NO: 19
TGGGGTCCTGAGGTCTTATG

Reverse
SEQ ID NO: 20
TCTCGAAGATGTCCACGTCA

Forward
SEQ ID NO: 21
GTGGCATCAGAAATGGGTCT

Reverse
SEQ ID NO: 22
AGGGCAAAGGTATCCTGCTT

Forward
SEQ ID NO: 23
TGACCCAGGATGAGGGTATC

Reverse
SEQ ID NO: 24
TCTCGAAGATGTCCACGTCA

Forward
SEQ ID NO: 25
GGAGACTGTGCCTTTGTCCA

Reverse
SEQ ID NO: 26
CTCTGTCAGCCAGGGACAT

Other sets of primers can be readily designed by the skilled artisan and/or are known in the art.

Probes for detecting ACAA1 can be derived from any number of sources depending on the desired use (e.g., using the above described primers and appropriate reagents). Other examples of probes include

SEQ ID NO: 27
CGGTTCTCAAGGACGTGAAT

SEQ ID NO: 28
AGTGACATCCCGGAGACTGT

SEQ ID NO: 29
GTGGCATCAGAAATGGGTCT

SEQ ID NO: 30
AGCTGAGATTGTGCCTGTGA

SEQ ID NO: 31
ATCAATGAGGCCTTTGCAAG

SEQ ID NO: 32
ACAGAGGGAACCCTGGAAAT

SEQ ID NO: 33
GATTGCCTGATTCCTATGGG

SEQ ID NO: 34
GTCCAAGGCAGAAGAGTTGG

SEQ ID NO: 35
ATGCCATCCCAGTAGCTTTG

SEQ ID NO: 36
GCCTGTGGGATAACCTCTGA

SEQ ID NO: 37
AAACTGAAGCCTGCCTTCAA

SEQ ID NO: 38
ATAGACAGTGTTCGTCGGGG

A probe for detecting a ACAA1 nucleic acid that was used on the microarray has a sequence as in SEQ ID NO:39

GCTACGCAGACAGTCCTGCTGCTCTAGCAGCAAGGCAGTAACACCACAA
AAGCAAAACCA

Other probes to ACAA1 are known in the art and/or can be readily designed by the skilled artisan.

Antibodies against ACAA1 include, but are not limited to, Rabbit polyclonal anti-ACAA1 Cat# HPA006764 from atlas antibodies (just recognizes the first transcript); and Mouse polyclonal antibody raised against a full-length human ACAA1 protein. Catalog #: H00000030-B01 from abnova (MaxPab).

Example 8

AP1M2

AP1M2 (adaptor-related protein complex 1, mu 2 subunit) also known as D9Ertd818e, HSMU1B, MU-1B, MU1B) was found to be overexpressed in endometrial cancer primary tissue as compared to normal endometrial tissue by the microarray experiment described in Example 1. Further studies using RT-PCR demonstrated that AP1M2 was overexpressed in primary endometrial cancer tissue as compared to normal endometrial tissue and it was surprisingly found that AP1M2 was overexpressed in samples obtained from uterine fluid (e.g., aspirates) from patients having endometrial cancer by the method described in Examples 2-4. Example 5 shows that AP1M2 can be combined with other biomarkers to give excellent predictive power for diagnosis of endometrial cancer.

AP1M2 is a subunit of the heterotetrameric clathrin adaptor-related protein complex 1 (AP-1), that play pivotal roles in many vesicle trafficking pathways within the cell. This protein is capable of interacting with tyrosine-based sorting signals. AP1 is expressed exclusively in epithelial cells. All AP complexes comprise two large subunits of 100-130 kDa ($\alpha$ and $\beta$1 in AP1), a medium subunit of 50 kDa ($\mu$l in AP1), and a small subunit of 17-20 kDa ($\sigma$1 in AP1). PMID: 10338135

In clathrin-coated vesicles, AP-2 is located between the lipid bilayer and clathrin lattice, and presumably is anchoring clathrin to membrane. AP1M2 is member of the adaptor medium chain family termed Mu1B, which is specifically expressed in polarized epithelial cells and some exocrine cells. Mu1B is most closely related to the ubiquitously-expressed Mu1A subunit of AP-1 (79% identity at the amino acid level).

The sequence of an mRNA corresponding to AP1M2 is given in ENSEMBL accession number ENST00000250244 and has a sequence as in SEQ ID NO:40

```
GGCGCTTCCGCAGGAAGAAGGAAGCGGCGCCGCCATCGCCTCCCGGCGCTCCCTCCCCGACTCCTAAGTC

CTTCGGCCGCCACCATGTCCGCCTCGGCTGTCTTCATTCTGGACGTTAAGGGCAAGCCATTGATCAGCCG

CAACTACAAGGGCGATGTGGCCATGAGCAAGATTGAGCACTTCATGCCTTTGCTGGTACAGCGGGAGGAG

GAAGGCGCCCTGGCCCCGCTGCTGAGCCACGGCCAGGTCCACTTCCTATGGATCAAACACAGCAACCTCT

ACTTGGTGGCCACCACATCGAAGAATGCCAATGCCTCCCTGGTGTACTCCTTCCTGTATAAGACAATAGA

GGTATTCTGCGAATACTTCAAGGAGCTGGAGGAGGAGAGCATCCGGGACAACTTTGTCATCGTCTACGAG

TTGCTGGACGAGCTCATGGACTTTGGCTTCCCGCAGACCACCGACAGCAAGATCCTGCAGGAGTACATCA

CTCAGCAGAGCAACAAGCTGGAGACGGGCAAGTCACGGGTGCCACCCACTGTCACCAACGCTGTGTCCTG

GCGCTCCGAGGGTATCAAGTATAAGAAGAACGAGGTCTTCATTGATGTCATAGAGTCTGTCAACCTGCTG

GTCAATGCCAACGGCAGCGTCCTTCTGAGCGAAATCGTCGGTACCATCAAGCTCAAGGTGTTTCTGTCAG

GAATGCCAGAGCTGCGGCTGGGCCTCAATGACCGCGTGCTCTTCGAGCTCACTGGCCGCAGCAAGAACAA

ATCAGTAGAGCTGGAGGATGTAAAATTCCACCAGTGCGTGCGGCTCTCTCGCTTTGACAACGACCGCACC

ATCTCCTTCATCCCGCCTGATGGTGACTTTGAGCTCATGTCATACCGCCTCAGCACCCAGGTCAAGCCAC

TGATCTGGATTGAGTCTGTCATTGAGAAGTTCTCCCACAGCCGCGTGGAGATCATGGTCAAGGCCAAGGG

GCAGTTTAAGAAACAGTCAGTGGCCAACGGTGTGGAGATATCTGTGCCTGTACCCAGCGATGCCGACTCC

CCCAGATTCAAGACCAGTGTGGGCAGCGCCAAGTATGTGCCGGAGAGAAACGTCGTGATTTGGAGTATTA

AGTCTTTCCCGGGGGGCAAGGAGTACTTGATGCGAGCCCACTTTGGCCTCCCCAGTGTGGAAAAGGAAGA

GGTGGAGGGCCGGCCCCCCATCGGGGTCAAGTTTGAGATCCCCTACTTCACCGTCTCTGGGATCCAGGTC

CGATACATGAAGATCATTGAGAAAAGTGGTTACCAGGCCCTGCCCTGGGTTCGCTACATCACCCAGAGTG

GCGATTACCAACTTCGTACCAGCTAGAAGGGAGAAGAGATGGGGGCTTGAACACGGGGCTTCCTTACAGC

CCCGGATGCAGATTTTAGAGGGAGGGCAGGTGCGGGCTGTGTGTGTCTGTGAGGGCAGGTCCTGGACT

TGGCAGTTTCTTGCTCCCAGCACCCGCCCCTTCCTCACCTCTTCCTTATTCCATAGGCTGGGAGAGAAAC

TCTCTGCTTCCCTCGCCCTTGGAGCTTTCCCCATCCCCCTGATTTTATATGAAGAAATAGAAGAGGGGCT

TGAAGTCCCCCTCGCGAGTGCCTTCTTGCAATTACCTGCCTTAGCGGGTGTTGCGGGTCCCTCCTTCACA

GCCGCTGAGCCCAGAGGTCCCGCTGGCCCCTCCTCTGAATTTTAGGATGTCATTAAAAAGATGAATCTA
```

The corresponding amino acid sequence is given in ENSEMBL accession no. ENSP00000250244 and has a sequence as in SEQ ID NO:41

```
MSASAVFILDVKGKPLISRNYKGDVAMSKIEHFMPLLVQREEEGALAPLLSHGQVHFLWIKHSNLYLVATTSKNA

NASLVYSFLYKTIEVFCEYFKELEEES

IRDNFVIVYELLDELMDFGFPQTTDSKILQEYITQQSNKLETGKSRVPPTVTNAVSWR

SEGIKYKKNEVFIDVIESVNLLVNANGSVLLSEIVGTIKLKVFLSGMPELRLGLNDRV

LFELTGRSKNKSVELEDVKFHQCVRLSRFDNDRTISFIPPDGDFELMSYRLSTQVKPL

IWIESVIEKFSHSRVEIMVKAKGQFKKQSVANGVEISVPVPSDADSPRFKTSVGSAKY

VPERNVVIWSIKSFPGGKEYLMRAHFGLPSVEKEEVEGRPPIGVKFEIPYFTVSGIQV

RYMKIIEKSGYQALPWVRYITQSGDYQLRTS
```

Primers for amplifying the sequence ENST00000250244 can be designed using primer design software such as Oligo Calc.

Examples of primer pairs for amplifying AP1M2 include:

Forward
SEQ ID NO: 42
CGCCACCATGTCCGCCTCGGCTG

Reverse
SEQ ID NO: 43
GCTCAATCTTGCTCATGGCCAC (Ex2)

Forward
SEQ ID NO: 44
CAGGTCCACTTCCTATGGATC (ex2)

Reverse
SEQ ID NO: 45
CAAAGTTGTCCCGGATGCTC (Ex4)

Forward
SEQ ID NO: 46
CGCTCCGAGGGTATCAAG (EX5)

Reverse
SEQ ID NO: 47
CTTGCTGCGGCCAGTGAGC (ex6-7)

Forward
SEQ ID NO: 48
GACTTTGAGCTCATGTCATACC (Ex7)

Reverse
SEQ ID NO: 49
CTTAATACTCCAAATCACGACG (Ex9)

Forward
SEQ ID NO: 50
GTTTGAGATCCCCTACTTC (Ex10)

Reverse
SEQ ID NO: 51
GCCTGGTAACCACTTTTCTCAATG (Ex11)

Forward
SEQ ID NO: 52
CTGGGTTCGCTACATCACC (Ex11)

Reverse
SEQ ID NO: 53
GCCCCGTGTTCAAGC (Ex12)

Forward
SEQ ID NO: 54
CATGCCTTTGCTGGTACAG (Ex2)

Reverse
SEQ ID NO: 55
GAGTACACCAGGGAGGCATTG (Ex3)

Forward
SEQ ID NO: 56
CTCCCTGGTGTACTCCTTC (Ex3)

Reverse
SEQ ID NO: 57
GCTGTCGGTGGTCTGCGGGAA G (Ex4)

Forward
SEQ ID NO: 58
CAGCAAGATCCTGCAGGAG (Ex4-5)

Reverse
SEQ ID NO: 59
CAGGTTGACAGACTCTATG (Ex5)

Other sets of primers can be readily designed by the skilled artisan and/or are known in the art.

Probes for detecting AP1M2 can be derived from any number of sources depending on the desired use (e.g., using the above described primers and appropriate reagents). Examples of probes include:

SEQ ID NO: 60
ATGAAGAAATAGAAGAGGGGCTTGAAGTCCTCCTCGCGAGTGCCTTCTT GCAATTACCTG

SEQ ID NO: 61
CCAGGTCCACTTCCTATGGATCAAACACAGCAACCTCTACTTGGTGGCC ACCACATCG

SEQ ID NO: 62
GACAATAGAGGTATTCTGCGAATACTTCAAGGAGCTGGAGGAG

SEQ ID NO: 63
CAATGACCGCGTGCTCTTCGAGCTCACTGGCCGCAGCAAGAACAAATCA GTAGA

SEQ ID NO: 64
TTTCCCGGGGGCAAGGAGTACTTGATGCGAGCCCACTTTGGCCTCCCC AGTGTGG

Other probes to AP1M2 are known in the art and/or can be readily designed by the skilled artisan.

Antibodies against AP1M2 include, but are not limited to, Proteintech Group, Inc. Cat#10618-1-AP1M2 which is an affinity purified rabbit polyclonal antibody with an antigen which was a recombinant AP1M2 protein that included the amino acids 1-320 of the protein and from Abnova Cat# H00010053-B01, which is a mouse polyclonal antibody against the full length protein.

Example 9

CGN

CGN (also known as DKFZp779N1112, FLJ39281, and KIAA1319) was found to be overexpressed in endometrial cancer primary tissue as compared to normal endometrial tissue by the microarray experiment described in Example 1. Further studies using RT-PCR demonstrated that CGN was overexpressed in primary endometrial cancer tissue as compared to normal endometrial tissue and it was surprisingly found that CGN was overexpressed in samples obtained from uterine fluid (e.g., aspirates) from patients having endometrial cancer by the method described in Examples 2-4. Example 5 shows that CGN can be combined with other biomarkers to give excellent predictive power for diagnosis of endometrial cancer.

The sequence of an mRNA corresponding to CGN is given in ENSEMBL accession number ENST00000271636 and has a sequence as in SEQ ID NO:65

ENSG00000143375: gene, just one transcript
ENST00000271636
GAGGGAGCTCCGAGGACGAGGGGGAGGGCCGGAGCTGCGCGTGCTGCTTTGCCCGAGCCCGAGCCCGAGC

CCGAGCCCGAGCCCGAGCCCGAGCCCGAACGCAAGCCTGGGAGCGCGGAGCCCGGCTAGGGACTCCTCCT

-continued

```
ATTTATGGAGCAGGCACCCAACATGGCTGAGCCCCGGGGCCCCGTAGACCATGGAGTCCAGATTCGCTTC

ATCACAGAGCCAGTGAGTGGTGCAGAGATGGGCACTCTACGTCGAGGTGGACGACGCCCAGCTAAGGATG

CAAGAGCCAGTACCTACGGGGTTGCTGTGCGTGTGCAGGGAATCGCTGGGCAGCCCTTTGTGGTGCTCAA

CAGTGGGGAGAAAGGCGGTGACTCCTTTGGGGTCCAAATCAAGGGGGCCAATGACCAAGGGGCCTCAGGA

GCTCTGAGCTCAGATTTGGAACTCCCTGAGAACCCCTACTCTCAGGTCAAGGGATTTCCTGCCCCCTCGC

AGAGCAGCACATCTGATGAGGAGCCTGGGGCCTACTGGAATGGAAAGCTACTCCGTTCCCACTCCCAGGC

CTCACTGGCAGGCCCTGGCCCAGTGGATCCTAGTAACAGAAGCAACAGCATGCTGGAGCTAGCCCCGAAA

GTGGCTTCCCCAGGTAGCACCATTGACACTGCTCCCCTGTCTTCAGTGGACTCACTCATCAACAAGTTTG

ACAGTCAACTTGGAGGCCAGGCCCGGGGTCGGACTGGCCGCCGAACACGGATGCTACCCCCTGAACAGCG

CAAACGGAGCAAGAGCCTGGACAGCCGCCTCCCACGGGACACCTTTGAGGAACGGGAGCGCCAGTCCACC

AACCACTGGACCTCTAGCACAAAATATGACAACCATGTGGGCACTTCGAAGCAGCCAGCCCAGAGCCAGA

ACCTGAGTCCTCTCAGTGGCTTTAGCCGTTCTCGTCAGACTCAGGACTGGGTCCTTCAGAGTTTTGAGGA

GCCGCGGAGGAGTGCACAGGACCCCACCATGCTGCAGTTCAAATCAACTCCAGACCTCCTTCGAGACCAG

CAGGAGGCAGCCCCACCAGGCAGTGTGGACCATATGAAGGCCACCATCTATGGCATCCTGAGGGAGGGAA

GCTCAGAAAGTGAAACCTCTGTGAGGAGGAAGGTTAGTTTGGTGCTGGAGAAGATGCAGCCTCTAGTGAT

GGTTTCTTCTGGTTCTACTAAGGCCGTGGCAGGGCAGGGTGAGCTTACCCGAAAAGTGGAGGAGCTACAG

CGAAAGCTGGATGAAGAGGTGAAGAAGCGGCAGAAGCTAGAGCCATCCCAAGTTGGGCTGGAGCGGCAGC

TGGAGGAGAAAACAGAAGAGTGCAGCCGACTGCAGGAGCTGCTGGAGAGGAGGAAGGGGGAGGCCCAGCA

GAGCAACAAGGAGCTCCAGAACATGAAGCGCCTCTTGGACCAGGGTGAAGATTTACGACATGGGCTGGAG

ACCCAGGTGATGGAGCTGCAGAACAAGCTGAAACATGTCCAGGGTCCTGAGCCTGCTAAGGAGGTGTTAC

TGAAGGACCTGTTAGAGACCCGGGAACTTCTGGAAGAGGTCTTGGAGGGGAAACAGCGAGTAGAGGAGCA

GCTGAGGCTGCGGGAGCGGGAGTTGACAGCCCTGAAGGGGGCCCTGAAAGAGGAGGTAGCCTCCCGTGAC

CAGGAGGTGGAACATGTCCGGCAGCAGTACCAGCGAGACACAGAGCAGCTCCGCAGGAGCATGCAAGATG

CAACCCAGGACCATGCAGTGCTGGAGGCCGAGAGGCAGAAGATGTCAGCCCTTGTGCGAGGGCTGCAGAG

GGAGCTGGAGGAGACTTCAGAGGAGACAGGGCATTGGCAGAGTATGTTCCAGAAGAACAAGGAGGATCTT

AGAGCCACCAAGCAGGAACTCCTGCAGCTGCGAATGGAGAAGGAGGAGATGGAAGAGGAGCTTGGAGAGA

AGATAGAGGTCTTGCAGAGGGAATTAGAGCAGGCCCGAGCTAGTGCTGGAGATACTCGCCAGGTTGAGGT

GCTCAAGAAGGAGCTGCTCCGGACACAGGAGGAGCTTAAGGAACTGCAGGCAGAACGGCAGAGCCAGGAG

GTGGCTGGGCGACACCGGGACCGGGAGTTGGAGAAGCAGCTGGCGGTCCTGAGGGTCGAGGCTGATCGAG

GTCGGGAGCTGGAAGAACAGAACCTCCAGCTACAAAAGACCCTCCAGCAACTGCGACAGGACTGTGAAGA

GGCTTCCAAGGCTAAGATGGTGGCCGAGGCAGAGGCAACAGTGCTGGGGCAGCGGCGGGCCGCAGTGGAG

ACGACGCTTCGGGAGACCCAGGAGGAAAATGACGAATTCCGCCGGCGCATCCTGGGTTTGGAGCAGCAGC

TGAAGGAGACTCGAGGTCTGGTGGATGGTGGGGAAGCGGTGGAGGCACGACTACGGGACAAGCTGCAGCG

GCTGGAGGCAGAGAAACAGCAGCTGGAGGAGGCCCTGAATGCGTCCCAGGAAGAGGAGGGGAGTCTGGCA

GCAGCCAAGCGGGCACTGGAGGCACGCCTAGAGGAGGCTCAGCGGGGCTGGCCCGCCTGGGCAGGAGC

AGCAGACACTGAACCGGGCCCTGGAGGAGGAAGGGAAGCAGCGGAGGTGCTCCGGCGAGGCAAGGCTGA

GCTGGAGGAGCAGAAGCGTTTGCTGGACAGGACTGTGGACCGACTGAACAAGGAGTTGGAGAAGATCGGG

GAGGACTCTAAGCAAGCCCTGCAGCAGCTCCAGGCCCAGCTGGAGGATTATAAGGAAAAGGCCCGGCGGG

AGGTGGCAGATGCCCAGCGCCAGGCCAAGGATTGGGCCAGTGAGGCTGAGAAGACCTCTGGAGGACTGAG

CCGACTTCAGGATGAGATCCAGAGGCTGCGGCAGGCCCTGCAGGCATCCCAGGCTGAGCGGGACACAGCC
```

-continued

```
CGGCTGGACAAAGAGCTACTGGCCCAGCGACTGCAGGGGCTGGAGCAAGAGGCAGAGAACAAGAAGCGTT

CCCAGGACGACAGGGCCCGGCAGCTGAAGGGTCTCGAGGAAAAAGTCTCACGGCTGGAAACAGAGTTAGA

TGAGGAGAAGAACACCGTGGAGCTGCTAACAGATCGGGTGAATCGTGGCCGGGACCAGGTGGATCAGCTG

AGGACAGAGCTCATGCAGGAAAGGTCTGCTCGGCAGGACCTGGAGTGTGACAAAATCTCCTTGGAGAGAC

AGAACAAGGACCTGAAGACCCGGTTGGCCAGCTCAGAAGGCTTCCAGAAGCCTAGTGCCAGCCTCTCTCA

GCTTGAGTCCCAGAATCAGTTGTTGCAGGAGCGGCTACAGGCTGAAGAGAGGGAGAAGACAGTTCTGCAG

TCTACCAATCGAAAACTGGAGCGGAAAGTTAAAGAACTATCCATCCAGATTGAAGACGAGCGGCAGCATG

TCAATGACCAGAAAGACCAGCTAAGCCTGAGGGTGAAGGCTTTGAAGCGTCAGGTGGATGAAGCAGAAGA

GGAAATTGAGCGACTGGACGGCCTGAGGAAGAAGGCCCAGCGTGAGGTGGAGGAGCAGCATGAGGTCAAT

GAACAGCTCCAGGCCCGGATCAAGTCTCTGGAGAAGGACTCCTGGCGCAAAGCTTCCCGCTCAGCTGCTG

AGTCAGCTCTCAAAAACGAAGGGCTGAGCTCAGATGAGGAATTCGACAGTGTCTACGATCCCTCGTCCAT

TGCATCACTGCTTACGAGAGCAACCTACAGACCAGCTCCTGTTAGCTCGTGGTCCTCAAGGACTCAGAA

ACCAGGCTCGAGGCCTATCCCAGCAAGTGCTGCTCTGCTCTGCCCACCCTGGGTTCTGCATTCCTATGGG

TGACCCAATTATTCAGACCTAAGACAGGGAGGGGTCAGAGTGATGGTGATAAAAAAAAAAAATCATCAGC

AATAAGCTGATAGATGGACTTTCCACTGTAGGAGTGGACATTTCAAGCCAACTGAGCCTTTTCCTCAAGT

GCCGACACCTCCCTCATCTCTCTTATAGTGGAAGGATGGTCAGCATTAGGCTGATGGGGACTGAGAAGGA

TAGGAAGGGATAGAAATTGCCATGTGTATAAAGCTTTATTCTTTAGCCCTTAACCCTAAGGCTCAGGGAA

ATACCCTATGTTATTGTGCTCCCTGGATTCCTGCAACTCATTTTCCTTCCACTCTGGAGCAGGGTGAGGG

GAATGTTATGGGTAACAGACATGCAGGCATGGCTCTACCCATTTCTTTGCACAAGTATGGGGCCCATGTG

GTAGTCCCCATACCCCTCCAGTTCCTATATTTTTGTCTTCTTCCTTTCCCCTCTTTGCCATTCCTACCTT

GCATTTTCCTGTCAGTGCCTTAGCCAAGGCAAGGAGATAAGGATGCTCTTCTTGCTTTTTATATCTGCA

CATTCATACCTCTCCAAAGACCAGCTTTTCCCCAGCCAGGGCCCTCAGCCTTCCCTGCTGCCCCAGTGAT

TGATTGAGAGAGCTGTTGGGGTTTCTCTGCCAATGACCCCTGGGAGAGGGACTTTGGTAGGGTCATGATA

AAGTGGCGGGGGTCTGGTCCTGCTCAGGGTTTTCATCCTTCCTCCTCTCCCTCCTCTGTGACTGTGGATA

TGGTTATAAGGTGGTTGCACCTGGGAGCCCTGACAACTGGCTGCACAAATTCCAAAAGTAAAGGTGTCAG

TCCCTGTGGCCTTCCTTGGGGCTTCTCTGACCACATGTGCCCAACTTCAATAAGAGAACCAAGGGACCCT

CATTTTCTGAGGTGCTTGGCTCTGATTCAGGGCTTTGCAAGGGGTTAGAAGCTGACTGTAAAAATGGGAA

GAGGCAACGGAAGACATTTATTTCTCCTTTGGATTTTGGGGAGAACCAAGCCCTGGTAGGGAAGAGGTAA

GGGGGATGATTCACCTCCATATTTCCTAAGCAGGTTGTATAGGGAGCCGGTGGCAGGAGGAAGGCTGTTT

TCACAAATGACTTGTAATGTCGTGATTAAAAAAATTCCTATATTCTTCTGCAAATCAAACGTTCTTTCCC

AATCCAATCCAGCCTTGGTTTTATTTTAAATTAAATATTAAAATTACACATTTATATTGAAAAAAAAAA

AAAAAAAAAAAAAAAAAAAAAA
```

The start and stop codons are indicated in bold.

The corresponding amino acid sequence is given in ENSEMBL accession no. ENSP00000271636 and has a sequence as in SEQ ID NO:66

MEQAPNMAEPRGPVDHGVQIRFITEPVSGAEMGTLRRGGRRPAKDARAS
TYGVAVRVQGIAGQPFVVLNSGEKGGDSFGVQIKGANDQGASGALSSDL
ELPENPYSQVKGFPAPSQSSTSDEEPGAYWNGKLLRSHSQASLAGPGPV
DPSNRSNSMLELAPKVASPGSTIDTAPLSSVDSLINKFDSQLGGQARGR
TGRRTRMLPPEQRKRSKSLDSRLPRDTFEERERQSTNHWTSSTKYDNHV
GTSKQPAQSQNLSPLSGFSRSRQTQDWVLQSFEEPRRSAQDPTMLQFKS
TPDLLRDQQEAAPPGSVDHMKATIYGILREGSSESETSVRRKVSLVLEK
MQPLVMVSSGSTKAVAGQGELTRKVEELQRKLDEEVKKRQKLEPSQVGL
ERQLEEKTEECSRLQELLERRKGEAQQSNKELQNMKRLLDQGEDLRHGL
ETQVMELQNKLKHVQGPEPAKEVLLKDLLETRELLEEVLEGKQRVEEQL
RLRERELTALKGALKEEVASRDQEVEHVRQQYQRDTEQLRRSMQDATQD

-continued

HAVLEAERQKMSALVRGLQRELEETSEETGHWQSMFQKNKEDLRATKQE

LLQLRMEKEEMEEELGEKIEVLQRELEQARASAGDTRQVEVLKKELLRT

QEELKELQAERQSQEVAGRHRDRELEKQLAVLRVEADRGRELEEQNLQL

QKTLQQLRQDCEEASKAKMVAEAEATVLGQRRAAVETTLRETQEENDEF

RRRILGLEQQLKETRGLVDGGEAVEARLRDKLQRLEAEKQQLEEALNAS

QEEEGSLAAAKRALEARLEEAQRGLARLGQEQQTLNRALEEEGKQREVL

RRGKAELEEQKRLLDRTVDRLNKELEKIGEDSKQALQQLQAQLEDYKEK

ARREVADAQRQAKDWASEAEKTSGGLSRLQDEIQRLRQALQASQAERDT

ARLDKELLAQRLQGLEQEAENKKRSQDDRARQLKGLEEKVSRLETELDE

EKNTVELLTDRVNRGRDQVDQLRTELMQERSARQDLECDKISLERQNKD

LKTRLASSEGFQKPSASLSQLESQNQLLQERLQAEEREKTVLQSTNRKL

ERKVKELSIQIEDERQHVNDQKDQLSLRVKALKRQVDEAEEEIERLDGL

RKKAQREVEEQHEVNEQLQARIKSLEKDSWRKASRSAAESALKNEGLSS

DEEFDSVYDPSSIASLLTESNLQTSSC

Primers for amplifying the sequence CGN can be designed using primer design software such as Oligo Calc. Examples of primer pairs for amplifying CGN include those in

```
                                        SEQ ID NO: 67
Forward  GCTTTAGCCGTTCTCGTCA SEQ ID NO: 68
Reverse  CTGGTCTCGAAGGAGGTCTG SEQ ID NO: 69
Forward  CAGACCTCCTTCGAGACCAG SEQ ID NO: 70
Reverse  TTCCTCCTCACAGAGGTTTCA SEQ ID NO: 71
Forward  TACAGCGAAAGCTGGATGAA SEQ ID NO: 72
Reverse  AGTCGGCTGCACTCTTCTGT SEQ ID NO: 73
Forward  TGCAGAACAAGCTGAAACAT SEQ ID NO: 74
Reverse  GCTGCTCCTCTACTCGCTGT SEQ ID NO: 75
Forward  GGGCATTGGCAGAGTATGTT SEQ ID NO: 76
Reverse  TTCCATCTCCTCCTTCTCCA SEQ ID NO: 77
Forward  CAGCAACTGCGACAGGACT SEQ ID NO: 78
Reverse  CATTTTCCTCCTGGGTCTCC SEQ ID NO: 79:
Forward  CTGAGCTGGAGGAGCAGAAG SEQ ID NO: 80
Reverse  TGCAGGGCTTGCTTAGAGTC SEQ ID NO: 81
Forward  TGGAGCAAGAGGCAGAGAAC SEQ ID NO: 82
Reverse  ACTCTGTTTCCAGCCGTGAG
```

Other sets of primers can be readily designed by the skilled artisan and/or are known in the art.

Probes for detecting CGN can be derived from any number of sources depending on the desired use (e.g., using the above described primers and appropriate reagents). Other examples of probes include

```
                                        SEQ ID NO: 83
CAGGACTGGGTCCTTCAGAG

SEQ ID NO: 84
CAGGCAGTGTGGACCATATG

SEQ ID NO: 85
GCTAGAGCCATCCCAAGTTG

SEQ ID NO: 86
TGAGCCTGCTAAGGAGGTGT

SEQ ID NO: 87
TAGAGCCACCAAGCAGGAAC

SEQ ID NO: 88
TTCCAAGGCTAAGATGGTGG

SEQ ID NO: 89
GACAGGACTGTGGACCGACT

SEQ ID NO: 90
TGAAGGGTCTCGAGGAAAAA

Probe from the array
                                        SEQ ID NO: 91
GGGAAGAGGTAAGGGGATGATTCACCTCCATATTTCCTAAGCAGGTTG
TATAGGGAGCC
```

Antibodies to CGN include, but are not limited to Rabbit Anti-Human Cingulin (CGN) Polyclonal, Unconjugated Cat# LS-C22229-100, from lifespan bioscience (C-terminal region); and Mouse Anti-Human Cingulin (CGN) Monoclonal, Unconjugated, Clone 6a40 Cat# LS-C22230-100, from Lifespan Bioscience (C-terminal region).

Example 10

DDR1

DDR1 was found to be overexpressed in endometrial cancer primary tissue as compared to normal endometrial tissue by the microarray experiment described in Example 1. Further studies using RT-PCR demonstrated that DDR1 was overexpressed in primary endometrial cancer tissue as compared to normal endometrial tissue and it was surprisingly found that DDR1 was overexpressed in samples obtained from uterine fluid (e.g., aspirates) from patients having endometrial cancer by the method described in Examples 2-4. Example 5 shows that DDR1 can be combined with other biomarkers to give excellent predictive power for diagnosis of endometrial cancer.

The sequence of an mRNA corresponding to DDR1 is given in ENSEMBL accession no. ENST00000376570 and has a sequence as in SEQ ID NO:92

```
   1 GTCTTCCCCTCGTGGGCCCTGAGCGGGACTGCAGCCAGCCCCCTGGGGCGCCAGCTTTG
  61 AGGCCCCCGACAGCTGCTCTCGGGAGCCGCCTCCCGACACCCGAGCCCCGCCGGCGCCTC
 121 CCGCTCCCGGCTCCCGGCTCCTGGCTCCCTCCGCCTCCCCCGCCCCTCGCCCCGCCGCC
 161 AAGAGGCCCCGCTCCCGGGTCGGACGCCTGGGTCTGCCGGGAAGAGCGATGAGAGGTGTC
 241 TGAAGGTGGCTATTCACTGAGCGATGGGGTTGGACTTGAAGGAATGCCAAGAGATGCTGC
 301 CCCCACCCCCTTAGGCCCGAGGGATCAGGAGCTATGGGACCAGAGGCCCTGTCATCTTTA
 361 CTGCTGCTGCTCTTGGTGGCAAGTGGAGATGCTGACATGAAGGGACATTTTGATCCTGCC
 421 AAGTGCCGCTATGCCCTGGGCATGCAGGACCGGACCATCCCAGACAGTGACATCTCTGCT
 431 TCCAGCTCCTGGTCAGATTCCACTGCCGCCCGCCACAGCAGGTTGGAGAGCAGTGACGGG
 541 GATGGGGCCTGGTGCCCCGCAGGGTCGGTGTTTCCCAAGGAGGAGGAGTACTTGCAGGTG
 601 GATCTACAACGACTGCACCTGGTGGCTCTGGTGGGCACCCAGGGACGGCATGCCGGGGGC
 661 CTGGGCAAGGAGTTCTCCCGGAGCTACCGGCTGCGTTACTCCCGGGATGGTCGCCGCTGG
 721 ATGGGCTGGAAGGACCGCTGGGGTCAGGAGGTGATCTCAGGCAATGAGGACCCTGAGGGA
 781 GTGGTGCTGAAGGACCTTGGGCCCCCCATGGTTGCCCGACTGGTTCGCTTCTACCCCCGG
 841 GCTGACCGGGTCATGAGCGTCTGTCTGCGGGTAGAGCTCTATGGCTGCCTCTGGAGGGAT
 901 GGACTCCTGTCTTACACCGCCCCTGTGGGGCAGACAATGTATTTATCTGAGGCCGTGTAC
 961 CTCAACGACTCCACCTATGACGGACATACCGTGGGCGGACTGCAGTATGGGGGTCTGGGC
1021 CAGCTGGCAGATGGTGTGGTGGGGCTGGATGACTTTAGGAAGAGTCAGGAGCTGCGGGTC
1081 TGGCCAGGCTATGACTATGTGGGATGGAGCAACCACAGCTTCTCCAGTGGCTATGTGGAG
1141 ATGGAGTTTGAGTTTGACCGGCTGAGGGCCTTCCAGGCTATGCAGGTCCACTGTAACAAC
1201 ATGCACACGCTGGGAGCCCGTCTGCCTGGCGGGGTGGAATGTCGCTTCCGGCGTGGCCCT
1261 GCCATGGCCTGGGAGGGGAGCCCATGCGCCACAACCTAGGGGGCAACCTGGGGACCCC
1321 AGAGCCCGGGCTGTCTCAGTGCCCCTTGGCGGCCGTGTGGCTCGCTTTCTGCAGTGCCGC
1381 TTCCTCTTTGCGGGGCCCTGGTTACTCTTCAGCGAAATCTCCTTCATCTCTGATGTGGTG
1441 AACAATTCCTCTCCGGCACTGGGAGGCACCTTCCCGCCAGCCCCTGGTGGCCGCCTGGC
1501 CCACCTCCCACCAACTTCAGCAGCTTGGAGCTGGAGCCCAGAGGCCAGCAGCCCGTGGCC
1561 AAGGCCGAGGGGAGCCCGACCGCCATCCTCATCGGCTGCCTGGTGGCCATCATCCTGCTC
1621 CTGCTGCTCATCATTGCCCTCATGCTCTGGCGGCTGCACTGGCGCAGGCTCCTCAGCAAG
1681 GCTGAACGGAGGGTGTTGGAAGAGGAGCTGACGGTTCACCTCTCTGTCCCTGGGGACACT
1741 ATCCTCATCAACAACCGCCCAGGTCCTAGAGAGCCACCCCCGTACCAGGAGCCCCGGCCT
1801 CGTGGGAATCCGCCCCACTCCGCTCCCTGTGTCCCCAATGGCTCTGCCTACAGTGGGGAC
1861 TATATGGAGCCTGAGAAGCCAGGCGCCCCGCTTCTGCCCCCACCTCCCCAGAACAGCGTC
1921 CCCCATTATGCCGAGGCTGACATTGTTACCCTGCAGGGCGTCACCGGGGGCAACACCTAT
1588 CCCCATTATGTCGAGGCTGACATTGTTACCCTGCAGGGCGTCACCGGGGGCAACACCTAT
1981 GCTGTGCCTGCACTGCCCCCAGSGGCAGTCGGGGATGGGCCCCCCAGAGTGGATTTCCCT
1648 GCTGTGCCTGCACTGCCCCCAGGGGCAGTCGGGGATGGGCCCCCCAGAGTGGATTTCCCT
2041 CGATCTCGACTCCGCTTCAAGGAGAAGCTTGGCGAGGGCCAGTTTGGGGAGGTGCACCTG
1708 CGATCTCGACTCCGCTTCAAGGAGAAGCTTGGCGAGGGCCAGTTTGGGGAGGTGCACCTG
2101 TGTGAGGTCGACAGCCCTCAAGATCTGGTTAGTCTTGATTTCCCCCTTAATGTGCGTAAG
1768 TGTGAGGTCGACAGCCCTCAAGATCTGGTTAGTCTTGATTTCCCCCTTAATGTGCGTAAG
2161 GGACACCCTTTGCTGGTAGCTGTCAAGATCTTACGGCCAGATGCCACCAAGAATGCCAGG
```

-continued

```
1828  GGACACCCTTTGCTGGTAGCTGTCAAGATCTTACGGCCAGATGCCACCAAGAATGCCAGG

2221  AATGATTTCCTGAAAGAGGTGAAGATCATGTCGAGGCTCAAGGACCCAAACATCATTCGG

1888  AATGATTTCCTGAAAGAGGTGAAGATCATGTCGAGGCTCAAGGACCCAAACATCATTCGG

2281  CTGCTGGGCGTGTGTGTGCAGGACGACCCCCTCTGCATGATTACTGACTACATGGAGAAC

1948  CTGCTGGGCGTGTGTGTGCAGGACGACCCCCTCTGCATGATTACTGACTACATGGAGAAC

2341  GGCGACCTCAACCAGTTCCTCAGTGCCCACCAGCTGGAGGACAAGGCAGCCGAGGGGCC

2008  GGCGACCTCAACCAGTTCCTCAGTGCCCACCAGCTGGAGGACAAGGCAGCCGAGGGGCC

2401  CCTGGGGACGGGCAGGCTGCGCAGGGGCCCACCATCAGCTACCCAATGCTGCTGCATGTG

2068  CCTGGGGACGGGCAGGCTGCGCAGGGGCCCACCATCAGCTACCCAATGCTGCTGCATGTG

2461  GCAGCCCAGATCGCCTCCGGCATGCGCTATCTGGCCACACTCAACTTTGTACATCGGGAC

2128  GCAGCCCAGATCGCCTCCGGCATGCGCTATCTGGCCACACTCAACTTTGTACATCGGGAC

2521  CTGGCCACGCGGAACTGCCTAGTTGGGGAAAATTTCACCATCAAAATCGCAGACTTTGGC

2188  CTGGCCACGCGGAACTGCCTAGTTGGGGAAAATTTCACCATCAAAATCGCAGACTTTGGC

2581  ATGAGCCGGAACCTCTATGCTGGGGACTATTACCGTGTGCAGGGCCGGGCAGTGCTGCCC

2248  ATGAGCCGGAACCTCTATGCTGGGGACTATTACCGTGTGCAGGGCCGGGCAGTGCTGCCC

2641  ATCCGCTGGATGGCCTGGGAGTGCATCCTCATGGGGAAGTTCACGACTGCGAGTGACGTG

2308  ATCCGCTGGATGGCCTGGGAGTGCATCCTCATGGGGAAGTTCACGACTGCGAGTGACGTG

2701  TGGGCCTTTGGTGTGACCCTGTGGGAGGTGCTGATGCTCTGTAGGGCCCAGCCCTTTGGG

2368  TGGGCCTTTGGTGTGACCCTGTGGGAGGTGCTGATGCTCTGTAGGGCCCAGCCCTTTGGG

2761  CAGCTCACCGACGAGCAGGTCATCGAGAACGCGGGGGAGTTCTTCCGGGACCAGGGCCGG

2428  CAGCTCACCGACGAGCAGGTCATCGAGAACGCGGGGGAGTTCTTCCGGGACCAGGGCCGG

2821  CAGGTGTACCTGTCCCGGCCGCCTGCCTGCCCGCAGGGCCTATATGAGCTGATGCTTCGG

2488  CAGGTGTACCTGTCCCGGCCGCCTGCCTGCCCGCAGGGCCTATATGAGCTGATGCTTCGG

2881  TGCTGGAGCCGGGAGTCTGAGCAGCGACCACCCTTTTCCCAGCTGCATCGGTTCCTGGCA

2548  TGCTGGAGCCGGGAGTCTGAGCAGCGACCACCCTTTTCCCAGCTGCATCGGTTCCTGGCA

2941  GAGGATGCACTCAACACGGTGTGAATCACACATCCAGCTGCCCCTCCCTCAGGGAGCGAT

3001  CCAGGGGAAGCCAGTGACACTAAAACAAGAGGACACAATGGCACCTCTGCCCTTCCCCTC

3061  CCGACAGCCCATCACCTCTAATAGAGGCAGTGAGACTGCAGGTGGGCTGGGCCCACCCAG

3121  GGAGCTGATGCCCCTTCTCCCCTTCCTGGACACACTCTCATGTCCCCTTCCTGTTCTTCC

3181  TTCCTAGAAGCCCCTGTCGCCCACCCAGCTGGTCCTGTGGATGGGATCCTCTCCACCCTC

3241  CTCTAGCCATCCCTTGGGAAGGGTGGGGAGAAATATAGGATAGACACTGGACATGGCCC

3301  ATTGGAGCACCTGGGCCCCACTGGACAACACTGATTCCTGGAGAGGTGGCTGCGCCCCA

3361  GCTTCTCTCTCCCTGTCACACACTGGACCCCACTGGCTGAGAATCTGGGGGTGAGGAGGA

3421  CAAGAAGGAGAGGAAAATGTTTCCTTGTGCCTGCTCCTGTACTTGTCCTCAGCTTGGGCT

3481  TCTTCCTCCTCCATCACCTGAAACACTGGACCTGGGGGTAGCCCCGCCCCAGCCCTCAGT

3541  CACCCCCACTTCCCACTTGCAGTCTTGTAGCTAGAACTTCTCTAAGCCTATACGTTTCTG

3601  TGGAGTAAATATTGGGATTGGGGGAAAGAGGGAGCAACGGCCCATAGCCTTGGGGTTGG

3661  ACATCTCTAGTGTAGCTGCCACATTGATTTTTCTATAATCACTTGGGGTTTGTACATTTT

3721  TGGGGGGAGAGACACAGATTTTTACACTAATATATGGACCTAGCTTGAGGCAATTTTAAT

3781  CCCCTGCACTAGGCAGGTAATAATAAAGGTTGACTTTTCC
```

The corresponding amino acid sequence is given in ENSEMBL accession no. EP0000365754 and has a sequence as in SEQ ID NO:93

```
  1 MGPEALSSLLLLLLVASGDADMKGHFDPAKCRYALGMQDRTIPDSDISASSSWSDSTAAR

61 HSRLESSDGDGAWCPAGSVFPKEEEYLQVDLQRLHLVALVGTQGRHAGGLGKEFSRSYRL

121 RYSRDGRRWMGWKDRWGQEVISGNEDPEGVVLKDLGPPMVARLVRFYPRADRVMSVCLRV

181 ELYGCLWRDGLLSYTAPVGQTMYLSEAVYLNDSTYDGHTVGGLQYGGLGQLADGVVGLDD

241 FRKSQELRVWPGYDYVGWSNHSFSSGYVEMEFEFDRLRAFQAMQVHCNNMHTLGARLPGG

301 VECRFRRGPAMAWEGEPMRHNLGGNLGDPRARAVSVPLGGRVARFLQCRFLFAGPWLLFS

361 EISFISDVVNNSSPALGGTFPPAPWWPPGPPPTNFSSLELEPRGQQPVAKAEGSPTAILI

421 GCLVAIILLLLLIIALMLWRLHWRRLLSKAERRVLEEELTVHLSVPGDTILINNRPGPRE

481 PPPYQEPRPRGNPPHSAPCVPNGSAYSGDYMEPEKPGAPLLPPPPQNSVPHYAEADIVTL

541 QGVTGGNTYAVPALPPGAVGDGPPRVDFPRSRLRFKEKLGEGQFGEVHLCEVDSPQDLVS

601 LDFPLNVRKGHPLLVAVKILRPDATKNARNDFLKEVKIMSRLKDPNIIRLLGVCVQDDPL

661 CMITDYMENGDLNQFLSAHQLEDKAAEGAPGDGQAAQGPTISYPMLLHVAAQIASGMRYL

721 ATLNFVHRDLATRNCLVGENFTIKIADFGMSRNLYAGDYYRVQGRAVLPIRWMAWECILM

781 GKFTTASDVWAFGVTLWEVLMLCRAQPFGQLTDEQVIENAGEFFRDQGRQVYLSRPPACP

841 QGLYELMLRCWSRESEQRPPFSQLHRFLAEDALNTV
```

Primers for amplifying the sequence DDR1 can be designed using primer design software such as Oligo Calc and/or Primer 3.

Examples of primer pairs for amplifying DDR1 include those in

```
                            SEQ ID NO: 94
    Forward CATCTCTGCTTCCAGCTCCT

SEQ ID NO: 95
    Reverse TACTCCTCCTCCTTGGGAAA

SEQ ID NO: 96
    Forward AGCTACCGGCTGCGTTACT

SEQ ID NO: 97
    Reverse CTTCAGCACCACTCCCTCAG

SEQ ID NO: 98
    Forward CGTCTGTCTGCGGGTAGAG

SEQ ID NO: 99
    Reverse CCGTCATAGGTGGAGTCGTT

SEQ ID NO: 100
    Forward CAACGACTCCACCTATGACG

SEQ ID NO: 101
    Reverse TGCTCCATCCCACATAGTCA

SEQ ID NO: 102
    Forward TGACTATGTGGGATGGAGCA

SEQ ID NO: 103
    Reverse CCAGCGTGTGCATGTTGTTA

SEQ ID NO: 104
    Forward TGTCTCAGTGCCCCTTGG

SEQ ID NO: 105
    Reverse GTGCCGGAGAGGAATTGTT

SEQ ID NO: 106
    Forward ACCTCCCACCAACTTCAGC

SEQ ID NO: 107
    Reverse CAGCAGGAGCAGGATGATG

SEQ ID NO: 108
    Forward CATCATCCTGCTCCTGCTG

SEQ ID NO: 109
    Reverse CCAGGGACAGAGAGGTGAAC

SEQ ID NO: 110
    Forward ACCGCCCAGGTCCTAGAG

SEQ ID NO: 111
    Reverse CGGTAGGCTGGATTGGAGA

SEQ ID NO: 112
    Forward CACCCTTTGCTGGTAGCTGT

SEQ ID NO: 113
    Reverse CGAATGATGTTTGGGTCCTT
```

Other sets of primers can be readily designed by the skilled artisan and/or are known in the art.

Probes for detecting DDR1 can be derived from any number of sources depending on the desired use (e.g., using the above described primers and appropriate reagents). Other examples of probes include

```
    SEQ ID NO: 114    ACAGCAGGTTGGAGAGCAGT
    SEQ ID NO: 115    GTCAGGAGGTGATCTCAGGC
    SEQ ID NO: 116    CTCTATGGCTGCCTCTGGAG
    SEQ ID NO: 117    GTGGGGCTGGATGACTTTAG
    SEQ ID NO: 118    AGTTTGAGTTTGACCGGCTG
    SEQ ID NO: 119    CCCTGGTTACTCTTCAGCGA
```

-continued

| SEQ ID NO: 120 | CTTGGAGCTGGAGCCCAG |
| SEQ ID NO: 121 | AGGGTGTTGGAAGAGGAGCT |
| SEQ ID NO: 122 | ACTCTGCTCCCTGTGTCCC |
| SEQ ID NO: 123 | GCCAGGAATGATTTCCTGAA |

A probe used to detect the DDR1 nucleic acid that was used on the microarray has a sequence as in SEQ ID NO:124

ATTGGGATTGGGGGGAAAGAGGGAGCAACGGCCCATAGCCTTGGGGTT
GGACATCTCTAG

Other probes to DDR1 are known in the art and/or can be readily designed by the skilled artisan.

Antibodies against DDR1 include, but are not limited to, Rabbit polyclonal antibody to MCK10 from abcam cat# ab5508 epitope: aa31-47; and Mouse Anti-Human DDR1 Polyclonal Antibody, Unconjugated from abnova cat# H00000780-A01 against full length.

Example 11

EPS8L2

EPS8L2 (EPS8-like 2 also known as AI042819, AW545405, Eps8l2_predicted, Eps8l2 predicted, EPS8R2, FLJ16738, FLJ21935, FLJ22171, MGC126530, MGC3088) was found to be overexpressed in endometrial cancer primary tissue as compared to normal endometrial tissue by the microarray experiment described in Example 1. Further studies using RT-PCR demonstrated that EPS8L2 was overexpressed in primary endometrial cancer tissue as compared to normal endometrial tissue and it was surprisingly found that EPS8L2 was overexpressed in samples obtained from uterine fluid (e.g., aspirates) from patients having endometrial cancer by the method described in Examples 2-4. Example 5 shows that EPS8L2 can be combined with other biomarkers to give excellent predictive power for diagnosis of endometrial cancer.

The EPS8L2 gene encodes a protein that is related to epidermal growth factor receptor pathway substrate 8 (EPS8), a substrate for the epidermal growth factor receptor. The eps8Ls define a novel family of proteins responsible for functional redundancy in the RTK-activated signaling pathway leading to actin remodeling. Members of this family link growth factor stimulation to actin organization. Members of the eps8 family share a modular organization consisting of a putative PTB domain, a central SH3 domain and a C-terminal effector region. The SH3 domains of eps8Ls display unique binding preferences for peptides containing a proline-X-X-aspartate-tyrosine (pXXDY) consensus and constitute a phylogenetically distinct subfamily within the SH3 domain family. (PMID: 14565974).

Although EPS8L2 function is unknown, gene expression analyses of breast and thyroid cancers identified Eps8, another member of the family, as a novel putative oncogene and also it was implicated in tumor cell migration in fibrosarcoma cells. (PMID: 16618726) (PMID: 17075124) (PMID: 15289329)

The sequence of an mRNA corresponding to EPS8L2 is given in ENSEMBL accession no. ENST00000318562 and SEQ ID NO:125

ACTCCGCAACCTGTCGCTCAGGTTCCTCCTCTCCCGGCCCCGCCCCGGCCCGGCCCCGCCGAGCGTCCCA

CCCGCCCGCGGGAGACCTGGCGCCCCGGCCGAGGCGCGAACAGACGGACGCACCGGCGAGCGCCGAGGGG

ACAGGCCGAGCGCGGGGCGCCGGAGGCAGGTGTGGGACAGGCACTGGCCTCAGACCGGGGCCACACTGAG

GTCTGCCCTTCTCCCGCTGGCCGCCACCCAAGACACCATGAGCCAGTCCGGGGCCGTGAGCTGCTGCCCG

GGTGCCACCAATGGCAGCCTGGGCCGGTCCGACGGTGTGGCCAAGATGAGCCCCAAGGACCTGTTTGAGC

AGAGGAAGAAGTATTCCAACTCCAACGTCATCATGCACGAGACCTCGCAGTACCACGTCCAGCACCTGGC

CACATTCATCATGGACAAGAGCGAAGCCATCACGTCTGTGGACGACGCCATCCGGAAGCTGGTGCAGCTG

AGCTCCAAGGAGAAGATCTGGACCCAGGAGATGCTGCTGCAGGTGAACGACCAGTCGCTGCGGCTGCTGG

ACATCGAGTCACAGGAGGAGCTGGAAGACTTCCCGCTGCCCACGGTGCAGCGCAGCCAGACGGTCCTCAA

CCAGCTGCGCTACCCGTCTGTGCTGCTGCTCGTGTGCCAGGACTCGGAGCAGAGCAAGCCGGATGTCCAC

TTCTTCCACTGCGATGAGGTGGAGGCAGAGCTGGTGCACGAGGACATCGAGAGCGCGTTGGCCGACTGCC

GGCTGGGCAAGAAGATGCGGCCGCAGACCCTGAAGGGACACCAGGAGAAGATTCGGCAGCGGCAGTCCAT

CCTGCCTCCTCCCCAGGGCCCGGCGCCCATCCCCTTCCAGCACCGCGGCGGGGATTCCCCGGAGGCCAAG

AATCGCGTGGGCCCGCAGGTGCCACTCAGCGAGCCAGGTTTCCGCCGTCGGGAGTCGCAGGAGGAGCCGC

GGGCCGTGCTGGCTCAGAAGATAGAGAAGGAGACGCAAATCCTCAACTGCGCCCTGGACGACATCGAGTG

GTTTGTGGCCCGGCTGCAGAAGGCAGCCGAGGCTTTCAAGCAGCTGAACCAGCGGAAAAAGGGGAAGAAG

AAGGGCAAGAAGGCGCCAGCAGAGGGCGTCCTCACACTGCGGGCACGGCCCCCCTCTGAGGGCGAGTTCA

TCGACTGCTTCCAGAAAATCAAGCTGGCGATTAACTTGCTGGCAAAGCTGCAGAAGCACATCCAGAACCC

CAGCGCCGCGGAGCTCGTGCACTTCCTCTTCGGGCCTCTGGACCTGATCGTCAACACCTGCAGTGGCCCA

GACATCGCACGCTCCGTCTCCTGCCCACTGCTCTCCCGAGATGCCGTGGACTTCCTGCGCGGCCACCTGG

```
TCCCTAAGGAGATGTCGCTGTGGGAGTCACTGGGAGAGAGCTGGATGCGGCCCCGTTCCGAGTGGCCGCG
GGAGCCACAGGTGCCCCTCTACGTGCCCAAGTTCCACAGCGGCTGGGAGCCTCCTGTGGATGTGCTGCAG
GAGGCCCCTGGGAGGTGGAGGGGCTGGCGTCTGCCCCCATCGAGGAGGTGAGTCCAGTGAGCCGACAGT
CCATAAGAAACTCCCAGAAGCACAGCCCCACTTCAGAGCCCACCCCCCCGGGGGATGCCCTACCACCAGT
CAGCTCCCCACATACTCACAGGGGCTACCAGCCAACACCAGCCATGGCCAAGTACGTCAAGATCCTGTAT
GACTTCACAGCCCGAAATGCCAACGAGCTATCGTGCTCAAGGATGAGGTCCTAGAGGTGCTGGAGGACG
GCCGGCAGTGGTGGAAGCTGCGCAGCCGCAGCGGCCAGGCGGGGTACGTGCCCTGCAACATCCTAGGCGA
GGCGCGACCGGAGGACGCCGGCGCCCCGTTCGAGCAGGCCGGTCAGAAGTACTGGGGCCCCGCCAGCCCG
ACCCACAAGCTACCCCCAAGCTTCCCGGGGAACAAAGACGAGCTCATGCAGCACATGGACGAGGTCAACG
ACGAGCTCATCCGGAAAATCAGCAACATCAGGGCGCAGCCACAGAGGCACTTCCGCGTGGAGCGCAGCCA
GCCCGTGAGCCAGCCGCTCACCTACGAGTCGGGTCCGGACGAGGTCCGCGCCTGGCTGGAAGCCAAGGCC
TTCAGCCCGCGGATCGTGGAGAACCTGGGCATCCTGACCGGGCCGCAGCTCTTCTCCCTCAACAAGGAGG
AGCTGAAGAAAGTGTGCGGCGAGGAGGGCGTCCGCGTGTACAGCCAGCTCACCATGCAGAAGGCCTTCCT
GGAGAAGCAGCAAAGTGGGTCGGAGCTGGAAGAACTCATGAACAAGTTTCATTCCATGAATCAGAGGAGG
GGGGAGGACAGCTAGGCCCAGCTGCCTTGGGCTGGGGCCTGCGGAGGGGAAGCCCACCCACAATGCATGG
AGTATTATTTTTATATGTGTATGTATTTTGTATCAAGGACACGGAGGGGGTGTGGTGCTGGCTAGAGGTC
CCTGCCCCTGTCTGGAGGCACAACGCCCATCCTTAGGCCAAACAGTACCCAAGGCCTCAGCCCACACCAA
GACTAATCTCAGCCAAACCTGCTGCTTGGTGGTGCCAGCCCCTTGTCCACCTTCTCTTGAGGCCACAGAA
CTCCCTGGGGCTGGGGCCTCTTTCTCTGGCCTCCCCTGTGCACCTGGGGGGTCCTGGCCCCTGTGATGCT
CCtCCATCCCCACCCACTTCTACATCCATCCACACCCCAGGGTGAGCTGGAGCTCCAGGCTGGCCAGGCT
GAACCTCGCACACACGCAGAGTTCTGCTCCCTGAGGGGGGCCCGGGAGGGGCTCCAGCAGGAGGCCGTGG
GTGCCATTCGGGGAAAGTGGGGAACGCACACACACTTCACCTGCAAGGGCCGACAACGCAGGGGACACC
GTGCCGGCTTCAGACACTCCCAGCGCCCACTCTTACAGGCCCAGGACTGGAGCTTTCTCTGGCCAAGTTT
CAGGCCAATGATCCCCGCATGGTGTTGGGGGTGCTGGTGTGTCTTGGTGCCTGGACTTGAGTCTCACCCT
ACAGATGAGAGGTGGCTGAGGCACCAGGGCTAAGCAATTAAACCAGTTAAGTCTCCCAGGAAAAAAAAAA
AAAAAA
```

The start and stop codons are indicated in bold as well as the position corresponding to the microarray probe.

The corresponding amino acid sequence is given in ENSEMBL accession no. ENSP00000320828 and has a sequence as in SEQ ID NO:126

MSQSGAVSCCPGATNGSLGRSDGVAKMSPKDLFEQRKKYSNSNVIMHE
TSQYHVQHLATFIMDKSEAITSVDDAIRKLVQLSSKEKIWTQEMLLQV
NDQSLRLLDIESQEELEDFPLPTVQRSQTVLNQLRYPSVLLLVCQDSE
QSKPDVHFFHCDEVEAELVHEDIESALADCRLGKKMRPQTLKGHQEKI
RQRQSILPPPOGPAPIPFQHRGGDSPEAKNRVGPQVPLSEPGFRRRES
QEEPRAVLAQKIEKETQILNCALDDIEWFVARLQKAAEAFKOLNORKK
GKKKGKKAPAEGVLTLRARPPSEGEFIDCFQKIKLAINLLAKLQKHIQ
NPSAAELVHFLFGPLDLIVNTCSGPDIARSVSCPLLSRDAVDFLRGHL
VPKEMSLWESLGESWMRPRSEWPREPOVPLYVPKFHSGWEPPVDVLQE
APWEVEGLASAPIEEVSPVSRQSIRNSQKHSPTSEPTPPGDALPPVSS
PHTHRGYQPTPAMAKYVKILYDFTARNANELSVLKDEVLEVLEDGRQW
WKLRSRSGOAGYVPCNILGEARPEDAGAPFEQAGQKYWGPASPTHKLP
PSFPGNKDELMQHMDEVNDELIRKISNIRAQPQRHFRVERSQPVSQPL
TYESGPDEVRAWLEAKAFSPRIVENLGILTGPQLFSLNKEELKKVCGE
EGVRVYSQLTMQKAFLEKQQSGSELEELMNKFHSMNQRRGEDS

Primers for amplifying the sequence ENST00000318562 can be designed using primer design software such as Oligo Calc and/or Primer 3. Examples of primer pairs for amplifying EPS8L2 include:

```
                                                    SEQ ID NO: 127
Forward GAG ACC TGG CGC CCC GGC (Ex1)

SEQ ID NO: 128
Reverse GTG GCC CCG GTC TGA GGC (Ex2)
```

```
                                                  SEQ ID NO: 129
Forward GAG CCA GTC CGG GGC CGT G (Ex2)

SEQ ID NO: 130
Reverse CTT GGG GCT CAT CTT GGC (Ex3)

SEQ ID NO: 131
Forward CGA CGG TGT GGC CAA GAT GAG (Ex3

SEQ ID NO: 132
Reverse CGT GGT ACT GCG AGG TC (Ex4)

SEQ ID NO: 133
Forward CTCCAACGTCATCATGCAC (Ex4)

SEQ ID NO: 134
Reverse GATGGCGTCGTCCACAGAC (Ex5)

SEQ ID NO: 135
Forward CAGTCGCTGCGGCTGCTGG (Ex5)

SEQ ID NO: 136
Reverse GGACCGTCTGGCTGCGCTG (Ex6)

SEQ ID NO: 137
Forward GATGTCCACTTCTTCCACTGC (Ex6)

SEQ ID NO: 138
Reverse CCGAATCTTCTCCTGGTGTC (Ex8)

SEQ ID NO: 139
Forward GAGGCCAAGAATCGCGTGGGC (Ex8)

SEQ ID NO: 140
Reverse GTCCAGGGCGCAGTTGAGG (Ex10)

SEQ ID NO: 141
Forward CGACTGCTTCCAGAAAATC (Ex11)

SEQ ID NO: 142
Reverse CGAAGAGGAAGTGCACGAG (Ex12)

SEQ ID NO: 143
Forward GATGTCGCTGTGGGAGTCAC (Ex13)

SEQ ID NO: 144
Reverse GAGGGGCACCTGTGGCTC (Ex14)

SEQ ID NO: 145
Forward GGTGGAGGGGCTGGCGTC (Ex14)

SEQ ID NO: 146
Reverse GGCTCTGAAGTG GGGCTGTG (Ex15)
```

Other sets of primers can be readily designed by the skilled artisan and/or are known in the art.

Probes for detecting EPS8L2 can be derived from any number of sources depending on the desired use (e.g., using the primers described above and the appropriate reagents). Examples of probes include:

```
                                                  SEQ ID NO: 147
GCTTCCCGGGGAACAAAGACGAGCTCATGCAGCACATGGACGAGGTCA
ACGACGAGCTCA

SEQ ID NO: 148
GCAGAGCTGGTGCACGAGGACATCGAGAGCGCGTTGGCCGACTGCCGG

SEQ ID NO: 149
GCCGTCGGGAGTCGCAGGAGGAGCCGCGGGCCGTGCTGGCTCAGAAGA
TAG

SEQ ID NO: 150
GCTCGTGTGCCAGGACTCGGAGCAGAGCAAGCCGGATGTCCAC

SEQ ID NO: 151
GTACAGCCAGCTCACCATGCAGAAGGCCTTCCTGGAGAAGCAGCAAAG
```

Other probes to EPS8L2 are known in the art and/or can be readily designed by the skilled artisan.

Antibodies against EPS8L2 include, but are not limited to, Abnova Cat# H00064787-M01 which is a mouse monoclonal antibody raised against a partial recombinant EPS8L2 (615 a.a.~715 a.a) and Abnova Cat# H00064787-B01 which is a mouse polyclonal antibody raised against a full-length human EPS8L2 protein.

Example 12

FASTKD1

FASTKD1 was found to be overexpressed in endometrial cancer primary tissue as compared to normal endometrial tissue by the microarray experiment described in Example 1. Further studies using RT-PCR demonstrated that FASTKD1 was overexpressed in primary endometrial cancer tissue as compared to normal endometrial tissue and it was surprisingly found that FASTKD1 was overexpressed in samples obtained from uterine fluid (e.g., aspirates) from patients having endometrial cancer by the method described in Examples 2-4. Example 5 shows that FASTKD1 can be combined with other biomarkers to give excellent predictive power for diagnosis of endometrial cancer.

The sequence of an mRNA corresponding to FASTKD1 is given in ENSEMBL accession no. ENST00000260971 and has a sequence as in SEQ ID NO:152

```
  1 ATAAACCCTGAGATATGAGGGTTGGGCGAGACATCCGAGCCTGTTTCGTTCCGTGTTGGG

61 ACCAGGAATAACCCTGACTTCTGAGCTTTCATAACCCCAGGATCCTCCAGAAAATTTGCG

121 GCGCGCTGAGGGAAAACCTTGCTGAAGCTGTACATTGGAATGCGTTTACAGTGAATGTAA

181 TGGAAGCAAAATACATGAAGGAAAAACTGTTATTTGTATCCCTGCTTATTGCACCTGACG

241 ACTAGTTGCAGATGGTTTTGTTTACCTAAGAAAACTTGTGATATAAATGAAAAAAACACC

301 TGTTTTCCTAGAGTCATTGGTTACAAATATGCTTCGTCTAAGAGCTATTTGTCCATTCTC

361 CTGGAGAGTGTTTCAATTTCGACCCATCAGTTGTGAACCACTAATTATTCAGATGAATAA

421 GTGTACAGATGAGGAGCAAATGTTTGGTTTTATTGAAAGAAACAAAGCCATACTTTCAGA

481 AAAGCAAGTGGGATGTGCATTTGATATGCTTTGGAAGCTTCAAAAGCAGAAGACCAGCCT

541 GTTAAAAAATGCTGAGTATGTCAGAGACCATCCTCAATTTCTTACTCTTCATAATTTAGC
```

```
 601 TACAAATAAATTCAAATTAATGAATGACGATACCCTGGTGAATGTGTTATACGTCACACA
 661 ACAGTTTGCTGGTGAGGCCCATGACCCGCTAGTTGAAGCACTAGTTACAGAAGCATGGAG
 721 AAGGCTAGAAAGGTTTGATATTAAACTGCTCTCAGAATTTTCCTCTTGCCTAGCAGATCA
 781 GCATTTGTATTTTAGTCCATTAATGGGAAAAATAGCTGATATTGTTCATAGGAACTTGGA
 841 AACCACACAGGACTTAAGTTCCTTGTCTGTCTTGATGGTCAACATATCTTCTTTAATATC
 901 ACGACATTTTCAACAACAACTGGTGAACAAAACAGAACTTCTTTTTGACACCATAGATTC
 961 TTCTGAGGTCAACGTTGCAAAAAGCATAGCAAAGTTTCTTCGAAATGTTAGATATCGTTA
1021 TCAACCACTATTAGAAAGATGTAATAACGTATTTTTAAGTAATGTGGACCACCTTGATTT
1081 GGATTCCATCAGTAAAATACTTAGTGTATACAAATTTCTACAATTTAATAGTTTTGAATT
1141 TATTATAATGGCTAAAAAGAAGCTAACTGAAATGATTCCTCTGTGTAATCATCCTGCTAG
1201 CTTTGTAAAATTGTTTGTAGCATTGGGACCCATTGCAGGACCTGAAGAAAAGAAACAACT
1261 TAAATCAACTATGTTATTGATGTCAGAGGACCTAACTGGCGAGCAAGCCCTGGCAGTGTT
1321 GGGAGCAATGGGAGATATGGAAAGCAGAAACTCATGTCTGATTAAAAGAGTTACTTCAGT
1381 TCTGCATAAACATTTGGATGGCTATAAACCATTAGAGTTGTTGAAGATAACTCAAGAATT
1441 AACTTTTCTGCATTTCCAAAGGAAGGAGTTTTTTGCGAAACTTAGAGAATTACTGCTTAG
1301 TTATTTGAAAAATAGTTTCATACCAACTGAGGTGTCTGTTCTGGTCCGTGCTATTTCCCT
1561 GCTCCCTTCTCCTCACTTGGACGAAGTGGGGATATCCCGAATTGAAGCCGTTTTACCACA
1621 GTGTGACCTAAATAACCTGAGTAGTTTTGCCACATCTGTTTTAAGATGGATTCAGCATGA
1681 TCACATGTATTTGGATAATATGACTGCGAAACAACTGAAACTACTTCAAAAATTAGATCA
1741 CTATGGTCGTCAGAGACTACAACACAGCAACAGTTTGGATCTGTTACGGAAGGAACTTAA
1801 ATCTCTCAAAGGAAACACGTTTCCTGAGTCACTTCTTGAAGAAATGATTGCTACTTTACA
1361 GCATTTCATGGATGATATTAATTACATAAATGTTGGGGAGATTGCATCTTTTATTTCTAG
1921 TACTGATTACCTCAGTACTTTGCTACTAGATAGGATAGCCTCAGTGGCTGTTCAGCAGAT
1981 TGAAAAGATCCATCCTTTTACAATCCCTGCTATTATTCGTCCATTCAGCGTATTGAACTA
2041 TGATCCACCTCAAAGGGATSAATTTTTGGGAACTTGCGTGCAACATCTTAATTCTTACTT
2101 AGGTATATTGGATCCTTTTATATTAGTGTTTCTTGGTTTCTCTTTGGCCACACTTGAATA
2161 TTTTCCAGAAGATCTGCTAAAGGCAATTTTTAACATCAAATTCTTAGCTAGATTGGATTC
2221 TCAACTTGAAAGTRTTGGTGGCATGGATGGAACACAACAGCAGATTTTTAAAATGTTAGC
2281 AGAGGTACTAGGAGGAATCAATTGTGTAAAAGCCTCGGTTCTTACGCCTTATTACCACAA
2341 AGTAGATTTTGAGTGTATCTTGGATAAAAGAAAAAAACCTCTTCCGTATGGAAGCCATAA
2401 TATAGCATTGGGACAACTACCAGAAATGCCCTGGGAATCAAATATCGAAATAGTTGGATC
2461 AAGGCTGCCACCAGGGGCTGAAAGGATTGCTTTGGAATTTTTGGATTCAAAAGCACTTTG
2521 TAGAAATATCCCTCACATGAAAGGAAAATCTGCTATGAAAAAACGACATTTGGAAATTCT
2581 GGGGTATCGTGTAATTCAGATTTCCCAGTTTGAATGGAACTCTATGGCACTGTCAACAAA
2641 GGATGCTCGGATGGACTACCTGAGAGAATGTATATTTGGAGAAGTCAAGTCATGTTTGTA
2701 GTTTTATTTAAAATGAATGTTATCGTGTGTTACATTTGGACCTATTTTAATAAAGTGGC
2761 CTGTCTC
```

The corresponding amino acid sequence is given in ENSEMBL accession no. ENSP00000260971 and has a sequence as in SEQ ID NO:153

```
  1 MKKTPVFLESLVTNMLRLRAICPFSWRVFQFRPISCEPLIIQMNKCTDEEQMFGFIERNK

61 AILSEKQVGCAFDMLWKLQKQKTSLLKNAEYVRDHPQFLTLHNLATNKFKLMNDDTLVNV

121 LYVTQQFAGEAHDPLVEALVTEAWRRLERFDIKLLSEFSSCLADQHLYESPLMGKIADIV

181 HRNLETTQDLSSLSVLMVNISSLISRHFQQQLVNKTELLFDTIDSSEVNVAKSIAKFLRN

241 VRYRYQPLLERCNNVFLSNVDHLDLDSISKILSVYKFLQFNSFEFIIMAKKKLTEMIPLC

301 NHPASFVKLFVALGPIAGPEEKKQLKSTMLLMSEDLTGEQALAVLGAMGDMESRNSCLIK

361 RVTSVLHKHLDGYKPLELLKITQELTFLHFQRKEFFAKLRELLLSYLKNSFIPTEVSVLV

421 RAISLLPSPHLDEVGISRIEAVLPQCDLNNLSSFATSVLRWIQHDHMYLDNMTAKQLKLL

481 QKLDHYGRQRLQHSNSLDLLRKELKSLKGNTFPESLLEEMIATLQHFMDDINYINVGEIA

541 SFISSTDYLSTLLLDRIASVAVQQIEKIHPFTIPAIIRPFSVLNYDPPQRDEFLGTCVQH

601 LNSYLGILDPFILVFLGFSLATLEYFPEDLLKAIFNIKFLARLDSQLESIGGMDGTQQQI

661 FKMLAEVLGGINCVKASVLTPYYHKVDFECILDKRKKPLPYGSHNIALGQLPEMPWESNI

721 EIVGSRLPPGAERIALEFLDSKALCRNIPHMKGKSAMKKRHLEILGYRVIQISQFEWNSM

781 ALSTKDARMDYLRECIFGEVKSCL
```

Primers for amplifying a FASTKD1 nucleic acid sequence can be designed using primer design software such as Oligo Calc and/or Primer 3.

Examples of primer pairs for amplifying a FASTKD1 nucleic acid include those in

```
         SEQ ID NO: 154
Forward: TGAATGACGATACCCTGGTG

SEQ ID NO: 155
Reverse: AGCCTTCTCCATGCTTCTGT

SEQ ID NO: 156
Forward: CCATGACCCGCTAGTTGAAG

SEQ ID NO: 157
Reverse: TGATCTGCTAGGCAAGAGGAA

SEQ ID NO: 158
Forward: TTCCTCTTGCCTAGCAGATCA

SEQ ID NO: 159
Reverse: TGTTGACCATCAAGACAGACA

SEQ ID NO: 160
Forward: TCCTCTGTGTAATCATCCTGCT

SEQ ID NO: 161
Reverse: CTCGCCAGTTAGGTCCTCTG

SEQ ID NO: 162
Forward: GGAGCAATGGGAGATATGGA

SEQ ID NO: 163
Reverse: TTCCTTTGGAAATGCAGAAAA

SEQ ID NO: 164
Forward: TGCATTTCCAAAGGAAGGAG

SEQ ID NO: 165
Reverse: CAAGTGAGGAGAAGGGAGCA

SEQ ID NO: 166
Forward: AAATGTTGGGGAGATTGCAT

SEQ ID NO: 167
Reverse: TCAATACGCTGAATGGACGA

SEQ ID NO: 168
Forward: GATCCACCTCAAAGGGATGA

SEQ ID NO: 169
Reverse: GGCCAAAGAGAAACCAAGAA

SEQ ID NO: 170
Forward: GTGTTTCTTGGTTTCTCTTTGG

SEQ ID NO: 171
Reverse: CTGTTGTGTTCCATCCATGC

SEQ ID NO: 172
Forward: GCATTGGGACAACTACCAGAA

SEQ ID NO: 173
Reverse: GTATGGGAGCGCAAAAGAAG

SEQ ID NO: 174
Forward: TGTGTTGCTTCATATTTGTACCC

SEQ ID NO: 175
Reverse: CATAGCAGATTTTCCTTTCATGTG

SEQ ID NO: 176
Forward: TGACCGCTTCTGTCAACAAT

SEQ ID NO: 177
Reverse: TGAATCCAAAAATTCCAAAGC
```

Other sets of primers can be readily designed by the skilled artisan and/or are known in the art.

Probes for detecting FASTKD1 can be derived from any number of sources depending on the desired use (e.g., using the above described primers and appropriate reagents). Other examples of probes include

```
SEQ ID NO: 178    GACCCGCTAGTTGAAGCACT

SEQ ID NO: 179    ACAGAAGCATGGAGAAGGCT

SEQ ID NO: 180    GAACTTGGAAACCACACAGGA

SEQ ID NO: 181    TTGTAGCATTGGGACCCATT

SEQ ID NO: 182    TGCATAAACATTTGGATGGC

SEQ ID NO: 183    TTCTGGTCCGTGCTATTTCC
```

```
SEQ ID NO: 184    GTGGCTGTTCAGCAGATTGA

SEQ ID NO: 185    GAACTTGCGTGCAACATCTT

SEQ ID NO: 186    CCAGAAGATCTGCTAAAGGCA

SEQ ID NO: 187    TGCCCTGGGAATCAAATATC

SEQ ID NO: 188    GGATTGCTTTGGAATTTTTGG

SEQ ID NO: 189    ATGGATGGAACACAACAGCA
```

A probe for detecting a FASTKD1 nucleic acid that was used on the microarray has a sequence as in SEQ ID NO:190

TGAATGGAACTCTATGGCACTGTCAACAAAGGATGCTCGGATGGACTA
CCTGAGAGA

Other probes to FASTKD1 are known in the art and/or can be readily designed by the skilled artisan.

Antibodies against FASTKD1 include, but are not limited to, Mouse Anti-Human FLJ21901 Polyclonal Antibody Cat# H00079675-A01 against de N-terminal (from aa 2-100).

Example 13

IKBKE

IKBKE (inhibitor of kappa light polypeptide gene enhancer in B-cells, kinase epsilon) also known as IKK-I; IKKE; IKKI; KIAA0151; MGC125294; MGC125295; MGC125297, was found to be overexpressed in endometrial cancer primary tissue as compared to normal endometrial tissue by the microarray experiment described in Example 1. Further studies using RT-PCR demonstrated that IKBKE was overexpressed in primary endometrial cancer tissue as compared to normal endometrial tissue and it was surprisingly found that IKBKE was overexpressed in samples obtained from uterine fluid (e.g., aspirates) from patients having endometrial cancer by the method described in Example 4. Example 5 shows that IKBKE can be combined with other biomarkers to give excellent predictive power for diagnosis of endometrial cancer.

IKBKE is a member of the large IkB kinase complex capable of phosphorylating IkB. IKK phosphorylates only one of two serine residues in IκBα necessary for ubiquitination and degradation of IκBα. The degradation of IkBα exposes however, the nuclear localization signals on NF-kB, leading to its translocation to the nucleus, where it binds to specific promoters and activates transcription. (PMID: 10882136).

The sequence of an mRNA corresponding to IKBKE is given in ENSEMBL accession no. ENST00000367120 and has a sequence as in SEQ ID NO:191

```
GAGAGAGCTGAGAGCCAGGACTCAGTGCTGAGCTTGGTGTCCCACCGCCACAAGGAGGCAGGGAAGAAAC

CCACTAGTCCCAGCTCCTGGGGTGGCACAGACATTGCAACTGGCCCTGCCTGTGGGTCCTAGGGGCCCTT

GGCTACCAGGAGGCTAAGAACACTGCTCATGAATGACAGTGAGCCCTGAAAGCTCTGGGGGTGTCACCCA

GTCCCACAAGCCTGCATCCCCTGCAGTGGAGATGGGCTCAGCTCCTGGACGTGCCACAGACAGAAAGCAT

AACATACACTCGCCAGGAAGAGCCTTTGCCTGACTCAGGGCAGCTCAGAGTGTGGGGCAGAAGGTGACCA

GCCAGCTCAGGGCAGGAGATGCAGAGCACAGCCAATTACCTGTGGCACACAGATGACCTGCTGGGGCAGG

GGGCCACTGCCAGTGTGTACAAGGCCCGCAACAAGAAATCCGGAGAGCTGGTTGCTGTGAAGGTCTTCAA

CACTACCAGCTACCTGCGGCCCCGCGAGGTGCAGGTGAGGGAGTTTGAGGTCCTGCGGAAGCTGAACCAC

CAGAACATCGTCAAGCTCTTTGCGGTGGAGGAGACGGGCGGAAGCCGGCAGAAGGTACTGGTGATGGAGT

ACTGCTCCAGTGGGAGCCTGCTGAGTGTGCTGGAGAGCCCTGAGAATGCCTTTGGGCTGCCTGAGGATGA

GTTCCTGGTGGTGCTGCGCGTGTGTGGTGGCCGGCATGAACCACCTGCGGGAGAACGGCATTGTGCATCGC

GACATCAAGCCGGGGAACATCATGCGCCTCGTAGGGGAGGAGGGCAGAGCATCTACAAGCTGACAGACT

TCGGCGCTGCCCGGGAGCTGGATGATGATGAGAAGTTCGTCTCGGTCTATGGGACTGAGGAGTACCTGCA

TCCCGACATGTATGAGCGGGCGGTGCTTCGAAAGCCCCAGCAAAAAGCGTTCGGGGTGACTGTGGATCTC

TGGAGCATTGGAGTGACCTTGTACCATGCAGCCACTGGCAGCCTGCCCTTCATCCCCTTTGGTGGGCCAC

GGCGGAACAAGGAGATCATGTACCGGATCACCACGGAGAAGCCGGCTGGGGCCATTGCAGGTGCCCAGAG

GCGGGAGAACGGGCCCCTGGAGTGGAGCTACACCCTCCCCATCACCTGCCAGCTGTCACTGGGGCTGCAG

AGCCAGCTGGTGCCCATCCTGGCCAACATCCTGGAGGTGGAGCAGGCCAAGTGCTGGGGCTTCGACCAGT

TCTTTGCGGAGACCAGTGACATCCTGCAGCGAGTTGTCGTCCATGTCTTCTCCCTGTCCCAGGCAGTCCT

GCACCACATCTATATCCATGCCCACAACACGATAGCCATTTTCCAGGAGGCCGTGCACAAGCAGACCAGT

GTGGCCCCCCGACACCAGGAGTACCTCTTTGAGGGTCACCTCTGTGTCCTCGAGCCCAGCGTCTCAGCAC

AGCACATCGCCCACACGACGGCAAGCAGCCCCCTGACCCTCTTCAGCACAGCCATCCCTAAGGGGCTGGC

CTTCAGGGACCCTGCTCTGGACGTCCCCAAGTTCGTCCCCAAAGTGGACCTGCAGGCGGATTACAACACT
```

-continued

```
GCCAAGGGCGTGTTGGGCGCCGGCTACCAGGCCCTGCGGCTGGCACGGGCCCTGCTGGATGGGCAGGAGC
TAATGTTTCGGGGGCTGCACTGGGTCATGGAGGTGCTCCAGGCCACATGCAGACGGACTCTGGAAGTGGC
AAGGACATCCCTCCTCTACCTCAGCAGCAGCCTGGGAACTGAGAGGTTCAGCAGCGTGGCTGGAACGCCT
GAGATCCAGGAACTGAAGGCGGCTGCAGAACTGAGGTCCAGGCTGCGGACTCTAGCGGAGGTCCTCTCCA
GATGCTCCCAAAATATCACGGAGACCCAGGAGAGCCTGAGCAGCCTGAACCGGGAGCTGGTGAAGAGCCG
GGATCAGGTACATGAGGACAGAAGCATCCAGCAGATTCAGTGCTGTTTGGACAAGATGAACTTCATCTAC
AAACAGTTCAAGAAGTCTAGGATGAGGCCAGGGCTTGGCTACAACGAGGAGCAGATTCACAAGCTGGATA
AGGTGAATTTCAGTCATTTAGCCAAAAGACTCCTGCAGGTGTTCCAGGAGGAGTGCGTGCAGAAGTATCA
AGCGTCCTTAGTCACACACGGCAAGAGGATGAGGGTGGTGCACGAGACCAGGAACCACCTGCGCCTGGTT
GGCTGTTCTGTGGCTGCCTGTAACACAGAAGCCCAGGGGGTCCAGGAGAGTCTCAGCAAGCTCCTGGAAG
AGCTATCTCACCAGCTCCTTCAGGACCGAGCAAAGGGGGCTCAGGCCTCGCCGCCTCCCATAGCTCCTTA
CCCCAGCCCTACACGAAAGGACCTGCTTCTCCACATGCAAGAGCTCTGCGAGGGGATGAAGCTGCTGGCA
TCTGACCTCCTGGACAACAACCGCATCATCGAACGGCTAAATAGAGTCCCAGCACCTCCTGATGTCTGAG
CTCCATGGGGCACATGAGGCATCCTGAAGCATTAGAATGATTCCAACACTGCTCTTCTGCACCATGAGAC
CAACCCAGGGCAAGATCCCATCCCATCACATCAGCCTACCTCCCTCCTGGCTGCTGGCCAGGATGTCGCC
AGCATTACCTTCCACTGCCTTTCTCCCTGGGAAGCAGCACAGCTGAGACTGGGCACCAGGCCACCTCTGT
TGGGACCCACAGGAAAGAGTGTGGCAGCAACTGCCTGGCTGACCTTTCTATCTTCTAGGCTCAGGTAC
TGCTCCTCCATGCCCATGGCTGGGCCGTGGGGAGAAGAAGCTCTCATACGCCTTCCCACTCCCTCTGGTT
TATAGGACTTCACTCCCTAGCCAACAGGAGAGGAGGCCTCCTGGGGTTTCCCCAGGGCAGTAGGTCAAAC
GACCTCATCACAGTCTTCCTTCCTCTTCAAGCGTTTCATGTTGAACACAGCTCTCTCCGCTCCCTTGTGA
TTTCTGAGGGTCACCACTGCCAGCCTCAGGCAACATAGAGAGCCTCCTGTTCTTTCTATGCTTGGTCTGA
CTGAGCCTAAAGTTGAGAAAATGGGTGGCCAAGGCCAGTGCCAGTGTCTTGGGGCCCCTTTGGCTCTCCC
TCACTCTCTGAGGCTCCAGCTGGTCCTGGGACATGCAGCCAGGACTGTGAGTCTGGGCAGGTCCAAGGCC
TGCACCTTCAAGAAGTGGAATAAATGTGGCCTTTGCTTCTGTT
```

The start and stop codons are indicated in bold.

The corresponding amino acid sequence is given in ENSEMBL accession no. ENSP00000356087 and has a sequence as in SEQ ID NO:192

MQSTANYLWHTDDLLGQGATASVYKARNKKSGELVAVKVFNTTSYLRP
REVQVREFEVLRKLNHQNIVKLFAVEETGGSRQKVLVMEYCSSGSLLS
VLESPENAFGLPEDEFLVVLRCVVAGMNHLRENGIVHRDIKPGNIMRL
VGEEGQSIYKLTDFGAARELDDDEKFVSVYGTEEYLHPDMYERAVLRK
PQQKAFGVTVDLWSIGVTLYHAATGSLPFIPFGGPRRNKEIMYRITTE
KPAGAIAGAQRRENGPLEWSYTLPITCQLSLGLQSQLVPILANILEVE
QAKCWGFDQFFAETSDILQRVVVHVFSLSQAVLHHIYIHAHNTIAIFQ
EAVHKQTSVAPRHQEYLFEGHLCVLEPSVSAQHIAHTTASSPLTLFST
AIPKGLAFRDPALDVPKFVPKVDLQADYNTAKGVLGAGYQALRLARAL
LDGQELMFRGLHWVMEVLQATCRRTLEVARTSLLYLSSSLGTERFSSV
AGTPEIQELKAAAELRSRLRTLAEVLSRCSQNITETQESLSSLNRELV
KSRDQVHEDRSIQQIQCCLDKMNFIYKQFKKSRMRPGLGYNEEQIHKL

-continued

DKVNFSHLAKRLLQVFQEECVQKYQASLVTHGKRMRVVHETRNHLRLV
GCSVAACNTEAQGVQESLSKLLEELSHQLLQDRAKGAQASPPPIAPYP
SPTRKDLLLHMQELCEGMKLLASDLLDNNRIIERLNRVPAPPDV

Primers for amplifying the sequence ENST00000367120 can be designed using primer design software such as Oligo Calc and/or Primer 3.

Examples of primer pairs for amplifying IKBKE include:

```
                                          SEQ ID NO: 193
Forward GTGCCACAGACAGAAAGCATAAC (EX2)

SEQ ID NO: 194
Reverse GGCTGTGCTCTGCATCTC (ex3)

SEQ ID NO: 195
Forward GGGGCCACTGCCAGTGTG (ex3)

SEQ ID NO: 196
Reverse GCAGGTAGCTGGTAGTGTTGAAG (ex4)

SEQ ID NO: 197
Forward GAGGTCCTGCGGAAGCTGAAC (ex4)

SEQ ID NO: 198
Reverse CACTCAGCAGGCTCCCACTG (ex5)
```

-continued

```
                                        SEQ ID NO: 199
Forward CCTGAGGATGAGTTCCTGGTG (ex5)

SEQ ID NO: 200
Reverse GTCGCGATGCACAATGCCGTTC (ex6)

SEQ ID NO: 201
Forward GGATGATGATGAGAAGTTCGTCTC

SEQ ID NO: 202
Reverse GAACGCTTTTTGCTGGGGC (ex7)

SEQ ID NO: 203
Forward CATCCCCTTTGGTGGGCCAC (ex7)

SEQ ID NO: 204
Reverse CCGTTCTCCCGCCTCTGG (ex8)

SEQ ID NO: 205
Forward CCTGGAGTGGAGCTACACC (ex8)

SEQ ID NO: 206
Reverse CACTTGGCCTGCTCCACCTC (ex9)

SEQ ID NO: 207
Forward GTCCCAGGCAGTCCTGCAC (ex9)

SEQ ID NO: 208
Reverse GACGCTGGGCTCGAGGACAC (ex10)

SEQ ID NO: 209
Forward GACCCTCTTCAGCACAGCCAT C

SEQ ID NO: 210
Reverse GCCGCAGGGCCTGGTAGC (ex12)

SEQ ID NO: 211
Forward GATCCAGGAACTGAAGGCGGC (ex14)

SEQ ID NO: 212
Reverse CCTGATCCCGGCTCTTCAC (ex15)
```

Other sets of primers can be readily designed by the skilled artisan and/or are known in the art.

Probes for detecting IKBKE can be derived from any number of sources depending on the desired use (e.g., using the primers described above and the appropriate reagents).

Other examples of probes include:

```
                                        SEQ ID NO: 213
CTCCTGTTCTTTCTATGCTTGGTCTGACTGAGCCTAAAGTTGAGAAAAT

SEQ ID NO: 214
GGGTGGCCAAG

SEQ ID NO: 215
CATCACCTGCCAGCTGTCACTGGGGCTGCAGAGCC

SEQ ID NO: 216
CTATATCCATGCCCACAACACGATAGCCATTTTCC

SEQ ID NO: 217
GGACGTCCCCAAGTTCGTCCCCAAAGTGGACCTGCAGGCG

SEQ ID NO: 218
GGTCCAGGAGAGTCTCAGCAAGCTCCTGGAAGAGCTATCTCAC
```

Other probes to IKBKE are known in the art and/or can be readily designed by the skilled artisan.

Antibodies against IKBKE include, but are not limited to, Abcam Cat# ab37596 which is a rabbit polyclonal antibody with an antigen that was a KLH conjugated synthetic peptide selected within a.a. 700-800 of human IKKE; and Abcam Cat# ab12142 which is a mouse monoclonal antibody against a synthetic peptide corresponding to a.a. residues 175-188, 525-540, or 567-580 of human IKK iota/IKK epsilon.

Example 14

PHKG2

PHKG2 was found to be overexpressed in endometrial cancer primary tissue as compared to normal endometrial tissue by the microarray experiment described in Example 1. Further studies using RT-PCR demonstrated that PHKG2 was overexpressed in primary endometrial cancer tissue as compared to normal endometrial tissue and it was surprisingly found that PHKG2 was overexpressed in samples obtained from uterine fluid (e.g., aspirates) from patients having endometrial cancer by the method described in Examples 2-4. Example 5 shows that PHKG2 can be combined with other biomarkers to give excellent predictive power for diagnosis of endometrial cancer.

The sequence of an mRNA corresponding to PHKG2 is given in ENSEMBL accession no. ENST00000328273 and has a sequence as in SEQ ID NO:218

```
  1 AAGGTGAGCGACTGCAGGCAAACCCGGCGACAGCGCAGCTCGCGTCGACCCTGGCTCCTC
 61 TGCCTGCCCCCTCAGGCCCCCGCCTCCTTCAGGATGACGCTGGACGTGGGGCCGGAGGAT
121 GAGCTGCCCGACTGGGCCGCCGCCAAAGAGTTTTACCAGAAGTACGACCCTAAGGACGTC
181 ATCGGCAGAGGAGTGAGCTCTGTGGTCCGCCGTTGTGTTCATCGAGCTACTGGCCACGAG
241 TTTGCGGTGAAGATTATGGAAGTGACAGCTGAGCGGCTGAGTCCTGAGCAGCTGGAGGAG
301 GTGCGGGAAGCCACACGGCGAGAGACACACATCCTTCGCCAGGTCGCCGGCCACCCCCAC
361 ATCATCACCCTCATCGATTCCTACGAGTCTTCTAGCTTCATGTTCCTGGTGTTTGACCTG
421 ATGCGGAAGGGAGAGCTGTTTGACTATCTCACAGAGAAGGTGGCCCTCTCTGAAAAGGAA
481 ACCAGGTCCATCATGCGGTCTCTGCTGGAAGCAGTGAGCTTTCTCCATGCCAACAACATT
541 GTGCATCGAGATCTGAAGCCCGAGAATATTCTCCTAGATGACAATATGCAGATCCGACTT
601 TCAGATTTCGGGTTCTCCTGCCACTTGGAACCTGGCGAGAAGCTTCGAGAGTTGTGTGGG
661 ACCCCAGGGTATCTAGCGCCAGAGATCCTTAAATGCTCCATGGATGAAACCCACCCAGGC
721 TATGGCAAGGAGGTCGACCTCTGGGCCTGTGGGGTGATCTTGTTCACACTCCTGGCTGGC
781 TCGCCACCCTTCTGGCACCGGCGGCAGATCCTGATGTTACGCATGATCATGGAGGGCCAG
```

-continued

```
 841 TACCAGTTCAGTTCCCCCGAGTGGGATGACCGTTCCAGCACTGTCAAAGACCTGATCTCC
 901 AGGCTGCTGCAGGTGGATCCTGAGGCACGCCTGACAGCTGAGCAGGCCCTACAGCACCCC
 961 TTCTTTGAGCGTTGTGAAGGCAGCCAACCCTGGAACCTCACCCCCCGCCAGCGGTTCCGG
1021 GTGGCAGTGTGGACAGTGCTGGCTGCTGGACGAGTGGCCCTAAGCACCCATCGTGTACGG
1061 CCACTGACCAAGAATGCACTGTTGAGGGACCCTTATGCGCTGCGGTCAGTGCGGCACCTC
1141 ATCGACAACTGTGCCTTCCGGCTCTACGGGCACTGGGTAAAGAAAGGGGAGCAGCAGAAC
1201 CGGGCGGCTCTCTTTCAGCACCGGCCCCCTGGGCCTTTTCCCATCATGGGCCCTGAAGAG
1261 GAGGGAGACTCTGCTGCTATAACTGAGGATGAGGCCGTGCTTGTGCTGGGCTAGGACCTC
1321 AACCCCAGGGATTCCCAGGAAGCAGAACTCTCCAGAAGAAGGGTTTTGATCATTCCAGCT
1381 CCTCTGGGCTCTGGCCTCTGGCCTCAGGCCCACTAATGATCCTGCTACCCTCTTGAAGAC
1441 CAGCCCGGTACCTCTCTCCCCACTGGCCAGGACTCTGAGATCAGAGCTGGGGTGGAAGGG
1501 AGCCATTCTGAACGCCACGCCTGGCCCGGTCAGTGCTGCATGCACTGCATATGAAATAAA
1561 ATCTGCTACACGCCAGGG
```

The start and stop codons are indicated in bold.
The corresponding amino acid sequence is given in ENSEMBL accession no. ENSP00000329968 and has a sequence as in SEQ ID NO:219

```
  1- MTLDVGPEDELPDWAAAKEFYQKYDPKDVIGRGVSSVVRRCVHRATGHEFAVKIMEVTAE
 61  RLSPEQLEEVREATRRETHILRQVAGHPHIITLIDSYESSSFMFLVFDLMRKGELFDYLT
121  EKVALSEKETRSIMRSLLEAVSFLHANNIVHRDLKPENTLLDDNMQIRLSDFGFSCHLEP
181  GEKLRELCGTPGYLAPEILKCSMDETHPGYGKEVDLWACGVILFTLLAGSPPFWHRRQIL
241  MLRMIMEGQYQFSSPEWDDRSSTVKDLISRLLQVDPEARLTAEQALQHPFFERCEGSQPW
301  NLTPRQRFRVAVWTVLAAGRVALSTHRVRPLTKNALLRDPYALRSVRHLIDNCAFRLYGH
361  WVKKGEQQNRAALFQHRPPGPFPIMGPEEEGDSAAITEDEAVLVLG
```

Primers for amplifying the sequence PHKG2 can be designed using primer design software such as Oligo Calc.
Examples of primer pairs for amplifying PHKG2 include those in

```
                                                SEQ ID NO: 220
                forward CCGCCAAAGAGTTTTACCAG
                                                SEQ ID NO: 221
                reverse TCCATAATCTTCACCGCAAA
                                                SEQ ID NO: 222
                forward GGCGAGAGACACACATCCTT
                                                SEQ ID NO: 223
                reverse CAAACACCAGGAACATGAAGC
                                                SEQ ID NO: 224
                forward GCTTCATGTTCCTGGTGTTTG
                                                SEQ ID NO: 225
                reverse TTTTCAGAGAGGGCCACCTT
                                                SEQ ID NO: 226
                forward GGAAGGGAGAGCTGTTTGACT
                                                SEQ ID NO: 227
                reverse TGTTGTTGGCATGGAGAAAG
                                                SEQ ID NO: 228
                forward TCAGATTTCGGGTTCTCCTG
                                                SEQ ID NO: 229
                reverse ATAGCCTGGGTGGGTTTCAT
                                                SEQ ID NO: 230
                forward ATGAAACCCACCCAGGCTAT
                                                SEQ ID NO: 231
                reverse TGCGTAACATCAGGATCTGC
                                                SEQ ID NO: 232
                forward CGTTCCAGCACTGTCAAAGA
                                                SEQ ID NO: 233
                reverse: CCTTCACAACGCTCAAAGAA
                                                SEQ ID NO: 234
                forward ACCCCTTCTTTGAGCGTTGT
                                                SEQ ID NO: 235
                reverse CGTACACGATGGGTGCTTAG
```

Other sets of primers can be readily designed by the skilled artisan and/or are known in the art.

Probes for detecting PHKG2 can be derived from any number of sources depending on the desired use (e.g., using the above described primers and appropriate reagents). Other examples of probes include

| | |
|---|---|
| SEQ ID NO: 236 | CCGTTGTGTTCATCGAGCTA |
| SEQ ID NO: 237 | CATCACCCTCATCGATTCCT |
| SEQ ID NO: 238 | GGAAGGGAGAGCTGTTTGACT |
| SEQ ID NO: 239 | AGGAAACCAGGTCCATCATG |
| SEQ ID NO: 240 | CAGGGTATCTAGCGCCAGAG |
| SEQ ID NO: 241 | CCTGTGGGGTGATCTTGTTC |
| SEQ ID NO: 242 | ACAGCTGAGCAGGCCCTAC |
| SEQ ID NO: 243 | GTTGTGGCAGTGTGGACAGT |

A probe for detecting a PHKG2 nucleic acid that was used on the microarray has a sequence as in

SEQ ID NO: 244
CTCAACCCCAGGGATTCCCAGGAAGCAGAACTCTCCAGAAGAAGGGTTTGATGATTTCCA

Other probes to PHKG2 are known in the art and/or can be readily designed by the skilled artisan.

Antibodies against PHKG2 include, but are not limited to, Mouse monoclonal antibody Anti-PHKG2 against full length protein Cat# WH0005261M1 from SIGMA; PHKG2 antibody—N-terminal Cat# ab71129 from abcam; and PHKG2 antibody Cat# ab28642 against a region between amino acids 8-57 of human PHKG2 from abcam.

Example 15

P4HB

P4HB was found to be overexpressed in endometrial cancer primary tissue as compared to normal endometrial tissue by the microarray experiment described in Example 1. Further studies using RT-PCR demonstrated that P4HB was overexpressed in primary endometrial cancer tissue as compared to normal endometrial tissue and it was surprisingly found that P4HB was overexpressed in samples obtained from uterine fluid (e.g., aspirates) from patients having endometrial cancer by the method described in Examples 2-4. Example 5 shows that P4HB can be combined with other biomarkers to give excellent predictive power for diagnosis of endometrial cancer.

The sequence of an mRNA corresponding to P4HB is given in ENSEMBL accession no. ENST00000331483 and has a sequence as in SEQ ID NO:245

```
   1 GAGCCTCGAAGTCCGCCGGCCAATCGAAGGCGGGCCCCAGCGGCGCGTGCGCGCCGCGGC
  61 CAGCGCGCGCGGGCGGGGGGCAGGCGCGCCCCGGACCCAGGATTTATAAAGGCGAGGCC
 121 GGGACCGGCGCGCGCTCTCGTCGCCCCCGCTGTCCCGGCGGCGCCAACCGAAGCGCCCCG
 181 CCTGATCCGTGTCCGACATGCTGCGCCGCGCTCTGCTGTGCCTGGCCGTGGCCGCCCTGG
 241 TGCGCGCCGACGCCCCGAGGAGGAGGACCACGTCCTGGTGCTGCGGAAAAGCAACTTCG
 301 CGGAGGCGCTGGCGGCCCACAAGTACCTGCTGGTGGAGTTCTATGCCCCTTGGTGTGGCC
 361 ACTGCAAGGCTCTGGCCCCTGAGTATGCCAAAGCCGCTGGGAAGCTGAAGGCAGAAGGTT
 421 CCGAGATCAGGTTGGCCAAGGTGGACGCCACGGAGGAGTCTGACCTGGCCCAGCAGTACG
 481 GCGTGCGCGGCTATCCCACCATCAAGTTCTTCAGGAATGGAGACACGGCTTCCCCCAAGG
 541 AATATACAGCTGGCAGAGAGGCTGATGACATCGTGAACTGGCTGAAGAAGCGCACGGGCC
 601 CGGCTGCCACCACCCTGCCTGACGGCGCAGCTGCAGAGTCCTTGGTGGAGTCCAGCGAGG
 661 TGGCTGTCATCGGCTTCTTCAAGGACGTGGAGTCGGACTCTGCCAAGCAGTTTTTGCAGG
 721 CAGCAGAGGCCATCGATGACATACCATTTGGGATCACTTCCAACAGTGACGTGTTCTCCA
 781 AATACCAGCTCGACAAAGATGGGGTTGTCCTCTTTAAGAAGTTTGATGAAGGCCGGAACA
 841 ACTTTGAAGGGGAGGTCACCAAGGAGAACCTGCTGGACTTTATCAAACACAACCAGCTGC
 901 CCCTTGTCATCGAGTTCACCGAGCAGACAGCCCCGAAGATTTTTGGAGGTGAAATCAAGA
 961 CTCACATCCTGCTGTTCTTGCCCAAGAGTGTGTCTGACTATGACGGCAAACTGAGCAACT
1021 TCAAAACAGCAGCCGAGAGCTTCAAGGGCAAGATCCTGTTCATCTTCATCGACAGCGACC
1081 ACACCGACAACCAGCGCATCCTCGAGTTCTTTGGCCTGAAGAAGGAAGAGTGCCCGGCCG
1141 TGCGCCTCATCACCCTGGAGGAGGAGATGACCAAGTACAAGCCCGAATCGGAGGAGCTGA
1201 CGGCAGAGAGGATCACAGAGTTCTGCCACCGCTTCCTGGAGGGCAAAATCAAGCCCCACC
1261 TGATGAGCCAGGAGCTGCCGGAGGACTGGGACAAGCAGCCTGTCAAGGTGCTTGTTGGGA
1321 AGAACTTTGAAGACGTGGCTTTTGATGAGAAAAAAAACGTCTTTGTGGAGTTCTATGCCC
1381 CATGGTGTGGTCACTGCAAACAGTTGGCTCCCATTTGGGATAAACTGGGAGAGACGTACA
```

```
-continued
1441 AGGACCATGAGAACATCGTCATCGCCAAGATGGACTCGACTGCCAACGAGGTGGAGGCCG

1501 TCAAAGTGCACAGCTTCCCCACACTCAAGTTCTTTCCTGCCAGTGCCGACAGGACGGTCA

1561 TTGATTACAACGGGGAACGCACGCTGGATGGTTTTAAGAAATTCCTGGAGAGCGGTGGCC

1621 AGGATGGGGCAGGGGATGATGACGATCTCGAGGACCTGGAAGAAGCAGAGGAGCCAGACA

1681 TGGAGGAAGACGATGATCAGAAAGCTGTGAAAGATGAACTGTAATACGCAAAGCCAGACC

1741 CGGGCGCTGCCGAGACCCCTCGGGGGCTGCACACCCAGCAGCAGCGCACGCCTCCGAAGC

1801 CTGCGGCCTCGCTTGAAGGAGGGCGTCGCCGGAAACCCAGGGAACCTCTCTGAAGTGACA

1861 CCTCACCCCTACACACCGTCCGTTCACCCCCGTCTCTTCCTTCTGCTTTTCGGTTTTTGG

1921 AAAGGGATCCATCTCCAGGCAGCCCACCCTGGTGGGCTTGTTTCCTGAAACCATGATGT

1981 ACTTTTTCATACATGAGTCTGTCCAGAGTGCTTGCTACCGTGTTCGGAGTCTCGCTGCCT

2041 CCCTCCCGCGGGAGGTTTCTCCTCTTTTTGAAAATTCCGTCTGTGGGATTTTTAGACATT

2101 TTTCGACATCAGGGTATTTGTTCCACCTTGGCCAGGCCTCCTCGGAGAAGCTTGTCCCCC

2161 GTGTGGGAGGGACGGAGCCGGACTGGACATGGTCACTCAGTACCGCCTGCAGTGTCGCCA

2221 TGACTGATCATGGCTCTTGCATTTTTGGGTAAATGGAGACTTCCGGATCCTGTCAGGGTG

2281 TCCCCCATGCCTGGAAGAGGAGCTGGTGGCTGCCAGCCCTGGGGCCCGGCACAGGCCTGG

2341 GCCTTCCCCTTCCCTCAAGCCAGGGCTCCTCCTCCTGTCGTGGGCTCATTGTGACCACTG

2401 GCCTCTCTACAGCACGGCCTGTGGCCTGTTCAAGGCAGAACCACGACCCTTGACTCCCGG

2461 GTGGGGAGGTGGCCAAGGATGCTGGAGCTGAATCAGACGCTGACAGTTCTTCAGGCATTT

2521 CTATTTCACAATCGAATTGAACACATTGGCCAAATAAAGTTGAAATTTTACCACCTGT
```

The start and stop codons are indicated in bold as well as the position corresponding to the microarray probe.

The corresponding amino acid sequence is given in ENSEMBL accession no. ENSP00000327801 and has a sequence as in SEQ ID NO:246

```
  1 MLRRALLCLAVAALVRADAPEEEDHVLVLRKSNFAEALAAHKYLLVEFYAPWCGHCKALA

61 PEYAKAAGKLKAEGSEIRLAKVDATEESDLAQQYGVRGYPTIKFFRNGDTASPKEYTAGR

121 EADDIVNWLKKRTGPAATTLPDGAAAESLVESSEVAVIGFFKDVESDSAKQFLQAAEAID

181 DIPFGITSNSDVFSKYQLDKDGVVLFKKFDEGRNNFEGEVTKENLLDFIKHNQLPLVIEF

241 TEQTAPKIFGGEIKTHILLFLPKSVSDYDGKLSNFKTAAESFKGKILFIFIDSDHTDNQR

301 ILEFFGLKKEECPAVRLITLEEEMTKYKPESEELTAERITEFCHRFLEGK1KPHLMSQEL

361 PEDWDKQPVKVLVGKNFEDVAFDEKKNVFVEFYAPWCGHCKQLAPIWDKLGETYKDHENI

421 VIAKMDSTANEVEAVKVHSFPTLKFFPASADRTVIDYNGERTLDGFKKFLESGGQDGAGD

481 DDDLEDLEEAEEPDMEEDDDQKAVKDEL
```

Primers for amplifying the sequence P4HB can be designed using primer design software such as Oligo Calc and/or Primer 3.

Examples of primer pairs for amplifying P4HB include those in

SEQ ID NO: 247:
Forward GCTGCGGAAAAGCAACTTC

SEQ ID NO: 248
Reverse CTGATCTCGGAACCTTCTGC

SEQ ID NO: 249
Forward GGCTATCCCACCATCAAGTT

SEQ ID NO: 250
Reverse TCTTCAGCCAGTTCACGATG

SEQ ID NO: 251
Forward GCAGAGTCCTTGGTGGAGTC

SEQ ID NO: 252
Reverse TGGAAGTGATCCCAAATGGT

SEQ ID NO: 253
Forward ACCATTTGGGATCACTTCCA

Reverse GGTGACCTCCCCTTCAAAGT                    SEQ ID NO: 254

Forward CCCCTTGTCATCGAGTTCAC                   SEQ ID NO: 255

Reverse TGCTCAGTTTGCCGTCATAG                   SEQ ID NO: 256

Forward TCACATCCTGCTGTTCTTGC                   SEQ ID NO: 257

Reverse GTCGCTGTCGATGAAGATGA                   SEQ ID NO: 258

Forward GACGGCAGAGAGGATCACAG                   SEQ ID NO: 259

Reverse TTCTTCCCAACAAGCACCTT                   SEQ ID NO: 260

Forward AGCCTGTCAAGGTGCTTGTT                   SEQ ID NO: 261

Reverse CAAATGGGAGCCAACTGTTT                   SEQ ID NO: 262

Forward ACAGCTTCCCCACACTCAAG                   SEQ ID NO: 263

Reverse CACCGCTCTCCAGGAATTT                    SEQ ID NO: 264

Forward GCACGCTGGATGGTTTTAAG                   SEQ ID NO: 265

Reverse TCATCGTCTTCCTCCATGTCT                  SEQ ID NO: 266

Other sets of primers can be readily designed by the skilled artisan and/or are known in the art.

Probes for detecting P4HB can be derived from any number of sources depending on the desired use (e.g., using the above described primers and appropriate reagents). Other examples of probes include

CACAAGTACCTGCTGGTGGA                          SEQ ID NO: 267

GGCTTCCCCCAAGGAATATA                          SEQ ID NO: 268

GCTTCTTCAAGGACGTGGAG                          SEQ ID NO: 269

CTCGACAAAGATGGGGTTGT                          SEQ ID NO: 270

TCACATCCTGCTGTTCTTGC                          SEQ ID NO: 271

CTATGACGGCAAACTGAGCA                          SEQ ID NO: 272

AAAATCAAGCCCCACCTGAT                          SEQ ID NO: 273

TGAAGACGTGGCTTTTGATG                          SEQ ID NO: 274

GGTCATTGATTACAACGGGG                          SEQ ID NO: 275

ATGACGATCTCGAGGACCTG                          SEQ ID NO: 276

A probe for detecting a P4HB nucleic acid that was used on the microarray has a sequence as in

GGCATTTCTATTTCACAATCGAATTGAACACATTGGCCAAATAAAGTTGA     SEQ ID NO: 277
AATTTTCCCC

Other probes to P4HB are known in the art and/or can be readily designed by the skilled artisan.

Antibodies against P4HB include, but are not limited to, anti P4HB Cat# ab31811 de abcam (rabbit polyclonal) against residues 400 to 500; and PDI (P4HB) Mouse anti-Human Monoclonal Antibody from Lifespan Biosciences Cat# LS-C38385.

Example 16

P2RX4

P2RX4 was found to be overexpressed in endometrial cancer primary tissue as compared to normal endometrial tissue by the microarray experiment described in Example 1. Further studies using RT-PCR demonstrated that P2RX4 was overexpressed in primary endometrial cancer tissue as compared to normal endometrial tissue as described in Example 2. It was surprisingly found that P2RX4 was overexpressed in samples obtained from uterine fluid (e.g., aspirates) from patients having endometrial cancer by the method described in Example 4. Example 5 shows that P2RX4 can be combined with other biomarkers to give excellent predictive power for diagnosis of endometrial cancer.

P2RX4
(also known as P2X4; P2X4R; P2RX4)
P2X purinoceptor 4 (P2X4)(ATP receptor)(Purinergic receptor
ENSG00000135124

The sequence of an mRNA corresponding to P2RX4 is given in ENSEMBL accession no. ENST00000337233 and has a sequence as in SEQ ID NO:278

```
  1 AAGTGCTGGGATGACAGGTGTGAGCCACCGCCCCGGCCCCTCGCCCGCCTTTTGAAGGA

61 GCCTTTCGTCCTCAAGGGCGAGGCCACTCCCCCCCGCGAGTTCCATGCCCCCTAGAGGG

121 TCATCGTTCCCGACGGGAGGTGGCGCCCTCCCCGGGCCCCGGGCCCCGACCGCCCGTG

181 CTGCCTCCTTCCGGGCCCTCCTCCGCGATGACGGCGCCGCCAGCAGGCCAGGCGGACTGG

241 GCGGGGCTCCGAGCGGGACTGGGACCCAGACCGACTAGGGGACTGGGAGCGGGCGGCGC

301 GGCCATGGCGGGCTGCTGCGCCGCGCTGGCGGCCTTCCTGTTCGAGTACGACACGCCGCG

361 CATCGTGCTCATCCGCAGCCGCAAAGTGGGGCTCATGAACCGCGCCGTGCAACTGCTCAT
```

```
-continued
 421 CCTGGCCTACGTCATCGGGTGGGTGTTTGTGTGGGAAAAGGGCTACCAGGAAACTGACTC

481 CGTGGTCAGCTCCGTTACGACCAAGGTCAAGGGCGTGGCTGTGACCAACACTTCTAAACT

541 TGGATTCCGGATCTGGGATGTGGCGGATTATGTGATACCAGCTCAGGAGGAAAACTCCCT

601 CTTCGTCATGACCAACGTGATCCTCACCATGAACCAGACACAGGGCCTGTGCCCCGAGAT

661 TCCAGATGCGACCACTGTGTGTAAATCAGATGCCAGCTGTACTGCCGGCTCTGCCGGCAC

721 CCACAGCAACGGAGTCTCAACAGGCAGGTGCGTAGCTTTCAACGGGTCTGTCAAGACGTG

781 TGAGGTGGCGGCCTGGTGCCCGGTGGAGGATGACACACACGTGCCACAACCTGCTTTTTT

841 AAAGGCTGCAGAAAACTTCACTCTTTTGGTTAAGAACAACATCTGGTATCCCAAATTTAA

901 TTTCAGCAAGAGGAATATCCTTCCCAACATCACCACTACTTACCTCAAGTCGTGCATTTA

961 TGATGCTAAAACAGATCCCTTCTGCCCCATATTCCGTCTTGGCAAAATAGTGGAGAACGC

1021 AGGACACAGTTTCCAGGACATGGCCGTGGAGGGAGGCATCATGGGCATCCAGGTCAACTG

1081 GGACTGCAACCTGGACAGAGCCGCCTCCCTCTGCTTGCCCAGGTACTCCTTCCGCCGCCT

1141 CGATACACGGGACGTTGAGCACAACGTATCTCCTGGCTACAATTTCAGGTTTGCCAAGTA

1201 CTACAGAGACCTGGCTGGCAACGAGCAGCGCACGCTCATCAAGGCCTATGGCATCCGCTT

1261 CGACATCATTGTGTTTGGGAAGGCAGGGAAATTTGACATCATCCCCACTATGATCAACAT

1321 CGGCTCTGGCCTGGCACTGCTAGGCATGGCGACCGTGCTGTGTGACATCATAGTCCTCTA

1381 CTGCATGAAGAAAGACTCTACTATCGGGAGAAGAAATATAAATATGTGGAAGATTACGA

1441 GCAGGGTCTTGCTAGTGAGCTGGACCAGTGAGGCCTACCCCACACCTGGGCTCTCCACAG

1501 CCCCATCAAAGAACAGAGAGGAGGAGGAGGGAGAAATGGCCACCACATCACCCCAGAGAA

1561 ATTTCTGGAATCTGATTGAGTCTCCACTCCACAAGCACTCAGGGTTCCCCAGCAGCTCCT

1621 GTGTGTTGTGTGCAGGATCTGTTTGCCCACTCGGCCCAGGAGGTCAGCAGTCTGTTCTTG

1681 GCTGGGTCAACTCTGCTTTTCCCGCAACCTGGGGTTGTCGGGGGAGCGCTGGCCCGACGC

1741 AGTGGCACTGCTGTGGCTTTCAGGGCTGGAGCTGGCTTTGCTCAGAAGCCTCCTGTCTCC

1801 AGCTCTCTCCAGGACAGGCCCAGTCCTCTGAGGCACGGCGGCTCTGTTCAAGCACTTTAT

1861 GCGGCAGGGGAGGCCGCCTGGCTGCAGTCACTAGACTTGTAGCAGGCCTGGGCTGCAGGC

1921 TTCCCCCCGACCATTCCCTGCAGCCATGCGGCAGAGCTGGCATTTCTCCTCAGAGAAGCG

1981 CTGTGCTAAGGTGATCGAGGACCAGACATTAAAGCGTGATTTTCTT
```

The start and stop codons are indicated in bold as well as the position corresponding to the microarray probe.

The corresponding amino acid sequence is given in ENSEMBL accession no. ENSP00000336607 and has a sequence as in SEQ ID NO:279

```
  1 MAGCCAALAAFLFEYDTPRIVLIRSRKVGLMNRAVQLLILAYVIGWVFVWEKGYQETDSV

61 VSSVTTKVKGVAVTNTSKLGFRIWDVADYVIPAQEENSLFVMTNVILTMNQTQGLCPEIP

121 DATTVCKSDASCTAGSAGTHSNGVSTGRCVAFNGSVKTCEVAAWCPVEDDTHVPQPAFLK

181 AAENFTLLVKNNIWYPKFNFSKRNILPNITTTYLKSCIYDAKTDPFCPIFRLGKIVENAG

241 HSFQDMAVEGGIMGIQVNWDCNLDRAASLCLPRYSFRRLDTRDVEHNVSPGYNFRFAKYY

301 RDLAGNEQRTLIKAYGIRFDIIVFGKAGKFDIIPTMINIGSGLALLGMATVLCDIIVLYC

361 MKKRLYYREKKYRKYVEDYEQGLASELDQ
```

ENST00000359949
ENSP00000353032

```
                                                   SEQ ID NO: 280
  1 MAGCCAALAAFLFEYDTPRIVLIRSRKVGLMNRAVQLLILAYVIGWVFVWEKGYQETDSV

61 VSSVTTKVKGVAVTNTSKLGFRIWDVADYVIPAQEENSLFVMTNVILTMNQTQGLCPEIP

121 DATTVCKSDASCTAGSAGTHSNVVCTLIPAFLKAAENFTLLVKNNIWYPKFNFSKRNILP

181 NITTTYLKSCIYDAKTDPFCPIFRLGKIVENAGHSFQDMAVEGGIMGIQVNWDCNLDRAA

241 SLCLPRYSFRRLDTRDVEHNVSPGYNFRFAKYYRDLAGNEQRTLIKAYGIRFDIIVFGKA

301 GKFDIIPTMINIGSGLALLGMATVLCDIIVLYCMKKRLYYREKKYKYVEDYEQGLASELD

361 Q
```

Examples of primer pairs for amplifying P2RX4 include:

```
                                       SEQ ID NO: 281
Forward AACTGCTCATCCTGGCCTAC SEQ ID NO: 282
Reverse GTCGTAACGGAGCTGACCAC SEQ ID NO: 283
Forward GGATGTGGCGGATTATGTG SEQ ID NO: 284
Reverse CCTGTGTCTGGTTCATGGTG SEQ ID NO: 285
Forward AGATTCCAGATGCGACCACT SEQ ID NO: 286
Reverse CAGACCCGTTGAAAGCTACG SEQ ID NO: 287
Forward TCTGTCAAGACGTGTGAGGTG SEQ ID NO: 288
Reverse CCAAAAGAGTGAAGTTTTCTGC SEQ ID NO: 289
Forward TTTTGGTTAAGAACAACATCTGG SEQ ID NO: 290
Reverse ATATGGGGCAGAAGGGATCT SEQ ID NO: 291
Forward CGCTTCGACATCATTGTGTT SEQ ID NO: 292
Reverse TAGCAGTGCCAGGCCAGAG SEQ ID NO: 293
Forward GAAAAGACTCTACTATCGGGAGAA SEQ ID NO: 294
Reverse CTGTTCTTTGATGGGGCTGT
```

Other sets of primers can be readily designed by the skilled artisan and/or are known in the art.

Probes for detecting P2RX4 derived from any number of sources depending on the desired use (e.g., using the above described primers and appropriate reagents).

Other examples of probes include:

```
                                       SEQ ID NO: 295
        TTGTGTGGGAAAAGGGCTAC

SEQ ID NO: 296
        TTCGTCATGACCAACGTGAT

SEQ ID NO: 297
        TCAGATGCCAGCTGTACTGC

SEQ ID NO: 298
        GTGGAGGATGACACACACGT

SEQ ID NO: 299
        TCCTTCCCAACATCACCACT

SEQ ID NO: 300
        GAAGGCAGGGAAATTTGACA

SEQ ID NO: 301
        GGGTCTTGCTAGTGAGCTGG
```

A probe for detecting a P2RX4 nucleic acid that was used on the microarray has a sequence as in

```
                                       SEQ ID NO: 302
CTCCTCAGAGAAGCGCTGTGCTAAGGTGATCGAGGACCAGACATTAAAGC
GTGATTTTCT
```

Other probes to P2RX4 are known in the art and/or can be readily designed by the skilled artisan.

Antibodies to P2RX4, include, but are not limited to, Mouse Anti-Human P2RX4 Maxpab polyclonal, unconjugated from Novus Biologicals, P2RX4 (1 a.a.~388 a.a) full-length human protein, H00005025-B01, and Goat Anti-P2RX4 polyclonal, unconjugated from Novus Biologicals, NBP1-00141, Synthetic peptide, SEQ ID NO:303 YREKKYKYVEDYEQ, representing the C Terminus of the sequence according to NP_002551.2

Example 17

PPFIBP2

PPFIBP2 was found to be overexpressed in endometrial cancer primary tissue as compared to normal endometrial tissue by the microarray experiment described in Example 1. Further studies using RT-PCR demonstrated that PPFIBP2 was overexpressed in primary endometrial cancer tissue as compared to normal endometrial tissue as described in Example 2. It was surprisingly found that PPFIBP2 was overexpressed in samples obtained from uterine fluid (e.g., aspirates) from patients having endometrial cancer by the method described in Example 4. Example 5 shows that PPFIBP2 can be combined with other biomarkers to give excellent predictive power for diagnosis of endometrial cancer.

PPPFIBP2

The sequence of an mRNA corresponding to PPPFIBP2 is given in ENSEMBL accession no. ENST00000299492 and has a sequence as in SEQ ID NO:304

```
   1 GCAGGCTTCTTCGGTGCCCGAGAGGGAGCGGGTGCCCAAGGGGGTGGTCCCTGTGGCAGG
  61 TCCCGGGGTGGGGGCGCGGCGCTCCGGGAAGAGCCTTCCGCAGGTCCCCGCCCCGTCACG
 121 TGGGCGCCGGCCCCGGCCGCTGCGGTCGGTCCGCTGGTTGGTCGGGCGCTTGGTCCGGCA
 181 GTTGGTCGGTGGGCCAGTGGCCCGTCGCTCGCTTCTGGGCTCTCATGTTTGAAGGTGGGA
 241 GGGACACGGGAGCGGCCCGCACACCTGAGCCGCCCGGAGAGGAGCCTCGGCCCCGTACCC
 301 AGTAAGAAGAGGAGGAGGCCAGGCAGGCAAAAGGAGTCATGGCTTCTGATGCTAGTCATG
 361 CGCTGGAAGCTGCCCTGGAGCAAATGGACGGGATCATTGCAGGCACTAAAACAGGTGCAG
 421 ATCTTAGTGATGGTACTTGTGAGCCTGGACTGGCTTCCCCGGCCTCCTACATGAACCCCT
 481 TCCCGGTGCTCCATCTCATCGAGGACTTGAGGCTGGCCTTGGAGATGCTGGAGCTTCCTC
 541 AGGAGAGAGCAGCCCTCCTGAGCCAGATCCCTGGCCCAACAGCTGCCTACATAAAGGAAT
 601 GGTTTGAAGAGAGCTTGTCCCAGGTAAACCACCACAGTGCTGCTAGTAATGAAACCTACC
 661 AGGAACGCTTGGCACGTCTAGAAGGGGATAAGGAGTCCCTCATATTGCAGGTGAGTGTCC
 721 TCACAGACCAAGTAGAAGCCCAGGGAGAAAAGATTCGAGACCTGGAAGTGTGTCTGGAAG
 781 GACACCAGGTGAAACTCAATGCTGCTGAAGAGATGCTTCAACAGGAGCTGCTAAGCCGCA
 841 CATCTCTTGAGACCCAGAAGCTCGATCTGATGACTGAAGTGTCTGAGCTGAAGCTCAAGC
 901 TGGTTGGCATGGAGAAGGAGCAGAGAGAGCAGGAGGAGAAGCAGAGAAAAGCAGAGGAGT
 961 TACTGCAAGAGCTCAGGCACCTCAAAATCAAAGTGGAAGAGTTGGAAAATGAAAGGAATC
1021 AGTATGAATGGAAGCTAAAGGCCACTAAGGCTGAAGTCGCCCAGCTGCAAGAACAGGTGG
1081 CCCTGAAAGATGCAGAAATTGAGCGTCTGCACAGCCAGCTCTCCCGGACAGCAGCTCTCC
1141 ACAGTGAGAGTCACACAGAGAGAGACCAAGAAATTCAACGTCTGAAAATGGGGATGGAAA
1201 CTTTGCTGCTTGCCAATGAAGATAAGGACCGTCGGATAGAGGAGCTTACGGGGCTGTTAA
1261 ACCAGTACCGGAAGGTAAAGGAGATTGTGATGGTCACTCAAGGGCCTTCGGAGAGAACTC
1321 TCTCAATCAATGAAGAACCGGAGGGAGGTTTCAGCAAGTGGAACGCTACAAATAAGG
1381 ACCCTGAAGAATTATTTAAACAAGAGATGCCTCCAAGATGTAGCTCTCCTACAGTGGGGC
1441 CACCTCCATTGCCACAGAAATCACTGGAAACCAGGGCTCAGAAAAAGCTCTCTTGTAGTC
1501 TAGAAGACTTGAGAAGTGAATCTGTGGATAAGTGTATGGATGGGAACCAGCCCTTCCCGG
1561 TGTTAGAACCCAAGGACAGCCCTTTCTTGGCGGAGCACAAATATCCCACTTTACCTGGGA
1621 AGCTTTCAGGAGCCACGCCCAATGGAGAGGCTGCCAAATCTCCTCCCACCATCTGCCAGC
1681 CTGACGCCACGGGGAGCAGCCTGCTGAGGCTGAGAGACACAGAAAGTGGCTGGGACGACA
1741 CTGCTGTGGTCAATGACCTCTCATCCACATCATCGGGCACTGAATCAGGTCCTCAGTCTC
1801 CTCTGACACCAGATGGTAAACGGAATCCCAAAGGCATTAAGAAGTTCTGGGGAAAAATCC
1861 GAAGAACTCAGTCAGGAAATTTCTACACTGACACGCTGGGGATGGCAGAGTTTCGACGAG
1921 GTGGGCTCCGGGCAACCGCAGGGCCAAGACTCTCTAGGACCAGGGACTCCAAGGGACAGA
1981 AAAGTGACGCCAATGCCCCCTTTGCCCAGTGGAGCACAGAGCGTGTGTGCATGGCTGG
2041 AGGACTTTGGCCTGGCTCAGTATGTGATCTTTGCCAGGCAGTGGGTATCTTCTGGCCACA
2101 CCTTATTGACAGCCACCCCTCAGGACATGGAAAAGGAGCTAGGAATTAAGCACCCACTCC
2161 ACAGGAAGAAGCTTGTTTTAGCAGTGAAAGCCATCAACACCAAACAGGAGGAGAAGTCTG
2221 CACTGCTAGACCACATTTGGGTGACAAGGTGGCTTGATGATATTGGCTTACCCCAGTACA
2281 AAGACCAGTTTCATGAATCTAGAGTTGACAGACGAATGCTGCAATACCTAACTGTGAACG
2341 ATTTACTCTTCTTAAAAGTCACCAGCCAACTACATCATCTCAGCATCAAATGTGCCATTC
2401 ACGTGCTGCATGTCAACAAGTTCAACCCCCACTGCCTGCACCGGCGGCCAGCTGATGAGA
```

-continued

```
2461 GTAACCTTTCTCCTTCAGAAGTTGTACAGTGGTCCAACCACAGGGTGATGGAGTGGTTAC

2521 GATCTGTGGACCTGGCAGAGTATGCACCCAATCTTCGAGGGAGTGGAGTCCATGGAGGCC

2581 TCATTATCCTGGAGCCACGCTTCACTGGGGACACCCTGGCTATGCTTCTCAACATCCCCC

2641 CACAAAAGACGCTCCTCAGGCGCCACCTGACCACCAAGTTCAATGCCTTGATTGGTCCGG

2701 AGGCTGAACAGGAGAAGCGAGAGAAAATGGCCTCACCAGCTTACACACCACTGACCACCA

2761 CAGCCAAAGTCCGGCCAAGGAAACTAGGATTTTCACACTTCGGAAACATAAGAAAAAAGA

2821 AGTTCGATGAATCGACGGACTACATTTGCCCAATGGAGCCCAGTGACGGTGTCAGTGATA

2881 GTCACAGGGTCTACAGTGGCTACCGGGGCCTCAGCCCCCTTGATGCCCCTGAACTGGATG

2941 GGCTGGACCAGGTGGGACAGATTAGCTGATGCCCTTGTCACCTGCCCTCTGTGCACCCTG

3001 AGAGCTCACAGTAACACTGTGTGTGTCACCATATAACTGCACCTCACCCCCGCACGTGTG

3061 CATGACTCGCAGAGAATATTCCAGCAATTGTGTACCCCTGGGCCAGTCTCTTTGAACCCT

3121 GAGGGTGGCCAGGATCTGGAGCTGCATCTCTAAGGGGCCAGGCTTTGGGGACCATTGCCA

3181 AAGGTGGACTCAGGAGGAAAGACACTTAAAGACACTTTTACATGTCTAGTAATTCTTGAT

3241 GTTCATCTTCAGCACCAGTGGAAACACATGAACTTCGATGCAGGTCCAGAGACCATGGAC

3301 ACTCCCACGAGGCTCAGCTCTCAGGCACCCCCTACACTTCAGTTGAGGGAAAAGCTCAAG

3361 TGCCTTAGGCCCGTGGACCACAGTCTTGGCTGAGATCAAAGGGATGAGCAACAGGGACTT

3421 CTGCCACAGTGACAATGGAATTGTGTTGTGCCTTACTTCAGAGGTGGTCTCTTCTTTCTT

3481 GTAATAAAAGCAATATTTATGC
```

The start and stop codons are indicated in bold as well as the position corresponding to the microarray probe.

The corresponding amino acid sequence is given in ENSEMBL accession no. ENSP00000299492 and has a sequence as in SEQ ID NO:305

```
  1 MASDASHALEAALEQMDGIIAGTKTGADLSDGTCEPGLASPASYMNPFPVLHLIEDLRLA

61 LEMLELPQERAALLSQIPGPTAAYIKEWFEESLSQVNHHSAASNETYQERLARLEGDKES

121 LILQVSVLTDQVEAQGEKIRDLEVCLEGHQVKLNAAEEMLQQELLSRTSLETQKLDLMTE

181 VSELKLKLVGMEKEQREQEEKQRKAEELLQELRHLKIKVEELENERNQYEWKLKATKAEV

241 AQLQEQVALKDAEIERLHSQLSRTAALHSESHTERDQEIQRLKMGMETLLLANEDKDRRI

301 EELTGLLNQYRKVKEIVMVTQGPSERTLSINEEEPEGGFSKWNATNKDPEELFKQEMPPR

361 CSSPTVGPPPLPQKSLETRAQKKLSCSLEDLRSESVDKCMDGNQPFPVLEPKDSPFLAEH

421 KYPTLPGKLSGATPNGEAAKSPPTICQPDATGSSLLRLRDTESGWDDTAVVNDLSSTSSG

481 TESGPQSPLTPDGKRNPKGIKKFWGKIRRTQSGNFYTDTLGMAEFRRGGLRATAGPRLSR

541 TRDSKGQKSDANAPFAQWSTERVCAWLEDFGLAQYVIFARQWVSSGHTLLTATPQDMEKE

601 LGIKHPLHRKKLVLAVKAINTKQEEKSALLDHIWVTRWLDDIGLPQYKDQFHESRVDRRM

661 LQYLTVNDLLFLKVTSQLHHLSIKCAIHVLHVNKFNPHCLHRRPADESNLSPSEVVQWSN

721 HRVMEWLRSVDLAEYAPNLRGSGVHGGLIILEPRFTGDTLAMLLNIPPQKTLLRRHLTTK

781 FNALIGPEAEQEKREKMASPAYTPLTTTAKVRPRKLGFSHFGNIRKKKFDESTDYICPME

841 PSDGVSDSHRVYSGYRGLSPLDAPELDGLDQVGQIS
```

Primers for amplifying the sequence ENST00000299492 can be designed using primer design software such as Oligo Calc and/or Primer 3.

Examples of primer pairs for amplifying PPFIBP2 include:

```
                              SEQ ID NO: 306
1)    Forward  GCTAGTCATGCGCTGGAAG SEQ ID NO: 307
      Reverse  GAAGCTCCAGCATCTCCAAG SEQ ID NO: 308
2)    Forward  CCCAGGTAAACCACCACAGT SEQ ID NO: 309
      Reverse  CTGGTGTCCTTCCAGACACA SEQ ID NO: 310
3)    Forward  TGTGTCTGGAAGGACACCAG SEQ ID NO: 311
      Reverse  TCCTCCTGCTCTCTCTGCTC SEQ ID NO: 312
4)    Forward  AAGAGCTCAGGCACCTCAAA SEQ ID NO: 313
      Reverse  CTCACTGTGGAGAGCTGCTG SEQ ID NO: 314
5)    Forward  AAACTTTGCTGCTTGCCAAT SEQ ID NO: 315
      Reverse  TTGAGTGACCATCACAATCTCC SEQ ID NO: 316
6)    Forward  TCTCTCAATCAATGAAGAAGAACC -continued
                              SEQ ID NO: 317
      Reverse  TCCAGTGATTTCTGTGGCAAT SEQ ID NO: 318
7)    Forward  GCCTCCAAGATGTAGCTCTCC SEQ ID NO: 319
      Reverse  TCCACAGATTCACTTCTCAAGTC SEQ ID NO: 320
8)    Forward  CGGAGCACAAATATCCCACT SEQ ID NO: 321
      Reverse  CTTTGGGATTCCGTTTACCA SEQ ID NO: 322
9)    Forward  TGGTAAACGGAATCCCAAAG SEQ ID NO: 323
      Reverse  TTGGAGTCCCTGGTCCTAGA SEQ ID NO: 324
10)   Forward  TCTAGGACCAGGGACTCCAA SEQ ID NO: 325
      Reverse  GGGTGGCTGTCAATAAGGTG
```

Other sets of primers can be readily designed by the skilled artisan and/or are known in the art.

Probes for detecting PPFIBP2 derived from any number of sources depending on the desired use (e.g., using the above described primers and appropriate reagents).

Other examples of probes include:

Probe:

```
                              SEQ ID NO: 326
      CAGGCACTAAAACAGGTGCA

SEQ ID NO: 327
      AGGGGATAAGGAGTCCCTCA

SEQ ID NO: 328
      TTGAGACCCAGAAGCTCGAT

SEQ ID NO: 329
      GAAATTGAGCGTCTGCACAG

SEQ ID NO: 330
      TTACGGGCTGTTAAACCAG

SEQ ID NO: 331
      CAGCAAGTGGAACGCTACAA

SEQ ID NO: 332
      TGCCACAGAAATCACTGGAA

SEQ ID NO: 333
      ACACAGAAAGTGGCTGGGAC

SEQ ID NO: 334
      TTCTACACTGACACGCTGGG

SEQ ID NO: 335
      GGCCTGGCTCAGTATGTGAT
```

A probe for detecting PPFIBP2 nucleic acid that was used on the microarray has a sequence as in SEQ ID NO:336

```
AGATCAAAGGGATGAGCAACAGGGACTTCTGCCACAGTGACAATGGAATTGTGTTGTGCC
```

Other probes to PPP1R16A are known in the art and/or can be readily designed by the skilled artisan.

1) Antibodies:
2) Mouse Anti-Human PPFIBP2 Monoclonal Antibody, Unconjugated, Clone 3A5, Abnova Corporation, PPFIBP2 (NP_003612, 1 a.a.~101 a.a) partial recombinant protein with GST tag. MW of the GST tag alone is 26 KDa.
3) Rabbit Anti-Human PPFIBP2 Purified—MaxPab Polyclonal Antibody, Unconjugated, Abnova Corporation, PPFIBP2 (NP_003612.1, 1 a.a.~876 a.a) full-length human protein.

Example 18

PPP1R16A

PPP1R16A (protein phosphatase 1, regulatory (inhibitor) subunit 16A) also known as MGC14333 and MYPT3 was found to be overexpressed in endometrial cancer primary tissue as compared to normal endometrial tissue by the microarray experiment described in Example 1. Further studies using RT-PCR demonstrated that PPP1R16A was overexpressed in primary endometrial cancer tissue as compared to normal endometrial tissue as described in Example 2. It was surprisingly found that PPP1R16A was overexpressed in samples obtained from uterine fluid (e.g., aspirates) from patients having endometrial cancer by the method described in Example 4. Example 5 shows that PPP1R16A can be combined with other biomarkers to give excellent predictive power for diagnosis of endometrial cancer.

PPP1R16A, also named Myosin phosphatase targeting subunit 3 (MYPT3) is a membrane located protein which having 524 amino acid residues, in which five Ankyrin repeats and a consensus PP1 binding site are located within the N-terminal 300 amino acid residues. The C-terminal region with 224 residues contains two possible Src homology 3 binding sites and a prenylation motif (CaaX). These structural features suggest that R16A could be a scaffold protein regulating protein-protein interactions as well as cellular signalling. (PMID: 18202305)

The sequence of an mRNA corresponding to PPP1R16A is given in ENSEMBL accession no. ENST00000292539 and has a sequence as in SEQ ID NO:337

```
GTGAAAAGAGGACTCTCAGGGGCTCACAGGGGCTCTCACTGCTGGTTGGCCCTGCCCTCCCTTCCCCCTC
AGCAGGGTGCCCGGAAGCTGGAACCTTGTTATCTGGGTAATTAGTTTCAGACCCTGCACTGAGGCCGGCC
AGGTCTCGGGGCTGCCTCCCATAGGTTGTGCACCCTGACCCCGAGAGGGAGGCGAGGCGCTGCTTGTCGA
CAGCTAGAGGCTGGCCTGGGGAGCAGGTTTGGGGTGCCCTCCCACACTGCCCTCCCTGCCCCGGCCCATG
CCCCCCAGGGCTGCCTGGGCCTGGTTATTGTGTGGGGCCTCCTGACCCAGCCAAGGGCACGAAGCTCTGG
GAAGGGGATGCCCCCGAGGGTGCCAGTCCAGCTAGCTGCCCCACCCCTCAGGCCCAGCCTGGCCCCCAAG
CTCCCCACTCTGGTGCCCCGAGCAGCCCTGTGGGCAAGCAGCCGCCGCCATGGCCGAGCACCTGGAGCTG
CTGGCAGAGATGCCCATGGTGGGCAGGATGAGCACACAGGAGCGGCTGAAGCATGCCCAGAAGCGGCGCG
CCCAGCAGGTGAAGATGTGGGCCCAGGCTGAGAAGGAGGCCCAGGGCAAGAAGGGTCCTGGGGAGCGTCC
CCGGAAGGAGGCAGCCAGCCAAGGGCTCCTGAAGCAGGTCCTCTTCCCTCCCAGTGTTGTCCTTCTGGAG
GCCGCTGCCCGAAATGACCTGGAAGAAGTCCGCCAGTTCCTTGGGAGTGGGGTCAGCCCTGACTTGGCCA
ACGAGGACGCCTGACGGCCCTGCACCAGTGCTGCATTGATGATTTCCGAGAGATGGTGCAGCAGCTCCT
GGAGGCTGGGGCCAACATCAATGCCTGTGACAGTGAGTGCTGGACGCCTCTGCATGCTGCGGCCACCTGC
GGCCACCTGCACCTGGTGGAGCTGCTCATCGCCAGTGGCGCCAATCTCCTGGCGGTCAACACCGACGGGA
ACATGCCCTATGACCTGTGTGATGATGAGCAGACGCTGGACTGCCTGGAGACTGCCATGGCCGACCGTGG
CATCACCCAGGACAGCATCGAGGCCGCCCGGGCCGTGCCAGAACTGCGCATGCTGGACGACATCCGGAGC
CGGCTGCAGGCCGGGGCAGACCTCCATGCCCCCTGGACCACGGGGCCACGCTGCTGCACGTCGCAGCCG
CCAACGGGTTCAGCGAGGCGGCTGCCCTGCTGCTGGAACACCGAGCCAGCCTGAGCGCTAAGGACCAAGA
CGGCTGGGAGCCGCTGCACGCCGCGGCCTACTGGGGCCAGGTGCCCCTGGTGGAGCTGCTCGTGGCGCAC
GGGGCCGACCTGAACGCAAAGTCCCTGATGGACGAGACGCCCCTTGATGTGTGCGGGGACGAGGAGGTGC
GGGCCAAGCTGCTGGAGCTGAAGCACAAGCACGACGCCCTCCTGCGCGCCCAGAGCCGCCAGCGCTCCTT
GCTGCGCCGCCGCACCTCCAGCGCCGGCAGCCGCGGGAAGGTGGTGAGGCGGGTGAGCCTAACCCAGCGC
ACCGACCTGTACCGCAAGCAGCACGCCCAGGAGGCCATCGTGTGGCAACAGCCGCCGCCCACCAGCCCGG
AGCCGCCCGAGGACAACGATGACCGCCAGACAGGCGCAGAGCTCAGGCCGCCGCCCCCGGAGGAGGACAA
CCCCGAAGTGGTCAGGCCGCACAATGGCCGAGTAGGGGGCTCCCCAGTGCGGCATCTATACTCCAAGCGA
CTAGACCGGAGTGTCTCCTACCAGCTGAGCCCCTGGACAGCACCACCCCCCACACCCTGGTCCACGACA
AGGCCCACCACACCCTGGCTGACCTGAAGCGCCAGCGAGCTGCTGCCAAGCTGCAGCGACCCCCACCTGA
GGGGCCCGAGAGCCCTGAGACAGCTGAGCCTGGCCTGCCTGGTGACACGGTGACCCCCCAGCCTGACTGT
GGCTTCAGGGCAGGCGGGACCCACCCCTGCTCAAGCTCACAGCCCCGGCGGTGGAGGCTCCCGTGGAGA
GGAGGCCGTGCTGCCTGCTCATGTGAGGCTGTTGCTCAGCATGCAGGGGCCCTGTCGCGGGCACAGCCCA
AGGCTGCCTCCCCACGGTGCGTGCCCTGGTGCTGCGGGTGCAGCACGGAAACCCCGGCTTCTACTGTACA
GGACACTGGCCCCTCTCAGGTCAGAAGACATGCCTGGAGGGATGTCTGGCTGCAAAGACTATTTTTATCC
TGCAACTCTTGATAAAGGGCTGTTTTGCCATGGAAAAAAAAAAAAAAAAAAAAAAAAAAAAAAAAAAAAA
AAAAAAAAAAAAAAAA
```

The start and stop codons are indicated in bold as well as the position corresponding to the microarray probe.

The corresponding amino acid sequence is given in ENSEMBL accession no. ENSP00000292539 and has a sequence as in SEQ ID NO:338

MAEHLELLAEMPMVGRMSTQERLKHAQKRRAQQVKMWAQAEKEA

QGKKGPGERPRKEAASQGLLKQVLFPPSVVLLEAAARNDLEEVRQFLGSG

VSPDLANEDGLTALHQCCIDDFREMVQQLLEAGANINACDSECWTPLHAA

ATCGHLHLVELLIASGANLLAVNTDGNMPYDLCDDEQTLDCLETAMADRG

ITQDSIEAARAVPELRMLDDIRSRLQAGADLHAPLDHGATLLHVAAANGF

SEAAALLLEHRASLSAKDQDGWEPLHAAAYWGQVPLVELLVAHGADLNAK

SLMDETPLDVCGDEEVRAKLLELKHKHDALLRAQSRQRSLLRRRTSSAGS

RGKVVRRVSLTQRTDLYRKQHAQEAIVWQQPPPTSPEPPEDNDDRQTGAE

LRPPPPEEDNPEVVRPHNGRVGGSPVRHLYSKRLDRSVSYQLSPLDSTTP

HTLVHDKAHHTLADLKRQRAAAKLQRPPPEGPESPETAEPGLPGDTVTPQ

PDCGFRAGGDPPLLKLTAPAVEAPVERRPCCLLM

Primers for amplifying the sequence ENST00000292539 can be designed using primer design software such as Oligo Calc and/or Primer 3.

Examples of primer pairs for amplifying PPP1R16A include:

```
                                           SEQ ID NO: 339
       Forward GTGTTGTCCTTCTGGAGGCCG (Ex2)

SEQ ID NO: 340
       Reverse GCCGTCAGGCCGTCCTCGTTG (Ex3)

SEQ ID NO: 341
       Forward GCTGCCCGAAATGACCTGG (Ex3)

SEQ ID NO: 342
       Reverse CGGAAATCATCAATGCAGC (Ex5)

SEQ ID NO: 343
       Forward GACGCCTCTGCATGCTGCGG (Ex5)

SEQ ID NO: 344
       Reverse CACAGGTCATAGGGCATGTTC (Ex6)

SEQ ID NO: 345
       Forward GATGAGCAGACGCTGGACTG (Ex6)

SEQ ID NO: 346
       Reverse CTCCGGATGTCGTCCAGC (Ex7)

SEQ ID NO: 347
       Forward CAGGCCGGGGCAGACCTC

SEQ ID NO: 348
       Reverse GGCTCGGTGTTCCAGCAGCAG

SEQ ID NO: 349
       Forward GGGAGCCGCTGCACGCC

SEQ ID NO: 350
       Reverse CCCGCACCTCCTCGTCCC

SEQ ID NO: 351
       Forward CTGCGCGCCCAGAGCCGC

SEQ ID NO: 352
       Reverse GCGTGCTGCTTGCGGTAC

SEQ ID NO: 353
       Forward GCCAGACAGGCGCAGAGCTC
```

```
                                           SEQ ID NO: 354
       Reverse CTACTCGGCCATTGTGCG
```

Other sets of primers can be readily designed by the skilled artisan and/or are known in the art.

Probes for detecting PPP1R16A derived from any number of sources depending on the desired use (e.g., using the above described primers and appropriate reagents).

Other examples of probes include:

```
                                           SEQ ID NO: 355
       TCTACTGTACAGGACACTGGCCCCTCTCAGGTCAGAAGACATGCCTGGAG
       GGATGTCTGGCTGCAAAGACTATTTTTATCC

SEQ ID NO: 356
       CTGACGGCCCTGCACCAGTGCTGCATTGATGATTTCC

SEQ ID NO: 357
       GACTGCCATGGCCGACCGTGGCATCACCCAG

SEQ ID NO: 358
       GCTCGTGGCGCACGGGGCCGACCTGAACGC

SEQ ID NO: 359
       GCGCCGGCAGCCGCGGGAAGGTGGTGAGG
```

Other probes to PPP1R16A are known in the art and/or can be readily designed by the skilled artisan.

Antibodies against PPP1R16A include, but are not limited to, Abnova Corporation Cat# H00084988-M06 which is a mouse monoclonal antibody raised against a partial recombinant PPP1R16A: 429 a.a.~529 a.a; and from Abnova Cat# H00084988-B01 which is a mouse polyclonal raised against a full-length human PPP1R16A protein.

Example 19

RASSF7

RASSF7, Ras association (RalGDS/AF-6) domain family (N-terminal) member 7 also known as 2400009B11RIK, AW210608, C11ORF13, HRAS1, HRC1, MGC126069, MGC126070, and RGD1306244 was found to be overexpressed in endometrial cancer primary tissue as compared to normal endometrial tissue by the microarray experiment described in Example 1. Further studies using RT-PCR demonstrated that RASSF7 was overexpressed in primary endometrial cancer tissue as compared to normal endometrial tissue as described in Example 2. It was surprisingly found that RASSF7 was overexpressed in samples obtained from uterine fluid (e.g., aspirates) from patients having endometrial cancer by the method described in Example 4. Example 5 shows that RASSF7 can be combined with other biomarkers to give excellent predictive power for diagnosis of endometrial cancer.

RASSF7 is a member of a new Ras effector family characterise for the presence of a RA domain in their sequence. Although they interact either directly or indirectly with activated Ras, their role in mediating its biological effects remains unclear. What is clear is that they seem to modulate some of the growth inhibitory responses mediated by Ras and may serve as tumour suppressor genes. In fact, it is been described that members of the family are silenced in tumours by methylation of their promoters. (PMID: 17692468).

The sequence of an mRNA corresponding to RASSF7 is given in ENSEMBL accession no. ENST00000344375 and has a sequence as in SEQ ID NO:360

GAATTCGGGGGAGGGGGCAGTGTCCTCCGAGCCAGGACAGGCATGTTGTTGGGACTGGCGGCCATGGAG

CTGAAGGTGTGGGTGGATGGCATCCAGCGTGTGGTCTGTGGGGTCTCAGAGCAGACCACCTGCCAGGAAG

TGGTCATCGCACTAGCCCAAGCAATAGGCCAGACTGGCCGCTTTGTGCTTGTGCAGCGGCTTCGGGAGAA

GGAGCGGCAGTTGCTGCCACAAGAGTGTCCAGTGGGCGCCCAGGCCACCTGCGGACAGTTTGCCAGCGAT

GTCCAGTTTGTCCTGAGGCGCACAGGGCCCAGCCTAGCTGGGAGGCCCTCCTCAGACAGCTGTCCACCCC

CGGAACGCTGCCTAATTCGTGCCAGCCTCCCTGTAAAGCCACGGGCTGCGCTGGGCTGTGAGCCCCGCAA

AACACTGACCCCCGAGCCAGCCCCCAGCCTCTCACGCCCTGGGCCTGCGGCCCCTGTGACACCCACACCA

GGCTGCTGCACAGACCTGCGGGGCCTGGAGCTCAGGGTGCAGAGGAATGCTGAGGAGCTGGGCCATGAGG

CCTTCTGGGAGCAAGAGCTGCGCCGGGAGCAGGCCCGGGAGCGAGAGGGACAGGCACGCCTGCAGGCACT

AAGTGCGGCCACTGCTGAGCATGCCGCCCGGCTGCAGGCCCTGGACGCTCAGGCCCGTGCCCTGGAGGCT

GAGCTGCAGCTGGCAGCGGAGGCCCCTGGGCCCCCCTCACCTATGGCATCTGCCACTGAGCGCCTGCACC

AGGACCTGGCTGTTCAGGAGCGGCAGAGTGCGGAGGTGCAGGGCAGCCTGGCTCTGGTGAGCCGGGCCCT

GGAGGCAGCAGAGCGAGCCTTGCAGGCTCAGGCTCAGGAGCTGGAGGAGCTGAACCGAGAGCTCCGTCAG

TGCAACCTGCAGCAGTTCATCCAGCAGACCGGGGCTGCGCTGCCACCGCCCCACGGCCTGACAGGGGCC

CTCCTGGCACTCAGGGCCCTCTGCCTCCAGCCAGAGAGGAGTCCCTCCTGGGCGCTCCCTCTGAGTCCCA

TGCTGGTGCCCAGCCTAGGCCCCGAGGTGGCCCCCATGACGCAGAACTCCTGGAGGTAGCAGCAGCTCCT

GCCCCAGAGTGGTGTCCTCTGGCAGCCCAGCCCCAGGCTCTGTGACAGCCTAGTGAGGGCTGCAAGACCA

TCCTGCCCGGACCACAGAAGGAGAGTTGGCGGTCACAGAGGGCTCCTCTGCCAGGCAGTGGGAAGCCCTG

GGTTTGGCCTCAGGAGCTGGGGGTGCAGTGGGGGACTGCCCTAGTCCTTGCCAGGTCGCCCAGCACCCTG

GAGAAGCATGGGGCGTAGCCAGCTCGGAACTTGCCAGGCCCCAAAGGCCACGACTGCCTGTTGGGGACAG

GAGATGCATGGACAGTGTGCTCAAGCTGTGGGCATGTGCTTGCCTGCGGGAGAGGTCCTTCACTGTGTGT

ACACAGCAAGAGCATGTGTGTGCCACTTCCCCTACCCCAACGTGAAAACCTCAATAAACTGCCCGAAGC

The corresponding amino acid sequence is given in ENSEMBL accession no. ENSP00000344226 and has a sequence as in SEQ ID NO:361

MLLGLAAMELKVWVDGIQRVVCGVSEQTTCQEVVIALAQAIGQTGRFVLVQRLREKERQLLPQECPVGAQ

ATCGQFASDVQFVLRRTGPSLAGRPSSDSCPPPERCLIRASLPVKPRAALGCEPRKTLTPEPAPSLSRPG

PAAPVTPTPGCCTDLRGLELRVQRNAEELGHEAFWEQELRREQAREREGQARLQALSAATAEHAARLQAL

DAQARALEAELQLAAEAPGPPSPMASATERLHQDLAVQERQSAEVQGSLALVSRALEAAERALQAQAQEL

EELNRELRQCNLQQFIQQTGAALPPPPRPDRGPPGTQGPLPPAREESLLGAPSESHAGAQPRPRGGPHDA

ELLEVAAAPAPEWCPLAAQPQAL

Primers for amplifying the sequence ENST00000344375 can be designed using primer design software such as Oligo Calc and/or Primer 3.

Examples of primer pairs for amplifying RASSF7 include:

| | | SEQ ID NO: 362 |
|---|---|---|
| Forward | CTGCCAGGAAGTGGTCATC (Ex1) | |
| | | SEQ ID NO: 363 |
| Reverse | GCCGCTGCACAAGCACA (ex2) | |
| | | SEQ ID NO: 364 |
| Forward | CATGGAGCTGAAGGTG (ex1) | |

-continued

| | | SEQ ID NO: 365 |
|---|---|---|
| Reverse | CTCAGGACAAACTGGAC (ex2) | |
| | | SEQ ID NO: 366 |
| Forward | GCCACTGAGCGCCTGC (Ex2) | |
| | | SEQ ID NO: 367 |
| Reverse | GTCTGCTGGATGAACTG (EX3) | |
| | | SEQ ID NO: 368 |
| Forward | CAG CAG AGC GAG CCT TGC AG | |
| | | SEQ ID NO: 369 |
| Reverse | CTG AGT GCC AGG AGG GC (Ex3) | |

| | | |
|---|---|---|
| Forward | CAC GGC CTG ACA GGG GCC (Ex3) | SEQ ID NO: 370 |
| Reverse | GCC TAG GCT GGG CAC (EX4) | SEQ ID NO: 371 |
| Forward | CTCTGAGTCCCATGCTGG (EX4) | SEQ ID NO: 372 |
| Reverse | GACACCACTCTGGGGC (EX5) | SEQ ID NO: 373 |
| Forward | TGCCCAGCCTAGGCCC (EX4) | SEQ ID NO: 374 |
| Reverse | GCCAGAGGACACCACTC (EX5) | SEQ ID NO: 375 |

Other sets of primers can be readily designed by the skilled artisan and/or are known in the art.

Probes for detecting RASSF7 can be derived from any number of sources depending on the desired use (e.g., using the above described primers and appropriate reagents). Other examples of probes include:

SEQ ID NO: 376
GAGAGGTCCTTCACTGTGTGTACACAGCAAGAGCATGTGTGTGCCACTTC

SEQ ID NO: 377
AGTGTCCTCCGAGCCAGGACAGGCATGTTGTTGGGACTGGCGGCCATGGAG

SEQ ID NO: 378
GAGCCGGGCCCTGGAGGCAGCAGAGCGAGCCTTGCAGGCTCAGGCTCAGGA
GCTG

SEQ ID NO: 379
CGGCCTGACAGGGGCCCTCCTGGCACTCAGGGCCCTCTGCCTCCAGCCAGA
GAGGAG

SEQ ID NO: 380
GAGGAGCTGGGCCATGAGGCCTTCTGGGAGCAAGAGCTGCGCCGGGAGCAG
GCCCGGGAG

Other probes to RASSF7 are known in the art and/or can be readily designed by the skilled artisan.

Antibodies against RASSF7 include, but are not limited to, LifeSpan BioSciences. Cat# LS-C31793-100 which is a rabbit polyclonal antibody; and from Novus Biologivals Cat#NB100-93434, which is a goat polyclonal anti-RASSF7 against the epitope SEQ ID NO:381 CTDLRGLELRVQRN.

Example 20

RNF183

RNF183 was found to be overexpressed in endometrial cancer primary tissue as compared to normal endometrial tissue by the microarray experiment described in Example 1. Further studies using RT-PCR demonstrated that RNF183 was overexpressed in primary endometrial cancer tissue as compared to normal endometrial tissue as described in Example 2. It was surprisingly found that RNF183 was overexpressed in samples obtained from uterine fluid (e.g., aspirates) from patients having endometrial cancer by the method described in Example 4. Example 5 shows that RNF183 can be combined with other biomarkers to give excellent predictive power for diagnosis of endometrial cancer.

The sequence of an mRNA corresponding to RNF183 is given in ENSEMBL accession no. ENST00000297894 and has a sequence as in SEQ ID NO:382

CGATTCAGGGGAGGGAGCAACTGGAGCCTCAGGCCCTCCAGAGTAGTCTGCCTGACCACCCTGGAGCCCA
CAGAAGCCCAGGACGTCTCCCGCGAAGCCTCCCCGTGTGTGGCTGAGGATGGCTGAGCAGCAGGGCCGGG
AGCTTGAGGCTGAGTGCCCCGTCTGCTGGAACCCCTTCAACAACACGTTCCATACCCCCAAAATGCTGGA
TTGCTGCCACTCCTTCTGCGTGGAATGTCTGGCCCACCTCAGCCTTGTGACTCCAGCCCGGCGCCGCCTG
CTGTGCCCACTCTGTCGCCAGCCCACAGTGCTGGCCTCAGGGCAGCCTGTCACTGACTTGCCCACGGACA
CTGCCATGCTCGCCCTGCTCCGCCTGGAGCCCCACCATGTCATCCTGGAAGGCCATCAGCTGTGCCTCAA
GGACCAGCCCAAGAGCCGCTACTTCCTGCGCCAGCCTCAAGTCTACACGCTGGACCTTGGCCCCCAGCCT
GGGGGCCAGACTGGGCCGCCCCCAGACACGGCCTCTGCCACCGTGTCTACGCCCATCCTCATCCCCAGCC
ACCACTCTTTGAGGGAGTGTTTCCGCAACCCTCAGTTCCGCATCTTTGCCTACCTGATGGCCGTCATCCT
CAGTGTCACTCTGTTGCTCATATTCTCCATCTTTTGGACCAAGCAGTTCCTTTGGGGTGTGGGGTGAGTG
CTGTTCCCAGACAAGAAACCAAACCTTTTTCGGTTGCTGCTGGGTATGGTGACTACGGAGCCTCATTTGG
TATTGTCTTCCTTTGTAGTGTTGTTTATTTTACAATCCAGGGATTGTTCAGGCCATGTGTTTGCTTCTGG
GAACAATTTTAAAAAAAAACAAAAAAACGAAAAGCTTGAAGGACTGGGAGATGTGGAGCGACCTCCGGGT
GTGAGTGTGGCGTCATGGAAGGGCAGAGAAGCGGTTCTGACCACAGAGCTCCACAGCAAGTTGTGCCAAA
GGGCTGCACAGTGGTATCCAGGAACCTGACTAGCCCAAATAGCAAGTTGCATTTCTCACTGGAGCTGCTT
CAAAATCAGTGCATATTTTTTGAGTTGCTCTTTTACTATGGGTTGCTAAAAAAAAAAAAAAATTGGGA
AGTGAGCTTCAATTCTGTGGGTAAATGTGTGTTTGTTTCTCTTTGAATGTCTTGCCACTGGTTGCAGTAA
AAGTGTTCTGTATTCATTAAAAAAAAAAAAAAAAAAAAAAAAAAAA

The corresponding amino acid sequence is given in ENSEMBL accession no. ENSP00000297894 and has a sequence as in SEQ ID NO:383

MAEQQGRELEAECPVCWNPFNNTFHTPKMLDCCHSFCVECLAHLSLVTPARRRLLCPLCRQPTVLASGQPVTDLP

TDTAMLALLRLEPHHVILEGHQLCLKDQPKSRYFLRQPQVYTLDLGPQPGGQTGPPPDTASATVSTPILIPSHHS

LRECFRNPQFRIFAYLMAVILSVTLLLIFSIFWTKQFLWGVG

Primers for amplifying the sequence RNF183 can be designed using primer design software such as Oligo Calc.

Examples of primer pairs for amplifying RNF183 include those in

```
Forward    GAGAAGCTGGGCTGGAG (EXON3)              SEQ ID NO: 384
Reverse    CAGCCACACACGGGGA (EXON4)               SEQ ID NO: 385
Forward    CAGCTGTGTGCTAAGAACAAAG (EXON3)         SEQ ID NO: 386
Reverse    GCCCTGCTGCTCAGCCATC (EXON4)            SEQ ID NO: 387
Forward    GCAGAAGGCAGCGAGGAC (EXON3)             SEQ ID NO: 388
Reverse    GGCAGCAATCCAGCATTTTG (EXON4)           SEQ ID NO: 389
Forward    CTGCGTGGAATGTCTGGCC (EXON4)            SEQ ID NO: 390
Reverse    CAAGTCAGTGACAGGCTGC (EXON4)            SEQ ID NO: 391
Forward    GTCTACACGCTGGACCTTG (EXON4)            SEQ ID NO: 392
Reverse    GATGCGGAACTGAGGGTTG (EXON4)            SEQ ID NO: 393
Forward    CTACCTGATGGCCGTCATC (EXON4)            SEQ ID NO: 394
Reverse    CCAGCAGCAACCGAAAAAG (EXON4)            SEQ ID NO: 395
Forward    CATGCGTGCAGGGCTGCA (EXON1)             SEQ ID NO: 396
Reverse    GTGCTGCTCTCCCAGGG (EXON2)              SEQ ID NO: 397
Forward    CCG TGGAATCGATTCCCAG (EXON2)           SEQ ID NO: 398
Reverse    CTGTTTCTCATATGGGTCATTCG (EXON3)        SEQ ID NO: 399
```

Other sets of primers can be readily designed by the skilled artisan and/or are known in the art.

Probes for detecting RNF183 can be derived from any number of sources depending on the desired use (e.g., using the above described primers and appropriate reagents). Other examples of probes include

```
ATGGCTGAGCAGCAGGGCCGGGAGCTTGAGGCTGAGTGCCC    SEQ ID NO: 400

GCCCACGGACACTGCCATGCTCGCCCTGCTCC             SEQ ID NO: 401

GGACCAGCCCAAGAGCCGCTACTTCCTGCGCCAGCCT        SEQ ID NO: 402

CGCTGGACCTTGGCCCCCAGCCTGGGGGCCAG             SEQ ID NO: 403

GTTCCTTTGGGGTGTGGGGTGAGTGCTG                 SEQ ID NO: 404
```

A probe for detecting RNF183 nucleic acid that was used on the microarray has a sequence as in SEQ ID NO:405

CAGTGGTATCCAGGAACCTGACTAGCCCAAATAGCAAGTTGCATTTCTCA CTGGAGCTGC

Other probes to RNF183 are known in the art and/or can be readily designed by the skilled artisan.

Example 21

SIRT6

SIRT6 was found to be overexpressed in endometrial cancer primary tissue as compared to normal endometrial tissue by the microarray experiment described in Example 1. Further studies using RT-PCR demonstrated that SIRT6 was overexpressed in primary endometrial cancer tissue as compared to normal endometrial tissue as described in Example 2. It was surprisingly found that SIRT6 was overexpressed in samples obtained from uterine fluid (e.g., aspirates) from patients having endometrial cancer by the method described in Example 4. Example 5 shows that SIRT6 can be combined with other biomarkers to give excellent predictive power for diagnosis of endometrial cancer.

The sequence of an mRNA corresponding to SIRT6 is given in ENSEMBL accession no. ENST00000269860 and has a sequence as in SEQ ID NO:406

```
  1 GCTTCCGGCGGAAGCGGCCTCAACAAGGGAAACTTTATTGTTCCCGTGGGGCAGTCGAGG
 61 ATGTCGGTGAATTACGCGGCGGGGCTGTCGCCGTACGCGGACAAGGGCAAGTGGGCCTC
121 CCGGAGATCTTCGACCCCCCGGAGGAGCTGGAGCGGAAGGTGTGGGAACTGGCGAGGCTG
181 GTCTGGCAGTCTTCCAGTGTGGTGTTCCACACGGGTGCCGGCATCAGCACTGCCTCTGGC
```

```
-continued
 241 ATCCCCGACTTCAGGGACAAACTGGCAGAGCTCCACGGGAACATGTTTGTGGAAGAATGT

301 GCCAAGTGTAAGACGCAGTACGTCCGAGACACAGTCGTGGGCACCATGGGCCTGAAGGCC

361 ACGGGCCGGCTCTGCACCGTGGCTAAGGCAAGGGGGCTGCGAGCCTGCAGGGGAGAGCTG

421 AGGGACACCATCCTAGACTGGGAGGACTCCCTGCCCGACCGGGACCTGGCACTCGCCGAT

481 GAGGCCAGCAGATCCGGCCCAGCGGGAACCTGCCGCTGGCTACCAAGCGCCGGGGAGGCC

541 GCCTGGTCATCGTCAACCTGCAGCCCACCAAGCACGACCGCCATGCTGACCTCCGCATCC

601 ATGGCTACGTTGACGAGGTCATGACCCGGCTCATGAAGCACCTGGGGCTGGAGATCCCCG

661 CCTGGGACGGCCCCCGTGTGCTGGAGAGGGCGCTGCCACCCCTGCCCCGCCCGCCCACCC

721 CCAAGCTGGAGCCCAAGGAGGAATCTCCCACCCGGATCAACGGCTCTATCCCCGCCGGCC

781 CCAAGCAGGAGCCCTGCGCCCAGCACAACGGCTCAGAGCCCGCCAGCCCCAAACGGGAGC

841 GGCCCACCAGCCCTGCCCCCCACAGACCCCCCAAAAGGGTGAAGGCCAAGGCGGTCCCCA

901 GCTGACCAGGGTGCTTGGGGAGGGTGGGGCTTTTTGTAGAAACTGTGGATTCTTTTTCTC

961 TCGTGGTCTCACTTTGTTACTTGTTTCTGTCCCCGGGAGCCTCAGGGCTCTGAGAGCTGT

1021 GCTCCAGGCCAGGGGTTACACCTGCCCTCCGTGGTCCCTCCCTGGGCTCCAGGGGCCTCT

1081 GGTGCGGTTCCGGGAAGAAGCCACACCCCAGAGGTGACAGGTGAGCCCCTGOCACACCCC

1141 AGCCTCTGACTTGCTGTGTTGTCCAGAGGTGAGGCTGGGCCCTCCCTGGTCTCCAGCTTA

1201 AACAGGAGTGAACTCCCTCTGTCCCCAGGGCCTCCCTTCTGGGCCCCTACAGCCCACCC

1261 TACCCCTCCTCCATGGGCCCTGCAGGAGGGGAGACCCACCTTGAAGTGGGGATCAGTAG

1321 AGGCTTGCACTGCCTTTGGGGCTGGAGGGAGACGTGGGTCCACCAGGCTTCTGGAAAAGT

1381 CCTCAATGCAATAAAAACAATTTCTTTCTTGCA
```

The start and stop codons are indicated in bold as well as the position corresponding to the microarray probe.

The corresponding amino acid sequence is given in ENSEMBL accession no. ENSP00000269860 and has a sequence as in SEQ ID NO:407

```
  1 MSVNYAAGLSPYADKGKCGLPEIFDPPEELERKVWELARLVWQSSSVVFHTGAGISTASG

61 IPDFRDKLAELHGNMFVEECAKCKTQYVRDTVVGTMGLKATGRLCTVAKARGLRACRGEL

121 RDTILDWEDSLPDRDLALADEASRSGPAGTCRWLPSAGEAAWSSSTCSPPSTTAMLTSAS

181 MATLTRS
```

Primers for amplifying the sequence SIRT6 can be designed using primer design software such as Oligo Calc and/or Primer 3.

Examples of primer pairs for amplifying SIRT6 include those in

| | SEQ ID NO: 408 |
|---|---|
| Forward | TTGTGGAAGAATGTGCCAAG |
| | SEQ ID NO: 409 |
| Reverse | CCTTAGCCACGGTGCAGAG |
| | SEQ ID NO: 410 |
| Forward | TCTTCCAGTGTGGTGTTCCA |
| | SEQ ID NO: 411 |
| Reverse | TTGGCACATTCTTCCACAAA |
| | SEQ ID NO: 412 |
| Forward | AGCTGAGGGACACCATCCTA |
| | SEQ ID NO: 413 |
| Reverse | GCAGGTTGACGATGACCAG |
| | SEQ ID NO: 414 |
| Forward | GCTTCCTGGTCAGCCAGA |
| | SEQ ID NO: 415 |
| Reverse | ATGTACCCAGCGTGATGGAC |
| | SEQ ID NO: 416 |
| Forward | GCTTCCTGGTCAGCCAGA |
| | SEQ ID NO: 417 |
| Reverse | CTAGGATGGTGTCCCTCAGC |
| | SEQ ID NO: 418 |
| Forward | GAGAGCTGAGGGACACCATC |
| | SEQ ID NO: 419 |
| Reverse | GTACCCAGCGTGATGGACAG |
| | SEQ ID NO: 420 |
| Forward | AGGATGTCGGTGAATTACGC |

-continued

```
                              SEQ ID NO: 421
    Reverse          AAAGGTGGTGTCGAACTTGG
```

Other sets of primers can be readily designed by the skilled artisan and/or are known in the art.

Probes for detecting SIRT6 can be derived from any number of sources depending on the desired use (e.g., using the above described primers and appropriate reagents). Other examples of probes include

```
                                     SEQ ID NO: 422
              TGTAAGACGCAGTACGTCCG

SEQ ID NO: 423
              GACTTCAGGGACAAACTGGC

SEQ ID NO: 424
              ACTGGGAGGACTCCCTGC

SEQ ID NO: 425
              TGTAAGACGCAGTACGTCCG

SEQ ID NO: 426
              TGTAAGACGCAGTACGTCCG

SEQ ID NO: 427
              TAGACTGGGAGGACTCCCTG

SEQ ID NO: 428
              GAGTCTGGACCATGGAGGAG
```

A probe to detect SIRT6 nucleic acid that was used on the microarray has a sequence as in SEQ ID NO:429

```
GAAGTGGGGGATCAGTAGAGGCTTGCACTGCCTTTGGGGCTGGAGGGAGA
```

Other probes to SIRT6 are known in the art and/or can be readily designed by the skilled artisan.

Antibodies against SIRT6 include, but are not limited to, Rabbit polyclonal anti-SIRT6 against de C-terminal Cat#2590 from Cell Signalling Technology; and Mouse monoclonal antibody raised against a partial recombinant SIRT6 141 a.a.~251 a.a Catalog #:H00051548-M01 from abnova.

Example 22

TJP3

TJP3, tight junction protein 3 (zona occludens 3) also known as MGC119546, ZO-3, ZO3 was found to be overexpressed in endometrial cancer primary tissue as compared to normal endometrial tissue by the microarray experiment described in Example 1. Further studies using RT-PCR demonstrated that TJP3 was overexpressed in primary endometrial cancer tissue as compared to normal endometrial tissue as described in Example 2. It was surprisingly found that TJP3 was overexpressed in samples obtained from uterine fluid (e.g., aspirates) from patients having endometrial cancer by the method described in Example 4. Example shows that TJP3 can be combined with other biomarkers to give excellent predictive power for diagnosis of endometrial cancer.

TJP3 (ZO-3) was first identified as a 130 kDa protein that coimmunoprecipitates with ZO-1. It is a member of the MAGUK proteins (MEMBRANE-associated guanylate kinase-like homologues). These proteins are implicated in the formation and maintenance of supramolecular complexes at specific areas of the cell surface called tight junctions. Tight junctions locate at the most apical part of lateral membranes of simple epithelial cells, and are considered to be involved in barrier and fence functions.

Cloning and sequencing cDNAs encoding MAGUK proteins showed that all have three PDZ domains (PDZ1 to –3), one SH3 domain, and one guanylate kinase-like (GUK) domain in this order from their NH2 termini (PMID: 10966866). Among these domains, PDZ domains bind to COOH-terminal ends of various proteins, especially integral membrane proteins, most of which end in valine. Thus, MAGUKs can cross-link multiple integral membrane proteins at the cytoplasmic surface of plasma membranes to establish specialized membrane domains. ZO-3 has also been reported to associate with ZO-1, but not with ZO-2, although the domains responsible for ZO-3/ZO-1 interaction remain unidentified. ZO-3 was also shown to directly bind to the cytoplasmic domain of occludin (Haskins et al. 1998).

The sequence of an mRNA corresponding to TJP3 is given in ENSEMBL accession no. ENST00000262968 and has a sequence as in SEQ ID NO:430

```
ATGAACCTGTGTGGCCTCATGCCCATCTTCCCCGCTCCCCTCGACCAGGTGGCTGACATGGAGGAGCTGA

CCATCTGGGAACAGCACACGGCCACACTGTCCAAGGACCCCCGCCGGGGCTTTGGCATTGCGATCTCTGG

AGGCCGAGACCGGCCCGGTGGATCCATGGTTGTATCTGACGTGGTACCTGGAGGGCCGGCGGAGGGCAGG

CTACAGACAGGCGACCACATCGTCATGGTGAACGGGGTTTCCATGGAGAATGCCACCTCCGCGTTTGCCA

TTCAGATACTCAAGACCTGCACCAAGATGGCCAACATCACAGTGAAACGTCCCCGGAGGATCCACCTGCC

CGCCACCAAAGCCAGCCCCTCCAGCCCAGGGCGCCAGGACTCGGATGAAGACGATGGGCCCCAGCGGGTG

GAGGAGGTGGACCAGGGCCGGGCTATGACGGCGACTCATCCAGTGGCTCCGGCCGCTCCTGGGACGAGC

GCTCCCGCCGGCCGAGGCCTGGTCGCCGGGGCCGGGCCGGCAGCCATGGGCGTAGGAGCCCAGGTGGTGG

CTCTGAGGCCAACGGGCTGGCCCTGGTGTCCGGCTTTAAGCGGCTGCCACGGCAGGACGTGCAGATGAAG

CCTGTGAAGTCAGTGCTGGTGAAGAGGAGAGACAGCGAAGAGTTTGGCGTCAAGCTGGGCAGTCAGATCT

TCATCAAGCACATTACAGATTCGGGCCTGGCTGCCCGGCACCGTGGGCTGCAGGAAGGAGATCTCATTCT

ACAGATCAACGGGGTGTCTAGCCAGAACCTGTCACTGAACGACACCCGGCGACTGATTGAGAAGTCAGAA

GGGAAGCTAAGCCTGCTGGTGCTGAGAGATCGTGGGCAGTTCCTGGTGAACATTCCGCCTGCTGTCAGTG
```

-continued

```
ACAGCGACAGCTCGCCATTGGAGGAAGGCGTGACCATGGCTGATGAGATGTCCTCTCCCCCTGCAGACAT
CTCGGACCTCGCCTCGGAGCTATCGCAGGCACCACCATCCCACATCCCACCACCACCCCGGCATGCTCAG
CGGAGCCCCGAGGCCAGCCAGACCGACTCTCCCGTGGAGAGTCCCCGGCTTCGGCGGGAAAGTTCAGTAG
ATTCCAGAACCATCTCGGAACCAGATGAGCAACGGTCAGAGTTGCCCAGGGAAAGCAGCTATGACATCTA
CAGAGTGCCCAGCAGTCAGAGCATGGAGGATCGTGGGTACAGCCCCGACACGCGTGTGGTCCGCTTCCTC
AAGGGCAAGAGCATCGGGCTGCGGCTGGCAGGGGGCAATGACGTGGGCATCTTCGTGTCCGGGGTGCAGG
CGGGCAGCCCGGCCGACGGGCAGGGCATCCAGGAGGGAGATCAGATTCTGCAGGTGAATGACGTGCCATT
CCAGAACCTGACACGGGAGGAGGCAGTGCAGTTCCTGCTGGGGCTGCCACCAGGCGAGGAGATGGAGCTG
GTGACGCAGAGGAAGCAGGACATTTTCTGGAAAATGGTGCAGTCCCGCGTGGGTGACTCCTTCTACATCC
GCACTCACTTTGAGCTGGAGCCCAGTCCACCGTCTGGCCTGGGCTTCACCCGTGGCGACGTCTTCCACGT
GCTGGACACGCTGCACCCCGGCCCCGGGCAGAGCCACGCACGAGGAGGCCACTGGCTGGCGGTGCGCATG
GGTCGTGACCTGCGGGAGCAAGAGCGGGGCATCATTCCCAACCAGAGCAGGGCGGAGCAGCTGGCCAGCC
TGGAAGCTGCCCAGAGGGCCGTGGGAGTCGGGCCCGGCTCCTCCGCGGGCTCCAATGCTCGGGCCGAGTT
CTGGCGGCTGCGGGGTCTTCGTCGAGGAGCCAAGAAGACCACTCAGCGGAGCCGTGAGGACCTCTCAGCT
CTGACCCGACAGGGCCGCTACCCGCCCTACGAACGAGTGGTGTTGCGAGAAGCCAGTTTCAAGCGCCCGG
TAGTGATCCTGGGACCCGTGGCCGACATTGCTATGCAGAAGTTGACTGCTGAGATGCCTGACCAGTTTGA
AATCGCAGAGACTGTGTCCAGGACCGACAGCCCCTCCAAGATCATCAAACTAGACACCGTGCGGGTGATT
GCAGAAAAAGACAAGCATGCGCTCCTGGATGTGACCCCCTCCGCCATCGAGCGCCTCAACTATGTGCAGT
ACTACCCCATTGTGGTCTTCTTCATCCCCGAGAGCCGGCCGGCCCTCAAGGCACTGCGCCAGTGGCTGGC
GCCTGCCTCCCGCCGCAGCACCCGTCGCCTCTACGCACAAGCCCAGAAGCTGCGAAAACACAGCAGCCAC
CTCTTCACAGCCACCATCCCTCTGAATGGCACGAGTGACACCTGGTACCAGGAGCTCAAGGCCATCATTC
GAGAGCAGCAGACGCGGCCCATCTGGACGGCGGAAGATCAGCTGGATGGCTCCTTGGAGGACAACCTAGA
CCTCCCTCACCACGGCCTGGCCGACAGCTCCGCTGACCTCAGCTGCGACAGCCGCGTTAACAGCGACTAC
GAGACGGACGGCGAGGGCGGCGCGTACACGGATGGCGAGGGCTACACAGACGGCGAGGGGGGCCCTACA
CGGATGTGGATGATGAGCCCCCGGCTCCAGCCCTGGCCCGGTCCTCGGAGCCCGTGCAGGCAGATGAGTC
CCAGAGCCCGAGGGATCGTGGGAGAATCTCGGCTCATCAGGGGGCCCAGGTGGACAGCCGCCACCCCCAG
GGACAGTGGCGACAGGACAGCATGCGAACCTATGAACGGGAAGCCCTGAAGAAAAAGTTTATGCGAGTAC
ATGATGCGGAGTCCTCCGATGAAGACGGCTATGACTGGGGTCCGGCCACTGACCTGTGA
```

The corresponding amino acid sequence is given in ENSEMBL accession no. ENSP00000262968 and has a sequence as in SEQ ID NO:431

```
MNLCGLMPIFPAPLDQVADMEELTIWEQHTATLSKDPRRGFGIA
ISGGRDRPGGSMVVSDVVPGGPAEGRLQTGDHIVMVNGVSMENATSAFAI
QILKTCTKMANITVKRPRRIHLPATKASPSSPGRQDSDEDDGPQRVEEVD
QGRGYDGDSSSGSGRSWDERSRRPRPGRRGRAGSHGRRSPGGGSEANGLA
LVSGFKRLPRQDVQMKPVKSVLVKRRDSEEFGVKLGSQIFIKHITDSGLA
ARHRGLQEGDLILQINGVSSQNLSLNDTRRLIEKSEGKLSLLVLRDRGQF
LVNIPPAVSDSDSSPLEEGVTMADEMSSPPADISDLASELSQAPPSHIPP
PPRHAQRSPEASQTDSPVESPRLRRESSVDSRTISEPDEQRSELPRESSY
DIYRVPSSQSMEDRGYSPDTRVVRFLKGKSIGLRLAGGNDVGIFVSGVQA
GSPADGQGIQEGDQILQVNDVPFQNLTREEAVQFLLGLPPGEEMELVTQR
KQDIFWKMVQSRVGDSFYIRTHFELEPSPPSGLGFTRGDVFHVLDTLHPG
PGQSHARGGHWLAVRMGRDLREQERGIIPNQSRAEQLASLEAAQRAVGVG
PGSSAGSNARAEFWRLRGLRRGAKKTTQRSREDLSALTRQGRYPPYERVV
LREASFKRPVVILGPVADIAMQKLTAEMPDQFEIAETVSRTDSPSKIIKL
DTVRVIAEKDKHALLDVTPSAIERLNYVQYYPIVVFFIPESRPALKALRQ
WLAPASRRSTRRLYAQAQKLRKHSSHLFTATIPLNGTSDTWYQELKAIIR
EQQTRPIWTAEDQLDGSLEDNLDLPHHGLADSSADLSCDSRVNSDYETDG
EGGAYTDGEGYTDGEGGPYTDVDDEPPAPALARSSEPVQADESQSPRDRG
RISAHQGAQVDSRHPQGQWRQDSMRTYEREALKKKFMRVHDAESSDEDGY
DWGPATDL
```

Primers for amplifying the sequence ENST00000262968 can be designed using primer design software such as Oligo Calc and/or Primer 3.

Examples of primer pairs for amplifying TJP3 include:

Forward CCCTCGACCAGGTGGCTGAC (Exon1) SEQ ID NO: 432

Reverse CCTCCAGAGATCGCAATGC (Exon2) SEQ ID NO: 433

Forward GTATCTGACGTGGTACCTG (Exon2) SEQ ID NO: 434

Reverse GGCAAACGCGGAGGTGGCATT C (Exon3) SEQ ID NO: 435

Forward CGGGGTTTCCATGGAGAATG (Exon3) SEQ ID NO: 436

Reverse GCGGGCAGGTGGATCCTCC (Exon4) SEQ ID NO: 437

Forward GCAGGACGTGCAGATGAAGC (Exon4) SEQ ID NO: 438

Reverse CCCGAATCTGTAATGTGCTTG (Exon5) SEQ ID NO: 439

Forward GTGGGCTGCAGGAAGGAGATC (Exon5) SEQ ID NO: 440

Reverse GAACTGCCCACGATCTCTCAGC (Exon6) SEQ ID NO: 441

Forward GATCGTGGGCAGTTCCTGG (Exon6) SEQ ID NO: 442

Reverse GATGTCTGCAGGGGGAGAGG (Exon7) SEQ ID NO: 443

Forward CACCCCGGCATGCTCAGCG (Exon7) SEQ ID NO: 444

Reverse CCGAGATGGTTCTGGAATC (Exon8) SEQ ID NO: 445

Forward GAGTCCCCGGCTTCGGCGG (Exon8) SEQ ID NO: 446

Reverse CGATCCTCCATGCTCTGACTG (Exon9) SEQ ID NO: 447

Forward GTG CAG GCG GGC AGC CCG (Exon10) SEQ ID NO: 448

Reverse GTC CTG CTT CCT CTG CGT C (Exon11) SEQ ID NO: 449

Forward CGAGAGCAGCAGACGCGGCC SEQ ID NO: 450

Reverse GAGGTCAGCGGAGCTGTCG SEQ ID NO: 451

Other sets of primers can be readily designed by the skilled artisan and/or are known in the art.

Probes for detecting TJP3 can be derived from any number of sources depending on the desired use (e.g., using the above described primers and appropriate reagents).

Other examples of probes include:

CAGGGACAGTGGCGACAGGACAGCATGCGAACCTATGAACGGGAAGCCCT GAAGAAAAAG SEQ ID NO: 452

GAACAGCACACGGCCACACTGTCCAAGGACCCCCGCCGGGGC SEQ ID NO: 453

ACCAAGATGGCCAACATCACAGTGAAACGTCCCCGGAGGATCCACCTGCC CGCC SEQ ID NO: 454

CAGTGACAGCGACAGCTCGCCATTGGAGGAAGGCGTGACCATGGCTGATG AGAT SEQ ID NO: 455

CGAGTGGTGTTGCGAGAAGCCAGTTTCAAGCGCCCGGTAGTGATCCTGGG ACCC SEQ ID NO: 456

Other probes to TJP3 are known in the art and/or can be readily designed by the skilled artisan.

Antibodies against include, but are not limited to, TJP3 are commercially available from e.g., Abnova Cat# H00027134-A01 which is a mouse polyclonal antibody raised against a partial recombinant TJP3 having the sequence SEQ ID NO:457 DEPPA-PALARSSEPVQADESQSPRDRGRISAHQ-GAQVDSRHPQGQWRQDS MRTYEREALKKKFM-RVHDAESSDEDGYDWGPATDL (NP_055243, 868 a.a.~953 a.a); from LifeSpanBiosciences Cat# LS-C18593 which is a rabbit polyclonal against a synthetic peptide derived from the C-terminus of the human TJP3 (ZO-3) protein; and from LifeSpanBiosciences Cat#LS-050518 which is a rabbit polyclonal against a synthetic peptide derived from the C-terminus of the human TJP3 (ZO-3) protein.

Example 23

EFEMP2

EFEMP2 also known as FBLN4, MBP1, and UPH1 was found to be underexpressed in endometrial cancer primary tissue as compared to normal endometrial tissue by the microarray experiment described in Example 1. Further studies using RT-PCR demonstrated that EFEMP2 was underexpressed in primary endometrial cancer tissue as compared to normal endometrial tissue as described in Example 2. It was surprisingly found that EFEMP2 was underexpressed in samples obtained from uterine fluid (e.g., aspirates) from patients having endometrial cancer by the method described in Example 4. Example 5 shows that EFEMP2 can be combined with other biomarkers to give excellent predictive power for diagnosis of endometrial cancer.

ENSG00000172638: Just One Transcript

The sequence of an mRNA corresponding to EFEMP2 is given in ENSEMBL accession number ENST00000307998 and has a sequence as in SEQ ID NO:458.

GGGGCG

CTTCCTGGGGCCGCGCGTCCAGGGAGCTGTGCCGTCCGCCCGTCCGTCTG

CCCGCAGGCATTGCCCGAGC

CAGCCGAGCCGCCAGAGCCGCGGGCCGCGGGGGTGTCGCGGGCCCAACCC

CAGGATGCTCCCCTGCGCCT

CCTGCCTACCCGGGTCTCTACTGCTCTGGGCGCTGCTACTGTTGCTCTTG

GGATCAGCTTCTCCTCAGGA

```
TTCTGAAGAGCCCGACAGCTACACGGAATGCACAGATGGCTATGAGTGGG

ACCCAGACAGCCAGCACTGC

CGGGATGTCAACGAGTGTCTGACCATCCCTGAGGCCTGCAAGGGGGAAAT

GAAGTGCATCAACCACTACG

GGGGCTACTTGTGCCTGCCCCGCTCCGCTGCCGTCATCAACGACCTACAC

GGCGAGGGACCCCCGCCACC

AGTGCCTCCCGCTCAACACCCCAACCCCTGCCCACCAGGCTATGAGCCCG

ACGATCAGGACAGCTGTGTG

GATGTGGACGAGTGTGCCCAGGCCCTGCACGACTGTCGCCCCAGCCAGGA

CTGCCATAACTTGCCTGGCT

CCTATCAGTGCACCTGCCCTGATGGTTACCGCAAGATCGGGCCCGAGTGT

GTGGACATAGACGAGTGCCG

CTACCGCTACTGCCAGCACCGCTGCGTGAACCTGCCTGGCTCCTTCCGCT

GCCAGTGCGAGCCGGGCTTC

CAGCTGGGGCCTAACAACCGCTCCTGTGTTGATGTGAACGAGTGTGACAT

GGGGGCCCCATGCGAGCAGC

GCTGCTTCAACTCCTATGGGACCTTCCTGTGTCGCTGCCACCAGGGCTAT

GAGCTGCATCGGGATGGCTT

CTCCTGCAGTGATATTGATGAGTGTAGCTACTCCAGCTACCTCTGTCAGT

ACCGCTGCGTCAACGAGCCA

GGCCGTTTCTCCTGCCACTGCCCACAGGGTTACCAGCTGCTGGCCACACG

CCTCTGCCAAGACATTGATG

AGTGTGAGTCTGGTGCGCACCAGTGCTCCGAGGCCCAAACCTGTGTCAAC

TTCCATGGGGCTACCGCTG

CGTGGACACCAACCGCTGCGTGGAGCCCTACATCCAGGTCTCTGAGAACC

GCTGTCTCTGCCCGGCCTCC

AACCCTCTATGTCGAGAGCAGCCTTCATCCATTGTGCACCGCTACATGAC

CATCACCTCGGAGCGGAGCG

TGCCCGCTGACGTGTTCCAGATCCAGGCGACCTCCGTCTACCCCGGTGCC

TACAATGCCTTTCAGATCCG

TGCTGGAAACTCGCAGGGGACTTTTACATTAGGCAAATCAACAACGTCA

GCGCCATGCTGGTCCTCGCC

CGGCCGGTGACGGGCCCCGGGAGTACGTGCTGGACCTGGAGATGGTCAC

CATGAATTCCCTCATGAGCT

ACCGGGCCAGCTCTGTACTGAGGCTCACCGTCTTTGTAGGGGCCTACACC

TTCTGAGGAGCAGGAGGGAG

CCACCCTCCCTGCAGCTACCCTAGCTGAGGAGCCTGTTGTGAGGGGCAGA

ATGAGAAAGGCAATAAAGGG

AGAAAGAAAGTCCTGGTGGCTGAGGTGGGCGGGTCACACTGCAGGAAGCC

TCAGGCTGGGGCAGGGTGGC

ACTTGGGGGGGCAGGCCAAGTTCACCTAAATGGGGGTCTCTATATGTTCA

GGCCCAGGGGCCCCCATTGA

CAGGAGCTGGGAGCTCTGCACCACGAGCTTCAGTCACCCCGAGAGGAGAG

GAGGTAACGAGGAGGGCGGA

CTCCAGGCCCCGGCCCAGAGATTTGGACTTGGCTGGCTTGCAGGGGTCCT

AAGAAACTCCACTCTGGACA

GCGCCAGGAGGCCCTGGGTTCCATTCCTAACTCTGCCTCAAACTGTACAT

TTGGATAAGCCCTAGTAGTT

CCCTGGGCCTGTTTTTCTATAAAACGAGGCAACTGGACTGTT
```

The corresponding amino acid sequence is given in ENSEMBL accession no. ENSP00000309953 and has a sequence as in SEQ ID NO:459

```
MLPCASCLPGSLLLWALLLLLLGSASPQDSEEPDSYTECTDGYE

WDPDSQHCRDVNECLTIPEACKGEMKCINHYGGYLCLPRSAAVINDLHGE

GPPPPVPPAQHPNPCPPGYEPDDQDSCVDVDECAQALHDCRPSQDCHNLP

GSYQCTCPDGYRKIGPECVDIDECRYRYCQHRCVNLPGSFRCQCEPGFQL

GPNNRSCVDVNECDMGAPCEQRCFNSYGTFLCRCHQGYELHRDGFSCSDI

DECSYSSYLCQYRCVNEPGRFSCHCPQGYQLLATRLCQDIDECESGAHQC

SEAQTCVNFHGGYRCVDTNRCVEPYIQVSENRCLCPASNPLCREQPSSIV

HRYMTITSERSVPADVFQIQATSVYPGAYNAFQIRAGNSQGDFYIRQINN

VSAMLVLARPVTGPREYVLDLEMVTMNSLMSYRASSVLRLTVFVGAYTF
```

Examples of primer pairs for amplifying EFEMP2 include those in

```
                                        SEQ ID NO: 460
         Forward TGCTCTTGGGATCAGCTTCT
                                        SEQ ID NO: 461
         Reverse CCTCAGGGATGGTCAGACAC
                                        SEQ ID NO: 462
         Forward TGCCCACCAGGCTATGAG
                                        SEQ ID NO: 463
         Reverse CAGGCAAGTTATGGCAGTCC
                                        SEQ ID NO: 464
         Forward AACTTGCCTGGCTCCTATCA
                                        SEQ ID NO: 465
         Reverse GTGCTGGCAGTAGCGGTAG
                                        SEQ ID NO: 466
         Forward GGCCTAACAACCGCTCCT
                                        SEQ ID NO: 467
         Reverse CGACACAGGAAGGTCCCATA
                                        SEQ ID NO: 468
         Forward TATGGGACCTTCCTGTGTCG
                                        SEQ ID NO: 469
         Reverse GATGCAGCGGTACTGACAGA
                                        SEQ ID NO: 470
         Forward GTCAGTACCGCTGCATCAAC
                                        SEQ ID NO: 471
         Reverse CGCACCAGACTCACACTCAT
```

```
                                          SEQ ID NO: 472
Forward GTGGAGCCCTACATCCAGGT SEQ ID NO: 473
Reverse TCCGAGGTGATGGTCATGTA
```

Other sets of primers can be readily designed by the skilled artisan and/or are known in the art.

Probes for detecting EFEMP2 can be derived from any number of sources depending on the desired use (e.g., using the above described primers and appropriate reagents). Other examples of probes include The probe used on the microarray has a sequence as in SEQ ID NO:474
TTCATCCATTGTGCACCGCTACATGAC-CATCACCTCGGAGCGGAGCGTGC
SEQ ID NO:475 GAAGAGCCCGACAGCTACAC
SEQ ID NO:476 CAGGCAAGTTATGGCAGTCC
SEQ ID NO:477 CCTGATGGTTACCGCAAGAT
SEQ ID NO:478 GTGAACGAGTGTGACATGGG
SEQ ID NO:479 ATGGCTTCTCCTGCAGTGAT
SEQ ID NO:480 ACGCCTCTGCCAAGACATT
SEQ ID NO:481 ATGTCGAGAGCAGCCTTCAT Antibodies to EFEMP2 include Mouse Anti-Human EFEMP2 MaxPab® Polyclonal Antibody, Unconjugated Cat# H00030008-B01 against full length human EFEMP2; Anti-EFEMP2 Monoclonal Antibody, Unconjugated, Clone 2C8 Cat# H00030008-M01 against a partial protein, 26aa-443aa; and Rabbit Anti-Human EFEMP2 Polyclonal Antibody, Unconjugated Cat# ab74873 against a Synthetic peptide derived from an internal region of human EFEMP2.

Example 24

SOCS2

SOCS2 also known as CIS2, Cish2, SOCS-2, SSI-2, SSI2, and STATI2 was found to be underexpressed in endometrial cancer primary tissue as compared to normal endometrial tissue by the microarray experiment described in Example 1. Further studies using RT-PCR demonstrated that SOCS2 was underexpressed in primary endometrial cancer tissue as compared to normal endometrial tissue as described in Example 2. It was surprisingly found that SOCS2 was underexpressed in samples obtained from uterine fluid (e.g., aspirates) from patients having endometrial cancer by the method described in Example 4. Example 5 shows that SOCS2 can be combined with other biomarkers to give excellent predictive power for diagnosis of endometrial cancer.

The sequence of an mRNA corresponding to SOCS2 is given in ENSEMBL accession number ENST00000340600 and has a sequence as in SEQ ID NO:482

```
   1 AGCCGCGGCCTCAACTAAAAGTGGCCATTGACCTTTCAAGCTTTCGAGCAGTGATGCAAT
  61 AGAATAGTATTTCAAAGAAAAATGCTTATCGAAATTTTGGATCCGGTTTTCCCGTGATTG
 121 TTAAGGGTTTCTTTTAAAAAGTAGGTCACATTTCAAGTAGGTCATATTTCGGGGGCGGGT
 181 GCGCAGACAAGGAGATGAGTTTCCACTAAGGCCAGGGGGCCTCCAACGGGGTTGGAGGTG
 241 AGAATCCCAGGTAGGGTAGAGGTGCCGAGATCCTTCCGAATCCCAGCCCTGGGGCGTCAG
 301 CCCTGCAGGGAATGGCAGAGACACTCTCCGGACTGAGGGAACCGAGGCCAGTCACCAAGC
 361 CCCTTCCGGGCGCGCAGGCGATCAGTGGGTGACCGCGGCTGCGAGGGACTTTGTCATCCG
 421 TCCTCCAGGATCTGGGGAGAAAGAGCCCCATCCCTTCTCTCTCTGCCACCATTTCGGACA
 481 CCCCGCAGGGACTCGTTTTGGGATTCGCACTGACTTCAAGGAAGGACGCGAACCCTTCTC
 541 TGACCCCAGCTCGGGCGGCCACCTGTCTTTGCCGCGGTGACCCTTCTCTCATGACCCTGC
 601 GGTGCCTTGAGCCCTCCGGGAATGGCGGGAAGGGACGCGGAGCCAGTGGGGACCGCGG
 661 GGTCGGCGGAGGAGCCATCCCCGCAGGCGGCGCGTCTGGCGAAGGCCCTGCGGGAGCTCG
 721 GTCAGACAGGATGGTACTGGGGAAGTATGACTGTTAATGAAGCCAAAGAGAAATTAAAAG
 781 AGGCACCAGAAGGAACTTTCTTGATTAGAGATAGCTCGCATTCAGACTACCTACTAACAA
 841 TATCTGTTAAAACATCAGCTGGACCAACTAATCTTCGAATCGAATACCAAGACGGAAAAT
 901 TCAGATTGGACTCTATCATATGTGTCAAATCCAAGCTTAAACAATTTGACAGTGTGGTTC
 961 ATCTGATCGACTACTATGTTCAGATGTGCAAGGATAAGCGGACAGGTCCAGAAGCCCCCC
1021 GGAACGGCACTGTTCACCTTTATCTGACCAAACCGCTCTACACGTCAGCACCATCTCTGC
1081 AGCATCTCTGTAGGCTCACCATTAACAAATGTACCGGTGCCATCTGGGGACTGCCTTTAC
1141 CAACAAGACTAAAAGATTACTTGGAAGAATATAAATTCCAGGTATAAATGTTTCTCTTTT
1201 TTTAAACATGTCTCACATAGAGTATCTCCGAATGCAGCTATGTAAAAGAGAACCAAAACT
1261 TGAGTGCTCTGGATAACTATATGGAATGCTTTCTAAGAACAGCTGAAGCTAATCTAATTT
1321 AAATTTAACAGCTTGAAGAGGTAGCTAGGTGTTTAAAGTTCCTCCAGATACTTTTACCTG
1381 AGTGATGCTTCCCTTCCTAAGGCTGACCAAGACCTGTTGATCCTTTTAGATTAAAAATAA
```

```
1441 AATGTCGCATGTAAAGGCTGAAGTCGCGTTTTATCAGAATGCCTTGCCTTCTTAGGTTCT

1501 TTTCCATTATGTCAAAGGTCCAGGCTCCAGTAGGAGAGAAAGAACTCCTCATAGGAATAC

1561 TGAAGAAGTGGGAAGGAACCAAGCTGACACAGGCCTCACTGCAATTTGATATGCCTGCTG

1621 ATCAGAGTCTCTTGGGCATTTTATATTTTGCATTCTGATGTACCTAGGAGTTTTGTTAAA

1681 CAGATGATGTATGTGAGTATTTATCCCATTTTATGCAATTAACCAAATCAACCAAAAAAA

1741 GTGACCATGAAGTCCTGTATTTGTCTTTTTACTACATGTAGGAACTCTCATGTGAATGAG

1801 TACTGTAGTAATCCATTCTATGGGAGCCTTATTTCAGAAATATTTCAAACTGGTGCAAAT

1861 GGAAAAGACTTTCTCTTTTCCTTTAAAGCTAAAGACAAGAATATCATGCTATACAGGTGC

1921 AACTCAATCCCCGTTAATAAAAACCAATGTAGGTATAGGCATTCTACCCTTTGAAATAGC

1981 TGTGTCCCAACCTGTTGCCATTGATTTTTTGGAAATGGCTTTAGAAATATCCAAGTTGTC

2041 CTTGAATTGTCTAACCATGGACATAAACAGTTGTCTCCCTTCTACTGTGTAGAATACTTT

2101 GACTTAATTTTCTTCCAGATACAGGGGGATACCTGCCTGTTTTTCAAAGTGTTTATTTAC

2161 TGCTGTTACTATTTGATTAGAATGTATTAAATAAAAAAAACCTGATTTCT
```

The start and stop codons are indicated in bold.

The corresponding amino acid sequence is given in ENSEMBL accession no. ENSP00000339428 and has a sequence as in SEQ ID NO:483

```
  1 MTLRCLEPSGNGGEGTRSQWGTAGSAEEPSPQAARLAKALRELGQTGWYWGSMTVNEAKE

61 KLKEAPEGTFLIRDSSHSDYLLTISVKTSAGPTNLRIEYQDGKFRLDSIICVKSKLKQFD

121 SVVHLIDYYVQMCKDKRTGPEAPRNGTVHLYLTKPLYTSAPSLQHLCRLTINKCTGAIWG

181 LPLPTRLKDYLEEYKFQV
```

Examples of primer pairs for amplifying SOCS2 include those in

```
                              SEQ ID NO: 484
Forward AGTCACCAAGCCCCTTCC

SEQ ID NO: 485
Reverse GCTCTTTCTCCCCAGATCCT

SEQ ID NO: 486
Forward GGGACTGCCTTTACCAACAA

SEQ ID NO: 487
Reverse TTTACATAGCTGCATTCGGAGA
```

Other sets of primers can be readily designed by the skilled artisan and/or are known in the art (e.g., using Oligo Calc and/or Primer 3).

Probes for detecting SOCS2 can be derived from any number of sources depending on the desired use (e.g., using the above described primers and appropriate reagents). Other examples of probes include The probe used on the microarray has a sequence as in SEQ ID NO:488
AGTGTGGTTCATCTGATCGACTACTAT-GTTCAGATGTGCAAGGATAAGCGGA CAGGTCCA
SEQ ID NO:489 GACTTTGTCATCCGTCCTCC
SEQ ID NO:490 ACTTGGAAGAATATAAATTCCAGGT Antibodies to SOCS2 include, but are not limited to, Mouse Anti-Human SOCS2 Polyclonal Antibody, Unconjugated Cat# H00008835-A01 against a partial protein: 99aa-198aa; Mouse Anti-Human SOCS2 Monoclonal Antibody, Unconjugated, Clone 3E7 Cat# H00008835-M01 against a partial protein: 99aa-198aa; Rabbit Anti-Human SOCS2 Polyclonal Antibody, Unconjugated Cat# ab74533 against the C-terminal part of the protein.

Example 25

DCN

DCN also known as CSCD, DSPG2, PG40, PGII, PGS2, and SLRR1B was found to be underexpressed in endometrial cancer primary tissue as compared to normal endometrial tissue by the microarray experiment described in Example 1. Further studies using RT-PCR demonstrated that DCN was underexpressed in primary endometrial cancer tissue as compared to normal endometrial tissue as described in Example 2. It was surprisingly found that DCN was underexpressed in samples obtained from uterine fluid (e.g., aspirates) from patients having endometrial cancer by the method described in Example 4. Example 5 shows that DCN can be combined with other biomarkers to give excellent predictive power for diagnosis of endometrial cancer.

Six transcripts from gene ENSG00000011465 but only 4 of them hybridize with our array probe, the following ones:

The sequence of an mRNA corresponding to DCN is given in ENSEMBL accession number ENST00000052754 and has a sequence as in SEQ ID NO:491

```
   1 GAATCTACAATAAGACAAATTTCAAATCAAGTTGCTCCACTATACTGCATAAGCAGTTTA
  61 GAATCTTAAGCAGATGCAAAAAGAATAAAGCAAATGGGAGGAAAAAAAGGCCGATAAAG
 121 TTTCTGGCTACAATACAAGAGACATATCATTACCATATGATCTAATGTGGGTGTCAGCCG
 181 GATTGTGTTCATTGAGGGAAACCTTATTTTTAACTGTGCTATGGAGTAGAAGCAGGAGG
 241 TTTTCAACCTAGTCACAGAGCAGCACCTACCCCCTCCTCCTTTCCACACCTGCAAACTCT
 301 TTTACTTGGGCTGAATATTTAGTGTAATTACATCTCAGCTTTGAGGGCTCCTGTGGCAAA
 361 TTCCCGGATTAAAAGGTTCCCTGGTTGTGAAAATACATGAGATAAATCATGAAGGCCACT
 421 ATCATCCTCCTTCTGCTTGCACAAGTTTCCTGGGCTGGACCGTTTCAACAGAGAGGCTTA
 481 TTTGACTTTATGCTAGAAGATGAGGCTTCTGGGATAGGCCCAGAAGTTCCTGATGACCGC
 541 GACTTCGAGCCCTCCCTAGGCCCAGTGTGCCCCTTCCGCTGTCAATGCCATCTTCGAGTG
 601 GTCCAGTGTTCTGATTTGGGTCTGGACAAAGTGCCAAAGGATCTTCCCCCTGACACAACT
 661 CTGCTAGACCTGCAAAACAACAAAATAACCGAAATCAAAGATGGAGACTTTAAGAACCTG
 721 AAGAACCTTCACGCATTGATTCTTGTCAACAATAAAATTAGCAAAGTTAGTCCTGGAGCA
 781 TTTACACCTTTGGTGAAGTTGGAACGACTTTATCTGTCCAAGAATCAGCTGAAGGAATTG
 841 CCAGAAAAAATGCCCAAAACTCTTCAGGAGCTGCGTGCCCATGAGAATGAGATCACCAAA
 901 GTGCGAAAAGTTACTTTCAATGGACTGAACCAGATGATTGTCATAGAACTGGGCACCAAT
 961 CCGCTGAAGAGCTCAGGAATTGAAAATGGGGCTTTCCAGGGAATGAAGAAGCTCTCCTAC
1021 ATCCGCATTGCTGATACCAATATCACCAGCATTCCTCAAGGTCTTCCTCCTTCCCTTACG
1081 GAATTACATCTTGATGGCAACAAAATCAGCAGAGTTGATGCAGCTAGCCTGAAAGGACTG
1141 AATAATTTGGCTAAGTTGGGATTGAGTTTCAACAGCATCTCTGCTGTTGACAATGGCTCT
1201 CTGGCCAACACGCCTCATCTGAGGGAGCTTCACTTGGACAACAACAAGCTTACCAGAGTA
1261 CCTGGTGGGCTGGCAGAGCATAAGTACATCCAGGTTGTCTACCTTCATAACAACAATATC
1321 TCTGTAGTTGGATCAAGTGACTTCTGCCCACCTGGACACAACACCAAAAAGGCTTCTTAT
1381 TCGGGTGTGAGTCTTTTCAGCAACCCGGTCCAGTACTGGGAGATACAGCCATCCACCTTC
1441 AGATGTGTCTACGTGCGCTCTGCCATTCAACTCGGAAACTATAAGTAATTCTCAAGAAG
1501 CCCTCATTTTTATAACCTGGCAAATCTTGTTAATGTCATTGCTAAAAAATAAATAAAAG
1561 CTAGATACTGGAAACCTAACTGCAATGTGGATGTTTTACCCACATGACTTATTATGCATA
1621 AAGCCAAATTTCCAGTTTAAGTAATTGCCTACAATAAAAAGAAATTTTGCCTGCCATTTT
1681 CAGAATCATCTTTTGAAGCTTTCTGTTGATGTTAACTGAGCTACTAGAGATATTCTTATT
1741 TCACTAAATGTAAAATTTGGAGTAAATATATATGTCAATATTTAGTAAAGCTTTTCTTTT
1801 TTAATTTCCAGGAAAAAATAAAAAGAGTATGAGTCTTCTGTAATTCATTGAGCAGTTAGC
1861 TCATTTGAGATAAAGTCAAATGCCAAACACTAGCTCTGTATTAATCCCCATCATTACTGG
1921 TAAAGCCTCATTTGAATGTGTGAATTCAATACAGGCTATGTAAAATTTTTACTAATGTCA
1981 TTATTTTGAAAAATAAATTTAAAAATACATTCAAAATTACTATTGTATACAAGCTTAAT
2041 TGTTAATATTCCCTAAACACAATTTTATGAAGGGAGAAGACATTGGTTTGTTGACAATAA
2101 CAGTACATCTTTTCAAGTTCTCAGCTATTTCTTCTACCTCTCCCTATCTTACATTTGAGT
2161 ATGGTAACTTATGTCATCTATGTTGAATGTAAGCTTATAAAGCACAAAGCATACATTTCC
2221 TGACTGGTCTAGAGAACTGATGTTTCAATTTACCCCTCTGCTAAATAAATATTAAAACTA
2281 TCATGTG
```

The stop codon is indicated in bold as well as the position corresponding to the microarray probe.

The corresponding amino acid sequence is given in ENSEMBL accession no. ENSP00000052754 and has a sequence as in SEQ ID NO:492

```
  1 MKATIILLLLAQVSWAGPFQQRGLFDFMLEDEASGIGPEVPDDRDFEPSLGPVCPFRCQC
 61 HLRVVQCSDLGLDKVPKDLPPDTTLLDLQNNKITEIKDGDFKNLKNLHALILVNNKISKV
121 SPGAFTPLVKLERLYLSKNQLKELPEKMPKTLQELRAHENEITKVRKVTFNGLNQMIVIE
181 LGTNPLKSSGIENGAFQGMKKLSYIRIADTNITSIPQGLPPSLTELHLDGNKISRVDAAS
241 LKGLNNLAKLGLSFNSISAVDNGSLANTPHLRELHLDNNKLTRVPGGLAEHKYIQVVYLH
301 NNNISVVGSSDFCPPGHNTKKASYSGVSLFSNPVQYWEIQPSTFRCVYVRSAIQLGNYK
```

Primers for amplifying the sequence DCN can be designed using primer design software such as Oligo Calc and/or Primer 3. Examples of primer pairs for amplifying DCN include those in

```
                                        SEQ ID NO: 493
Forward AGCTTTGAGGGCTCCTGTG SEQ ID NO: 494
Reverse GCAAGCAGAAGGAGGATGAT SEQ ID NO: 495
Forward AATGCCATCTTCGAGTGGTC SEQ ID NO: 496
Reverse TGCAGGTCTAGCAGAGTTGTG SEQ ID NO: 497
Forward AACCGAAATCAAAGATGGAGA SEQ ID NO: 498
Reverse GTCCAGGTGGGCAGAAGTC SEQ ID NO: 499
Forward AATGCCATCTTCGAGTGGTC SEQ ID NO: 500
Reverse CTGCTGATTTTGTTGCCATC SEQ ID NO: 501
Forward TGGCAACAAAATCAGCAGAG SEQ ID NO: 502
Reverse GCCATTGTCAACAGCAGAGA SEQ ID NO: 503
Forward GGGCTGGCAGAGCATAAGTA SEQ ID NO: 504
Reverse GTCCAGGTGGGCAGAAGTC SEQ ID NO: 505
Forward AACCGAAATCAAAGATGGAGA SEQ ID NO: 506
Reverse CCAAAGGTGTAAATGCTCCAG SEQ ID NO: 507
Forward GAGATCACCAAAGTGCGAAA SEQ ID NO: 508
Reverse AAAGCCCCATTTTCAATTCC SEQ ID NO: 509
Forward AATGCCATCTTCGAGTGGTC SEQ ID NO: 510
Reverse AAAGCCCCATTTTCAATTCC
```

Other sets of primers can be readily designed by the skilled artisan and/or are known in the art.

Probes for detecting DCN can be derived from any number of sources depending on the desired use (e.g., using the above described primers and appropriate reagents). Other examples of probes include The probe used on the microarray has a sequence as in SEQ ID NO:511
TTTAACTGTGCTATGGAGTAGAAGCAG-GAGGTTTTCAACCTAGTCACAGAGCAGC ACC
SEQ ID NO:512 TTCCCGGATTAAAAGGTTCC
SEQ ID NO:513 AAGTGCCAAAGGATCTTCCC
SEQ ID NO:514 CCTGAAGAACCTTCACGTTG
SEQ ID NO:515 TCCTCCTTCCCTTACGGAAT
SEQ ID NO:516 ATGCAGCTAGCCTGAAAGGA
SEQ ID NO:517 CATCCAGGTTGTCTACCTTCA
SEQ ID NO:518 TGAAGAACCTTCACGCATTG
SEQ ID NO:519 TGTCATAGAACTGGGCACCA
SEQ ID NO:520 GTTCTGATTTGGAACTGGGC Antibodies to DCN include, but are not limited to, Mouse Anti-Human Decorin Monoclonal Antibody, Unconjugated Cat# ab54728, against recombinant full length protein; and Anti-DCN Monoclonal Antibody, Unconjugated, Clone 2B5-G5 Cat# H00001634-M02, against recombinant full length protein.

Additional Primers for the Biomarkers of the Invention:

```
ACAA1
                                        SEQ ID NO: 521
tcacgggagaagcaggatac SEQ ID NO: 522
cttgctctgggctcttgc SEQ ID NO: 523
ccagagattgcctgattcct SEQ ID NO: 524
cctgcttctcccgtgaaat SEQ ID NO: 525
agctgggggacatctgtgt SEQ ID NO: 526
cactcagaaactgggcgatt AP1M2
                                        SEQ ID NO: 527
cacatcgaagaatgccaatg SEQ ID NO: 528
gctccttgaagtattcgcaga SEQ ID NO: 529
tgctcttcgagctcactgg
``` cacgcactggtggaatttt SEQ ID NO: 530 gttcgctacatcacccagagt SEQ ID NO: 531 gtaaggaagccccgtgttc SEQ ID NO: 532

CGN gagcttacccgaaaagtgga SEQ ID NO: 533 tctagcttctgccgcttctt SEQ ID NO: 534 ggagatactcgccaggttga SEQ ID NO: 535 ccttaagctcctcctgtgtcc SEQ ID NO: 536 cctctgtgaggaggaaggttag SEQ ID NO: 537 ttagtagaaccagaagaaaccatcac SEQ ID NO: 538

DDR1 tagagagccaccccgta SEQ ID NO: 539 ccatatagtccccactgtaggc SEQ ID NO: 540 ccactctgctccctgtgtc SEQ ID NO: 541 ctggcttctcaggctccata SEQ ID NO: 542 tggggactattaccgtgtgc SEQ ID NO: 543 acgtcactcgcagtcgtg SEQ ID NO: 544

EPS8L2 gcagctcttctccctcaaca SEQ ID NO: 545 cccactttgctgcttctcc SEQ ID NO: 546 caagatgagccccaaggac SEQ ID NO: 547 tgatgacgttggagttggaa SEQ ID NO: 548 caaggatgaggtcctagaggtg SEQ ID NO: 549 gatgttgcagggcacgta SEQ ID NO: 550

FASTKD1 tggaaattctggggtatcgt SEQ ID NO: 551 gcatcctttgttgacagtgc SEQ ID NO: 552 cctgggaatcaaatatcgaaatag SEQ ID NO: 553 ccaaaaattccaaagcaatcc SEQ ID NO: 554 aagaattaacttttctgcatttcca SEQ ID NO: 555 cagaacagacacctcagttggt SEQ ID NO: 556

GMIP aaccctggccatggagac SEQ ID NO: 557 ccgccacttctcaatctcag SEQ ID NO: 558 cccagcaccacagtaccc SEQ ID NO: 559 ctctgtggagttggaatctcg SEQ ID NO: 560 ctggtggcccatctgttc SEQ ID NO: 561 ggttgttggcagacatcttgt SEQ ID NO: 562

IKBKE acagttcaagaagtctaggatgagg SEQ ID NO: 563 tggctaaatgactgaaattcacc SEQ ID NO: 564 ggacatccctcctctacctca SEQ ID NO: 565 ggatctcaggcgttccag SEQ ID NO: 566 ctgcctgaggatgagttcct SEQ ID NO: 567 gatgcacaatgccgttctc SEQ ID NO: 568

P2RX4 ccgttacgaccaaggtcaag SEQ ID NO: 569 tgacgaagagggagttttcc SEQ ID NO: 570 tctgtcaagacgtgtgaggtg SEQ ID NO: 571 agtgaagttttctgcagcctttα SEQ ID NO: 572 tctcctggctacaatttcagg SEQ ID NO: 573 atgccataggccttgatgag SEQ ID NO: 574

P4HB gcttcccccaaggaatataca SEQ ID NO: 575 tcttcagccagttcacgatg SEQ ID NO: 576 gcagggatgatgacgat SEQ ID NO: 577 cgtcttcctccatgtctgg SEQ ID NO: 578 ctggagggcaaaatcaagc SEQ ID NO: 579 ttcttcccaacaagcacctt SEQ ID NO: 580

PHKG2 gcagatccgactttcagatttc  SEQ ID NO: 581 ggggtcccacacaactctc  SEQ ID NO: 582 ttccagcactgtcaaagacct  SEQ ID NO: 583 aaagaagggtgctgtaggg  SEQ ID NO: 584 aggctatggcaaggaggtc  SEQ ID NO: 585 tgcgtaacatcaggatctgc  SEQ ID NO: 586

PPFIBP2 aggggataaggagtccctca  SEQ ID NO: 587 ctggtgtccttccagacaca  SEQ ID NO: 588 gaatggaagctaaaggccact  SEQ ID NO: 589 atctttcagggccacctgtt  SEQ ID NO: 590 aatcttcgagggagtggagtc  SEQ ID NO: 591 cagggtgtccccagtgaa  SEQ ID NO: 592

PPP1R16A ccctcccagtgttgtcctt  SEQ ID NO: 593 ccccactcccaaggaact  SEQ ID NO: 594 gagtgctggacgcctctg  SEQ ID NO: 595 ttgaccgccaggagattg  SEQ ID NO: 596 atgccctatgacctgtgtgat  SEQ ID NO: 597 gatgctgtcctgggtgatg  SEQ ID NO: 598

RASSF7 cactagcccaagcaataggc  SEQ ID NO: 599 cactcttgtggcagcaactg  SEQ ID NO: 600 cagcctggctctggtgag  SEQ ID NO: 601 ggagctctcggttcagctc  SEQ ID NO: 602 tctgcctccagccagaga  SEQ ID NO: 603 ctccaggagttctgcgtcat  SEQ ID NO: 604

RNF183 tccagagtagtctgcctgacc  SEQ ID NO: 605 catcctcagccacacacg  SEQ ID NO: 606 tccagagtagtctgcctgacc  SEQ ID NO: 607 tgttgttgaaggggttccag  SEQ ID NO: 608 tctgccaccgtgtctacg  SEQ ID NO: 609 cggaaacactccctcaaaga  SEQ ID NO: 610

SIRT6 agctgagggacaccatccta  SEQ ID NO: 611 atgtacccagcgtgatggac  SEQ ID NO: 612 aggatgtcggtgaattacgc  SEQ ID NO: 613 agaccagcctcgccagtt  SEQ ID NO: 614 ggtcagccagaacgtgga  SEQ ID NO: 615 gtggagctctgccagtttgt  SEQ ID NO: 616

TJP3 gtgggcatcttcgtgtcc  SEQ ID NO: 617 gaatggcacgtcattcacc  SEQ ID NO: 618 atctggacggcggaagat  SEQ ID NO: 619 ggtgagggaggtctaggttgt  SEQ ID NO: 620 tcatcaagcacattacagattcg  SEQ ID NO: 621 ggctagacaccccgttgat  SEQ ID NO: 622

EFEMP2 actcgcaggggacttttac  SEQ ID NO: 623 catgagggaattcatggtga  SEQ ID NO: 624 atcgggatggcttctcct  SEQ ID NO: 625 tgatgcagcggtactgaca  SEQ ID NO: 626 agtaccgctgcatcaacga  SEQ ID NO: 627 cgcaccagactcacactcat  SEQ ID NO: 628

SOCS2 ggagctcggtcagacagg  SEQ ID NO: 629 ctaatcaagaaagttccttctggtg  SEQ ID NO: 630 cagtcaccaagcccctcc  SEQ ID NO: 631

| | SEQ ID NO: 632 |
|---|---|
| aagggatggggctctttct | |
| | SEQ ID NO: 633 |
| ggagctcggtcagacagg | |
| | SEQ ID NO: 634 |
| gttccttctggtgcctctttt | |
| DCN | |
| | SEQ ID NO: 635 |
| ggagactttaagaacctgaagaacc | |
| | SEQ ID NO: 636 |
| cgttccaacttcaccaaagg | |
| | SEQ ID NO: 637 |
| ctgtcaatgccatcttcgag | |
| | SEQ ID NO: 638 |
| gatcctttggcactttgtcc | |
| | SEQ ID NO: 639 |
| caatatcaccagcattcctcaag | |
| | SEQ ID NO: 640 |
| ctgctgattttgttgccatc | |

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference. The mere mentioning of the publications and patent applications does not necessarily constitute an admission that they are prior art to the instant application.

Although the foregoing invention has been described in some detail by way of illustration and example for purposes of clarity of understanding, it will be obvious that certain changes and modifications may be practiced within the scope of the appended claims.

The invention claimed is:

1. An in vitro method for diagnosing endometrial cancer in a patient, comprising (a) performing reverse transcription on a uterine tissue or uterine fluid sample from the patient to synthesize cDNA, (b) contacting the cDNA with primers and reagents and specifically amplifying P4HB cDNA, (c) contacting the cDNA with primers and reagents and specifically amplifying GMIP cDNA, wherein the amplifying of P4HB cDNA and the amplifying of GMIP cDNA are not multiplex, and (d) detecting the level of the amplified P4HB cDNA and GMIP cDNA, wherein increased levels of P4HB cDNA and GMIP cDNA compared to a control value indicates the existence of endometrial cancer, wherein the P4HB primers are primer pairs selected from the group consisting of:

(i) Forward SEQ ID NO:247: GCTGCGGAAAAGCAACTTC and Reverse SEQ ID NO:248 CTGATCTCGGAACCTTCTGC;
(ii) Forward SEQ ID NO:249 GGCTATCCCACCATCAAGTT and Reverse SEQ ID NO:250 TCTTCAGCCAGTTCACGATG;
(iii) Forward SEQ ID NO:251 GCAGAGTCCTTGGTGGAGTC and Reverse SEQ ID NO:252 TGGAAGTGATCCCAAATGGT;
(iv) Forward SEQ ID NO:253 ACCATTTGGGATCACTTCCA and Reverse SEQ ID NO:254 GGTGACCTCCCCTTCAAAGT;
(v) Forward SEQ ID NO:255 CCCCTTGTCATCGAGTTCAC and Reverse SEQ ID NO:256 TGCTCAGTTTGCCGTCATAG;
(vi) Forward SEQ ID NO:257 TCACATCCTGCTGTTCTTGC and Reverse SEQ ID NO:258 GTCGCTGTCGATGAAGATGA;
(vii) Forward SEQ ID NO:259 GACGGCAGAGAGGATCACAG and Reverse SEQ ID NO:260 TTCTTCCCAACAAGCACCTT;
(viii) Forward SEQ ID NO:261 AGCCTGTCAAGGTGCTTGTT and Reverse SEQ ID NO:262 CAAATGGGAGCCAACTGTTT;
(ix) Forward SEQ ID NO:263 ACAGCTTCCCCACACTCAAG and Reverse SEQ ID NO:264 CACCGCTCTCCAGGAATTT; and
(x) Forward SEQ ID NO:265 GCACGCTGGATGGTTTTAAG and Reverse SEQ ID NO:266 TCATCGTCTTCCTCCATGTCT.

2. The method of claim 1 wherein said patient has a risk factor for endometrial cancer or is being screened for endometrial cancer.

3. The method of claim 1 wherein said sample from said patient is from a patient with abnormal uterine bleeding.

4. The method of claim 1 wherein said sample from said patient is from a patient having an endometrium with increased thickness.

5. The method of claim 1 wherein said sample from said patient is from a pre-menopausal, peri-menopausal, or post-menopausal patient.

6. The method of claim 1 further comprising contacting the cDNA with primers and reagents and specifically amplifying cDNA of a combination of at least one of the following markers: EFEMP2, SIRT6, FASTKD1 and DDR1, and determining the level of the amplified cDNA of the combination.

7. The method of claim 1 further comprising contacting the cDNA with primers and reagents and specifically amplifying cDNA of a combination of at least two of the following markers: EFEMP2, SIRT6, FASTKD1 and PHKG2, and determining the level of the amplified cDNA of the combination.

8. The method of claim 1 further comprising contacting the cDNA with primers and reagents and specifically amplifying cDNA of a combination of at least two of the following markers: EFEMP2, SIRT6, ACAA1, AP1M2, EPS8L2, IKBKE, P2RX4, PPFIBP2 and PPP1R16A, and determining the level of the amplified cDNA of the combination.

9. The method of claim 1, further comprising contacting the cDNA with primers and reagents and specifically amplifying IKBKE cDNA, and detecting the level of amplified IBKE cDNA.

10. The method of claim 1, further comprising contacting the cDNA with primers and reagents and specifically amplifying cDNA for a combination of markers selected from the group consisting of: SOCS2; IKBKE; IKBKE, and SOCS2; SOCS2, and EPS8L2; IKBKE, and EPS8L2; IKBKE, SOCS2, and DDR1; IKBKE, SOCS2, EPS8L2, and PPP1R16A; IKBKE, SOCS2, PHKG2, and RASSF7; IKBKE, SOCS2, EPS8L2, and DDR1; IKBKE, SOCS2, EPS8L2, PPP1R16A, and DDR1; IKBKE, SOCS2, and EPS8L2; DDR1, EPS8L2, IKBKE, P2RX4, PHKG2, PPP1R16A, RASSF7, SIRT6, TJP3, and SOCS2; and DDR1, EPS8L2, IKBKE, P2RX4, PHKG2, PPP1R16A, RASSF7, SIRT6, TJP3, RNF183 and SOCS2, and determining the level of the amplified cDNA of the combination.

11. The method of claim 1, further comprising contacting the cDNA with primers and reagents and specifically amplifying cDNA for a combination of markers selected from the group consisting of: IKBKE, SOCS2 and FASTKD1; IKBKE, SOCS2 and DDR1; IKBKE, SOCS2 and PHKG2; IKBKE, SOCS2 and SIRT6; IKBKE, SOCS2 and ACAA1; IKBKE, SOCS2 and EFEMP2; IKBKE, SOCS2 and EPS8L2; IKBKE, SOCS2 and P2RX4; IKBKE, SOCS2 and PPFIBP2; IKBKE, SOCS2 and PPP1R16A; IKBKE, SOCS2, ACAA1 and FASTKD1; IKBKE, SOCS2, PHKG2 and FASTKD1; IKBKE, SOCS2, SIRT6 and FASTKD1; IKBKE, and EFEMP2; ACAA1, AP1M2, EPS8L2, IKBKE, P2RX4, PPFIBP2, PPP1R16A, SIRT6, and EFEMP2; DDR1, FASTKD1, PHKG2, SIRT6, SOCS2, IKBKE, and EFEMP2; DDR1, FASTKD1, PHKG2, SIRT6, IKBKE, and EFEMP2; and EFEMP2, IKBKE, and FASTKD1, and determining the level of the amplified cDNA of the combination.

12. The method of claim 1, further comprising contacting the cDNA with primers and reagents and specifically amplifying for a combination of markers selected from the group consisting of: IKBKE, EFEMP2 and FASTKD1; IKBKE, EFEMP2 and DDR1; IKBKE, EFEMP2 and PHKG2; IKBKE, EFEMP2 and SIRT6; IKBKE, EFEMP2 and ACAA1; IKBKE, SOCS2 and EFEMP2; IKBKE, EFEMP2 and EPS8L2; IKBKE, EFEMP2 and P2RX4; IKBKE, EFEMP2 and PPFIBP2; IKBKE, EFEMP2 and PPP1R16A; IKBKE, EFEMP2, ACAA1 and FASTKD1; IKBKE, EFEMP2, PHKG2 and FASTKD1; and IKBKE, EFEMP2, SIRT6 and FASTKD 1, and determining the level of the amplified cDNA of the combination.

* * * * *